(12) United States Patent
Clayton et al.

(10) Patent No.: US 7,968,570 B2
(45) Date of Patent: *Jun. 28, 2011

(54) ISOINDOLONE COMPOUNDS AND THEIR USE AS METABOTROPIC GLUTAMATE RECEPTOR POTENTIATORS

(75) Inventors: Joshua Clayton, Toronto (CA); Fupeng Ma, Toronto (CA); Bradford Van Wagenen, Salt Lake City, UT (US); Radhakrishnan Ukkiramapandian, Salt Lake City, UT (US); Ian Egle, Toronto (CA); James Empfield, Wilmington, DE (US); Methvin Isaac, Toronto (CA); Abdelmalik Slassi, Toronto (CA); Gary Steelman, Wilmington, DE (US); Rebecca Urbanek, Wilmington, DE (US); Sally Walsh, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 550 days.

This patent is subject to a terminal disclaimer.

(21) Appl. No.: 11/659,149

(22) PCT Filed: Aug. 12, 2005

(86) PCT No.: PCT/US2005/028760
§ 371 (c)(1),
(2), (4) Date: Aug. 25, 2008

(87) PCT Pub. No.: WO2006/020879
PCT Pub. Date: Feb. 23, 2006

(65) Prior Publication Data
US 2009/0275578 A1    Nov. 5, 2009

Related U.S. Application Data

(60) Provisional application No. 60/601,125, filed on Aug. 13, 2004, provisional application No. 60/684,945, filed on May 27, 2005.

(51) Int. Cl.
*A61K 31/4409* (2006.01)
*C07D 401/14* (2006.01)

(52) U.S. Cl. .................................. 514/339; 546/275.4
(58) Field of Classification Search .................. None
See application file for complete search history.

(56) References Cited

U.S. PATENT DOCUMENTS

| 3,993,617 | A | 11/1976 | Schwan |
| 5,681,954 | A | 10/1997 | Yamamoto et al. |
| 2004/0242572 | A1 * | 12/2004 | Stenkamp et al. .......... 514/227.2 |

FOREIGN PATENT DOCUMENTS

| BE | 620 654 A | 1/1963 |
| EP | 1528923 A1 | 10/1978 |
| EP | 0 548 934 A | 6/1993 |
| EP | 0602814 A1 | 6/1994 |
| EP | 1431267 A1 | 6/2004 |
| WO | WO-92-17448 A1 | 4/1991 |
| WO | WO-99-26927 A | 6/1999 |
| WO | WO-02-10146 A1 | 2/2002 |
| WO | WO-03-087044 A2 | 10/2003 |
| WO | WO-2004-024702 A | 3/2004 |
| WO | WO-2004-087048 A2 | 10/2004 |
| WO | WO-2004-089897 A1 | 10/2004 |
| WO | WO-2005-040157 A | 5/2005 |
| WO | WO-2005-074643 A | 8/2005 |
| WO | WO-2005-085214 A | 9/2005 |
| WO | WO-2005-085216 A | 9/2005 |

OTHER PUBLICATIONS

Yamamoto et al. Org. Biomol. Chem. 2004, vol. 2, pp. 1287-1294.*
Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Yamamoto et al. Org. Biomol. Chem (2004); 2,1287-1294.*
CA 139:133427 Synthetic Communications 33(7), 1087-1094, 2003.
Yamamoto Y. et al: vol. 2, No. 9, May 2004, pp. 1287-1294, XP002357868.
Moreau a et al: Tetrahedron, vol. 60, No. 29, Jul. 12, 2004, pp. 6169-6176 XP002357869.
Hatt H H et al: Journal of the Chemical Society, 1952, pp. 199-205 XP002357871. Bohme H et al: Die Pharmazie, No. 25, 1970, pp. 283-289, XP002357872.
Mori M et al: Journal of Organic Chemistry, vol. 43, No. 9, Apr. 28, 1978, pp. 1864-1867, XP002357874.
Grigg R et al: Tetrahedron Letters, vol. 44, No. 37, Sep. 8, 2003, pp. 6979-6982, XP004447066.
Norman M H et al.: Journal of Medicinal Chemistry, vol. 39, No. 1, 1996, pp. 149-157, XP000982309.
Zhuang Z-P et al: Journal of Medicinal Chemistry, vol. 41, No. 2, Jan. 15, 1998, pp. 157-166, XP002357875.
Norman M H, et al: Journal of Medicinal Chemistry, vol. 36, No. 22, Oct. 29, 1993, pp. 3417-3423, XP002357876.
Ahn K H et al: Bioorganic & Medicinal Chemistry Letters, vol. 9, No. 10, May 17, 1999, pp. 1379-1384, XP004164896.

(Continued)

Primary Examiner — Rebecca L Anderson
Assistant Examiner — Alicia L Otton
(74) Attorney, Agent, or Firm — Kenneth F. Mitchell

(57) ABSTRACT

The present invention is directed to compounds of formula I:

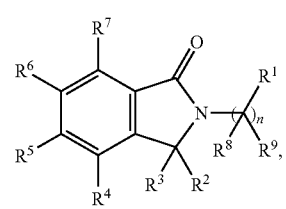

(I)

wherein $R^1$, $R^2$, $R^3$, $R^4$, $R^5$, $R^6$, $R^7$, $R^8$, $R^9$ and n are as defined for formula I in the description. The invention also relates to processes for the preparation of the compounds and to new intermediates employed in the preparation, pharmaceutical compositions containing the compounds, and to the use of the compounds in therapy.

4 Claims, No Drawings

OTHER PUBLICATIONS

Sugimoto H et al: Journal of Medicinal Chemistry, vol. 35, No. 24, 1992, pp. 4542-4548, XP002319779.
Mayer P et al: Journal of Medicinal Chemistry, vol. 43, Sep. 19, 2000, pp. 3653-3664, XP001183987.
Breytenbach J C et al: Bioorganic & Medicinal Chemistry Letters, vol. 10, No. 15, Aug. 7, 2000, pp. 1629-1631, XP004213210.
Anderson P S et al: Journal of Organic Chemistry, vol. 44, No. 9, 1979, pp. 1519-1515, XP002981802.
Luzzio F A et al: Tetrahedron Letters, vol. 40, No. 11, Mar. 12, 1999, pp. 2087-2090, XP002357870.
CA 133:150436, Tetrahedron Letters, 41(20), 3891-3893, 2000.
CA 83:9678, Chemical & Pharmaceutical Bulletin, 23(1), 184-187, 1975.
CA 79:105030, Roczniki Chemii, 47(5), 937-942, 1973.

* cited by examiner

ISOINDOLONE COMPOUNDS AND THEIR USE AS METABOTROPIC GLUTAMATE RECEPTOR POTENTIATORS

CROSS REFERENCE TO RELATED APPLICATIONS

This application is related to U.S. Provisional Application 60/601,125, filed Aug. 13, 2004, and U.S. Provisional Application 60/684,945, filed May 27, 2005, each of which is incorporated herein by reference in its entirety.

BACKGROUND OF THE INVENTION

The present invention relates to novel compounds that function as potentiators of glutamate receptors, methods for their preparation, pharmaceutical compositions containing them and their use in therapy.

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolim., 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Members of the mGluR family of receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365; Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

SUMMARY OF THE INVENTION

The invention satisfies this need and others by providing, as one object, compounds of formula I,

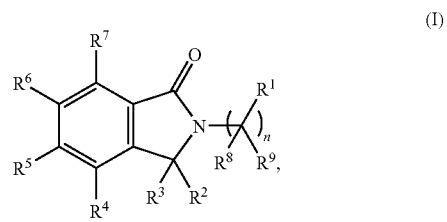

(I)

wherein:
$R^1$ is a 3- to 7-membered ring that may contain one or more heteroatoms independently selected from the group consisting of N, O and S, wherein said ring may be substituted by one or more A;
$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;
$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkylOR$^{10}$, $OC_{2-6}$-alkylOR$^{10}$, $C_{1-6}$-alkyl(CO)R$^{10}$, $OC_{1-6}$-alkyl(CO)R$^{10}$, $C_{0-6}$-alkylCO$_2$R$^{10}$, $OC_{1-6}$-alkylCO$_2$R$^{10}$, $C_{1-6}$-alkylcyano, $OC_{2-6}$-alkylcyano, $C_{0-6}$-alkylNR$^{10}$R$^{11}$, $OC_{2-6}$-alkylNR$^{10}$R$^{11}$, $C_{1-6}$-alkyl(CO)R$^{10}$, $OC_{1-6}$-alkyl(CO)NR$^{10}$R$^{11}$, $C_{0-6}$-alkylNR$^{10}$(CO)R$^{11}$, $OC_{2-6}$-alkylNR$^{10}$(CO)R$^{11}$, $C_{0-6}$-alkylNR$^{10}$(CO)NR$^{10}$R$^{11}$, $C_{0-6}$-alkylSR$^{10}$, $OC_{2-6}$-alkylSR$^{10}$, $C_{0-6}$-alkyl(SO)R$^{10}$, $OC_{2-6}$-alkyl(SO)R$^{10}$, $C_{0-6}$-alkylSO$_2$R$^{10}$, $OC_{2-6}$-alkylSO$_2$R$^{10}$, $C_{1-6}$-alkyl(SO$_2$)NR$^{10}$R$^{11}$, $OC_{2-6}$-alkyl(SO$_2$)NR$^{10}$R$^{11}$, $C_{0-6}$-alkylNR$^{10}$(SO$_2$)R$^{11}$, $OC_{2-6}$-alkylNR$^{10}$(SO$_2$)R$^{11}$, $C_{0-6}$-alkylNR$^{10}$(SO$_2$)NR$^{10}$R$^{11}$, $OC_{2-6}$-alkylNR$^{10}$(SO$_2$)NR$^{10}$R$^{11}$, $(CO)NR$^{10}$R$^{11}$, $O(CO)$ NR$^{10}$R$^{11}$, NR$^{10}$OR$^{11}$, $C_{0-6}$-alkylNR$^{10}$(CO)OR$^{11}$, $OC_{2-6}$-alkylNR$^{10}$(CO)OR$^{11}$, SO$_3$R$^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;
$R^5$ is selected from the group consisting of H, F, Cl, Br, I, nitro, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$- cycloalkyl, aryl, $C_{1-6}$-alkylaryl, $C_{1-6}$-alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$alkylheterocycloalkyl, C(O)H, $(CO)R^{10}$, $O(CO)R^{10}$, $O(CO)OR^{10}$, $C(O)OR^{10}$, $O(CN)OR^{10}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}OR^{11}$, $C_{0-6}$-alkyl$SR^{10}$), $OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}OR^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $C_{2-6}$-alkynyl, and $OC_{2-6}$-alkynyl, or, where n is greater than 1, two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from allyl, halo, hydroxyl, Oalkyl, haloalkyl and Ohaloalkyl;

A is selected from the group consisting of H, hydroxy, P, Cl, Br, I, nitro, cyano, oxo, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{11}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}OR^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $OC_{2-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}OR^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$; and n is selected from the group consisting of 1, 2, 3, 4, 5, 6, 7, and 8;

The invention also provides, in addition to a compound of formula I, a pharmaceutically acceptable salt, hydrate, solvate, optical isomer, or combination thereof.

It should be understood that notwithstanding the strictures of formula I, the invention does not include the following compounds:

4-[(5-bromo-1,3-dihydro-1-oxo-2H-isoindol-2-yl)methyl]-1-piperidinecarboxylic acid 1,1-dimethylethyl ester, 5-bromo-2,3-dihydro-2-(4-piperidinylmethyl)-1H-Isoindol-1-one, 4-[(5-chloro-1,3-dihydro-1-oxo-2H-isoindol-2-yl)methyl]-1-Piperidinecarboxylic acid, 5-chloro-2,3-dihydro-2-(4-piperidinylmethyl)-1H-Isoindol-1-one, 4-[(1,3-dihydro-5-methoxy-1-oxo-2H-isoindol-2-yl)methyl]-1-Piperidinecarboxylic acid 1,1-dimethylethyl ester, 2,3-dihydro-5-methoxy-2-(4-piperidinylmethyl)-1H-Isoindol-1-one, 4-[(5-cyano-1,3-dihydro-1-oxo-2H-isoindol-2-yl)methyl]-1-Piperidinecarboxylic acid 1,1-dimethylethyl ester, 2,3-dihydro-1-oxo-2-(4-piperidinylmethyl)-1H-Isoindole-5-carbonitrile, 4-[(5-fluoro-1,3-dihydro-1-oxo-2H-isoindol-2-yl)methyl]-1-Piperidinecarboxylic acid 1,1-dimethylethyl ester, 5-fluoro-2,3-dihydro-2-(4-piperidinylmethyl)-1H-Isoindol-1-one, 2,3-dihydro-5-(methoxymethyl)-2-(phenylmethyl)-1H-Isoindol-1-one, 2,3-dihydro-5-hydroxy-2-[2-(4-morpholinyl)ethyl]-1H-isoindol-1-one, 2-[[(2R)-4,4-diethoxy-1-[(1S)-1-phenylethyl]-2-piperidinyl]methyl]-2,3-dihydro-7-methoxy-1H-isoindol-1-one, 2,3-dihydro-7-methoxy-2-[[(2R)-4-oxo-1-[(1S)-1-phenylethyl]-2-piperidinyl]methyl]-1H-isoindol-1-one,

[[7-chloro-2,3-dihydro-1-oxo-2-(phenylmethyl)-1H-isoindol-5-yl]oxy]-acetic acid,

[[7-chloro-2,3-dihydro-1-oxo-2-(phenylmethyl)-1H-isoindol-5-yl]oxy]-acetic acid ethyl ester, 5-fluoro-2,3-dihydro-2-[3-[4-(2-methoxyphenyl)-1-piperazinyl]propyl]-1H-isoindol-1-one,

[[2,3-dihydro-2-[2-(4-morpholinyl)ethyl]1-oxo-1H-isoindol-5-yl]oxy]-acetic acid ethyl ester, Ethyl-(2-benzyl-3-oxo-2,3-dihydro-1H-isoindol-1-yl)-acetate, Ethyl-(2-cyclopropylmethyl-3-oxo-2,3-dihydro-1H-isoindol-1-yl)-acetate, (5-Phenoxymethyl-2-(1-phenyl-3-methyl-butyl)-3-oxo-2,3-dihydro-1H-isoindol-1-yl)-acetic acid, 5,6-Dimethoxy-1-oxo-N-2-(4-(2-methoxyphenyl)-1-piperazinyl)ethyl-isoindole, 5,6-Dimethoxy-1-(3,4-dimethoxy)benzyl-3-oxo-2-(4-(2-methoxyphenyl)-1-piperazinyl)ethyl-isoindole, 2,3-Dihydro-3-allyl-3-hydroxy-2-benzyl-1H-isoindol-1-one, 2,3-Dihydro-2-benzyl-3-methyl-1H-isoindol-1-one, 2,3-Dihydro-2,3-dibenzyl-1H-isoindol-1-one, 2,3-Dihydro-3-allyl-2-benzyl-1H-isoindol-1-one,
2,3-Dihydro-2-benzyl-3-((1-hydroxy)butyl)-3-methyl-1H-isoindol-1-one,
2,3-Dihydro-2-benzyl-3-((1-hydroxy-1-methyl)ethyl)-3-methyl-1H-isoindol-1-one,
Methyl-(2,3-dihydro-3-methyl-3-oxo-2-benzyl-1H-isoindol-1-yl)-acetate,
Methyl-(2,3-dihydro-3-phenyl-3-oxo-2-benzyl-1H-isoindol-1-yl)-acetate,
Methyl-(2,3-dihydro-3-(furan-2-yl)-3-oxo-2-benzyl-1H-isoindol-1-yl)-acetate,
Methyl-(2,3-dihydro-3-methyl-3-oxo-2-((2-phenyl)ethyl)-1H-isoindol-1-yl)-acetate,
Methyl-(2,3-dihydro-3-phenyl-3-oxo-2-((2-phenyl)ethyl)-1H-isoindol-1-yl)-acetate,
Methyl-(2,3-dihydro-3-(furan-2-yl)-3-oxo-2-((2-phenyl)ethyl)-1H-isoindol-1-yl)-acetate,
2,3-Dihydro-3-phenyl-2,3-dibenzyl-1H-isoindol-1-one,
2,3-Dihydro-2,3,3-tribenzyl-1H-isoindol-1-one,
2,3-Dihydro-2,3-dibenzyl-1H-isoindol-1-one or
2,3-Dihydro-3,3-dimethyl-2-benzyl-1H-isoindol-1-one.

Another object of the invention is to provide a pharmaceutical composition comprising a compound according to formula I together with a pharmaceutically acceptable carrier or excipient.

Yet another object of the invention is a method for the treatment or prevention of neurological and psychiatric disorders associated with glutamate dysfunction in an animal in need of such treatment. The method comprises the step of administering to the animal a therapeutically effective amount of a compound of formula I or a pharmaceutical composition thereof.

Still another object of the invention is the use of a compound according to formula I, or a pharmaceutically acceptable salt or solvate thereof, for the manufacture of a medicament for the treatment of any of the conditions discussed herein.

Another object of the invention provides a compound of formula I, or a pharmaceutically acceptable salt or solvate thereof, for use in therapy.

The invention additionally provides processes for the preparation of compounds of formula I. General and specific processes are discussed in more detail below.

DETAILED DESCRIPTION OF THE PREFERRED EMBODIMENTS

The present invention is based upon the discovery of compounds that exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction.

Definitions

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "$C_{m-n}$" or "$C_{m-n}$ group" used alone or as a prefix, refers to any group having m to n carbon atoms, and having 0 to n multivalent heteroatoms selected from O, S and N, wherein m and n are 0 or positive integers, and n>m. For example, "$C_{1-6}$" would refer to a chemical group having 1 to 6 carbon atoms, and having 0 to 6 multivalent heteroatoms selected from O, S and N.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "alkyl" general includes both saturated alkyl and unsaturated alkyl.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more poly-unsaturated carbon rings having aromatic character, (e.g., 4n+2 delocalized electrons) and comprising 5 up to about 14 carbon atoms, which serves to links two structures together.

The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl" used alone or as a suffix or prefix, refers to a radical formed as a result of replacing one or more carbon atom of an alkyl with one or more heteroatoms selected from N, O and S.

The term "heteroaromatic" used alone or as a suffix or prefix, refers to a ring-containing structure or molecule having one or more multivalent heteroatoms, independently selected from N, O and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone Or as a suffix or prefix, refers to a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

The term "3- to 7-membered ring that may contain one or more heteroatoms independently selected from the group consisting of N, O and S" refers to ring as described which may be saturated, partially unsaturated or aromatic. Non-limiting examples of such rings would include pyridine, piperazine, thiophene, dihydro pyridine and the like. Similarly the term "5- to 7-membered ring that may contain one or more heteroatoms independently selected from the group consisting of N, O and S" refers to ring as described which may be saturated, partially unsaturated or aromatic. Non-limiting examples of such rings would include pyridine, piperazine, thiophene, dihydro pyridine and the like.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —R'OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, —NRC(=O)OR, —R'$NR_2$, oxo (=O), imino (=NR), thio (=S), and oximino (=N—OR), wherein each "R" is hydrogen or a $C_{1-12}$hydrocarbyl and "R'" is a $C_{1-12}$hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to groups, structures, or molecules that are substituted and to those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means —C(=O)—R, wherein R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

"Halogen" includes fluorine, chlorine, bromine and iodine.

"Halogenated," used as a prefix of a group, means one or more hydrogens on the group is replaced with one or more halogens.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

Compounds

Compounds of the invention conform generally to formula I:

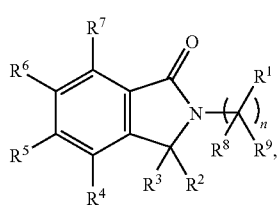

(I)

wherein:
$R^1$ is a 3- to 7-membered ring that may contain one or more heteroatoms independently selected from the group consisting of N, O and S, wherein said ring may be substituted by one or more A;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkylOR^{10}$, $OC_{2-6}$-alkylOR^{10}$, $C_{1-6}$-alkyl(CO)R^{10}$, $OC_{1-6}$-alkyl(CO)R^{11}$, $C_{0-6}$-alkylCO_2R^{10}$), $OC_{1-6}$-alkylCO_2R^{10}$, $C_{1-6}$-alkylcyano, $OC_{2-6}$-alkylcyano, $C_{0-6}$-alkylNR^{10}R^{11}$, $OC_{2-6}$-alkylNR^{10}R^{11}$, $C_{1-6}$-alkyl(CO)NR^{10}R^{11}$, $OC_{1-6}$-alkyl(CO)NR^{10}R^{11}$, $C_{0-6}$-alkylNR^{10}(CO)R^{11}$, $OC_{2-6}$-alkylNR^{10}(CO)R^{11}$, $C_{0-6}$-alkylNR^{10}(CO)NR^{10}R^{11}$, $C_{0-6}$-alkylSR^{10}$, $OC_{2-6}$-alkylSR^{10}$, $C_{0-6}$-alkyl(SO)R^{10}$, $OC_{2-6}$-alkyl(SO)R^{10}$, $C_{0-6}$-alkylSO_2R^{10}$, $OC_{2-6}$-alkylSO_2R^{10}$, $C_{0-6}$-alkyl(SO_2)NR^{10}R^{11}$, $OC_{2-6}$-alkyl(SO_2)NR^{10}R^{10}$, $C_{0-6}$-alkylNR^{10}(SO_2)R^{11}$, $OC_{2-6}$-alkylNR^{10}(SO_2)R^{11}$, $C_{0-6}$-alkylNR^{10}(SO_2)NR^{10}R^{11}$, $OC_{2-6}$-alkylNR^{10}(SO_2)NR^{10}R^{11}$, $(CO)NR^{10}R^{11}$, $O(CO)NR^{10}R^{11}$, $NR^{10}OR^{11}$, $C_{0-6}$-alkylNR^{10}(CO)OR^{11}$, $OC_{2-6}$-alkylNR^{10}(CO)OR^{11}$, $SO_3R^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of H, F, Cl, Br, I, nitro, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $C_{1-6}$-alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$-alkylheterocycloalkyl, $C(O)H$, $(CO)R^{10}$, $O(CO)R^{10}$, $O(CO)OR^{10}$, $C(O)OR^{10}$, $O(CN)OR^{10}$, $C_{1-6}$-alkylOR^{10}$; $OC_{2-6}$-alkylOR^{10}$, $C_{1-6}$-alkyl(CO)R^{10}$, $OC_{1-6}$-alkyl(CO)R^{10}$, $C_{0-6}$-alkylCO_2R^{10}$, $C_{1-6}$-alkylcyano, $OC_{2-6}$-alkylcyano, $C_{0-6}$-alkylNR^{10}R^{11}$, $OC_{2-6}$-alkylNR^{10}R^{11}$, $C_{1-6}$-alkyl(CO)NR^{10}R^{11}$, $OC_{1-6}$-alkyl(CO)NR^{10}R^{11}$, $C_{0-6}$-alkylNR^{10}(CO)R^{11}$, $OC_{2-6}$-alkylNR^{10}(CO)R^{11}$, $C_{0-6}$-alkylNR^{10}(CO)NR^{10}R^{11}$, $C_{0-6}$-alkylSR^{10}$, $OC_{2-6}$-alkylSR^{10}$, $C_{0-6}$-alkyl(SO)R^{10}$, $OC_{2-6}$-allyl(SO)R^{10}$, $C_{0-6}$-alkylSO_2R^{10}$, $OC_{2-6}$-alkylSO_2R^{10}$, $C_{0-6}$-alkyl(SO_2)NR^{10}R^{11}$, $OC_{2-6}$-alkyl(SO_2)NR^{11}$, $C_{0-6}$-alkylNR^{10}(SO_2)R^{11}$, $OC_{2-6}$-alkylNR^{10}(SO_2)R^{11}$, $C_{0-6}$-alkylNR^{10}(SO_2)NR^{10}R^{11}$, $OC_{2-6}$-alkylNR^{10}(SO_2)NR^{10}R^{11}$, $(CO)NR^{10}R^{11}$, $O(CO)NR^{10}R^{11}$, $NR^{10}OR^{11}$, $C_{0-6}$-alkylNR^{10}(CO)OR^{11}$, $OC_{2-6}$-alkylNR^{10}(CO)OR^{11}$, $SO_3R^{10}$ and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$alkenyl, $OC_{2-6}$-alkenyl, $C_{2-6}$-alkynyl, and $OC_{2-6}$-alkynyl, or, where n is greater than 1, two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$alkylaryl, $OC_{0-6}$-alkylaryl, $C_{0-6}$-alkyl-heterocycloalkyl, $OC_{1-6}$-alkyl-heterocycyoalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-4}$-alkyl$CO_2R'''$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR(CO)R^{10}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$; and n is selected from the group consisting of 1, 2, 3, 4, 5, 6, 7, and 8;

or a pharmaceutically acceptable salt, hydrate, solvate, optical isomer, or combination thereof;

with the proviso that the compound is not:

4-[(5-bromo-1,3-dihydro-1-oxo-2H-isoindol-2-yl)methyl]-1-piperidinecarboxylic acid 1,1-dimethylethyl ester, 5-bromo-2,3-dihydro-2-(4-piperidinylmethyl)-1H-Isoindol-1-one, 4-[(5-chloro-1,3-dihydro-1-oxo-2H-isoindol-2-yl)methyl]-1-Piperidinecarboxylic acid, 5-chloro-2,3-dihydro-2-(4-piperidinylmethyl)-1H-Isoindol-1-one, 4-[(1,3-dihydro-5-methoxy-1-oxo-2H-isoindol-2-yl)methyl]-1-Piperidinecarboxylic acid 1,1-dimethylethyl ester, 2,3-dihydro-5-methoxy-2-(4-piperidinylmethyl)-1H-Isoindol-1-one, 4-[(5-cyano-1,3-dihydro-1-oxo-2H-isoindol-2-yl)methyl]-1-Piperidinecarboxylic acid 1,1-dimethylethyl ester, 2,3-dihydro-1-oxo-2-(4-piperidinylmethyl)-1H-Isoindole-5-carbonitrile, 4-[(5-fluoro-1,3-dihydro-1-oxo-2H-isoindol-2-yl)methyl]-1-Piperidinecarboxylic acid 1,1-dimethylethyl ester, 5-fluoro-2,3-dihydro-2-(4-piperidinylmethyl)-1H-Isoindol-1-one, 2,3-dihydro-5-(methoxymethyl)-2-(phenylmethyl)-1H-Isoindol-1-one, 2,3-dihydro-5-hydroxy-2-[2-(4-morpholinyl)ethyl]-1H-isoindol-1-one, 2-[[(2R)-4,4-diethoxy-1-[(1S)-1-phenylethyl]-2-piperidinyl]methyl]-2,3-dihydro-7-methoxy-1H-isoindol-1-one, 2,3-dihydro-7-methoxy-2-[[(2R)-4-oxo-1-[(1S)-1-phenylethyl]-2-piperidinyl]methyl]-1H-isoindol-1-one,

[[7-chloro-2,3-dihydro-1-oxo-2-(phenylmethyl)-1H-isoindol-5-yl]oxy]-acetic acid,

[[7-chloro-2,3-dihydro-1-oxo-2-(phenylmethyl)-1H-isoindol-5-yl]oxy]-acetic acid ethyl ester, 5-fluoro-2,3-dihydro-2-[3-[4-(2-methoxyphenyl)-1-piperazinyl]propyl]-1H-isoindol-1-one,

[[2,3-dihydro-2-[2-(4-morpholinyl)ethyl]1-oxo-1H-isoindol-5-yl]oxy]-acetic acid ethyl ester, Ethyl-(2-benzyl-3-oxo-2,3-dihydro-1H-isoindol-1-yl)-acetate, Ethyl-(2-cyclopropylmethyl-3-oxo-2,3-dihydro-1H-isoindol-1-yl)-acetate, (5-Phenoxymethyl-2-(1-phenyl-3-methyl-butyl)-3-oxo-2,3-dihydro-1H-isoindol-1-yl)-acetic acid, 5,6-Dimethoxy-1-oxo-N-2-(4-(2-methoxyphenyl)-1-piperazinyl)ethyl-isoindole, 5,6-Dimethoxy-1-(3,4-dimethoxy)benzyl-3-oxo-2-(4-(2-methoxyphenyl)-1-piperazinyl)ethyl-isoindole, 2,3-Dihydro-3-allyl-3-hydroxy-2-benzyl-1H-isoindol-1-one, 2,3-Dihydro-2-benzyl-3-methyl-1H-isoindol-1-one, 2,3-Dihydro-2,3-dibenzyl-1H-isoindol-1-one, 2,3-Dihydro-3-allyl-2-benzyl-1H-isoindol-1-one, 2,3-Dihydro-2-benzyl-3-((1-hydroxy)butyl)-3-methyl-1H-isoindol-1-one, 2,3-Dihydro-2-benzyl-3-((1-hydroxy-1-methyl)ethyl)-3-methyl-1H-isoindol-1-one, Methyl-(2,3-dihydro-3-methyl-3-oxo-2-benzyl-1H-isoindol-1-yl)-acetate, Methyl-(2,3-dihydro-3-phenyl-3-oxo-2-benzyl-1H-isoindol-1-yl)-acetate, Methyl-(2,3-dihydro-3-(furan-2-yl)-3-oxo-2-benzyl-1H-isoindol-1-yl)-acetate, Methyl-(2,3-dihydro-3-methyl-3-oxo-2-((2-phenyl)ethyl)-1H-isoindol-1-yl)-acetate, Methyl-(2,3-dihydro-3-phenyl-3-oxo-2-((2-phenyl)ethyl)-1H-isoindol-1-yl)-acetate, Methyl-(2,3-dihydro-3-(furan-2-yl)-3-oxo-2-((2-phenyl)ethyl)-1H-isoindol-1-yl)-acetate, 2,3-Dihydro-3-phenyl-2,3-dibenzyl-1H-isoindol-1-one, 2,3-Dihydro-2,3,3-tribenzyl-1H-isoindol-1-one, 2,3-Dihydro-2,3-dibenzyl-1H-isoindol-1-one or 2,3-Dihydro-3,3-dimethyl-2-benzyl-1H-isoindol-1-one.

Other compounds of the invention conform generally to formula I:

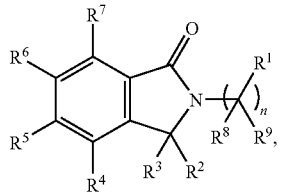

wherein $R^1$, $R^2$, $R^3$, $R^4$, $R^5$, $R^6$, $R^7$, $R^8$, $R^9$ and n are defined as hereinabove. In a preferred embodiment, n is 1, 2, or 3. When n is greater than 1, two or more of $R^8$ and $R^9$ on adjacent carbon atoms can be missing so as to form partially or fully unsaturated moieties. Thus, for example, when n is 2 and two adjacent $R^8$ and $R^9$ are missing, the moiety is an alkenyl group. When four adjacent $R^8$ and $R^9$ are missing, the moiety is an alkynyl group. All of these combinations are contemplated. Most preferably, n is 1. In this context, $R^8$ and $R^9$ preferably are each H.

Another preferred subset of compounds are those in which $R^4$ and $R^6$ in formula I are each H. Thus, the aromatic portion of the isoindolone core in this embodiment can be di-substituted at most.

In another embodiment, $R^1$ is a 5- to 7-membered ring that is selected from the group consisting of aryl, $C_{3-8}$-cycloalkyl, cycloalkenyl, and heterocyclyl optionally substituted by one or more A selected from the group consisting of F, Cl, Br, I, $OC_{1-6}$-alkylhalo, and $OC_{0-6}$-alkylaryl. Exemplary rings in this context include but are not limited to phenyl, naphthyl, $C_{3-8}$-cycloalkyl, cycloalkenyl, furanyl, tetrahydrofuranyl, thiophenyl, pyridyl, oxadiazolyl, quinolinyl, piperazinyl, and tetrahydropyranyl. Preferably, $R^1$ is phenyl optionally substituted by one or more A selected from the group consisting of F, Cl, Br, I, $OC_{1-6}$-alkylhalo, and $OC_{0-6}$-alkylaryl.

In another embodiment, $R^1$ is phenyl optionally substituted by one or more A selected from the group consisting of F, Cl, Br, I, $OC_{1-6}$-alkylhalo, and $OC_{0-6}$-alkylaryl. Additionally, $R^2$, $R^3$, $R^4$, $R^6$, $R^8$, and $R^9$ are each H and n is 1. Preferred values for $R^7$ include H, Cl, Br, I, $C_{1-6}$-alkyl, and $OC_{1-4}$-alkyl, preferably H, Cl, Br, I, —$CH_3$, and —$OCH_3$, and most preferably Cl, Br, I, and —$OCH_3$.

In yet another embodiment, $R^1$ is a $C_{3-8}$-cycloalkyl group. Preferably, $R^1$ is cyclopropyl. In this embodiment, n is preferably 1, 2, or 3, and most preferably is 1.

Another preferred subset of compounds are those in which $R^5$ is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{1-6}$-alkylaryl, and a 5- to 7-membered ring that may contain one or more heteroatoms independently selected from the group consisting of N, O and S. In this embodiment, $R^5$ may be substituted by one or more A, and any cycloalkyl or aryl is optionally fused to a 5- to 7-membered ring that may contain one or more heteroatoms independently selected from the group consisting of C, N, O and S. Preferably, $R^5$ is selected from $C_{1-6}$-alkylaryl and a 5- to 7-membered ring that may contain one or more heteroatoms independently selected from the group consisting of N, O and S, wherein $R^5$ may be substituted by one or more A. More preferably, $R^5$ is a 5- to 7-membered ring that may contain one or more heteroatoms independently selected from the group consisting of N, O and S, which ring is substituted by one or more A selected from the group consisting of $C_{1-6}$-alkyl-heterocyclyl and a 5- to 7-membered ring that may contain one or more heteroatoms independently selected from the group consisting of N, O and S.

In yet another embodiment, n is 1, 2, or 3; $R^4$, $R^6$, $R^8$ and $R^9$ are each H; $R^1$ is selected from the group consisting of aryl, $C_{3-8}$-cycloalkyl, cycloalkenyl, and heterocyclyl optionally substituted by one or more A selected from the group consisting of F, Cl, Br, I, $OC_{1-6}$-alkylhalo, and $OC_{0-6}$-alkylaryl; $R^7$ is selected from the group consisting of H, Cl, Br, I, $C_{1-6}$-alkyl, and $OC_{1-4}$-alkyl, and $R^5$ is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{1-6}$-alkylaryl, and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S.

In another embodiment, n is 1, 2, or 3; $R^4$, $R^6$, $R^8$ and $R^9$ are each H; $R^1$ is selected from phenyl, naphthyl, $C_{3-8}$-cycloalkyl, cycloalkenyl, furanyl, tetrahydrofuranyl, thiophenyl, pyridyl, oxadiazolyl, quinolinyl, piperazinyl, and tetrahydropyranyl optionally substituted by one or more A selected from the group consisting of F, Cl, Br, I, $OC_{1-6}$-alkylhalo, and $OC_{0-6}$-alkylaryl; $R^7$ is selected from Cl, Br, I, and —$OCH_3$, and $R^5$ is selected from $C_{1-6}$-alkylaryl and a 5- to 7-membered ring that may contain one or more heteroatoms independently selected from the group consisting of N, O and S, wherein $R^5$ may be substituted by one or more A.

In a still further embodiment, n is 1, 2, or 3; $R^4$, $R^6$, $R^8$ and $R^9$ are each H; $R^1$ is phenyl optionally substituted by one or more A selected from the group consisting of F, Cl, Br, I, $OC_{1-6}$-alkylhalo, and $OC_{0-6}$-alkylaryl; $R^7$ is selected from the group consisting of H, Cl, Br, J, $C_{1-6}$-alkyl, and $OC_{1-4}$-alkyl, and $R^5$ is a 5- to 7-membered ring that may contain one or more heteroatoms independently selected from the group consisting of N, O and S, wherein the 5- to 7-membered ring is substituted by one or more A selected from the group consisting of $C_{1-6}$-alkyl-heterocyclyl and a 5- to 7-membered ring that may contain one or more heteroatoms independently selected from the group consisting of N, O and S.

In another embodiment, n is 1; $R^2$, $R^3$, $R^4$, $R^6$, $R^8$ and $R^9$ are each H; $R^1$ is phenyl optionally substituted by one or more A selected from the group consisting of F, Cl, Br, I, $OC_{1-6}$-alkylhalo, and $OC_{0-6}$-alkylaryl; $R^7$ is selected from Cl, Br, I, and —$OCH_3$, and $R^5$ is selected from $C_{1-6}$-alkylaryl and a 5- to 7-membered ring that may contain one or more heteroatoms independently selected from the group consisting of N, O and S, wherein $R^5$ may be substituted by one or more A.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of formula I. The optically active forms of the compound of the invention may be prepared, for example, by chiral chromatographic separation of a racemate, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of formula I. It will further be understood that the present invention encompasses tautomers of the compounds of formula I.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the following compounds, their pharmaceutically acceptable salts, hydrates, solvates, optical isomers, and combinations thereof:

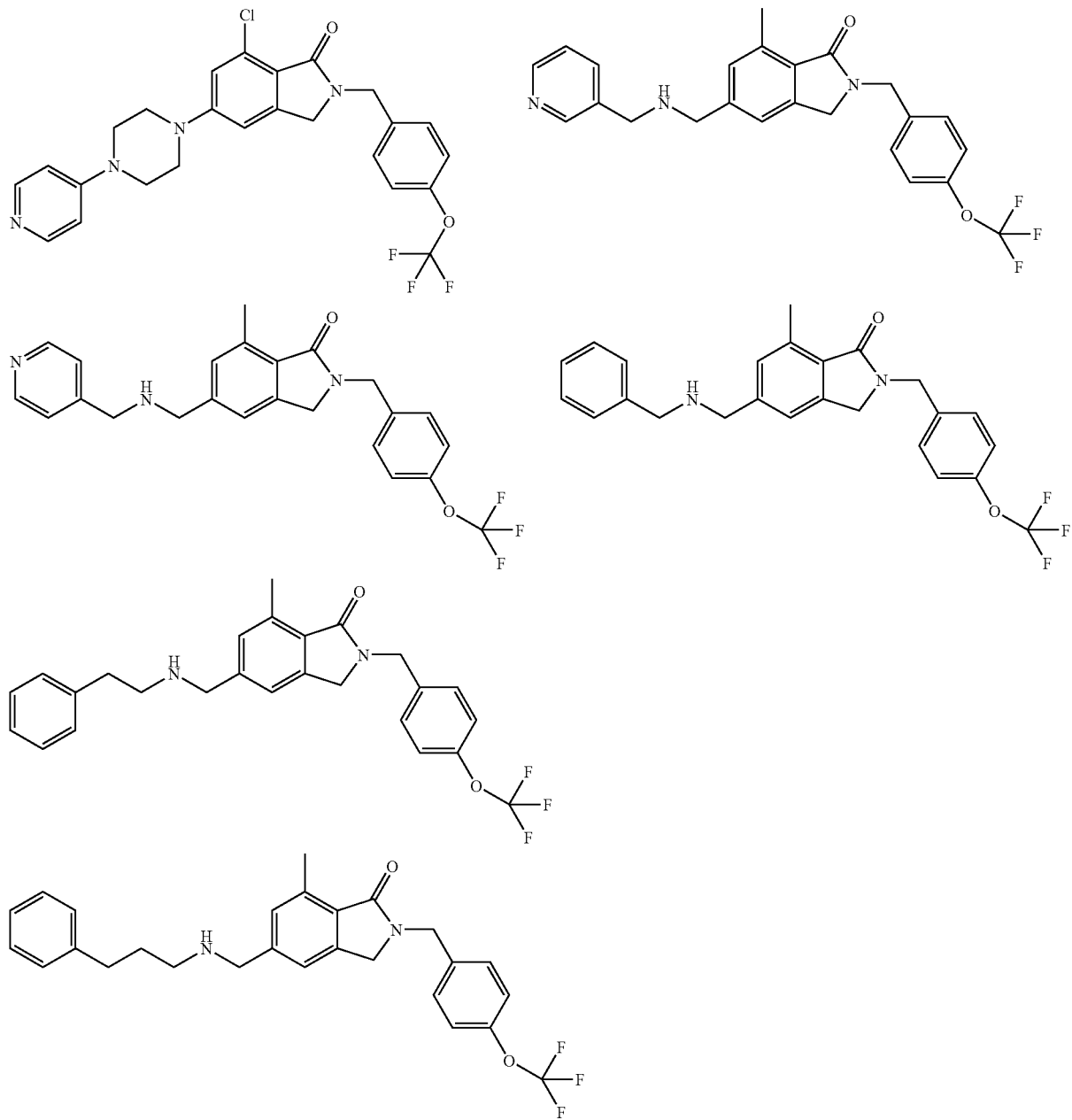

-continued
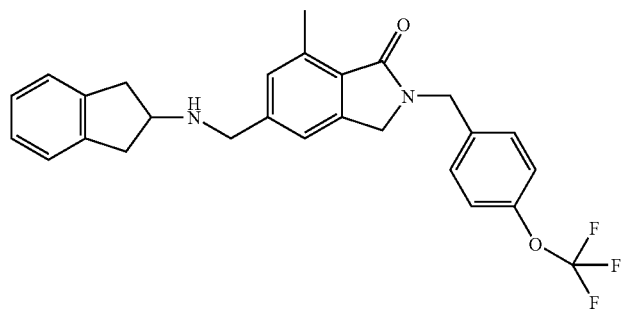
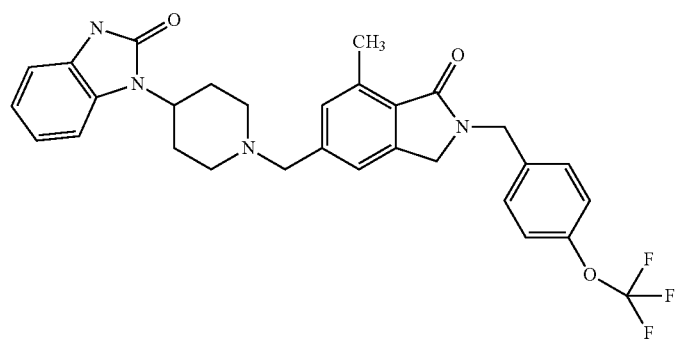
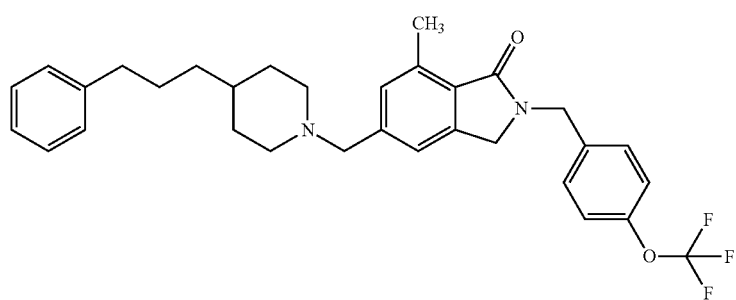
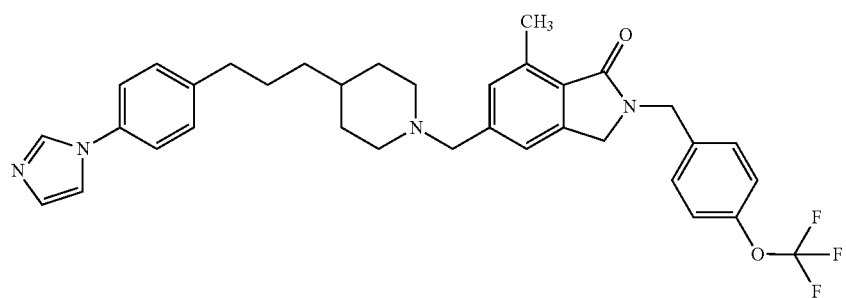
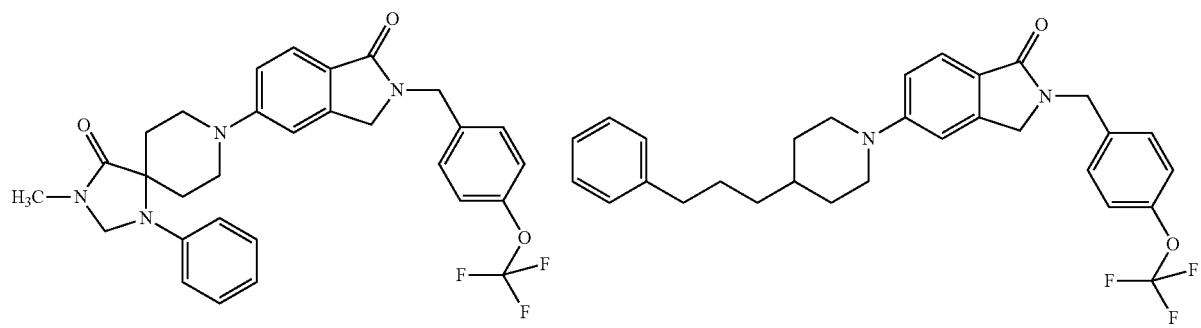

-continued
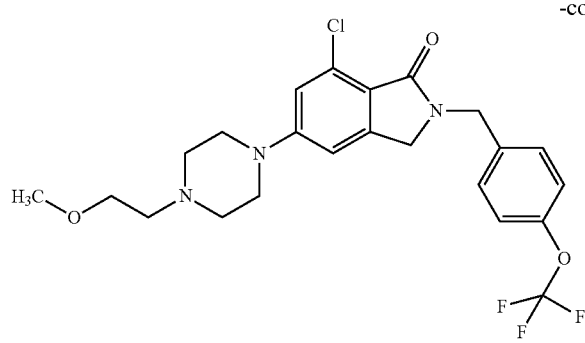
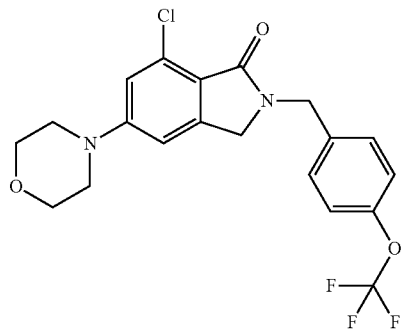
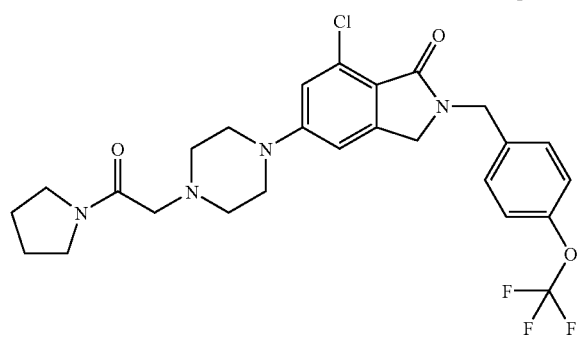
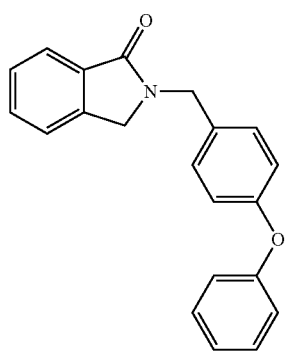
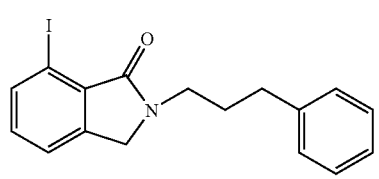
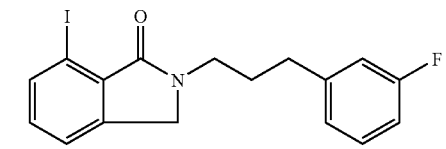
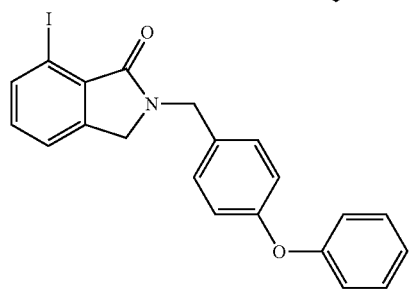
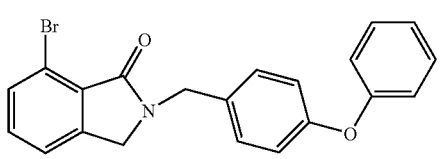
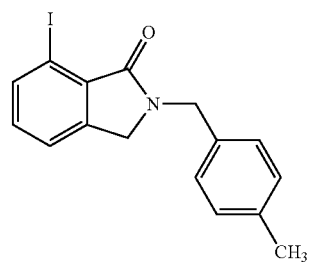
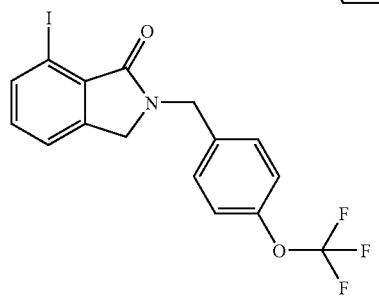
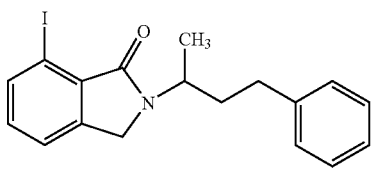
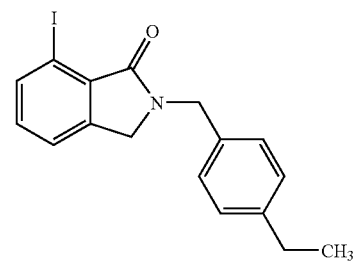
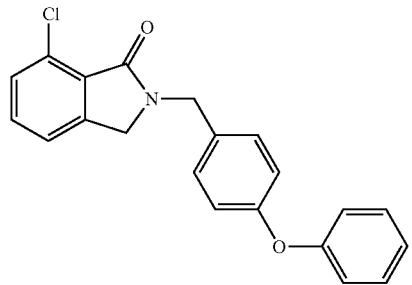
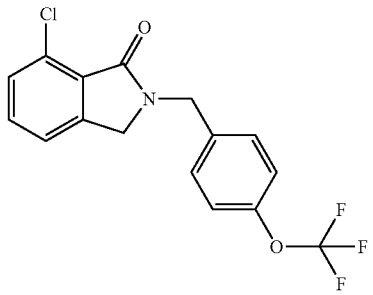

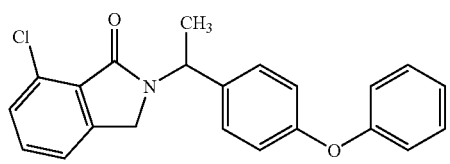
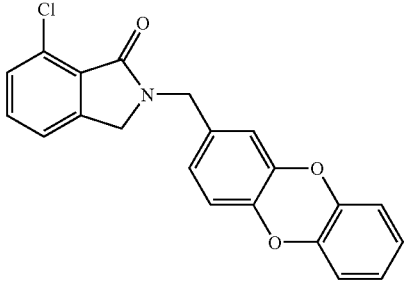
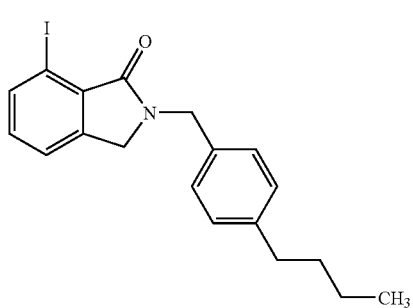
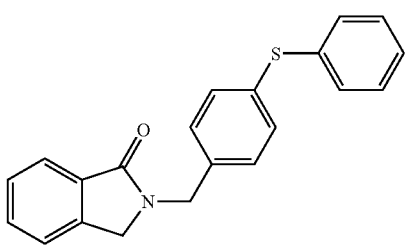
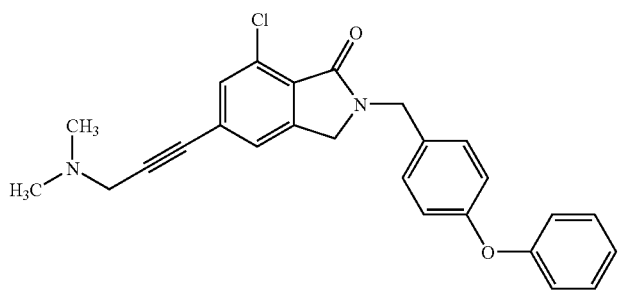
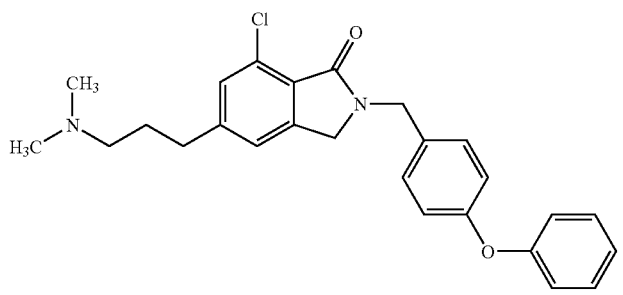
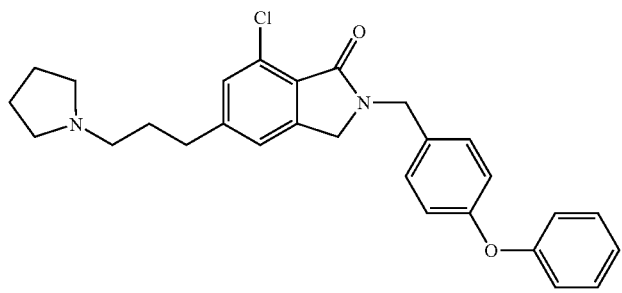

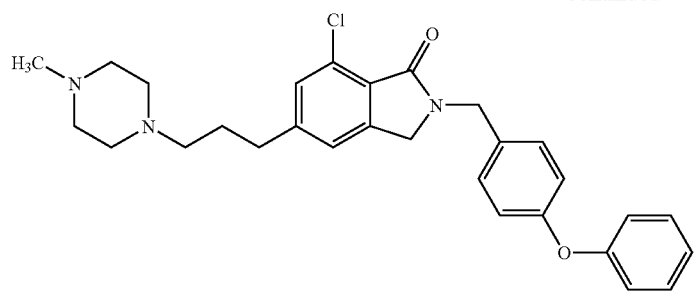
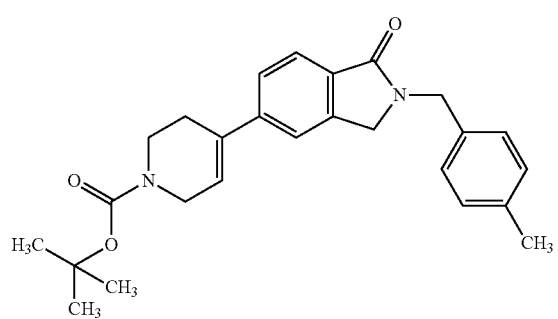
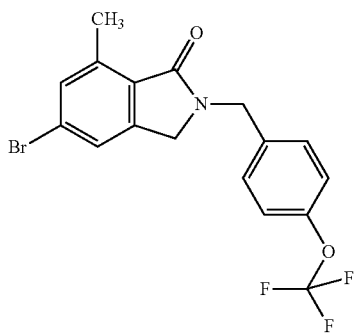
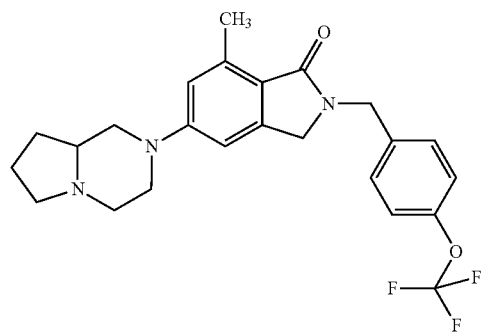
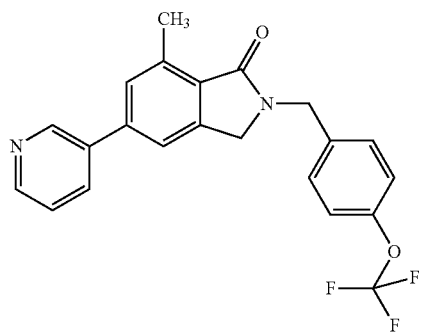
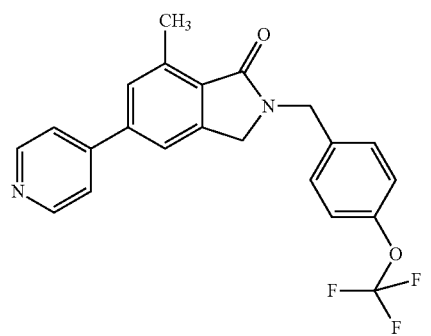
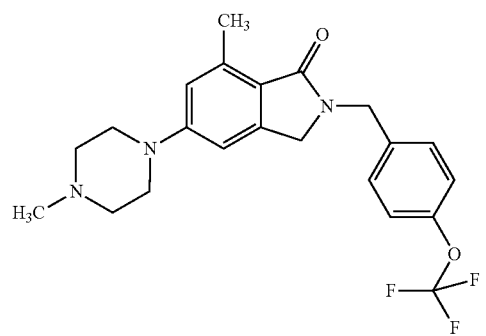
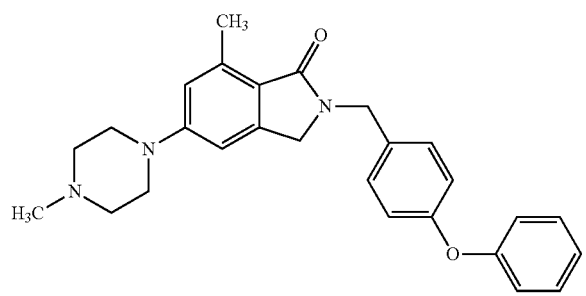
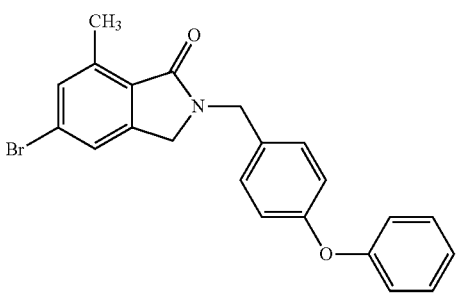

25
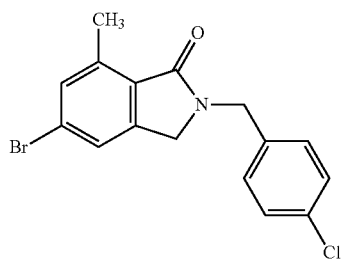
26
-continued
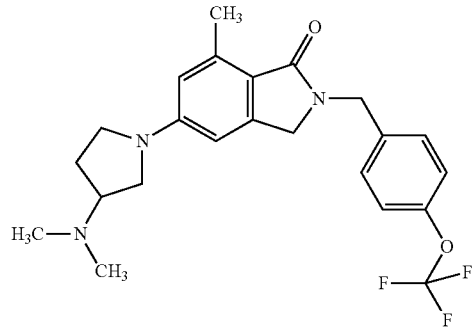
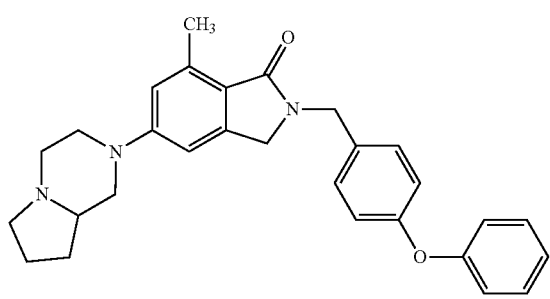
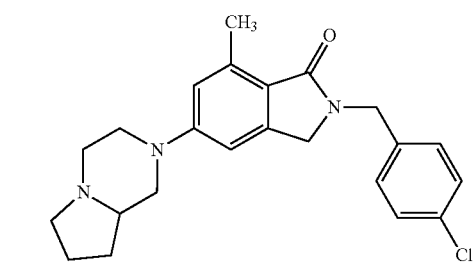
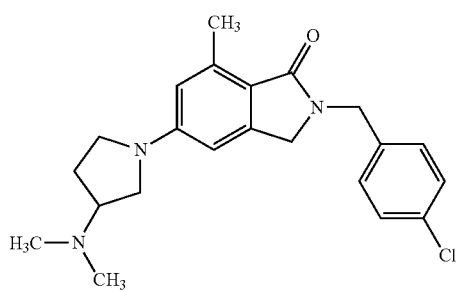
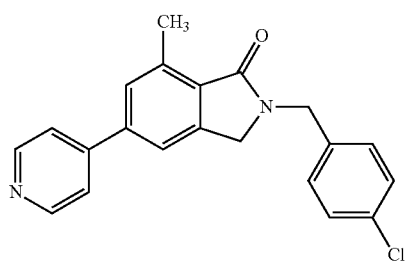
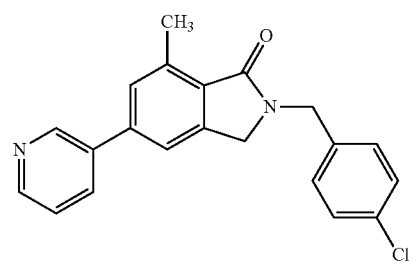
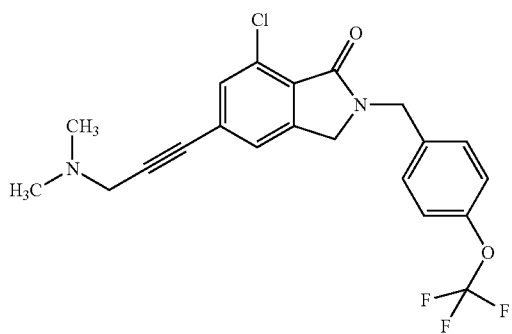
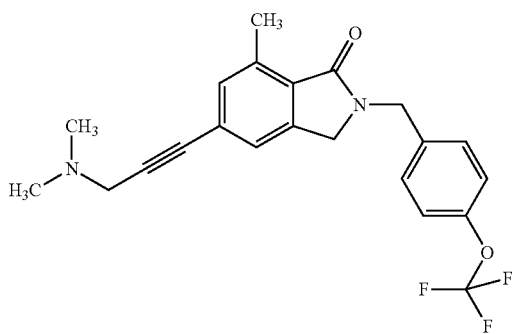

-continued
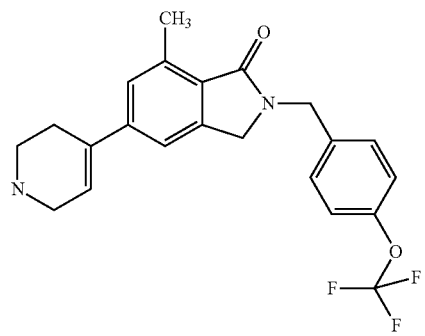
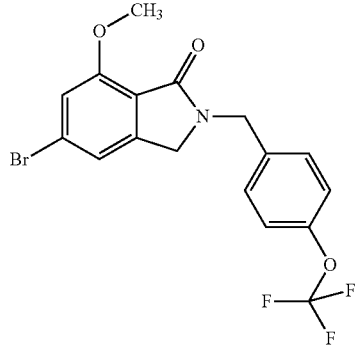
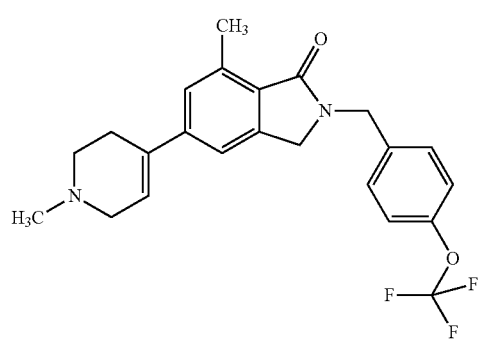
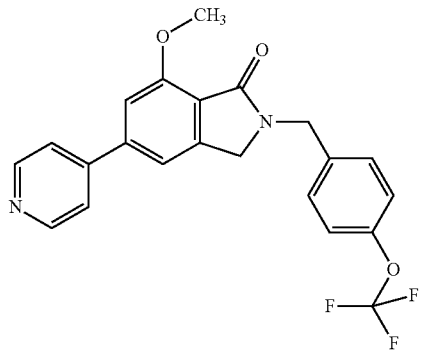
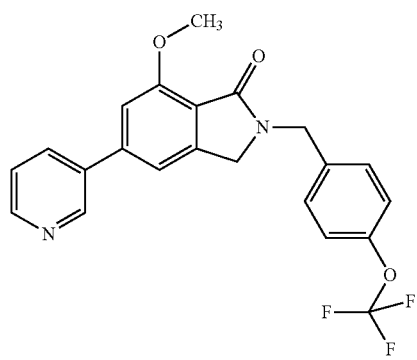
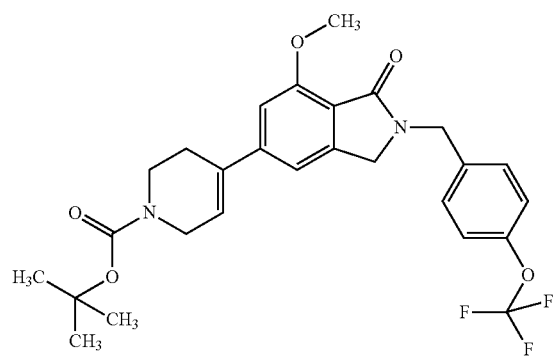
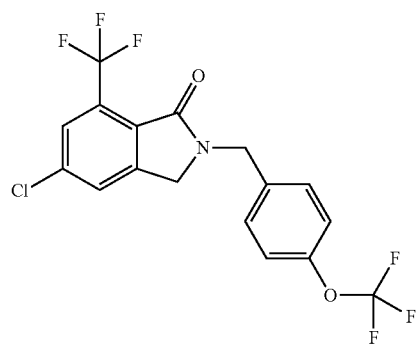
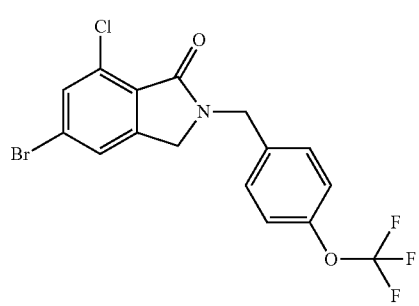
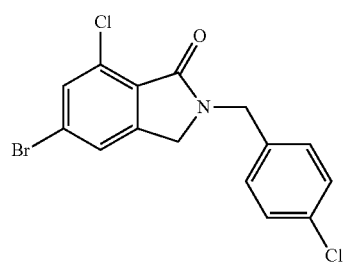
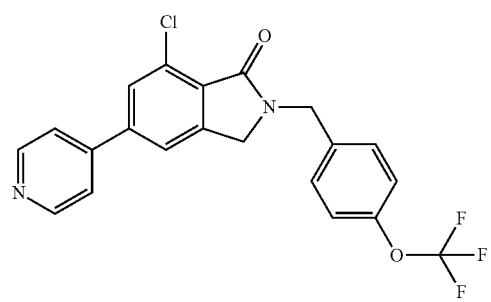

-continued
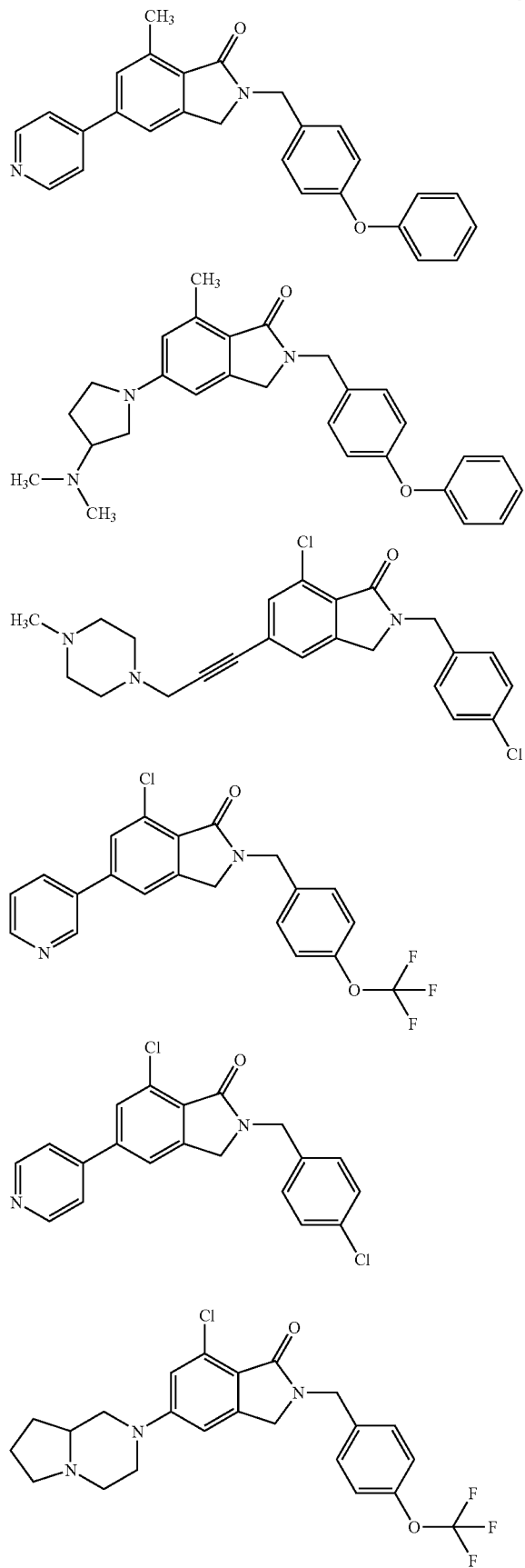

-continued
31
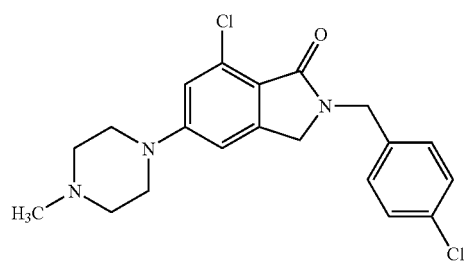
32
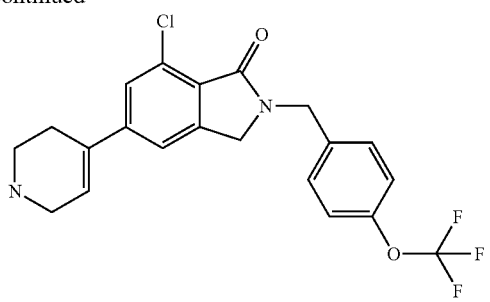
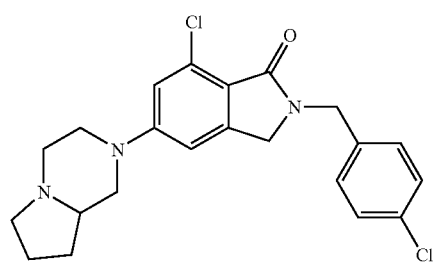
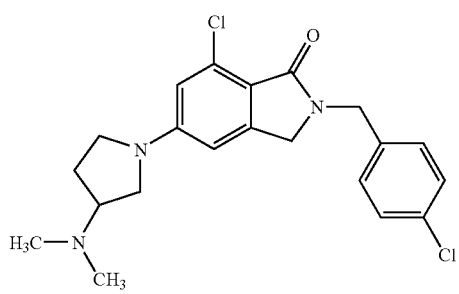
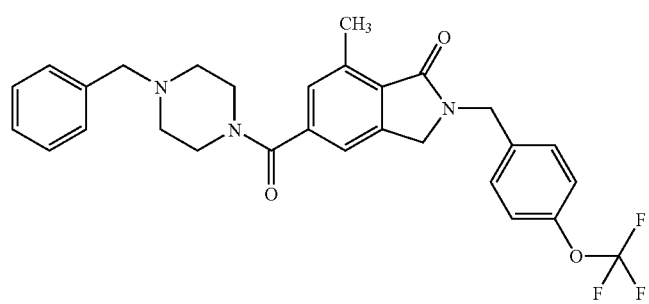
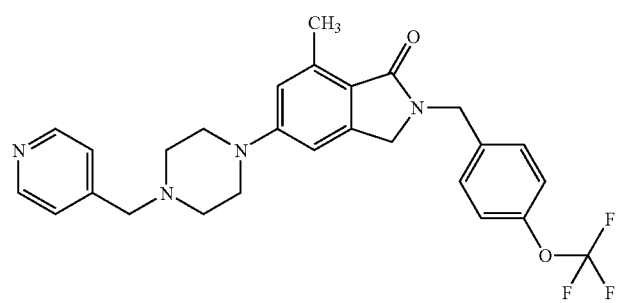
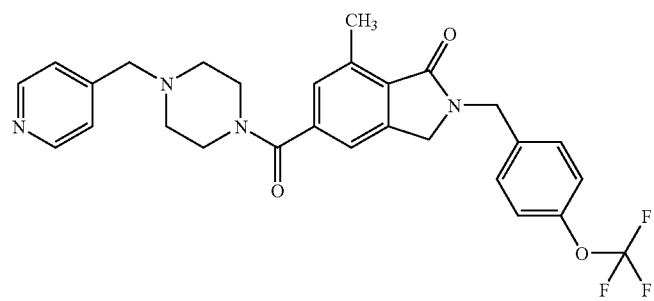

33
34
-continued
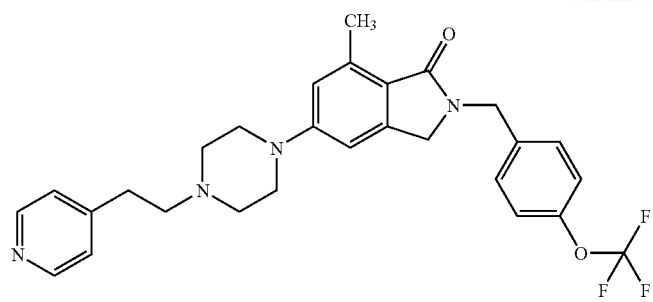
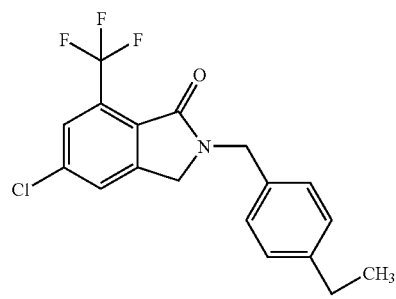
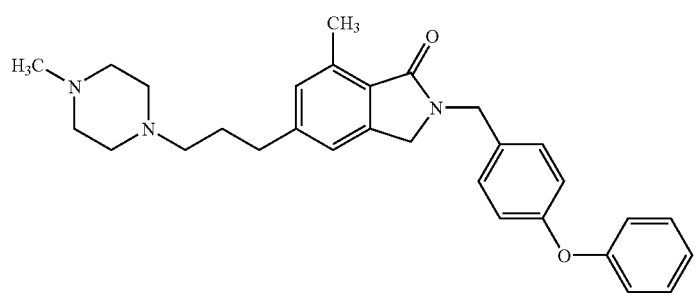
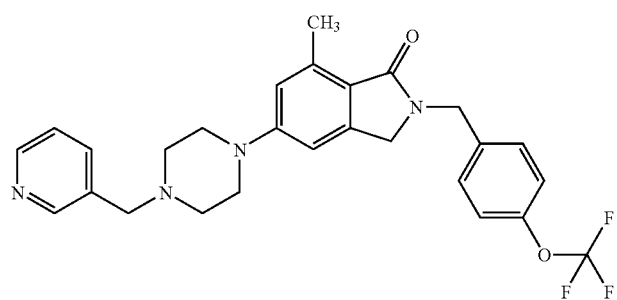
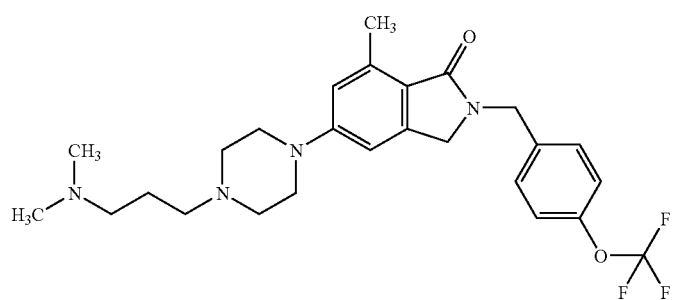
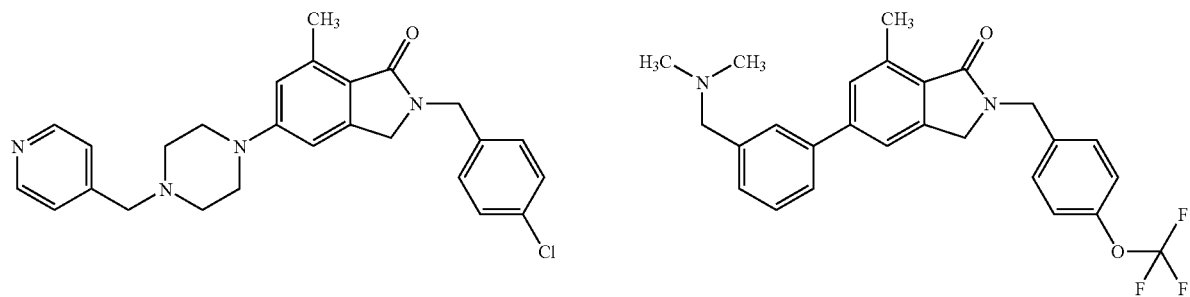

35
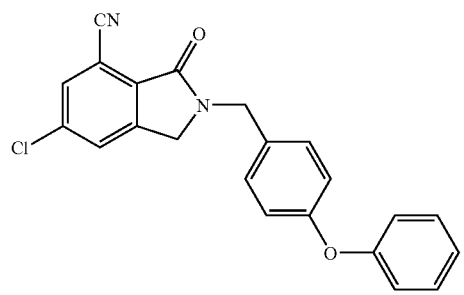
36
-continued
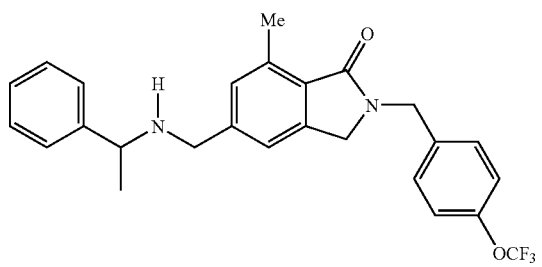
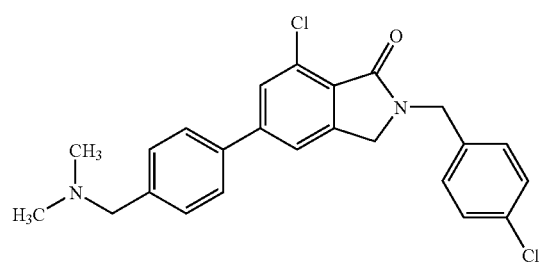
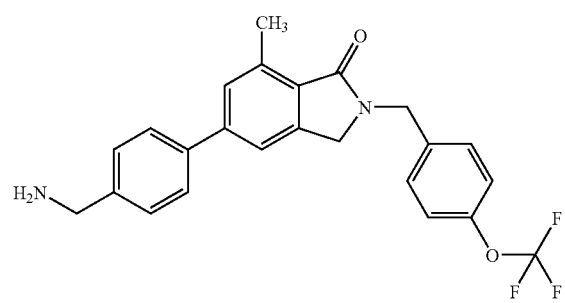
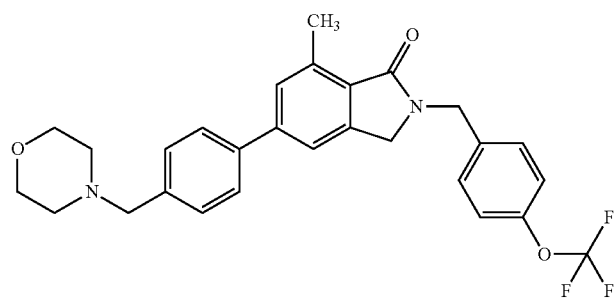
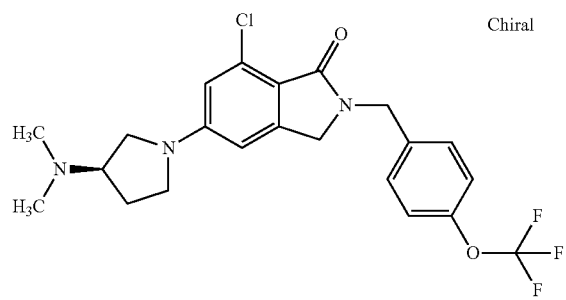
Chiral
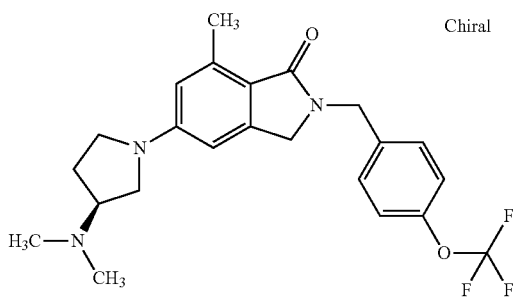
Chiral
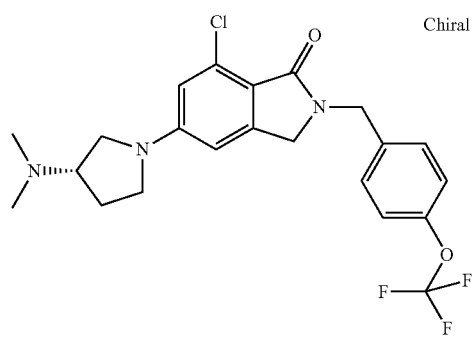
Chiral
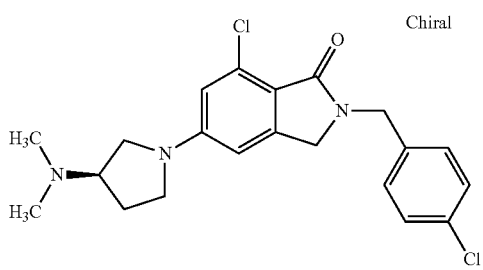
Chiral 37
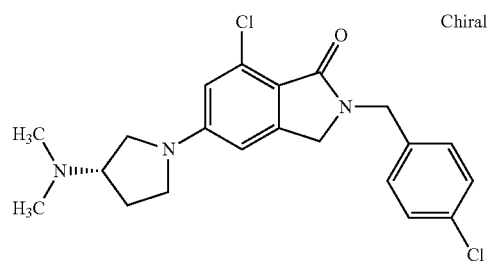
38
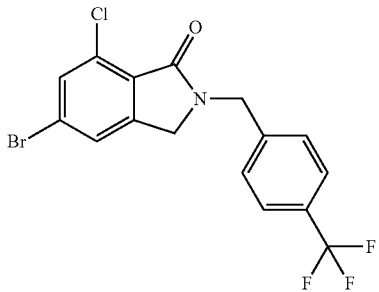
-continued
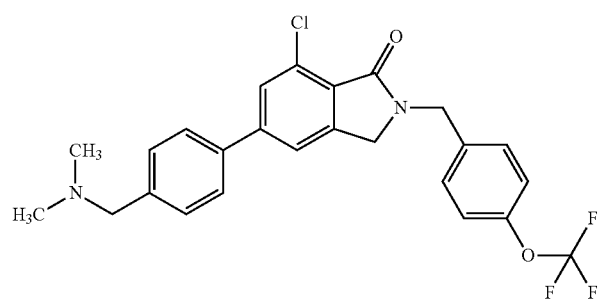
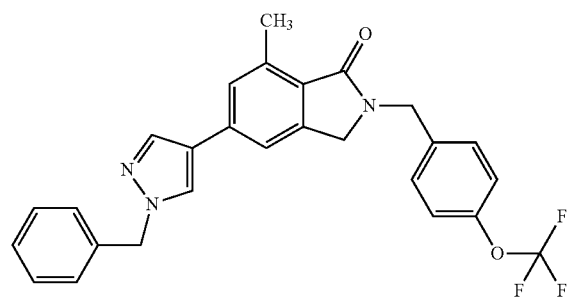
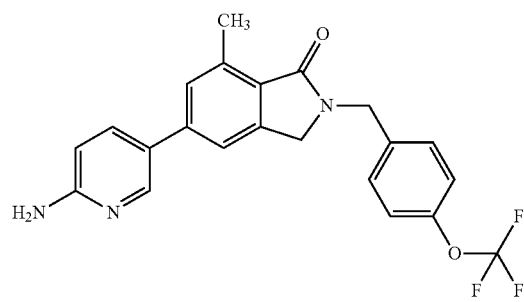
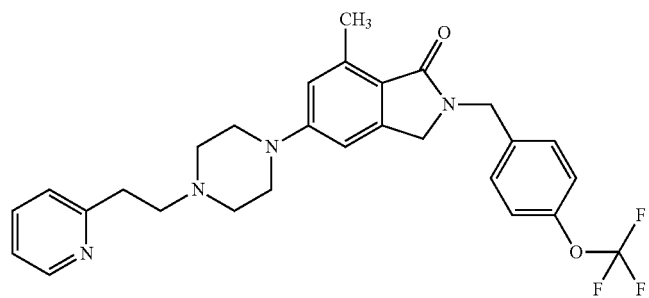
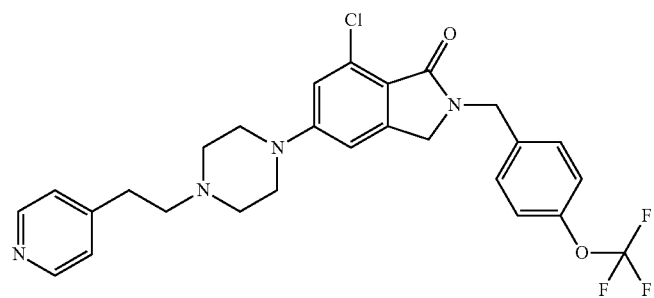
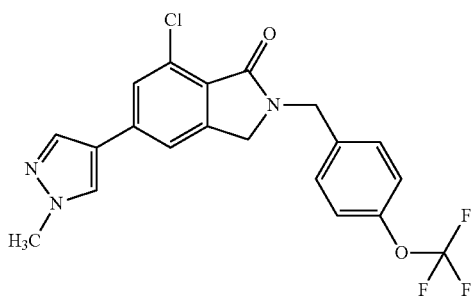

-continued
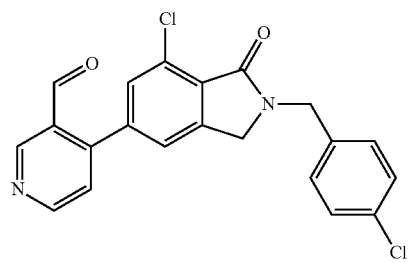
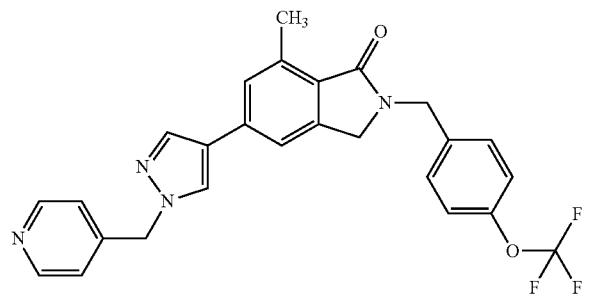
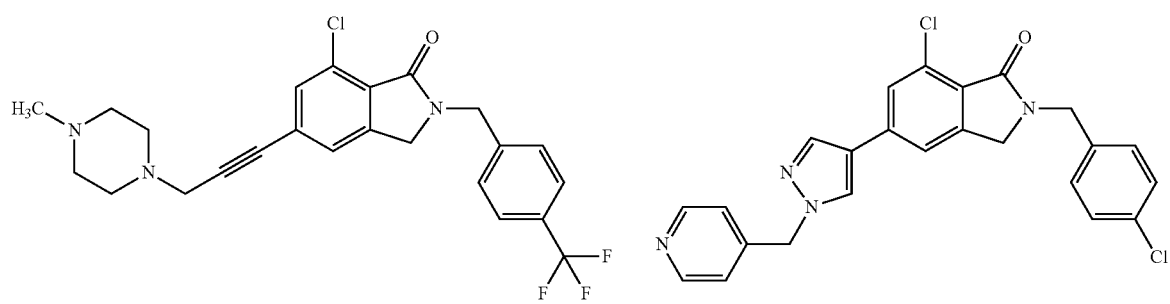
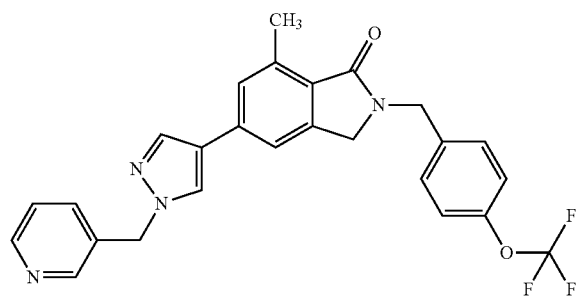
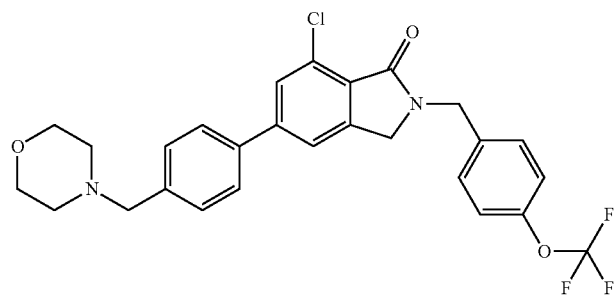
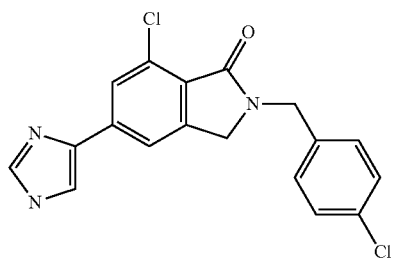
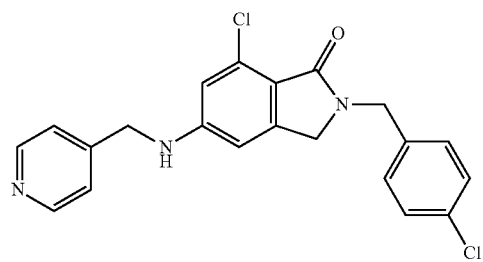
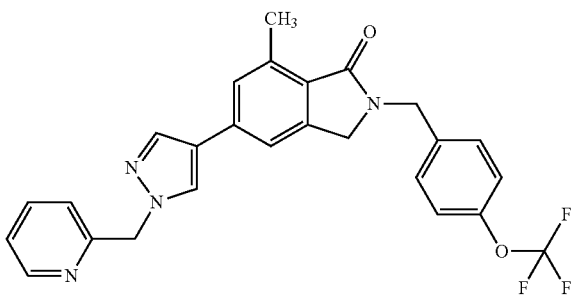

-continued
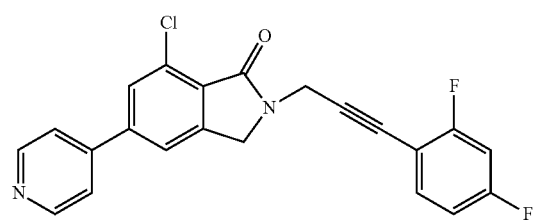
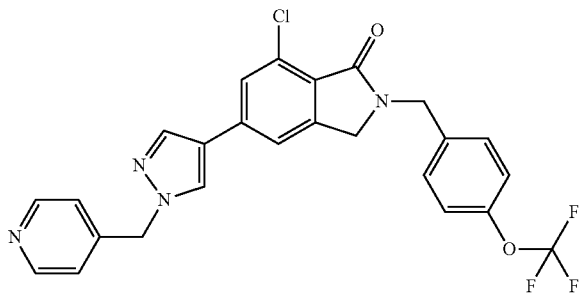
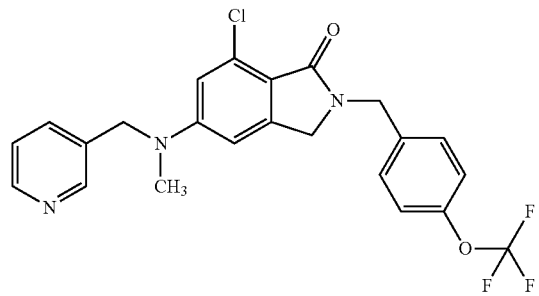
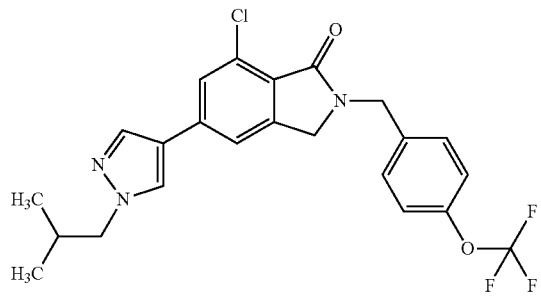
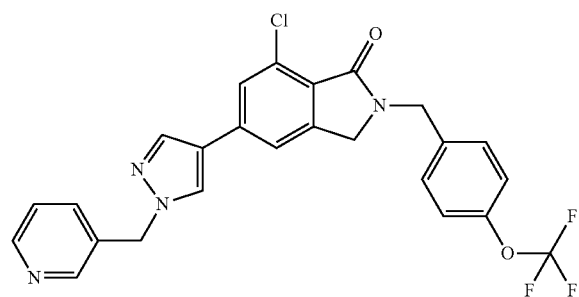
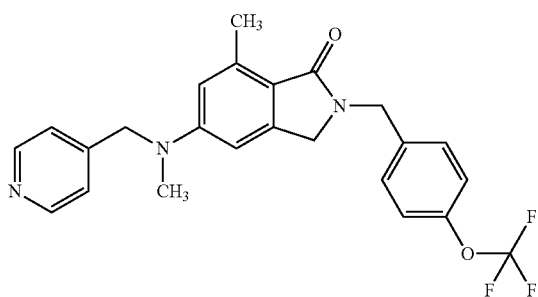
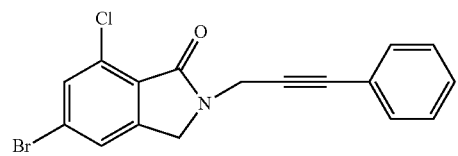
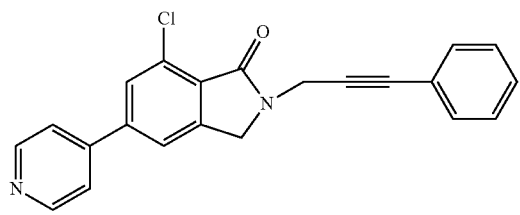
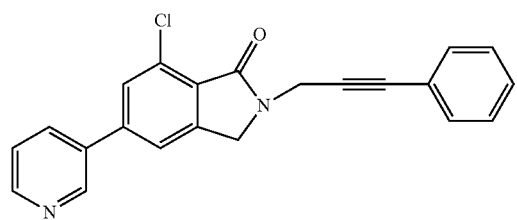
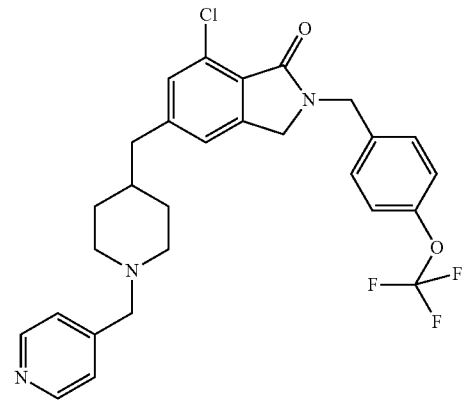
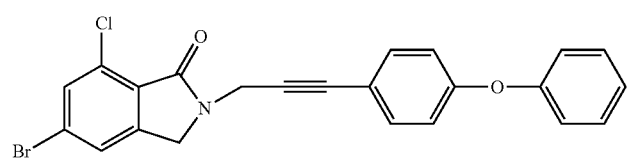

-continued
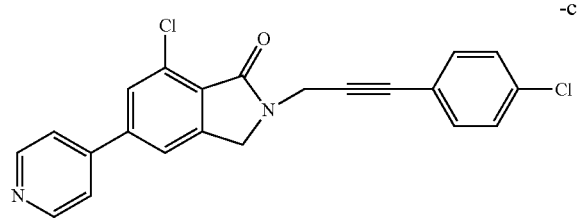
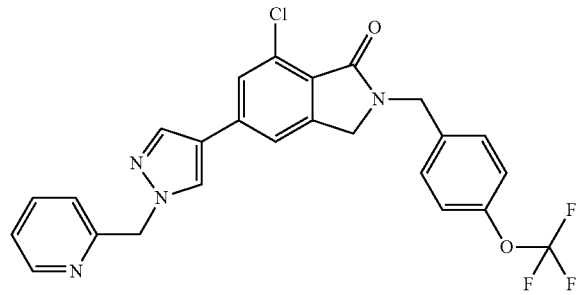
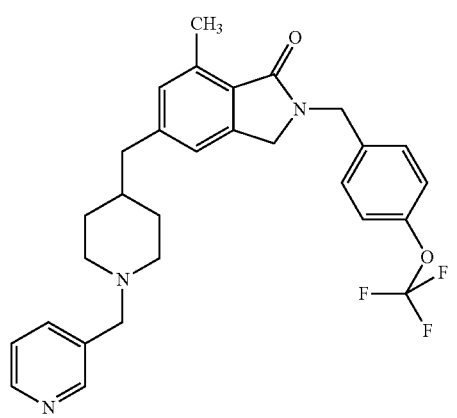
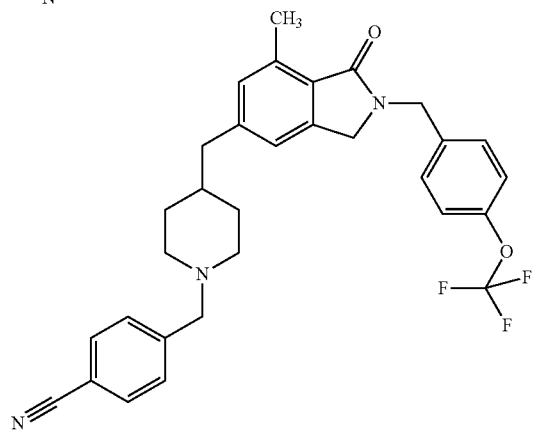
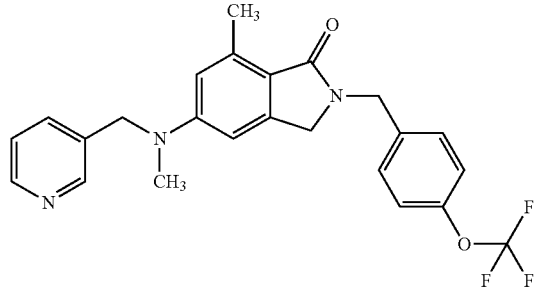
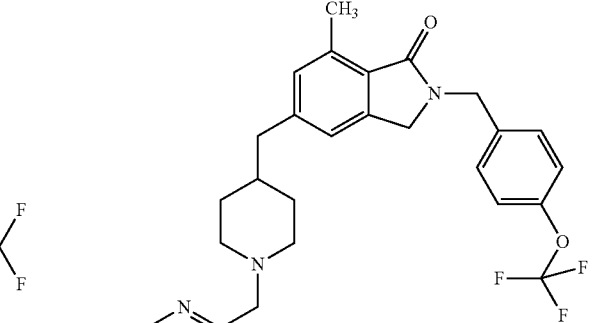
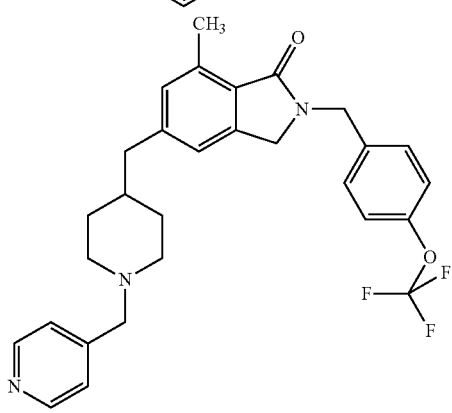
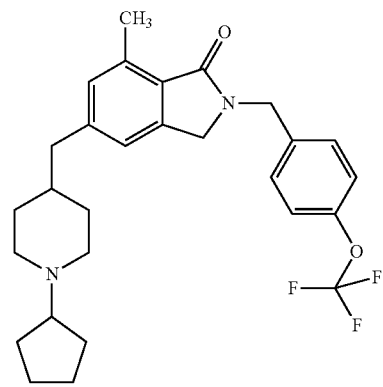
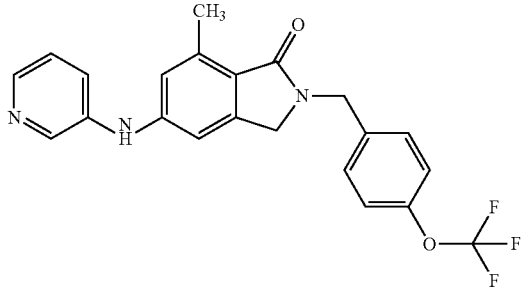

-continued
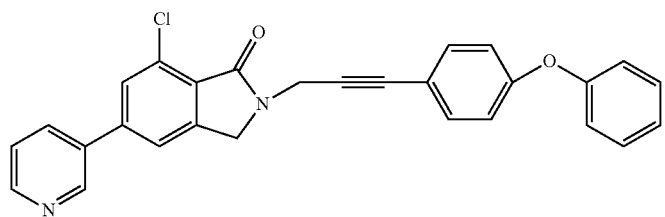
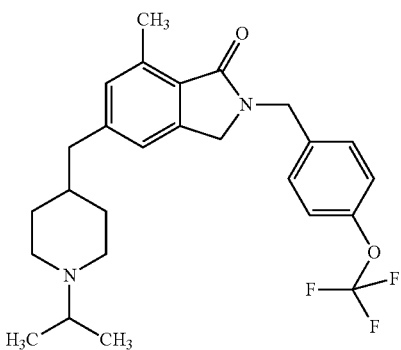
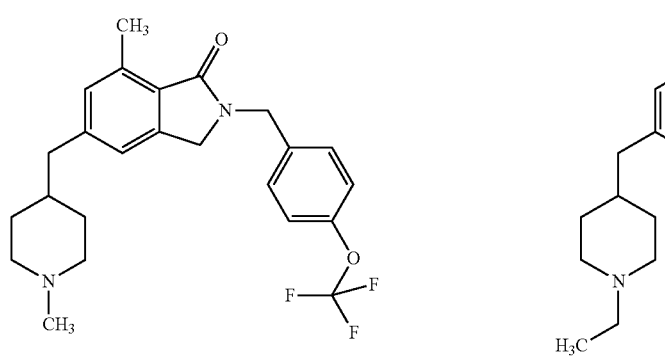
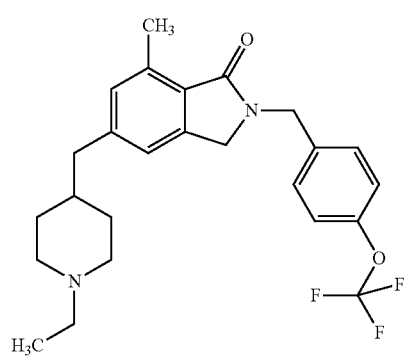
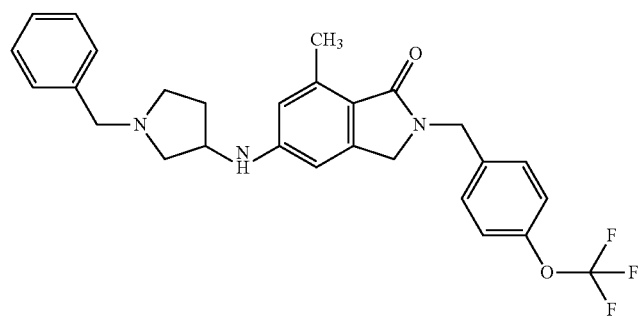
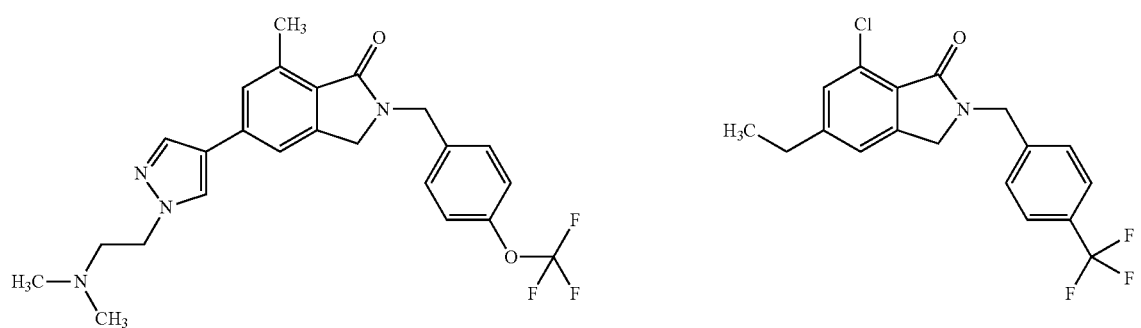
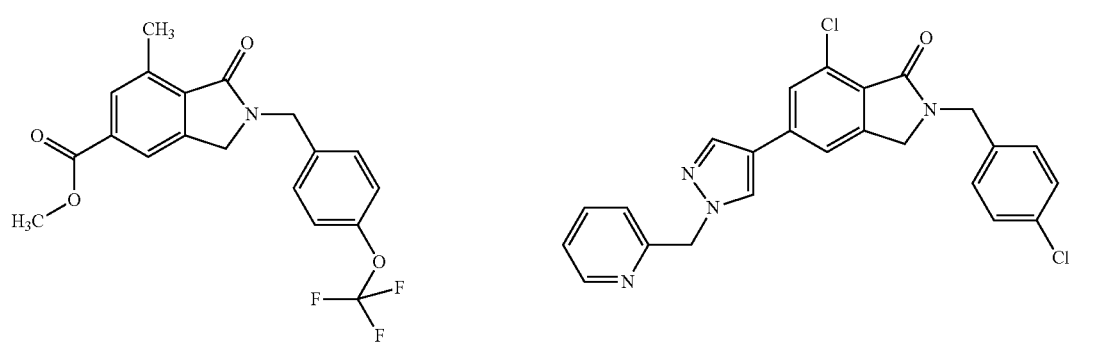

-continued
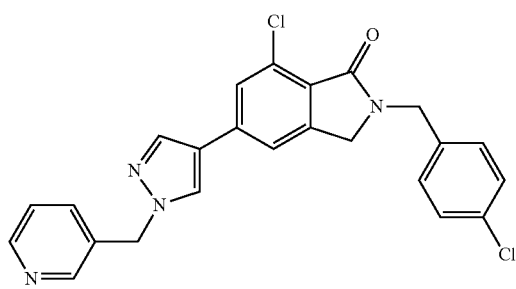
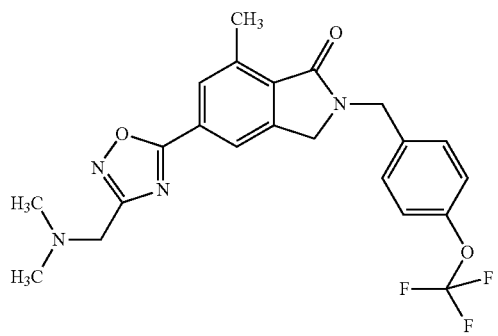
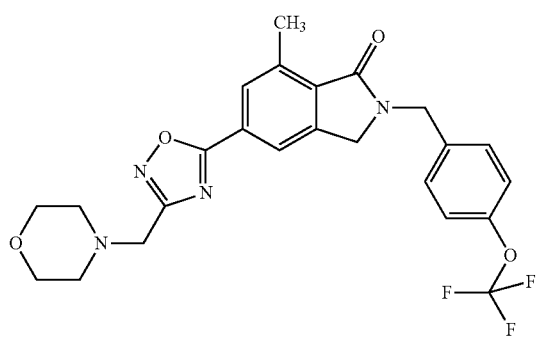
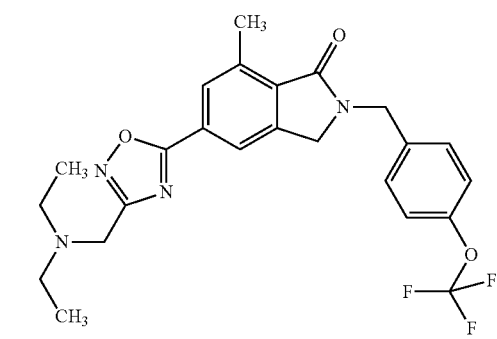
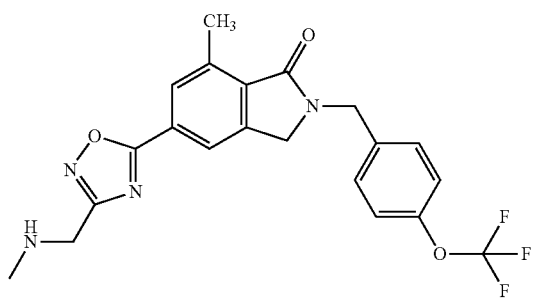
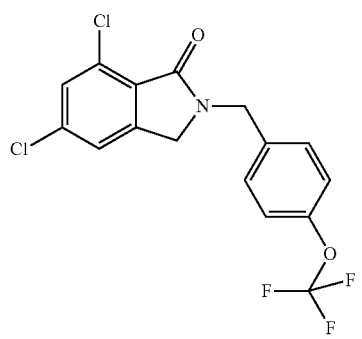
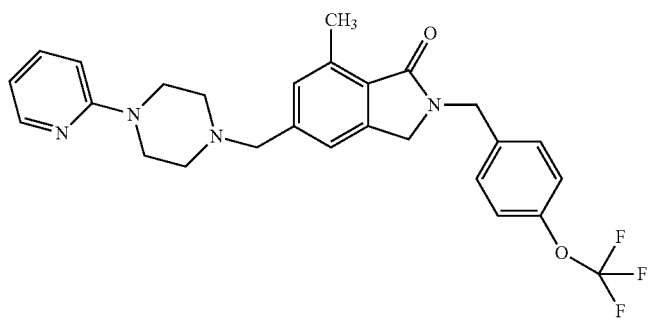
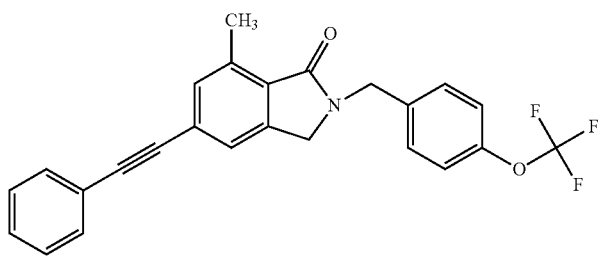
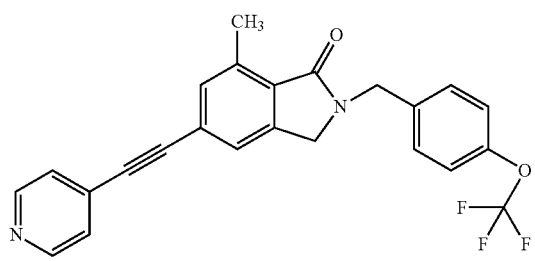

-continued
| 49 | 50 |
|---|---|
| 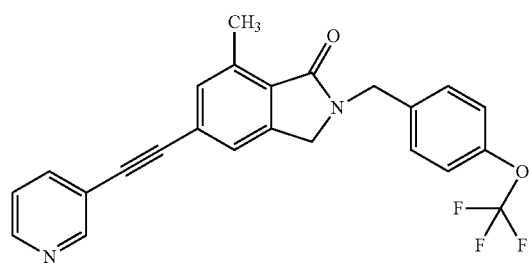 | 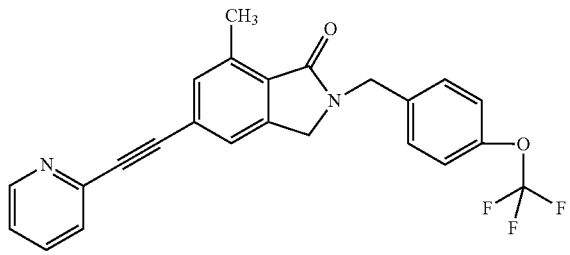 |
| 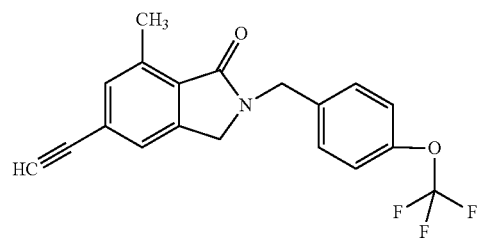 | 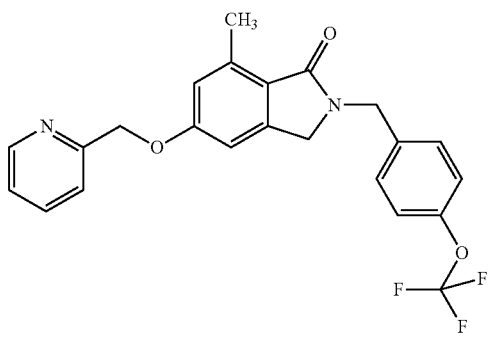 |
| 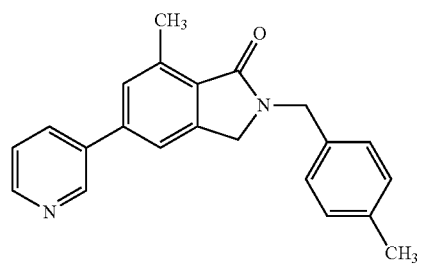 | 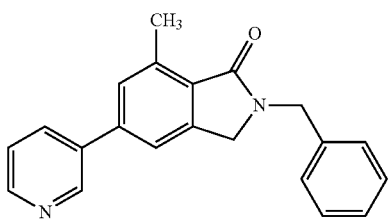 |
| 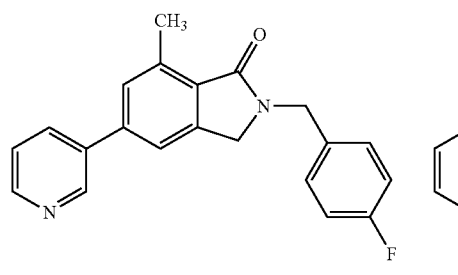 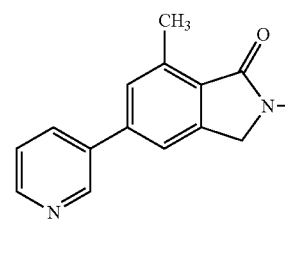 | 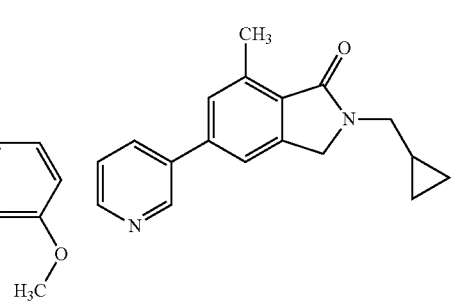 |
| 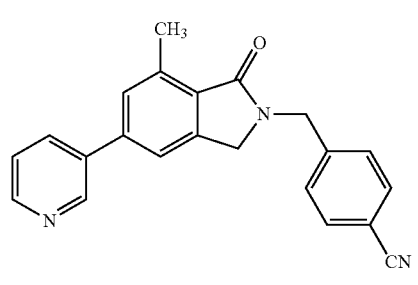 | 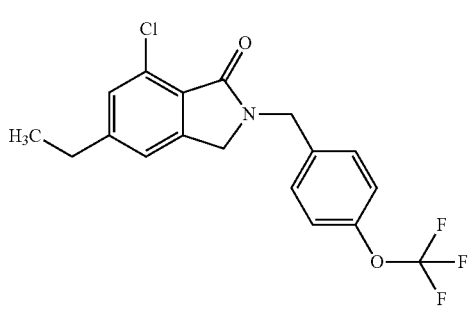 |

51
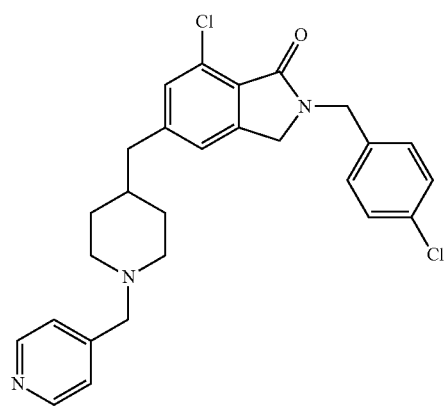
52
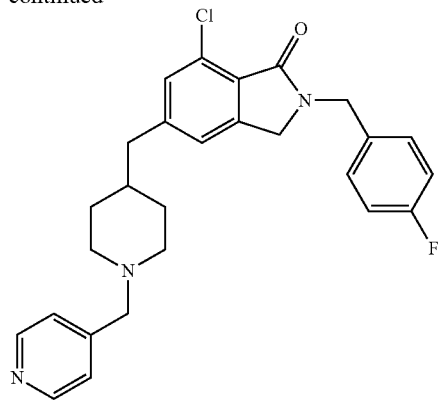
-continued
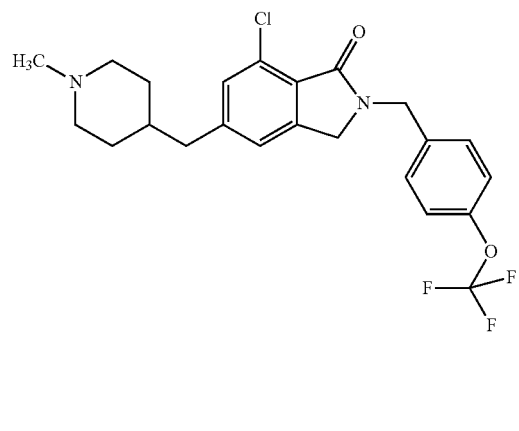
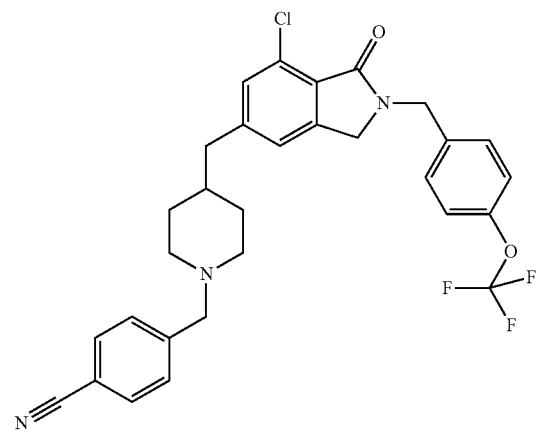
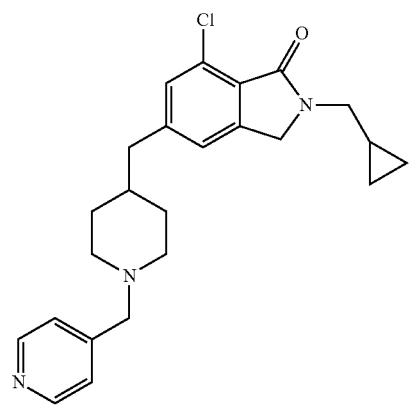
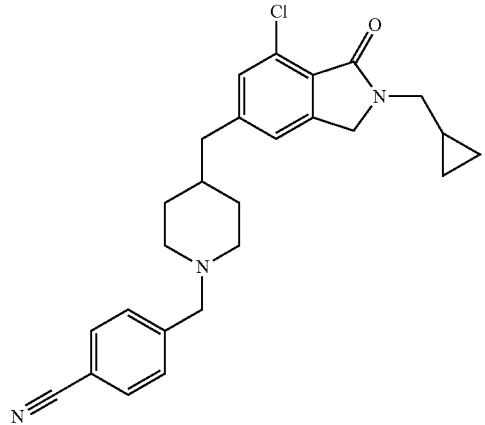
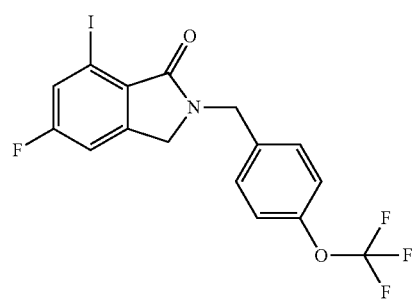
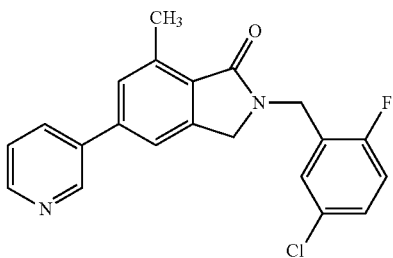

53
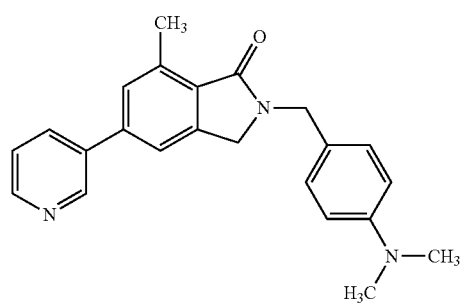
54
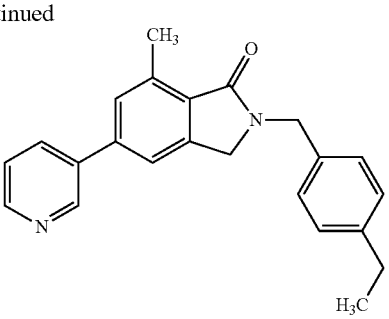
-continued
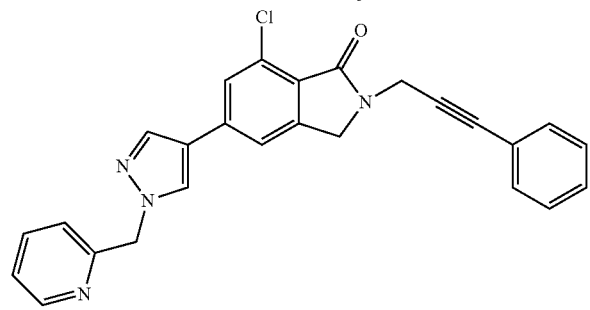
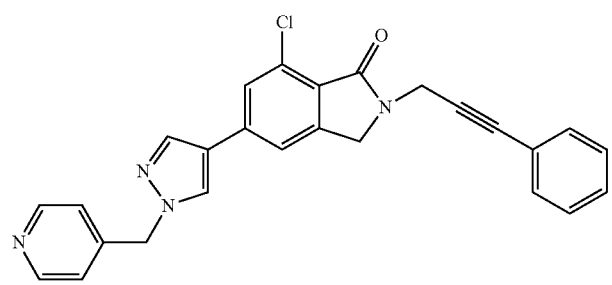
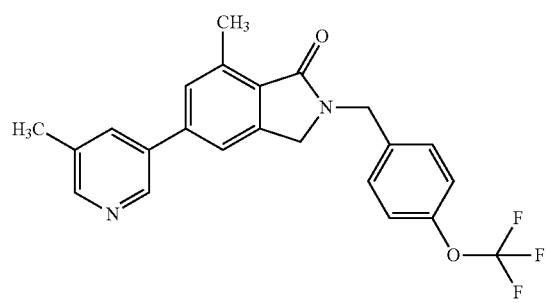
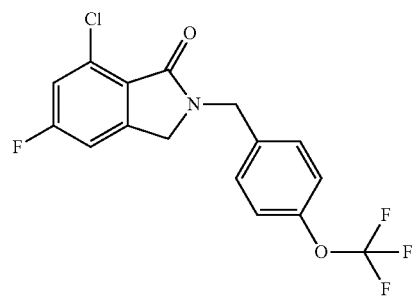
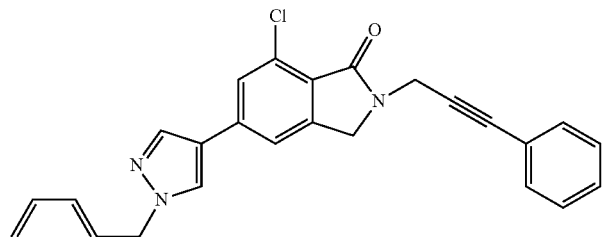
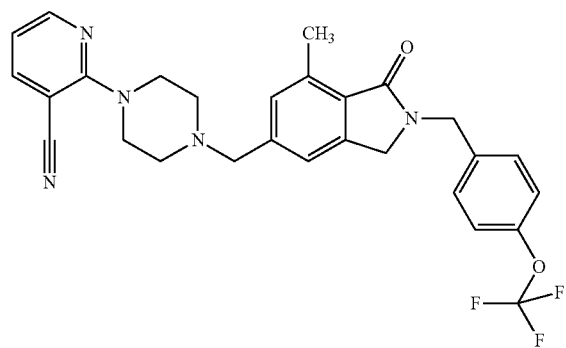

55
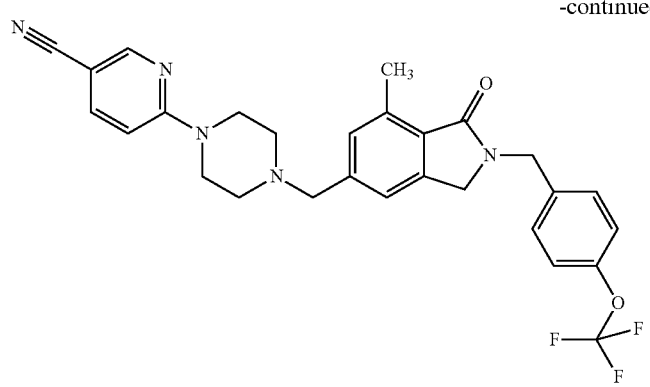
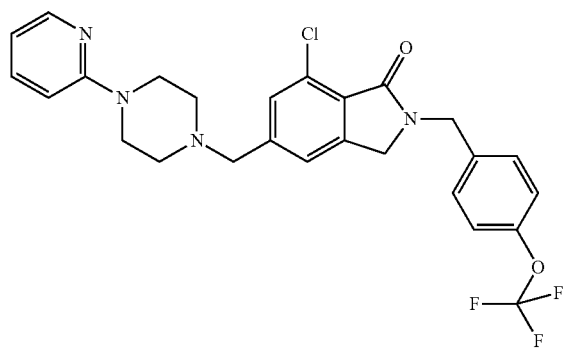
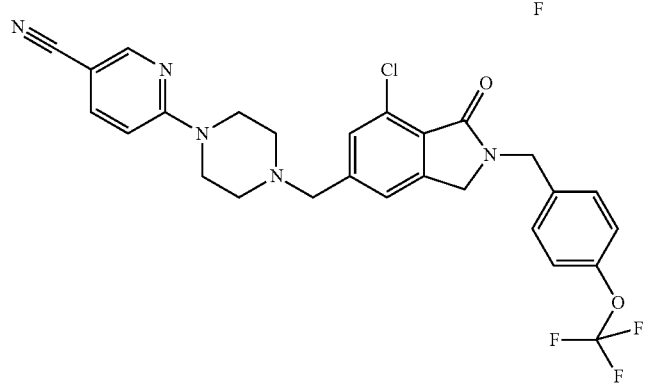
56
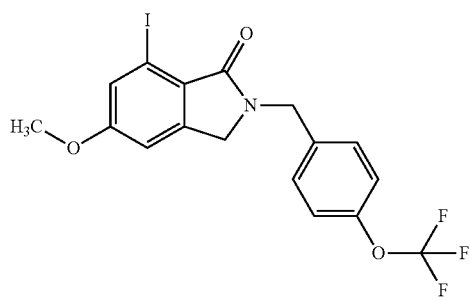
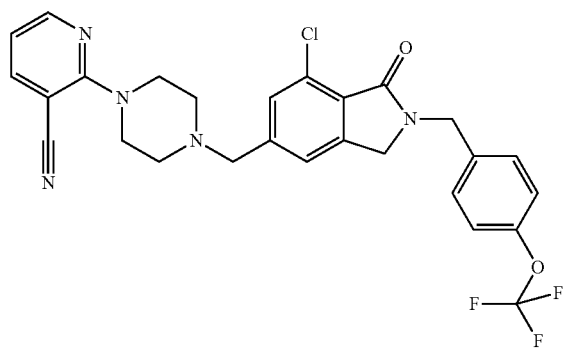
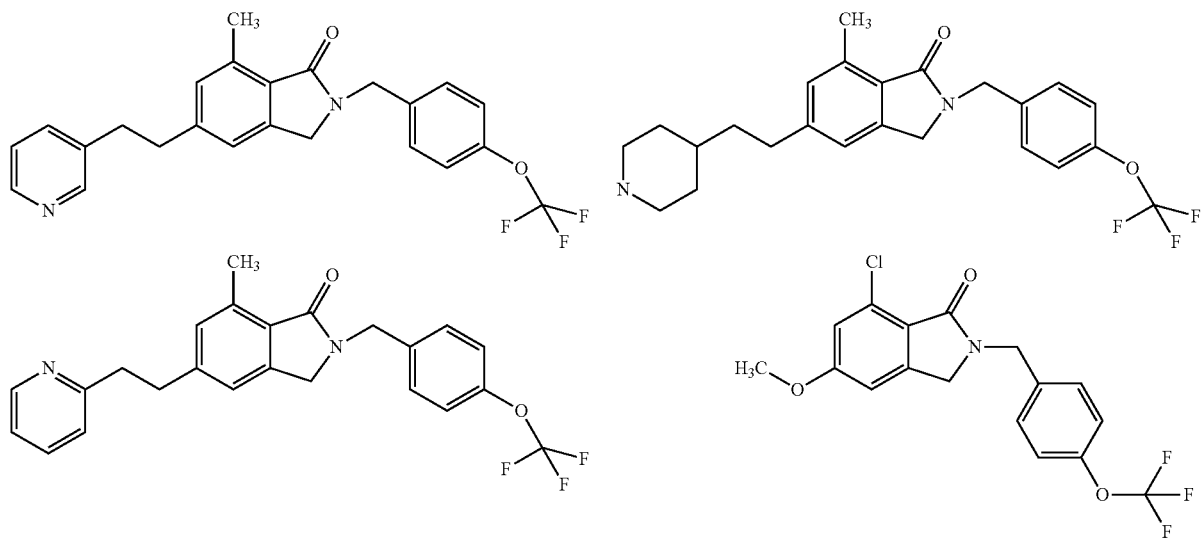

-continued
57
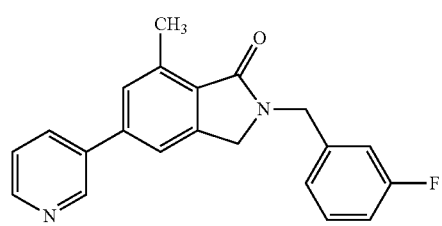
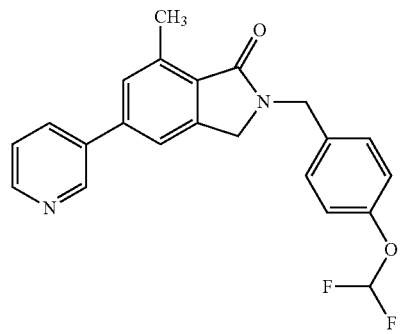
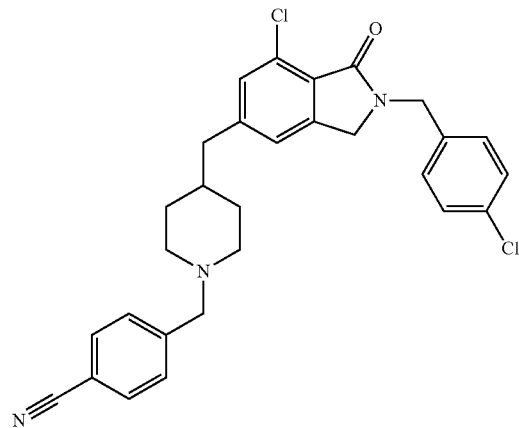
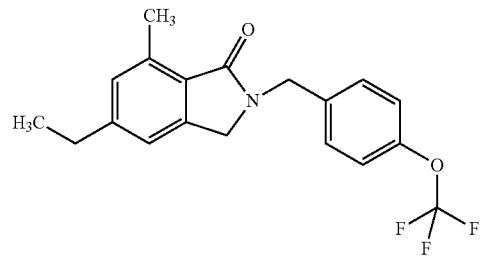
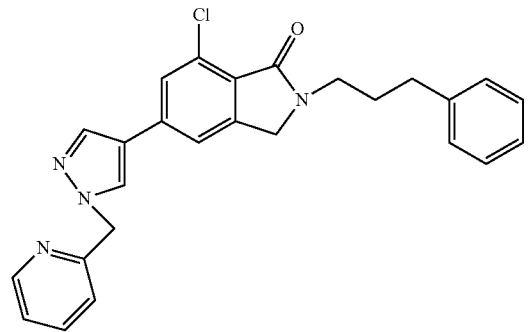
58
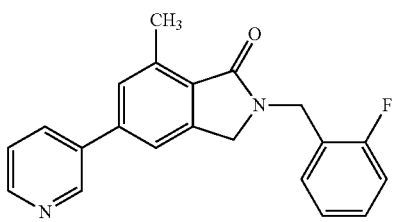
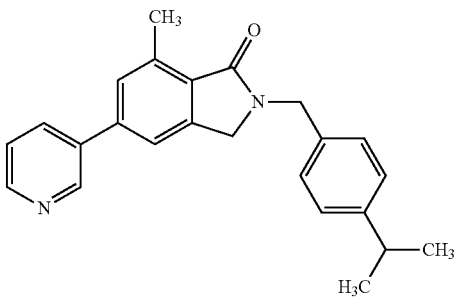
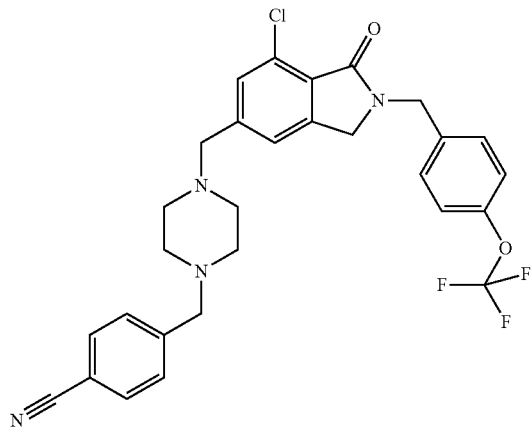
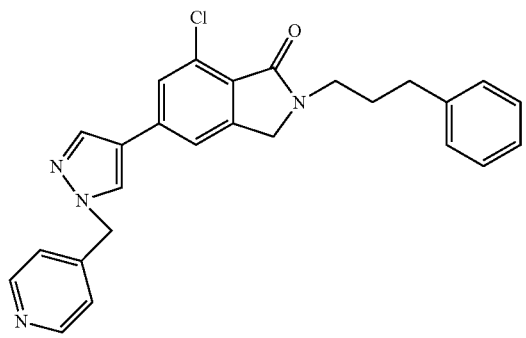
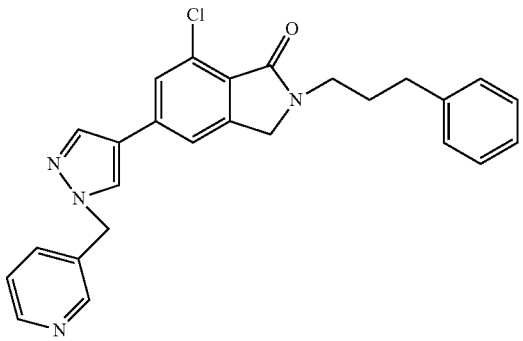

-continued
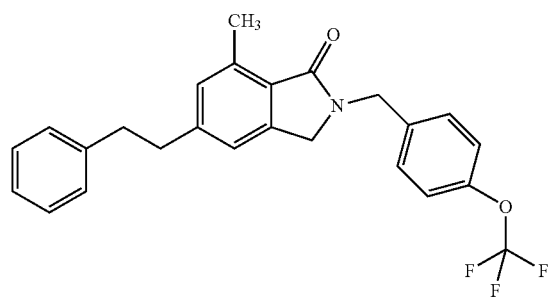
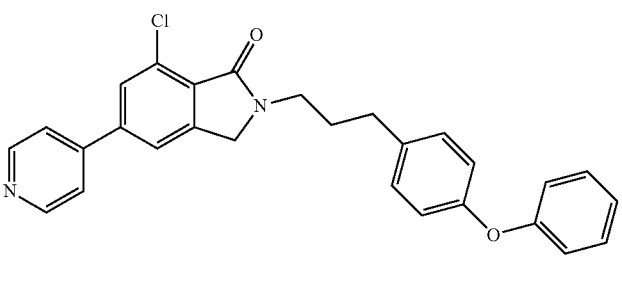
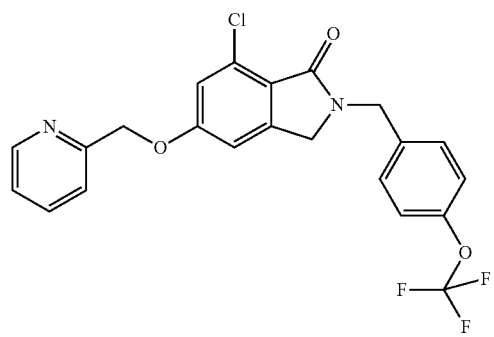
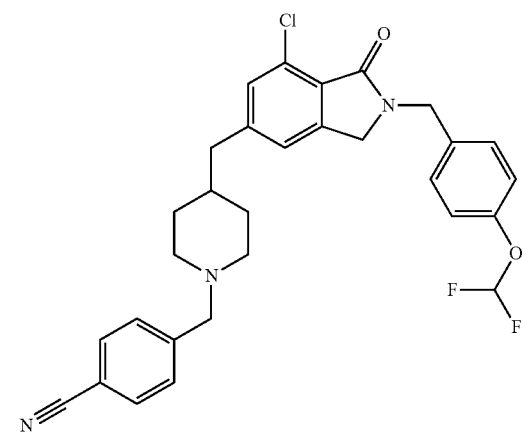
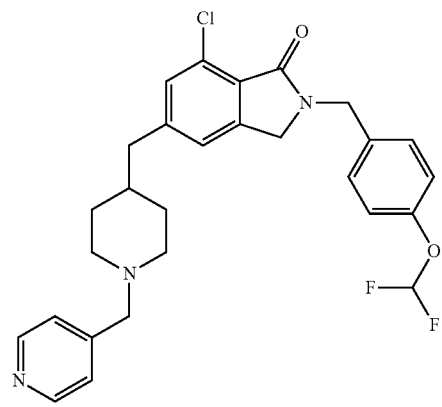
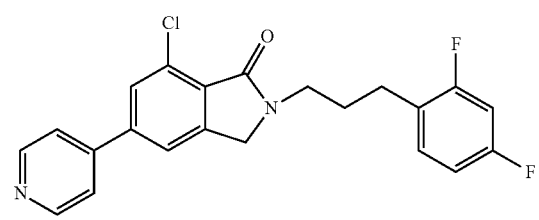
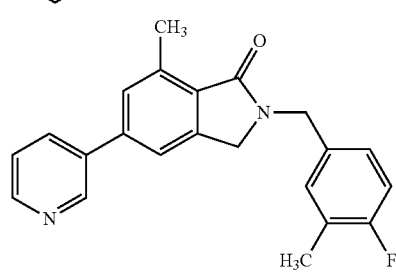
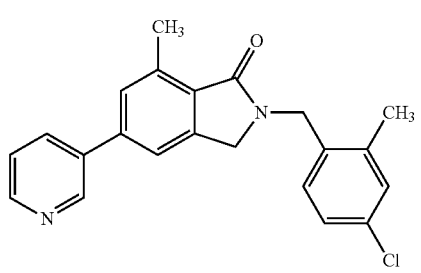
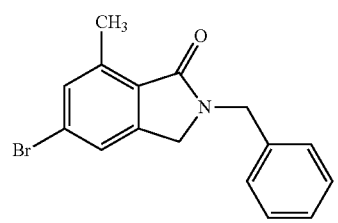
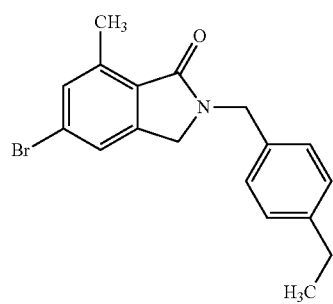

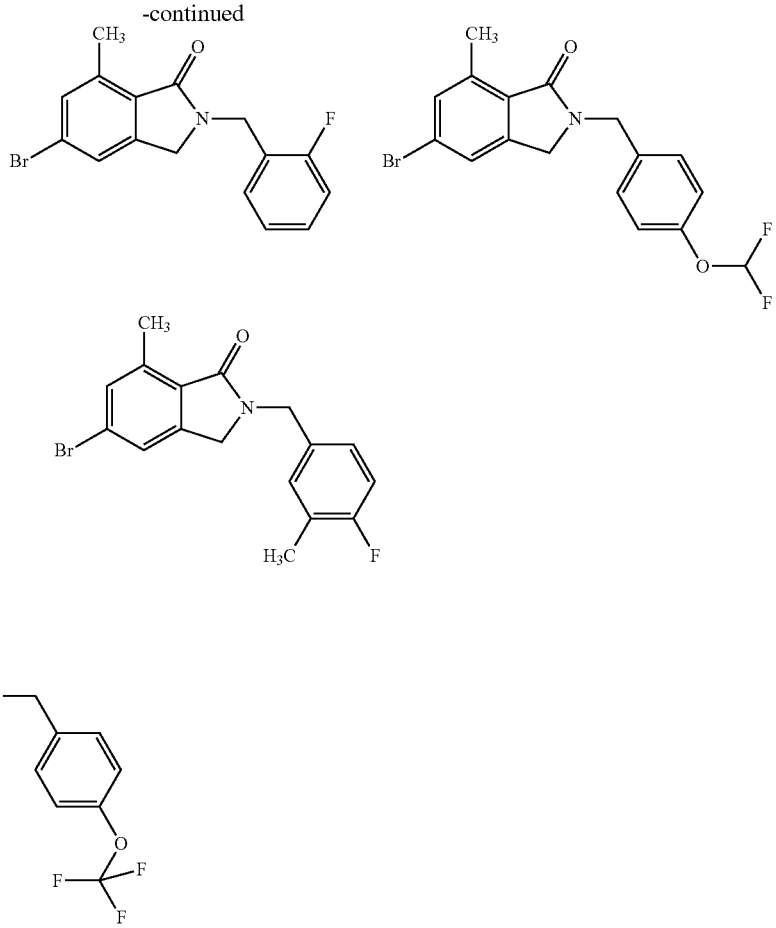

Specific examples of the present invention include the following compounds, their pharmaceutically acceptable salts, hydrates, solvates, optical isomers, and combinations thereof:

7-Chloro-5-(4-pyridin-4-yl-piperazin-1-yl)-2-(4-trifluoromethoxy-benzyl)-2,3-dihydro-isoindol-1-one;
7-Methyl-5-{[(pyridine-3-ylmethyl)-amino]-methyl}-2-(4-trifluoromethoxy-benzyl)-2,3-dihydro-isoindol-1-one;
7-Methyl-5-{[(pyridine-4-ylmethyl)-amino]-methyl}-2-(4-trifluoromethoxy-benzyl)-2,3-dihydro-isoindol-1-one;
5-(Benzylamino-methyl)-7-methyl-2-(4-trifluoromethoxy-benzyl)-2,3-dihydro-isoindol-1-one;
7-Methyl-5-(phenethylamino-methyl)-2-(4-trifluoromethoxy-benzyl)-2,3-dihydro-isoindol-1-one;
7-Methyl-5-[(3-phenyl-propylamino)-methyl]-2-(4-trifluoromethoxy-benzyl)-2,3-dihydro-isoindol-1-one;
5-(Indan-2-ylaminomethyl)-7-methyl-2-(4-trifluoromethoxy-benzyl)-2,3-dihydro-isoindol-1-one;
1-{1-[7-Methyl-1-oxo-2-(4-trifluoromethoxybenzyl)-2,3-dihydro-1H-isoindol-5-ylmethyl]-piperidin-4-yl}-1,3-dihydro-benzoimidazol-2-one;
7-Methyl-5-[4-(3-phenylpropyl)-piperidin-1-ylmethyl]-2-(4-trifluoromethoxy-benzyl)-2,3-dihydroisoindol-1-one;
5-{4-[3-(4-Imidazol-1-yl-phenyl)-propyl]-piperidin-1-ylmethyl}-7-methyl-2-(4-trifluoromethoxy-benzyl)-2,3-dihydroisoindol-1-one;
3-Methyl-8-[1-oxo-2-(4-trifluoromethoxy-benzyl)-2,3-dihydro-1H-isoindol-5-yl]-1-phenyl-1,3,8-triaza-spiro[4.5]decan-4-one;
5-[4-(3-Phenyl-propyl)-piperidin-1-yl]-2-(4-trifluoromethoxy-benzyl)-2,3-dihydro-isoindol-1-one;
7-Chloro-5-[4-(2-methoxy-ethyl)-piperazin-1-yl]-2-(4-trifluoromethoxy-benzyl)-2,3-dihydro-isoindol-1-one;
7-Chloro-5-morpholin-4-yl-2-(4-trifluoromethoxy-benzyl)-2,3-dihydro-isoindol-1-one;
7-Chloro-5-[4-(2-oxo-2-pyrrolidin-1-yl-ethyl)-piperazin-1-yl]-2-(4-trifluoromethoxy-benzyl)-2,3-dihydro-isoindol-1-one;
2-(4-phenoxy-benzyl)-2,3-dihydro-isoindol-1-one;
7-Iodo-2-(3-phenyl-propyl)-2,3-dihydro-isoindol-1-one;
2-[3-(3-Fluoro-phenyl)-propyl]-7-iodo-2,3-dihydro-isoindol-1-one;
7-Iodo-2-(4-phenoxy-benzyl)-2,3-dihydro-isoindol-1-one;
7-Bromo-2-(4-phenoxy-benzyl)-2,3-dihydro-isoindol-1-one;
7-Iodo-2-(4-methyl-benzyl)-2,3-dihydro-isoindol-1-one;
7-Iodo-2-(4-trifluoromethoxy-benzyl)-2,3-dihydro-isoindol-1-one;
7-Iodo-2-(1-methyl-3-phenyl-propyl)-2,3-dihydro-isoindol-1-one;
7-Iodo-2-(4-ethyl-benzyl)-2,3-dihydro-isoindol-1-one;
7-Chloro-2-(4-phenoxy-benzyl)-2,3-dihydro-isoindol-1-one;
7-Chloro-2-(4-trifluoromethoxy-benzyl)-2,3-dihydro-isoindol-1-one;
7-chloro-2-[1-(4-phenoxyphenyl)-ethyl]-2,3-dihydroisoindol-1-one;
7-Chloro-2-dibenzo[1,4]dioxin-2-ylmethyl-2,3-dihydro-isoindol-1-one;
7-Iodo-2-(4-butyl-benzyl)-2,3-dihydro-isoindol-1-one;

2-(4-Phenylsulfanyl-benzyl)-2,3-dihydro-isoindol-1-one;
7-Chloro-5-(3-dimethylamino-prop-1-ynyl)-2-(4-phenoxy-benzyl)-2,3-dihydro-isoindol-1-one;
7-Chloro-5-(3-dimethylamino-propyl)-2-(4-phenoxy-benzyl)-2,3-dihydro-isoindol-1-one;
7-Chloro-2-(4-phenoxy-benzyl)-5-(3-pyrrolidin-1-yl-propyl)-2,3-dihydro-isoindol-1-one;
7-Chloro-5-[3-(4-methyl-piperazin-1-yl)-propyl]-2-(4-phenoxy-benzyl)-2,3-dihydro-isoindol-1-one;
4-[2-(4-Methylbenzyl)-1-oxo-2,3-dihydro-1H-isoindol-5-yl]-3,6-dihydro-2H-pyridine-1-carboxylic acid tert-butyl ester;
5-Bromo-7-methyl-2-(4-trifluoromethoxy-benzyl)-2,3-dihydro-isoindol-1-one;
5-(Hexahydropyrrolo[1,2-a]pyrazin-2-yl)-7-methyl-2-(4-trifluoromethoxybenzyl)-2,3-dihydroisoindol-1-one;
7-Methyl-5-pyridin-3-yl-2-(trifluoromethoxybenzyl)-2,3-dihydroisoindol-1-one;
7-Methyl-5-pyridin-4-yl-2-(trifluoromethoxybenzyl)-2,3-dihydroisoindol-1-one;
7-Methyl-5-(4-methyl piperazine-1-yl)-2-(4-trifluoromethoxybenzyl)-2,3-dihydroisoindol-1-one;
7-Methyl-5-(4-methylpiperazin-1-yl)-2-(phenoxybenzyl)-2,3-dihydroisoindol-1-one;
5-Bromo-7-methyl-2-(4-phenoxy-benzyl)-2,3-dihydro-isoindol-1-one;
5-Bromo-7-methyl-2-(4-chloro-benzyl)-2,3-dihydro-isoindol-1-one;
5-(3-dimethylaminopyrollidin-1-yl)-7-methyl-2-(4-trifluoromethoxybenzyl)-2,3-dihydroisoindol-1-one;
5-(Hexahydropyrrolo[1,2-a]pyrazin-2-yl)-7-methyl-2-(4-phenoxybenzyl)-2,3-dihydroisoindol-1-one;
2-(4-Chlorobenzyl)-5-(hexahydropyrrolo[1,2-a]pyrazin-2-yl)-7-methyl-2,3-dihydroisoindol-1-one;
2-(4-chlorobenzyl)-5-(3-dimethylaminopyrollidin-1-yl)-7-methyl-2,3-dihydroisoindol-1-one;
7-Methyl-5-(octahydropyrrolo[1,2-a]pyrazin-2-yl)-2-(4-trifluoromethoxybenzyl)-2,3-dihydroisoindol-1-one;
2-(4-chlorobenzyl)-7-methyl-5-pyridin-4-yl-2,3-dihydroisoindol-1-one;
2-(4-chlorobenzyl)-7-methyl-5-pyridin-3-yl-2,3-dihydroisoindol-1-one;
7-Chloro-5-(3-dimethylamino-prop-1-ynyl)-2-(4-trifluoromethoxy-benzyl)-2,3-dihydro-isoindol-1-one;
5-(3-Dimethylamino-prop-1-ynyl)-7-methyl-2-(4-trifluoromethoxy-benzyl)-2,3-dihydro-isoindol-1-one;
7-Methyl-5-(1,2,3,6-pyridin-4-yl)-2-(4-trifluoromethoxy-benzyl)-2,3-dihydroisoindol-1-one;
Bromo-7-methoxy-2-(4-trifluoromethoxybenzyl)-2,3-dihydroisoindol-1-one;
7-Methyl-5-(1-methyl-1,2,3,6-pyridin-4-yl)-2-(4-trifluoromethoxybenzyl)-2,3-dihydroisoindol-1-one;
7-Methoxy-5-pyridin-4-yl-2-(4-trifluoromethoxybenzyl)-2,3-dihydroisoindol-1-one;
7-Methoxy-5-pyridin-3-yl-2-(4-trifluoromethoxybenzyl)-2,3-dihydroisoindol-1-one;
4-[7-Methoxy-1-oxo-2-(4-trifluoromethoxy-benzyl)-2,3-dihydro-1H-isoindol-5-yl]-3,6-dihydro-2H-pyridine-1-carboxylic acid tert-butyl ester;
5-chloro-2-(4-trifluoromethoxy-benzyl)-7-trifluoromethyl-2,3-dihydro-isoindol-1-one;
5-Bromo-7-chloro-2-(4-trifluoromethoxy-benzyl)-2,3-dihydro-isoindol-1-one;
5-Bromo-7-chloro-2-(4-chloro-benzyl)-2,3-dihydro-isoindol-1-one;
7-Chloro-5-pyridin-4-yl-2-(4-trifluoromethoxy-benzyl)-2,3-dihydro-isoindol-1-one;
7-Methyl-2-(4-phenoxy-benzyl)-5-pyridin-4-yl-2,3-dihydro-isoindol-1-one;
7-Methyl-2-(4-phenoxy-benzyl)-5-pyridin-3-yl-2,3-dihydro-isoindol-1-one;
5-(3-Dimethylamino-pyrrolidin-1-yl)-7-methyl-2-(4-phenoxy-benzyl)-2,3-dihydro-isoindol-1-one;
7-Chloro-2-(4-chloro-benzyl)-5-[3-(4-methyl-piperazin-1-yl)-prop-1-ynyl]-2,3-dihydro-isoindol-1-one;
7-Chloro-2-(4-chloro-benzyl)-5-[3-(4-methyl-piperazin-1-yl)-propyl]-2,3-dihydro-isoindol-1-one;
7-Chloro-5-pyridin-3-yl-2-(4-trifluoromethoxy-benzyl)-2,3-dihydro-isoindol-1-one;
5-(4-Dimethylaminomethyl-phenyl)-7-methyl-2-(4-trifluoromethoxy-benzyl)-2,3-dihydro-isoindol-1-one;
7-Chloro-2-(4-chloro-benzyl)-5-pyridin-4-yl-2,3-dihydro-isoindol-1-one;
7-Chloro-5-(4-methyl-piperazin-1-yl)-2-(4-trifluoromethoxy-benzyl)-2,3-dihydro-isoindol-1-one;
7-Chloro-5-(hexahydro-pyrrolo[1,2-a]pyrazin-2-yl)-2-(4-trifluoromethoxy-benzyl)-2,3-dihydro-isoindol-1-one;
7-Chloro-2-(4-chloro-benzyl)-5-pyridin-3-yl-2,3-dihydro-isoindol-1-one;
7-Chloro-2-(4-chlorobenzyl)-5-(4-methyl-piperazin-1-yl)-2,3-dihydroisoindol-1-one;
7-Chloro-2-(4-chloro-benzyl)-5-(hexahydro-pyrrolo[1,2-a]pyrazin-2-yl)-2,3-dihydro-isoindol-1-one;
7-Chloro-2-(4-chloro-benzyl)-5-(3-dimethylamino-pyrrolidin-1-yl)-2,3-dihydro-isoindol-1-one;
7-Chloro-2-(4-chloro-benzyl)-5-(3-dimethylamino-pyrrolidin-1-yl)-2,3-dihydro-isoindol-1-one;
7-Methyl-5-(4-pyridin-4-ylmethyl-piperazin-1-yl)-2-(4-trifluoromethoxy-benzyl)-2,3-dihydro-isoindol-1-one;
7-Methyl-5-(4-pyridin-4-ylmethyl-piperazine-1-carbonyl)-2-(4-trifluoromethoxy-benzyl)-2,3-dihydro-isoindol-1-one;
7-Methyl-5-[4-(2-pyridin-4-yl-ethyl)-piperazin-1-yl]-2-(4-trifluoromethoxybenzyl)-2,3-dihydro-isoindol-1-one;
5-chloro-2-(4-ethyl-benzyl)-7-trifluoromethyl-2,3-dihydro-isoindol-1-one;
7-Methyl-5-[3-(4-methyl-piperazin-1-yl)-propyl]-2-(4-phenoxy-benzyl)-2,3-dihydro-isoindol-1-one;
7-Methyl-5-(4-pyridin-3-ylmethyl-piperazin-1-yl)-2-(4-trifluoromethoxy-benzyl)-2,3-dihydroisoindol-1-one;
5-[4-(3-Dimethylamino-propyl)-piperazin-1-yl]-7-methyl-2-(4-trifluoromethoxy-benzyl)-2,3-dihydro-isoindol-1-one;
2-(4-Chloro-benzyl)-7-methyl-5-(4-pyridin-4-ylmethyl-piperazin-1-yl)-2,3-dihydro-isoindol-1-one;
5-(3-Dimethylaminomethyl-phenyl)-7-methyl-2-(4-trifluoromethoxy-benzyl)-2,3-dihydro-isoindol-1-one;
6-Chloro-3-oxo-2-(4-phenoxy-benzyl)-2,3-dihydro-1H-isoindole-4-carbonitrile;
7-Methyl-5-[(1-phenyl-ethylamino)-methyl]-2-(4-trifluoromethoxy-benzyl)-2,3-dihydro-isoindol-1-one;
5-(4-Aminomethyl-phenyl)-7-methyl-2-(4-trifluoromethoxy-benzyl)-2,3-dihydro-isoindol-1-one;
7-Methyl-5-(4-morpholin-4-ylmethyl-phenyl)-2-(4-trifluoromethoxy-benzyl)-2,3-dihydro-isoindol-1-one;
7-Chloro-5-(3-dimethylamino-pyrrolidin-1-yl)-2-(4-trifluoromethoxy-benzyl)-2,3-dihydro-isoindol-1-one;
(S)-5-(3-Dimethylamino-pyrrolidin-1-yl)-7-methyl-2-(4-trifluoromethoxy-benzyl)-2,3-dihydro-isoindol-1-one;
7-Chloro-5-(3-dimethylamino-pyrrolidin-1-yl)-2-(4-trifluoromethoxy-benzyl)-2,3-dihydro-isoindol-1-one;
7-Chloro-2-(4-chloro-benzyl)-5-(3-dimethylamino-pyrrolidin-1-yl)-2,3-dihydro-isoindol-1-one;

7-Chloro-2-(4-chloro-benzyl)-5-(3-dimethylamino-pyrrolidin-1-yl)-2,3-dihydro-isoindol-1-one;
5-Bromo-7-chloro-2-(4-trifluoromethyl-benzyl)-2,3-dihydro-isoindol-1-one;
7-Chloro-5-(4-dimethylaminomethyl-phenyl)-2-(4-trifluoromethoxy-benzyl)-2,3-dihydro-isoindol-1-one;
5-(1'-Benzyl-1H-pyrazol-4-yl)-7-methyl-2-(4-trifluoromethoxy-benzyl)-2,3-dihydro-isoindol-1-one;
5-(6-Amino-pyridin-3-yl)-7-methyl-2-(4-trifluoromethoxy-benzyl)-2,3-dihydro-isoindol-1-one;
7-Methyl-5-[4-(2-pyridin-2-yl-ethyl)-piperazin-1-yl]-2-(4-trifluoromethoxy-benzyl)-2,3-dihydro-isoindol-1-one;
7-Chloro-5-[4-(2-pyridin-4-yl-ethyl)-piperazin-1-yl]-2-(4-trifluoromethoxy-benzyl)-2,3-dihydro-isoindol-1-one;
7-Chloro-5-(1-methyl-1H-pyrazol-4-yl)-2-(4-trifluoromethoxy-benzyl)-2,3-dihydro-isoindol-1-one;
4-[7-Chloro-2-(4-chloro-benzyl)-1-oxo-2,3-dihydro-1H-isoindol-5-yl]-pyridine-3-carbaldehyde;
7-Methyl-5-(1-pyridin-4-ylmethyl-1H-pyrazol-4-yl)-2-(4-trifluoromethoxy-benzyl)-2,3-dihydro-isoindol-1-one;
7-Chloro-5-[3-(4-methyl-piperazin-1-yl)-prop-1-ynyl]-2-(4-trifluoromethyl-benzyl)-2,3-dihydro-isoindol-1-one;
7-Chloro-2-(4-chloro-benzyl)-5-(1-pyridin-4-ylmethyl-1H-pyrazol-4-yl)-2,3-dihydro-isoindol-1-one;
7-Methyl-5-(1-pyridin-3-ylmethyl-1H-pyrazol-4-yl)-2-(4-trifluoromethoxy-benzyl)-2,3-dihydro-isoindol-1-one;
7-Chloro-5-(4-morpholin-4-ylmethyl-phenyl)-2-(4-trifluoromethoxy-benzyl)-2,3-dihydro-isoindol-1-one;
7-Chloro-2-(4-chloro-benzyl)-5-(1H-imidazol-4-yl)-2,3-dihydro-isoindol-1-one;
7-Chloro-2-(4-chloro-benzyl)-5-[(pyridin-4-ylmethyl)-amino]2,3-dihydro-isoindol-1-one;
7-Methyl-5-(1-pyridin-2-ylmethyl-1H-pyrazol-4-yl)-2-(4-trifluoromethoxy-benzyl)-2,3-dihydro-isoindol-1-one;
7-Chloro-5-(1-pyridin-4-ylmethyl-1H-pyrazol-4-yl)-2-(4-trifluoromethoxy-benzyl)-2,3-dihydro-isoindol-1-one;
7-Chloro-S-(methyl-pyridin-3-ylmethyl-amino)-2-(4-trifluoromethoxy-benzyl)-2,3-dihydro-isoindol-1-one;
7-Chloro-5-(1-isobutyl-1H-pyrazol-4-yl)-2-(4-trifluoromethoxy-benzyl)-2,3-dihydro-isoindol-1-one;
7-Methyl-5-(methyl-pyridin-4-ylmethyl-amino)-2-(4-trifluoromethoxy-benzyl)-2,3-dihydro-isoindol-1-one;
7-Chloro-5-(1-pyridin-4-ylmethyl-piperidin-4-ylmethyl)-2-(4-trifluoromethoxy-benzyl)-2,3-dihydro-isoindol-1-one;
7-Chloro-5-(1-pyridin-2-ylmethyl-1H-pyrazol-4-yl)-2-(4-trifluoromethoxy-benzyl)-2,3-dihydro-isoindol-1-one;
7-Methyl-5-(1-pyridin-2-ylmethyl-piperidin-4-ylmethyl)-2-(4-trifluoromethoxy-benzyl)-2,3-dihydro-isoindol-1-one;
7-methyl-5-(1-pyridin-3-ylmethyl-piperidin-4-ylmethyl)-2-(4-trifluoromethoxy-benzyl)-2,3-dihydro-isoindol-1-one;
7-methyl-5-(1-pyridin-4-ylmethyl-piperidin-4-ylmethyl)-2-(4-trifluoromethoxy-benzyl)-2,3-dihydro-isoindol-1-one;
4-{4-[7-methyl-1-oxo-2-(4-trifluoromethoxy-benzyl)-2,3-dihydro-1H-isoindol-5-ylmethyl]-piperidin-1-ylmethyl}-benzonitrile;
5-(1-cyclopentyl-piperidin-4-ylmethyl)-7-methyl-2-(4-trifluoromethoxy-benzyl)-2,3-dihydro-isoindol-1-one;
7-Methyl-5-(methyl-pyridin-3-ylmethyl-amino)-2-(4-trifluoromethoxy-benzyl)-2,3-dihydro-isoindol-1-one;
7-Methyl-pyridin-3-ylamino)-2-(4-trifluoromethoxy-benzyl)-2,3-dihydro-isoindol-1-one;
5-(1-isopropyl-piperidin-4-ylmethyl)-7-methyl-2-(4-trifluoromethoxy-benzyl)-2,3-dihydro-isoindol-1-one;
7-Methyl-5-(1-methyl-piperidin-4-ylmethyl)-2-(4-trifluoromethoxy-benzyl)-2,3-dihydro-isoindol-1-one;
5-(1-Ethyl-piperidin-4-ylmethyl)-7-methyl-2-(4-trifluoromethoxy-benzyl)-2,3-dihydro-isoindol-1-one;
5-(1-Benzyl-pyrrolidin-3-ylamino)-7-methyl-2-(4-trifluoromethoxy-benzyl)-2,3-dihydro-isoindol-1-one;
5-[1-(2-Dimethylamino-ethyl)-1H-pyrazol-4-yl]-7-methyl-2-(4-trifluoromethoxy-benzyl)-2,3-dihydro-isoindol-1-one;
7-Chloro-5-ethyl-2-(4-trifluoromethyl-benzyl)-2,3-dihydro-isoindol-1-one;
7-Methyl-1-oxo-2-(4-trifluoromethoxy-benzyl)-2,3-dihydro-1H-isoindole-5-carboxylic acid methyl ester;
7-Chloro-2-(4-chloro-benzyl)-5-(1-pyridin-2-ylmethyl-1H-pyrazol-4-yl)-2,3-dihydro-isoindol-1-one;
7-Chloro-2-(4-chloro-benzyl)-5-(1-pyridin-3-ylmethyl-1H-pyrazol-4-yl)-2,3-dihydro-isoindol-1-one;
5-(3-Dimethylaminomethyl-[1,2,4]oxadiazol-5-yl)-7-methyl-2-(4-trifluoromethoxy-benzyl)-2,3-dihydro-isoindol-1-one;
7-Methyl-5-(3-morpholin-4-ylmethyl-[1,2,4]oxadiazol-5-yl)-2-(4-trifluoromethoxy-benzyl)-2,3-dihydro-isoindol-1-one;
5-(3-Diethylaminomethyl-[1,2,4]oxadiazol-5-yl)-7-methyl-2-(4-trifluoromethoxy-benzyl)-2,3-dihydro-isoindol-1-one;
7-Methyl-5-(3-methylaminomethyl-[1,2,4]oxadiazol-5-yl)-2-(4-trifluoromethoxy-benzyl)-2,3-dihydro-isoindol-1-one;
5,7-Dichloro-2-(4-trifluoromethoxy-benzyl)-2,3-dihydro-isoindol-1-one;
7-Chloro-5-ethyl-2-(4-trifluoromethyl-benzyl)-2,3-dihydro-isoindol-1-one;
7-Methyl-S-(pyridine-2-ylmethoxy)-2-(4-trifluoromethoxy-benzyl)-2,3-dihydro-isoindol-1-one;
7-Methyl-2-(4-methyl-benzyl)-5-pyridin-3-yl-2,3-dihydro-isoindol-1-one;
2-Benzyl-7-methyl-5-pyridin-3-yl-2,3-dihydro-isoindol-1-one;
2-(4-Fluoro-benzyl)-7-methyl-5-pyridin-3-yl-2,3-dihydro-isoindol-1-one;
2-(4-Methoxy-benzyl)-7-methyl-5-pyridin-3-yl-2,3-dihydro-isoindol-1-one;
2-Cyclopropylmethyl-7-methyl-5-pyridin-3-yl-2,3-dihydro-isoindol-1-one;
4-[(7-methyl-1-oxo-5-pyridin-3-yl-1,3-dihydro-2H-isoindol-2-yl)methyl]benzonitrile;
7-chloro-5-ethyl-2-(4-trifluoromethoxy-benzyl)-2,3-dihydro-isoindol-1-one;
7-Chloro-2-(4-chloro-benzyl)-5-(1-pyridin-ylmethyl-piperidin-4-ylmethyl-2,3-dihydro-isoindol-1-one;
7-Chloro-2-(4-fluoro-benzyl)-5-(1-pyridin-ylmethyl-piperidin-4-ylmethyl-2,3-dihydro-isoindol-1-one;
7-Chloro-5-(1-methyl-piperidin-4-ylmethyl)-2-(4-trifluoromethoxy-benzyl)-2,3-dihydro-isoindol-1-one;
4-{4-[7-chloro-1-oxo-2-(4-trifluoromethoxy-benzyl)-2,3-dihydro-1H-isoindol-5-ylmethyl]-piperidin-1-ylmethyl}-benzonitrile;
7-chloro-2-cyclopropylmethyl-5-(1-pyridine-4-ylmethyl-piperidin-4-ylmethyl)-2,3-dihydro-isoindol-1-one;
4-[4-(7-chloro-2-cyclopropylmethyl-1-oxo-2,3-dihydro-1H-isoindol-5-ylmethyl)-piperidine-1-ylmethyl]-benzonitrile;
5-Fluoro-7-iodo-2-(4-trifluoromethoxy-benzyl)-2,3-dihydro-isoindol-1-one;
2-(5-Chloro-2-fluoro-benzyl)-7-methyl-5-pyridin-3-yl-2,3-dihydro-isoindol-1-one;
2-(4-Dimethylamino-benzyl)-7-methyl-5-pyridin-3-yl-2,3-dihydro-isoindol-1-one;
2-(4-Ethyl-benzyl)-7-methyl-5-pyridin-3-yl-2,3-dihydro-isoindol-1-one;

7-Chloro-2-(3-phenylprop-2-ynyl)-5-(1-pyridin-2-ylmethyl-1H-pyrazol-4-yl)-2,3-dihydroisoindol-1-one;
5-Fluoro-7-chloro-2-(4-trifluoromethoxy-benzyl)-2,3-dihydro-isoindol-1-one;
2-{4-[7-methyl-1-oxo-2-(4-trifluoromethoxy-benzyl)-2,3-dihydro-1H-isoindol-5-ylmethyl]-piperazin-1-ylmethyl}-nicotinonitrile;
6-{4-[7-methyl-1-oxo-2-(4-trifluoromethoxy-benzyl)-2,3-dihydro-1H-isoindol-5-ylmethyl]-piperazin-1-ylmethyl}-nicotinonitrile;
7-Iodo-5-methoxy-2-(4-trifluoromethoxy-benzyl)-2,3-dihydro-isoindol-1-one;
7-chloro-5-(4-pyridin-2-yl-piperazin-1-ylmethyl)-2-(4-trifluoromethoxy-benzyl)-2,3-dihydro-isoindol-1-one;
2-{4-[7-chloro-1-oxo-2-(4-trifluoromethoxy-benzyl)-2,3-dihydro-1H-isoindol-5-ylmethyl]-piperazin-1-ylmethyl}-nicotinonitrile;
6-{4-[7-chloro-1-oxo-2-(4-trifluoromethoxy-benzyl)-2,3-dihydro-1H-isoindol-5-ylmethyl]-piperazin-1-ylmethyl}-nicotinonitrile;
7-chloro-5-methoxy-2-(4-trifluoromethoxy-benzyl)-2,3-dihydro-isoindol-1-one;
2-(3-Fluoro-benzyl)-7-methyl-5-pyridin-3-yl-2,3-dihydro-isoindol-1-one;
2-(2-Fluoro-benzyl)-7-methyl-5-pyridin-3-yl-2,3-dihydro-isoindol-1-one;
2-(4-Difluoromethoxy-benzyl)-7-methyl-5-pyridin-3-yl-2,3-dihydro-isoindol-1-one;
2-(4-Isopropyl-benzyl)-7-methyl-5-pyridin-3-yl-2,3-dihydro-isoindol-1-one;
7-chloro-2-(4-chloro-benzyl)-1-oxo-2,3-dihydro-1H-isoindol-5-ylmethyl]-piperidin-1-ylmethyl}-benzonitrile;
4-{4-[7-chloro-1-oxo-2-(4-trifluoromethoxy-benzyl)-2,3-dihydro-1H-isoindol-5-ylmethyl]-piperazin-1-methyl}-nicotinonitrile;
7-Chloro-2-(3-phenylpropyl)-5-(1-pyridin-2-ylmethyl-1H-pyrazol-4-yl)-2,3-dihydroisoindol-1-one;
7-Chloro-5-(pyridin-2-ylmethoxy)-2-(4-trifluoromethoxy-benzyl)-2,3-dihydro-isoindol-1-one;
4-{4-[7-chloro-2-(4-difluoromethoxy-benzyl)-1-oxo-2,3-dihydro-1H-isoindol-5-ylmethyl]-piperidin-1-ylmethyl}-benzonitrile;
7-Chloro-2-(4-difluoromethoxy-benzyl)-5-(1-pyridin-ylmethyl-piperidin-4-ylmethyl-2,3-dihydro-isoindol-1-one;
2-(4-Fluoro-3-methyl-benzyl)-7-methyl-5-pyridin-3-yl-2,3-dihydro-isoindol-1-one;
2-(4-Chloro-2-methyl-benzyl)-7-methyl-5-pyridin-3-yl-2,3-dihydro-isoindol-1-one;
2-Benzyl-5-bromo-7-methyl-2,3-dihydro-isoindol-1-one;
5-Bromo-2-(4-ethyl-benzyl)-7-methyl-2,3-dihydro-isoindol-1-one;
5-Bromo-2-(3-fluoro-benzyl)-7-methyl-2,3-dihydro-isoindol-1-one;
5-Bromo-2-(2-fluoro-benzyl)-7-methyl-2,3-dihydro-isoindol-1-one;
5-Bromo-2-(4-difluoromethoxy-benzyl)-7-methyl-2,3-dihydro-isoindol-1-one;
5-Bromo-2-(4-isopropyl-benzyl)-7-methyl-2,3-dihydro-isoindol-1-one;
5-Bromo-2-(4-fluoro-3-methyl-benzyl)-7-methyl-2,3-dihydro-isoindol-1-one; and
7-Methyl-5-[3-(1-methyl-piperidin-4-yl)-propyl]-2-(4-trifluoromethoxy-benzyl)-2,3-dihydro-isoindol-1-one.

Pharmaceutical Composition

The compounds of the present invention may be formulated into conventional pharmaceutical composition comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or table disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

We have discovered that the compounds of the present invention exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction in an animal.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to formula I or a pharmaceutically acceptable salt or solvate thereof, is administered to a patient in need of such treatment. The invention also provides a compound of formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders.

In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracically, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of formula I, or salts thereof, are useful as pharmacological tools in the development and standardisation of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

Process for Preparing

Compounds of the present invention can be prepared by various synthetic processes. The selection of a particular process to prepare a given compound is within the purview of the person of skill in the art. The choice of particular structural features and/or substituents may therefore influence the selection of one process over another.

Within these general guidelines, the following processes can be used to prepare exemplary subsets of compounds of this invention. Unless indicated otherwise, the variables described in the following schemes and processes have the same definitions as those given for formula I above.

In one process, for example, a compound of formula Ia:

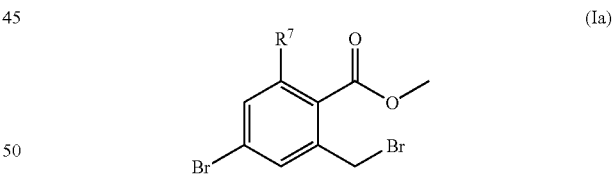

(Ia)

is cyclized in the presence of an amine of the formula $R^1(CR^8R^9)_n NH_2$ to give a compound of formula Ib:

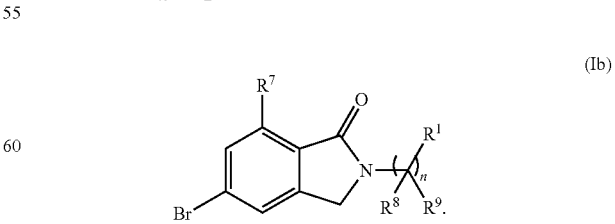

(Ib)

A compound of formula Ib is then cross-coupled with a suitable reagent containing $R^5$ to yield a compound according to formula Ic:

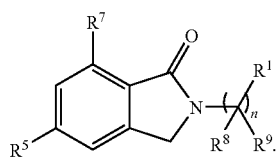

(Ic)

In one embodiment of this process, 5-substituted-7-methyl isoindolones are synthesized as depicted in Scheme 1 below. 4-bromo-2,6-dimethylaniline is converted to the corresponding nitrile under Sandmeyer reaction conditions. The nitrile is then hydrolyzed to the acid in a stepwise fashion. The amide can be obtained by basic hydrolysis. The amide is then diazotized and hydrolyzed with nitrososulphuric acid to provide the benzoic acid, which is subsequently protected as the methyl ester using standard conditions. The benzylic methyl group is monobrominated with N-bromosuccinimide using benzoyl peroxide as the radical initiator. This resultant intermediate is cyclized to the isoindolone with the appropriate amine in the presence of a base such as potassium carbonate. Finally, substituent $R^5$ was introduced at C5 of the isoindolone using typical Buchwald, Suzuki or Stille cross-coupling reaction conditions and reagents.

Scheme 1

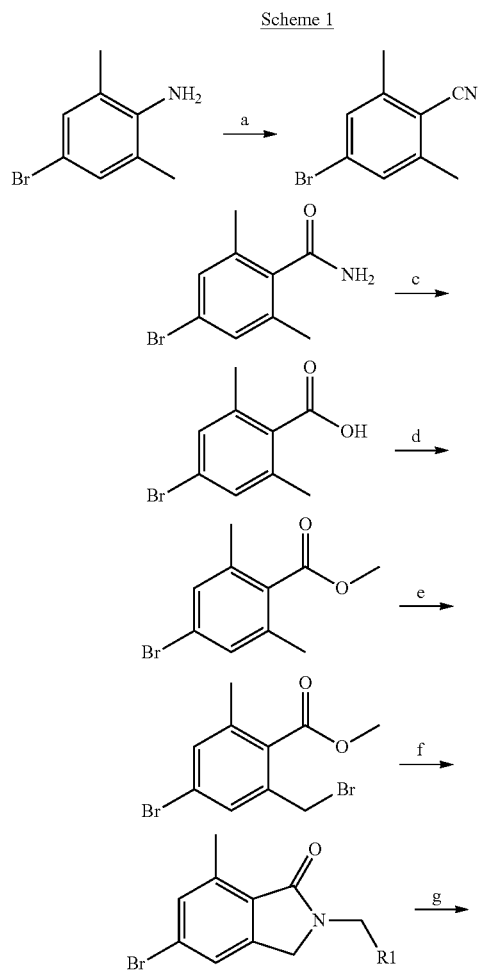

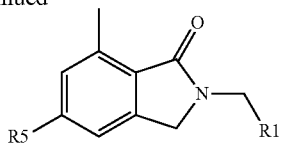

a NaCN, CuCN, HCl;
b NaOH;
c nitrososulphuric acid;
d MeI, K$_2$CO$_3$;
e NBS, (PhCO$_2$)$_2$;
f R1CH$_2$NH$_2$, K$_2$CO$_3$;
g R5H, BINAP, PdCl$_2$(dppf), NaOtBu OR R5B(OH)$_2$, PdCl$_2$(dppf), K$_2$CO$_3$ OR R5SnBu$_3$, Pd(PPh$_3$)$_4$ In another embodiment of this process, 5-substituted-7-chloro isoindolones are synthesized as depicted in Scheme 2 below. 4-bromo-2-methylbenzoic acid is chlorinated ortho to the acid using N-chlorosuccinimide and a palladium catalyst. In the manner analogous to that described above (Scheme 1), this acid was then esterified, brominated, and cyclized to yield the isoindolone intermediate. Substituent $R^5$ is introduced similarly.

Scheme 2

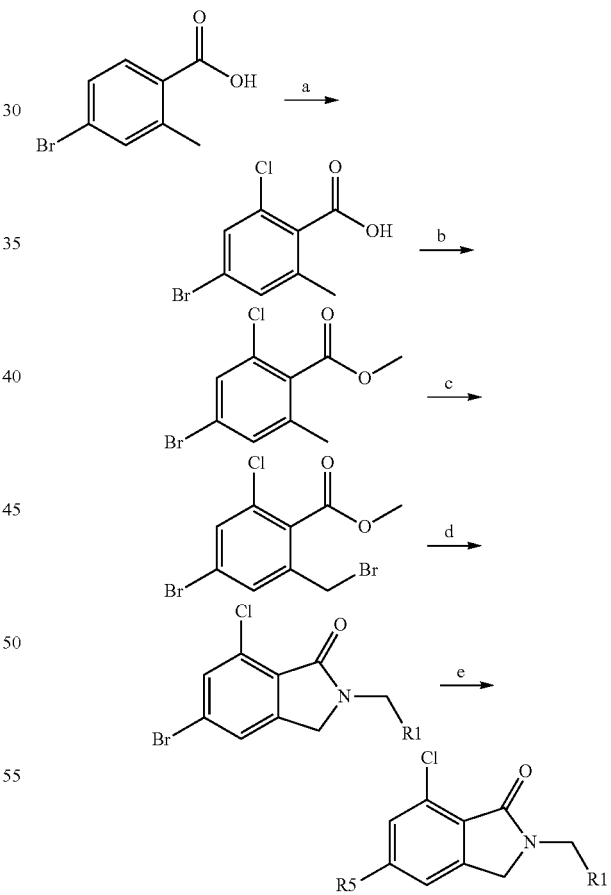

a NCS, Pd(OAc)$_2$;
b MeI, K$_2$CO$_3$;
c NBS, (PhCO$_2$)$_2$;
d R1CH$_2$NH$_2$, K$_2$CO$_3$;
e R5H, BINAP, PdCl$_2$(dppf), NaOtBu OR R5B(OH)$_2$, PdCl$_2$(dppf), K$_2$CO$_3$ OR R5SnBu$_3$, Pd(PPh$_3$)$_4$ In yet another embodiment of this process, isoindolones that are substituted with an amide at C5 can be prepared as depicted in Scheme 3 below. Thus, an appropriately substituted 5-bromoisoindolone is converted to the corresponding nitrile using zinc cyanide in the presence of a palladium catalyst. The nitrile is then hydrolyzed under basic conditions to provide the benzoic acid, which was then coupled with various amines using methodologies that are well-known in the art to provide the final compounds.

Scheme 3

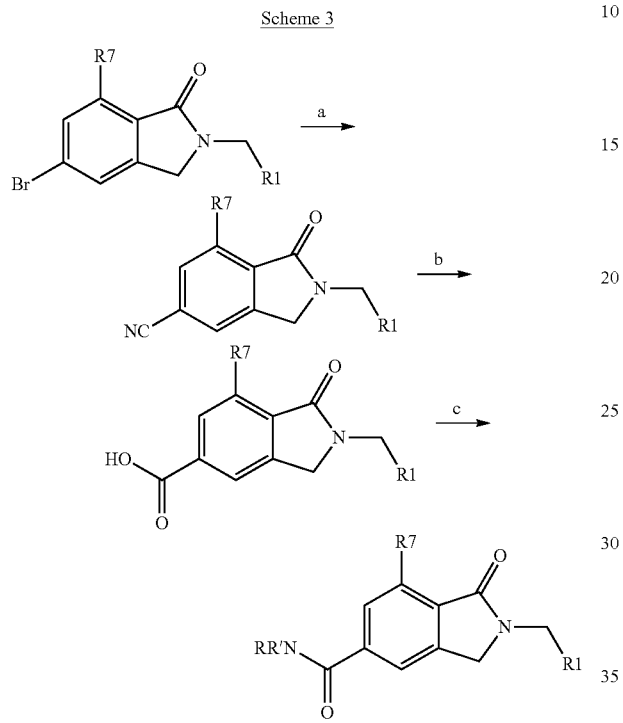

a Zn(CN)$_2$, Pd(PPh$_3$)$_4$;
b NaOH;
c RR'NH, EDCl

In still another embodiment, the process as described above can be adapted for the preparation of amino-propargyl and amino-alkyl isoindolones. Thus, suitable 5-bromoisoindolones are first subjected to Sonogashira coupling conditions with various propargyl amines as shown in Scheme 4. The resulting alkyne then can be hydrogenated using routine methodologies to provide the amino-alkyl substituted product. In Scheme 4, R and R' correspond to substituents as defined herein for $R^{10}$ and $R^{11}$.

Scheme 4

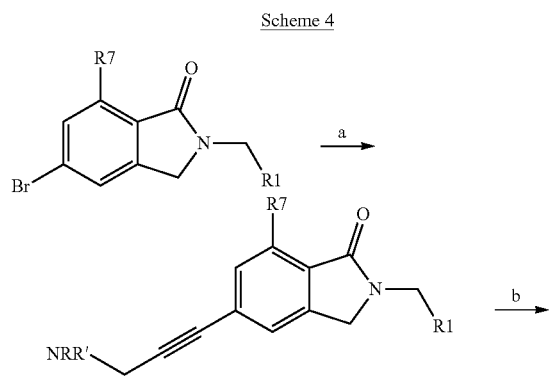

-continued

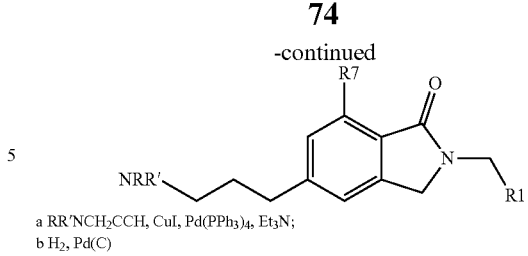

a RR'NCH$_2$CCH, CuI, Pd(PPh$_3$)$_4$, Et$_3$N;
b H$_2$, Pd(C)

Another process according to this invention adapts some of the foregoing synthetic methodology for the preparation of compounds bearing N-propargylic substituents. Thus, a compound of the formula Ia:

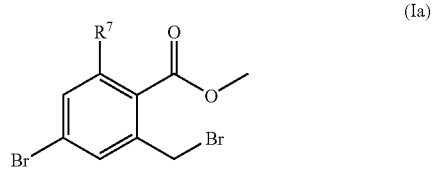
(Ia)

is cyclized in the presence of propargyl amine into a compound of the formula Id:

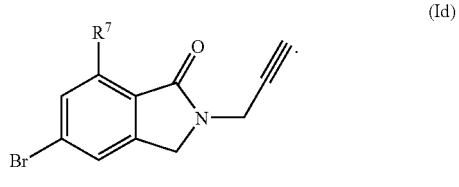
(Id)

Coupling a compound of formula Id with a reagent comprising $R^1$ gives a compound of formula Ie:

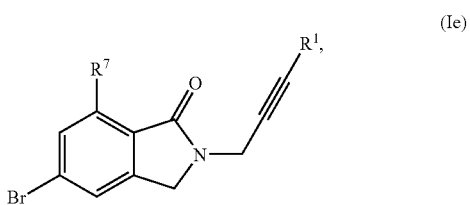
(Ie)

$R^1$ preferably is an aryl group. A compound of formula Ie is then cross-coupled with a reagent comprising $R^5$, thereby yielding a compound according to formula If:

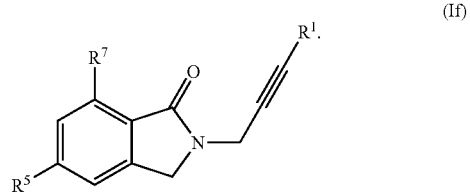
(If)

One embodiment of this process is shown in Scheme 5 below. The terminal alkyne is coupled with various aryl groups using standard Sonogashira coupling conditions. Finally, substituent $R^5$ was introduced at C5 using typical Buchwald, Suzuki or Stille cross-coupling reaction conditions as indicated in Scheme 5.

Scheme 5

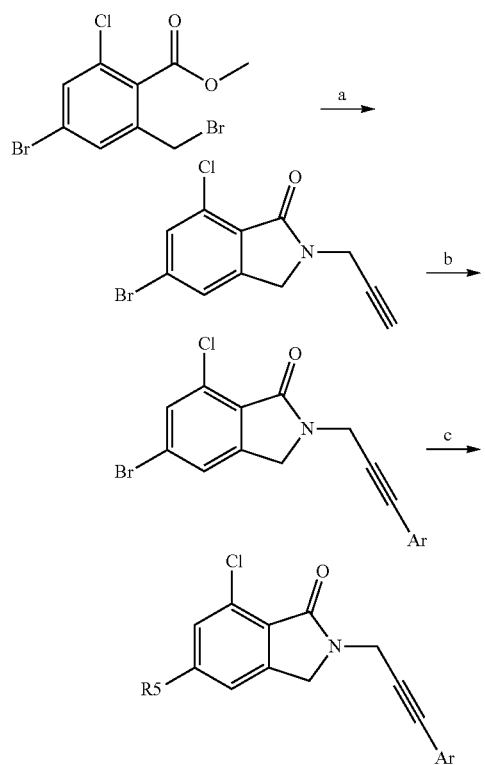

a propargyl amine, K₂CO₃;
b ArI, CuI, Pd(PPh₃)₄, Et₃N;
c R5H, BINAP, PdCl₂(dppf), NaOtBu OR R5B(OH)₂, PdCl₂(dppf), K₂CO₃ OR R5SnBu₃, Pd(PPh₃)₄

Another process of the invention contemplates the preparation of compounds of formula I that are unsubstituted on the isoindolone aromatic ring. This subset of compounds are be straightforwardly prepared as depicted below in Scheme 6. Thus, phthalimide is reduced, for example with tin under acidic conditions, to provide isoindolinone. This intermediate is alkylated with various electrophiles under basic conditions to provide the desired final products. In Scheme 6, X can be any suitable leaving group such as, for example, halo, such as bromo and iodo; and tosylate.

Scheme 6

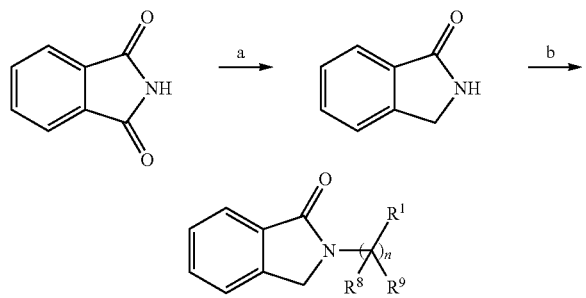

a Sn, HCl, AcOH;
b R¹(CR⁸R⁹)ₙX, Cs₂CO₃, 18-crown-6

Many variations of the foregoing processes and additions thereto appear throughout the examples that follow. The person of ordinary skill in the art thus will appreciate that the compounds of this invention can be prepared by following or adapting one or more of the processes disclosed herein.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson autopreparative HPLC with a diode array detector using an XTerra MS C8, 19×300 mm, 7 mm as column.

Purification by a chromatotron was performed on rotating silica gel/gypsum (Merck, 60 PF-254 with calcium sulphate) coated glass sheets, with coating layer of 1, 2, or 4 mm using a TC Research 7924T chromatotron.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns. Microwave heating was performed in a Smith Synthesizer Single-mode microwave cavity producing continuous irradiation at 2450 MHz (Personal Chemistry AB, Uppsala, Sweden).

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

Fluorometric Imaging Plate Reader (FLIPR) analysis was used to detect allosteric activators of mGluR2 via calcium mobilization. A clonal HEK 293 cell line expressing a chimeric mGluR2/CaR construct comprising the extracellular and transmembrane domains of human mGluR2 and the intracellular domain of the human calcium receptor, fused to the promiscuous chimeric protein $G_{\alpha qi5}$ was used. Activation of this construct by agonists or allosteric activators resulted in stimulation of the PLC pathway and the subsequent mobilization of intracellular $Ca^{2+}$ which was measured via FLIPR analysis. At 24-hours prior to analysis, the cells were trypsinized and plated in DMEM at 100,000 cells/well in black sided, clear-bottom, collagen I coated, 96-well plates. The plates were incubated under 5% $CO_2$ at 37° C. overnight. Cells were loaded with 6 µM fluo-3 acetoxymethylester (Molecular Probes, Eugene Oreg.) for 60 minutes at room temperature. All assays were performed in a buffer containing 126 mM NaCl, 5 mM KCl, 1 mM $MgCl_2$, 1 mM $CaCl_2$, 20 mM Hepes, 0.06 µM DCG-IV (a Group II mGluR selective agonist), supplemented with 1.0 mg/ml D-glucose and 1.0 mg/ml BSA fraction IV (pH 7.4).

FLIPR experiments were done using a laser setting of 0.8 W and a 0.4 second CCD camera shutter speed. Extracellular fluo-3 was washed off and cells were maintained in 160 µL of buffer and placed in the FLIPR. An addition of test compound (0.01 µM to 30 µM in duplicate) was made after 10 seconds of baseline fluorescent readings were recorded on FLIPR. Fluorescent signals were then recorded for an additional 75 seconds at which point a second addition of DCG-IV (0.2 µM) was made and fluorescent signals were recorded for an additional 65 seconds. Fluorescent signals were measured as the peak height of the response within the sample period. Data was analyzed using Assay Explorer, and $EC_{50}$ and $E_{max}$ values (relative to maximum DCG-IV effect) were calculated using a four parameter logistic equation.

A $[^{35}S]$-GTPγS binding assay was used to functionally assay mGluR2 receptor activation. The allosteric activator activity of compounds at the human mGluR2 receptor were measured using a $[^{35}S]$-GTPγS binding assay with membranes prepared from CHO cells which stably express the human mGluR2. The assay is based upon the principle that agonists bind to G-protein coupled receptors to stimulate GDP-GTP exchange at the G-protein. Since $[^{35}S]$-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 µg protein) were incubated with test compound (3 nM to 300 µM) for 15 minutes at room temperature prior to the addition of 1 µM glutamate, and incubated for 30 min at 30° C. in 500 µl assay buffer (20 mM HEPES, 100 mM NaCl, 10 mM $MgCl_2$), containing 30 µM GDP and 0.1 nM $[^{35}S]$-GTPγS (1250 Ci/mmol). Reactions were carried out in triplicate in 2 ml polypropylene 96-well plates. Reactions were terminated by vacuum filtration using a Packard 96-well harvester and Unifilter-96, GF/B filter microplates. The filter plates were washed 4×1.5 ml with ice-cold wash buffer (10 mM sodium phosphate buffer, pH 7.4). The filter plates were dried and 35 µl of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

Generally, the compounds of the present invention were active in assays described herein at concentrations (or with $EC_{50}$ values) less than 10 µM.

PREPARATION OF INTERMEDIATES FOR EXAMPLES

Example 1

4-Fluoro-2-methylbenzonitrile

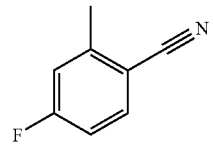

5-Fluoro-2-iodotoluene (3 g, 12.7 mmol) was stirred in DMF (40 mL) under argon and $Zn(CN)_2$ (1.94 g, 16.5 mmol) and $Pd(PPh_3)_4$ (1.47 g, 1.27 mmol) were added. The reaction was stirred at 80° C. for 1.5 hours. The reaction was partitioned between ethyl acetate and water and the organic layer was washed with brine and dried over anhydrous $Na_2SO_4$. The solvent was removed under reduced pressure to afford a yellow solid (2.90 g), confirmed by GC MS.

Example 2

4-Bromo-2,6-dimethylbenzonitrile

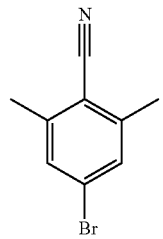

4-Bromo-2,6-dimethylphenylamine (10 g, 500 mmol) was suspended in concentrated HCl (10 mL) and crushed ice (41 g) and cooled to 0° C. $NaNO_2$ (3.52 g, 51 mmol) in water (10 mL) was added, maintaining a temperature of 0° C. and the reaction was stirred for 30 minutes. A solution of copper cyanide (5.60 g, 62.5 mmol) in water (25 mL) and sodium cyanide (7.79 g, 159 mmol) in water (12 mL) were cooled to 0° C. in a separate flask. The concentrated HCl mixture was neutralized with sodium carbonate and the resulting diazonium salt mixture was added to the copper cyanide and sodium cyanide solution along with toluene (100 mL) under vigorous stirring, maintaining a temperature of 0° C. for 1 hour, followed by stirring at room temperature for 4 hours. The reaction mixture was heated to 50° C. and then cooled to room temperature. The reaction was partitioned between water and toluene and the organic layers were combined and washed with water and dried over anhydrous $Na_2SO_4$. The product was purified by column chromatography on silica (20% EtOAc/Hexanes) to afford a brown solid (8.10 g). $^1$H NMR (300 MHz, $CDCl_3$): δ 7.33 (s, 2H), 2.53 (s, 6H).

In a similar fashion, the following compounds were made:

| Example | Structure | Name | Yield | ¹H NMR |
|---------|-----------|------|-------|--------|
| 3 | 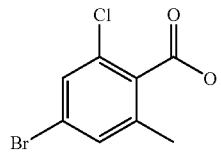 | 4-Bromo-2-methoxy-6-methyl-benzonitrile | 7.32 g (70%) brown solid | 7.08 (d, 1H), 6.97 (d, 1H), 3.93 (s, 3H), 2.50 (s, 3H) |
| 4 | 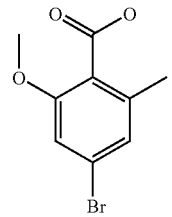 | 4-Bromo-2-chloro-6-methyl-benzonitrile | 1.69 g (44%) orange solid | N/A |

Example 5

4-Fluoro-2-methylbenzoic acid

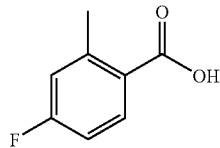

4-Fluoro-2-methylbenzonitrile (2.9 g), 5N NaOH (50 mL), and MeOH (50 mL) were set stirring at 100° C. for 18 hours. The solvent was removed under reduced pressure and the product was washed with CH₂Cl₂ and acidified to pH 1. The reaction was partitioned between ethyl acetate and water and the organic layer was washed with brine and dried over anhydrous Na₂SO₄ to yield a while solid (1.6 g). ¹H NMR (300 MHz, CDCl₃): δ 8.07-8.14 (m, 1H), 6.96-7.01 (m, 1H), 6.79-6.82 (m, 1H), 2.73 (br s, 3H).

Example 6

4-Bromo-2,6-dimethylbenzoic acid

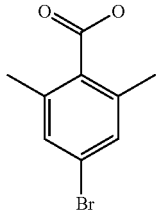

4-Bromo-2,6-dimethylbenzonitrile (4.0 g, 19 mmol) was stirred in MeOH (100 mL) and 5N NaOH (100 mL) at 100° C. for 12 hours. The reaction was cooled to room temperature and partitioned between CH₂Cl₂ and water and the organic layer was dried over anhydrous Na₂SO₄. The solvent was removed under reduced pressure and the resulting product was stirred in H₂PO₃ (20 mL) for 6 hours at 150° C. The reaction mixture was basified with 6M KOH, filtered and then acidified with 12M HCl. The reaction was partitioned between CH₂Cl₂ and water and the organic layer was dried over anhydrous Na₂-SO₄. The solvent was removed under reduced pressure to afford the product (2.81 g). ¹H NMR (300 MHz, CDCl₃): δ 7.22 (s, 2H), 6.17 (s, 1H), 5.67 (s, 1H), 2.36 (s, 6H).

Example 7

4-Bromo-2-chloro-6-methyl-benzoic acid

Water (5 mL) was chilled in an ice bath and nitrososulfuric acid was added dropwise. A suspension of 4-Bromo-2,6-dimethyl-benzamide (1.30 g, 5.23 mmol) in dichloromethane (10 mL) was added. The organic phase was dried over magnesium sulfate and concentrated. It was taken up in ethyl acetate and extracted three times with saturated sodium bicarbonate. The combined aqueous extracts were acidified with 6M hydrochloric acid and extracted three times with ethyl acetate. The combined organic extracts were washed with brine, dried over magnesium sulfate, filtered and concentrated to provide the title compound as a colourless solid (1.14 g, 88%). ¹H NMR CDCl₃: δ 7.48 (s, 1H), 7.35 (s, 1H), 2.45 (s, 3H).

Example 8

4-Bromo-2-methoxy-6-methylbenzoic acid

4-Bromo-2-methoxy-6-methylbenzamide (2.0 g, 8.2 mmol), dissolved in CH₂Cl₂, was added dropwise to nitrosyl sulfuric acid (14.0 mL) in water (6.0 mL) at 0° C. and stirred for 2 hours. The reaction mixture was poured over ice and extracted with CH₂Cl₂, and the solvent was removed under reduced pressure to afford a light pink solid (1.93 g, 96%). ¹H NMR (300 MHz, CDCl₃): δ 7.07 (s, 1H), 7.00 (s, 1H), 3.93 (s, 3H), 2.46 (s, 3H).

The following compounds were made in a similar fashion:

| Example | Structure | Name | Yield | ¹H NMR |
|---|---|---|---|---|
| 9 | 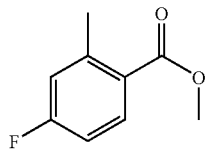 | 4-Bromo-2-methylbenzoic acid | 5.09 g (93%) colourless solid | 7.95 (d, 1H), 7.45 (m, 2H), 2.66 (s, 3H) |

Example 10

4-Fluoro-2-methyl-benzoic acid methyl ester

4-Fluoro-2-methylbenzoic acid (1.6 g, 10.3 mmol) was dissolved in CH$_2$Cl$_2$ (20 mL) and DMF (1 drop) and stirred as oxalyl chloride (10.3 mL, 20.8 mmol) was added. The reaction stirred for 15 minutes before the solvent was removed under reduced pressure. The product was dissolved in anhydrous CH$_2$Cl$_2$ and MeOH (5 mL) and stirred for a further 15 minutes. The solvent was removed under reduced pressure and purified by column chromatography on silica (2% EtOAc/Hexanes) to afford a colourless oil (1.33 g). ¹H NMR (300 MHz, CDCl$_3$): δ 7.95 (d, 1H), 6.96 (d, 1H), 6.75-6.77 (m, 1H), 3.86 (d, 3H), 2.62 (d, 3H).

The following products were made in a similar fashion:

Example 12

4-Bromo-2,6-dimethylbenzoic acid methyl ester

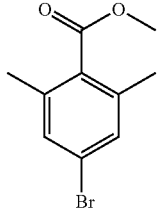

To a stirred solution of 4-bromo-2,6-dimethylbenzoic acid (2.81 g, 12.3 mmol) in DMF (30 mL) was added iodomethane (2.30 mL, 36.9 mmol) and potassium carbonate (5.09 g, 36.9 mmol) and reaction was stirred at room temperature for 1.5 hours. The reaction mixture was partitioned between water and ethyl acetate and the organic layer was washed with brine. The solvent was removed under reduced pressure to yield an amber oil (3.06 g). ¹H NMR (300 MHz, CDCl$_3$): δ 7.22 (S, 2H), 3.92 (s, 3H), 2.30 (s, 6H).

The following compounds were made in a similar fashion:

| Example | Structure | Name | Yield | ¹H NMR |
|---|---|---|---|---|
| 11 | 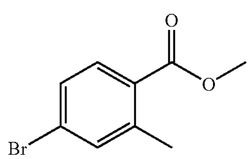 | 4-Bromo-2-methylbenzoic acid methyl ester | 5.00 g (92%) colourless oil | 7.80 (d, 1H), 7.42 (m, 2H), 3.91 (s, 3H), 2.60 (s, 3H) |

| Example | Structure | Name | Yield | ¹H NMR |
|---|---|---|---|---|
| 13 | 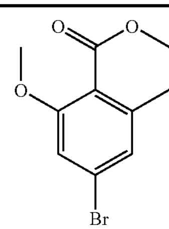 | 4-Bromo-2-methoxy-6-methyl benzoic acid methyl ester | 3.95 g (99%) brown solid | 7.00 (s, 1H), 6.92 (s, 1H), 3.92 (s, 3H), 3.83 (s, 3H), 2.28 (s, 3H) |

Example 14

4-Bromo-2-chloro-6-methylbenzoic acid methyl ester

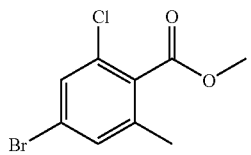

4-Bromo-2-chloro-6-methylbenzoic acid (1.10 g, 4.41 mmol) was dissolved in ethyl acetate (15 mL). A solution of diazomethane in diethyl ether was added until the yellow colour persisted. After fifteen minutes the reaction was quenched with acetic acid. After one hour, the mixture was washed with saturated sodium bicarbonate and brine, dried over magnesium sulfate, filtered and concentrated to provide the title compound as a yellow oil (1.31 g, 113%). $^1$H NMR CDCl$_3$: 7.43 (s, 1H), 7.31 (s, 1H), 3.94 (s, 3H), 2.33 (s, 3H).

Example 15

4-Bromo-2-chloro-6-methylphenylamine hydrobromide salt

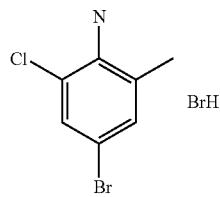

2-Chloro-6-methyl-phenylamine (5.00 g, 35.3 mmol) was dissolved in methanol (15 mL) and acetic acid was added (5 mL). The solution was chilled in an ice bath and a solution of bromine (1.8 mL) in acetic acid (15 mL) was added dropwise. After complete addition MeOH (5 mL) was added to dissolve the precipitated solid. The solvents were removed under reduced pressure and the residue was triturated with hexanes to provide the title compound as an off white solid (10.49 g, 99%). $^1$H NMR (300 MHz, MeOD): δ 7.42 (s, 1H), 7.28 (s, 1H), 2.42 (s, 3H).

Example 16

4-Bromo-2-methoxy-6-methyl phenylamine

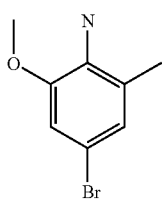

2-Methoxy-6-methyl phenylamine (10 g, 72.9 mmol) was set stirring in methanol (30 mL) and acetic acid (10 mL) at 0° C. Bromine (3.73 mL, 72.9 mmol) was dissolved in acetic acid (15 mL) and added dropwise to the reaction. The reaction was stirred for 2 hours and the solvent was removed under reduced pressure. The resulting residue was basified with 1N NaOH and partitioned with EtOAc. The organic layer was dried over anhydrous Na$_2$SO$_4$. The solvent was removed under reduced pressure and the product was purified by column chromatography (20% EtOAc/Hexanes) to afford a red-brown solid (6.86 g, 87%). $^1$H NMR (300 MHz, CDCl$_3$): δ 6.87 (d, 1H), 6.81 (d, 1H), 3.85 (s, 3H), 2.16 (s, 3H).

Example 17

4-Bromo-2-methoxy-6-methyl benzamide

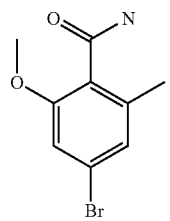

4-Bromo-2-methoxy-6-methyl benzonitrile (7.3 g, 32.4 mmol) was stirred in MeOH (100 mL) and 5N NaOH (100 mL) at 100° C. for 12 hours. The reaction was cooled to room temperature and the methanol was removed under reduced pressure. The reaction mixture was extracted with CH$_2$Cl$_2$ and the solvent was removed under reduced pressure to yield the product (7.13 g, 90%). $^1$H NMR (300 MHz, CDCl$_3$): δ 7.03 (d, 1H), 6.94 (d, 1H), 5.83 (br s, 2H), 3.85 (s, 3H), 2.39 (s, 3H).

Example 18

4-Bromo-2,6-dimethyl-benzamide

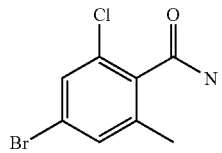

4-Bromo-2-chloro-6-methyl-benzonitrile (1.65 g, 7.16 mmol) was dissolved in methanol (20 mL) and 6M NaOH (20 mL) was added. The mixture was heated to reflux for seventeen hours. After cooling, the reaction was partitioned between diethyl ether and water. The organic phase was washed with water and brine, dried over magnesium sulfate, filtered and concentrated. Trituration with 10% EtOAc/Hexanes provided the title compound as a brick coloured solid (1.35 g, 76%). $^1$H NMR CDCl$_3$: δ 7.41 (s, 1H), 7.29 (s, 1H), 6.33 (br s, 1H), 5.90 (br s, 1H), 2.37 (s, 3H).

Example 19

2-Bromomethyl-4-methoxybenzoic acid methyl ester

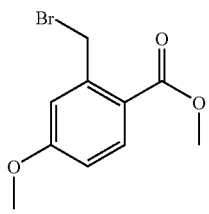

4-Fluoro-2-methyl-benzoic acid methyl ester (600 mg, 3.6 mmol), N-bromosuccinimide (635 mg, 3.6 mmol) and benzoyl peroxide (43 mg, 1.79 mmol) in $CCl_4$ (15 mL) was stirred at 90° C. for 3 hours. The reaction was cooled to room temperature, filtered, washed with $CCl_4$ and the solvent was removed under reduced pressure to provide a white solid. $^1$H NMR (300 MHz, $CDCl_3$): δ 8.01 (d, 1H), 6.99 (d, 1H), 6.88 (dd, 1H), 4.98 (s, 2H), 3.93 (s, 3H), 3.89 (s, 3H).

The following compounds were made in a similar fashion:

| Example | Structure | Name | Yield | $^1$H NMR |
|---|---|---|---|---|
| 20 | 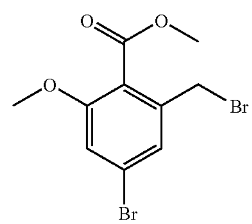 | 4-Bromo-2-bromomethyl-6-methoxybenzoic acid methyl ester | 3.74 g yellow oil | 7.20 (d, 1H), 7.05 (d, 1H), 4.44 (s, 2H), 3.96 (s, 3H), 3.86 (s, 3H) |
| 21 | 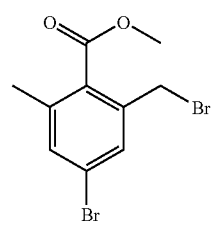 | 4-Bromo-2-bromomethyl-6-methylbenzoic methyl ester | 1.87 g yellow oil | 7.36 (d, 2H), 4.51 (s, 2H), 3.98 (s, 3H), 2.35 (s, 3H) |
| 22 | 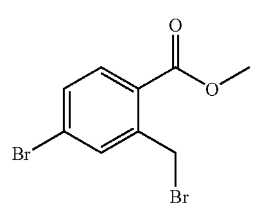 | 4-Bromo-2-bromomethyl-benzoic acid methyl ester | 3.70 g (55%) colourless solid | 7.87 (d, 1H), 7.65 (s, 1H), 7.53 (d of d, 1H), 4.92 (s, 2H), 3.96 (s, 3H) |
| 23 | 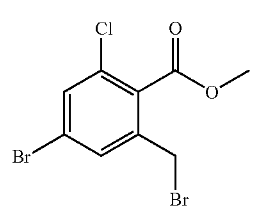 | 4-Bromo-2-bromomethyl-6-chloro-benzoic acid methyl ester | 2.06 g yellow oil | N/A |

Example K1

4-(Pyridin-3-yloxy)benzonitrile

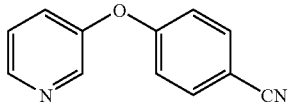

To a solution of 3-hydroxypyridine (2.1 g, 0.02 mmol) in NMP (20 mL) were added cesium carbonate (7.2 g, 0.02 mmol), 4-bromobenzonitrile (2.0 g, 0.01 mmol), 2,2,6,6-tetramethyl-3,5-heptanedione (0.23 mL, 0.001 mmol) and copper chloride (0.54 g, 0.005 mmol) at room temperature. The suspension was stirred at 120° C. for 6.5 hours. The reaction was cooled to room temperature and diluted with EtOAc (75 mL). The suspension was filtered and the filtrate washed with $H_2O$ (4×100 mL). Combined aqueous washes were extracted once with EtOAc (100 mL). Combined organic layer was washed with brine, dried over anhydrous $Na_2SO_4$, filtered and concentrated under reduced pressure. The product was purified by column chromatography (10-20% acetone in hexanes) to provide the title compound as an orange oil (1.53 g, 71%). $^1$H NMR (300 MHz, $CDCl_3$): δ 8.45-8.60 (m, 2H), 7.67 (d, 2H), 7.28-7.42 (m, 2H), 7.07 (d, 2H).

The following compounds were made in a similar fashion:

| Example | Structure | Name | Yield | $^1$H NMR |
|---|---|---|---|---|
| K2 | 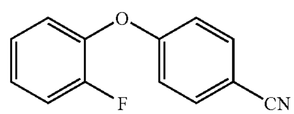 | 4-(2-Fluorophenoxy)-benzonitrile | 1.49 g (63%), yellow oil | 7.61 (d, 2H), 7.16-7.26 (m, 4H), 7.00 (d, 2H). |
| K3 | 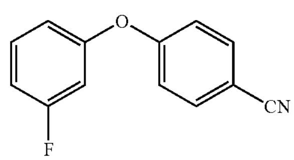 | 4-(3-Fluorophenoxy)-benzonitrile | 1.67 g (71%), white solid | 7.67 (d, 2H), 7.30-7.45 (m, 1H), 7.08 (d, 2H), 6.90-7.00 (m, 1H), 6.75-6.90 (m, 2H). |

Example K4

4-(Pyridin-3-yloxy)benzylamine hydrochloride

To a suspension of $LiAlH_4$ (0.46 g, 11.6 mmol) in THF (24 mL) at 0° C., was added a solution of 4-(pyridin-3-yloxy)benzonitrile in THF (13 mL) dropwise. The suspension was stirred at room temperature for 2 hours. The reaction was cooled to 0° C. and $Na_2SO_4 \cdot 10H_2O$ was added in portions until foaming stopped. The suspension was heated at 60° C. for 10 minutes, cooled to room temperature and filtered through Celite. The filtrate was cooled to 0° C. and 1M HCl in $Et_2O$ was added. The cloudy solution was concentrated under reduced pressure to provide the title compound as an orange solid (2.32 g, quantitative). $^1$H NMR (300 MHz, $CDCl_3$): δ 8.75 (d, 1H), 8.65 (d, 1H), 8.23 (dd, 1H), 8.03-8.10 (m, 1H), 7.65 (d, 2H), 7.36 (d, 2H), 4.02 (s, 2H).

The following compounds were made in a similar fashion:

| Example | Structure | Name | Yield | $^1$H NMR |
|---|---|---|---|---|
| K5 | 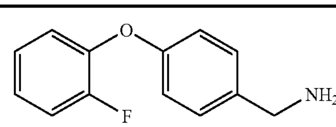 | 4-(2-Fluorophenoxy)-benzylamine | 1.45 g (quantitative), yellow oil | 7.29 (d, 2H), 7.00-7.20 (m, 4H), 6.97 (d, 2H), 3.87 (s, 2H), 1.52 (bs, 2H). |

| Example | Structure | Name | Yield | ¹H NMR |
|---|---|---|---|---|
| K6 | 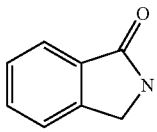 | 4-(3-Fluorophenoxy)-benzylamine | 1.72 g (quantitative), pale yellow oil | 7.34 (d, 2H), 7.26-7.32 (m, 1H), 7.03 (d, 2H), 6.76-6.80 (m, 2H), 6.68-6.71 (m, 1H), 3.90 (s, 2H), 1.45 (bs, 2H). |

Method 1

Step 1: Reduction of Phthalimide

Example 24

2,3-Dihydro-isoindol-1-one

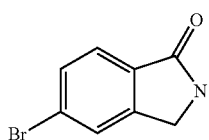

To a suspension of phthalimide (14.7 g, 100.0 mmol) in AcOH (150 mL) was added Sn⁰ (29.7 g, 250.0 mmol) and concentrated HCl (70 mL). The mixture was heated to reflux for two hours. The hot mixture was filtered and concentrated. The residue was taken up in $CH_2Cl_2$ and washed four times with 1M HCl, until no more precipitate was observed when saturated $NaHCO_3$ was added to the organic phase. The organic layer was washed once with saturated $NaHCO_3$, dried over $MgSO_4$, filtered and concentrated to provide the title compound as a pale yellow solid (7.00 g, 53%). ¹H NMR (300 MHz, $CDCl_3$): δ 8.08 (d of d, 1H), 7.52 (m, 3H), 4.50 (s, 2H).

Example 25

5-Bromo-2,3-dihydro-isoindol-1-one

4-Bromo-2-bromomethyl-benzoic acid methyl ester (3.70 g) was suspended in 2M $NH_3$ in MeOH (36 mL) and concentrated ammonium hydroxide (12 mL) for eighteen hours. The solid product was filtered to provide the title compound as a colourless solid (2.30 g, 90%). ¹H NMR (300M, $CDCl_3$): δ 7.68 (m, 3H), 4.44 (s, 2H).

The following compounds were made in the same fashion:

| Example | Structure | Name | Yield | ¹H NMR |
|---|---|---|---|---|
| J46 | 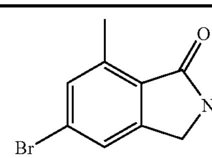 | 5-Bromo-7-methyl-2,3-dihydro-isoindol-1-one | 2.04 g 46% beige solid | 7.45 (s, 1H), 7.39 (s, 1H), 6.71, br s, 1H), 4.39 (s, 2H), 2.71, (s, 3H) |

Example 26

5-Methoxy-2,3-dihydro-isoindol-1-one

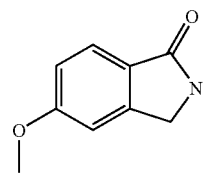

2-Bromomethyl-4-methoxy-benzoic acid methyl ester, 2% ammonia in MeOH (4 mL) and $NH_4OH$ (1.5 mL) were stirred for at 18 hours at room temperature. The reaction was partitioned between $CH_2Cl_2$ and water and the organic layer was washed with brine and dried over anhydrous $Na_2SO_4$. The solvent was removed under reduced pressure to afford a white solid (151 mg). ¹H NMR (300 MHz, $CDCl_3$): δ 7.80 (d, 2H), 7.02 (dd, 1H), 6.97 (s, 1H), 4.44 (s, 2H), 3.90 (s, 3H).

Example 27

2-Prop-2-ynyl-2,3-dihydro-isoindol-1-one

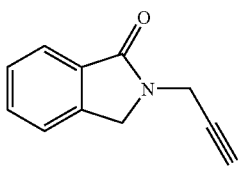

To 2,3-dihydro-isoindol-1-one (250.0 mg, 1.85 mmol) in acetonitrile (9 mL) was added propargyl bromide (308.6 uL, 2.77 mmol) and cesium carbonate (2.4 g, 7.39 mmol) and the mixture was allowed to stir at 80° C. for two hours. An aqueous workup was done to provide the title compound (303.3 mg, 96%).

Example 28

2-(4-Bromomethylbenzyl)-2,3-dihydroisoindol-1-one

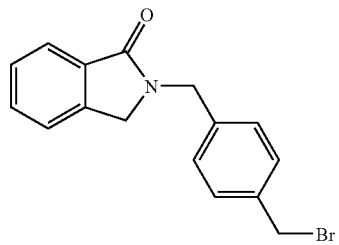

2,3-Dihydroisoindol-1-one (350 mg, 2.63 mmol), 1,4-bis-bromomethylbenzene (3.78 g, 14.3 mmol), $Cs_2CO_3$ (3.60 g, 11.1 mmol), in acetonitrile (20 mL), was stirred together at room temperature for 5 hours and 80° C. for 20 minutes. The reaction was partitioned between ethyl acetate and water and the organic layer was washed with brine and dried over anhydrous $Na_2SO_4$. The solvent was removed under reduced pressure and the product was purified by column chromatography (30% EtOAc/Hexanes) to afford a white solid (410 mg, 49%).
$^1$H NMR (300 MHz, $CDCl_3$): δ 7.92 (d, 1H), 7.49-7.55 (m, 2H), 7.37-7.42 (m, 3H), 7.28-7.31 (m, 2H), 4.82 (s, 2.03), 4.49 (s, 2H), 4.31 (s, 2H).

The following compounds were made in the same fashion:

| Example | Structure | Name | Yield | $^1$H NMR |
|---|---|---|---|---|
| J47 | 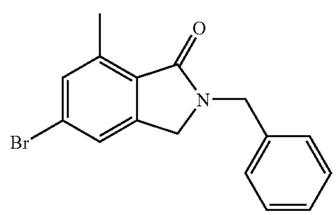 | 2-Benzyl-5-bromo-7-methyl-2,3-dihydro-isoindol-1-one | 89 mg 64% yellow oil | 7.37-7.29 (m, 6H), 4.77 (s, 2 h), 4.20 (s, 2H), 2.75 (s, 3H) |
| J48 | 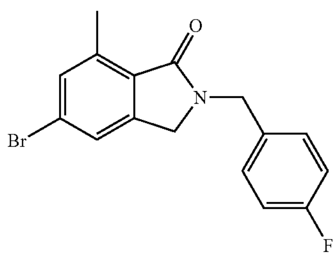 | 5-Bromo-2-(4-fluoro-benzyl)-7-methyl-2,3-dihydro-isoindol-1-one | 69 mg 47% yellow solid | 7.36 (d, 2H), 7.30-7.26 (m, 2H), 7.03 (dd, 2H), 4.73 (s, 2H), 4.19 (s, 2H), 2.74 (s, 3H) |
| J49 | 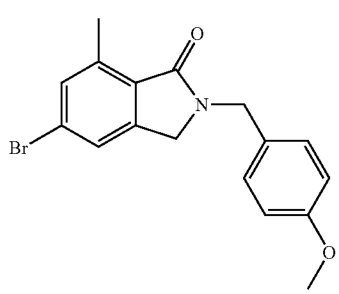 | 5-Bromo-2-(4-methoxy-benzyl)-7-methyl-2,3-dihydro-isoindol-1-one | 89 mg 58% yellow oil | 7.34 (d, 2H), 7.23 (dd, 2H), 6.87 (dd, 2H), 4.69 (s, 2H), 4.17 (s, 2H), 3.81 (s, 3H), 2.74 (s, 3H) |

-continued

| Example | Structure | Name | Yield | $^1$H NMR |
|---|---|---|---|---|
| J51 | 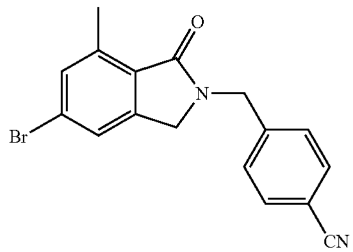 | 4-[(5-bromo-7-methyl-1-oxo-1,3-dihydro-2H-isoindol-2-yl)methyl]benzonitrile | 64 mg 43% yellow solid | 7.65 (d, 2H), 7.42-7.37 (m, 4H), 4.81 (s, 2H), 4.23 (s, 2H), 2.73 (s, 3H), |
| J52 | 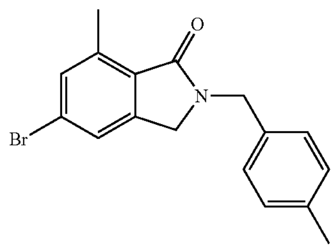 | 5-Bromo-7-methyl-2-(4-methyl-benzyl)-2,3-dihydro-isoindol-1-one | 115 mg 83% yellow oil | 7.34 (d, 2H), 7.21-7.14 (m, 4H), 4.72 (s, 2H), 4.18 (s, 2H), 2.75 (s, 3H), 2.34 (s, 3H) |

Example 29

5-Bromo-7-methyl-2-(4-phenoxybenzyl)-2,3-dihydroisoindol-1-one

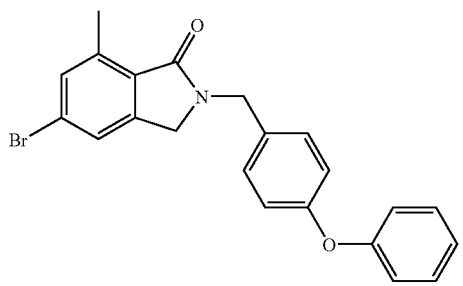

4-Bromo-2-bromomethyl-6-methylbenzoic acid methyl ester (762 mg, 2.37 mmol), 4-phenoxy benzylamine (0.543 mL, 3.56 mmol) and $K_2CO_3$ (981 mg, 7.10 mmol) were stirred in toluene (10 mL) at 95° C. for 12 hours. The reaction was partitioned between ethyl acetate and water and the organic layer was washed with brine and dried over anhydrous $Na_2$-$SO_4$. The solvent was removed under reduced pressure and the product was purified by column chromatography (10-25% EtOAc/Hexanes) to afford a yellow oil (650 mg). $^1$H NMR (300 MHz, CDCl$_3$): δ 7.35-7.38 (m, 4H), 7.32 (s, 1H), 7.26-7.29 (m, 1H), 7.15 (t, 1H), 6.99 (t, 4H), 4.74 (s, 2H), 4.23 (s, 2H), 2.75 (s, 3H).

The following compounds were made in the same fashion:

| Example | Structure | Name | Yield | $^1$H NMR | GTPγS EC50 |
|---|---|---|---|---|---|
| 30 | 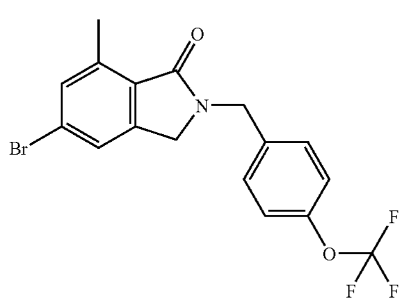 | 5-Bromo-7-methyl-2-(4-trifluoromethoxy-benzyl)-2,3-dihydro-isoindol-1-one | Yellow oil | 7.33-7.39 (m, 4H), 7.20 (d, 2H), 4.77 (s, 2H), 4.15 (s, 2H), 2.75 (s, 3H) | 0.37 |

-continued

| Example | Structure | Name | Yield | ¹H NMR | GTPγS EC50 |
|---|---|---|---|---|---|
| 31 | 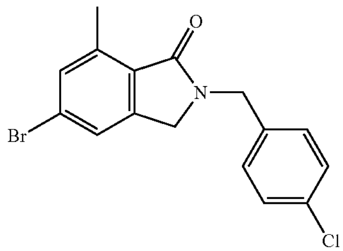 | 5-Bromo-2-(4-chlorobenzyl)-7-methyl-2,3-dihydroisoindol-1-one | 428 mg (42%) yellow solid | 7.23-7.39 (m, 6H), 4.73 (s, 2H), 4.20 (s, 2H), 2.74 (s, 3H) | 0.71 |
| 32 | 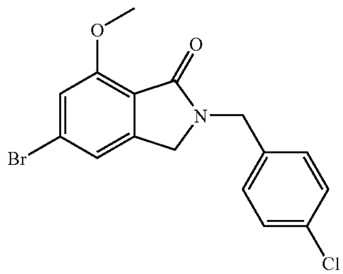 | 5-Bromo-2-(4-chloro-benzyl)-7-methoxy-2,3-dihydro-isoindol-1-one | 234 mg (32%) brown solid | 7.23-7.31 (m, 4H), 7.12 (s, 1H), 7.05 (s, 1H), 4.70 (s, 2H), 4.19 (s, 2H), 3.98 (s, 3H) | 2.80 |
| 33 | 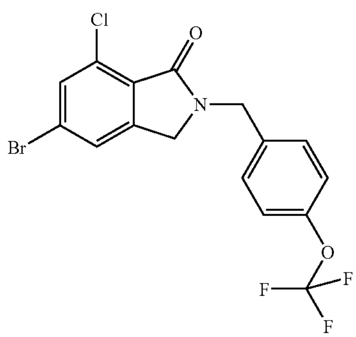 | 5-Bromo-7-chloro-2-(4-trifluoromethoxy-benzyl)-2,3-dihydro-isoindol-1-one | 0.50 g | 7.61 (s, 1H), 7.47 (s, 1H), 7.36 (d, 2H), 7.22 (d, 2H), 4.78 (s, 2H), 4.25 (s, 2H) | 0.14 |
| 34 | 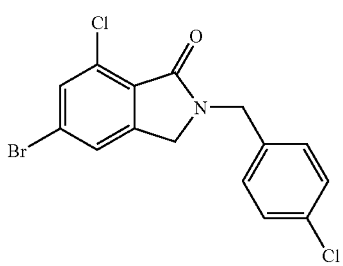 | 5-Bromo-7-chloro-2-(4-chloro-benzyl)-2,3-dihydro-isoindol-1-one | 0.42 g, 52% | 7.61 (s, 1H), 7.46 (s, 1H), 7.33 (d, 2H), 7.27 (d, 2H), 4.75 (s, 2H), 4.23 (s, 2H) | 0.47 |
| J50 | 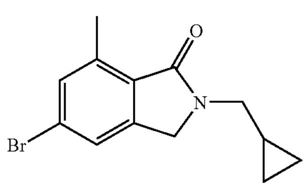 | 5-Bromo-2-cyclopropyl-methyl-7-methyl-2,3-dihydro-isoindol-1-one | 171 mg 49% colorless solid | 7.40 (s, 1H), 7.34 (s, 1H), 4.41 (s, 2H), 3.43 (d, 2H), 2.69 (s, 3H), 1.05-1.00 (m, 1H), 0.60-0.57 (m, 2H), 0.33-0.31 (m, 2H) | |

-continued

| Example | Structure | Name | Yield | ¹H NMR | GTPγS EC50 |
|---|---|---|---|---|---|
| J59 | 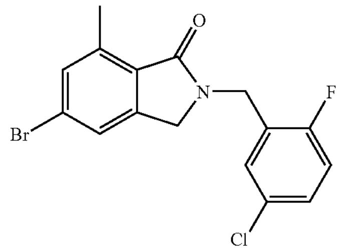 | 5-Bromo-2-(5-chloro-2-fluoro-benzyl)-7-methyl-2,3-dihydro-isoindol-1-one | 139 mg 41% colorless solid | 7.37 (d, 2H), 7.37-7.30 (m, 1H), 7.27-7.22 (m, 1H), 7.04 (d, 1H), 4.78 (s, 2H), 4.28 (s, 2H), 2.72 (s, 3H) | |
| J60 | 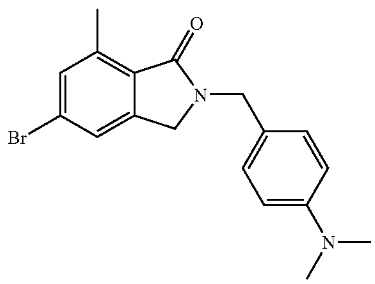 | 5-Bromo-2-(4-dimethylamino-benzyl)-7-methyl-2,3-dihydro-isoindol-1-one | 135 mg 40% orange solid | 7.35 (d, 2H), 7.19 (d, 2H), 6.70 (d, 2H), 4.66 (s, 2H), 4.16 (s, 2H), 2.95 (s, 6H), 2.74 (s, 3H) | |
| J61 | 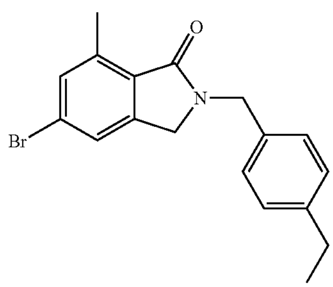 | 5-Bromo-2-(4-ethyl-benzyl)-7-methyl-2,3-dihydro-isoindol-1-one | 152 mg 48% yellow oil | 7.34 (d, 2H), 7.24-7.16 (m, 4H), 4.73 (s, 2H), 4.19 (s, 2H), 2.75 (s, 3H), 2.65 (q, 2H), 1.23 (t, 3H) | |
| J65 | 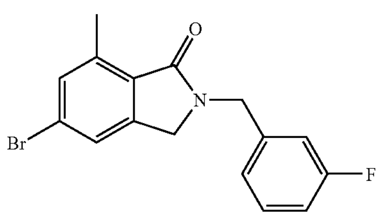 | 5-Bromo-2-(3-fluoro-benzyl)-7-methyl-2,3-dihydro-isoindol-1-one | 113 mg 36% colorless oil | 7.38 (dd, 2H), 7.31 (d, 1H), 7.06 (d, 1H), 7.00 (dd, 2H), 4.76 (s, 2H), 4.22 (s, 2H), 2.74 (s, 3H) | |
| J66 | 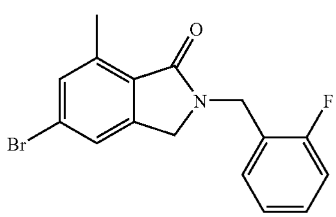 | 5-Bromo-2-(2-fluoro-benzyl)-7-methyl-2,3-dihydro-isoindol-1-one | 109 mg 35% colorless solid | 7.45 (s, 1H), 7.36-7.28 (m, 3H), 7.12 (m, 2H), 4.82 (s, 2H), 4.27 (s, 2H), 2.72 (s, 2H) | |
| J67 | 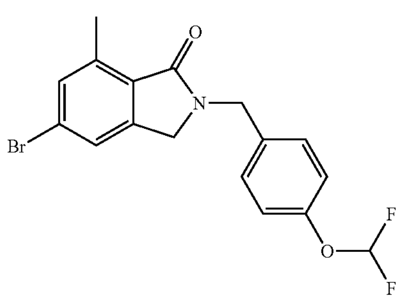 | 5-Bromo-2-(4-difluoromethoxy-benzyl)-7-methyl-2,3-dihydro-isoindol-1-one | 100 mg 28% yellow oil | 7.38-7.29 (m, 4H), 7.10 (dd, 2H), 6.75-6.62 (br t, 1H), 4.74 (s, 2H), 4.20 (s, 2H), 2.74 (s, 3H) | |

-continued

| Example | Structure | Name | Yield | ¹H NMR | GTPγS EC50 |
|---|---|---|---|---|---|
| J68 | 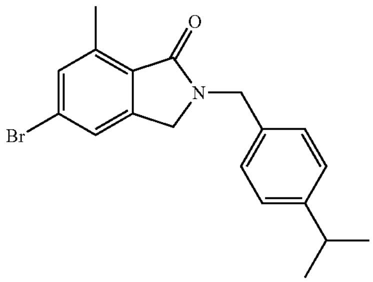 | 5-Bromo-2-(4-isopropyl-benzyl)-7-methyl-2,3-dihydro-isoindol-1-one | 143 mg 42% yellow oil | 7.44 (s, 1H), 7.35 (d, 2H), 7.23-7.19 (m, 3H), 4.73 (s, 2H), 4.19 (s, 2H), 2.92-2.89 (m, 1H), 2.88 (s, 3H), 1.24 (d, 6H) | |
| J73 | 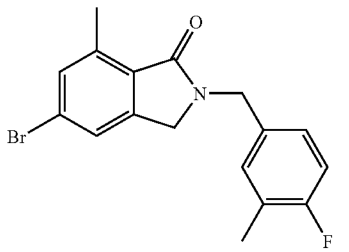 | 5-Bromo-2-(4-fluoro-3-methyl-benzyl)-7-methyl-2,3-dihydro-isoindol-1-one | 105 mg 32% colorless solid | 7.35 (d, 2H), 7.13-7.07 (m, 2H), 6.95 (t, 1H), 4.68 (s, 2H), 4.18 (s, 2H), 2.73 (s, 3H), 2.25 (s, 3H) | |
| J74 | 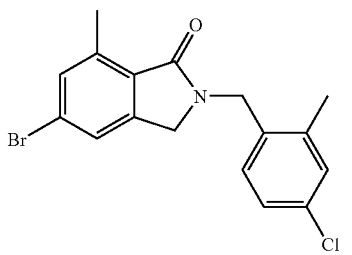 | 5-Bromo-2-(4-chloro-2-methyl-benzyl)-7-methyl-2,3-dihydro-isoindol-1-one | 133 mg 39% yellow oil | 7.35 (d, 2H), 7.19-7.01 (m, 3H), 4.28 (s, 2H), 4.11 (s, 2H), 2.37 (s, 3H), 2.33 (s, 3H) | |
| J75 | 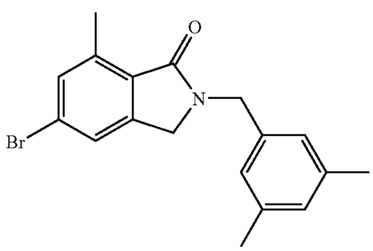 | 5-Bromo-2-(3,5-dimethyl-benzyl)-7-methyl-2,3-dihydro-isoindol-1-one | 137 mg 43% yellow oil | 7.44 (s, 1H), 7.33 (d, 2H), 6.92 (d, 2H), 4.68 (s, 2H), 4.18 (s, 2H), 2.74 (s, 3H), 2.30 (s, 6H) | |
| J80 | Chiral | 5-bromo-2-[(1R)-1-(4-chlorophenyl)ethyl]-7-methylisoindolin-1-one | 147 mg 43% yellow oil | 7.35-7.27 (m, 6H), 5.73 (q, 1H), 4.26 (d, 1H), 3.92 (d, 1H), 2.72 (s, 3H), 1.66 (d, 3H) | |
| J81 | Chiral | 5-bromo-2-[(1S)-1-(4-chlorophenyl)ethyl]-7-methylisoindolin-1-one | 144 mg 42% yellow oil | 7.36-7.30 (m, 6H), 5.73 (q, 1H), 4.26 (d, 1H), 3.93 (d, 1H), 2.72 (s, 3H), 1.66 (d, 3H) | |

| Example | Structure | Name | Yield | $^1$H NMR | GTPγS EC50 |
|---|---|---|---|---|---|
| J84 | Chiral | 5-bromo-2-[(1R)-1-cyclohexylethyl]-7-methylisoindolin-1-one | 116 mg 37% yellow solid | 7.41 (s, 1H), 7.40 (s, 1H), 4.22 (q, 2H), 4.17 (q, 1H), 2.72 (s, 3H), 1.82-1.76 (m, 2H), 1.68-1.64 (m, 2H), 1.46 (m, 2H), 1.26 (d, 3H), 1.18-1.03 (m, 5H) | |
| J85 | Chiral | 5-bromo-2-[(1S)-1-cyclohexylethyl]-7-methylisoindolin-1-one | 112 mg 36% colorless solid | 7.41 (s, 1H), 7.40 (s, 1H), 4.22 (q, 2H), 4.17 (q, 1H), 2.71 (s, 3H), 1.82-1.77 (m, 2H), 1.67-1.65 (m, 2H), 1.46 (m, 2H), 1.26 (d, 3H), 1.17-1.03 (m, 5H) | |
| J86 | Chiral | 5-bromo-2-[(1S)-1-(4-fluorophenyl)ethyl]-7-methylisoindolin-1-one | 116 mg 38% yellow oil | 7.36-7.31 (m, 4H), 7.07-7.01 (m, 2H), 5.74 (q, 1H), 4.26 (d, 1H), 3.92 (d, 1H), 2.73 (s, 3H), 1.67 (d, 3H) | |
| J90 | Chiral | 5-bromo-2-[(1R)-1-(4-fluorophenyl)ethyl]-7-methylisoindolin-1-one | 123 mg 38% yellow oil | 7.36-7.31 (m, 4H), 7.07-7.01 (m, 2H), 5.74 (q, 1H), 4.26 (d, 1H), 3.92 (d, 1H), 2.73 (s, 3H), 1.67 (d, 3H) | |
| M6 | 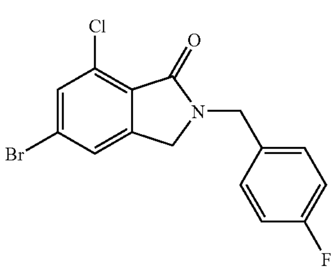 | 5-bromo-7-chloro-2-(4-fluorobenzyl)-2,3-dihydro-isoindol-1-one | 244 mg, 58.9%, yellow oil | 7.53 (s, 1H), 7.42 (s, 1H), 7.25-7.29 (m, 2H), 6.98-7.04 (2H), 4.70 (s, 2H), 4.20 (s, 2H) | |
| M15 | 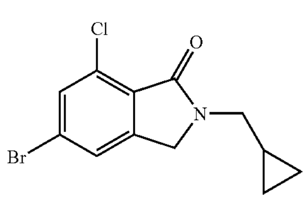 | 5-bromo-7-chloro-2-cyclopropyl-methyl-2,3-dihydro-isoindol-1-one | 237 mg, 67.4%, yellow oil | 7.48 (d, 2H), 4.40 (s, 2H), 3.40 (d, 2H), 0.97-1.02 (m, 1H), 0.52-0.58 (m, 2 h), 0.27-0.32 (m, 2H) | |

| Example | Structure | Name | Yield | ¹H NMR | GTPγS EC50 |
|---|---|---|---|---|---|
| M29 | 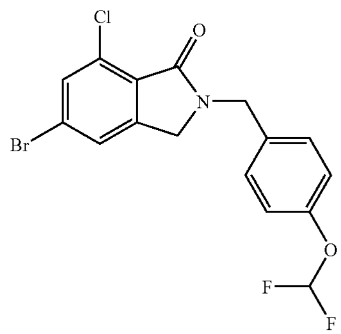 | 5-bromo-7-chloro-2-(4-difluoromethoxy-benzyl)2,3-dihydro-isoindol-1-one | 694.6 mg, 59.1%, yellow foam | 7.52 (s, 1H), 7.41-7.42 (m, 1H), 7.26-7.33 (m, 2H), 6.99-7.08 (m, 2H), 6.25-6.74 (t, 1H), 4.70 (s, 2H), 4.21 (s, 2H) | |
| M34 | 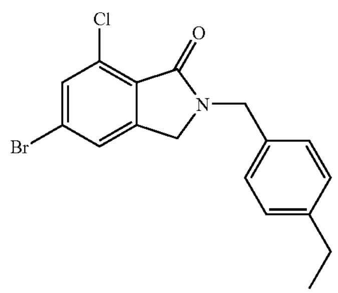 | 5-Bromo-7-chloro-2-(4-ethyl-benzyl)-2,3-dihydro-isoindol-1-one | 358.2 mg, 42%, yellow solid | 7.51-7.52 (m, 1H), 7.39-7.40 (m, 1H), 7.15-7.24 (m, 4H), 4.71 (s, 2H), 4.20 (s, 2H), 2.62 (q, 2H), 1.21 (t, 3H) | |
| K6 | 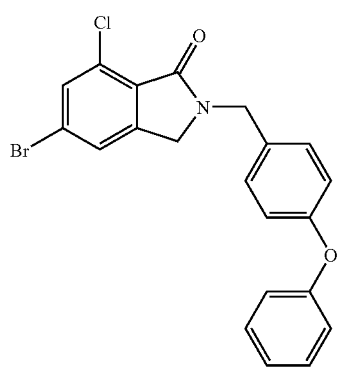 | 5-Bromo-7-chloro-2-(4-phenoxybenzyl)-2,3-dihydro-isoindol-1-one | 2.6 g, 50%, yellow solid | 7.60 (d, 1H), 7.46 (d, 1H), 7.28-7.38 (m, 4H), 7.13 (t, 1H), 7.00 (t, 4H), 4.77 (s, 2H), 4.25 (s, 2H). | |
| K7 | 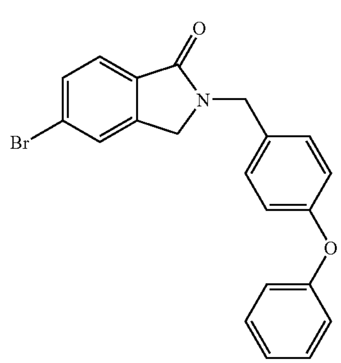 | 5-Bromo-2-(4-phenoxybenzyl)-2,3-dihydro-isoindol-1-one | 4.6 g, 52% pale yellow solid | 7.77 (d, 1H), 7.58-7.65 (m, 2H), 7.33-7.35 (m, 2H), 7.28 (d, 2H), 7.13 (t, 1H), 7.00 (t, 4H), 4.78 (s, 2H), 4.28 (s, 2H). | |

-continued

| Example | Structure | Name | Yield | ¹H NMR | GTPγS EC50 |
|---|---|---|---|---|---|
| K8 | 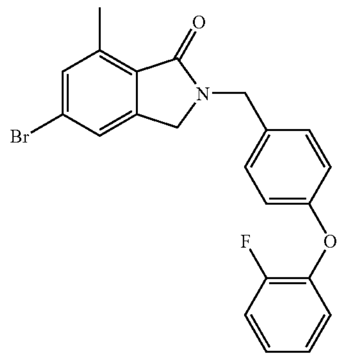 | 5-Bromo-2-[4-(2-fluorophenoxy)benzyl]-7-methyl-2,3-dihydro-isoindol-1-one | 0.80 g, 42%, yellow oil | 7.37 (d, 2H), 7.27 (d, 2H), 7.02-7.22 (m, 4H), 6.95 (d, 2H), 4.73 (s, 2H), 4.21 (s, 2H), 2.74 (s, 3H). | |
| K9 | 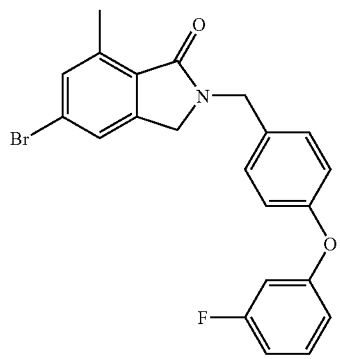 | 5-Bromo-2-[4-(3-fluorophenoxy)benzyl]-7-methyl-2,3-dihydro-isoindol-1-one | 0.58 g, 26%, yellow oil | 7.38 (d, 2H), 7.27-7.33 (m, 3H), 7.02 (d, 2H), 6.75-6.85 (m, 2H), 6.66-6.72 (m, 1H), 4.76 (s, 2H), 4.24 (s, 2H), 2.75 (s, 3H). | |
| K10 | 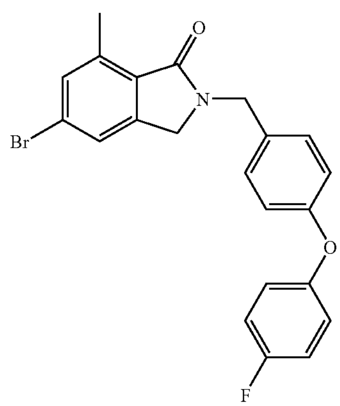 | 5-Bromo-2-[4-(4-fluorophenoxy)benzyl]-7-methyl-2,3-dihydro-isoindol-1-one | 0.38 g, 34%, yellow oil | 7.37 (d, 2H), 7.27 (d, 2H), 6.90-7.10 (m, 6H), 4.73 (s, 2H), 4.22 (s, 2H), 2.75 (s, 3H). | |
| K11 | 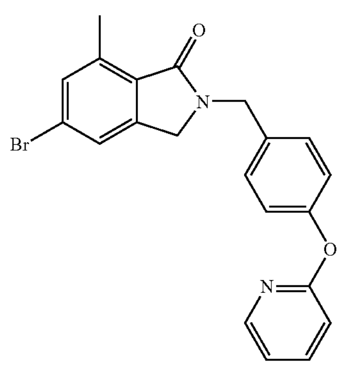 | 5-Bromo-7-methyl-2-[4-(pyridin-2-yloxy)benzyl]-2,3-dihydro-isoindol-1-one | 0.42 g, 40%, yellow oil | 8.17-8.22 (m, 1H), 7.67-7.75 (m, 1H), 7.33-7.39 (m, 4H), 7.13 (d, 2H), 7.00-7.05 (m, 1H), 6.93 (d, 2H), 4.77 (s, 2H), 4.25 (s, 2H), 2.75 (s, 3H). | |

| Example | Structure | Name | Yield | $^1$H NMR | GTPγS EC50 |
|---|---|---|---|---|---|
| K12 | 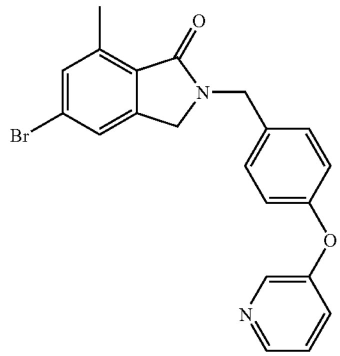 | 5-Bromo-7-methyl-2-[4-(pyridin-3-yloxy)benzyl]-2,3-dihydro-isoindol-1-one | 0.19 g, 9%, orange solid | 8.37-8.42 (m, 2H), 7.38 (d, 2H), 7.28-7.33 (m, 4H), 7.01 (d, 2H), 4.76 (s, 2H), 4.24 (s, 2H), 2.75 (s, 3H). | |
| I1 | 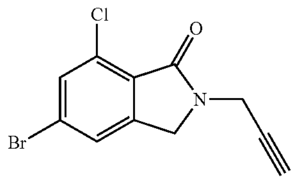 | 5-Bromo-7-chloro-2-prop-2-ynyl-2,3-dihydroisoindol-1-one | 1.69 g, 52%, off-white solid | 7.60 (s, 1H), 7.55 (s, 1H), 4.45 (s, 4H), 2.32 (s, 1H). | |

Example 35

7-Methyl-1-oxo-2-(4-trifluoromethoxy-benzyl)-2,3-dihydro-1H-isoindole-5-carbonitrile

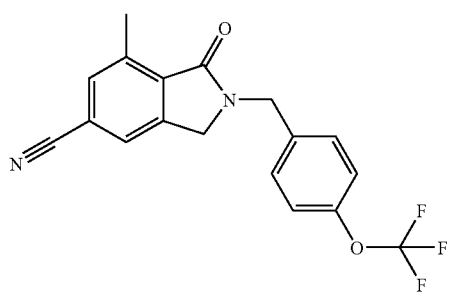

Method A

5-Bromo-7-methyl-2-(4-trifluoromethoxy-benzyl)-2,3-dihydro-isoindol-1-one (500 mg, 1.25 mmol) was set stirring in DMF (15 mL) under argon and Zn(CN)$_2$ (190 mg, 1.63 mmol) and Pd(PPh$_3$)$_4$ (289 mg, 0.25 mmol) were added. The reaction was stirred at 80° C. for 1.5 hours. The reaction was partitioned between ethyl acetate and water and the organic layer was washed with brine and dried over anhydrous Na$_2$SO$_4$. The solvent was removed under reduced pressure and the product was purified by column chromatography (40% EtOAc/Hexanes) to afford a yellow solid (356 mg, 82%). $^1$H NMR (300 MHz, CDCl$_3$): δ 7.53 (s, 2H), 7.36 (d, 2H), 7.22 (s, 2H), 4.80 (s, 2H), 4.30 (s, 2H), 2.81 (s, 3H).

The following compounds were made in the same fashion:

| Example | Structure | Name | Yield | $^1$H NMR |
|---|---|---|---|---|
| J125 | 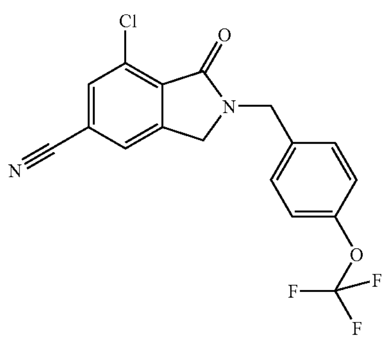 | 7-Chloro-1-oxo-2-(4-trifluoromethoxy-benzyl)-2,3-dihydro-1H-isoindole-5-carbonitrile | 2.06 g yellow solid 95% | 7.62 (d, 2H), 7.34 (d, 2H), 7.15 (d, 2H), 4.77 (s, 2H), 4.33 (s, 2H) |

| Example | Structure | Name | Yield | ¹H NMR |
|---------|-----------|------|-------|--------|
| M41 | 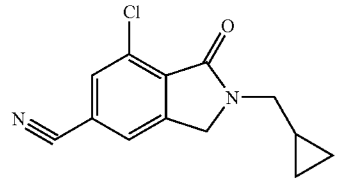 | 7-Chloro-2-cyclopropylmethyl-1-oxo-2,3-dihydro-1H-isoindole-5-carbonitrile | 142.6 mg, 49.4%, yellow solid, | 7.66 (d, 2H), 4.54 (s, 2H), 3.50 (d, 2H), 1.04-1.09 (m, 1H), 0.60-0.66 (m, 2H), 0.36-0.40 (m, 2H) |

Method B

This reaction was run in three equal batches. Three portions of 5-bromo-7-methyl-2-(4-trifluoromethoxybenzyl)-2,3-dihydroisoindol-1-one (3×0.66 g, net 5 mmol) were mixed with nickel bromide (3×0.43 g, net 6 mmol) and sodium cyanide (3×0.1 g, net 6 mmol) in N-methylpyrrolidine (NMP) (3×5 mL). The mixtures were microwaved for 15 minutes each at 200° C. The reactions were monitored by HPLC and residual starting material was found. The reactions were microwaved an additional 5 minutes each at 200° C. HPLC analysis showed complete consumption of the starting 5-bromo-7-methyl-2-(4-trifluoromethoxybenzyl)-2,3-dihydroisoindol-1-one. The combined reactions were partitioned between ethyl acetate and water. The organic phase was washed five times with brine and evaporated. Obtained 1.9 g of material which was purified by chromatography on a 40 g silica gel cartridge eluting with methylene chloride to give 1.2 g (77% yield) of 5-carbonitrile-7-methyl-2-(4-trifluoromethoxybenzyl)-2,3-dihydroisoindole-1-one as a tan solid.

Example 36

5-Aminomethyl-7-methyl-2-(4-trifluoromethoxybenzyl)-2,3-dihydroisoindol-1-one

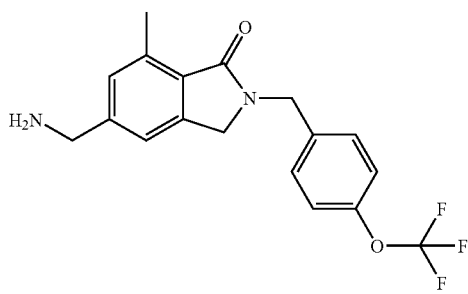

5-carbonitrile-7-methyl-2-(4-trifluoromethoxybenzyl)-2,3-dihydroisoindole-1-one (104 mg, 0.3 mmol) was dissolved in THF (10 mL), methanol (10 mL), and conc. Ammonium hydroxide (5 mL). Raney nickel was added and the mix was hydrogenated at 10 psig on Parr shaker for 5 hours. The catalyst was removed by vacuum filtration and the filtrate was evaporated. The residue was chromatographed on silica gel, eluting with a 0 to 10% gradient of methanol in methylene chloride, to give 90 mg (86% yield) of the title compound as a colorless oil. ¹H NMR (300.132 MHz, CDCl₃) δ 7.35-7.29 (m, 2H), 7.20-7.13 (m, 4H), 4.76 (s, 2H), 4.21 (s, 2H), 3.91 (s, 2H), 2.75 (s, 3H)

Example 37

5-Bromomethyl-7-methyl-2-(4-trifluoromethoxybenzyl)-2,3-dihydroisoindol-1-one

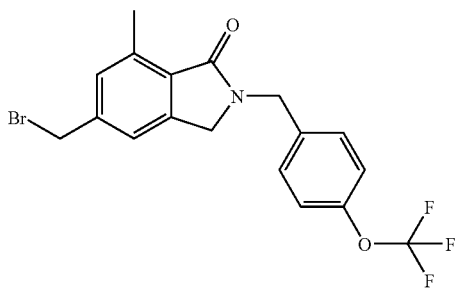

5-Aminomethyl-7-methyl-2-(4-trifluoromethoxybenzyl)-2,3-dihydroisoindol-1-one (0.5 g, 1.43 mmol) was dissolved in a solution of water (10 mL) and 48% HBr (1 mL). The solution was chilled in an ice bath. A solution of sodium nitrate (0.17 g, 2.4 mmol) in water (5 mL) was added dropwise. A white solid formed. The reaction was allowed to stand for 30 minutes, and then the water was decanted off. The solid was chromatographed on silica gel, eluting with methylene chloride, to give 0.42 g (70% yield) of the title compound as a white solid. ¹H NMR (300.132 MHz, CDCl₃) δ 7.23-7.15 (m, 4H), 7.35-7.30 (m, 2H), 4.76 (s, 2H), 4.48 (s, 2H), 4.22 (s, 2H), 2.75 (s, 3H)

Example 38

5-[(Benzylmethylamino)methyl]-7-methyl-2-(4-trifluoromethoxybenzyl)-2,3-dihydroisoindol-1-one

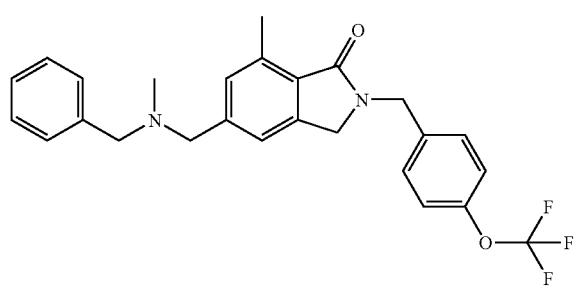

A solution of 5-bromomethyl-7-methyl-2-(4-trifluoromethoxybenzyl)-2,3-dihydroisoindol-1-one (50 mg, 0.12 mmol) in acetonitrile (3 mL) was added drop wise to N-methylbenzylamine (24 mg, 0.2 mmol) and diisopropylethylamine (0.17 mL, 1 mmol) in acetonitrile (5 mL). After 4 hours the reaction was evaporated. The residue was chromatographed on silica gel, eluting with 0 to 25% ethyl acetate in methylene chloride, to give 45 mg (83% yield) of 5-[(benzylmethylamino)methyl]-7-methyl-2-(4-trifluoromethoxybenzyl)-2,3-dihydroisoindol-1-one as a colorless oil. $^1$H NMR (300.132 MHz, CDCl$_3$) δ 7.37-7.28 (m, 6H), 7.25-7.14 (m, 5H), 4.75 (s, 2H), 4.21 (s, 2H), 3.53 (s, 2H), 3.52 (s, 2H), 2.74 (s, 3H), 2.18 (s, 3H).

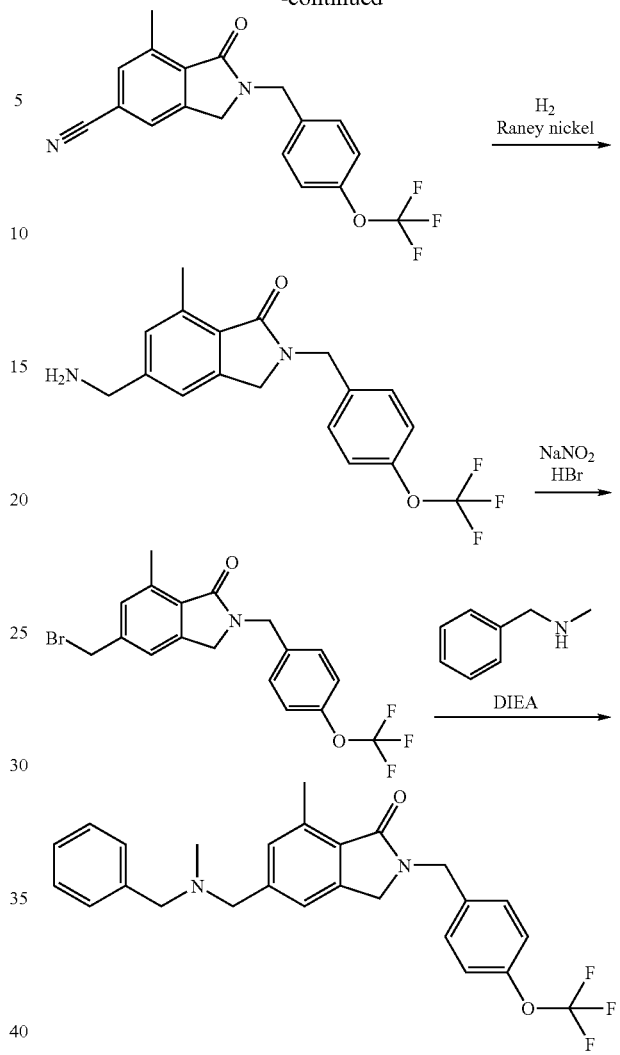

The compounds in the following table were synthesized in an analogous manner to the procedure according to Example 38, using the appropriate amine in the final synthetic step.

| Example | Structure | Name | Yield | NMR | GTPγS EC50 |
|---|---|---|---|---|---|
| 35 | 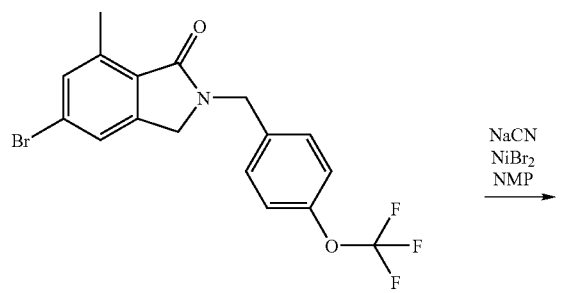 | 5-[(Benzylmethyl amino)-methyl]-7-methyl-2-(4-trifluoromethoxy-benzyl)-2,3-dihydro-isoindol-1-one | 45 mg (83%) colorless oil | 7.37-7.28 (m, 6H), 7.25-7.14 (m, 5H), 4.75 (s, 2H), 4.21 (s, 2H), 3.53 (s, 2H), 3.52 (s, 2H), 2.74 (s, 3H), 2.18 (s, 3H). | 0.07 |

-continued

| Example | Structure | Name | Yield | NMR | GTPγS EC50 |
|---|---|---|---|---|---|
| 39 | 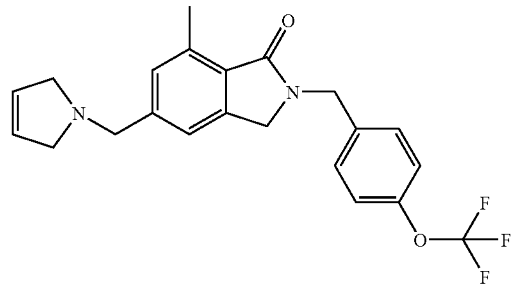 | 5-(2,5-Dihydro-pyrrol-1-ylmethyl)-7-methyl-2-(4-trifluoromethoxy-benzyl)-2,3-dihydro-isoindol-1-one | 37 mg (76%) liquid | 7.35 (s, 1H), 7.32 (s, 1H), 7.19 (dd, J = 12.5, 7.9 Hz, 4H), 5.79 (s, 2H), 4.76 (s, 2H), 4.20 (s, 2H), 3.84 (s, 2H), 3.49 (s, 4H), 2.74 (s, 3H) | 2.40 |
| 40 | 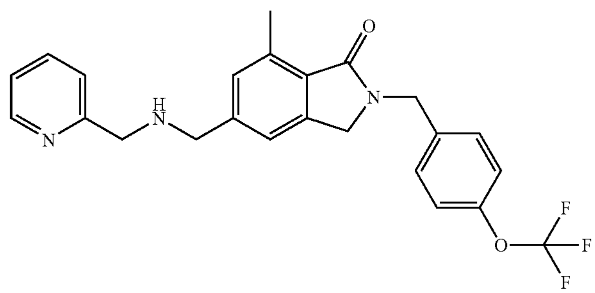 | 7-Methyl-5-{[(pyridine-2-ylmethyl)-amino]-methyl}-2-(4-trifluoromethoxy-benzyl)-2,3-dihydro-isoindol-1-one | 26 mg (49%) liquid | 8.56 (d, J = 4.7 Hz, 1H), 7.64 (td, J = 7.7, 1.8 Hz, 1H), 7.34-7.15 (m, 4H), 4.76 (s, 2H), 4.20 (s, 2H), 3.92 (s, 2H), 3.88 (s, 2H), 2.74 (s, 3H) | 1.45 |
| 41 | 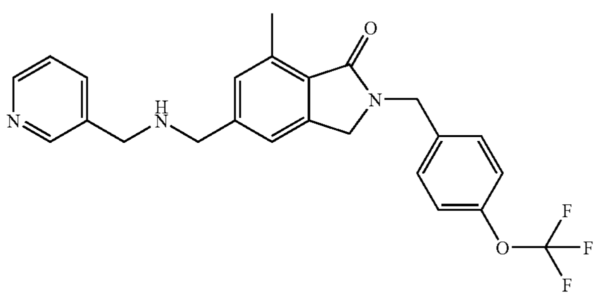 | 7-Methyl-5-{[(pyridine-3-ylmethyl)-amino]-methyl}-2-(4-trifluoromethoxy-benzyl)-2,3-dihydro-isoindol-1-one | 25 mg (47%) liquid | 8.57 (s, 1H), 8.51 (d, J = 4.0 Hz, 1H), 7.68 (d, J = 7.7 Hz, 1H), 7.35 (s, 1H), 7.32 (s, 1H), 7.28-7.24 (m, 2H), 7.21-7.15 (m, 4H), 4.76 (s, 2H), 4.21 (s, 2H), 3.84 (s, 2H), 3.82 (s, 2H), 2.75 (s, 3H) | 0.91 |
| 42 | 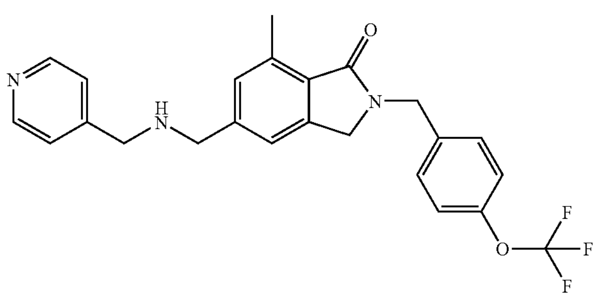 | 7-Methyl-5-{[(pyridine-4-ylmethyl)-amino]-methyl}-2-(4-trifluoromethoxy-benzyl)-2,3-dihydro-isoindol-1-one | 17 mg (32%) liquid | 8.56 (d, J = 5.7 Hz, 2H), 7.35 (s, 1H), 7.32 (s, 1H), 7.28 (d, J = 5.6 Hz, 2H), 7.20-7.15 (m, 4H), 4.76 (s, 2H), 4.21 (s, 2H), 3.83 (s, 2H), 3.83 (s, 2H), 2.75 (s, 3H) | 0.47 |
| 43 | 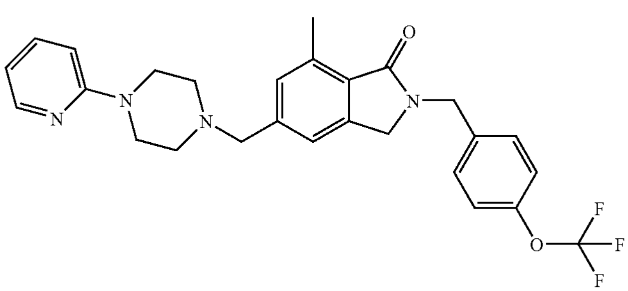 | 7-Methyl-5-(4-pyridin-2-yl-piperazin-1-ylmethyl)-2-(4-trifluoromethoxy-benzyl)-2,3-dihydro-isoindol-1-one | 44 mg (73%) gum | 8.19-8.16 (m, 1H), 7.46 (dd, J = 15.7, 1.9 Hz, 1H), 7.35 (s, 1H), 7.33 (s, 1H), 7.23-7.15 (m, 4H), 6.64-6.58 (m, 2H), 4.76 (s, 2H), 4.22 (s, 2H), 3.58-3.51 (m, 6H), 2.75 (s, 3H), 2.58-2.52 (m, 4H) | 0.05 |

-continued

| Example | Structure | Name | Yield | NMR | GTPγS EC50 |
|---|---|---|---|---|---|
| 44 | 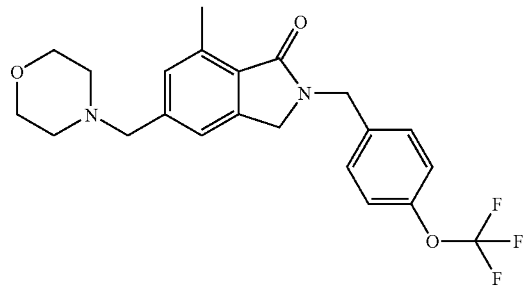 | 7-Methyl-5-morpholin-4-ylmethyl-2-(4-trifluoromethoxy-benzyl)-2,3-dihydro-isoindol-1-one | 40 mg (80%) liquid | 7.35 (s, 1H), 7.32 (s, 1H), 7.20-7.14 (m, 4H), 4.76 (s, 2H), 4.21 (s, 2H), 3.72-3.68 (m, 4H), 3.51 (s, 2H), 2.74 (s, 3H), 2.46-2.41 (m, 4H) | 0.59 |
| 45 | 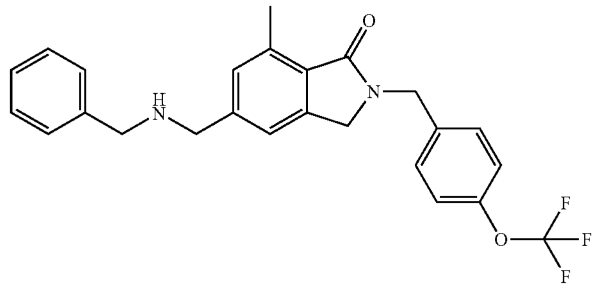 | 5-(Benzylamino-methyl)-7-methyl-2-(4-trifluoromethoxy-benzyl)-2,3-dihydro-isoindol-1-one | 31 mg (58%) liquid | 7.35-7.30 (m, 5H), 7.21-7.15 (m, 4H), 4.76 (s, 2H), 4.20 (s, 2H), 3.83 (s, 2H), 3.81 (s, 2H), 2.74 (s, 3H) | 0.39 |
| 46 | 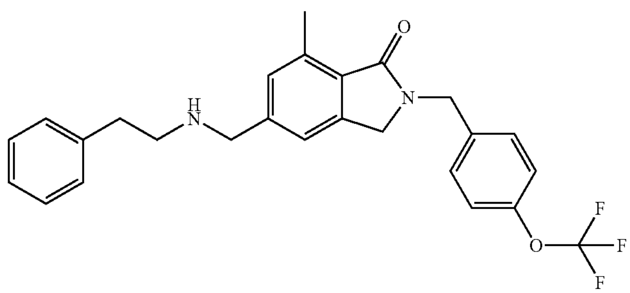 | 7-Methyl-5-(phenethylamino-methyl)-2-(4-trifluoromethoxy-benzyl)-2,3-dihydro-isoindol-1-one | 31 mg (57%) liquid | 7.35-7.09 (m, 11H), 4.75 (s, 2H), 4.18 (s, 2H), 3.82 (s, 2H), 2.93-2.79 (m, 4H), 2.72 (s, 3H) | 0.63 |
| 47 | 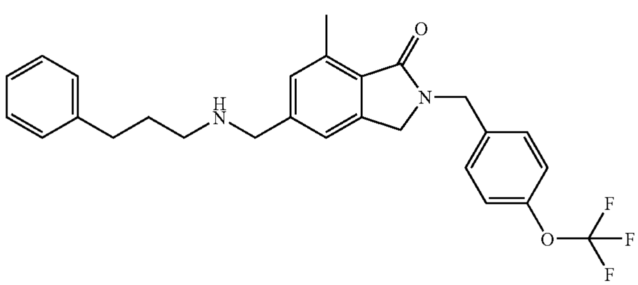 | 7-Methyl-5-[(3-phenyl-propylamino)-methyl]-2-(4-trifluoromethoxy-benzyl)-2,3-dihydro-isoindol-1-one | 31 mg (55%) liquid | 7.35-7.11 (m, 11H), 4.76 (s, 2H), 4.19 (s, 2H), 3.80 (s, 2H), 2.74 (s, 3H), 2.70-2.61 (m, 4H), 1.89-1.79 (m, 2H) | 0.34 |
| 48 | 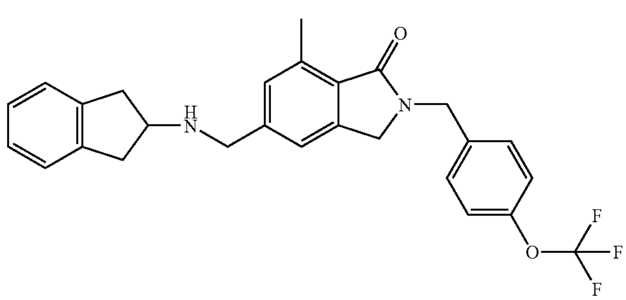 | 5-(Indan-2-ylaminomethyl)-7-methyl-2-(4-trifluoromethoxy-benzyl)-2,3-dihydro-isoindol-1-one | 19 mg (34%) liquid | 7.34 (s, 1H), 7.31 (s, 1H), 7.22-7.11 (m, 8H), 4.75 (s, 2H), 4.20 (s, 2H), 3.88 (s, 2H), 3.67 (quintet, J = 6.6 Hz, 1H), 3.17 (dd, J = 15.5, 7.0 Hz, 2H), 2.81 (dd, J = 15.5, 6.3 Hz, 2H), 2.74 (s, 3H) | 0.41 |

-continued

| Example | Structure | Name | Yield | NMR | GTPγS EC50 |
|---|---|---|---|---|---|
| 49 | 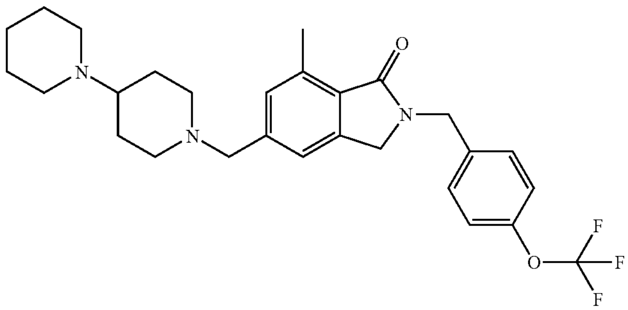 | 5-[1,4"]Bipiperidinyl-1"-ylmethyl-7-methyl-2-(4-trifluoromethoxy-benzyl)-2,3-dihydro-isoindol-1-one | 32 mg (53%) liquid | 7.35 (s, 1H), 7.32 (s, 1H), 7.19-7.12 (m, 4H), 4.75 (s, 2H), 4.20 (s, 2H), 3.49 (s, 2H), 2.91 (d, J = 11.3 Hz, 2H), 2.73 (s, 3H), 2.56-2.47 (m, 4H), 2.33-2.24 (m, 1H), 1.97 (t, J = 11.0 Hz, 2H), 1.83-1.38 (m, 10H) | 3.25 |
| 50 | 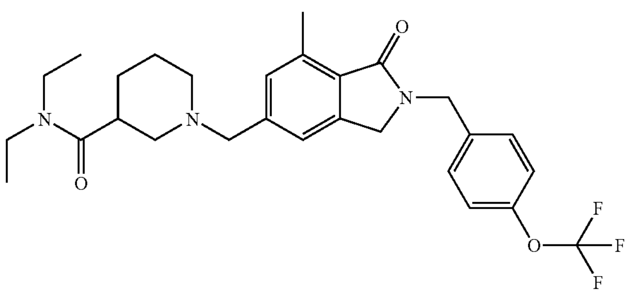 | 1-[7-Methyl-1-oxo-2-(4-trifluoromethoxy-benzyl)-2,3-dihydro-1H-isoindol-5-ylmethyl]-piperidine-3-carboxylic acid diethylamide | 46 mg (74%) liquid | 7.35 (s, 1H), 7.32 (s, 1H), 7.20-7.13 (m, 4H), 4.75 (s, 2H), 4.19 (s, 2H), 3.57-3.47 (m, 2H), 3.40-3.24 (m, 4H), 2.89-2.78 (m, 2H), 2.73 (s, 3H), 2.22 (t, J = 10.9 Hz, 1H), 2.04-1.94 (m, 1H), 1.80-1.48 (m, 5H), 1.10 (dt, J = 18.3, 7.1 Hz, 6H) | 1.81 |
| 51 | 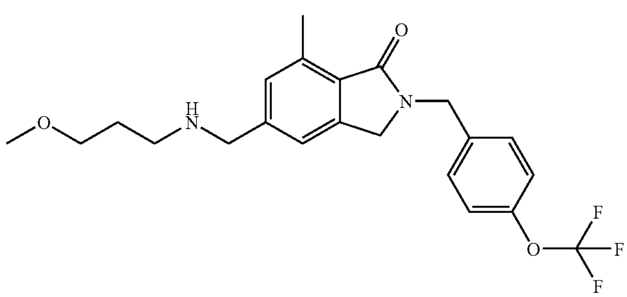 | 5-[(3-Methoxy-propylamino)-methyl]-7-methyl-2-(4-trifluoromethoxy-benzyl)-2,3-dihydro-isoindol-1-one | 32 mg (64%) liquid | 7.34 (s, 1H), 7.31 (s, 1H), 7.20-7.13 (m, 4H), 4.76 (s, 2H), 4.20 (s, 2H), 3.82 (s, 2H), 3.48-3.41 (m, 2H), 3.32 (s, 3H), 2.75-2.69 (m, 5H), 1.83-1.73 (m, 2H) | 1.80 |
| 52 | 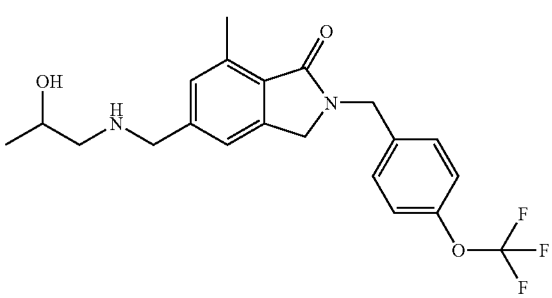 | 5-[(2-Hydroxy-propylamino)-methyl]-7-methyl-2-(4-trifluoromethoxy-benzyl)-2,3-dihydro-isoindol-1-one | 29 mg (49%) liquid | 7.35 (s, 1H), 7.32 (s, 1H), 7.20-7.13 (m, 4H), 4.76 (s, 2H), 4.21 (s, 2H), 3.90-3.76 (m, 3H), 2.77-2.69 (m, 4H), 2.45 (dd, J = 12.0, 9.3 Hz, 1H), 1.15 (d, J = 6.2 Hz, 3H) | 7.02 |

-continued

| Example | Structure | Name | Yield | NMR | GTPγS EC50 |
|---|---|---|---|---|---|
| 53 | 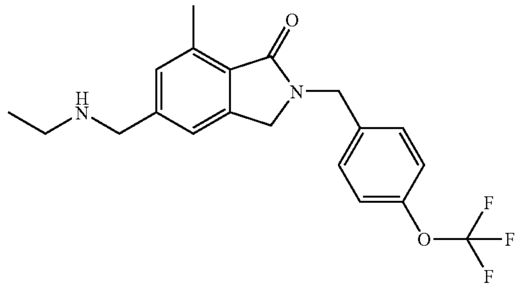 | 5-Ethylaminomethyl-7-methyl-2-(4-trifluoromethoxybenzyl)-2,3-dihydro-isoindol-1-one | 20 mg (44%) solid | 7.34 (s, 1H), 7.31 (s, 1H), 7.21-7.14 (m, 4H), 4.75 (s, 2H), 4.20 (s, 2H), 3.83 (s, 2H), 2.74 (s, 3H), 2.69 (q, J = 7.2 Hz, 2H), 1.15 (t, J = 7.1 Hz, 3H) | 6.31 |
| 54 | 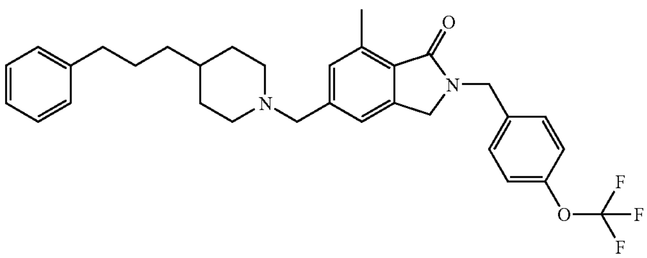 | 7-Methyl-5-[4-(3-phenylpropyl)-piperidin-1-ylmethyl]-2-(4-trifluoromethoxybenzyl)-2,3-dihydroisoindol-1-one | 35 mg (47%) gum | 7.33 (d, J = 8.6 Hz, 2H), 7.29-7.22 (m, 3H), 7.19-7.13 (m, 6H), 4.75 (s, 2H), 4.19 (s, 2H), 3.47 (s, 2H), 2.82 (d, J = 11.0 Hz, 2H), 2.73 (s, 3H), 2.58 (t, J = 7.7 Hz, 2H), 1.97-1.86 (m, 2H), 1.67-1.56 (m, 4H), 1.32-1.18 (m, 5H) | 0.10 |
| 55 | 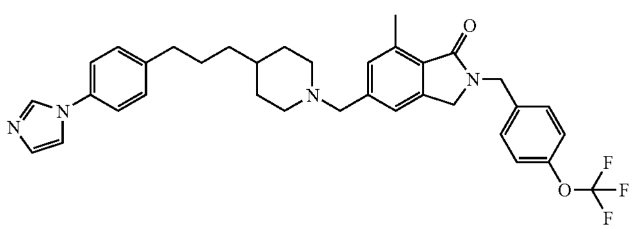 | 5-{4-[3-(4-Imidazol-1-yl-phenyl)-propyl]-piperidin-1-ylmethyl}-7-methyl-2-(4-trifluoromethoxybenzyl)-2,3-dihydroisoindol-1-one | 30 mg (36%) gum | 7.81 (s, 1H), 7.33 (d, J = 8.7 Hz, 2H), 7.31-7.22 (m, 5H), 7.19-7.13 (m, 5H), 4.75 (s, 2H), 4.19 (s, 2H), 3.48 (s, 2H), 2.83 (d, J = 10.7 Hz, 2H), 2.73 (s, 3H), 2.63 (t, J = 7.7 Hz, 2H), 1.98-1.87 (m, 2H), 1.70-1.58 (m, 4H), 1.33-1.17 (m, 5H) | 0.02 |
| 56 | 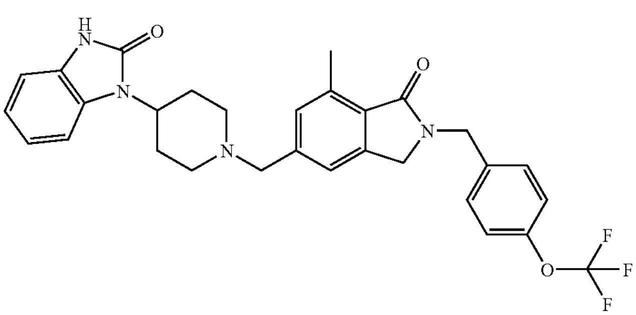 | 1-{1-[7-Methyl-1-oxo-2-(4-trifluoromethoxybenzyl)-2,3-dihydro-1H-isoindol-5-ylmethyl]-piperidin-4-yl}-1,3-dihydrobenzoimidazol-2-one | 45 mg (68%) solid | 8.37 (s, 1H), 7.34 (d, J = 8.6 Hz, 2H), 7.26-7.15 (m, 5H), 7.07-7.01 (m, 3H), 4.77 (s, 2H), 4.40-4.27 (m, 1H), 4.24 (s, 2H), 3.58 (s, 2H), 3.02 (d, J = 11.6 Hz, 2H), 2.77 (s, 3H), 2.56-2.39 (m, 2H), 2.18 (t, J = 11.1 Hz, 2H), 1.80 (d, J = 10.0 Hz, 2H) | 0.06 |

M39 5-Iodo-7-methyl-2-(4-trifluoromethoxy-benzyl)-2,3-dihydro-isoindol-1-one

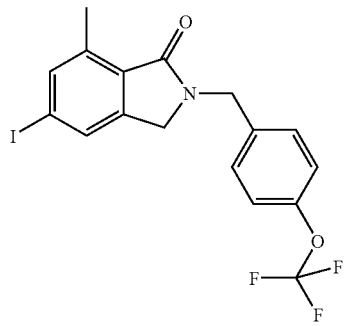

To a solution of 5-Bromo-7-methyl-2-(4-trifluoromethoxy-benzyl)-2,3-dihydro-isoindol-1-one (300 mg, 0.713 mmol) in butanol (3 ml), (1R,2R)—N,N'-dimethylcyclohexane-1,2-diamine (20 mg, 0.142 mmol), copper(I) iodide (13.6 mg, 0.07 mmol) and sodium iodide (214 mg, 1.43 mmol) were added. The resulting mixture was stirred at 120° C. overnight. After cooling, the mixture was diluted with ethyl acetate, washed with water, brine, dried over anhydrous sodium sulphate, filtered, concentrated. Column chromatography (30% EtOAc/Hexanes) provided the title compound as a yellow oil (274 mg, 85%). $^1$H NMR (300 MHz, CDCl$_3$): δ 7.55-7.57 (m, 2H), 7.30-7.35 (m, 2H), 7.16-7.20 (m, 2H), 4.74 (s, 2H), 4.318 (s, 2H), 2.69 (s, 3H).

The following compounds were made in the same fashion:

| Example | Name | Yield | $^1$H NMR |
|---|---|---|---|
| M45 | 4-[7-Methyl-1-oxo-2-(4-trifluoromethoxy-benzyl)-2,3-dihydro-1H-isoindol-5-yloxy]-piperidine-1-carboxylic acid tert-butyl ester | 12 mg, 5.8%, yellow oil | 7.32-7.35 (m, 2H), 7.18-7.20 (m, 2H), 6.74 (d, 2H), 4.75 (s, 2H), 4.40-4.53 (m, 1H), 4.19 (s, 2H), 3.65-3.72 (m, 2H), 3.34-3.41 (m, 2H), 2.73 (s, 3H), 1.90-1.92 (m, 2H), 1.76-1.79 (m, 2H), 1.48 (s, 9H) |
| M49 | 3-[7-Methyl-1-oxo-2-(4-trifluoromethoxy-benzyl)-2,3-dihydro-1H-isoindol-5-yloxymethyl]-morpholine-4-carboxylic acid tert-butyl ester | 46 mg, 11% yellow foam | 7.31-7.35 (m, 2H), 7.17-7.20 (m, 2H), 6.75-6.77 (m, 2H), 4.75 (s, 2H), 4.22-4.28 (m, 2H), 4.18 (s, 2H), 4.07-4.11 (m, 2H), 3.85-3.95 (m, 2H), 3.51-3.64 (m, 2H), 3.02-3.08 (m, 1H), 2.73 (s, 3H), 1.48 (s, 9H) |
| M51 | 4-[7-Methyl-1-oxo-2-(4-trifluoromethoxy-benzyl)-2,3-dihydro-1H-isoindol-5-yloxymethyl]-piperidine-1-carboxylic acid tert-butyl ester | 200 mg, 48%, yellow foam | 7.30-7.33 (m, 2H), 7.15-7.18 (m, 2H), 6.68-6.72 (m, 2H), 4.73 (s, 2H), 4.10-4.16 (m, 4H), 3.82 (d, 2H), 2.70-2.80 (m, 5H), 1.95-2.02 (m, 1H), 1.70-1.80 (m, 2H), 1.46 (s, 9H), 1.23-1.27 (m, 2H) |

Example 57

7-Methyl-1-oxo-2-(4-trifluoromethoxybenzyl)-2,3-dihydro-1H-isoindole-5-carbaldehyde

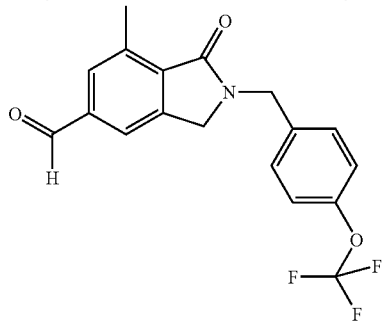

7-Methyl-1-oxo-2-(4-trifluoromethoxy-benzyl)-2,3-dihydro-1H-isoindole-5-carbonitrile (400.0 mg, 1.16 mmol) and $PtO_2$ (26.0 mg, 0.115 mmol) were added to formic acid (2 mL) and the mixture was heated at 60° C. for three hours. The NMR spectrum showed 40% conversion, so $PtO_2$ (50.0 mg) was added to the mixture and it was allowed to stir at 60° C. overnight. After cooling, the mixture was filtered through Celite® and concentrated. Column chromatography (30% EtOAc/Hexanes) provided the title compound as a white solid (357.5 mg, 88%). $^1$H NMR (300 MHz, $CDCl_3$): δ 10.08 (s, 1H), 7.71 (s, 2H), 7.35 (d, 3H), 7.19 (d, 3H), 4.80 (s, 2H), 4.32 (s, 2H), 2.83 (s, 3H).

The following compounds were made in the same fashion:

| Example | Structure | Name | Yield | $^1$H NMR |
|---|---|---|---|---|
| J126 | 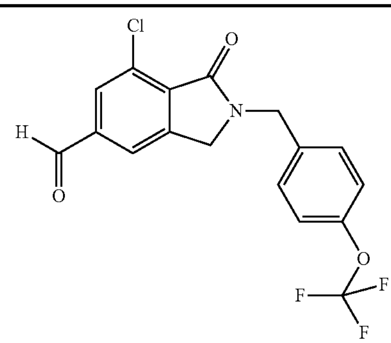 | 7-Chloro-1-oxo-2-(4-trifluoromethoxy-benzyl)-2,3-dihydro-1H-isoindole-5-carbaldehyde | 252 mg colorless solid | 10.02 (s, 1H), 7.86 (s, 1H), 7.79 (s, 1H), 7.37 (dd, 2H), 7.18 (dd, 2H), 4.79 (s, 2H), 4.35 (s, 2H) |
| 42 M | 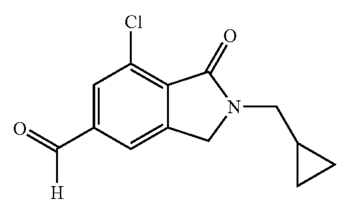 | 5-Acetyl-7-chloro-2-cyclopropylmethyl-2,3-dihydro-isoindol-1-one | 72.1 mg, 49.8%, off-white solid | 10.05 (s, 1H), 7.86-7.87 (m 2H), 4.55 (s, 2H), 3.49 (d, 2H), 1.03-1.06 (m, 1H), 0.59-0.62 (m, 2H), 0.34-0.36 (m, 2H) |

Example 58

7-Methyl-1-oxo-2-(4-trifluoromethoxy-benzyl)-2,3-dihydro-1H-isoindole-5-carboxylic acid

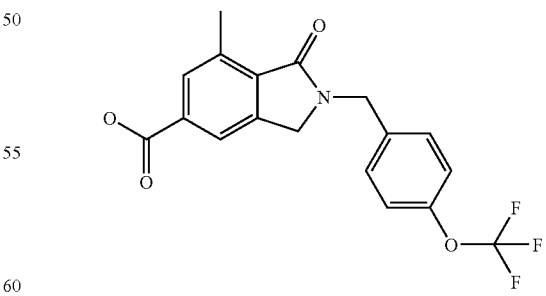

7-Methyl-1-oxo-2-(4-trifluoromethoxybenzyl)-2,3-dihydro-1H-isoindole-5-carbonitrile (103 mg, 0.30 mmol) was stirred at 100° C. in MeOH (10 mL) and 6N NaOH (10 mL) for 2.5 hours. The reaction was acidified with 1N HCl and partitioned between $CH_2Cl_2$ and water, and the organic layer was washed with brine and dried over anhydrous $Na_2SO_4$. The solvent was removed under reduced pressure to yield a white solid (69.0 mg, 64%). $^1$H NMR (300 MHz, CDCl$_3$): δ 7.96 (d, 2H), 7.37 (d, 2H), 7.21 (d, 2H), 4.82 (s, 2H), 4.32 (s, 2H), 2.84 (s, 3H).

Example 59

7-Methyl-1-oxo-2-(4-trifluoromethoxy-benzyl)-2,3-dihydro-1H-isoindole-5-carboxylic acid methyl ester

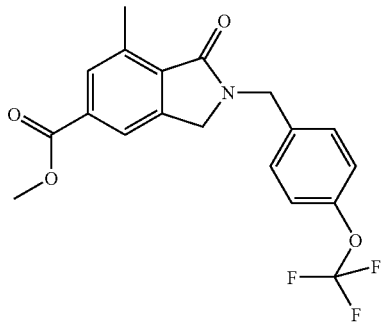

7-Methyl-1-oxo-2-(4-trifluoromethoxybenzyl)-2,3-dihydro-1H-isoindole-5-carboxylic acid (170.00 mg, 0.465 mmol) was mixed with potassium carbonate (193.0 mg, 1.40 mmol) and methyl iodide (199.0 mg, 1.40 mmol) in DMF (2.0 mL) over a weekend. The reaction mixture was diluted with ethyl acetate, and washed with water, brine, dried over sodium sulfate, filtered and concentrated to provide the title compound.

Example 60

7-Methyl-1-oxo-2-(4-trifluoromethoxy-benzyl)-2,3-dihydro-1H-isoindole-5-carboxylic acid hydrazide

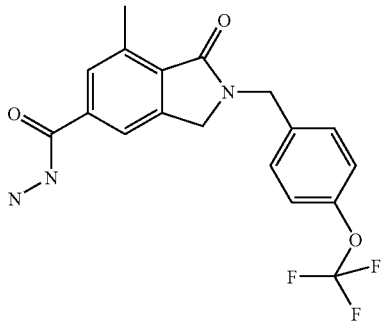

7-Methyl-1-oxo-2-(4-trifluoromethoxy-benzyl)-2,3-dihydro-1H-isoindole-5-carboxylic acid methyl ester (190.0 mg, 0.5 mmol) was mixed with hydrazine (in water) 125.0 mg, 2.50 mmol) in ethanol (0.5 mL) and the reaction was refluxed for five hours. The reaction was concentrated to provide the title compound as an off white solid (200.0 mg, 100%). $^1$H NMR (300 MHz, CDCl$_3$): δ 7.63 (s, 1H), 7.54 (broad s, 1H), 7.31 (m, 2H), 7.18 (d, 2H), 4.75 (s, 2H), 4.22 (s, 2H), 2.74 (s, 3H).

Example 61

5-(5-Chloromethyl-[1,3,4]oxadiazol-2-yl)-7-methyl-2-(4-trifluoromethoxy-benzyl)-2,3-dihydro-isoindol-1-one

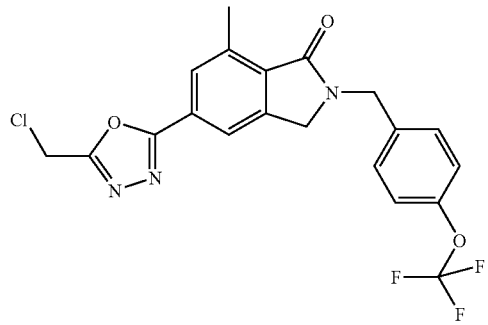

7-Methyl-1-oxo-2-(4-trifluoromethoxy-benzyl)-2,3-dihydro-1H-isoindole-5-carboxylic acid hydrazide (200.0 mg, 0.527 mmol) was stirred with trimethoxy chloroethane (2.0 mL) at 120° C. for two hours. The reaction was concentrated and column chromatography (50% EtOAc/Hexanes) provided the title compound as a yellow solid (28.0 mg). $^1$H NMR (300 MHz, CDCl$_3$): δ 7.94 (s, 2H), 7.38 (d, 2H), 7.21 (d, 2H), 4.81 (s, 4H), 4.34 (s, 2H), 2.85 (s, 3H).

Example 62

5-(3-Chloromethyl-[1,2,4]oxadiazol-5-yl)-7-methyl-2-(4-trifluoromethoxy-benzyl)-2,3-dihydro-isoindol-1-one

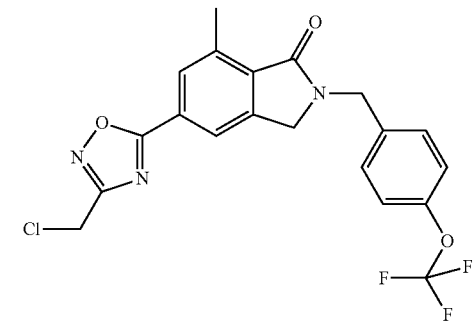

7-Methyl-1-oxo-2-(4-trifluoromethoxybenzyl)-2,3-dihydro-1H-isoindole-5-carboxylic acid (80.0 mg, 0.49 mmol), EDCI (104.0 mg, 0.54 mmol), HOBT (73.0 mg, 0.54 mmol) and 2-chloro-N-hydroxyacetamidine (59.0 mg, 0.54 mmol) were mixed in DMF (4.0 mL) over the weekend. The reaction mixture was diluted with EtOAc and washed with water, brine, dried over sodium sulfate, filtered and concentrated. The product was subjected to column chromatography (100% EtOAc). The product was heated to 135° C. in DMF for 1.5 hours. The reaction mixture was cooled and diluted with ethyl acetate, washed with water, brine, dried over sodium sulfate, filtered and concentrated. The product was purified by column chromatography to yield the title compound as a brown oil (63.0 mg, 33%). $^1$H NMR (300 MHz, CDCl$_3$): δ 8.01 (d, 2H), 7.37 (d, 2H), 7.21 (d, 2H), 4.81 (s, 2H), 4.69 (s, 2H), 4.34 (s, 2H), 2.85 (s, 3H).

anes) on SiO$_2$ pre-washed with 2% Et$_3$N/hexanes, using permanganate stain to provide the title compound as a yellow oil (11.86 g, 75%).

Example 63

4-Trifluoromethanesulfonyloxy-3,6-dihydro-2H-pyridine-1-carboxylic acid tert-butyl ester

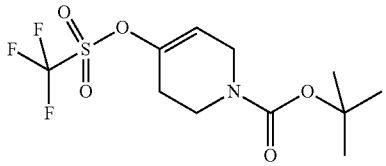

Diisopropylamine (8.4 mL, 60.0 mmol) was dissolved in anhydrous TH (250 mL) and the solution was chilled in an ice bath. To the solution was added dropwise 1.6M nBuLi in hexanes (38 mL, 60.0 mmol). After fifteen minutes, the ice bath was replaced with a dry ice/acetone bath and a solution of N-Boc-piperidone (9.96 g, 50.0 mmol) in anhydrous THF (120 mL) was added dropwise. After thirty minutes, a solution of N-phenyltrifluoromethanesulfonimide (19.6 g, 55.0 mmol) in anhydrous THF (60 mL) was added dropwise. After one hour, the chilling bath was removed. After three hours, the reaction was quenched with saturated sodium bicarbonate and diluted with ethyl acetate. The organic phase was washed twice with 1M sodium hydroxide and once with brine. It was dried over magnesium sulfate, filtered and stored overnight in the freezer. The following day, the product was concentrated and purified by column chromatography (5% EtOAc/Hex-

Example 64

4-(4,4,5,5-Tetramethyl-[1,3,2]dioxaborolan-2-yl)-3,6-dihydro-2H-pyridine-1-carboxylic acid tert butyl ester

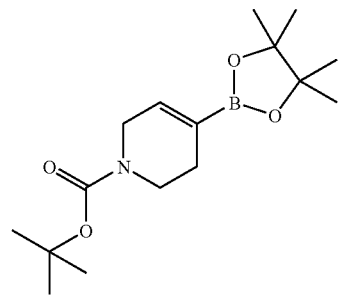

4-Trifluoromethanesulfonyloxy-3,6-dihydro-2H-pyridine-1-carboxylic acid tert-butyl ester (11.86 g, 37.6 mmol) was dissolved in anhydrous 1,4-dioxane (120 mL) and sodium acetate (9.25 g, 113.0 mmol), bis(pinacolato)diboron (10.50 g, 41.4 mmol) and Pd(dppf)Cl$_2$ (1.84 g, 2.26 mmol) were added. The mixture was immersed in a 80° C. oil bath for twenty-two hours. The cooled reaction was concentrated and the residue was partitioned between ethyl acetate and water. The organic phase was washed with water and brine, dried over magnesium sulfate, filtered and concentrated. Column chromatography (5% EtOAc/Hexanes) provided the title compound as a colourless solid (1.96 g, 17%). $^1$H NMR (300 MHz, CDCl$_3$): δ 6.43 (broad s, 1H), 3.96 (s, 2H), 3.45 (t, 2H), 2.22 (broad s, 2H), 1.47 (s, 9H), 1.28 (s, 12H).

The following compounds were made in a similar fashion:

| Example | Structure | Name | Yield | NMR |
|---|---|---|---|---|
| J101 | 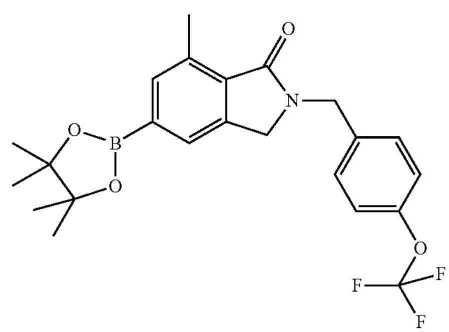 | 7-Methyl-5-(4,4,5,5-tetramethyl-[1,3,2]dioxaborolan-2-yl)-2-(4-tri-fluoromethoxy-benzyl)-2,3-dihydro-isoindol-1-one | 834 mg 76% yellow oil | 7.66 (d, 1H), 7.34 (d, 1H), 7.19 (d, 2H), 4.79 (s, 2H), 4.24 (s, 2H), 2.78 (s, 3H), 1.37 (s, 12H) |

Example 65

4-Methylene-piperidine-1-carboxylic acid tert-butyl ester

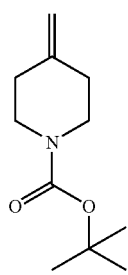

To a solution of methyl triphenylphosphonium bromide (5.4 g, 15.05 mmol) in THF (100 mL) was added slowly butyl lithium (2M, 15.05 mmol) at −78° C. The mixture was allowed to stir for one hour and N-Boc-piperidinone (2 g, 10.03 mmol) was added. The mixture was warmed to room temperature and stirred overnight. The THF was evaporated and the residue was partitioned between water and ethyl acetate. The organic layer was washed with brine and dried over sodium sulphate, filtered and concentrated. The compound was purified by column chromatography (30% Hexanes/EtOAc) to provide the title compound (1.96 g, 99%).

The following compounds were made in a similar fashion:

| Example | Structure | Name | Yield | NMR |
|---|---|---|---|---|
| M59 | 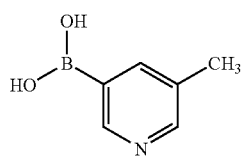 | 4-Allyl-piperidine-1-carboxylic acid tert-butyl ester | 1.2g, 40.3%, yellow oil | 5.67-5.76 (m, 1H), 4.96-4.99 (m, 1H), 4.92-4.94 (m, 1H), 4.02-4.06 (br, 2H), 2.62 (br, 2H), 1.95 (t, 2H), 1.59-1.63 (m, 2H), 1.41 (s, 9H), 1.25-1.36 (m, 1H), 1.01-1.07 (m, 2H) |

Example K42

3-Methylpyridine-5-boronic acid

To a solution of 5-bromo-3-picoline (0.25 g, 1.45 mmol) in Et₂O (5 mL) at −78° C., was added n-butyl lithium (1.6 M in hexanes, 0.92 mL, 1.48 mmol) dropwise. The mixture was stirred at −78° C. for 1 hour and then triisopropyl borate was added quickly. The mixture was stirred at −78° C. for 1 hour and then quenched with water (2 mL). The mixture was warmed up to room temperature overnight. Solvent was removed under reduced pressure to yield a yellow solid (0.25 g).

Example K43

7-Methyl-5-(5-methyl-pyridin-3-yl)-2-(4-phenoxy-benzyl)-2,3-dihydro-isoindol-1-one

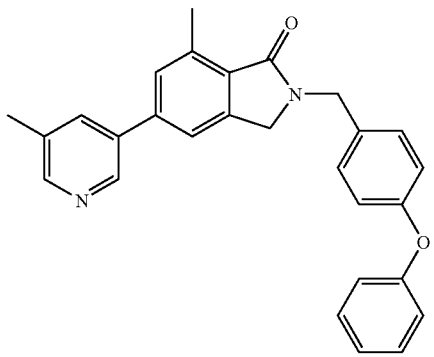

5-Bromo-7-methyl-2-(4-phenoxy-benzyl)-2,3-dihydro-isoindol-1-one (100.0 mg, 0.24 mmol), 3-methylpyridine-5-boronic acid (67.1 mg, 0.49 mmol), 2M sodium carbonate (1 mL) and Pd(PPh₃)₄ (37.0 mg, 0.045 mmol) were suspended in DME (1 mL), and the mixture was heated to 110° C. After 15 hours, the reaction mixture was cooled to room temperature. The cooled reaction mixture was partitioned between ethyl acetate and water. The aqueous phase was extracted with ethyl acetate and the combined organic phase was washed with brine, dried over sodium sulfate, filtered and concentrated under reduced pressure. The product was purified by column chromatography (30-35% EtOAc in hexanes) to provide the title compound as an off-white gum (64 mg, 62%.) $^1$H NMR (300 MHz, CDCl₃): δ 8.66 (d, 1H), 8.47 (d, 1H), 7.70 (s, 1H), 7.28-7.41 (m, 6H), 7.12 (t, 1H), 6.98-7.03 (m, 4H), 4.79 (s, 2H), 4.33 (s, 2H), 2.85 (s, 3H), 2.44 (s, 3H).

Example 66

4-[7-Chloro-1-oxo-2-(4-trifluoromethoxybenzyl)-2,3-dihydro-1H-isoindol-5-yl]-3,6-dihydro-2H-pyridine-1-carboxylic acid tert-butyl ester

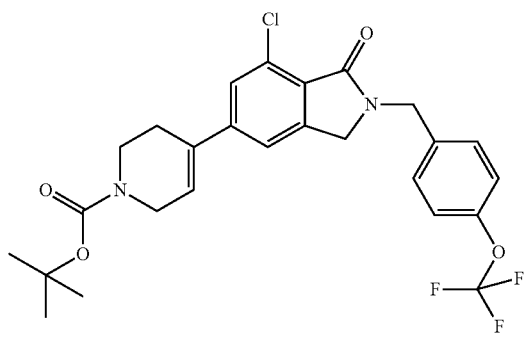

5-Bromo-7-chloro-2-(4-trifluoromethoxybenzyl)-2,3-dihydroisoindol-1-one (190.0 mg, 0.452 mmol), 4-(4,4,5,5-Tetramethyl-[1,3,2]-dioxaborolan-2-yl)-3,6-dihydro-2H-pyridine-1-carboxylic acid tert butyl ester (140.0 mg, 0.452 mmol), potassium carbonate (187.0 mg, 1.36 mmol), and PdCl$_2$(dppf) (37.0 mg, 0.045 mmol) were suspended in anhydrous dimethyl formamide (2 mL) and the mixture was heated to 110° C. After nineteen hours, the heating was stopped and the cooled reaction mixture was partitioned between ethyl acetate and water. The organic phase was washed with water and brine, dried over magnesium sulfate, filtered and concentrated. The product was purified by column chromatography (30% EtOAc/Hexanes) to provide the title compound as a colourless solid (55.0 mg, 23%.) $^1$H NMR (300 MHz, CDCl$_3$): δ 7.38 (m, 3H), 7.26 (s, 1H), 7.18 (d, 2H), 6.18 (broad s, 1H), 4.79 (s, 2H), 4.25 (s, 2H), 4.11 (broad s, 2H), 3.65 (t, 2H), 2.5 (broad s, 2H), 1.49 (s, 9H).

The following compounds were made in a similar fashion:

| Example | Structure | Name | Yield | NMR |
|---|---|---|---|---|
| J107 | 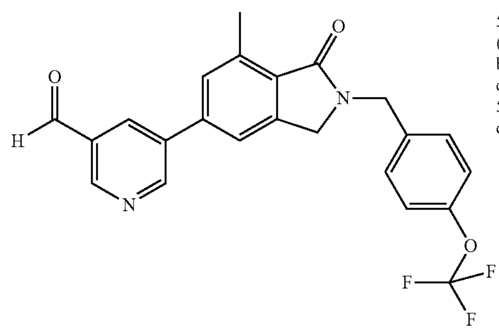 | 5-[7-Methyl-1-oxo-2-(4-trifluoromethoxybenzyl)-2,3-dihydro-1H-isoindol-5-yl]-pyridine-3-carbaldehyde | 91 mg 56% yellow oil | 10.21 (s, 1H), 9.08 (d, 2H), 8.36 (s, 1H), 7.47 (d, 2H), 7.38 (d, 2H), 7.21 (d, 2H), 4.82 (s, 2H), 4.34 (s, 2H), 2.86 (s, 3H) |
| K37 | 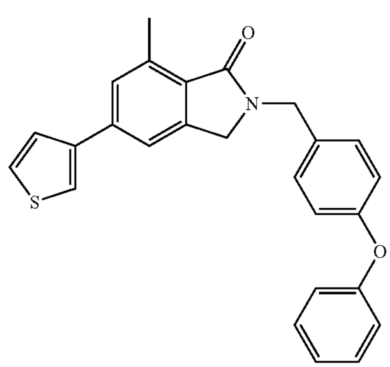 | 7-Methyl-2-(4-phenoxy-benzyl)-5-thiophen-3-yl-2,3-dihydro-isoindol-1-one | 20 mg, 25%, pale yellow oil | 7.52 (d, 1H), 7.28-7.45 (m, 8H), 7.12 (t, 1H), 6.98-7.03 (m, 4H), 4.78 (s, 2H), 4.29 (s, 2H), 2.82 (s, 3H) |

| Example | Structure | Name | Yield | NMR |
|---|---|---|---|---|
| K38 | 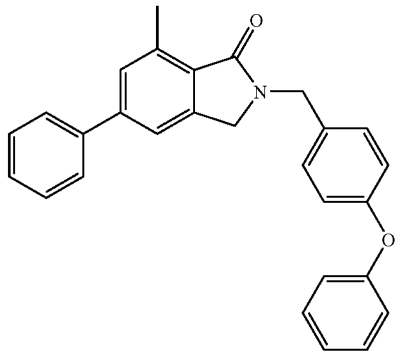 | 7-Methyl-2-(4-phenoxy-benzyl)-5-phenyl-2,3-dihydro-isoindol-1-one | 29 mg, 37% yellow oil | 7.58-7.62 (m, 2H), 7.28-7.48 (m, 9H), 7.13 (t, 1H), 6.98-7.03 (m, 4H), 4.79 (s, 2H), 4.31 (s, 2H), 2.84 (s, 3H) |
| K39 | 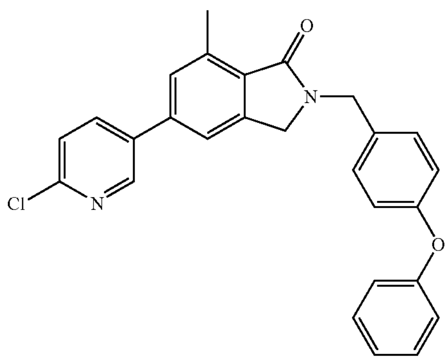 | 5-(6-Chloro-pyridin-3-yl)-7-methyl-2-(4-phenoxy-benzyl)-2,3-dihydro-isoindol-1-one | 15 mg, 17%, yellow gum | 8.61 (d, 1H), 7.87 (dd, 1H), 7.45 (d, 1H), 7.28-7.38 (m, 6H), 7.12 (t, 1H), 6.98-7.03 (m, 4H), 4.79 (s, 2H), 4.33 (s, 2H), 2.85 (s, 3H) |
| K40 | 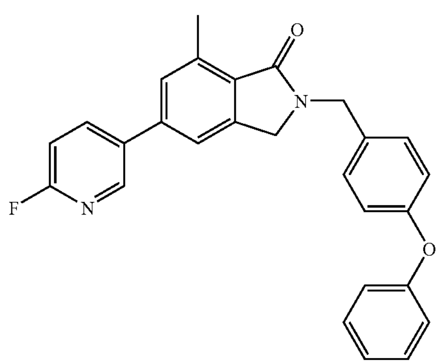 | 5-(6-Fluoro-pyridin-3-yl)-7-methyl-2-(4-phenoxy-benzyl)-2,3-dihydro-isoindol-1-one | 25 mg, 30% yellow solid | 8.44 (d, 1H), 7.95-8.05 (m, 1H), 7.28-7.38 (m, 6H), 7.15 (t, 1H), 6.98-7.03 (m, 5H), 4.79 (s, 2H), 4.33 (s, 2H), 2.85 (s, 3H) |
| K41 | 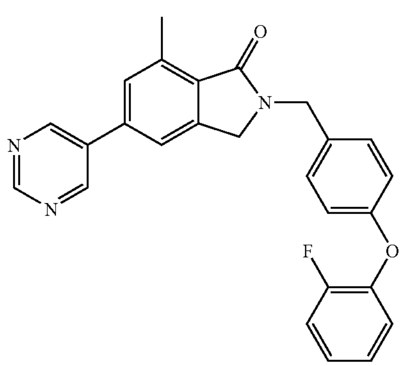 | 2-[4-(2-Fluoro-phenoxy)-benzyl]-7-methyl-5-pyrimidin-5-yl-2,3-dihydro-isoindol-1-one | 12 mg, 14%, white solid | 9.26 (s, 1H), 8.97 (s, 2H), 7.41 (s, 2H), 7.31 (d, 2H), 7.02-7.25 (m, 4H), 6.96 (d, 2H), 4.79, (s, 2H), 4.33 (s, 2H), 2.87 (s, 3H) |

Example 67

4-[7-Chloro-1-oxo-2-(4-trifluoromethoxy-benzyl)-2,3-dihydro-1H-isoindol-5-ylmethyl]-piperidine-1-carboxylic acid tert-butyl ester

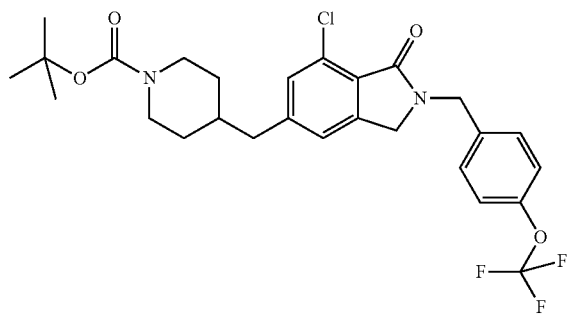

To a purged (argon) sample of 4-methylene-piperidine-1-carboxylic acid tert-butyl ester (51.6 mg, 0.26 mmol) was added 9-BBN. The mixture was stirred at 60° C. for one hour. After cooling to room temperature this solution was added to 5-bromo-7-chloro-2-(4-trifluoromethoxybenzyl)-2,3-dihydroisoindol-1-one (100.0 mg, 0.24 mmol), Pd(dppf)Cl$_2$ (5.9 mg, 0.0072 mmol), DMF (2.0 mL), potassium carbonate 943.1 mg, 0.31 mmol) and water (0.2 mL). The mixture was allowed to stir at 75° C. overnight. The mixture was then cooled to room temperature and poured into water (3 mL). The pH was adjusted to 11 with aqueous sodium hydroxide (3N). The product was extracted with ethyl acetate. The combined organic layers were washed with water three times, brine, dried over sodium sulphate, filtered and concentrated. Column chromatography (30% Ethyl acetate/hexanes) provided the title compound (54.9 mg, 44%).

Example 68

7-Chloro-5-piperidin-4-ylmethyl-2-(4-trifluoromethoxybenzyl)-2,3-dihydroisoindol-1-one

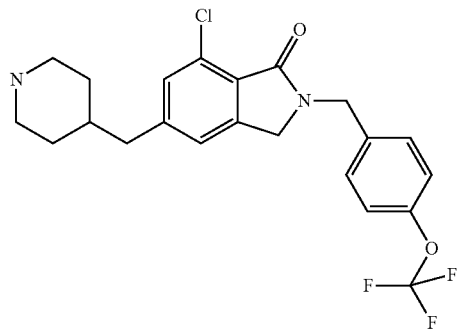

4-[7-Chloro-1-oxo-2-(4-trifluoromethoxybenzyl)-2,3-dihydro-1H-isoindol-5-ylmethyl]-piperidine-1-carboxylic acid tert-butyl ester (54.90 mg, 0.102 mmol) was stirred in dichloromethane (2 mL) and trifluoroacetic acid (2 mL) overnight. The reaction mixture was quenched with sodium carbonate to pH=8-9 and the free base was extracted with dichloromethane. The organic layer was washed with water, brine, dried over sodium sulfate, filtered and concentrated to provide the title compound (48.9 mg, 100%). $^1$H NMR (300 MHz, CDCl$_3$): δ 7.39 (d, 2H), 7.18 (d, 3H), 7.06 (s, 1H), 4.77 (s, 2H), 4.61 (broad s, 1H), 4.23 (s, 2H), 3.16 (d, 2H), 2.62 (m, 4H), 1.61 (d, 3H), 1.29 (m, 2H).

J3: 4-[4-(4,4,5,5-Tetramethyl-[1,3,2]dioxaborolan-2-yl)-benzyl]-morpholine

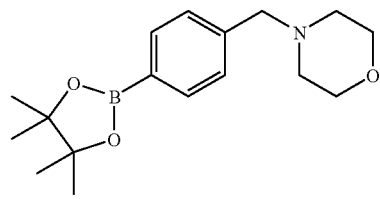

2-(4-Bromomethyl-phenyl)-4,4,5,5-tetramethyl-[1,3,2]dioxaborolane (200 mg, 0.673 mmol) was dissolved in THF (5 mL) and morpholine (0.088 mL, 1.01 mmol) was added. The mixture stirred overnight at room temperature and was then filtered and concentrated to afford the title compound (223 mg, 100%). $^1$H NMR (300 MHz, CDCl$_3$): δ 7.79 (d, 2H), 7.36 (d, 2H), 3.73 (t, 4H), 3.55 (s, 2H), 2.47 (t, 4H).

J19: 4-[4-(4,4,5,5-Tetramethyl-[1,3,2]dioxaborolan-2-yl)-pyrazol-1-ylmethyl]-pyridine

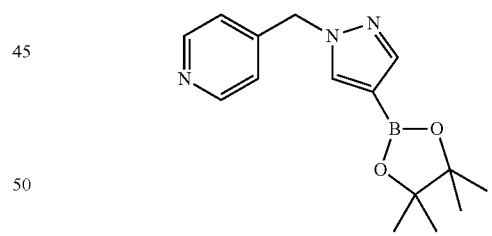

A mixture of 4-(4,4,5,5-Tetramethyl-[1,3,2]dioxaborolan-2-yl)-1H-pyrazole (750 mg, 0.387 mmol), 4-Chloromethylpyridine (740 mg, 0.581 mmol) and cesium carbonate (3.77 g, 1.16 mmol) was dissolved in acetonitrile (15 mL) was stirred overnight at room temperature. Stirring continued for 5 hrs at 60° C. and the reaction mixture was cooled, diluted with water and extracted with ethyl acetate. The organics were washed with brine, dried over anhydrous sodium sulfate, filtered and concentrated. Column chromatography (100% Ethyl acetate-4% 2M NH$_3$ in MeOH/CH$_2$Cl$_2$) provided the title compound (993 mg, 90%). $^1$H NMR (300 MHz, CDCl$_3$): δ 8.59-8.57 (m, 2H), 7.87 (s, 1H), 7.76 (s, 1H), 7.07-7.05 (m, 2H), 5.35 (s, 2H), 1.33 (s, 12H).

The following compounds were made in a similar fashion:

| Example | Structure | Name | Yield | NMR |
|---|---|---|---|---|
| J23 | 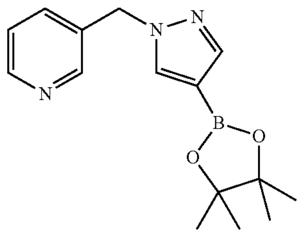 | 3-[4-(4,4,5,5-Tetramethyl-[1,3,2]dioxaborolan-2-yl)-pyrazol-1-ylmethyl]-pyridine | 316 mg 71% yellow oil | 8.57-8.56 (m, 2H), 7.85 (s, 1H), 7.73 (s, 1H), 7.28 (m, 2H), 5.35 (s, 2H), 1.33 (s, 12H). |
| J30 | 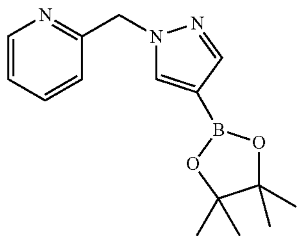 | 2-[4-(4,4,5,5-Tetramethyl-[1,3,2]dioxaborolan-2-yl)-pyrazol-1-ylmethyl]-pyridine | 622 mg 85% yellow oil | 8.57 (d, 1H), 7.87 (s, 1H), 7.84 (s, 1H), 7.65 (t, 1H), 7.25 (t, 1H), 7.01 (D, 1H), 5.48 (s, 2H), 1.33 (s, 12H). |

J25: 4-Tributylstannyl-1-trityl-1H-imidazole

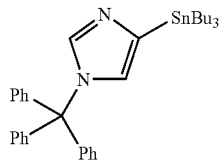

To a solution of 4-Iodo-1-trityl-1H-imidazole (5.0 g, 11.6 mmol) in dichloromethane (100 ml) added Ethylmagnesium bromide (3M in diethyl ether) (4.6 ml, 13.9 mmol). Stirred the reaction under argon atmosphere at room temperature for 1 h. At this point added tributyltin chloride (4.1 ml, 13.9 mmol) to the reaction mixture and left the resulting mixture stirring at room temperature overnight. The reaction mixture was diluted with dichloromethane (100 ml), successively washed with saturated ammonium chloride (100 ml), water (100 ml) and brine (100 ml). The organic phase was dried (sodium sulfate), filtered and concentrated in-vacuo to yield the crude title compound (2.35 g) as a white waxy solid.

J41: 1-(2-Chloro-ethyl)-4-(4,4,5,5-tetramethyl-[1,3,2]dioxaborolan-2-yl)-1H-pyrazole

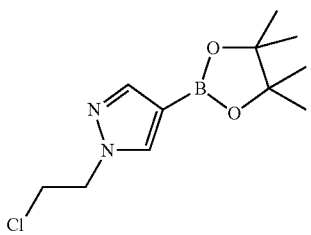

A mixture of 4-(4,4,5,5-Tetramethyl-[1,3,2]dioxaborolan-2-yl)-1H-pyrazole (560 mg, 2.89 mmol), 1-Bromo-2-chloroethane (0.36 mL, 4.39 mmol), and cesium carbonate (2.81 g, 8.67 mmol) in acetonitrile (20 mL) stirred at 62° C. for 4 hrs. The mixture was cooled, diluted with water and extracted with ethyl acetate. The organics were washed with water and brine, dried over anhydrous sodium sulfate, filtered and concentrated to afford the title compound (664 mg, 90%). $^1$H NMR (300 MHz, CDCl$_3$): δ 7.84 (s, 1H), 7.79 (s, 1H), 4.45 (t, 2H), 3.90 (t, 2H), 1.34 (s, 12H).

J42: Dimethyl-{2-[4-(4,4,5,5-tetramethyl-[1,3,2] dioxaborolan-2-yl)-pyrazol-1-yl]-ethyl}-amine

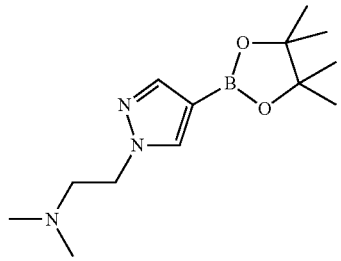

1-(2-Chloro-ethyl)-4-(4,4,5,5-tetramethyl-[1,3,2]dioxaborolan-2-yl)-1H-pyrazole (664 mg, 2.59 mmol) was dissolved in a 2M solution of dimethyl amine in THF (15.32 mL, 30.6 mmol) and stirred for 48 hrs at room temperature. A scoop of potassium iodide was added to the reaction flask and the mixture stirred at 75° C. for 48 hrs. The mixture was cooled, diluted with water and extracted with ethyl acetate. The organics were washed with water and brine, dried over anhydrous sodium sulfate, filtered and concentrated to afford the title compound (519 mg, 76%). $^1$H NMR (300 MHz, CDCl$_3$): δ 7.79 (d, 2H), 4.35 (t, 2H), 2.95 (t, 2H), 2.37 (s, 6H), 1.32 (s, 12H).

J95: [5-(4,4,5,5-tetramethyl-[1,3,2]dioxaborolan-2-yl)-pyridin-3-yl]-methanol

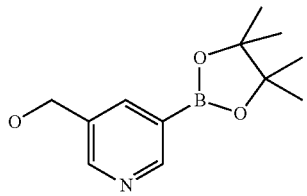

10% Pd/c (100 mg) was flushed with argon in a flask, and ethanol was carefully added. 5(4,4,5,5-Tetramethyl-[1,3,2] dioxaborolan-2-yl)-pyridine-3-carbaldehyde (100 mg, 0.429 mmol) and dimethylamine (429 µL, 0.858 mmol) were added and the mixture stirred for 3 hrs under hydrogen. The reaction mixture was filtered through celite and the filterate was concentrated to afford an orang solid (81 mg, 80%). $^1$H NMR (300 MHz, CDCl$_3$): δ 8.85 (d, 1H), 8.63 (d, 1H), 8.10 (d, 1M), 2.25 (s, 2H), 1.36 (s, 12H).

J97: Methanesulfonic acid 5-[7-methyl-1-oxo-2-(4-trifluoromethoxy-benzyl)-2,3-dihydro-1H-isoindol-5-yl]-pyridin-3-ylmethyl ester

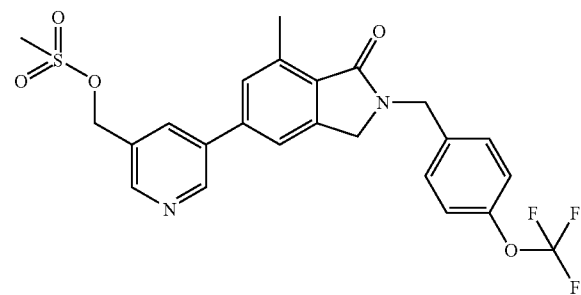

5-(5-Hydroxymethyl-pyridin-3-yl)-7-methyl-2-(4-trifluoromethoxy-benzyl)-2,3-dihydro-isoindol-1-one (72 mg, 0.168) was diluted with dichloromethane (5 mL) and the solution was cooled to 0° C. in an icebath. Triethyl amine (47 µL, 0.168 mmol) and methanesulfonyl chloride (19 µL, 0.252 mmol) were added and stirring continued for 1 hr at 0° C. The mixture was quenched with cold saturated sodium bicarbonate and the organics were dried over anhydrous sodium sulfate, filtered and concentrated to afford the title compound as black oil (70 mg, 100%). $^1$H NMR (300 MHz, CDCl$_3$): δ 8.01 (s, 1H), 7.43-7.37 (m, 5H), 7.23-7.20 (m, 3H), 5.37 (s, 2H), 4.83 (s, 2H), 4.34 (s, 2H), 3.09 (s, 3H), 2.86 (s, 3H).

The following compounds were made in a similar fashion:

| Example | Structure | Name | Yield | NMR |
|---|---|---|---|---|
| J118 | 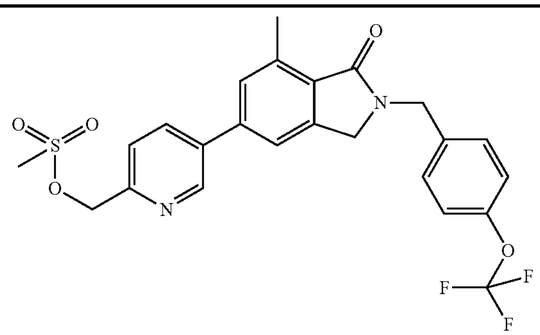 | Methanesulfonic acid 5-[7-methyl-1-oxo-2-(4-trifluoromethoxy-benzyl)-2,3-dihydro-1H-isoindol-5-yl]-pyridin-2-ylmethyl ester | 267 mg 100% red solid | 8.81 (br s, 1H), 7.94 (d, 1H), 7.56 (d, 1H), 7.40-7.34 (m, 4H), 7.18 (d, 2H), 5.37 (s, 2H), 4.79 (s, 2H), 4.31 (s, 2H), 3.68 (s, 3H), 2.82 (s, 3H) |

J108: 5-(5-Hydroxymethyl-pyridin-3-yl)-7-methyl-2-(4-trifluoromethoxy-benzyl)-2,3-dihydro-isoindol-1-one To a solution of 5-[7-Methyl-1-oxo-2-(4-trifluoromethoxy-benzyl)-2,3-dihydro-1H-isoindol-5-yl]-pyridine-3-carbaldehyde (91 mg, 0.212 mmol), in ethanol (10 mL) was added sodium borohydride (10 mg, 0.212 mmol). The mixture stirred for 4 hrs at room temperature and was poured into water and was extracted with ether. The organics were dried over anhydrous sodium sulfate, filtered and concentrated. The resulting residue was purified by column chromatography eluting with 30-100% ethyl acetate in hexanes. The isolated product stirred in 1N HCl/MeOH overnight and was neutralized with 1N NaOH, extracted with ether, and concentrated to afford the title compound (62 mg, 68%) as a yellow solid. $^1$H NMR (300 MHz, CDCl$_3$): δ 8.74 (s, 1H), 78.61 (s, 1H), 8.15 (s, 1H), 7.41-7.36 (m, 4H), 7.22 (d, 2H), 4.91 (s, 2H), 4.82 (s, 2H), 4.36 (s, 2H), 2.85 (s, 3H).

J115: 5-Bromo-2-methylpyridine-1-oxide

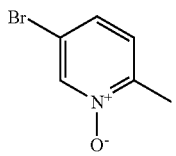

To a solution of 5-Bromo-2-methyl-pyridine (1.00 g, 5.80 mmol) in chloroform (10 mL) was slowly added 3-Chloro-benzenecarboperoxoic acid (1.004 g, 6.98 mmol) at 0° C. Stirring continued for 2 hrs at room temperature and the mixture was diluted with chloroform, washed with saturated sodium bicarbonate and water, dried over anhydrous sodium sulfate, filtered and concentrated to afford the title compound (1.14 g, 100%) as a yellow solid. $^1$H NMR (300 MHz, CDCl$_3$): δ 8.46 (s, 1H), 7.36 (d, 1H), 7.17 (d, 1H), 2.49 (s, 3H).

J116: (5-Bromo-pyridin-2-yl)-methanol

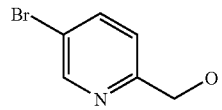

To a flask containing 5-Bromo-2-methyl-pyridine 1-oxide (1.14 g, 6.20 mmol) purged with argon was slowly added trifluoroacetic acid (10 mL). The mixture stirred for 0.5 hrs at room temperature and 0.5 hrs at 53° C. The mixture was cooled and diluted with saturated sodium bicarbonate. The aqueous solution stirred overnight at room temperature and was extracted with ethyl acetate, and concentrated to afford the title compound (895 mg, 77%) as a brown solid. $^1$H NMR (300 MHz, CDCl$_3$): δ 8.64 (s, 1H), 7.83 (d, 1H), 7.22 (d, 1H), 4.75 (s, 2H).

J127: 4-{[7-Chloro-1 oxo-2-(4-trifluoromethoxy-benzyl)-2,3-dihydro-1H-isoindol-5-ylamino]-methyl}-piperidine-1-carboxylic acid tert-butyl ester

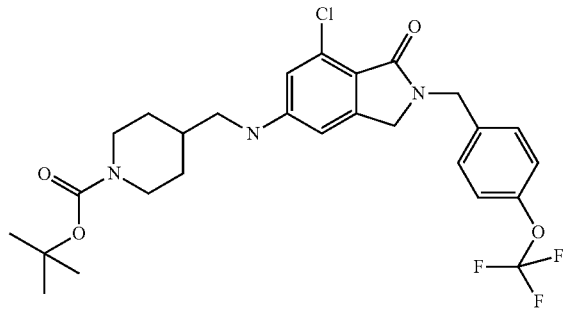

To a solution of 7-chloro-1-oxo-2-(4-trifluoromethoxy-benzyl)-2,3-dihydro-1H-isoindole-5-carbaldehyde (60 mg, 0.162 mmol) in methanol (1.6 mL) was added formic acid (0.02 ml), 4-Aminomethyl-piperidine-1-carboxylic acid tert-butyl ester (35 mg, 0.162 mmol), and Sodium cyanoborohydride (0.2 mL, 1M in THF) respectively. The mixture stirred at room temperature for 1 hour and was then diluted with water and extracted with ethyl acetate. The organic were washed with brine, dried over anhydrous sodium sulfate, filtered and concentrated. Column chromatography (56-60% ethyl acetate in hexanes) provided the title compound (47 mg, 52%). $^1$H NMR (300 MHz, CDCl$_3$): δ (7.35 (d, 4H), 7.18 (d, 2H), 4.77 (s, 2H), 4.25 (s, 2H), 4.13 (br s, 1H), 3.86 (s, 2H), 2.65 (t, 4H), 2.54 (d, 2H), 1.70 (t, 4H), 1.45 (s, 9H)

The following compound was made in a similar fashion:

| Example | Structure | Name | Yield | NMR |
|---|---|---|---|---|
| J130 | 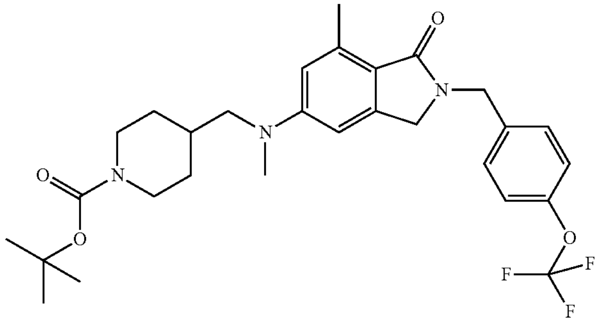 | 4-({Methyl-[7-methyl-1-oxo-2-(4-trifluoromethoxy-benzyl)-2,3-dihydro-1H-isoindol-5-yl]-amino}-methyl)-piperidine-1-carboxylic acid tert-butyl ester | 190 mg 67% colorless oil | 8.47 (s, 1H), 7.45-7.37 (m, 3H), 7.29 (d, 2H), 4.82 (s, 2H), 4.38 (s, 2H), 4.14 (s, 2H), 3.44-3.36 (m, 2H), 3.03-2.95 (m, 2H), 2.85 (d, 2H), 2.72 (s, 3H), 2.07-2.01 (m, 2H), 1.27-1.23 (m, 2H) |

| Example | Structure | Name | Yield | NMR |
|---|---|---|---|---|
| M1 | 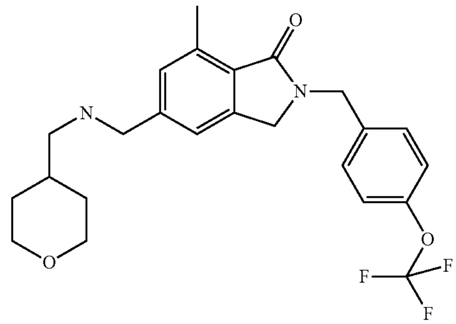 | 7-methyl-5-{[(tetrahydro-pyran-4-ylmethyl)amino]-methyl}-2-(4-trifluoromethoxy-benzyl)-2,3-dihydro-isoindo-1-one | 31.9 mg, 83.6% | 7.33-7.36 (m, 2H), 7.17-7.20 (m, 4H), 4.77 (s, 2H), 4.22 (s, 2H), 3.95-4.00 (m, 2H), 3.83 (s, 2H), 3.39 (dxt, 2H), 2.76 (s, 3H), 2.53 (d, 2H), 1.57-1.76 (m, 3H), 1.24-1.38 (m, 2H) |

Preparation of Final Compounds

Example 69

2-[3-(2,4-Difluoro-phenyl)-prop-2-ynyl]-2,3-dihydro-isoindol-1-one

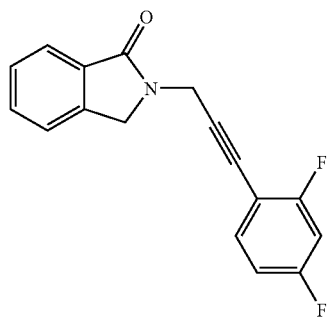

2-Prop-2-ynyl-2,3-dihydro-isoindol-1-one (50.0 mg, 0.29 mmol) was dissolved in triethylamine (2 mL). To this was added Pd(PPh$_3$)$_4$ (13 mg, 0.012 mmol), CuI (6.7 mg, 0.035 mmol) and 2,4-difluoro-1-iodo-benzene (52.0 µL, 0.438 mmol) and the reaction was allowed to stir overnight. The solvent was evaporated and the residue was purified by prep. TLC (30% EtOAc/Hexanes) to afford the title compound (20.0 mg, 24%) as a brown oil. $^1$H NMR (300 MHz, CDCl$_3$): δ 7.90 (d, 1H), 7.45 (m, 4H), 6.84 (t, 2H), 4.72 (s, 2H), 4.59 (s, 2H).

Example 70

2-[3-(2,4-Difluoro-phenyl)-propyl]-2,3-dihydro-isoindol-1-one

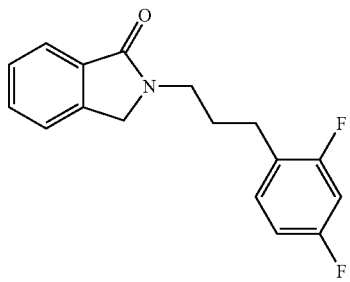

2-[3-(2,4-Difluoro-phenyl)-prop-2-ynyl]-2,3-dihydro-isoindol-1-one was dissolved in EtOH (5 mL) and a small amount of 10% Pd/C was added. A hydrogen balloon was attached to the flask and the system was evacuated and flushed three times. The reaction was allowed to stir for twenty-two hours. The reaction mixture was filtered and concentrated to provide the title compound as a colourless oil (13.0 mg).

Example 71

2-(4-Benzyloxybenzyl)-2,3-dihydroisoindol-1-one

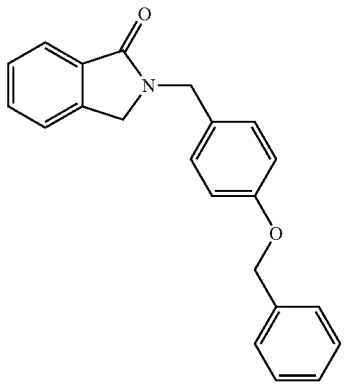

2,3-dihydro-isoindol-1-one (100 mg, 0.751 mmol) was dissolved in anhydrous acetonitrile and cesium carbonate (730 mg, 0.225 mmol) and 1-benzyloxy-4-chloroethylbenzene (349 mg, 0.150 mmol) were added to the solution and stirred at room temperature for 12 hours. The reaction was partitioned between ethyl acetate and water and the organic was washed with brine, dried over anhydrous sodium sulphate and concentrated. The compound was purified by column chromatography (20% ethyl acetate/hexanes) to yield a yellow solid (82 mg, 33%). $^1$H NMR (300 MHz, CDCl$_3$): δ 7.91 (d, 1H), 7.37-7.53 (m, 9H), 7.25-7.28 (m, 1H), 6.95 (d, 2H), 5.06 (d, 2H), 4.77 (d, 2H), 4.27 (d, 2H).

The following compounds were made in a similar fashion:

| Example | Structure | Name | Yield | NMR |
|---|---|---|---|---|
| 72 | 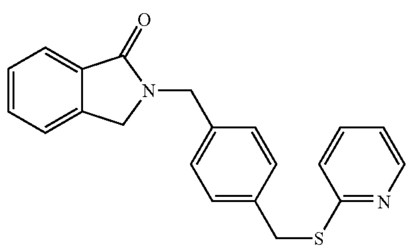 | 2-[4-(Pyridin-2-ylsulfanylmethyl)-benzyl]-2,3-dihydroisoindol-1-one | 36 mg (42%) off-white solid | 8.46 (d, 1H), 7.90 (d, 1H), 7.46-7.56 (m, 3H), 7.39 (d, 3H), 7.24-7.28 (m, 2H), 7.02 (d, 1H), 6.99 (t, 1H), 4.79 (s, 2H), 4.45 (s, 2H), 4.27 (s, 2H) |
| 73 | 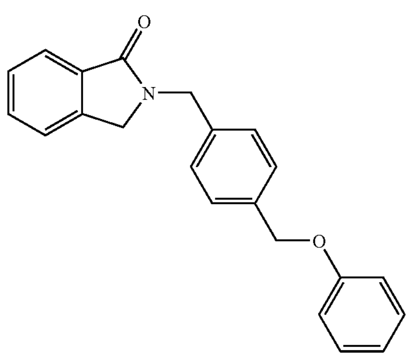 | 2-(4-Phenoxymethylbenzyl)-2,3-dihydroisoindol-1-one | 33 mg (42%) white solid | 7.91 (d, 1H), 7.42-7.54 (m, 5H), 7.28-7.36 (m, 4H), 6.97-7.00 (m, 3H), 5.06 (s, 2H), 4.84 (s, 2H), 4.30 (s, 2H) |
| 74 | 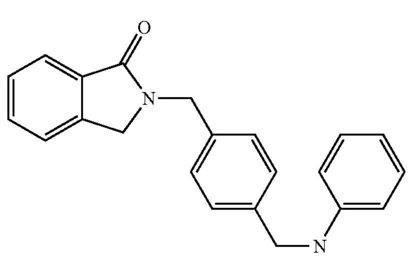 | 2-(4-Phenylaminomethylbenzyl)-2,3-dihydroisoindol-1-one | 20 mg (65%) white solid | 7.90 (d, 1H), 7.42-7.55 (m, 2H), 7.28-7.41 (m, 5H), 7.18 (t, 2H), 6.73 (t, 1H), 6.62 (dd, 2H), 4.83 (s, 2H), 7.35 (s, 2H), 4.29 (s, 2H) |

Example 75

5-Bromo-2-(4-methyl-benzyl)-2,3-dihydro-isoindol-1-one

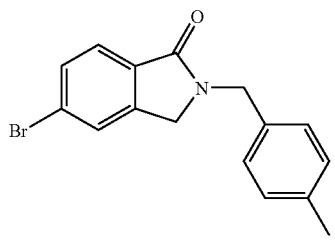

5-Bromo-2,3-dihydro-isoindol-1-one (1.0 g, 4.72 mmol), 1-bromomethyl-4-methyl-benzene (1.14 g, 6.14 mmol) and cesium carbonate (3.08 g, 9.44 mmol) were suspended in anhydrous NMP (10 mL). The mixture was immersed in a 60° C. oil bath for 16.5 hours. The cooled reaction mixture was poured into water and extracted with ethyl acetate. The organic phase was washed with water and brine, dried over magnesium sulfate, filtered and concentrated. Column chromatography (20% to 40% ethyl acetate/hexanes) provided the title compound as a yellow solid (1.18 g, 79%). $^1$H NMR CDCl$_3$: 7.76 (d, 1H), 7.62 (d, 1H), 7.55 (s, 1H), 4.76 (s, 2H), 4.24 (s, 2H), 2.35 (s, 3H).

Example 76

5-Methoxy-2-(4-methylbenzyl)-2,3-dihydroisoindol-1-one

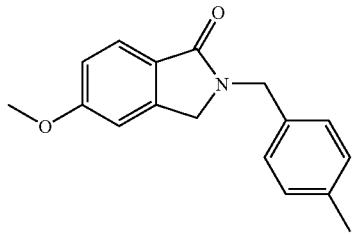

5-Methoxy-2,3-dihydroisoindol-1-one (40 mg, 0.25 mmol), Cs$_2$CO$_3$ (239 mg, 0.74 mmol), 1-bromomethyl-4-methylbenzene (68 mg, 0.37 mmol) in acetonitrile (4 mL) was allowed to stir at room temperature for 18 hours and at 70° C. for 4 hours. The reaction was partitioned between ethyl acetate and water and the organic layer was washed with brine and dried over anhydrous Na$_2$SO$_4$. The solvent was removed under reduced pressure and the product was purified by column chromatography (30% EtOAc/Hexanes) to afford a white solid (15 mg). $^1$H NMR (300 MHz, CDCl$_3$): δ 7.81 (d, 1H), 7.18 (q, 4H), 7.00 (dd, 1H), 6.87 (s, 1H), 4.75 (s, 2H), 4.21 (s, 2H), 3.87 (s, 3H), 2.34 (S, 3H).

Example 77

5-(3-Dimethylamino-prop-1-ynyl)-7-methyl-2-(4-trifluoromethoxy-benzyl)-2,3-dihydro-isoindol-1-one

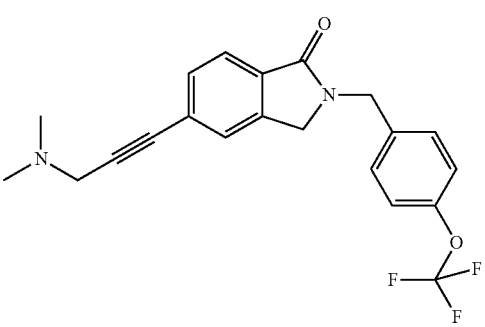

5-Bromo-7-methyl-2-(4-trifluoromethoxy-benzyl)-2,3-dihydro-isoindol-1-one (50 mg, 0.125 mmol), 1-dimethylamino-2-propyne (194 µL, 0.14 mmol), trimethylacteylene (20 µL, 0.14 mmol), Pd(PPh$_3$)$_2$Cl$_2$ (1.9 mg, 0.003 mmol) and copper iodide (1.0 mg, 0.006 mmol) were stirred together at 120° C. for 30 minutes. The reaction was cooled and partitioned between aqueous NaHCO$_3$ and EtOAc, and the organic was washed with 1N HCl and then basified with 1N NaOH, extracting with EtOAc. The solvent was removed under reduced pressure and purified on silica (2% ammonia in MeOH/EtOAc) to afford 2.8 mg (6%) of a yellow oil. $^1$H NMR (300 MHz, CDCl$_3$): δ 7.34 (d, 2H), 7.29 (d, 2H), 7.20 (d, 2H), 4.78 (s, 2H), 4.22 (s, 2H), 3.49 (s, 2H), 2.74 (s, 3H), 2.38 (s, 6H).

Example 78

4-[2-(4-Methylbenzyl)-1-oxo-2,3-dihydro-1H-isoindol-5-yl]-3,6-dihydro-2H-pyridine-1-carboxylic acid tert-butyl ester

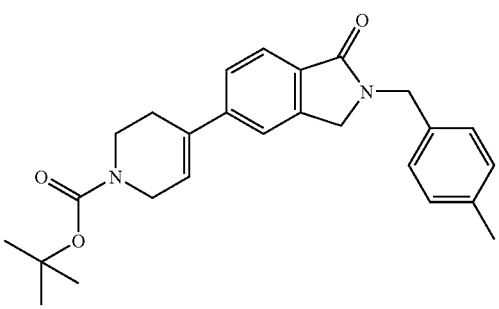

5-Bromo-2-(4-methyl-benzyl)-2,3-dihydro-isoindol-1-one (25 mg, 0.080 mmol), 4-boranate ester-3,6-dihydro-2H-pyridine-1-carboxylic acid tert-butyl ester (24 mg, 0.079 mmol), potassium carbonate (32 mg, 0.24 mmol), PdCl$_2$ (dppf) (3.8 mg, 0.005 mmol), was stirred in DMF (3 mL) at 110° C. for 18 hours, under argon. The cooled reaction was concentrated and the residue was partitioned between ethyl acetate and water. The organic phase was washed with water and brine, dried over magnesium sulfate, filtered and concentrated. Column chromatography (40% EtOAc/Hexanes) provided the title compound as a yellow solid (8.1 mg, 25%). ¹H NMR (300 MHz, CDCl₃): δ 7.85 (d, 1H), 7.49 (d, 1H), 7.36 (s, 1H), 7.20 (q, 4H), 6.11 (br s, 1H), 4.78 (s, 2H), 4.26 (s, 2H), 4.10 (dd, 2H, 3.66 (t, 2H), 2.53 (br s, 2H), 2.35 (s, 3H), 1.51 (s, 9H).

The following compounds were made in same the manner:

| Example | Structure | Name | Yield | NMR | GTPγS EC50 |
|---|---|---|---|---|---|
| 85 | 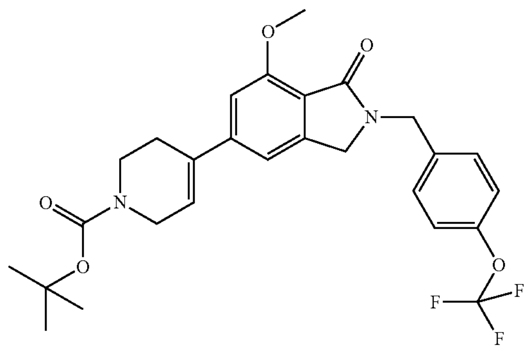 | 4-[7-Methoxy-1-oxo-2-(4-trifluoromethoxy-benzyl)-2,3-dihydro-1H-isoindol-5-yl]-3,6-dihydro-2H-pyridine-1-carboxylic acid tert-butyl ester | 122 mg (49%) colourless solid | 7.34-7.37 (m, 2H), 7.17 (d, 2H), 6.92 (d, 2H), 4.76 (s, 2H), 4.23 (s, 2H), 4.10-4.13 (m, 3H), 4.01 (s, 3H), 3.65 (t, 2H), 2.57 (br s, 2H), 1.51 (s, 9H) | 0.08 |
| 86 | 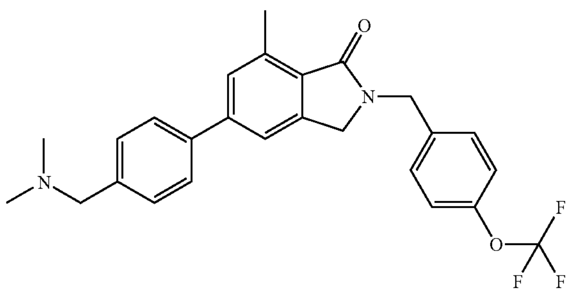 | 5-(4-Dimethylamino-methyl-phenyl)-7-methyl-2-(4-trifluoromethoxy-benzyl)-2,3-dihydro-isoindol-1-one | 75 mg (61%) brown solid | 7.56 (d, 2H), 7.36-7.45 (m, 6H), 7.19 (d, 2H), 4.81 (s, 2H), 4.30 (s, 2H), 3.49 (s, 2H, 2.83 (s, 3H), 2.29 (s, 6H) | 0.06 |
| 87 | 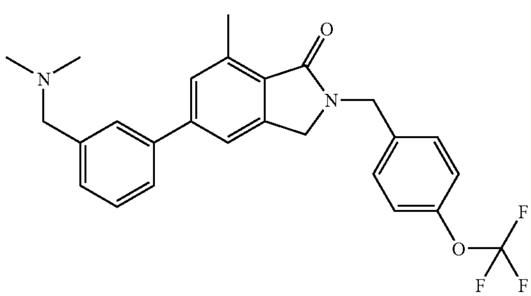 | 5-(3-Dimethylamino-methyl-phenyl)-7-methyl-2-(4-trifluoromethoxy-benzyl)-2,3-dihydro-isoindol-1-one | 60 mg (53%) brown oil | 7.55 (s, 1H), 7.39-7.43 (m, 3H), 7.19 (d, 2H), 5.05 (d, 1H), 4.32 (d, 1H), 4.14 (d, 1H), 2.64 (s, 3H) | 0.29 |
| J1 | 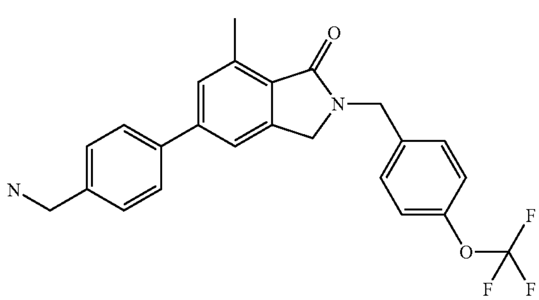 | 5-(4-Aminomethyl-phenyl)-7-methyl-2-(4-trifluoromethoxy-benzyl)-2,3-dihydro-isoindol-1-one | 60 mg 53% brown oil | 7.58 (dd, 2H), 7.38 (m, 6H), 7.20 (dd, 2H), 4.81 (s, 2H), 4.30 (s, 2H), 3.95 (s, 2H), 2.83 (s 3H) | |

-continued

| Example | Structure | Name | Yield | NMR | GTPγS EC50 |
|---|---|---|---|---|---|
| J2 | 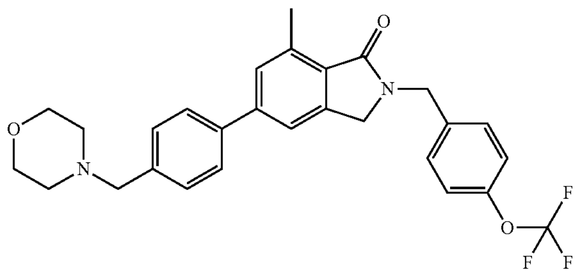 | 7-Methyl-5-(4-morpholin-4-ylmethyl-phenyl)-2-(4-trifluoromethoxy-benzyl)-2,3-dihydro-isoindol-1-one | 97 mg 78% brown oil | 7.55 (dd, 2H), 7.44-7.35 (m, 6H), 7.22 (dd, 2H), 4.81 (s, 2H), 4.30 (s, 2H), 3.75 (t, 4H), 3.57 (s, 2H), 2.83 (s, 3H), 2.50 (t, 4H) | |
| J9 | 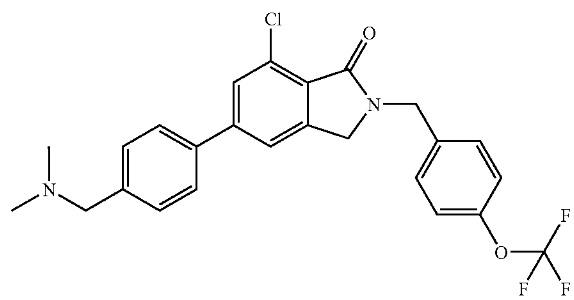 | 7-Chloro-5-(4-dimethylamino-methyl-phenyl)-2-(4-trifluoromethoxy-benzyl)-2,3-dihydro-isoindol-1-one | 35 mg 30% light brown solid | 7.64 (s, 1H), 7.55 (d, 2H), 7.49 (s, 4H), 7.44-7.38 (m, 4H), 7.21 (dd, 2H), 4.82 (s, 2H), 4.32 (s, 2H), 3.50 (s, 2H), 2.30 (s, 6H) | |
| J10 | 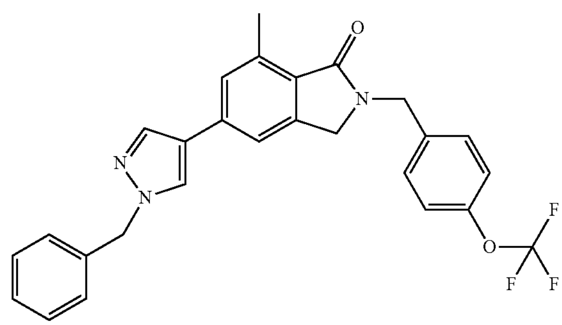 | 5-(1-Benzyl-1H-pyrazol-4-yl)-7-methyl-2-(4-trifluoromethoxy-benzyl)-2,3-dihydro-isoindol-1-one | 33 mg 37% yellow solid | 7.86 (d, 1H), 7.68 (d, 1H), 7.39-7.29 (m, 9H), 7.21 (dd, 2H), 5.36 (s, 2H), 4.78 (s, 2H), 4.23 (s, 2H), 2.77 (s, 3H) | |
| J13 | 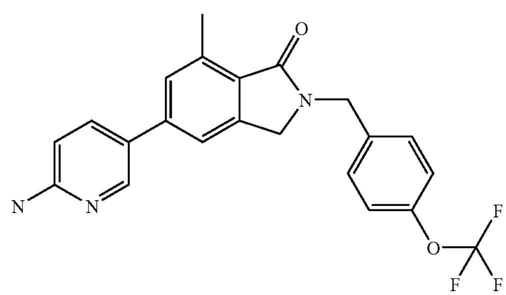 | 5-(6-Amino-pyridin-3-yl)-7-methyl-2-(4-trifluoromethoxy-benzyl)-2,3-dihydro-isoindol-1-one | 54 mg 70% beige solid | 8.33 (s, 1H), 7.68 (dd, 1H), 7.39.7.33 (m, 4H), 7.20 (d, 2H), 6.60 (d, 1H), 4.80 (s, 2H), 4.61 (s, 2H), 4.28 (s, 2H), 2.82 (s, 3H) | |
| J16 | 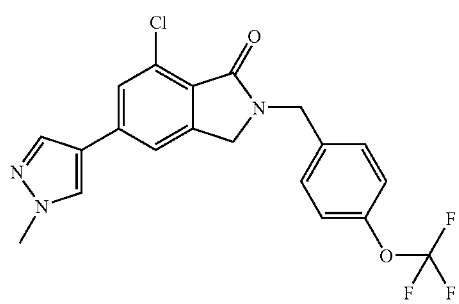 | 7-Chloro-5-(1-methyl-1H-pyrazol-4-yl)-2-(4-trifluoromethoxy-benzyl)-2,3-dihydro-isoindol-1-one | 34 mg 44% yellow oil | 7.79 (d, 1H) 7.67 (d, 1H), 7.37-7.30 (m, 4H), 7.21-7.18 (m, 2H), 4.78 (s, 2H), 4.25 (s, 2H), 3.97 (s, 3H), 2.77 (s, 3H | |

-continued

| Example | Structure | Name | Yield | NMR | GTPγS EC50 |
|---------|-----------|------|-------|-----|------------|
| J18 | 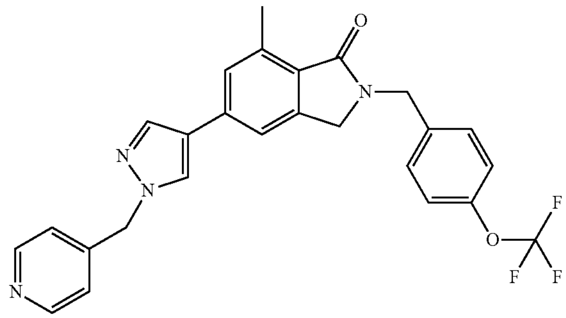 | 7-Methyl-5-(1-pyridin-4-ylmethyl-1H-pyrazol-4-yl)-2-(4-trifluoromethoxy-benzyl)-2,3-dihydro-isoindol-1-one | 36 mg 40% brown solid | 8.62 (br s, 2H), 8.03 (d, 1H), 7.75 (d, 1H), 7.37-7.32 (m, 4H), 7.21 (dd, 2H), 7.10 (d, 2H), 5.37 (s, 2H), 4.79 (s, 2H), 4.26 (s, 2H), 2.78 (s, 3H) | |
| J21 | 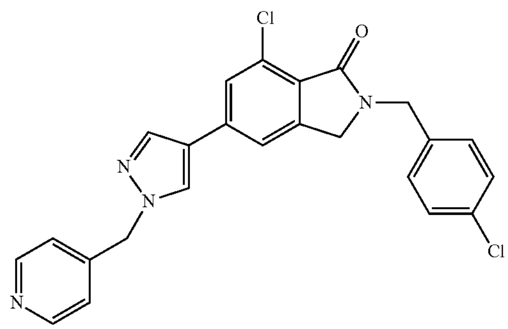 | 7-Chloro-2-(4-chloro-benzyl)-5-(1-pyridin-4-ylmethyl-1H-pyrazol-4-yl)-2,3-dihydro-isoindol-1-one | 48 mg 43% brown oil | 8.60 (br s, 2H), 7.88 (s, 1H), 7.78 (s, 1H), 7.50 (s, 1H), 7.37 (s, 1H), 7.33-7.25 (m, 4H), 7.21 (dd, 2H), 7.10 (d, 2H), 5.38 (s, 2H), 4.75 (s, 2H), 4.24 (s, 2H) | |
| J22 | 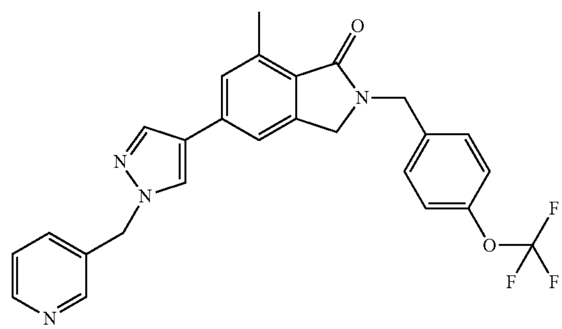 | 7-Methyl-5-(1-pyridin-3-ylmethyl-1H-pyrazol-4-yl)-2-(4-trifluoromethoxy-benzyl)-2,3-dihydro-isoindol-1-one | 67 mg 75% beige solid | 8.60 (br s, 2H), 7.91 (s, 1H), 7.85 (d, 1H), 7.71 (d, 1H), 7.58 (d, 1H), 7.36-7.30 (m, 5H), 7.19 (dd, 2H), 5.37 (s, 2H), 4.77 (s, 2H), 4.23 (s, 2H), 2.76 (s, 3H) | |
| J24 | 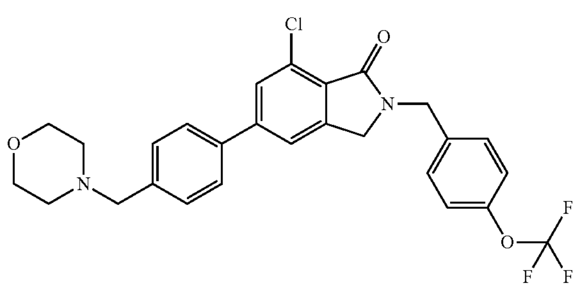 | 7-Chloro-5-(4-morpholin-4-ylmethyl-phenyl)-2-(4-trifluromethoxy-benzyl)-2,3-dihydro-isoindol-1-one | 61 mg 52% yellow oil | 7.62 (s, 1H), 7.53 (d, 2H), 7.48-7.35 (m, 5H), 7.21 (d, 2H), 4.82 (s, 2H), 4.32 (s, 2H), 3.74 (t, 4H) 3.55 (s, 2H), 2.49 (t, 4H) | |
| J29 | 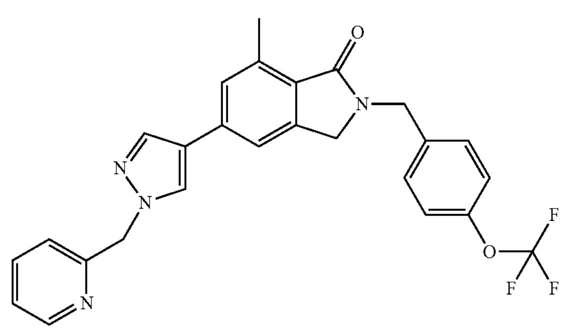 | 7-Methyl-5-(1-pyridin-2-ylmethyl-1H-pyrazol-4-yl)-2-(4-trifluoromethoxy-benzyl)-2,3-dihydro-isoindol-1-one | 30 mg 43% beige solid | 8.61 (d, 1H), 7.87 (d, 2H), 7.68 (t, 1H), 7.37-7.32 (m, 4H), 7.28-7.13 (m, 4H), 5.49 (s, 2H), 4.78 (s, 2H), 4.25 (s, 2H), 2.77 (s, 3H) | |

-continued

| Example | Structure | Name | Yield | NMR | GTPγS EC50 |
|---|---|---|---|---|---|
| J31 | 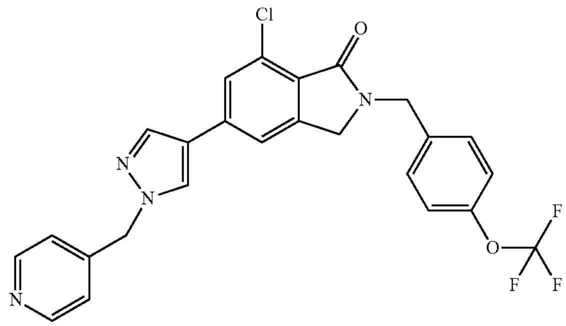 | 7-Chloro-5-(1-pyridin-4-ylmethyl-1H-pyrazol-4-yl)-2-(4-trifluoromethoxy-benzyl)-2,3-dihydro-isoindol-1-one | 37 mg 42% brown solid | 8.61 (dd, 2H), 7.89 (d, 1H), 7.78 (d, 1H), 7.61 (s, 1H), 7.51-7.47 (m, 3H), 7.20 (d, 2H), 7.13, (d, 2H), 5.38 (s, 2H), 4.79 (s, 2H), 4.26 (s, 2H) | |
| J33 | 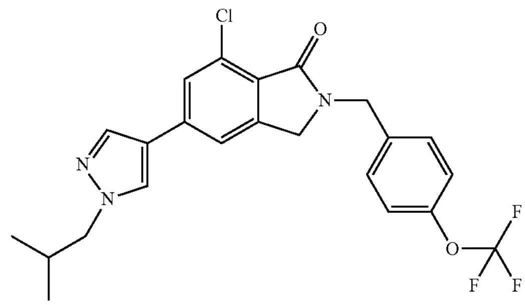 | 7-Chloro-5-(1-isobutyl-1H-pyrazol-4-yl)-2-(4-trifluoromethoxy-benzyl)-2,3-dihydro-isoindol-1-one | 40 mg 48% yellow oil | 7.80 (d, 1H), 7.69 (d, 1H), 7.50 (d, 1H), 7.38-7.35 (m, 3H), 7.20 (dd, 2H), 4.79 (s, 2H), 4.26 (s, 2H), 3.96 (d, 2H), 2.77-2.23 (m, 1H, 0.93 (d, 6H) | |
| J36 | 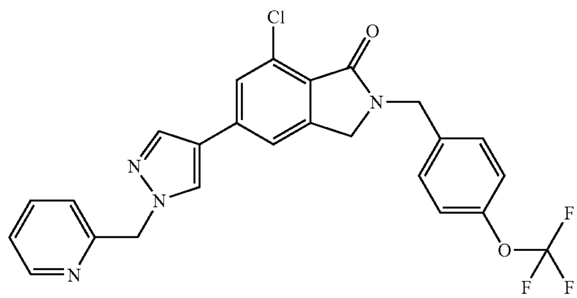 | 7-Chloro-5-(1-pyridin-2-ylmethyl-1H-pyrazol-4-yl)-2-(4-trifluoromethoxy-benzyl)-2,3-dihydor-isoindol-1-one | 39 mg 55% beige solid | 8.61 (br s, 1H), 7.88 (d, 2H), 7.71 (t 1H), 7.50 (s, 1H), 7.38-7.34 (m, 3H), 7.28 (s, 1H), 7.21-7.19 (m, 3H), 5.49 (s, 2H), 4.78 (s, 2H), 4.25 (s, 2H), | |
| J43 | 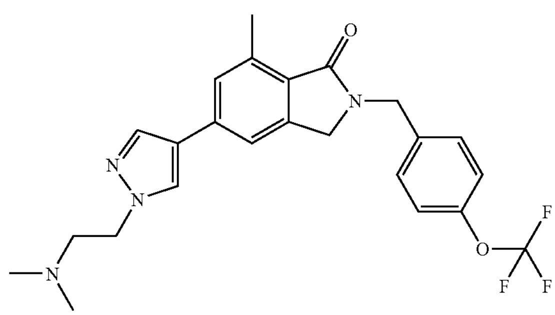 | 5-[1-(2-Dimethylamino-ethyl)-1H-pyrazol-4-yl]-7-methyl-2-(4-trifluoromethoxy-benzyl)-2,3-dihydro-isoindol-1-one | 35 mg 30% brown oil | 7.79 (dd, 2H), 7.37-7.31 (m, 4H), 7.20 (dd, 2H), 4.78 (s, 2H), 4.27 (t, 2H), 4.25 (s, 2H), 2.81 (t, 2H), 2.78 (s, 3H), 2.30 (s, 6H) | |
| J44 | 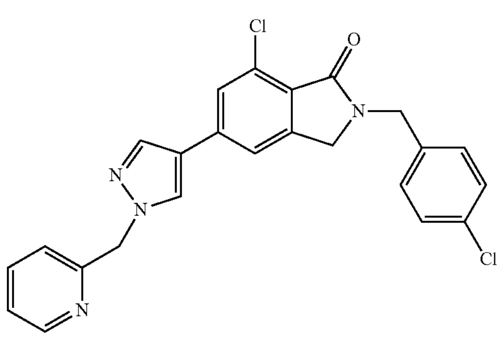 | 7-Chloro-2-(4-chloro-benzyl)-5-(1-pyridin-2-ylmethyl-1H-pyrazol-4-yl)-2,3-dihydro-isoindol-1-one | 15 mg 21% yellow oil | 8.61 (d, 1H), 7.87 (dd, 2H), 7.70 (d, 1H), 7.51 (d, 1H), 7.37 (d, 1H), 7.34-7.26 (m, 5H), 7.17 (d, 1H), 5.48 (s, 2H), 4.76 (s, 2H), 4.24 (s, 2H), | |

-continued

| Example | Structure | Name | Yield | NMR | GTPγS EC50 |
|---|---|---|---|---|---|
| J45 | 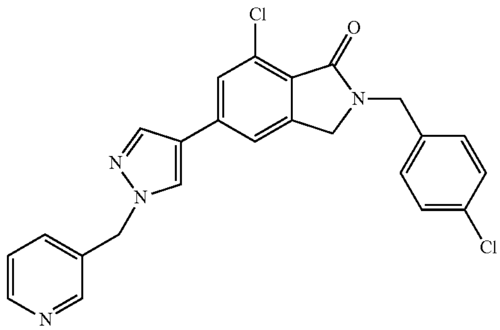 | 7-Chloro-2-(4-chloro-benzyl)-5-(1-pyridin-3-ylmethyl-1H-pyrazol-4-yl)-2,3-dihydro-isoindol-1-one | 31 mg 42% brown oil | 8.59 (br s, 2H), 7.88 (d, 1H), 7.77 (d, 1H), 7.50 (d, 1H), 7.37 (d, 1H), 7.32-7.24 (m, 4H), 7.10 (d, 2H), 5.38 (s, 2H), 4.74 (s, 2H), 4.24 (s, 2H), | |
| J53 | 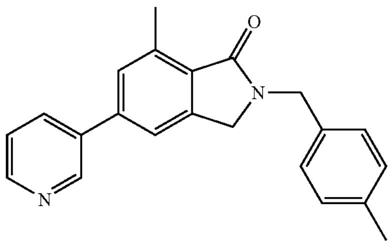 | 7-Methyl-2-(4-methyl-benzyl)-5-pyridin-3-yl-2,3-dihydro-isoindol-1-one | 33 mg 55% yellow oil | 8.84 (d, 1H), 8.63 (d, 1H), 7.87 (d, 1H), 7.42-7.38 (m, 3H) 7.23 (d, 2H), 7.16 (d, 2H), 4.77 (s, 2H), 4.29 (s, 2H), 2.85 (s, 3H), 2.35 (s, 3H) | |
| J54 | 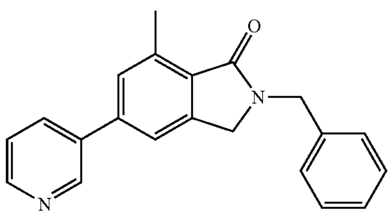 | 2-Benzyl-7-methyl-5-pyridin-3-yl-2,3-dihydro-isoindol-1-one | 45 mg 75% yellow oil | 8.85 (br s, 1H), 8.63 (br s, 1H), 7.88 (d, 1H), 7.41-7.29 (m, 8H), 4.82 (s, 2H), 4.30 (s, 2H), 2.85 (s, 3H) | |
| J55 | 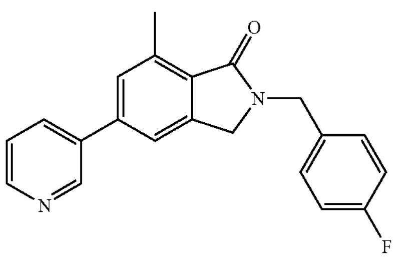 | 2-(4-Fluoro-benzyl)-7-methyl-5-pyridin-3-yl-2,3-dihydro-isoindol-1-one | 46 mg 77% yellow oil | 8.85 (d, 1H), 8.63 (d, 1H), 7.87 (d, 1H), 7.42-7.39 (m, 3H), 7.32-7.29 (m, 2H), 7.06-7.01 (m, 2H), 4.78 (s, 2H), 4.30 (s, 2H), 2.84 (s, 3H) | |
| J56 | 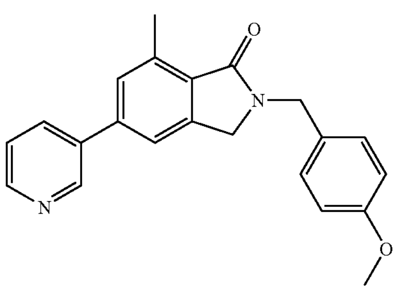 | 2-(4-Methoxy-benzyl)-7-methyl-5-pyridin-3-yl-2,3-dihydro-isoindol-1-one | 41 mg 68% yellow solid | 8.85 (br s, 1H), 8.63 (br s, 1H), 7.90-7.86 (m, 1H), 7.40-7.38 (m 3H), 7.27 (d, 2H), 6.88 (2, 2H), 4.75 (s, 2H), 4.28 (s, 2H), 3.81 (s, 3H), 2.85 (s, 3H) | |

| Example | Structure | Name | Yield | NMR | GTPγS EC50 |
|---|---|---|---|---|---|
| J57 | 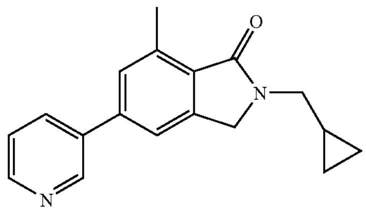 | 2-Cyclopropylmethyl-7-methyl-5-pyridin-3-yl-2,3-dihydro-isoindol-1-one | 38 mg 63% yellow solid | 8.87 (d, 1H), 8.64 (d, 1H), 7.89 (d, 1H), 7.42-7.38 (m, 3H), 4.52 (s, 2H), 3.49 (d, 2H), 2.81 (s, 3H), 1.07 (m, 1H), 0.62-0.58 (m, 2H), 0.38-0.35 (m, 2H) | |
| J58 | 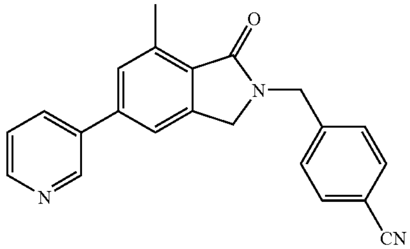 | 4-[(7-methyl-1-oxo-5-pyridin-3-yl-1,3-dihydro-2H-isoindol-2-yl)methyl]benzonitrile | 46 mg 77% yellow solid | 8.85 (d, 1H), 8.64 (d, 1H), 7.90-7.87 (m, 1H), 7.65 (d, 2H), 7.45-7.38 (m, 5H), 4.87 (s, 2H), 4.34 (s, 2H), 2.84 (s, 3H), 2.85 (s, 3H) | |
| J62 | 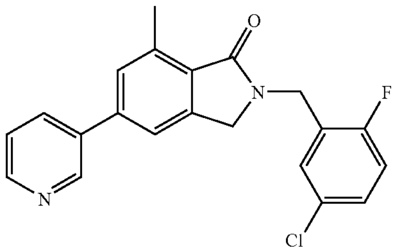 | 2-(5-Chloro-2-fluoro-benzyl)-7-methyl-5-pyridin-3-yl-2,3-dihydro-isoindol-1-one | 42 mg 70% colorless solid | 8.85 (d, 1H), 8.65 (d, 1H), 7.88 (d, 1H), 7.42-7.28 (m, 4H), 7.24 (m 1H), 7.05 t, 1H), 4.87 (s, 2H), 4.34 (s, 2H), 2.84 (s, 3H), 2.85 (s, 3H) | |
| J63 | 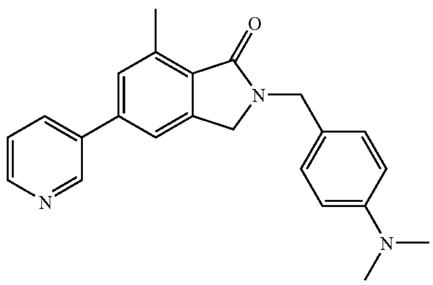 | 2-(4-Dimethylamino-benzyl)-7-methyl-5-pyridin-3-yl-2,3-dihydro-isoindol-1-one | 52 mg 87% brown oil | 8.84 (d, 1H), 8.63 (d, 1H), 7.86, (d, 1H), 7.41-7.36 (m, 3H), 7.23 (d, 2H), 6.72 (d, 2H), 4.71 (s, 2H), 4.27 (s, 2H), 2.95 (s, 6H), 2.85 (s, 3H) | |
| J64 | 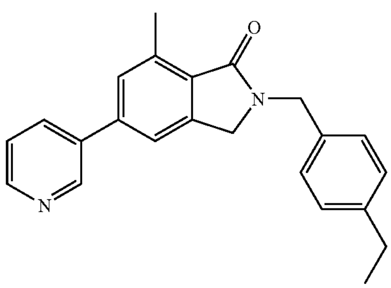 | 2-(4-Ethyl-benzyl)-7-methyl-5-pyridin-3-yl-2,3-dihydro-isoindol-1-one | 43 mg 72% yellow oil | 8.85 (br s, 1H), 8.64 (br s, 1H), 7.88 (d, 1H), 7.40-7.38 (m, 3H), 7.26 (dd, 2H), 7.19 (d, 2H), 4.78 (s, 2H), 4.30 (s, 2H), 2.85 (s, 3H), 2.65 (q, 2H), 1.26 (t, 3H) | |
| J69 | 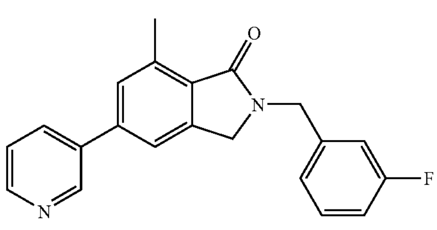 | 2-(3-Fluoro-benzyl)-7-methyl-5-pyridin-3-yl-2,3-dihydro-isoindol-1-one | 40 mg 69% brown oil | 8.85 (br s, 1H), 8.64 (br s, 1H), 7.88 (d, 1H), 7.42-7.28 (m, 4H), 7.11 (d, 1H), 7.00 (dd, 2H), 4.81 (s, 2H), 4.33 (s, 2H), 2.85 (s, 3H) | |

-continued

| Example | Name | Yield | NMR | GTPγS EC50 |
|---|---|---|---|---|
| J70 | 2-(2-Fluoro-benzyl)-7-methyl-5-pyridin-3-yl-2,3-dihydro-isoindol-1-one | 34 mg 59% yellow solid | 8.85 (br s, 1H), 8.64 (br s, 1H), 7.88 (d, 1H), 7.41-7.36 (m, 4H), 7.30-7.28 (m, 1H), 7.15-7.09 (m, 2H), 4.87 (s, 2H), 4.38 (s, 2H), 2.83 (s, 3H) | |
| J71 | 2-(4-Difluoromethoxy-benzyl)-7-methyl-5-pyridin-3-yl-2,3-dihydro-isoindol-1-one | 42 mg 70% colorless solid | 8.86 (br s, 1H), 8.65 (br s, 1H), 7.89 (d, 1H), 7.41-7.32 (m, 5H), 7.12 (dd, 2H), 6.75-6.26 (br t, 1H), 4.80 (s, 2H), 4.31 (s, 2H), 2.85 (s, 3H) | |
| J72 | 2-(4-Isopropyl-benzyl)-7-methyl-5-pyridin-3-yl-2,3-dihydro-isoindol-1-one | 26 mg 43% yellow oil | 8.86 (br s, 1H), 8.65 (br s, 1H), 7.88 (d, 1H), 7.41-7.38 (m, 3H), 7.28-7.20 (m, 4H), 4.78 (s, 2H), 4.31 (s, 2H), 2.93-2.89 (m, 1H), 2.85 (s, 3H), 1.26 (d, 6H) | |
| J76 | 2-(4-Fluoro-3-methyl-benzyl)-7-methyl-5-pyridin-3-yl-2,3-dihydro-isoindol-1-one | 35 mg 58% beige solid | 8.85 (br s, 1H), 8.63 (br s, 1H), 7.88 (d, 1H), 7.41-7.38 (m, 3H), 7.16-7.10 (m, 2H), 6.97 (t, 1H), 4.74 (s, 2H), 4.29 (s, 2H), 2.85 (s, 3H), 2.26 (s, 3H) | |
| J77 | 2-(4-Chloro-2-methyl-benzyl)-7-methyl-5-pyridin-3-yl-2,3-dihydro-isoindol-1-one | 38 mg 63% beige solid | 8.85 (br s, 1H), 8.64 (br s, 1H), 7.89 (d, 1H), 7.42-7.39 (m, 3H), 7.21-7.17 (m, 3H), 4.79 (s, 2H), 4.23 (s, 2H), 2.85 (s, 3H), 2.36 (s, 3H) | |

-continued

| Example | Structure | Name | Yield | NMR | GTPγS EC50 |
|---|---|---|---|---|---|
| J78 | 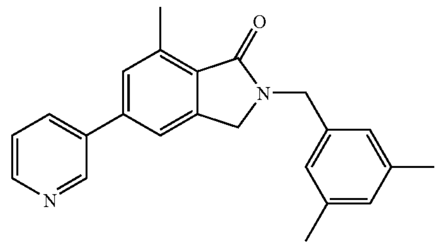 | 2-(3,5-Dimethyl-benzyl)-7-methyl-5-pyridine-3-yl-2,3-dihydro-isoindol-1-one | 23 mg 38% beige solid | 8.86 (br s, 1H), 8.64 (br s, 1H), 7.90 (d, 1H), 7.42-7.39 (m, 3H), 6.95 (s, 3H), 4.74 (s, 2H), 4.30 (s, 2H), 2.85 (s, 3H), 2.32 (s, 6H) | |
| J79 | 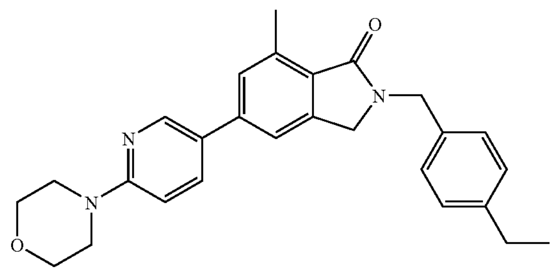 | 2-(4-Ethyl-benzyl)-7-methyl-5-(6-morpholin-4-yl-pyridin-3-yl)-2,3-dihydro-isoindol-1-one | 45 mg 61% yellow solid | 8.45 (d, 1H), 7.75 (d, 1H), 7.33 (d, 2H), 7.25 (dd, 2H), 7.19 (dd, 2H), 6.73 (d, 1H), 4.77 (s, 2H), 4.26 (s, 2H), 3.88-3.80 (m, 4H), 3.60-3.56 (m, 4H), 2.82 (s, 3H), 2.65 (q, 2H), 1.23 (t, 3H) | |
| J82 | Chiral | 2-[(1R)-1-(4-chlorophenyl)ethyl]-7-methyl-5-pyridin-3-ylisoindolin-1-one | 31 mg 52% colorless solid | 8.84 (br s, 1H), 8.63 (br s, 1H), 7.87 (d, 1H), 7.41-7.39 (m, 3H), 7.33 (s, 4H), 5.79 (q, 1H), 4.37 (d, 1H), 4.03 (d, 1H), 2.83 (s, 3H), 1.70 (d, 3H) | |
| J83 | Chiral | 2-[(1S)-1-(4-chlorophenyl)ethyl]-7-methyl-5-pyridin-3-ylisoindolin-1-one | 41 mg 68% colorless solid | 8.84 (br s, 1H), 8.63 (br s, 1H), 7.87 (d, 1H), 7.41-7.39 (m, 3H), 7.33 (s, 4H), 5.79 (q, 1H), 4.37 (d, 1H), 4.03 (d, 1H), 2.83 (s, 3H), 1.70 (d, 3H) | |
| J88 | Chiral | 2-(1-Cyclohexyl-ethyl)-7-methyl-5-pyridin-3-yl-2,3-dihydro-isoindol-1-one | 40 mg 63% colorless solid | 8.87 (br s, 1H), 8.63 (d, 1H), 7.90 (d, 1H), 7.45-7.39 (m, 3H), 4.34 (q, 2H), 4.21 (q, 1H), 2.82 (s, 3H), 1.90-1.86, (m, 2H), 1.68 (m, 2H), 1.55-1.50 (m, 2H), 1.30 (d, 3H), 1.28-1.06 (m, 5H) | |

| Example | Structure | Name | Yield | NMR | GTPγS EC50 |
|---|---|---|---|---|---|
| J89 | Chiral | (S)2-(1-Cyclohexyl-ethyl)-7-methyl-5-pyridin-3-yl-2,3-dihydro-isoindol-1-one | 49 mg 78% colorless solid | 8.87 (d, 1H), 8.64 (d, 1H), 7.90 (d, 1H), 7.46-7.38 (m, 3H), 4.33 (q, 2H), 4.21 (q, 1H), 2.82 (s, 3H), 1.88 (m, 2H), 1.68 (m, 2H), 1.55-1.50 (m, 2H), 1.30 (d, 3H), 1.25-1.06 (m, 5H) | |
| J91 | Chiral | 2-[(1R)-1-(4-fluorophenyl)ethyl]-7-methyl-5-pyridin-3-ylisoindolin-1-one | 34 mg 57% colorless solid | 8.83 (br s, 1H), 8.63 (d, 1H), 7.87 (d, 1H) 7.41-7.35 (m, 5H), 7.08-7.02 (m, 2H), 5.80 (q, 1H), 4.37 (d, 1H), 4.03 (d, 1H), 2.84 (s, 3H), 1.70 (d, 3H) | |
| J92 | Chiral | 2-[(1S)-1-(4-fluorophenyl)ethyl]-7-methyl-5-pyridin-3-ylisoindolin-1-one | 33 mg 55% colorless solid | 8.83 (br s, 1H), 8.63 (br s, 1H), 7.86 (d, 1H), 7.41-7.35 (m, 5H), 7.08-7.02 (m, 2H), 5.80 (q, 1H), 4.37 (d, 1H), 4.03 (d, 1H), 2.84 (s, 3H), 1.70 (d, 3H) | |
| J93 | 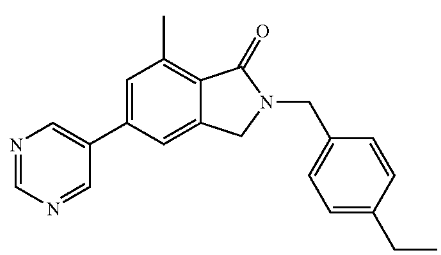 | 2-(4-Ethyl-benzyl)-7-methyl-5-pyrimidin-5-yl-2,3-dihydro-isoindol-1-one | 10 mg 17% brown oil | 9.25 (s, 1H), 8.96 (s, 2H), 7.40 (d, 2H), 7.27 (d, 2H), 7.19 (d, 2H), 4.79 (s, 2H), 4.32 (s, 2H), 2.87 (s, 3H), 2.65 (q, 2H), 1.24 (t, 3H) | |
| J94 | 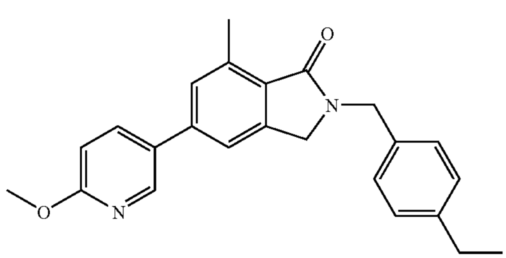 | 2-(4-Ethyl-benzyl)-5-(6-methoxy-pyridin-3-yl)-7-methyl-2,3-dihydro-isoindol-1-one | 89 mg 82% yellow oil | 8.38 (d, 1H), 7.79 (d, 1H), 7.33 (d, 2H), 7.27 (d, 2H), 7.18 (d, 2H), 6.84 (d, 1H), 4.77 (s, 2H), 4.28 (s, 2H), 4.00 (s, 3H), 2.83 (s, 3H), 2.65 (q, 2H), 1.26 (t, 3H) | |

| Example | Structure | Name | Yield | NMR | GTPγS EC50 |
|---|---|---|---|---|---|
| J96 | 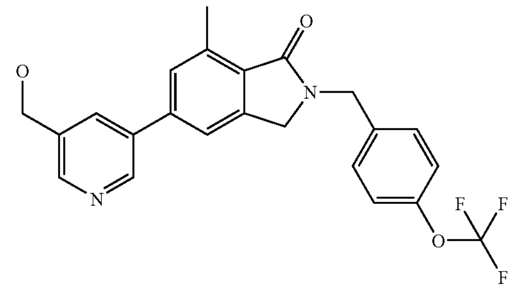 | 5-(5-Hydroxymethyl-pyridin-3-yl)-7-methyl-2-(4-trifluoromethoxy-benzyl)-2,3-dihydro-isoindol-1-one | 72 mg 55% brown oil | 8.74 (s, 1H), 8.60 (s, 1H), 7.94 (s, 1H), 7.41-7.35 (m, 4H), 7.22 (d, 2H), 4.84 (s, 2H), 4.80 (s, 2H), 4.30 (s, 2H), 2.90 (s, 3H) | |
| J99 | 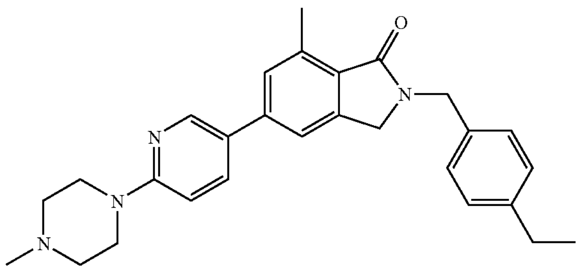 | 2-(4-Ethyl-benzyl)-7-methyl-5-[6-(4-methyl-piperazin-1-yl)-pyridin-3-yl]-2,3-dihydro-isoindol-1-one | 56 mg 73% brown solid | 8.45 (s, 1H), 7.73 (d, 1H), 7.32 (d, 2H), 7.24 (d, 2H), 7.18 (d, 2H), 6.74 (d, 1H), 4.77 (s, 2H), 4.26 (s, 2H), 3.65 (t, 4H), 2.82 (s, 3H), 2.65 (q, 2H), 2.56 (t, 4H), 2.38 (s, 3H), 1.24 (t, 3H) | |
| J102 | 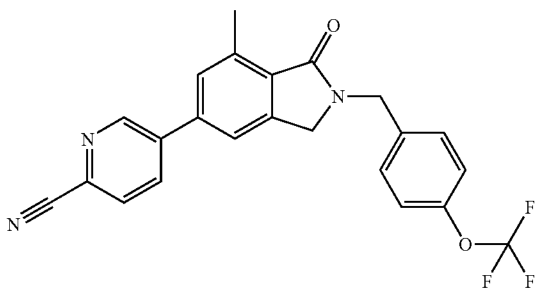 | 5-[7-Methyl-1-oxo-2-(4-trifluoromethoxy-benzyl)-2,3-dihydro-1H-isoindol-5-yl]-pyridine-2-carbonitrile | 39 mg 64% colorless solid | 8.95 (s, 1H), 8.02 (d, 1H), 7.81 (d, 1H), 7.44 (s, 2H), 7.37 (d, 2H), 7.23 (d, 2H), 4.83 (s, 2H), 4.35 (s, 2H), 2.87 (s, 3H) | |
| J103 | 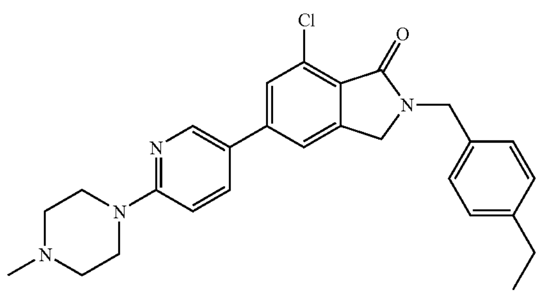 | 7-Chloro-2-(4-ethyl-benzyl)-5-[6-(4-methyl-piperazin-1-yl)-pyridin-3-yl]-2,3-dihydro-isoindol-1-one | 42 mg 42% brown solid | 8.42 (s, 1H), 7.69 (d, 1H), 7.52 (s, 1H), 7.37 (s, 1H), 7.26 (d, 2H), 7.18 (d, 2H), 6.73 (d, 1H), 4.77 (s, 2H), 4.27 (s, 2H), 3.65 (t, 4H), 2.65 (q, 2H), 2.55 (t, 4H), 2.37 (s, 3H), 1.25 (t, 3H) | |
| J104 | 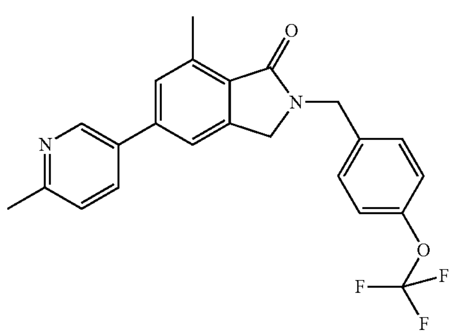 | 7-Methyl-5-(6-methyl-pyridin-3-yl)-2-(4-trifluoromethoxy-benzyl)-2,3-dihydro-isoindol-1-one | 31 mg 48% brown solid | 8.73 (s, 1H), 7.79 (d, 1H), 7.40-7.36 (m, 4H), 7.27-7.19 (m, 3H), 4.81 (s, 2H), 4.32 (s, 2H), 2.84 (s, 3H), 2.63 (s, 3H) | |

-continued

| Example | Structure | Name | Yield | NMR | GTPγS EC50 |
|---|---|---|---|---|---|
| J106 | 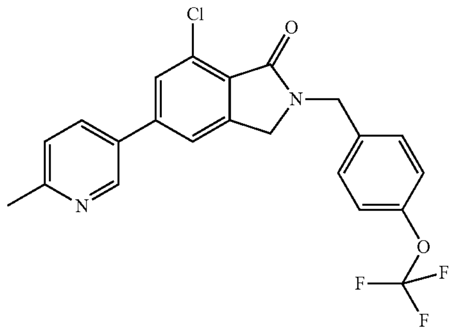 | 7-Chloro-5-(6-methyl-pyridin-3-yl)-2-(4-trifluoromethoxy-benzyl)-2,3-dihydro-isoindol-1-one | 24 mg 44% yellow solid | 8.72 (s, 1H), 7.78 (d, 1H), 7.61 (s, 1H), 7.48 (s, 1H), 7.39 (d, 2H), 7.28 (d, 2H), 7.21 (d, 2H), 4.83 (s, 2H), 4.34 (s, 2H), 2.63 (s, 3H) | |
| J111 | 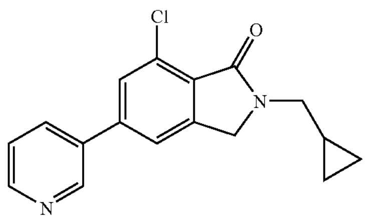 | 7-Chloro-2-cyclopropylmethyl-yl-5-pyridin-3-yl-2,3-dihydro-isoindol-1-one | 22 mg 55% yellow solid | 8.86 (s, 1H), 8.68 (d, 1H), 7.91 (d, 1H), 7.60 (s, 1H), 7.56 (s, 1H), 7.44 (t, 1H), 4.55 (s, 2H), 3.51 (d, 2H), 1.10-1.05 (m, 1H), 0.63-0.58 (m, 2H), 0.38-0.36 (m, 2H) | |
| J112 | 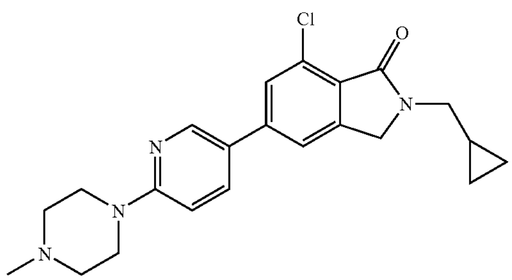 | 7-Chloro-2-cyclopropylmethyl-5-[6-(4-methyl-piperazin-1-yl)-pyridin-3-yl]-2,3-dihydro-isoindol-1-one | 28 mg 50% yellow solid | 8.45 (s, 1H), 7.72 (d, 1H), 7.52 (s, 1H), 7.46 (s, 1H), 7.74 (d, 1H), 4.51 (s, 2H), 3.66 (t, 4H), 3.49 (d, 2H), 2.56 (t, 4H), 2.38 (s, 3H), 1.06-1.04 (m, 1H), 0.63-0.57 (m, 2H), 0.38-0.33 (m, 2H) | |
| J113 | 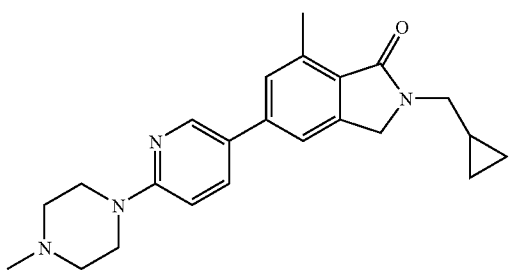 | 2-Cyclopropylmethyl-7-methyl-5-[6-(4-methyl-piperazin-1-yl)-pyridin-3-yl]-2,3-dihydro-isoindol-1-one | 17 mg 31% beige solid | 8.48 (s, 1H), 7.76 (d, 1H), 7.40 (s, 1H), 7.34 (s, 1H), 6.75 (d, 1H), 4.50 (s, 2H), 3.65 (t, 4H), 3.48 (d, 2H), 2.779 (s, 3H), 2.57 (t, 4H), 2.38 (s, 3H), 1.09-1.04 (m, 1H), 0.63-0.57 (m, 2H), 0.38-0.33 (m, 2H) | |
| J117 | 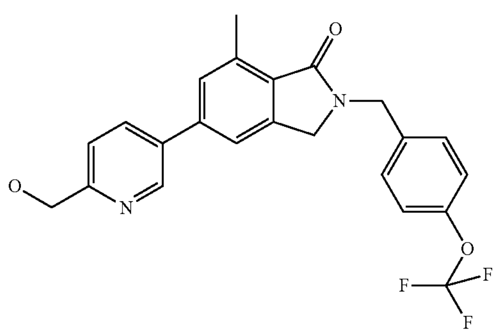 | 5-(6-Hydroxymethyl-pyridin-3-yl)-7-methyl-2-(4-trifluoromethoxy-benzyl)-2,3-dihydro-isoindol-1-one | 201 mg 20% brown solid | 8.78 (s, 1H), 7.89 (d, 1H), 7.41-7.36 (m, 5H), 7.21 (d, 2H), 4.85 (s, 2H), 4.82 (s, 2H), 4.32 (s, 2H), 3.80 (br s, 1H), 2.84 (s, 3H) | |

-continued

| Example | Structure | Name | Yield | NMR | GTPγS EC50 |
|---|---|---|---|---|---|
| J122 | Chiral | 2-(1-Cyclohexyl-ethyl)-7-methyl-5-[6-(4-methyl-piperazin-1-yl)-pyridin-3-yl]-2,3-dihydro-isoindol-1-one | 35 mg 73% brown solid | 8.46 (s, 1H), 7.75 (d, 1H), 7.38 (s, 1H), 7.33 (s, 1H), 6.74 (d, 1H), 4.30 (q, 2H), 4.21-4.17 (m, 1H), 3.65 (t, 4H), 2.79 (s, 3H), 2.57 (t, 4H), 2.38 (s, 3H), 2.01 (br s, 1H), 1.84-1.78 (m, 2H), 1.67-1.65 (m, 2H), 1.50-1.48 (m, 2H), 1.27 (d, 3H), 1.15-1.05 (m, 4H) | |
| 123 | 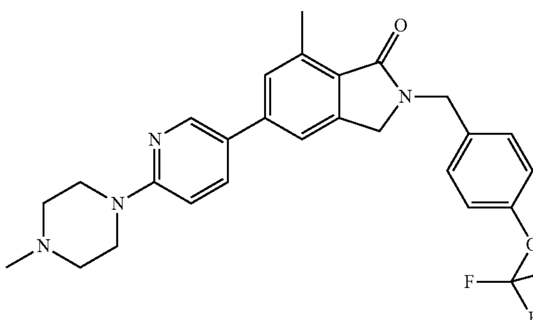 | 7-Methyl-5-[6-(4-methyl-piperazin-1-yl)-pyridin-3-yl]-2-(4-trifluoromethoxy-benzyl)-2,3-dihydro-isoindol-1-one | 71 mg 45% yellow solid | 8.45 (s, 1H), 7.73 (d, 1H), 7.37-7.34 (m, 4H), 7.20 (s, dH), 6.74 (d, 1H), 4.80 (s, 2H), 4.29 (s, 2H), 3.65 (t, 4H), 2.82 (s, 3H), 2.56 (t, 4H), 2.38 (s, 3H) | |
| J124 | 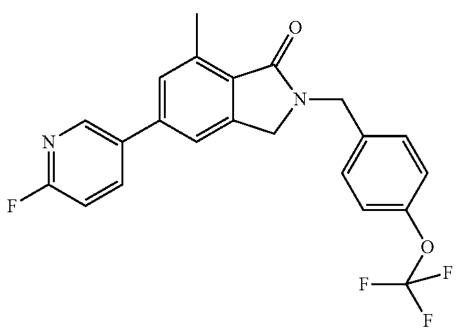 | 5-(6-Fluoro-pyridin-3-yl)-7-methyl-2-(4-trifluoromethoxy-benzyl)-2,3-dihydro-isoindol-1-one | 68 mg 73% white solid | 8.43 (s, 1H), 7.99 (t, 1H), 7.37 (dd, 4H), 7.22 (d, 2H), 7.05 (d, 1H), 4.82 (s, 2H), 4.32 (s, 2H), 2.84 (s, 3H) | |
| J129 | 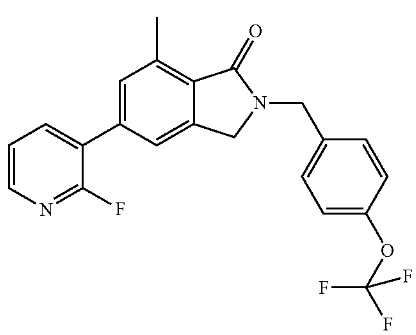 | 5-(2-Fluoro-pyridin-3-yl)-7-methyl-2-(4-trifluoromethoxy-benzyl)-2,3-dihydro-isoindol-1-one | 86 mg 74% colorless solid | 8.24 (s, 1H), 7.89 (t, 1H), 7.42-7.30 (m, 5H), 7.20 (d, 2H), 4.81 (s, 2H), 4.31 (s, 2H), 2.83 (s, 3H) | |

Example 79

4-[7-Chloro-1-oxo-2-(4-trifluoromethoxybenzyl)-2,3-dihydro-1H-isoindol-5-ylmethyl]-piperidine-1-carboxylic acid tert-butyl ester

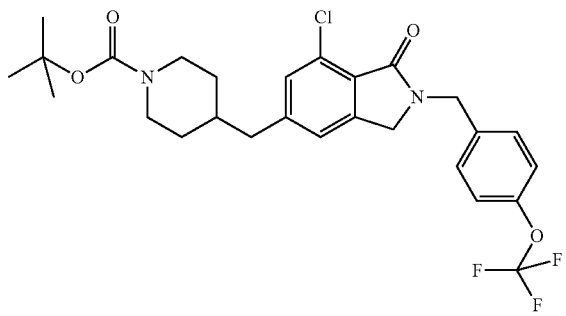

To a purged (Argon) sample of 4-Methylene-piperidine-1-carboxylic acid tert-butyl ester (51.6 mg, 0.26 mmol) was added 9-BBN. The mixture was stirred at 60° C. for one hour. After cooling to room temperature this solution was added to 5-bromo-7-chloro-2-(4 trifluoromethoxy-benzyl)-2,3-dihydro-isoindol-1-one (100.0 mg, 0.24 mmol), Pd(dppf)Cl$_2$ (5.9 mg, 0.0072 mmol), DMF (2.0 mL), potassium carbonate 943.1 mg, 0.31 mmol) and water (0.2 mL). The mixture was allowed to stir at 75° C. overnight. The mixture was then cooled to room temperature and poured into water (3 mL). The pH was adjusted to 11 with aqueous sodium hydroxide (3N). The product was extracted with ethyl acetate. The combined organic layers were washed with water three times, brine, dried over sodium sulphate, filtered and concentrated. Column chromatography (30% Ethyl acetate/hexanes) provided the title compound (54.9 mg, 44%).

The following compound was made in a similar fashion

| Example | Structure | Name | Yield | NMR |
|---|---|---|---|---|
| M2 | 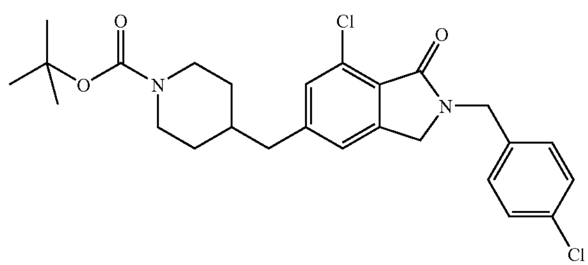 | 4-[7-Chloro-2-(4-chloro-benzyl)-1-oxo-2,3-dihydro-1H-isoindol-5-ylmethyl]-piperidine-1-carboxylic acid tert-butyl ester | 63 mg 47.7% colorless solid | 7.24-7.32 (m, 4H), 7.19 (s, 1H), 7.04 (m, 1H), 4.73 (s, 2H), 4.09-4.20 (m, 2H), 2.57-2.70 (m, 4H), 1.56-1.79 (, 3H), 1.45 (s, 9H), 1.05-1.20 (m, 2H) |
| M7 | 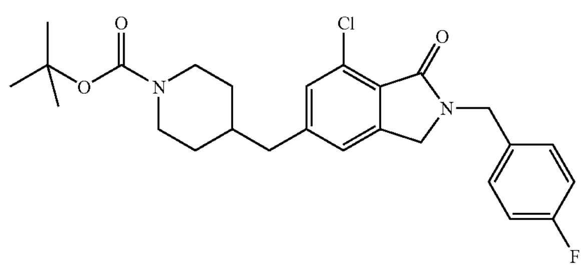 | 4-[7-Chloro-2-(4-fluoro-benzyl)-1-oxo-2,3-dihydro-1H-isoindol-5-ylmethyl]-piperidine-1-carboxylic acid tert-butyl ester | 47.2 mg, 36.9%, yellow solid | 7.29-7.33 (m, 2H), 7.19 (s, 1H), 6.99-7.05 (m, 3H), 4.74 (s, 2H), 4.20 (s, 2H), 3.90-4.11 (m, 2H), 2.57-2.63 (m, 4H), 1.46-1.61 (m, 3H), 1.45 (s, 9H), 1.15-1.27 (m, 2H) |
| M11 | 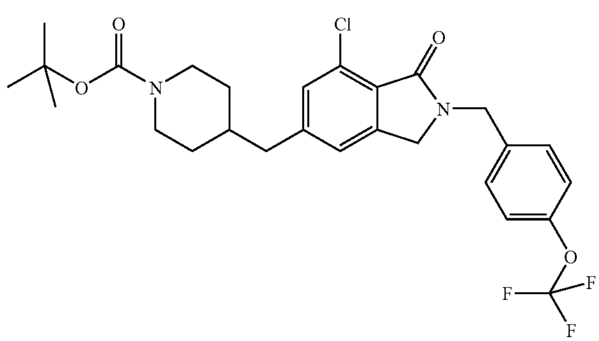 | 4-[7-Chloro-1-oxo-2-(4-trifluoromethoxy-benzyl)-2,3-dihydro-1H-isoindol-5-ylmethyl]-piperidine-1-carboxylic acid tert-butyl ester | 97.4 mg, 67%, yellow oil | 7.34-7.37 (m, 2H), 7.16-7.19 (m, 3H), 7.05 (s, 1H), 4.76 (s, 2H), 4.22 (s, 2H), 4.08-4.13 (m, 2H), 2.57-2.62 (m, 4H), 1.56-1.61 (m, 3H), 1.44 (s, 9H), 1.15-1.26 (m, 2H) |

-continued

| Example | Structure | Name | Yield | NMR |
|---|---|---|---|---|
| M16 | 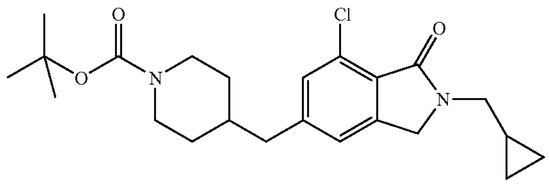 | 4-(7-chloro-2-cyclopropylmethyl-1-oxo-2,3-dihydro-1H-isoindol-5-ylmethyl)-piperidine-1-carboxylic acid tert-butyl-ester | 74.1 mg, 65.5%, yellow oil | 7.16 (s, 1H), 7.11 (s, 1h0, 4.42 (s, 2H), 4.10-4.13 (m, 2H), 3.45 (d, 2H), 2.58-2.63 (m, 4H), 1.58-1.62 (m, 3H), 1.45 (s, 9H), 0.99-1.22 (m, 3H), 0.54-0.58 (m, 2H), 0.32-0.34 (m, 2H) |
| M30 | 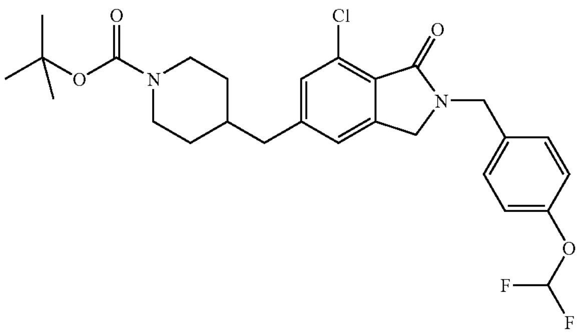 | 4-[7-Chloro-2-(4-difluoromethoxy-benzyl)-1-oxo-2,3-dihydro-1H-isoindol-5-ylmethyl]-piperidine-1-carboxylic acid tert-butyl ester | 94 mg, 40.4%, yellow oil | 7.30-7.34 (m, 2H), 7.18-7.19 (m, 1H), 7.05-7.10 (m, 3H), 6.25-6.74 (t, 1H), 4.74 (s, 2H), 4.21 (s, 2H), 4.11-4.13 (m, 2H), 2.56-2.70 (m, 4H), 1.80-1.95 (m, 1H), 1.47-1.60 (m, 3H), 1.46 (s, 9H), 1.02-1.24 (m, 1H) |
| M35 | 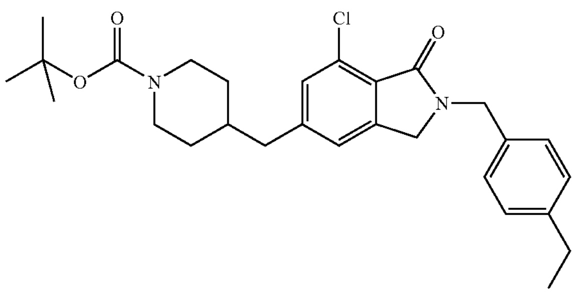 | 4-[7-Chloro-2-(4-ethyl-benzyl)-1-oxo-2,3-dihydro-1H-isoindol-5-ylmethyl]-piperidine-1-carboxylic acid tert-butyl ester | 72.1 mg, 55.3%, yellow foam | 7.23-7.26 (m, 2H), 7.15-7.18 (m, 3H), 7.03 (s, 1H), 4.74 (s, 2H), 4.19 (s, 2H), 4.02-4.12 (m, 2H), 2.56-2.67 (m, 6H), 1.82-1.92 (m, 2H), 1.52-1.67 (m, 3H), 1.47 (s, 9H), 1.25 (t, 3H), 1.15-1.20 (m, 2H) |
| M53 | 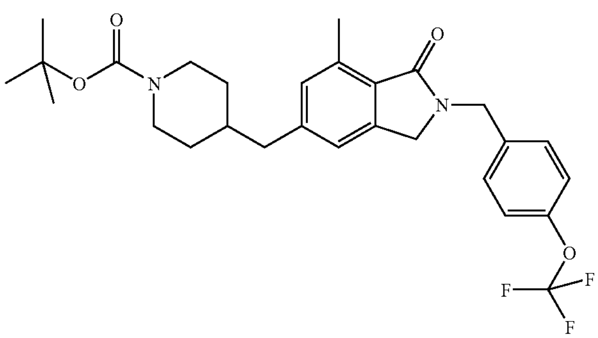 | 4-[7-Methyl-1-oxo-2-(4-trifluoromethoxy-benzyl)-2,3-dihydro-1H-isoindol-5-ylmethyl]-piperidine-1-carboxylic acid tert-butyl ester | 1.89 g, 64%, yellow foam | 7.25-7.28 (m, -H), 7.07-7.10 (m, 2H), 6.91 (s, 2H), 4.68 (s, 2H), 4.14 (m, 2H), 3.99-4.04 (m, 2H), 2.66 (s, 3H), 2.47-2.57 (m, 4H), 1.50-1.73 (m, 3H), 1.38 (s, 9H), 1.05-1.14 (m, 2H) |
| M60 | 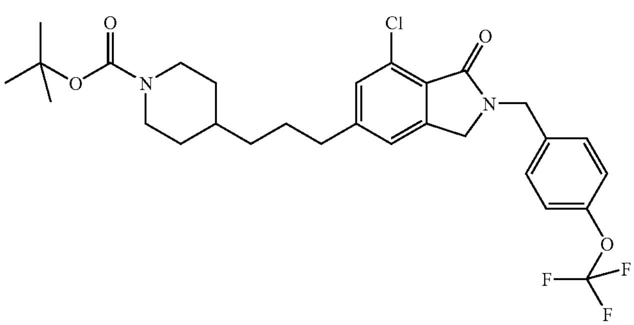 | 4-{3-[7-Chloro-1-oxo-2-(4-trifluoromethoxy-benzyl)-2,3-dihydro-1H-isoindol-5-yl]-propyl}-piperidine-1-carboxylic acid tert-butyl ester | 57.9 mg, 39%, yellow oil | 7.34-7.38 (m, 2H), 7.17-7.21 (m, 3H), 7.09 (s, 1H), 4.76 (s, 2H), 4.22 (s, 2H), 3.95-4.10 (br, 2H), 2.62-2.67 (m, 4), 1.61-1.65 (m, 4H), 1.45 (s, 9H), 1.23-1.28 (m, 3H), 1.10-1.15 (m, 2H) |

-continued

| Example | Structure | Name | Yield | NMR |
|---------|-----------|------|-------|-----|
| M64 | 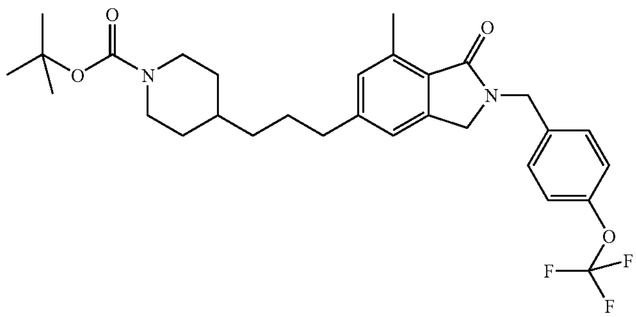 | 4-{3-[7-Methyl-1-oxo-2-(4-trifluoromethoxy-benzyl)-2,3-dihydro-1H-isoindol-5-yl]-propyl}-piperidine-1-carboxylic acid tert-butyl ester | 70.0 mg, 51.2%, yellow oil | 7.33-7.36 (m, 2H), 7.17-7.20 (m, 2H), 7.00-7.02 (d, 2H), 4.77 (s, 2H), 4.21 (s, 2H), 4.10-4.18 (m, 2H), 2.74 (s, 3H), 2.60-2.65 (m, 2H), 1.62-1.67 (m, 3H), 1.46 (s, 9H), 1.20-1.26 (m, 2H), 1.02-1.15 (m, 2H) |

Example 80

7-Chloro-5-piperidin-4-ylmethyl-2-(4-trifluoromethoxybenzyl)-2,3-dihydro-isoindol-1-one

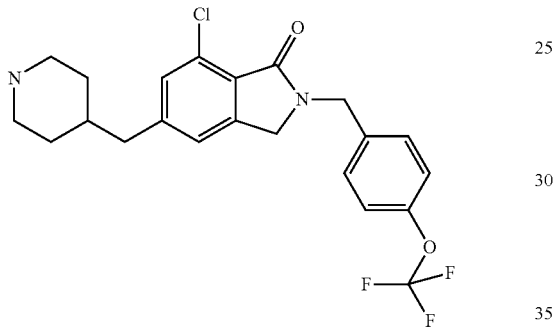

4-[7-Chloro-1-oxo-2-(4-trifluoromethoxybenzyl)-2,3-dihydro-1H-isoindol-5-ylmethyl]-piperidine-1-carboxylic acid tert-butyl ester (54.90 mg, 0.102 mmol) was stirred in dichloromethane (2 mL) and trifluoroacetic acid (2 mL) overnight. The reaction mixture was quenched with sodium carbonate to pH=8-9 and the free base was extracted with dichloromethane. The organic layer was washed with water, brine, dried over sodium sulfate, filtered and concentrated to provide the title compound (48.9 mg, 100%).

The following compound was made in a similar fashion

| Example | Structure | Name | Yield | NMR |
|---------|-----------|------|-------|-----|
| M3 | 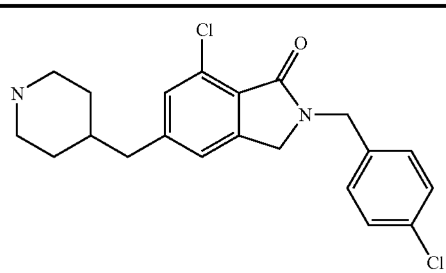 | [7-Chloro-2-(4-chloro-benzyl)-5-piperidin-4-ylmethyl-2,3-dihydro-isoindol-1-one | 50 mg 100% colorless oil | N/A |
| M8 | 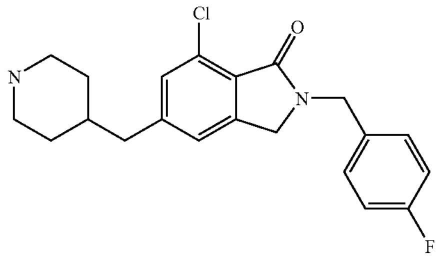 | [7-Chloro-2-(4-fluoro-benzyl)-5-piperidin-4-ylmethyl-2,3-dihydro-isoindol-1-one | 40 mg 100% colorless oil | N/A |

-continued

| Example | Structure | Name | Yield | NMR |
|---|---|---|---|---|
| M12 | 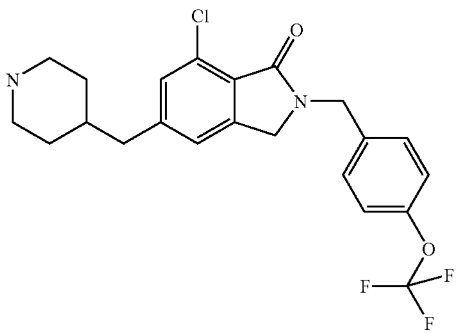 | [7-Chloro-5-piperidin-4-ylmethyl-2-(4-trifluoromethoxy-benzyl)-2,3-dihydro-isoindol-1-one | 45 mg 100% colorless oil | N/A |
| M17 | 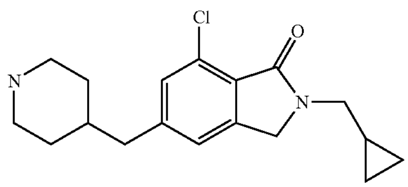 | 7-chloro-2-cyclopropylmethyl-5-piperidin-4-ylmethyl-2,3-dihydro-isoindol-1-one | 51 mg, 100%, yellow oil | N/A |
| M31 | 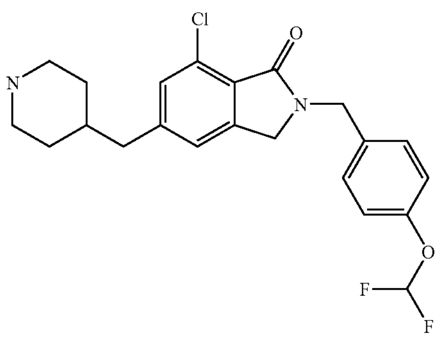 | [7-Chloro-2-(4-difluoromethoxy-benzyl)-5-piperidin-4-ylmethyl-2,3-dihydro-isoindol-1-one | 95 mg, 98%, yellow oil | N/A |
| M36 | 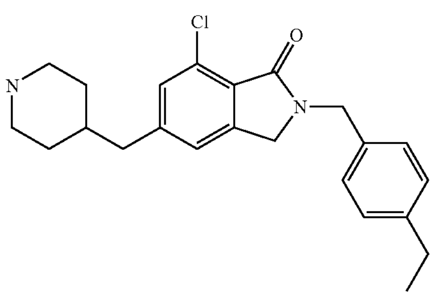 | 7-Chloro-2-(4-ethyl-benzyl)-5-piperidin-4-ylmethyl-2,3-dihydro-isoindol-1-one | 56 mg, 95%, yellow foam | N/A |
| M46 | 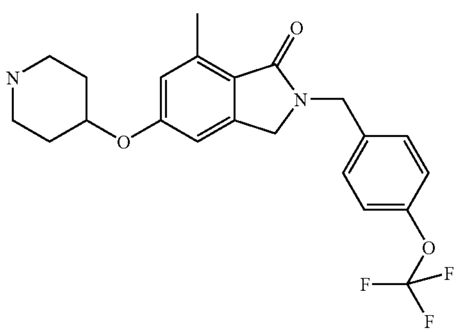 | 7-Methyl-piperidinedin-4-yloxy)-2-(4-trifluoromethoxy-benzyl)-2,3-dihydro-isoindol-1-one | 4.9 mg, 53%, yellow oil | 7.33-7.35 (m, 2H), 7.18-7.20 (m, 2H), 6.71-6.75 (m, 2H), 4.75 (s, 2H), 4.43-4.48 (m, 1H), 4.18 (s, 2H), 3.13-3.20 (m, 2H), 2.75-2.83 (m, 2H), 2.04-2.07 (m, 2H), 1.66-1.77 (m, 2H), 1.25-1.28 (m, 1H) |

-continued

| Example | Structure | Name | Yield | NMR |
|---|---|---|---|---|
| M50 | 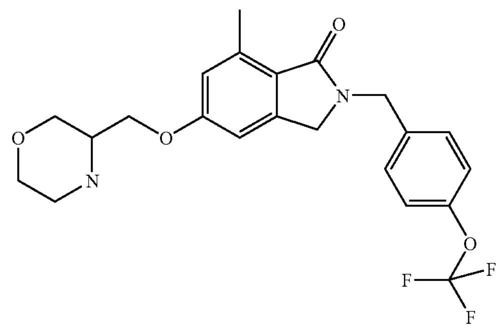 | 7-Methyl-5-(morpholin-3-ylmethoxy)-2-(4-trifluoromethoxy-benzyl)-2,3-dihydro-isoindol-1-one | 23.6 mg, 63%, yellow oil | 7.31-7.35 (m, 2H), 7.17-7.20 (m, 2H), 6.70-6.75 (m, 2H), 4.75 (s, 2H), 4.18 (s, 2H), 3.83-3.93 (m, 4H), 3.59-3.62 (m, 1H), 3.39-3.43 (m, 1H), 3.25-3.29 (m, 1H), 2.97-3.02 (m, 2H), 2.72 (s, 3H) |
| M52 | 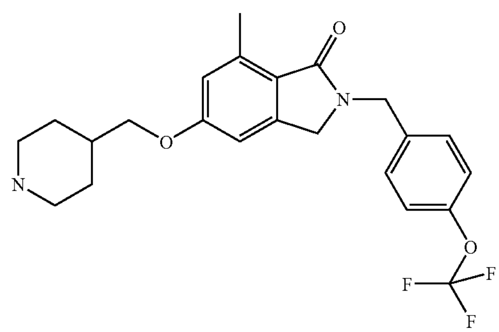 | 7-Methyl-5-(piperidine-4-ylmethoxy)-2-(4-trifluoromethoxy-benzyl)-2,3-dihydro-isoindol-1-one | 29.8 mg, 91.5%, yellow oil | 7.32-7.35 (m, 2H), 7.17-7.20 (m, 2H), 6.70-6.73 (m, 2H), 4.75 (s, 2H), 4.18 (s, 2H), 3.82 (d, 2H), 3.14-3.18 (m, 2H), 2.64-2.72 (m, 5H), 1.82-1.95 (m, 3H), 1.22-1.38 (m, 2H) |
| M54 | 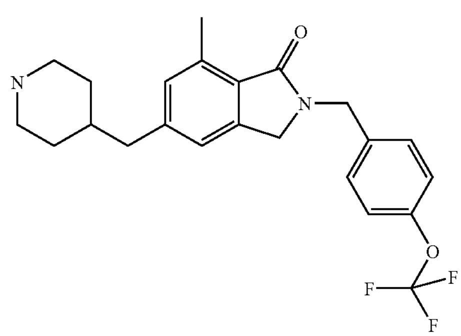 | 7-Methyl-5-piperidin-4-ylmethyl-2-(4-trifluoromethoxy-benzyl)-2,3-dihydro-isoindol-1-one | 1.56 g, 90%, yellow foam | 7.28-7.31 (m, 2H), 7.11-7.13 (m, 2H), 6.94 (s, 2H), 4.71 (s, 2H), 4.16 (s, 2H), 3.67 (br, 1H), 3.01-3.05 (m, 2H), 2.69 (s, 3H), 2.47-2.61 (m, 4H), 1.56-1.60 (m, 3H), 1.19-1.23 (m, 2H) |
| M61 | 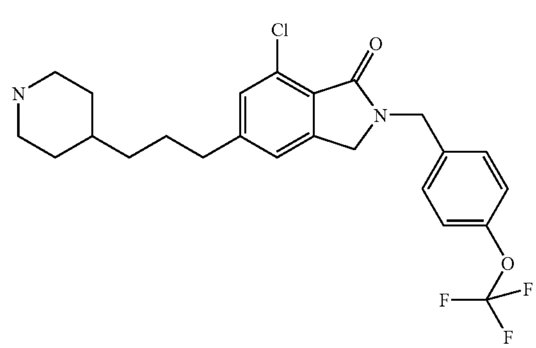 | 7-Chloro-5-(3-piperidin-4-yl-propyl)-2-(4-trifluoromethoxy-benzyl)-2,3-dihydro-isoindol-1-one | 55 mg, 90%, yellow oil | 7.31-7.35 (m, 2H), 7.17-7.22 (m, 3H), 7.09 (s, 1H), 4.76 (s, 2H), 4.22 (s, 2H), (m, 2H), 2.51-2.66 (m, 4H), 1.57-1.68 (m, 4H), 1.22-1.29 (m, 3H), 1.03-1.11 (m, 2H) |

-continued

| Example | Structure | Name | Yield | NMR |
|---|---|---|---|---|
| M65 | 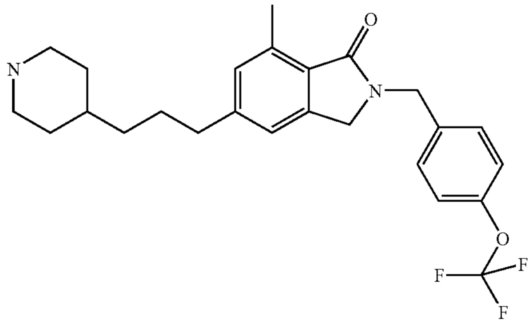 | 7-Methyl-5-(3-piperidin-4-yl-propyl)-2-(4-trifluoromethoxy-benzyl)-2,3-dihydro-isoindol-1-one | 39 mg, 65%, yellow oil | 7.32-7.36 (m, 2H), 7.16-7.22 (m, 2H), 6.99 (d, 2H), 4.77 (s, 2H), 4.20 (s, 2H), 3.22-3.25 (d, 2H), 2.59-2.77 (m, 5H), 1.51-1.79 (m, 4H), 1.24-1.42 (m, 5H) |

Example 81

7-Chloro-5-(4-methoxy-benzyloxy)-2-(4-trifluoromethoxy-benzyl)-2,3-dihydro-isoindol-1-one

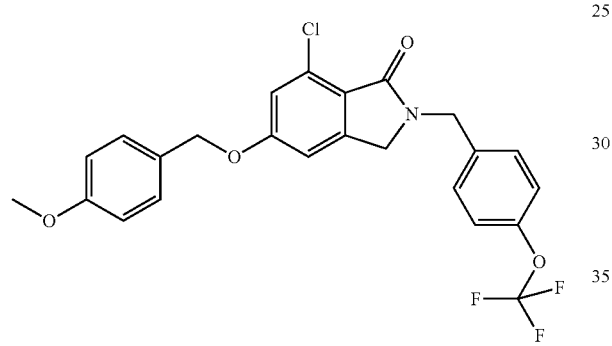

Palladium acetate (0.54 mg, 0.0024 mmol), racemic-2-(di-t-butylphosphino)-1,1'-binaphthyl (1.2 mg, 0.003 mmol), and cesium carbonate (58.6 mg, 0.18 mmol) were added to a vial and the vial was filled with Argon. Toluene (1.5 mL) was added and the vial was degassed with a pump and filled again with Argon. 5-Bromo-7-chloro-2-(4-trifluoromethoxy-benzyl)-2,3-dihydro-isoindol-1-one (50.0 mg, 0.12 mmol) and 4-methoxy-benzyl alcohol (33.2 mg, 0.24 mmol) were added and the mixture was stirred at 95° C. for forty-five hours. The cooled mixture was then diluted with diethyl ether and filtered through Celite®. Column chromatography (20% EtOAc/Hexanes to 100% EtOAc) provided the title compound (21.1 mg, 37%).

The following compound was made in a similar fashion:

| Example | Structure | Name | Yield | NMR | GTPγS EC50 |
|---|---|---|---|---|---|
| M26 | 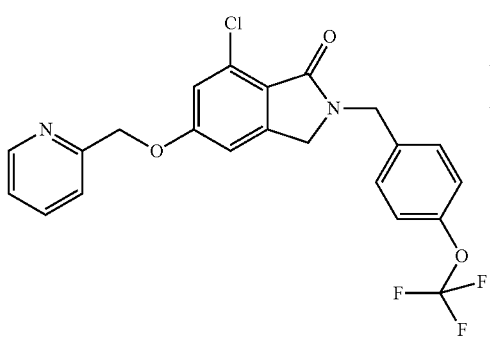 | 7-Chloro-5-(pyridin-2-ylmethoxy)-2-(4-trifluoromethoxy-benzyl)-2,3-dihydro-isoindol-1-one | 6.3 mg, 46.8%, white solid | 8.62 (m, 1H), 7.72-7.75 (m, 1H), 7.47-7.50 (m, 1H), 7.34-7.37 (m, 2H), 7.281 (m, 1H), 7.18-7.21 (m, 2H), 7.07-7.08 (m, 1H), 6.88-6.89 (m, 1H), 5.25 (s, 2H), 4.76 (m, 2H, 4.20 (s, 2H | |

| Example | Structure | Name | Yield | NMR | GTPγS EC50 |
|---|---|---|---|---|---|
| 82 | 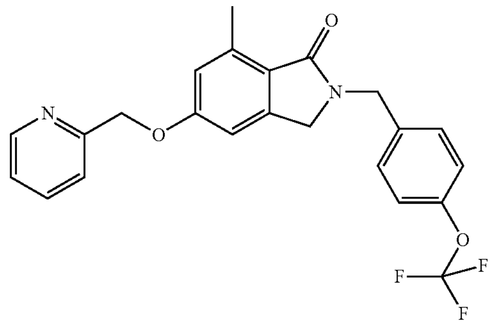 | 7-Methyl-5-(pyridine-2-ylmethoxy)-2-(4-trifluoromethoxy-benzyl)-2,3-dihydro-isoindol-1-one | 17.7 mg, 33%, yellow solid | $^1$H NMR CDCl$_3$: 8.64 (d, 1H), 7.97 (d, 2H, 7.75 (t of d, 1H), 7.45 (d, 1H, 7.36 (d, 2H), 7.22 (m, 1H, 7.20 (d, 2H,) 5.50 (s, 2H), 4.79 (s, 2H), 4.29 (s, 2H), 2.78 (s, 3H). | 0.10 |

M40 7-Methyl-5-(pyridin-4-ylmethoxy)-2-(4-trifluoromethoxy-benzyl)-2,3-dihydro-isoindol-1-one

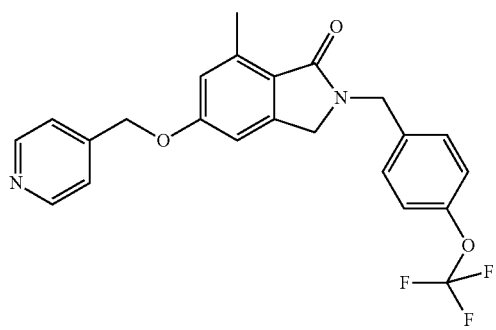

To a solution of 5-Iodo-7-methyl-2-(4-trifluoromethoxy-benzyl)-2,3-dihydro-isoindol-1-one (100 mg, 0.22 mmol) in toluene (3 ml), pyridin-4-yl-methanol (26.4 mg, 0.24 mmol), copper(I) iodide (40 mg, 0.022 mmol), cesium carbonate (143 mg, 0.44 mmol), and 1,10-phenanthroline (7.9 mg, 0.044 mmol) were added. The resulting mixture was refluxed overnight, After cooling, the mixture was filtered through Celite® and concentrated. Column chromatography (80% EtOAc/Hexanes to 10% MeOH/EtOAc) provided the title compound as a yellow oil (44.3 mg, 47%). $^1$H NMR (300 MHz, CDCl$_3$): δ 8.56 (br, 2H), 7.31-7.36 (m, 3H), 7.16-7.20 (m, 3H), 6.83 (s, 1H), 6.75 (s, 1H), 5.14 (s, 2H), 4.75 (s, 2H), 4.19 (s, 2H), 2.74 (s, 3H). GTPγS (0.0645).

Example 83

7-Chloro-5-hydroxy-2-(4-trifluoromethoxy-benzyl)-2,3-dihydro-isoindol-1-one

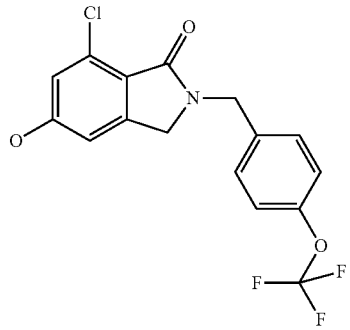

7-Chloro-5-(4-methoxy-benzyloxy)-2-(4-trifluoromethoxy-benzyl)-2,3-dihydro-isoindol-1-one (5.0 mg) was dissolved in a 1:1 mixture of trifluoroacetic acid and dichloromethane. The reaction was stirred over the weekend. The mixture was then washed with water, brine, dried over sodium sulfate, filtered and concentrated to provide the title compound (1.87 mg). $^1$H NMR (300 MHz, CDCl$_3$): δ 7.36 (d, 2H), 7.20 (d, 2H), 6.94 (s, 1H), 6.76 (s, 1H), 4.76 (s, 2H), 4.19 (s, 2H).

Example 84

Bromo-7-methoxy-2-(4-trifluoromethoxybenzyl)-2,3-dihydroisoindol-1-one

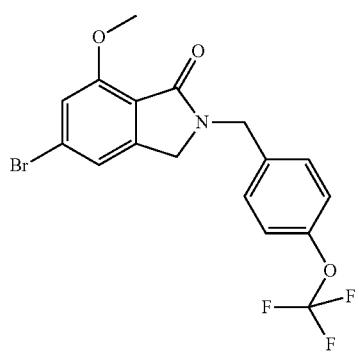

4-Bromo-2-bromomethyl-6-methylbenzoic acid methyl ester (762 mg, 2.37 mmol), 4-trifluoromethoxy benzylamine (0.543 mL, 3.56 mmol) and $K_2CO_3$ (981 mg, 7.10 mmol) were stirred in toluene (10 mL) at 95° C. for 12 hours. The reaction was partitioned between ethyl acetate and water and the organic layer was washed with brine and dried over anhydrous $Na_2SO_4$. The solvent was removed under reduced pressure and the product was purified by column chromatography (10-25% EtOAc/Hexanes) to afford a yellow oil (650 mg, 66%). $^1$H NMR (300 MHz, CDCl$_3$): δ 7.33-7.36 (m, 2H), 7.18 (d, 2H), 7.13 (s, 1H), 7.07 (s, 1H), 4.75 (s, 2H), 4.22 (s, 2H), 4.00 (s, 3H).

Example 88

7-Methyl-5-(1-methyl-1,2,3,6-pyridin-4-yl)-2-(4-trifluoromethoxybenzyl)-2,3-dihydroisoindol-1-one

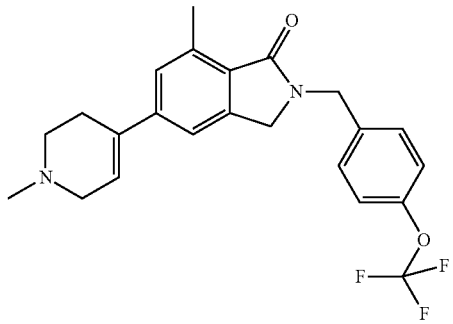

7-Methyl-5-(1,2,3,6-pyridin-4-yl)-2-(4-trifluoromethoxybenzyl)-2,3-dihydroisoindol-1-one (20 mg, 0.05 mmol), formaldehyde (2 mL), and formic acid (1 mL) was stirred together at room temperature for 1 hour and at 120° C. for 4 hours. The reaction mixture was neutralized with NaHCO$_3$ (aq.) and partitioned with CH$_2$Cl$_2$ and water. The organic layer was dried over anhydrous Na$_2$SO$_4$. The solvent was removed under reduced pressure and the product was purified by column chromatography (100% EtOAc-2% Ammonia in MeOH) to afford a yellow oil (7.4 mg, 37%). $^1$H NMR (300 MHz, CDCl$_3$): δ 7.32-7.37 (m, 2H), 7.20 (t, 4H), 6.12-6.15 (m, 1H), 4.78 (s, 2H), 4.23 (s, 2H), 3.13-3.16 (m, 2H), 2.76 (s, 3H), 2.68-2.71 (m, 2H), 2.60 (br s, 2H), 2.43 (s, 3H).

The following compound was made in the same fashion:

| Example | Structure | Name | Yield | NMR | GTPγS EC50 |
|---|---|---|---|---|---|
| 89 | 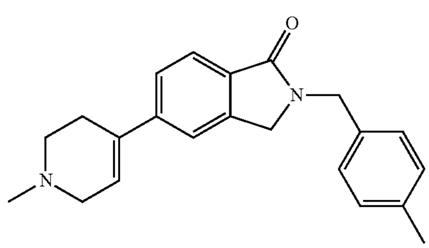 | 4-[2-(4-Methylbenzyl)-5-(1-methyl-1,2,3,6-tetrahydropyridin-4-yl)-2,3-dihydroisoindol-1-one | 12 mg (63%) yellow solid | 7.83 (d, 1H), 7.50 (dd, 1H), 7.37 (s, 1H), 7.17 (q, 4H), 6.13-6.15 (m, 1H), 4.91 (s, 2H), 4.24 (s, 2H), 3.14 (dd, 2H), 2.68-2.71 (m, 2H), 2.61-2.62 (m, 2H), 2.43 (3H), 2.34 (s, 3H) | 9.72 |
| 90 | 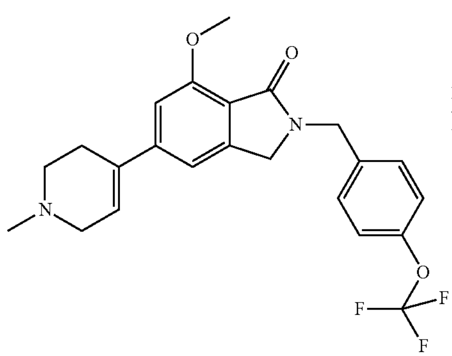 | 7-Methoxy-5-(1-methyl-1,2,3,6-tetrahydropyridin-4-yl)-2-(4-trifluoromethoxybenzyl)-2,3-dihydroisoindol-1-one | 29 mg (51%) brown oil | 7.35 (d, 2H), 7.16 (d, 2H), 6.92 (d, 2H), 6.12-6.15 (m, 1H), 4.75 (s, 2H), 4.22 (s, 2H), 4.00 (s, 2H), 3.13-3.16 (m, 2H), 2.67-2.71 (m, 2H), 2.58-2.60 (m, 2H), 2.42 (s, 3H), 1.97 (br s, 1H) | 3.82 |

Example 91

7-Methyl-5-(1,2,3,6-pyridin-4-yl)-2-(4-trifluoromethoxybenzyl)-2,3-dihydroisoindol-1-one

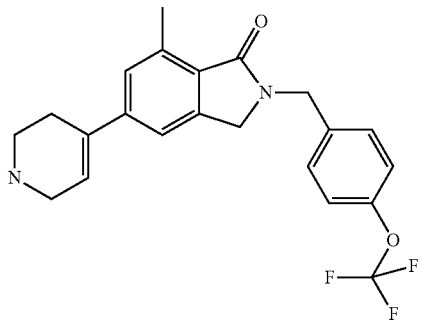

4-[7-Methyl-1-oxo-2-(4-trifluoromethoxy-benzyl)-2,3-dihydro-1H-isoindol-5-yl]-3,6-dihydro-2H-pyridine-1-carboxylic acid tert-butyl ester (445 mg, 0.88 mmol) was dissolved in formic acid (10 mL) and stirred at room temperature for 4 hours. The formic acid was removed under reduced pressure and the product was neutralized with NaHCO$_3$ and extracted with EtOAc. The organic layer was washed with 1N HCl and the aqueous layer was then basified, extracting with ethyl acetate. The organic layer was washed with brine, dried over anhydrous Na$_2$SO$_4$, filtered and concentrate to afford 127 mg (36%) of a yellow oil. $^1$H NMR (300 MHz, CDCl$_3$): δ 7.35 (d, 2H), 7.21 (t, 4H), 6.21 (br s, 1H), 4.78 (s, 2H), 4.24 (s, 2H), 3.51 (q, 2H), 3.13 (t, 2H), 2.77 (s, 3H), 2.43 (m, 2H).

The following compounds were made in the same fashion:

Example 93

2-(4-Methyl-benzyl)-5-pyridin-2-yl-2,3-dihydroisoindol-1-one

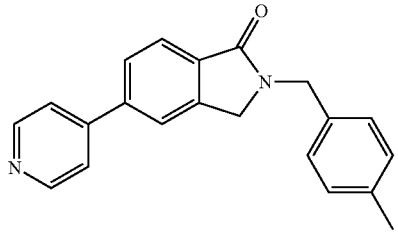

4-Tributylstannanylpyridine (37 mg, 0.032 mmol), 5-bromo-2-(4-methyl-benzyl)-2,3-dihydro-isoindol-1-one (50.0 mg, 0.16 mmol) and Pd(PPh$_3$)$_4$ (37 mg, 0.032 mmol) were dissolved in anhydrous toluene (4 mL). The mixture was immersed in a 100° C. oil bath. After eighteen hours, the reaction was cooled and the solvent was removed under reduced pressure. The compound was purified by column chromatography (50% EtOAc/Hexanes) to provide the title compound as a brown solid (17.0 mg, 35%). $^1$H NMR (300 MHz, CDCl$_3$): δ 8.72 (br s, 2H), 8.01 (d, 1H), 7.75 (dd, 1H), 7.62 (s, 1H), 7.53 (br s, 2H), 7.20 (q, 4H), 4.81 (s, 2H), 4.35 (s, 2H), 2.35 (s, 3H)

The following compounds were made using the above general procedure:

| Example | Structure | Name | Yield | NMR | GTPγS EC50 |
|---|---|---|---|---|---|
| 92 | 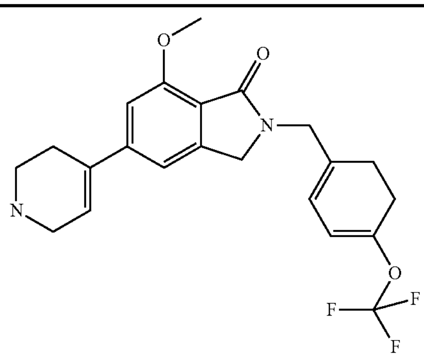 | 7-Methoxy-5-(1,2,3,6-tetrahydro-pyridin-4-yl)-2-(4-trifluoromethoxy-benzyl)-2,3-dihydro-isoindol-1-one | 96 mg brown oil | 7.35 (d, 2H), 7.17 (d, 2H), 6.92 (d, 2H), 6.21 (br s, 1H), 4.75 (s, 2H), 4.26 (s, 2H), 4.06 (s, 3H), 3.58 (br s, 2H), 3.13 (br s, 2H), 2.48 (s, 2H) | 1.36 |

| Example | Structure | Name | Yield | NMR | GTPγS EC50 |
|---|---|---|---|---|---|
| 94 | 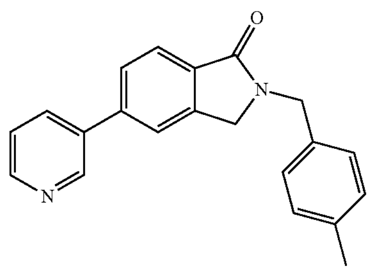 | 2-(4-Methylbenzyl)-5-pyridin-3-yl-2,3-dihydroisondol-1-one | 15 mg (31%) white solid | 8.82 (br s, 1H), 8.61 (br s, 1H), 8.01 (d, 1H), 7.90 (d, 1H), 6.69 (dd, 1H), 7.58 (s, 1H), 7.42 (dd, 1H), 7.20 (q, 4H), 4.81 (s, 2H), 4.35 (s, 2H), 2.35 (s, 3H) | 2.76 |
| 95 | 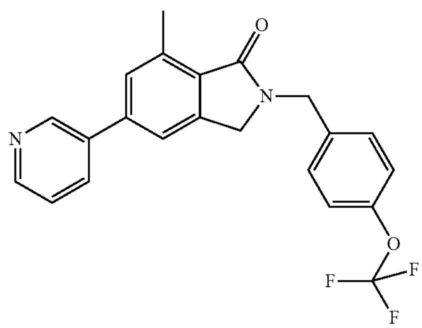 | 7-Methyl-5-pyridin-3-yl-2-(trifluoromethoxybenzyl)-2,3-dihydroisoindol-1-one | 20 mg (50%) yellow solid | 8.85 (s, 1H), 8.63 (dd, 1H), 7.88 (dd, 1H), 7.36-7.43 (m, 5H) 7.19 (d, 2H), 4.82 (s, 2H), 4.33 (s, 2H), 2.85 (s, 3H) | 0.05 |
| 96 | 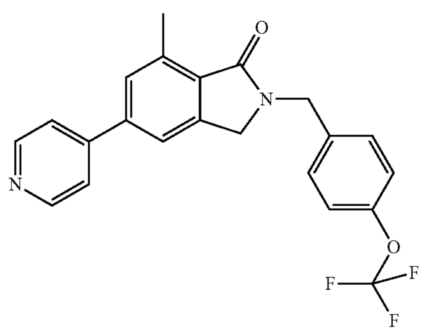 | 7-Methyl-5-pyridin-4-yl-2-(trifluoromethoxybenzyl)-2,3-dihydroisoindol-1-one | 45 mg (45%) yellow solid | 8.70 (br s, 2H), 7.54 (d, 2H), 7.46 (d, 2H), 7.35-7.39 (m, 2H), 7.19 (d, 2H), 4.81 (s, 2H), 4.32 (s, 2H), 2.85 (s, 3H) | 0.13 |
| 97 | 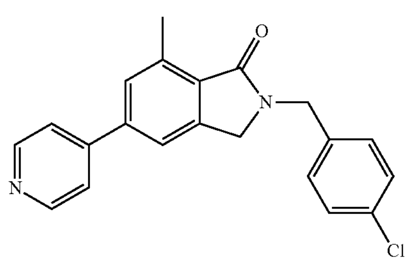 | 2-(4-chlorobenzyl)-7-methyl-5-pyridin-4-yl-2,3-dihydroisoindol-1-one | 20 mg (40%) white solid | 7.44-7.51 (m, 5H), 7.26-7.35 (m, 5H), 4.78 (s, 2H), 4.30 (s, 2H), 2.85 (s, 3H) | 0.30 |
| 98 | 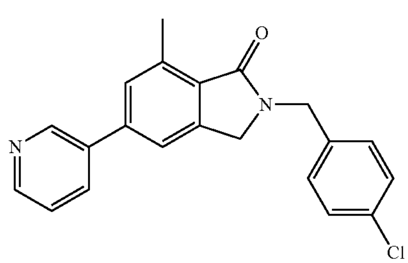 | 2-(4-chlorobenzyl)-7-methyl-5-pyridin-3-yl-2,3-dihydroisoindol-1-one | 31 mg (62%) yellow gum | 8.85 (br s, 1H), 8.64 (br s, 1H), 7.88 (d, 1H), 7.41 (d, 3H), 7.26-7.34 (m, 4H), 4.78 (s, 2H), 4.30 (s, 2H), 2.84 (s, 3H) | 0.10 |

-continued

| Example | Structure | Name | Yield | NMR | GTPγS EC50 |
|---|---|---|---|---|---|
| 99 | 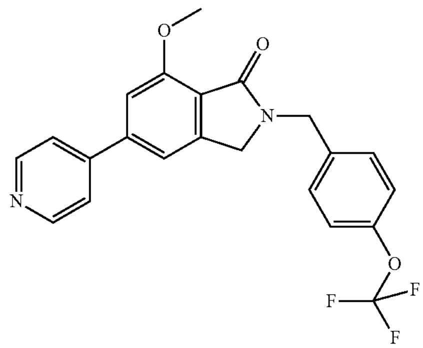 | 7-Methoxy-5-pyridin-4-yl-2-(4-trifluoromethoxy-benzyl)-2,3-dihydroisoindol-1-one | 65 mg (66%) white solid | 8.69 (d, 2H), 7.48 (d, 2H), 7.36 (d, 2H), 7.18 (d, 3H), 7.10 (s, 1H), 4.78 (s, 2H), 4.31 (s, 3H), 4.04 (s, 3H) | 0.40 |
| 100 | 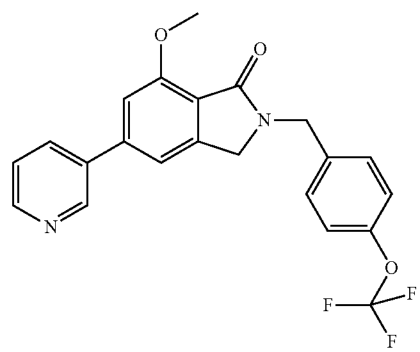 | 7-Methoxy-5-pyridin-3-yl-2-(4-trifluoromethoxy-benzyl)-2,3-dihydroisoindol-1-one | 66 mg (67%) off-white solid | 8.84 (br s, 1H), 8.65 (br s, 1H), 7.88 (d, 1H), 7.34-7.42 (m, 3H), 7.18 (s, 2H), 7.14 (d, 2H), 7.05 (s, 1H), 4.78 (s, 2H), 4.30 (s, 2H), 4.06 (s, 3H) | 0.22 |
| 101 | 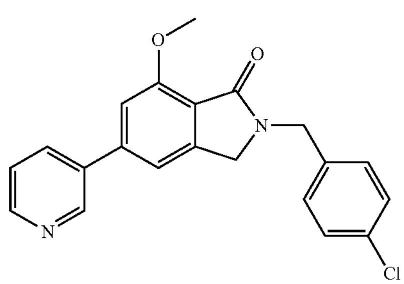 | 2-(4-Chloro-benzyl)-7-methoxy-5-pyridin-3-yl-2,3-dihydro-isoindol-1-one | 49 mg (84%) yellow oil | 8.84 (d, 1H), 8.64 (d, 1H), 7.88 (dt, 1H), 7.41 (q, 1H), 7.29 (s, 4H), 7.14 (s, 1H), 7.06 (s, 1H), 4.75 (s, 2H), 4.29 (s, 2H), 4.06 (s, 3H) | 1.16 |
| 102 | 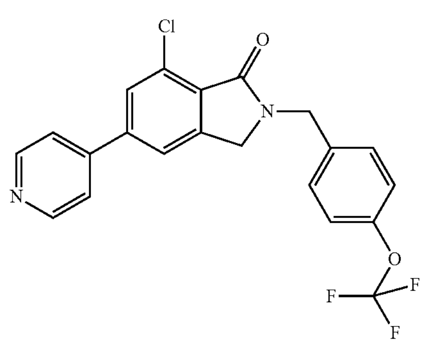 | 7-Chloro-5-pyridin-4-yl-2-(4-trifluoromethoxy-benzyl)-2,3-dihydro-isoindol-1-one | 18.0 mg, 48% colourless solid | 1H NMR CDCl$_3$: 8.73 (broad s, 2H), 7.67 (s, 1H), 7.50 (m, 3H), 7.39 (d, 2H), 7.22 (d, 2H), 4.83 (s, 2H), 4.35 (s, 2H) | 0.09 |

-continued

| Example | Structure | Name | Yield | NMR | GTPγS EC50 |
|---|---|---|---|---|---|
| 103 | 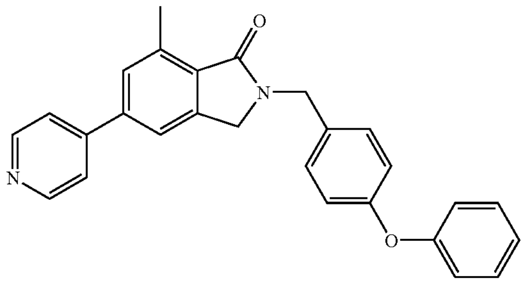 | 7-Methyl-2-(4-phenoxy-benzyl)-5-pyridin-4-yl-2,3-dihydro-isoindol-1-one | 32 mg (60%) yellow oil | 8.70 (br s, 2H), 7.50 (dd, 4H), 7.30-7.45 (m 4H), 7.12 (t, 1H), 6.98-7.02 (m, 4H), 4.79 (s, 2H), 4.33 (s, 2H), 2.85 (s, 3H) | 0.04 |
| 104 | 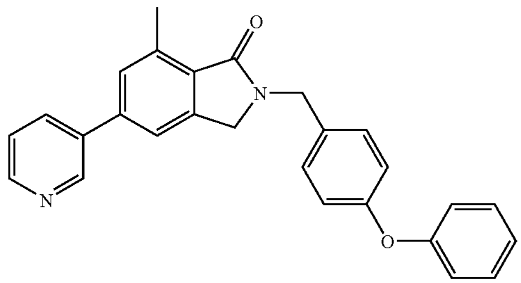 | 7-Methyl-2-(4-phenoxy-benzyl)-5-pyridin-3-yl-2,3-dihydro-isoindol-1-one | 32 mg (65%) yellow oil | 8.86 (br s, 1H), 8.65 (br s, s, 1H), 7.78 (d, 1H), 7.30-7.41 (m, 7H), 7.12 (t, 1H), 6.98-7.03 (m, 4H), 4.79 (s, 2H), 4.33 (s, 2H), 2.85 (3H) | 0.05 |
| 105 | 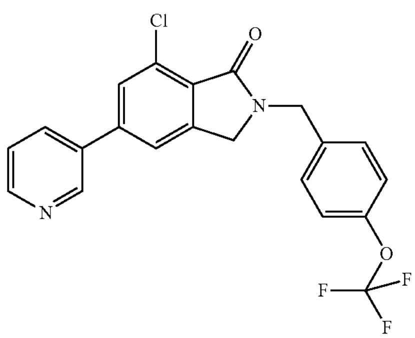 | 7-Chloro-5-pyridin-3-yl-2-(4-trifluoromethoxy-benzyl)-2,3-dihydro-isoindol-1-one | 24.0 mg, 60% colourless solid | 1HNMR MeOD: 8.83 (broad s, 1H), 8.62 (broad s, 1H), 8.17 (d, 1H), 7.76 (s, 2H), 7.60 (broad s, 1H), 7.45 (d, 2H), 7.28 (d, 2H), 4.83 (s, 2H), 4.45 (s, 2H) | 0.05 |
| 106 | 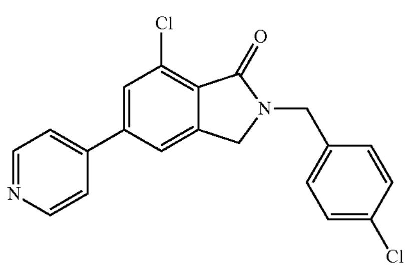 | 7-Chloro-2-(4-chloro-benzyl)-5-pyridin-4-yl-2,3-dihydro-isoindol-1-one | 33 mg (55%) yellow-brown oil | 8.72 (s, 2H), 7.66 (1H), 7.48-7.66 (m, 3H), 7.27-7.34 (m, 4H), 4.79 (s, 2H), 4.32 (s, 2H) | 0.13 |
| 107 | 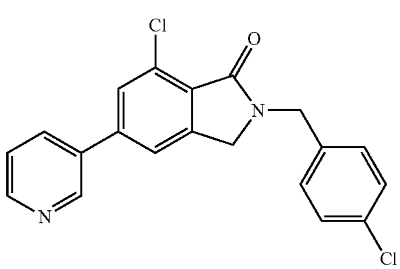 | 7-Chloro-2-(4-chloro-benzyl)-5-pyridin-3-yl-2,3-dihydro-isoindol-1-one | 23 mg (58%) white solid | 8.85 (br s, 1H), 8.69 (br s, 1H), 7.89 (d, 1H), 7.62 (s, 1H), 7.42-7.62 (m, 2H), 7.30-7.36 (m, 5H), 4.80 (s, 2H), 4.32 (s, 2H) | 0.36 |

| Example | Structure | Name | Yield | NMR | GTPγS EC50 |
|---|---|---|---|---|---|
| 108 | 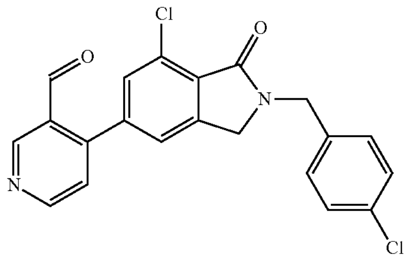 | 4-[7-Chloro-2-(4-chloro-benzyl)-1-oxo-2,3-dihydro-1H-isoindol-5-yl]-pyridine-3-carbaldehyde | 8.3 mg, 7.8%, colourless oil | 10.07 (s, 1H), 9.20 (s, 1H), 8.89 (d, 1H), 7.49 (s, 1H), 7.38-7.29 (m, 6H), 4.81 (s, 2H, 4.34 (s, 2H) | 0.46 |
| J87 | 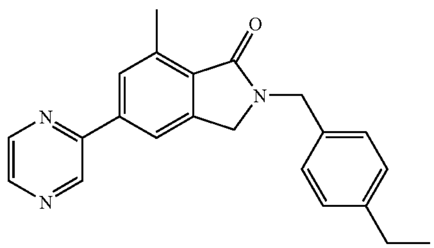 | 2-(4-Ethyl-benzyl)-7-methyl-5-pyrazin-2-yl-2,3-dihydro-isoindol-1-one | 39 mg 39% colorless solid | 9.06 (s, 1H), 8.67 (s, 1H), 8.57 (s, 1H), 7.85 (s, 2H), 7.27 (d, 2H), 7.19 (d, 2H), 4.79 (s, 2H), 4.32 (s, 2H), 2.88 (s, 3H), 2.65 (q, 2H), 1.24 (t, 3H) | |
| K13 | 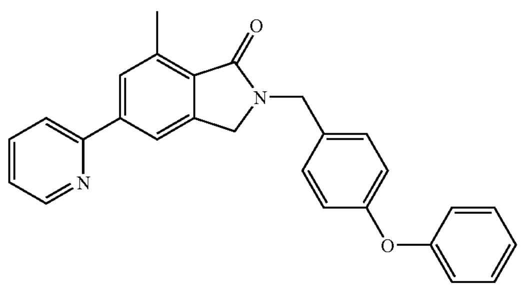 | 7-Methyl-2-(4-phenoxy-benzyl)-5-pyridin-2-yl-2,3-dihydro-isoindol-1-one | 48 mg, 60%, off-white semi-solid | 8.72 (d, 1H), 7.70-7.90 (m, 4H), 7.28-7.38 (m, 5H), 7.12 (t, 1H), 6.95-7.05 (m, 4H), 4.79 (s, 2H), 4.32 (s, 2H), 2.85 (s, 3H) | |
| K14 | 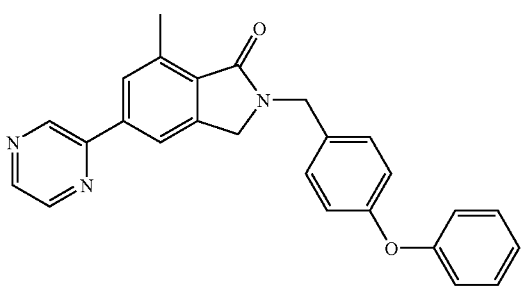 | 7-Methyl-2-(4-phenoxy-benzyl)-5-pyrazin-2-yl-2,3-dihydro-isoindol-1-one | 26 mg, 33%, off-white solid | 9.07 (s, 1H), 8.68 (d, 1H), 8.58 (d, 1H), 7.87 (s, 2H), 7.28-7.38 (m, 4H), 7.12 (t, 1H), 6.98-7.03 (m, 4H), 4.80 (s, 2H), 4.35 (s, 2H), 2.88 (s, 3H) | |
| K15 | 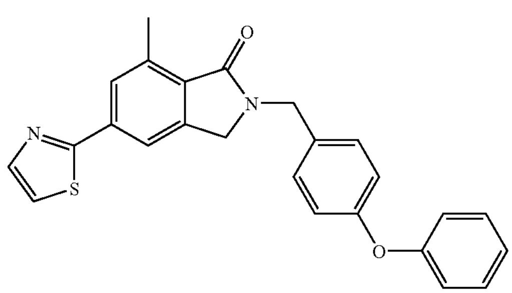 | 7-Methyl-2-(4-phenoxy-benzyl)-5-thiazol-2-yl-2,3-dihydro-isoindol-1-one | 25 mg, 31%, yellow oil | 7.92 (d, 1H), 7.84 (s, 1H), 7.81 (s, 1H), 7.28-7.41 (m, 5H), 7.12 (t, 1H), 6.98-7.03 (m, 4H), 4.78 (s, 2H), 4.32 (s, 2H), 2.84 (s, 3H) | |

| Example | Name | Yield | NMR | GTPγS EC50 |
|---|---|---|---|---|
| K16 | 2-(4-Phenoxy-benzyl)-5-pyridin-2-yl-2,3-dihydro-isoindol-1-one | 28 mg, 35%, off-white solid | 8.73 (d, 1H), 8.14 (s, 1H), 7.95-8.10 (m, 2H), 7.80-7.90 (m, 2H), 7.28-7.38 (m, 5H), 7.12 (t, 1H), 6.98-7.03 (m, 4H), 4.83 (s, 2H), 4.39 (s, 2H) | |
| K17 | 2-(4-Phenoxy-benzyl)-5-pyridin-3-yl-2,3-dihydro-isoindol-1-one | 40 mg, 50%, off-white solid | 8.88 (d, 1H), 7.78 (dd, 1H), 8.01 (d, 1H), 7.88-7.95 (m, 1H), 7.71 (d, 1H), 7.61 (s, 1H), 7.28-7.45 (m, 5H), 7.03 (t, 1H), 6.98-7.03 (m, 4H), 4.83 (s, 2H), 4.39 (s, 2H) | |
| K18 | 2-(4-Phenoxy-benzyl)-5-pyridin-4-yl-2,3-dihydro-isoindol-1-one | 22 mg, 28%, colourless oil | 8.71 (d, 2H), 8.00 (d, 1H), 7.72 (dd, 1H), 7.66 (d, 1H), 7.50-7.54 (m, 2H), 7.28-7.36 (m, 4H), 7.10 (t, 1H), 6.98-7.03 (m, 4H), 4.83 (s, 2H), 4.39 (s, 2H) | |
| K19 | 7-Chloro-2-(4-phenoxy-benzyl)-5-pyridin-2-yl-2,3-dihydro-isoindol-1-one | 42 mg, 42%, yellow solid | 8.73 (dd, 1H), 8.03 (d, 1H), 7.99 (d, 1H), 7.72-7.88 (m, 2H), 7.31-7.40 (m, 5H), 7.10 (t, 1H), 6.98-7.03 (m, 4H), 4.80 (s, 2H), 4.34 (s, 2H) | |
| K20 | 7-Chloro-2-(4-phenoxy-benzyl)-5-pyridin-3-yl-2,3-dihydro-isoindol-1-one | 49 mg, 49%, off-white solid | 8.85 (d, 1H), 8.70 (dd, 1H), 7.87-7.93 (m, 1H), 7.63 (d, 1H), 7.50 (d, 1H), 7.30-7.45 (m, 6H), 7.10 (t, 1H), 6.98-7.03 (m, 4H), 4.80 (s, 2H), 4.35 (s, 2H) | |

-continued

| Example | Structure | Name | Yield | NMR | GTPγS EC50 |
|---|---|---|---|---|---|
| K21 | 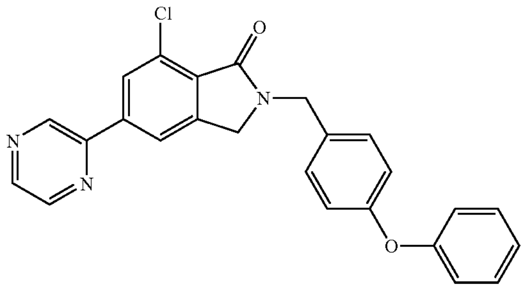 | 7-Chloro-2-(4-phenoxy-benzyl)-5-pyrazin-2-yl-2,3-dihydro-isoindol-1-one | 26 mg, 26%, pale yellow solid | 9.08 (d, 1H), 8.69-8.70 (m, 1H), 8.62 (d, 1H), 8.10 (s, 1H), 7.98 (s, 1H), 7.3-7.36 (m, 4H), 7.13 (t, 1H), 6.98-7.03 (m, 4H), 4.81 (s, 2H), 4.37 (s, 2H) | |
| K22 | 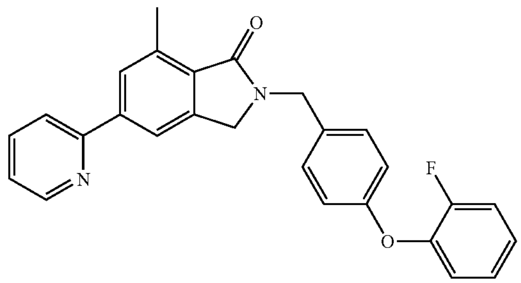 | 2-[4-(2-Fluoro-phenoxy)-benzyl]-7-methyl-5-pyridin-2-yl-2,3-dihydro-isoindol-1-one | 64 mg, 64%, pale yellow solid | 8.70-8.75 (m, 1H), 7.77-7.85 (m, 4H), 7.27-7.32 (m, 3H), 7.02-7.23 (m, 4H), 6.97 (d, 2H), 4.79 (s, 2H), 4.31 (s, 2H), 2.85 (s, 3H) | |
| K23 | 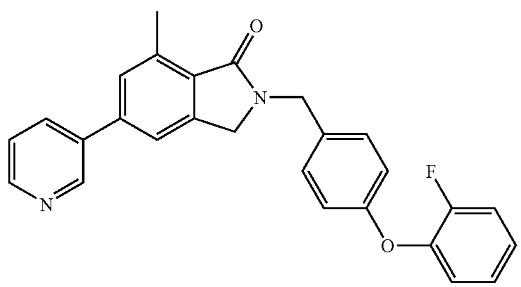 | 2-[4-(2-Fluoro-phenoxy)-benzyl]-7-methyl-5-pyridin-3-yl-2,3-dihydro-isoindol-1-one | 38 mg, 38%, pale yellow oil | 8.86 (d, 1H), 8.65 (dd, 1H), 7.85-7.92 (m, 1H), 7.38-7.41 (m, 3H), 7.30 (d, 2H), 7.02-7.23 (m, 4H), 6.96 (d, 2H), 4.79 (s, 2H), 4.32 (s, 2H), 2.85 (s, 3H) | |
| K24 | 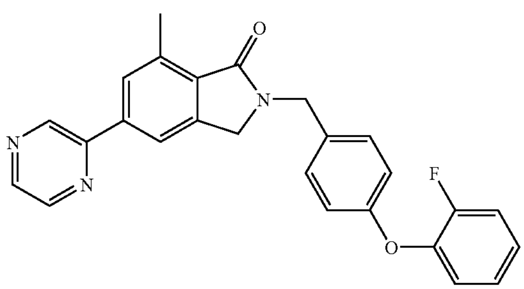 | 2-[4-(2-Fluoro-phenoxy)-benzyl]-7-methyl-5-pyrazin-2-yl-2,3-dihydro-isoindol-1-one | 24 mg, 24%, off-white solid | 9.07 (d, 1H), 8.68 (dd, 1H), 8.58 (d, 1H), 7.87 (s, 2H), 7.29 (d, 2H), 7.02-7.23 (m, 4H), 6.96 (d, 2H), 4.79 (s, 2H), 4.34 (s, 2H), 2.87 (s, 3H) | |
| K25 | 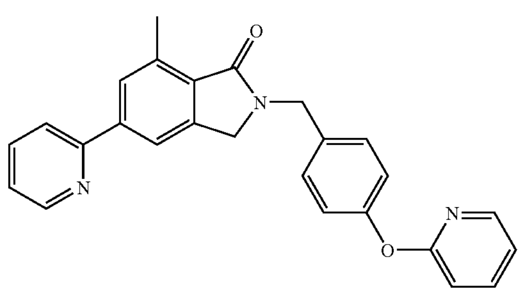 | 7-Methyl-5-pyridin-2-yl-2-[4-(pyridin-2-yloxy)-benzyl]-2,3-dihydro-isoindol-1-one | 57 mg, 57%, off-white solid | 8.73 (dd, 1H), 8.20 (dd, 1H), 7.65-7.86 (m, 5H), 7.38 (d, 2H), 7.28-7.30 (m, 1H), 7.14 (d, 2H), 6.95-7.05 (m, 1H), 6.94 (d, 1H), 4.82 (s, 2H), 4.35 (s, 2H), 2.86 (s, 3H) | |

-continued

| Example | Structure | Name | Yield | NMR | GTPγS EC50 |
|---|---|---|---|---|---|
| K26 | 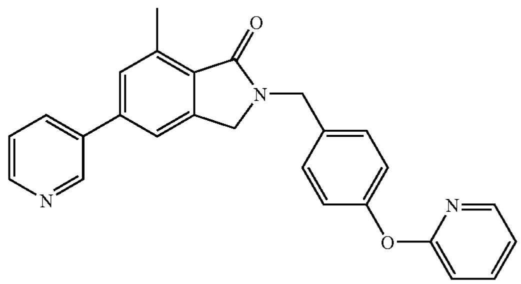 | 7-Methyl-5-pyridin-3-yl-2-[4-(pyridin-2-yloxy)-benzyl]-2,3-dihydro-isoindol-1-one | 43 mg, 43%, off-white gum | 8.85 (d, 1H), 8.65 (dd, 1H), 8.15-8.23 (m, 1H), 7.85-7.93 (m, 1H), 7.65-7.75 (m, 1H), 7.37-7.42 (m, 5H), 7.14 (d, 2H), 6.97-7.05 (m, 1H), 6.93 (d, 1H), 4.82 (s, 2H), 4.36 (s, 2H), 2.86 (s, 3H) | |
| K27 | 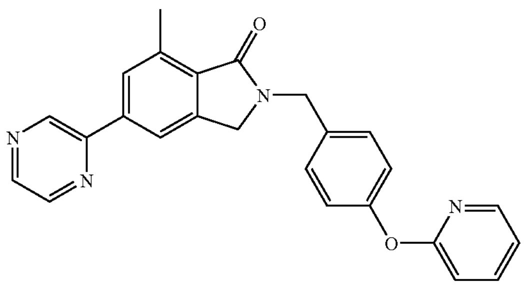 | 7-Methyl-5-pyrazin-2-yl-2-[4-(pyridin-2-yloxy)-benzyl]-2,3-dihydro-isoindol-1-one | 22 mg, 22%, off-white solid | 9.08 (d, 1H), 8.67-8.69 (m, 1H), 8.58 (d, 1H), 8.15-8.25 (m, 1H), 7.87 (s, 2H), 7.65-7.75 (m, 1H), 7.39 (d, 2H), 7.14 (d, 2H), 6.98-7.05 (m, 1H), 6.93 (d, 1H), 4.83 (s, 2H), 4.38 (s, 2H), 2.88 (s, 3H) | |
| K28 | 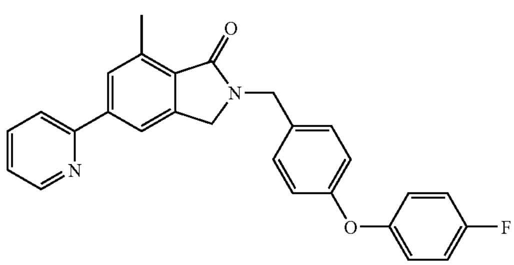 | 2-[4-(4-Fluoro-phenoxy)-benzyl]-7-methyl-5-pyridin-2-yl-2,3-dihydro-isoindol-1-one | 43 mg, 51%, yellow oil | 8.72-8.74 (m, 1H), 7.77-7.86 (m, 4H), 7.28-7.32 (m, 3H), 6.80-7.04 (m, 6H), 4.78 (s, 2H), 4.32 (s, 2H), 2.86 (s, 3H) | |
| K29 | 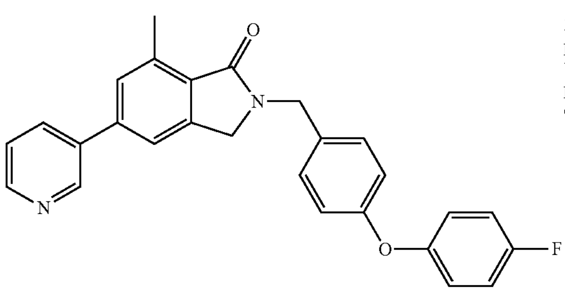 | 2-[4-(4-Fluoro-phenoxy)-benzyl]-7-methyl-5-pyridin-3-yl-2,3-dihydro-isoindol-1-one | 22 mg, 25%, yellow oil | 8.86 (d, 1H), 8.63-8.66 (m, 1H), 7.85-7.95 (m, 1H), 7.40-7.43 (m, 3H), 7.30 (d, 2H), 6.90-7.05 (m, 6H), 4.79 (s, 2H), 4.33 (s, 2H), 2.85 (s, 3H) | |
| K30 | 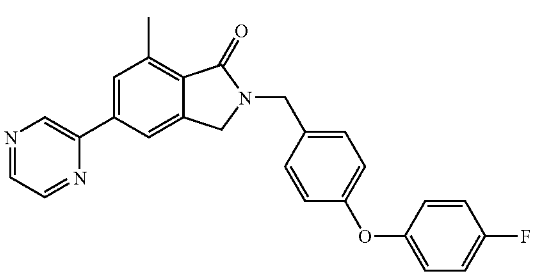 | 2-[4-(4-Fluoro-phenoxy)-benzyl]-7-methyl-5-pyrazin-2-yl-2,3-dihydro-isoindol-1-one | 21 mg, 25%, pale yellow solid | 9.07 (d, 1H), 8.67-8.69 (m, 1H), 8.58 (d, 1H), 7.87 (s, 2H), 7.31 (d, 2H), 6.90-7.08 (m, 6H), 4.79 (s, 2H), 4.34 (s, 2H), 2.87 (s, 3H) | |

-continued

| Example | Structure | Name | Yield | NMR | GTPγS EC50 |
|---|---|---|---|---|---|
| K31 | 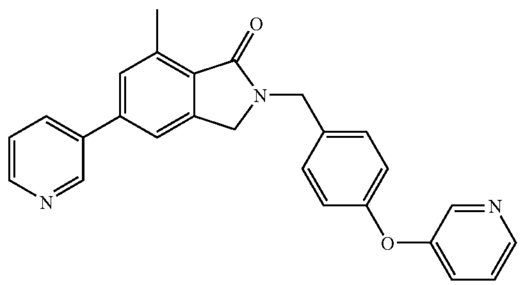 | 7-Methyl-5-pyridin-3-yl-2-[4-(pyridin-3-yloxy)-benzyl]-2,3-dihydro-isoindol-1-one | 34 mg, 38%, pale orange solid | 8.86 (d, 1H), 8.64-8.67 (m, 1H), 8.35-8.41 (m, 2H), 7.88-7.92 (m, 1H), 7.28-7.43 (m, 5H), 7.02 (d, 2H), 4.81 (s, 2H), 4.34 (s, 2H), 2.86 (s, 3H) | |
| K32 | 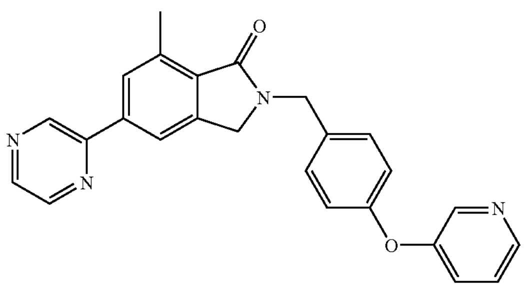 | 7-Methyl-5-pyrazin-2-yl-2-[4-(pyridin-3-yloxy)-benzyl]-2,3-dihydro-isoindol-1-one | 37 mg, 41%, pale orange solid | 9.08 (d, 1H), 8.65-8.69 (m, 1H), 8.58 (d, 1H), 8.35-8.42 (m, 2H), 7.87-7.89 (m, 2H), 7.34 (d, 2H), 7.28-7.30 (m, 2H), 7.03 (d, 2H), 4.82 (s, 2H), 4.36 (s, 2H), 2.88 (s, 3H) | |
| K33 | 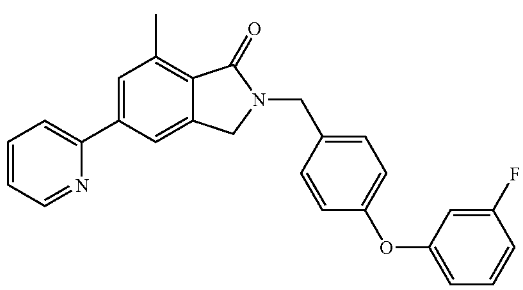 | 2-[4-(3-Fluoro-phenoxy)-benzyl]-7-methyl-5-pyridin-2-yl-2,3-dihydro-isoindol-1-one | 41 mg, 41%, colour-less oil | 8.70-8.75 (m, 1H), 7.75-7.88 (m, 4H), 7.25-7.37 (m, 4H), 7.03 (d, 2H), 6.75-6.85 (m, 2H), 6.65-6.73 (m, 1H), 4.81 (s, 2H), 4.14 (s, 2H), 2.86 (s, 3H) | |
| K34 | 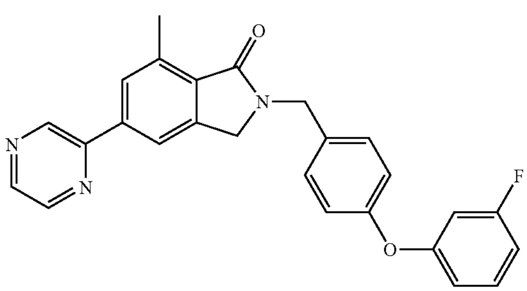 | 2-[4-(3-Fluoro-phenoxy)-benzyl]-7-methyl-5-pyrazin-2-yl-2,3-dihydro-isoindol-1-one | 27 mg, 27%, off-white solid | 9.08 (d, 1H), 8.67-8.69 (m, 1H), 8.58 (d, 1H), 7.87-7.89 (m, 2H), 7.35 (d, 2H), 7.27-7.29 (m, 1H), 7.03 (d, 2H), 6.75-6.83 (m, 2H), 6.68-6.72 (m, 1H), 4.81 (s, 2H), 4.36 (s, 2H), 2.88 (s, 3H) | |
| K35 | 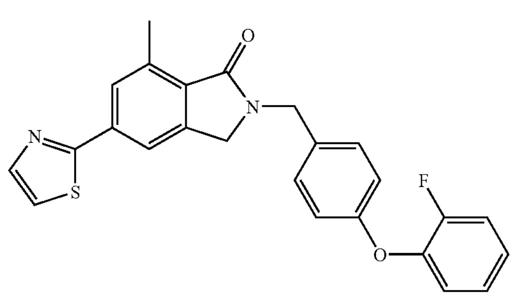 | 2-[4-(2-Fluoro-phenoxy)-benzyl]-7-methyl-5-thiazol-2-yl-2,3-dihydro-isoindol-1-one | 23 mg, 26%, yellow oil | 7.92 (d, 1H), 7.84 (s, 1H), 7.82 (s, 1H), 7.41 (d, 1H), 7.30 (d, 2H), 7.03-7.25 (m, 4H), 6.96 (d, 2H), 4.77 (s, 2H), 4.30 (s, 2H), 2.84 (s, 3H) | |

| Example | Structure | Name | Yield | NMR | GTPγS EC50 |
|---|---|---|---|---|---|
| K36 | 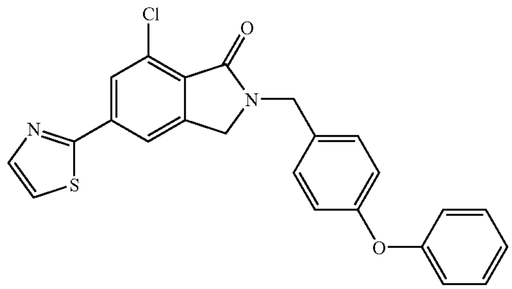 | 7-Chloro-2-(4-phenoxy-benzyl)-5-thiazol-2-yl-2,3-dihydro-isoindol-1-one | 38 mg, 37%, yellow solid | 8.01 (d, 1H), 7.92-7.95 (m, 2H), 7.46 (d, 1H), 7.30-7.36 (m, 4H), 7.13 (t, 1H), 6.96-7.05 (m, 4H), 4.79 (s, 2H), 4.33 (s, 2H) | |

Example 109

7-Methyl-5-(4-methyl piperazine-1-yl)-2-(4-trifluoromethoxybenzyl)-2,3-dihydroisoindol-1-one

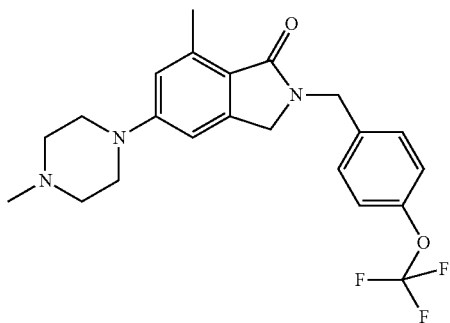

1-Methyl-piperazine (15 µL, 0.16 mmol), 5-Bromo-2-(4-methyl-benzyl)-2,3-dihydro-isoindol-1-one (43.0 mg, 0.11 mmol), NaO$^t$Bu (14.0 mg, 0.15 mmol), BINAP (6.7 mg, mmol) and Pd$_2$(dba)$_3$ (4.8 mg, 0.005 mmol) were dissolved in anhydrous toluene (2 mL). The mixture was immersed in a 110° C. oil bath. After eighteen hours, the reaction was cooled and poured into water and extracted with ethyl acetate. The organic phase was washed with brine, dried over MgSO$_4$, filtered and concentrated. The compound was purified by column chromatography (50% EtOAc/Hexanes) to provide the title compound as an orange solid (35.0 mg, 78%). $^1$H NMR (300 MHz, CDCl$_3$): δ 7.32-7.35 (m, 2H), 7.18 (d, 2H), 6.70 (d, 2H), 4.74 (s, 2H), 4.16 (s, 2H), 3.31 (t, 4H), 2.71 (s, 3H), 2.58 (t, 4H), 2.37 (s, 3H)

The following compounds were made using the above general procedure:

| Example | Structure | Name | Yield | NMR | GTPγS EC50 |
|---|---|---|---|---|---|
| 110 | 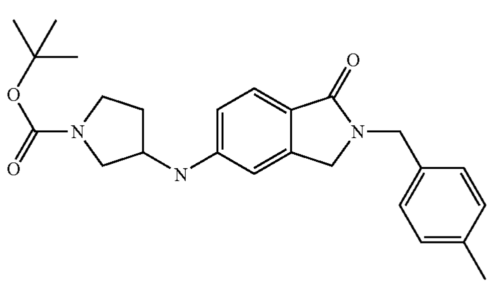 | 3-[2-(4-Methyl-benzyl)-1-oxo-2,3-dihydro-1H-isoindol-5-ylamino]-pyrrolidine-1-carboxylic acid tert-butyl ester | 78 mg (37%) colourless oil | 7.69 (d, 1H), 7.17 (q, 4H), 6.65 (d, 1H), 6.51 (s, 1H), 4.73 (s, 2H), 4.13 (m, 4H), 3.65 (m, 1H), 3.49 (m, 2H), 3.24 (m, 1H), 2.34 (s, 3H), 2.21 (m, 1H), 1.48 (s, 9H) | 2.52 |

-continued

| Example | Structure | Name | Yield | NMR | GTPγS EC50 |
|---|---|---|---|---|---|
| 111 | 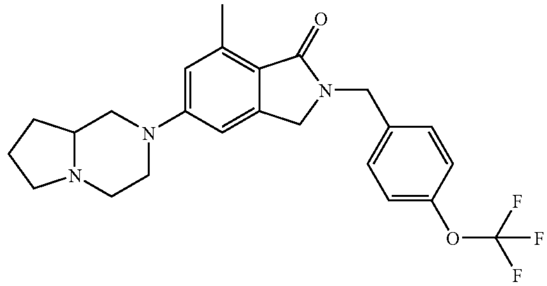 | 5-(Hexahydropyrrolo[1,2-a]pyrazin-2-yl)-7-methyl-2-(4-trifluoromethoxybenzyl)-2,3-dihydroisoindol-1-one | 14 mg (24%) brown oil | 7.26-7.35 (m, 2H), 7.16 (d, 2H), 6.72 (d, 2H), 4.74 (s, 2H), 4.16 (s, 2H), 3.87 (d, 1H), 3.85 (d, 1H), 3.16-3.20 (m, 2H), 3.02 (td, 1H), 2.63-2.71 (m, 3H), 2.41 (td, 1H), 2.20-2.29 (m, 4H), 1.55-1.95 (m, 3H) | 0.60 |
| 112 | 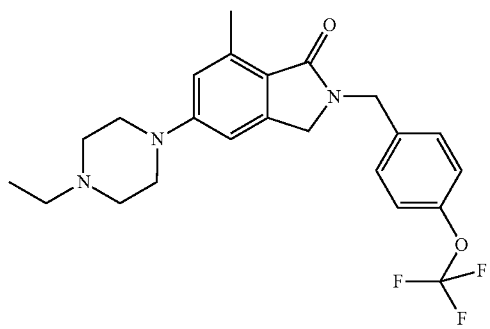 | 5-(4-Ethylpiperazin-1-yl)-7-methyl-2-(4-trifluoromethoxybenzyl)-2,3-dihydroisoindol-1-one | 20 mg (19%) yellow solid | 7.32-7.34 (m, 2H), 7.18 (d, 2H), 6.71 (d, 2H), 4.74 (s, 2H), 4.16 (s, 2H), 3.32 (t, 4H), 2.71 (s, 3H), 2.62 (t, 4H), 2.49 (q, 2H), 1.15 (t, 3H) | 0.68 |
| 113 | 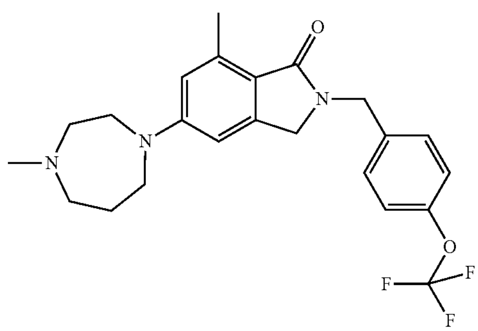 | 7-Methyl-5-(4-methyl-[1,4]-diazepan-1-yl)-2-(4-trifluoromethoxybenzyl)-2,3-dihydroisoindol-1-one | 17 mg (40%) yellow oil | 7.33 (d, 2H), 7.18 (d, 2H), 6.47 (d, 2H), 4.73 (s, 2H), 4.15 (s, 2H), 3.62 (t, 2H), 3.53 (t, 2H), 2.73 (t, 2H), 2.70 (s, 3H), 2.60 (t, 2H), 2.40 (s, 3H), 1.75 (quin, 2H) | 1.21 |
| 114 | 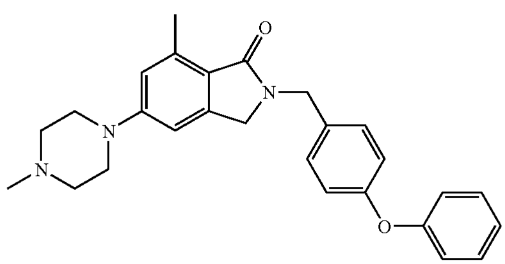 | 7-Methyl-5-(4-methylpiperazin-1-yl)-2-(4-phenoxybenzyl)-2,3-dihydroisoindol-1-one | 31 mg (72%) brown oil | 7.26-7.37 (m, 4H), 7.11 (t, 1H), 6.99 (t, 4H), 6.71 (d, 2H), 4.72 (s, 2H), 4.17 (s, 2H), 3.31 (t, 4H), 2.71 (s, 3H), 2.58 (t, 4H), 2.37 (s, 3H) | 0.28 |
| 115 | 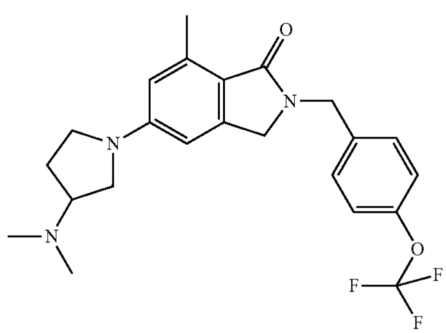 | 5-(3-dimethylamino-pyrollidin-1-yl)-7-methyl-2-(4-trifluoromethoxybenzyl)-2,3-dihydroisoindol-1-one | 30 mg (70%) yellow oil | 7.33 (d, 2H), 7.17 (d, 2H), 6.32 (d, 2H), 4.73 (s, 2H), 4.15 (s, 4H), 3.46-3.56 (m, 2H), 3.34-3.38 (m, 1H), 3.19 (t, 1H), 2.71 (quin, 1H), 2.65 (s, 3H), 2.33 (s, 6H) | 0.30 |

-continued

| Example | Name | Yield | NMR | GTPγS EC50 |
|---|---|---|---|---|
| 116 | 5-(Hexahydro-pyrrolo[1,2-a]pyrazin-2-yl)-7-methyl-2-(4-phenoxybenzyl)-2,3-dihydroisoindol-1-one | 13 mg (29%) yellow oil | 7.24-7.35 (m, 5H), 7.11 (t, 1H), 6.94-7.00 (m, 4H), 6.70 (d, 2H), 4.70 (s, 2H), 4.15 (s, 2H), 3.86 (d, 1H), 3.68 (d, 1H), 3.13-3.17 (m, 2H), 2.99 (td, 1H), 2.37 (td, 1H), 1.51-2.22 (m, 8H), 1.24-1.27 (m, 1H) | 0.18 |
| 117 | 2-(4-chlorobenzyl)-7-methyl-5-(4-methylpiperazin-1-yl)-2,3-dihydroisoindol-1-one | 24 mg (57%) orange solid | 7.21-7.32 (m, 4H), 6.70 (d, 2H), 4.70 (s, 2H), 4.14 (s, 2H), 3.30 (t, 4H), 2.70 (s, 3H), 2.58 (t, 4H), 2.37 (s, 3H) | 1.45 |
| 118 | 2-(4-Chlorobenzyl)-5-(hexahydropyrrolo[1,2-a]pyrazin-2-yl)-7-methyl-2,3-dihydroisoindol-1-one | 39 mg (57%) brown oil | 7.29 (dd, 4H), 6.70 (d, 2H), 4.70 (s, 2H), 4.14 9s, 2H), 3.86 (d, 1H), 3.71 (d, 1H), 3.14-3.18 (m, 2H), 2.99 (td, 1H), 2.71 (s, 3H), 2.37 (td, 1H), 2.16-2.22 (m, 3H), 1.87-1.93 (m, 4H) | 0.81 |
| 119 | 2-(4-chlorobenzyl)-5-(3-dimethylamino-pyrollidin-1-yl)-7-methyl-2,3-dihydroisoindol-1-one | 32 mg (58%) brown oil | 7.27 (dd, 4H), 6.32 (d, 2H), 4.70 (s, 2H), 4.12 (s, 2H), 3.49-3.56 (m, 2H), 3.34-3.37 (m, 1H), 3.20 (t, 1H), 2.83 (quin, 1H) 2.70 (s, 3H), 2.33 (s, 6H), 1.98-2.28 (m, 1H), 1.96 (q, 1H) | 0.42 |

-continued

| Example | Structure | Name | Yield | NMR | GTPγS EC50 |
|---|---|---|---|---|---|
| 120 | 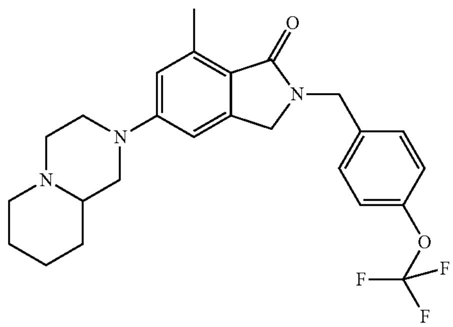 | 7-Methyl-5-(octahydropyrrolo[1,2-a]pyrazin-2-yl)-2-(4-trifluoromethoxy-benzyl)-2,3-dihydroisoindol-1-one | 27 mg (47%) yellow solid | 7.31 (t, 2H), 7.17 (d, 2H), 6.69 (d, 2H), 4.74 (s, 2H), 4.16 (s, 2H), 3.66 (d, 1H), 3.60 (d, 1H), 3.01 (td, 1H), 2.90 (t, 2H), 2.71 (s, 3H), 2.61 (t, 1H), 2.37 (td, 1H), 2.04-2.09 (m, 3H), 1.80 (br s, 1H), 1.62-1.69 (m, 3H), 1.27-1.36 (m, 3H) | 0.55 |
| 121 | 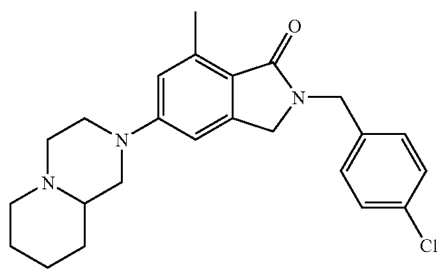 | 2-(4-Chlorobenzyl)-5-(octahydropyrrolo[1,2-a]pyrazin-2-yl-7-methyl-2,3-dihydroisoindol-1-one | 23 mg (39%) brown solid | 7.21-7.31 (m, 4H), 6.68 (d, 2H), 4.70 (s, 2H), 4.15 (s, 2H), 3.64 (d, 1H), 3.54 (d, 1H), 3.03 (td, 1H), 2.92 (t, 1H), 2.70 (s, 3H), 2.63 (t, 1H), 2.38 (td, 1H), 2.06-2.11 (m, 2H), 1.80 (br s, 1H), 1.63-1.69 (m, 3H), 1.25-1.38 (m, 4H) | 1.23 |
| 122 | 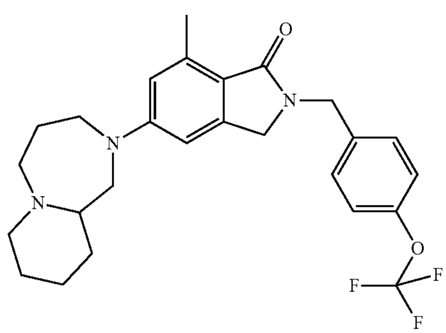 | 7-Methyl-5-(octahydropyrido[1,2-a][1,4]diazepin-2-yl)-2-(4-trifluoromethoxy-benzyl)-2,3-dihydroisoindol-1-one | 7.2 mg (12%) yellow oil | 7.33 (d, 2H), 7.17 (d, 2H), 6.41 (d, 2H), 4.73 (d, 1H), 4.16 (s, 2H), 3.40-3.42 (m, 4H), 2.90-2.94 (m, 1H), 2.71 (s, 3H), 2.20-2.30 (m, 2H), 2.07-2.19 (m, 2H), 1.82-1.93 (m, 2H), 1.64-1.70 (m, 2H), 1.30-1.36 (m, 2H) | 3.55 |
| 123 | 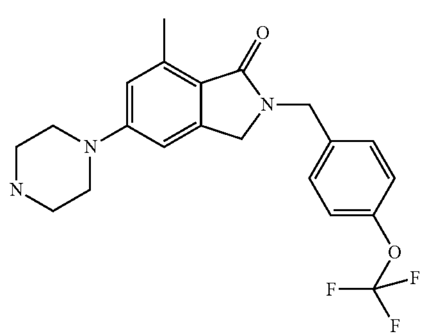 | 7-Methyl-5-piperazin-1-yl-2-(4-trifluoromethoxy-benzyl)-2,3-dihydroisoindol-1-one | 27 mg (45%) yellow gum | 7.33 (d, 2H), 7.17 (d, 2H), 6.70 (d, 2H), 4.74 (s, 2H), 4.16 (s, 2H), 3.26-3.29 (m, 4H), 3.05-3.08 (m, 4H), 2.71 (s, 3H) | 3.85 |

| Example | Structure | Name | Yield | NMR | GTPγS EC50 |
|---|---|---|---|---|---|
| 124 | 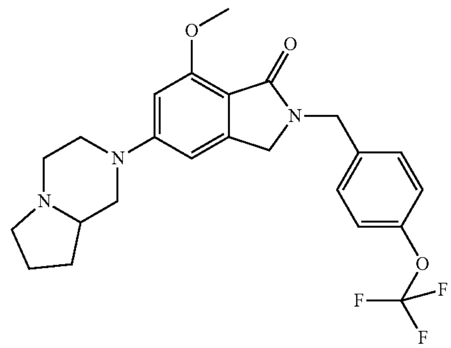 | 5-(Hexahydropyrrolo[1,2-a]pyrazin-2-yl)-7-methoxy-2-(4-trifluoromethoxy-benzyl)-2,3-dihydroisoindol-1-one | 37 mg (34%) yellow oil | 7.31-7.34 (m, 2H), 7.15 (d, 2H), 6.41 (d, 2H), 4.71 (s, 2H), 4.15 (s, 2H), 3.97 (s, 3H), 3.83 (d, 1H), 3.68 (d, 1H), 3.14-3.18 (m, 2H), 3.02 (td, 1H), 2.66 (t, 1H), 2.27 (td, 2H), 2.17-2.22 (m, 2H), 1.52-1.91 (m, 3H) | 1.91 |
| 125 | 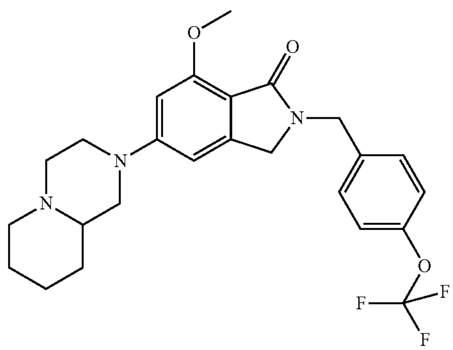 | 7-Methoxy-5-(octahydropyrrolo[1,2-a]pyrazin-2-yl)-2-(4-trifluoromethoxy-benzyl)-2,3-dihydroisoindol-1-one | 31 mg (27%) brown oil | 7.33 (d, 2H), 7.15 (d, 2H), 6.39 (d, 2H), 4.71 (s, 2H), 4.15 (s, 2H), 3.97 (s, 3H), 3.63 (d, 1H), 3.52 (d, 1H), 3.04 (td, 1H), 2.63 (t, 2H), 2.63 (1H), 2.38 (td, 1H), 2.04-2.10 (m, 2H), 1.62-1.69 (m, 3H), 1.25-1.33 (m, 3H) | 4.98 |
| 126 | 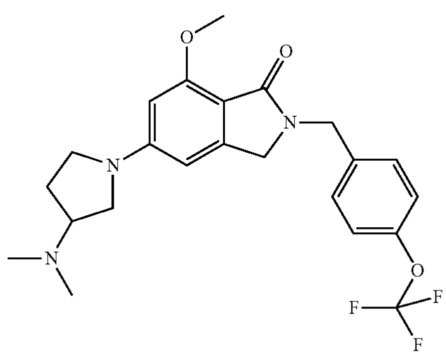 | 5-(3-Dimethylamino pyrrolidin-1-yl)-7-methoxy-2-(4-trifluoromethoxy-benzyl)-2,3-dihydroisoindol-1-one | 38 mg (35%) brown solid | 7.32 (d, 2H), 7.14 (d, 2H), 6.06 (s, 1H), 5.95 (s, 1H), 4.70 (s, 2H), 4.13 (s, 2H), 3.96 (s, 3H), 5.51 (q, 2H), 3.37 (q, 1H), 3.20 (t, 1H), 2.86 (quin, 1H), 2.33 (s, 6H), 2.22-2.29 (m, 1H), 1.95 (quin, 1H) | 2.52 |
| 127 | 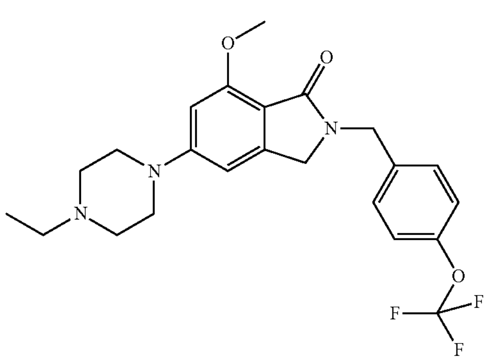 | 5-(4-Ethylpiperazin-1-yl)-7-methoxy-2-(4-trifluoromethoxy-benzyl)-2,3-dihydroisoindol-1-one | 56 mg (52%) light brown solid | 7.34 (d, 2H), 7.15 (d, 2H), 6.42 (d, 2H), 4.72 (s, 2H), 4.15 (s, 2H), 3.97 (s, 3H), 3.31-3.34 (m, 4H), 2.62 (t, 4H), 2.50 (q, 2H), 1.15 (t, 3H) | 4.68 |

-continued

| Example | Structure | Name | Yield | NMR | GTPγS EC50 |
|---|---|---|---|---|---|
| 128 | 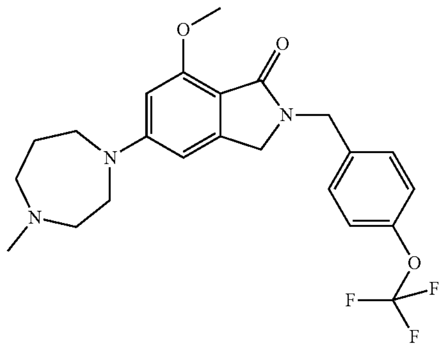 | 7-Methoxy-5-(4-methyl-[1,4]-diazepan-1-yl)-2-(4-triflouoromethoxy-benzyl)-2,3-dihydro-isoindol-1-one | 137 mg (100%) brown gum | 7.34 (d, 2H), 7.15 (d, 2H), 6.21 (s, 1H), 6.13 (s, 1H), 4.71 (s, 2H), 4.14 (s, 2H), 3.96 (s, 3H), 3.64 (t, 2H), 3.54 (t, 2H), 2.77 (t, 2H), 2.63 (t, 2H), 2.43 (s, 3H), 2.08 (q, 2H) | 5.04 |
| 129 | 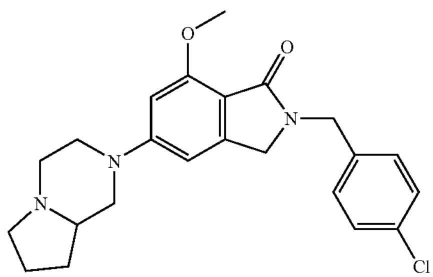 | 2-(4-Chloro-benzyl)-5-(hexahydro-pyrrolo]1,2-a]pyrazin-2-yl)-7-methoxy-2,3-dihydro-isoindol-1-one | 35 mg (27%) brown gum | 7.24-7.29 (m, 4H), 6.41 (d, 2H), 4.68 (s, 2H), 4.13 (s, 2H), 3.97 (s, 3H), 3.83 (d, 1H), 3.68 (d, 1H), 3.14-3.18 (m, 2H), 3.02 (td, 1H), 2.66 (t, 1H), 2.20 (td, 2H), 2.17-2.23 (m, 2H), 1.52-1.96 (m, 3H) | 6.34 |
| 130 | 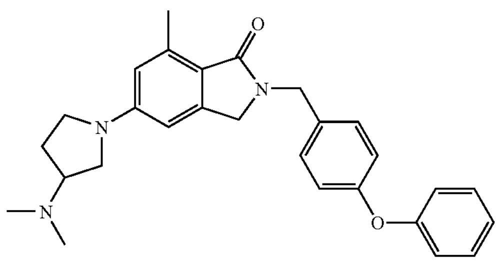 | 5-(3-Dimethylamino-pyrrolidin-1-yl)-7-methyl-2-(4-phenoxy-benzyl)-2,3-dihydro-isoindol-1-one | 7.3 mg (14%) yellow oil | 7.26-7.37 (m, 6H), 7.11 (t, 1H), 6.96-7.02 (m, 4H), 6.32 (d, 2H), 4.71 (2H), 4.16 (s, 2H), 3.46-3.57 (m, 2H), 3.35-3.38 (m, 1H), 3.20 (t, 1H), 2.82-2.92 (m, 1H), 2.71 (s, 3H), 2.34 (s, 6H), 2.19-2.23 (m, 1H) | 0.10 |
| 131 | 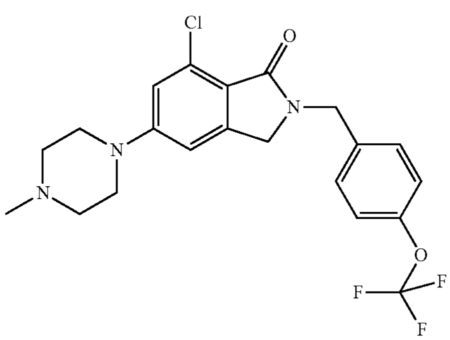 | 7-Chloro-5-(4-methyl-piperizin-1-yl)-2-(4-trifluoromethoxy-benzyl)-2,3-dihydro-isoindol-1-one | 14.0 mg, 34% colour-less solid | 1H NMR CDCl3: 7.35 (d, 2H), 7.18 (d, 2H), 6.89 (s, 1H), 6.72 (s, 1H), 4.75 (s, 2H), 4.16 (s, 2H), 3.32 (m, 4H), 2.58 (m, 4H), 2.37 (s, 3H) | 0.61 |

| Example | Structure | Name | Yield | NMR | GTPγS EC50 |
|---|---|---|---|---|---|
| 132 | 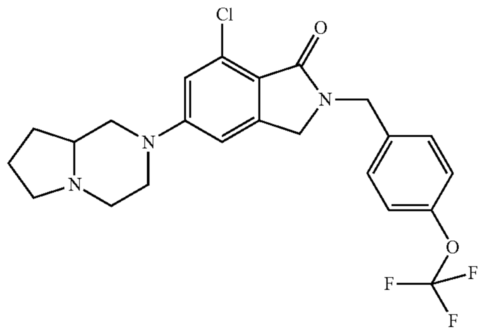 | 7-Chloro-5-(hexahydro-pyrrolo[1,2-a]pyrazin-2-yl)-2-(4-trifluoromethoxy-benzyl)-2,3-dihydro-isoindol-1-one | 23.0 mg, 52%, yellow solid | 7.35 (d, 2H), 7.18 (d, 2H), 6.90 (s, 1H), 6.73 (1H), 4.75 (s, 2H), 4.16 (s, 2H), 3.85 (d, 1H), 3.70 (d, 1H), 3.58 (broad s, 1H), 3.40 (broad s, 1H), 3.17 (d, 2H), 3.04 (t of d, 1H), 2.68 (t, 1H), 2.23 (m, 3H), 1.90 (m, 2H) | 0.48 |
| 133 | 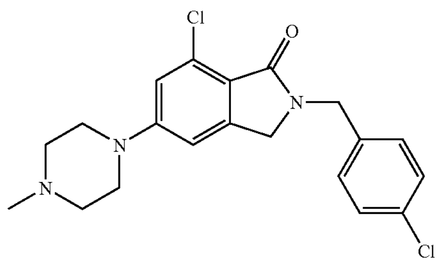 | 7-Chloro-2-(4-chlorobenzyl)-5-(4-methyl-piperazin-1-yl)-2,3-dihydroisoindol-1-one | 4.9 mg (12%) yellow solid | 7.24-7.32 (m, 4H), 6.89 (s, 1H), 6.71 (s, 1H), 7.72 (s, 2H), 4.14 (s, 2H), 3.32 (t, 4H), 2.57 (t, 4H), 2.37 (s, 3H) | 0.59 |
| 134 | 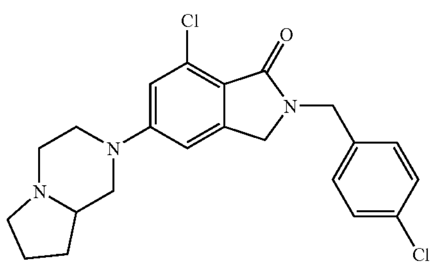 | 7-Chloro-2-(4-chloro-benzyl)-5-(hexahydro-pyrrolo[1,2-a]pyrazin-2-yl)-2,3-dihydro-isoindol-1-one | 4.6 mg (12%) brown solid | 7.24-7.32 (m, 6H), 6.90 (s, 1H), 6.72 (s, 1H), 7.72 (s, 2H), 4.14 (s, 2H), 3.83 (d, 1H), 3.68 (d, 1H), 3.05-3.19 (m, 2H), 3.04 (td, 1H), 2.66 (td, 1H), 1.84-1.98 (m, 2H), 1.52-1.54 (m, 2H) | 0.61 |
| 135 | 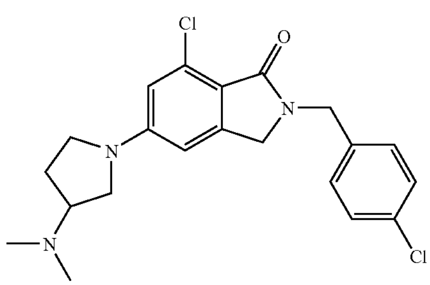 | 7-Chloro-2-(4-chloro-benzyl)-5-(3-dimethylamino-pyrolidin-1-yl)-2,3-dihydro-isoindol-1-one | 7.1 mg (15%) brown oil | 7.24-7.32 (m, 6H), 6.52 (s, 1H), 6.34 (s, 1H), 4.70 (s, 2H), 4.12 (s, 2H), 3.46-3.55 (m, 2H), 3.36 (td, 1H), 3.20 (t, 1H), 2.90 (quin, 1H), 2.34 (s, 6H) | 0.61 |
| 136 | 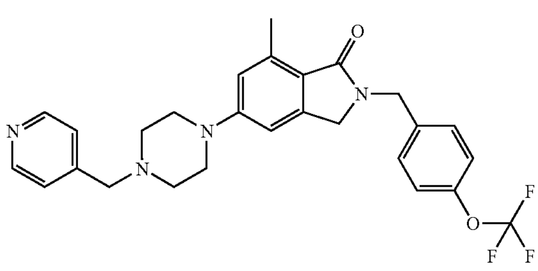 | 7-Methyl-5-(4-pyridin-4-ylmethyl-piperazin-1-yl)-2-(4-trifluoromethoxy-benzyl)-2,3-dihydro-isoindol-1-one | 64 mg (52%) yellow solid | 8.58 (br s, 2H), 7.39 (br s, 4H), 7.16 (br s, 2H), 6.69 (d, 2H), 4.73 (s, 2H), 4.09 (br s, 2H), 3.57 (br s, 2H), 3.30 (br s, 4H), 2.70 (br s, 3H), 2.62 (br s, 4H) | 0.70 |

| Example | Structure | Name | Yield | NMR | GTPγS EC50 |
|---|---|---|---|---|---|
| 137 | 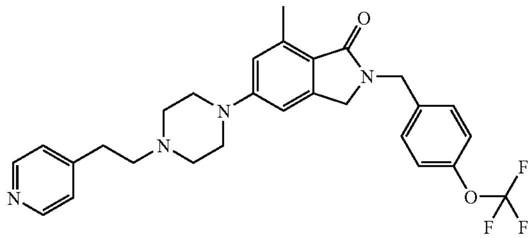 | 7-Methyl-5-[4-(2-pyridin-4-yl-ethyl)-piperazin-1-yl[-2-(4-trifluoromethoxy-benzyl)-2,3-dihydro-isoindol-1-one | 378 mg (30%) brown oil | 8.52 (s, 2H), 7.28-7.43 (m, 3H), 7.19 (s, 4H) 6.70 (d, 2H), 4.74 (s, 2H), 4.16 (s, 2H), 3.44 (s, 4H), 2.85 (br s, 2H), 2.68-2.71 (m, 8H) | 0.10 |
| 138 | 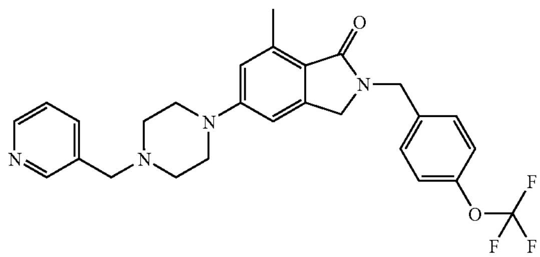 | 7-Methyl-5-(4-pyridin-3-ylmethyl-piperazin-1-yl)-2-(4-trifluoromethoxy-benzyl)-2,3-dihydro-isoindol-1-one | 90 mg (73%) brown oil | 8.59-8.66 (m, 2H), 7.71 (d, 1H), 7.31-7.34 (m, 3H), 7.16-7.18 (m, 2H), 6.70 (d, 2H), 4.73 (s, 2H), 4.11 (s, 2H), 3.58 (s, 2H), 3.28 (s, 4H), 2.70 (s, 3H), 2.61 (s, 4H) | 0.36 |
| 139 | 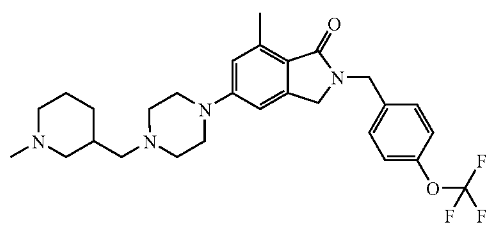 | 7-Methyl-5-[4-(1-methyl-piperidin-3-ylmethyl)-piperazin-1-yl]-2-(4-trifluoromethoxy-benzyl)-2,3-dihydro-isoindol-1-one | 46 mg (35%) yellow solid | 7.32 (d, 2H), 7.17 (d, 2H), 6.69 (d, 2H), 4.73 (s, 2H, 4.15 (s, 2H), 3.27 (t, 4H), 2.99 (d, 1H), 2.80 (d, 1H), 2.70 (s, 3H), 2.56 (pent, 2H), 2.49 (pent, 2H), 2.28 (s, 3H), 2.20-2.23 (m, 3H), 1.85-2.97 (m, 2H), 1.59-1.73 (m, 4H) | 1.05 |
| 140 | 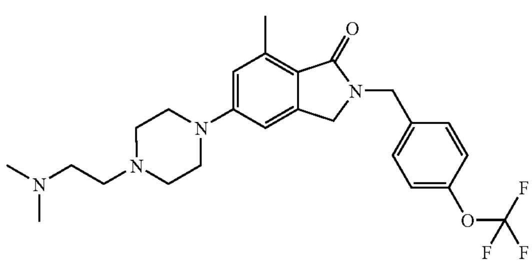 | 5-[4-(2-Dimethylamino-ethyl)-piperazin-1-yl]-7-methyl-2-(4-trifluoro-methoxy-benzyl)-2,3-dihydro-isoindol-1-one | 55 mg (46%) yellow solid | 7.32 (d, 2H), 7.17 (d, 2H), 6.69 (d, 2H), 4.74 (s, 2H), 4.16 (s, 2H), 3.30 (t, 4H), 2.70 (s, 3H), 2.64 (t, 4H), 2.49-2.55 (m, 4H), 2.28 (s, 6H) | 1.20 |
| 141 | 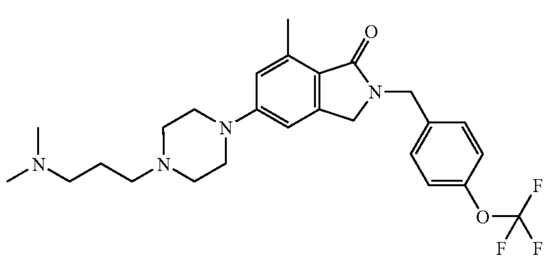 | 5-[4-(3-Dimethylamino-propyl)-piperazin-1-yl]-7-methyl-2-(4-trifluoro-methoxy-benzyl)-2,3-dihydro-isoindol-1-one | 44 mg (36%) yellow solid | 7.32 (d, 2H), 7.17 (d, 2H), 6.70 (d, 2H), 4.74 (s, 2H), 4.16 (s, 2H), 3.30 (t, 4H), 2.70 (s, 3H), 2.60 (t, 4H), 2.44 (t, 2H), 2.31 (t, 3H), 2.25 (s, 6H), 1.72 (quin, 2H) | 0.75 |

| Example | Structure | Name | Yield | NMR | GTPγS EC50 |
|---|---|---|---|---|---|
| 142 | 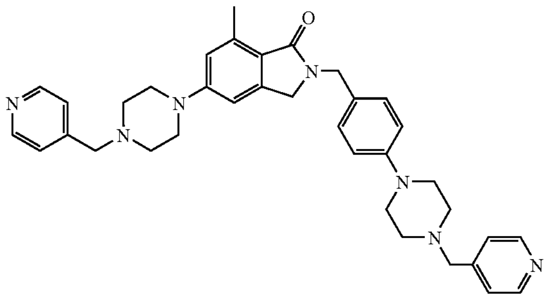 | 7-Methyl-5-(4-pyridin-4-ylmethyl-piperazin-1-yl)-2-[4-(4-pyridin-4-ylmethyl-piperazin-1-yl)-benzyl]-2,3-dihydro-isoindol-1-one | 9.9 mg yellow oil | 8.58 (br s, 4H), 7.32 (d, 5H), 7.20 (d, 2H), 6.89 (d, 2H), 6.74 (s, 2H), 6.63 (s, 2H), 4.68 (s, 2H), 4.12 (s, 2H), 3.58 (s, 4H), 3.29 (t, 4H), 3.20 (t, 4H), 2.71 (s, 3H), 2.60-2.64 (m, 8H) | 4.04 |
| 143 | 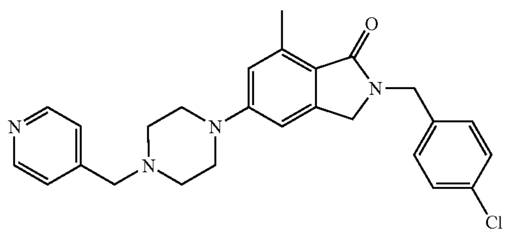 | 2-(4-Chloro-benzyl)-7-methyl-5-(4-pyridin-4-ylmethyl-piperazin-1-yl)-2,3-dihydro-isoindol-1-one | 62 mg (49%) yellow solid | 8.58 (d, 2H), 7.22-7.33 (m, 6H), 6.69 (d, 2H), 4.70 (s, 2H), 4.14 (s, 2H), 3.58 (s, 2H), 3.30 (t, 4H), 2.70 (s, 3H), 2.61 (t, 4H) | 0.42 |
| 144 | 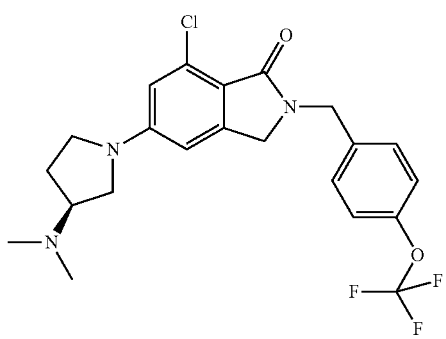 | 7-Chloro-5-(3-dimethylamino-pyrrolidin-1-yl)-2-(4-trifluoromethoxy-benzyl)-2,3-dihydro-isoindol-1-one | 45.1 mg, 42% yellow solid | 7.34 (d, 2H), 7.17 (d, 2H), 6.51 (s, 1H), 6.34 (s, 1H), 4.73 (s, 2H), 4.14 (s, 2H), 3.48 (q, 2H), 03.35 (m, 1H), 3.18 (t, 1H), 2.86 (m, 1H), 2.33 (s, 6H), 2.26 (m, 1H) 1.96 (m, 1H) | 0.31 |
| 145 | 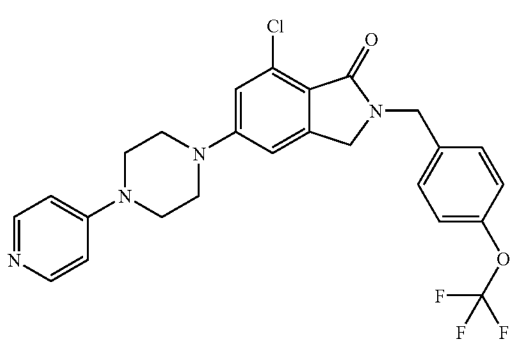 | 7-Chloro-5-(4-pyridin-4-yl-piperazin-1-yl)-2-(4-trifluoromethoxy-benzyl)-2,3-dihydro-isoindol-1-one | 19 mg (17%) solid | 8.37 (d, J = 8.2 Hz, 2H), 7.34 (d, J = 8.5 Hz, 2H), 7.18 (d, J = 8.1 Hz, 2H), 6.89-6.84 (m, 3H), 6.69 (s, 1H), 4.75 (s, 2H), 4.18 (s, 2H), 3.86-3.79 (m, 4H), 3.62-3.56 (m, 4H) | 0.40 |

-continued

| Example | Structure | Name | Yield | NMR | GTPγS EC50 |
|---|---|---|---|---|---|
| 146 | 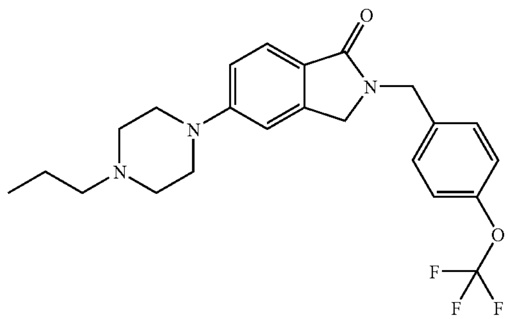 | 5-(4-Propyl-piperazin-1-yl)-2-(4-trifluoromethoxy-benzyl)-2,3-dihydro-isoindol-1-one | 21 mg (19%) solid | 7.74 (d, J = 8.6 Hz, 1H), 7.31 (d, J = 8.6 Hz, 2H), 7.16 (d, J = 8.1 Hz, 2H), 6.99 (dd, J = 8.6, 2.1 Hz, 1H), 6.82 (d, J = 1.5 Hz, 7H), 4.76 (s, 2H), 4.19 (s, 2H), 3.30 (t, J = 5.0 Hz, 4H), 2.58 (t, J = 5.0 Hz, 4H), 2.35 (t, J = 7.7 Hz, 2H), 0.93 (t, J = 7.4 Hz, 3H) | 4.42 |
| 147 | 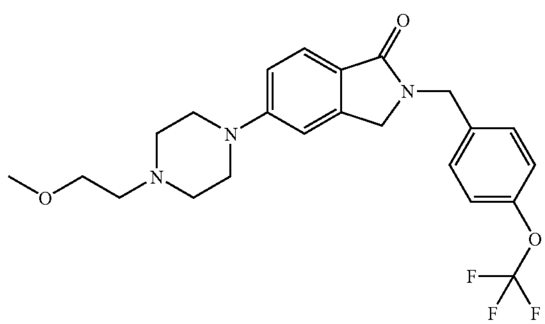 | 5-[4-(2-Methoxy-ethyl)-piperazin-1-yl]-2-(4-trifluoromethoxy-benzyl)-2,3-dihydro-isoindol-1-one | 38 mg (33%) solid | 7.73 (d, J = 8.6 Hz, 1H), 7.31 (d, J = 8.6 Hz, 2H), 7.16 (d, J = 8.2 Hz, 2H), 6.98 (dd, J = 8.6, 2.0 Hz, 1H), 6.82 (d, J = 1.4 Hz, 1H), 4.76 (s, 2H), 4.19 (s, 2H), 3.55 (t, J = 5.5 Hz, 2H), 3.37 (s, 3H), 3.32 (t, J = 5.0 Hz, 4H), 2.68-2.61 (m, 6H) | 6.57 |
| 148 | 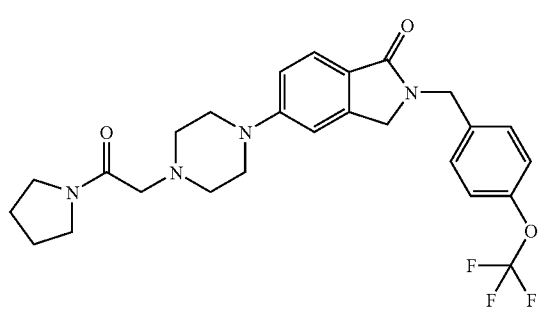 | 5-[4-(2-Oxo-2-pyrrolidin-1-yl-ethyl)-piperazin-1-yl]-2-(4-trifluoromethoxy-benzyl)-2,3-dihydro-isoindol-1-one | 39 mg (30%) solid | 7.73 (d, J = 8.6 Hz, 1H), 7.31 (d, J = 8.7 Hz, 2H), 7.16 (d, J = 8.7 Hz, 2H), 7.01-6.96 (m, 1H), 6.82 (s, 1H), 4.76 (s, 2H), 4.19 (s, 2H), 3.49 (t, J = 6.9 Hz, 4H), 3.33 (t, J = 5.0 Hz, 4H), 3.18 (s, 2H), 2.72 (t, J = 6.3 Hz, 4H), 1.91 (dq, J = 24.3, 6.5 Hz, 4H) | 6.78 |

-continued

| Example | Structure | Name | Yield | NMR | GTPγS EC50 |
|---|---|---|---|---|---|
| 149 | 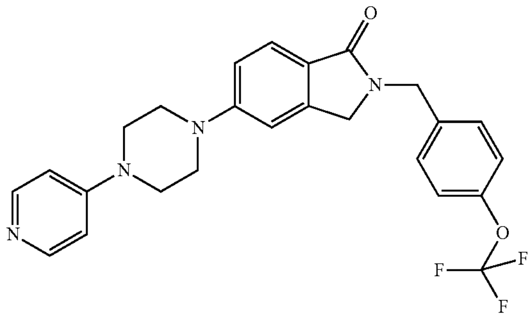 | 5-(4-Pyridin-4-yl-piperazin-1-yl)-2-(4-trifluoromethoxy-benzyl)-2,3-dihydro isoindol-1-one | 60 mg (49%) | 8.32 (d, J = 6.3 Hz, 2H), 7.78 (d, J = 8.5 Hz, 1H), 7.32 (d, J = 8.6 Hz, 2H), 7.17 (d, J = 8.2 Hz, 2H), 7.01 (d, J = 8.6 Hz, 1H), 6.85 (s, 1H), 6.69 (d, J = 6.5 Hz, 2H), 4.77 (s, 2H), 4.21 (s, 2H), 3.49 (dd, J = 20.2, 3.7 Hz, 8H) | 9.83 |
| 150 | 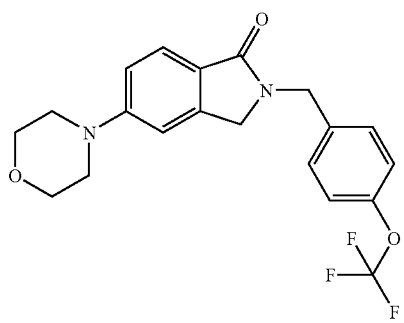 | 5-Morpholin-4-yl-2-(4-trifluoromethoxy-benzyl)-2,3-dihydro-isoindol-1-one | 90 mg (80%) solid | 7.76 (d, J = 8.6 Hz, 1H), 7.32 (d, J = 8.6 Hz, 2H), 7.17 (d, J = 8.0 Hz, 2H), 6.98 (dd, J = 8.5, 2.1 Hz, 1H), 6.83 (d, J = 1.8 Hz, 1H), 4.76 (s, 2H), 4.20 (s, 2H), 3.86 (t, J = 4.9 Hz, 4H), 3.24 (t, J = 4.9 Hz, 4H) | 8.76 |
| 151 | 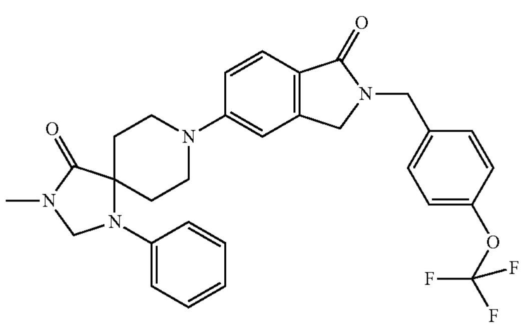 | 3-Methyl-8-[1-oxo-2-(4-trifluoromethoxy-benzyl)-2,3-dihydro-1H-isoindol-5-yl]-1-phenyl-1,3,8-triaza-spiro[4.5]decan-4-one | 1.22 mg (86%) solid | 7.77 (d, J = 8.6 Hz, 1H), 7.33 (d, J = 8.6 Hz, 2H), 7.17 (d, J = 8.2 Hz, 2H), 7.14-7.00 (m, 3H), 6.88 (s, 1H), 6.77 (t, J = 7.3 Hz, 1H), 6.58 (d, J = 8.2 Hz, 2H), 4.78 (s, 2H), 4.68 (s, 2H), 4.21 (s, 2H), 3.85-3.79 (m, 4H), 3.02 (s, 3H), 2.76-2.63 (m, 2H), 1.73-1.66 (m, 2H) | 0.48 |

-continued

| Example | Structure | Name | Yield | NMR | GTPγS EC50 |
|---|---|---|---|---|---|
| 152 | 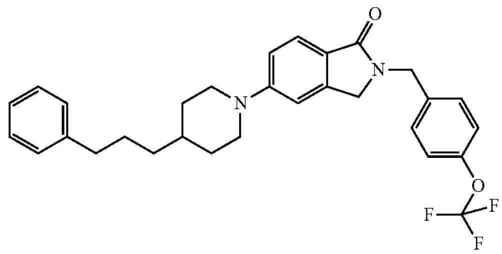 | 5-[4-(3-Phenyl-propyl)-piperidin-1-yl]-2-(4-trifluoromethoxy-benzyl)-2,3-dihydro-isoindol-1-one | 102 mg (78%) solid | 7.71 (d, J = 8.6 Hz, 1H), 7.33-7.27 (m, 4H), 7.20-7.13 (m, 5H), 6.97 (dd, J = 8.6, 2.0 Hz, 1H), 6.82-6.79 (m, 1H), 4.75 (s, 2H), 4.17 (s, 2H), 3.78 (d, J = 12.8 Hz, 2H), 2.79 (t, J = 12.3 Hz, 2H), 2.61 (t, J = 7.7 Hz, 2H), 1.81-1.59 (m, 4H), 1.37-1.21 (m, 4H) | 0.51 |
| 153 | 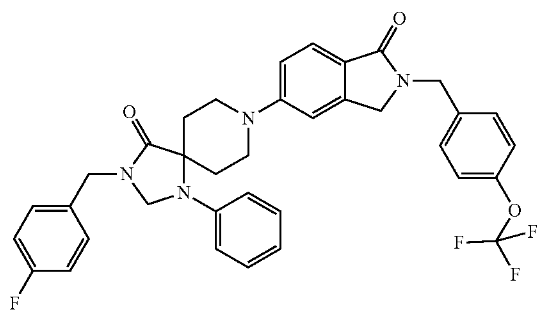 | 3-(4-Fluoro-benzyl)-8-[1-oxo-2-(4-trifluoromethoxy-benzyl)-2,3-dihydro-1H-isoindol-5-yl]-1-phenyl-1,3,8-triaza-spiro[4.5]decan-4-one | 125 mg (75%) solid | 7.78 (d, J = 8.6 Hz, 1H), 7.33 (d, J = 8.6 Hz, 2H), 7.31-7.26 (m, 2H), 7.17 (d, J = 8.1 Hz, 2H), 7.09-7.02 (m, 27H), 6.90-6.87 (m, 1H), 6.75 (t, J = 7.3 Hz, 1H), 6.53 (d, J = 8.1 Hz, 2H), 4.78 (s, 2H), 4.57 (d, J = 8.6 Hz, 4H), 4.21 (s, 2H), 3.87-3.80 (m, 4H), 2.76-2.63 (m, 2H), 1.72 (d, J = 13.9 Hz, 2H) | 2.64 |
| 154 | 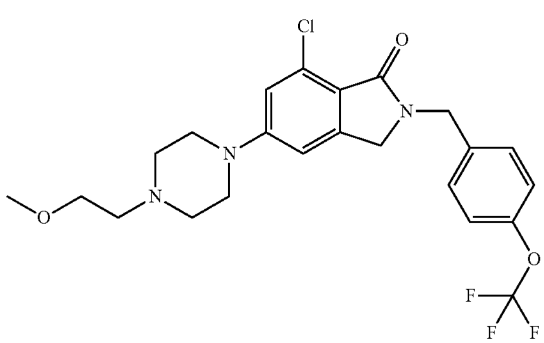 | 7-Chloro-5-[4-(2-methoxy-ethyl)-piperazin-1-yl]-2-(4-trifluoromethoxy-benzyl)-2,3-dihydro-isoindol-1-one | 15 mg (13%) solid | 7.34 (d, J = 8.4 Hz, 2H), 7.18 (d, J = 7.9 Hz, 2H), 6.90 (s, 1H), 6.73 (s, 1H), 4.75 (s, 2H), 4.17 (s, 2H), 3.95 (s, 2H), 3.73-3.57 (m, 7H), 3.52-3.33 (m, 4H), 2.05-1.85 (m, 5H) | 0.21 |

| Example | Structure | Name | Yield | NMR | GTPγS EC50 |
|---|---|---|---|---|---|
| 155 | 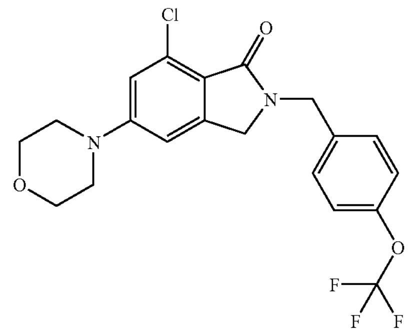 | 7-Chloro-5-morpholin-4-yl-2-(4-trifluoromethoxy-benzyl)-2,3-dihydro-isoindol-1-one | 10 mg (7%) solid | 7.34 (d, J = 8.6 Hz, 2H), 7.17 (d, J = 8.2 Hz, 2H), 6.87 (d, J = 1.9 Hz, 1H), 6.71-6.68 (m, 1H), 4.74 (s, 2H), 4.15 (s, 2H), 3.84 (t, J = 4.9 Hz, 4H), 3.24 (t, J = 4.9 Hz, 4H) | 0.52 |
| 156 | 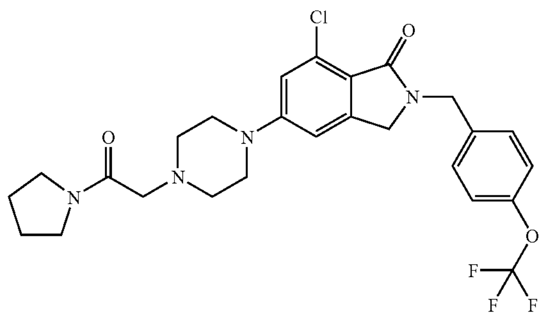 | 7-Chloro-5-[4-(2-oxo-2-pyrrolidin-1-yl-ethyl)-piperazin-1-yl]-2-(4-trifluoromethoxy-benzyl)-2,3-dihydro-isoindol-1-one | 19 mg (26%) solid | 7.34 (d, J = 8.4 Hz, 2H), 7.18 (d, J = 7.9 Hz, 2H), 6.90 (s, 1H), 6.73 (s, 1H), 4.75 (s, 2H), 4.17 (s, 2H), 3.95 (s, 2H), 3.73-3.56 (m, 11H), 3.53-3.44 (m, 2H), 3.41-3.33 (m, 2H), 2.06-1.84 (m, 5H) | 0.32 |
| J4 | 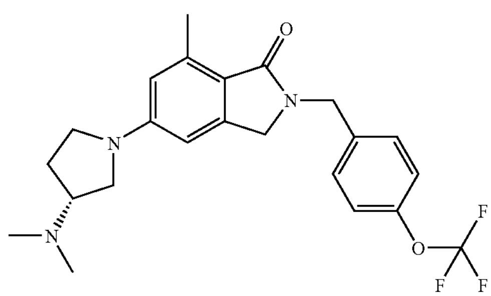 | (S)-5-(3-Dimethylamino-pyrrolidin-1-yl)-7-methyl-2-(4-trifluoromethoxy-benzyl)-2,3-dihydro-isoindol-1-one | 30 mg 28% brown oil | 7.33 (dd, 2H), 7.17 (d, 2H), 6.32 (d, 2H), 4.73 (s, 2H), 4.15 (s, 2H), 3.57-3.50 (m, 2H), 3.38-3.34, (m, 1H), 3.20 (t, 1H), 2.86 (m, 1H), 2.71 (s, 3H), 2.34 (s, 6H), 2.29-2.23 (m, 1H), 1.98-1.95 (m, 1H) | |
| J5 | Chiral | R-5-(3-Dimethylamino-pyrrolidin-1-yl)-7-methyl-2-(4-trifluoromethoxy-benzyl)-2,3-dihydro-isoindol-1-one | 34 mg 31% brown oil | 7.33 (dd, 2H), 7.19 (d, 2H), 6.32 (d, 2H), 4.73 (s, 2H), 4.15 (s, 2H), 3.57-3.50 (m, 2H), 3.37-3.35, (m, 1H), 3.20 (t, 1H), 2.86 (m, 1H), 2.71 (s, 3H), 2.34 (s, 6H), 2.29-2.25 (m, 1H), 1.98-1.95 (m, 1H) | |

-continued

| Example | Structure | Name | Yield | NMR | GTPγS EC50 |
|---|---|---|---|---|---|
| J6 | Chiral | 7-Chloro-5-(3-dimethylamino-pyrrolidin-1-yl)-2-(4-trifluoromethoxy-benzyl)-2,3-dihydro-isoindol-1-one | 89 mg 78% yellow oil | 7.35 (dd, 2H), 7.18 (d, 2H), 6.53 (d, 1H), 6.35 (d, 1H), 4.74 (s, 2H), 4.15 (s, 2H), 3.51 (m, 2H), 3.35 (m, 1H), 3.19 (t, 1H), 2.86 (m, 1H), 2.33 (s, 6H), 2.28 (m, 1H), 1.96, (m, 1H) | |
| J7 | Chiral | 7-Chloro-2-(4-chloro-benzyl)-5-(3-dimethylamino-pyrrolidin-1-yl)-2,3-dihydro-isoindol-1-one | 8.5 mg 8% yellow oil | 7.35-7.24 (m, 4H), 6.52 (d, 1H), 6.34 (d, 1H), 4.71 (s, 2H), 4.13 (s, 2H), 3.56-3.50 (m, 2H), 3.37-3.34 (m, 1H), 3.18 (t, 1H), 2.87 (m, 1H), 2.33 (s, 6H), 2.30-2.28 (m, 1H), 1.97, (m, 1H) | |
| J8 | Chiral | 7-Chloro-2-(4-chloro-benzyl)-5-(3-dimethylamino-pyrrolidin-1-yl)-2,3-dihydro-isoindol-1-one | 20 mg 18% yellow oil | 7.28 (m, 4H), 6.51 (d, 1H), 6.34 (d, 1H), 4.70 (s, 2H), 4.14 (s, 2H), 3.49 (m, 2H), 3.35 (m, 1H), 3.18 (t, 1H), 2.86 (m, 1H), 2.33 (s, 6H), 2.28 (m, 1H), 1.95, (m, 1H) | |
| J11 | 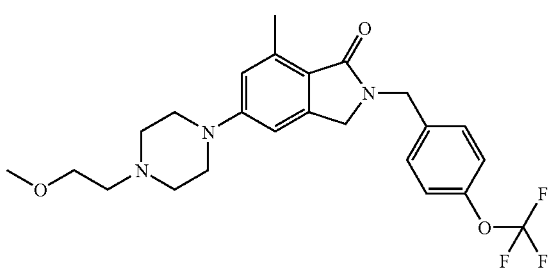 | 5-[4-(2-Methoxy-ethyl)-piperazin-1-yl]-7-methyl-2-(4-trifluoromethoxy-benzyl)-2,3-dihydro-isoindol-1-one | 23 mg 23% red solid | 7.33 (dd, 2H), 7.19 (d, 2H), 6.73 (s, 1H), 6.67 (s, 1H), 4.74 (s, 2H), 4.16 (s, 2H), 3.57 (t, 2H), 3.39 (s, 3H), 3.34 (t, 4H), 2.71 (s, 3H), 2.68-2.63 (m, 6H) | |
| J12 | 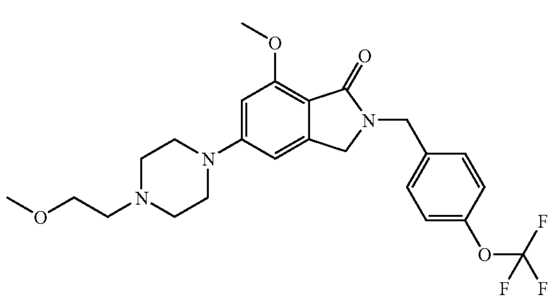 | 7-Methoxy-5-[4-(2-(methoxy-ethyl)-piperazin-1-yl]-2-(4-trifluoromethoxy-benzyl)-2,3-dihydro-isoindol-1-one | 31 mg 36% yellow oil | 7.34 (d, 2H), 7.16 (d, 2H), 6.40 (d, 2H), 4.72 (s, 2H), 4.15 (s, 2H), 3.97 (s, 3H), 3.57 (t, 2H), 3.39 (s, 3H), 3.-5 - 3.34 (t, 4H), 2.71 (s, 3H), 2.68-2.63 (m, 6H) | |

-continued

| Example | Structure | Name | Yield | NMR | GTPγS EC50 |
|---|---|---|---|---|---|
| J14 | 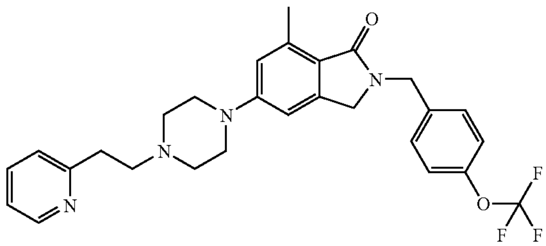 | 7-Methyl-5-[4-(2-pyridin-2-yl-ethyl)-piperazin-1-yl]-2-(4-trifluoromethoxy-benzyl)-2,3-dihydro-isoindol-1-one | 39 mg 41% brown oil | 8.56-8.54 (m, 1H), 7.62-7.59 (m, 1H), 7.34-7.32 (m, 2H), 7.23-7.15 (m, 4H), 6.71 (d, 2H), 4.74 (s, 2H), 4.16 (s, 2H), 3.33 (t, 4H), 3.07-3.02 (m, 2H), 2.87-2.82 (m, 2H), 2.72-2.69 (m, 7H) | |
| J15 | 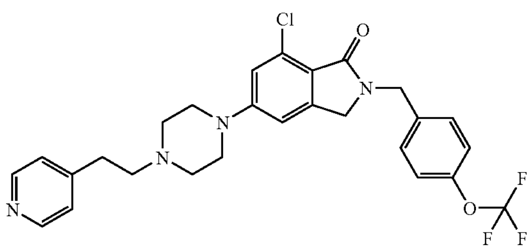 | 7-Chloro-5-[3-(2-pyridin-4-yl-ethyl)-piperazin-1-yl]-2-(4-trifluoromethoxy-benzyl)-2,3-dihydro-isoindol-1-one | 8 mg 3.7% yellow oil | 8.53 (dd, 2H), 7.37-7.33 (m, 2H), 7.20-7.16 (m, 4H), 6.90 (s, 1H), 6.73 (s, 1H), 4.75 (s, 2H), 4.17 (s, 2H), 3.33 (t, 4H), 2.87-2.82 (m, 2H), 2.71-2.65 (m, 6H) | |
| J17 | 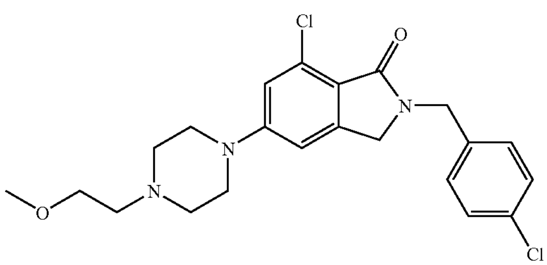 | 7-Chloro-2-(4-chloro-benzyl)-5-[4-(2-methoxy-ethyl)-piperazin-1-yl]-2,3-dihydro-isoindol-1-one | 31 mg 36% beige solid | 7.32-7.23 (m, 4H), 6.87 (d, 1H), 6.69 (d, 1H), 4.71 (s, 2H), 4.14 (s, 2H), 3.58-3.54 (m, 2H), 3.38 (s, 3H), 3.33 (t, 4H), 2.68-2.63 (m, 6H) | |
| J20 | 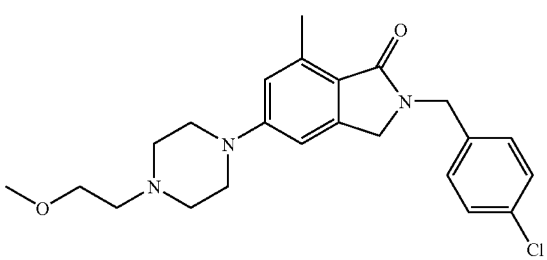 | 2-(4-Chloro-benzyl)-5-[4-(2-methoxy-ethyl)-piperazin-1-yl]-7-methyl-2,3-dihydro-isoindol-1-one | 61 mg 70% brown oil | 7.29-7.20 (m, 4H), 6.68 (d, 2H), 4.68 (s, 2H), 4.12 (s, 2H) 3.55 (t, 2H), 3.37 (s, 3H), 3.30 (t, 4H), 2.68 (s, 3H), 2.66-2.61 (m, 6H) | |
| J27 | 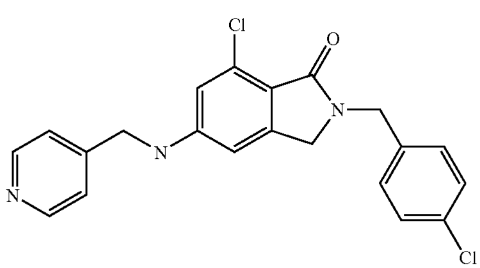 | 7-Chloro-2-(4-chloro-benzyl)-5-[(pyridin-4-ylmethyl)-amino]2,3-dihydro-isoindol-1-one | 17 mg 40% yellow solid | 8.61-8.58 (br s, 2H), 7.30-7.21 (m, 6H), 6.62 (s, 1H), 6.34 (s, 1H), 4.89 (t, 1H) 4.67 (s, 2H), 4.42 (d, 2H), 4.07 (s, 2H) | |

| Example | Name | Yield | NMR | GTPγS EC50 |
|---|---|---|---|---|
| J28 | 7-Chloro-2-(4-chloro-benzyl)-5-(2-pyridin-4-yl-4,5-dihydro-imidazol-1-yl)-2,3-dihydro-isoindol-1-one | 8 mg 17% colorless oil | 8.65 (d, 2H), 7.38 (d, 2H), 7.33-7.22 (m, 4H), 6.85 (d, 1H), 6.46 (d, 1H), 4.69 (s, 2H) 4.10 (s, 4H), 4.03 (s, 2H), | |
| J32 | 7-Chloro-5-(methyl-pyridin-3-ylmethyl-amino)-2-(4-trifluoromethoxy-benzyl)-2,3-dihydro-isoindol-1-one | 12 mg 18% orange solid | 8.61-8.58 (br d, 2H), 7.52 (d, 1H), 7.36-7.30 (m, 3H), 7.18 (d, 2H), 6.73 (d, 1H), 6.52 (d, 1H), 4.73 (s, 2H) 4.63 (s, 2H), 4.13 (d, 2H), 3.13 (s, 3H) | |
| J34 | 7-Chloro-5-(methyl-pyridin-4-ylmethyl-amino)-2-(4-trifluoromethoxy-benzyl)-2,3-dihydro-isoindol-1-one | 38 mg 54% yellow solid | 8.56 (br s, 2H), 7.74 (d, 1H), 7.33 (d, 2H), 7.18-7.14 (m, 4H), 6.78 (dd, 1H), 6.59 (d, 1H), 4.76 (s, 2H) 4.62 (s, 2H), 4.18 (s, 2H), 3.17 (s, 3H) | |
| J35 | 7-Methyl-5-(methyl-pyridin-4-ylmethyl-amino)-2-(4-trifluoromethoxy-benzyl)-2,3-dihydro-isoindol-1-one | 40 mg 57% yellow oil | 8.56 (br s, 2H), 7.32 (d, 2H, 7.36-7.30 (m, 3H), 7.18-7.14 (m, 4H), 6.50 (s, 1H), 6.42 (s, 1H), 4.73 (s, 2H) 4.60 (s, 2H), 4.13 (d, 2H), 3.14 (s, 3H), 2.69 (s, 3H) | |
| J37 | 7-Methyl-5-(methyl-pyridin-4-ylmethyl-amino)-2-(4-trifluoromethoxy-benzyl)-2,3-dihydro-isoindol-1-one | 21 mg 32% yellow oil | 8.56 (br s, 2H), 7.51 (d, 2H), 7.34-7.28 (m, 3H), 7.17 (d, 2H), 6.54 (s, 1H), 6.48 (s, 1H), 4.73 (s, 2H) 4.63 (s, 2H), 4.13 (d, 2H), 3.11 (s, 3H), 2.69 (s, 3H) | |

| Example | Structure | Name | Yield | NMR | GTPγS EC50 |
|---|---|---|---|---|---|
| J38 | 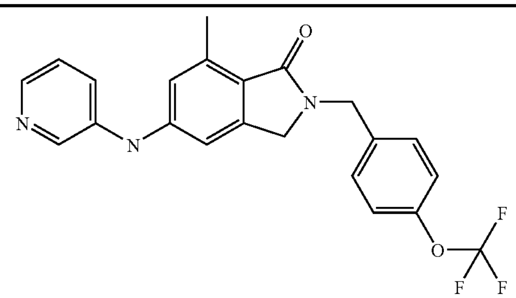 | 7-Methyl-pyridin-3-ylamino)-2-(4-trifluoromethoxy-benzyl)-2,3-dihydro-isoindol-1-one | 30 mg 48% yellow solid | | |
| J39 | 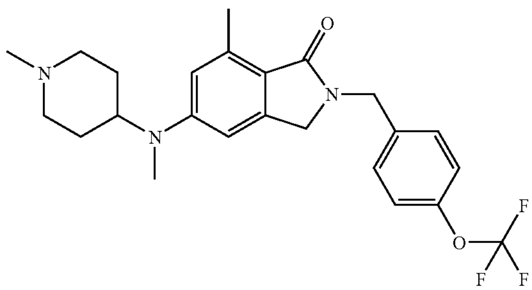 | 7-Methyl-5-[methyl-(1-methyl-piperidin-4-yl)-amino]-2-(4-trifluoromethoxy-benzyl)-2,3-dihydro-isoindol-1-one | 60 mg 54% yellow oil | | |
| J40 | 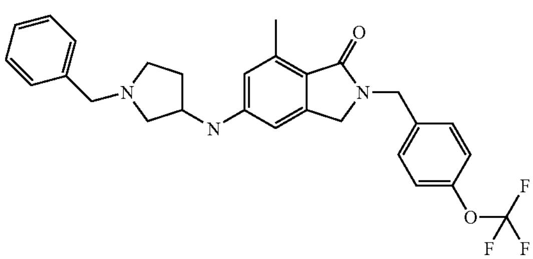 | 5-(1-Benzyl-pyrrolidin-3-ylamino)-7-methyl-2-(4-trifluoromethoxy-benzyl)-2,3-dihydro-isoindol-1-one | 87 mg 70% yellow gum | | |

Example 157

7-Methoxy-5-(1-methyl-piperidin-4-yl)-2-(4-trifluoromethoxy-benzyl)-2,3-dihydro-isoindol-1-one

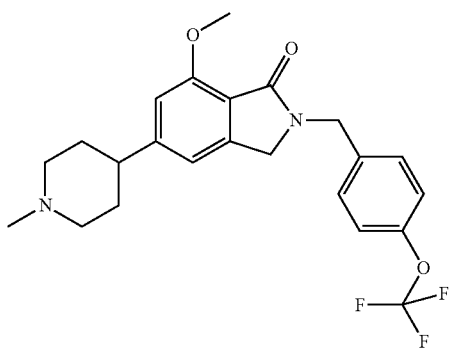

7-Methoxy-5-(1-methyl-1,2,3,6-tetrahydro-pyridin-4-yl)-2-(4-trifluoromethoxy-benzyl)-2,3-dihydro-isoindol-1-one (17 mg, 0.040 mmol) was stirred in methanol for 20 minutes under argon before a small scoop of palladium on carbon was added and the reaction atmosphere was changed to hydrogen. The reaction was allowed to stir for 18 hours under hydrogen. The reaction was filtered and the solvent was removed under reduced pressure to yield 7.2 mg (42%) of a yellow oil. $^1$H NMR (300 MHz, CDCl$_3$): δ 7.35 (d, 2H), 7.16 (d, 2H), 6.74 (d, 2H), 4.74 (s, 2H), 4.20 (s, 2H), 3.98 (s, 3H), 3.50 (s, 2H), 2.98-3.01 (m, 2H), 2.53-2.60 (m, 1H), 2.04-2.11 (m, 2H), 1.75-1.87 (m, 5H).

The following compounds were made in the same manner:

| Example | Structure | Name | Yield | NMR | GTPγS EC50 |
|---|---|---|---|---|---|
| 158 | 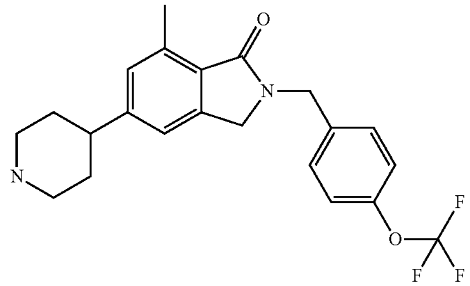 | 7-Methyl-5-piperidin-4-yl-2-(4-trifluoromethoxy-benzyl)-2,3-dihydro-isoindol-1-one | 19.2 mg (90%) yellow oil | 7.34 (d, 2H), 7.18 (d, 2H), 7.07-7.10 (m, 2H), 4.77 (s, 2H), 4.22 (2H), 3.18-3.20 (m, 1H), 2.98-3.01 (m, 1H), 2.75 (s, 4H), 2.34 (s, 1H), 2.02-2.18 (m, 2H) | 2.02 |
| 159 | 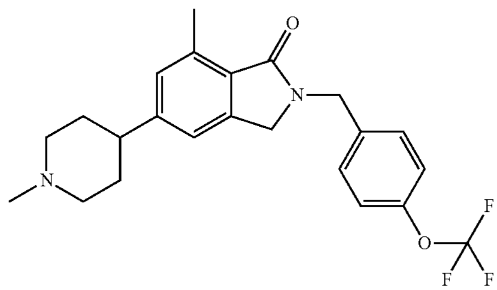 | 7-Methyl-5-(1-methyl-piperidin-4-yl)-2-(4-trifluoromethoxy-benzyl)-2,3-dihydro-isoindol-1-one | 15 mg (54%) yellow oil | 7.34 (d, 2H), 7.18 (d, 2H), 7.09 (d, 2H), 4.77 (s, 2H), 4.22 (s, 2H), 3.14 (d, 2H), 2.74 (s, 3H), 2.45 (sm 3H), 2.21 (t, 2H), 1.89-2.00 (m, 5H) | 1.28 |

Example 160

7-Methyl-5-(4-methyl-piperazine-1-carbonyl)-2-(4-trifluoromethoxy-benzyl)-2,3-dihydro-isoindol-1-one

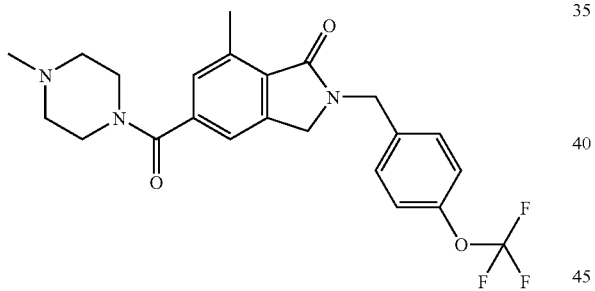

7-Methyl-1-oxo-2-(4-trifluoromethoxy-benzyl)-2,3-dihydro-1H-isoindole-5-carboxylic acid (35 mg, 0.096 mmol), 1-methylpiperazine (12 µL, 0.11 mmol), EDCI (20 mg, 0.11 mmol), HOBT (14 mg, 0.11 mmol) were stirred in DMF (5 mL) for 18 hours at room temperature. The reaction mixture was partitioned between EtOAc and water, and the organic layer was washed with brine, dried over anhydrous sodium sulphate, filtered and concentrated to yield 25 mg of a brown solid (70%). $^1$H NMR (300 MHz, CDCl$_3$): δ 7.34-7.37 (m, 2H), 7.19-7.24 (m, 4H), 4.79 (s, 2H), 4.24 (s, 2H), 3.84 (br s, 2H), 3.44 (br s, 2H), 2.79 (s, 3H), 2.55 (br s, 2H), 2.36 (s, 5H).

The following compounds were made in the same fashion:

| Ex. | Structure | Name | Yield | NMR | GTPγS EC50 |
|---|---|---|---|---|---|
| 161 | 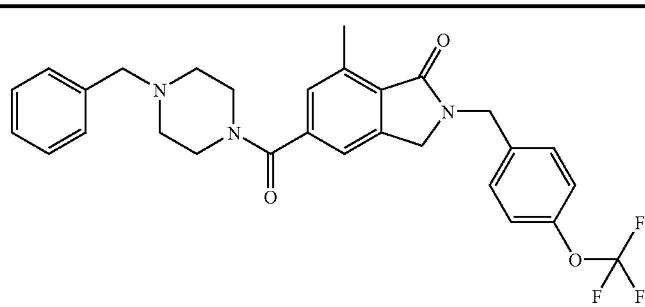 | 5-(4-Benzyl-piperazine-1-carbonyl)-7-methyl-2-(4-trifluoromethoxy-benzyl)-2,3-dihydro-isoindol-1-one | 60 mg (100%) brown oil | 7.30-7.36 (m, 7H), 7.18-7.23 (m, 4H), 4.79 (s, 2H), 4.26 (s, 2H), 3.81 (br s, 2H), 3.55 (s, 2H), 3.40 (s, 2H), 2.90 (s, 3H), 2.55 (br s, 2H), 2.38 (br s, 2H) | 0.63 |

-continued

| Ex. | Structure | Name | Yield | NMR | GTPγS EC50 |
|---|---|---|---|---|---|
| 162 | 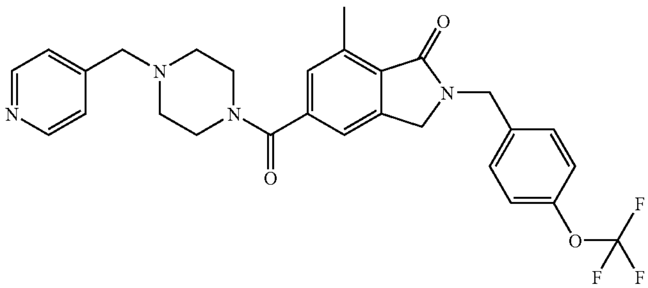 | 7-Methyl-5-(4-pyridin-4-ylmethyl-piperazine-1-carbonyl)-2-(4-trifluoromethoxy-benzyl)-2,3-dihydro-isoindol-1-one | 43 mg (100%) amber oil | 8.50 (br s, 2H), 7.09-7.35 (m, 8H), 4.78 (s, 2H), 4.25 (s, 2H), 3.75 (br s, 2H), 3.55 (s, 2H), 3.42 (br s, 2H), 2.78 (s, 3H), 2.62 (br s, 2H), 2.39 (br s, 2H) | 0.55 |
| 163 | 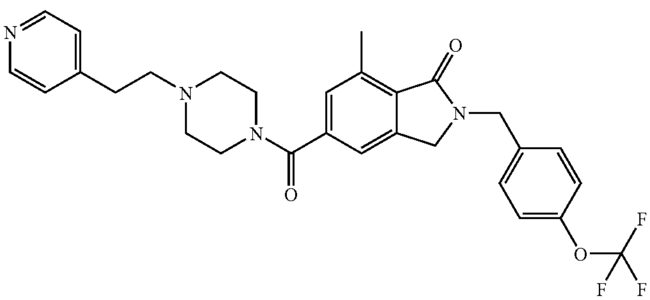 | 7-Methyl-5-[4-(2-pyridin-4-yl-ethyl)piperazine-1-carbonyl]-2-(4-trifluoromethoxy-benzyl)-2,3-dihydro-isoindol-1-one | 39 mg (87%) yellow oil | 8.50 (br s, 2H), 7.08-7.36 (m, 8H), 7.79 (s, 2H), 4.26 (s, 2H), 3.81 (br s, 2H), 3.41 (br s, 2H), 2.79 (s, 4H), 2.63-2.68 (m, 4H), 2.30-2.36 (m, 2H) | 1.21 |

Example 164

7-Methyl-5-(1-methyl-piperidin-4-ylmethyl)-2-(4-trifluoromethoxy-benzyl)-2,3-dihydro-isoindol-1-one

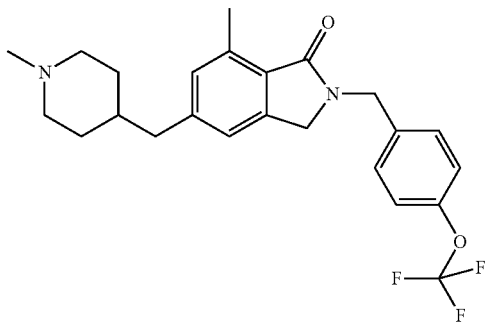

7-Methyl-5-piperidin-4-ylmethyl-2-(4-trifluoromethoxy-benzyl)-2,3-dihydro-isoindol-1-one (50.0 mg, 0.124 mmol) was dissolved in methanol (0.2 mL) and acetic acid (0.2 mL) and 37% formaldehyde (0.2 mL) was added at room temperature. The mixture was stirred for ten minutes and sodium cyanoborohydride (1M in THF, 0.2 mL, 0.20 mmol) was added and the mixture was allowed to stir overnight at room temperature. The reaction was diluted with dichloromethane, washed with sodium bicarbonate (sat) and brine dried over sodium sulphate, filtered and concentrated. Column chromatography provided the title compound as an off white foam (23.8 mg, 44%). $^1$H NMR (300 MHz, CDCl$_3$): δ 7.37 (d, 2H), 7.21 (d, 2H), 6.99 (d, 2H), 4.77 (s, 2H), 4.22 (s, 2H), 2.91 (d, 1H), 2.77 (m, 4H), 2.58 (d, 2H), 2.30 (m, 3H), 1.99 (m, 1H), 1.67-1.27 (m, 6H).

The following compound was made in a similar fashion

| Example | Structure | Name | Yield | NMR |
|---|---|---|---|---|
| M4 | 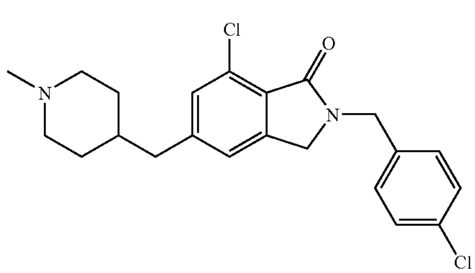 | 7-Chloro-2-(4-chloro-benzyl)-5-(1-methyl-piperidin-4-ylmethyl)-2,3-dihydro-isoindol-1-one | 17.6 mg 70.8% brown oil | 7.22-7.34 (m, 5H), 7.13 (s, 1H), 4.75 (s, 2H), 4.42 (s, 2H), 4.25 (s, 2H), 3.56-3.61 (m, 2H), 2.84 (s, 3H), 2.70-2.72 (m, 3H), 1.70-1.95 (m, 4H) |

| Example | Structure | Name | Yield | NMR |
| --- | --- | --- | --- | --- |
| M9 | 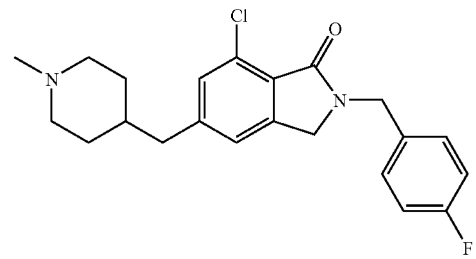 | 7-Chloro-2-(4-fluoro-benzyl)-5-(1-methyl-piperidin-4-ylmethyl)-2,3-dihydro-isoindol-1-one | 18 mg 97.7% brown oil | 7.28-7.33 (m, 2H), 7.24 (s, 1H), 7.14 (s, 1H), 7.02-7.08 (m, 2H), 4.76 (s, 2H), 4.42 (s, 2H), 3.55-3.63 (m, 2H), 2.86 (s, 3H), 2.71-2.73 (, 3H), 1.75-1.87 (m, 4H) |
| M13 | 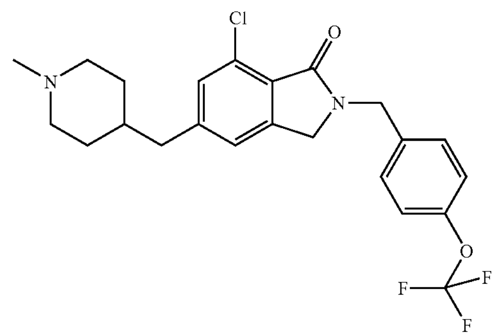 | 7-Chloro-5-(1-methyl-piperidin-4-ylmethyl)-2-(4-trifluoromethoxy-benzyl)-2,3-dihydro-isoindol-1-one | 25.6 mg 94.2% brown oil | 7.34-7.37 (m, 2H), 7.19-7.22 (m, 3H), 7.11 (s, 1H), 4.76 (m, 2H), 4.41 (s, 2H), 3.12-3.17 (m, 2H), 2.65 (d, 2H), 2.50 (s, 3h), 2.28 (dxt, 2H), 1.26-1.77 (m, 5H) |
| M18 | 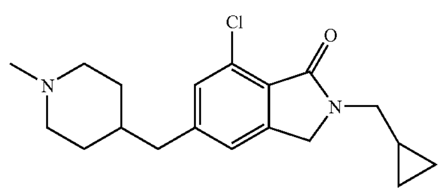 | 7-chloro-2-cyclopropylmethyl-5-(1-methyl-piperidin-4-ylmethyl)2,3-dihydro-isoindol-1-one | 19.6 mg, 99.8%, brown oil | 7.18-7.20 (d, 2H), 4.50 (s, 2H), 3.47 (d, 2H), 3.32-3.36 (m, 2H), 2.66-2.71 (m, 5H), 2.50 (t, 2h), 1.60-1.85 (m, 5H), 1.02-1.15 (m, 1H), 0.58-0.62 (m, 2H), 0.32-0.38 (m, 2H) |
| M56 | 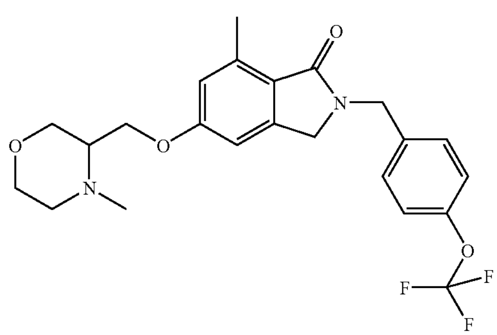 | 7-Methyl-5-(4-methyl-morpholin-3-yl methoxy)-2-(4-trifluoromethoxy-benzyl)-2,3-dihydro-isoindol-1-one | 17.8 mg, 92%, yellow oil | 7.32-7.35 (m, 2H), 7.18-7.20 (m, 2H), 6.75 (d, 2H), 4.75 (s, 2H), 4.37 (s, 1H), 4.19 (s, 2H), 3.93-4.08 (m, 4H), 3.54-3.84 (m, 2H), 2.78-2.82 (m, 2H), 2.72 (s, 3H), 2.63-2.70 (m, 1H), 2.44 (s, 3H), |

-continued

| Example | Structure | Name | Yield | NMR |
|---|---|---|---|---|
| M57 | 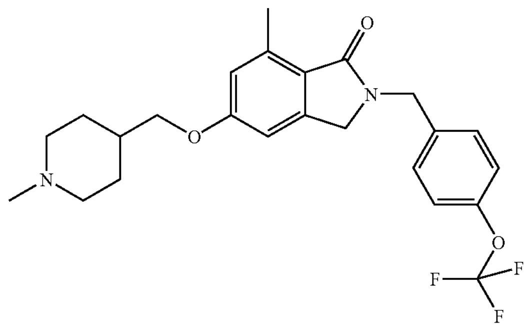 | 7-Methyl-5-(1-methyl-piperidin-4-yl methoxy)-2-(4-trifluoromethoxy-benzyl)-2,3-dihydro-isoindol-1-one | 27.7 mg, 100%, yellow oil | 7.31-7.35 (m, 2H), 6.18-6.20 (m, 2H), 6.72 (d, 2H), 4.76 (s, 2H), 4.35 (s, 2H), 4.19 (s, 2H), 3.85 (d, 2H), 2.99-3.03 (m, 2H), 2.71 (s, 2H), 2.37 (s, 2H), 2.07-2.16 (m, 2H), 1.85-1.92 (m, 3H), 1.46-1.50 (m, 2H) |
| M62 | 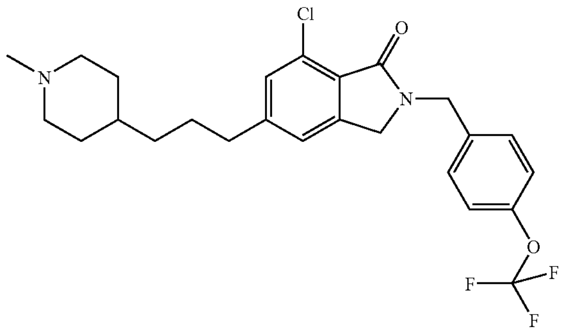 | 7-Chloro-5-[3-(1-methyl-piperidin-4-yl)-propyl]-2-(4-trifluoromethoxy-benzyl)-2,3-dihydro-isoindol-1-one | 51.3 mg, 100%, yellow oil | 7.34-7.39 (m, 2H), 7.18-7.22 (m, 3H), 7.09 (s, 1H), 4.78 (s, 2H), 4.23 (s, 2H), 2.98-3.02 (m, 2H), 2.64 (m, 2H), 2.37 (s, 3H), 2.05-2.13 (m, 2H), 1.61-1.74 (m, 4H), 1.27-1.40 (m, 5H) |
| M66 | 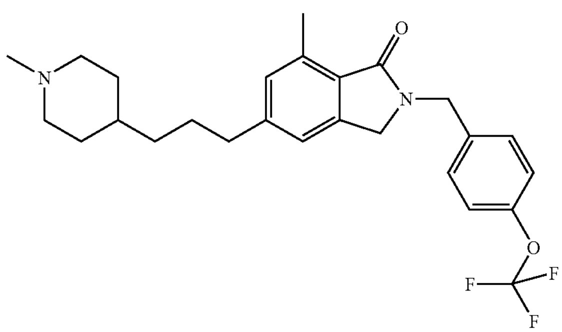 | 7-Methyl-5-[3-(1-methyl-piperidin-4-yl)-propyl]-2-(4-trifluoromethoxy-benzyl)-2,3-dihydro-isoindol-1-one | 8.9 mg, 56%, colorless oil | 7.33-7.37 (m, 2H), 7.16-7.21 (m, 2H), 7.00 (d, 2H), 4.76 (s, 2H), 4.21 (s, 2H), 2.83-2.87 (m, 2H), 2.74 (s, 3H), 2.62 (t, 2H), 2.27 (s, 3H), 1.85-1.92 (m, 2H), 1.61-1.68 (m, 4H), 1.20-1.31 (m, 5H) |

Example 165

7-Methyl-5-morpholin-4-ylmethyl-2-(4-trifluoromethoxy-benzyl)-2,3-dihydro-isoindol-1-one

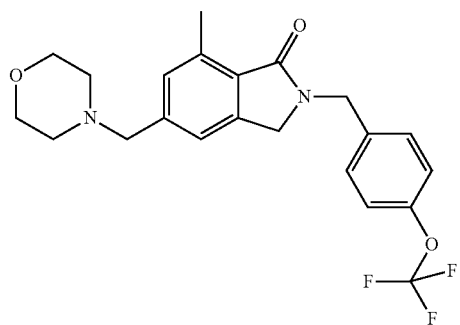

Morpholine (8.2 mg, 0.094 mmol) was dissolved in dichloromethane (2.0 mL) and 7-Methyl-1-oxo-2-(4-trifluoromethoxy-benzyl)-2,3-dihydro-1H-isoindole-5-carbaldehyde (30.0 mg, 0.085 mmol) was added. The mixture was stirred for ten minutes and sodium triacetoxy borohydride (29.7 mg, 0.14 mmol) was added and the reaction was allowed to stir overnight. The reaction was then diluted with dichloromethane, washed with saturated sodium bicarbonate and brine, dried over sodium sulfate, filtered and concentrated. Column chromatography (20% MeOH/EtOAc) provided the title compound as a colourless oil (13.3 mg, 37%). $^1$H NMR (300 MHz, CDCl$_3$): δ 7.35 (d, 2H), 7.19 (d, 4H), 4.78 (s, 2H), 4.23 (s, 2H), 3.72 (t, 4H), 3.53 (s, 2H), 2.76 (s, 3H), 2.45 (t, 4H).

The following compounds were made in a similar manner:

| Example | Structure | Name | Yield | NMR | GTPγS EC50 |
|---|---|---|---|---|---|
| 166 | 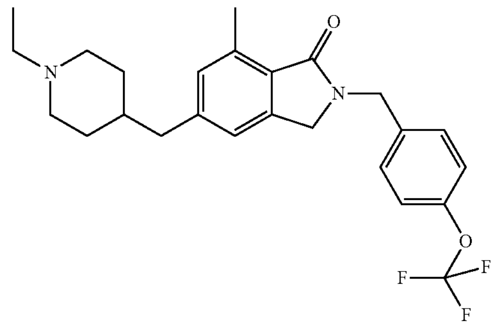 | 5-(1-Ethyl-piperidin-4-ylmethyl)-7-methyl-2-(4-trifluorometh-oxy-benzyl)-2,3-dihydro-isoindol-1-one | 23.0 mg, 41%, brown oil | 7.35 (d, 2H), 7.19 (d, 2H), 6.99 (d, 2H), 4.77 (s, 2H), 4.21 (s, 2H), 2.95 (d, 2H), 2.93 (s, 3H), 2.69 (m, 2H), 2.64 (d, 2H), 2.40 (q, 2H), 1.86 (t, 1H), 1.64 (m, 2H), 1.36 (m, 2H), 1.10 (t, 3H) | 0.52 |
| 167 | 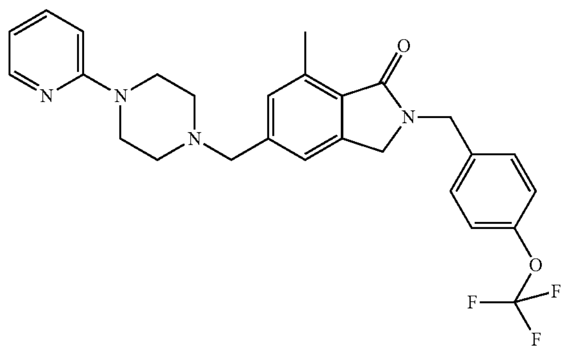 | 7-Methyl-5-(4-pyridin-2-yl-piperazin-1-ylmethyl)-2-(4-trifluorometh-oxy-benzyl)-2,3-dihydro-isoindol-1-one | 26.1 mg, 62%, colour-less oil | 8.19 (d, 1H), 7.48 t of d, 1H), 7.36 (d, 2H), 7.21 (t, 4H), 6.63 (t, 2H), 4.78 (s, 2H), 4.24 (s, 2H), 3.57 (m, 6H), 2.77 (s, 3H), 2.57 (t, 4H) | 0.14 |
| J100 | 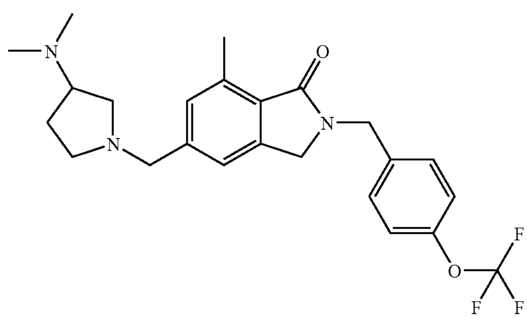 | 5-(3-Dimethylamino-pyrrolidin-1-ylmethyl)-7-methyl-2-(4-trifluorometh-oxy-benzyl)-2,3-dihydro-isoindol-1-one | 15 mg 20% brown oil | 7.34 (d, 2H), 7.19 (d, 4H), 4.77 s, 2H), 4.22 (s, 2H), 3.68-3.56 (m, 2H), 2.87-2.71 (m, 6H), 2.52-2.49 (m, 1H), 2.34-2.32 (m, 1H), 2.21 (s, 6H), 1.99 (m, 1H), 1.74-1.72 (m, 1H) | |
| M21 | 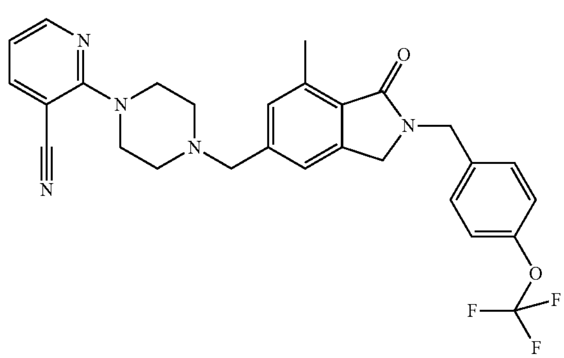 | 2-{4-[7-methyl-1-oxo-2-(4-trifluorometh-oxy-benzyl)-2,3-dihydro-1H-isoindol-5-ylmethyl]-piperazin-1-ylmethyl}-nicotinonitrile | 29.0 mg, yellow oil, 97.6% | 8.33-8.36 (m, 1H), 7.75-7.79 (m, 1H), 7.34-7.37 (m, 2H), 7.18-7.23 (m, 4H), 6.74-6.78 (m, 1H), 4.78 (m, 2H), 4.24 (m, 2H), 3.73-3.76 (m, 4H), 3.60 (s, 2H), 2.77 (s, 3H), 2.59-2.63 (m, 2H), | |

-continued

| Example | Structure | Name | Yield | NMR | GTPγS EC50 |
|---|---|---|---|---|---|
| M22 | 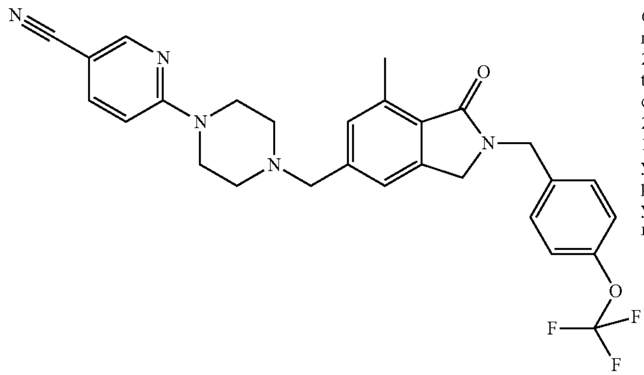 | 6-{4-[7-methyl-1-oxo 2-(4-trifluoromethoxy-benzyl)-2,3-dihydro-1H-isoindol-5-ylmethyl]-piperazin-1-ylmethyl}-nicotinonitrile | 29.9 mg, 99%, yellow oil | 8.41 (m, 1H), 7.59-7.63 (m, 1H), 7.34-7.37 (m, 2H), 7.18-7.22 (m, 4H), 6.59 (d, 1H), 4.78 (s, 2H), 4.24 (s, 2H), 3.69-3.71 (m, 4H), 3.58 (s, 2H), 2.76 (s, 3H), 2.52-2.56 (m, 4H) | |
| M23 | 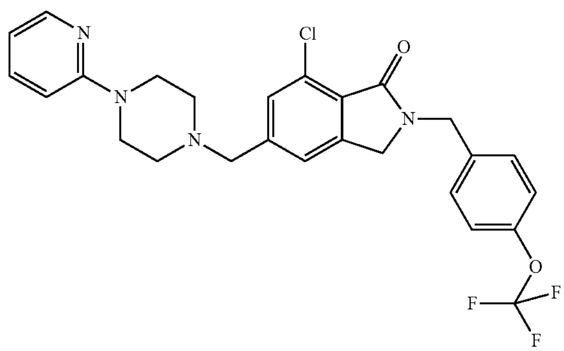 | 7-chloro-5-(4-pyridin-2-yl-piperazin-1-ylmethyl)-2-(4-trifluoromethoxy-benzyl)-2,3-dihydro-isoindol-1-one | 25.4 mg, 90.9%, yellow oil | 8.19-8.21 (m, 1H), 7.34-7.49 (m, 5H), 7.18-7.21 (m, 2H), 6.62-6.66 (m, 2H), 4.79 (s, 2H), 4.26 (s, 2H), 3.70 (s, 2H), 3.54-3.59 (m, 4H), 2.55-2.58 (m, 4H) | |
| M24 | 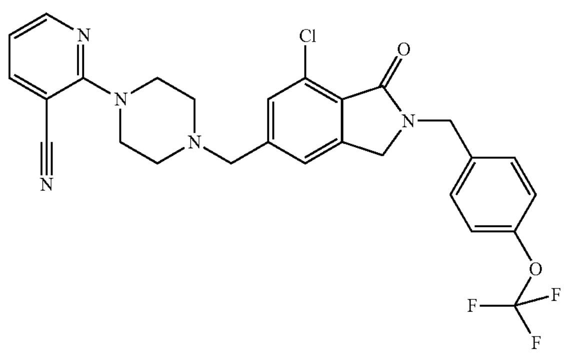 | 2-{4-[7-chloro-1-oxo-2-(4-trifluoromethoxy-benzyl)-2,3-dihydro-1H-isoindol-5-ylmethyl]-piperazin-1-ylmethyl}-nicotinonitrile | 24.4 mg, 83.4%, yellow oil | 8.34-8.36 (m, 1H), 7.76-7.79 (m, 1H), 7.32-7.44 (m, 4H), 7.19-7.21 (m, 2H), 6.75-6.79 (m, 1H), 4.79 (s, 2H), 4.26 (s, 2H), 3.73-3.76 (m, 4H), 3.60 (s, 2H), 2.59-2.62 (m, 4H) | |
| M25 | 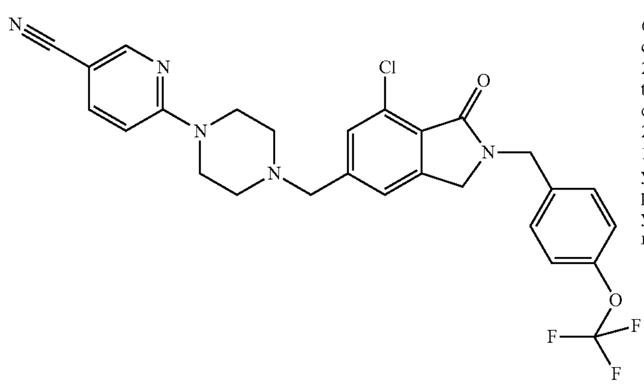 | 6-{4-[7-chloro-1-oxo-2-(4-trifluoromethoxy-benzyl)-2,3-dihydro-1H-isoindol-5-ylmethyl]-piperazin-1-ylmethyl}-nicotinonitrile | 27.2 mg, 92.9%, yellow oil | 8.40-8.41 (m, 1H), 7.60-7.63 (m, 1H), 7.31-7.44 (m, 4H), 7.19-7.21 (m, 2H), 6.58-6.61 (m, 1H) 4.79 (s, 2H), 4.26 (s, 2H), 3.68-3.72 (m, 4H), 3.59 (s, 2H), 2.53-2.56 (m, 4H) | |

-continued

| Example | Name | Yield | NMR | GTPγS EC50 |
|---|---|---|---|---|
| M28 | 4-{4-[7-chloro-1-oxo-2-(4-trifluoromethoxy-benzyl)-2,3-dihydro-1H-isoindol-5-ylmethyl]-piperazin-1-methyl}-nicotinonitrile | 17.9 mg, 32.4%, yellow oil | 7.60-7.63 (m, 2H), 7.34-7.47 (m, 5H), 7.27-7.28 (m, 1H), 7.18-7.21 (m, 2H), 4.78 (m, 2H), 4.24 (s, 2H), 3.55-3.57 (m, 4H), 2.48-2.53 (m, 8H) | |
| M43 | 2-[4-(7-Chloro-2-cyclopropyl-methyl-1-oxo-2,3-dihydro-1H-isoindol-5-yl-methyl)-piperazin-1-yl]-nicotinonitrile | 41.9 mg, 99%, yellow oil | 8.24-8.36 (m, 1H), 7.76-7.79 (m, 1H), 7.37-7.40 (d, 2H), 6.75-6.79 (m, 1H), 4.46 (s, 2H), 3.74-3.77 (m, 4H), 3.62 (s, 2H), 3.47 (d, 2H), 2.60-2.64 (m, 4H), 1.03-1.16 (m, 1H), 0.56-0.62 (m, 2H), 0.32-0.37 (m, 2H) | |
| M44 | 6-[4-(7-Chloro-2-cyclopropyl-methyl-1-oxo-2,3-dihydro-1H-isoindol-5-yl-methyl)-piperazin-1-yl]-nicotinonitrile | 34 mg, 80%, white foam | 8.40 (d, 1H), 7.58-7.62 (m, 1H), 7.34-7.70 (m, 2H), 6.60 (d, 1H), 4.46 (s, 2H), 3.69-3.72 (m, 4H), 3.60 (s, 2H), 3.46 (d, 2H, 2.54-2.57 (m, 4H), 1.02-1.10 (m, 1H), 0.55-0.61 (m, 2H), 0.32-0.37 (m, 2H) | |
| M47 | 7-Chloro-5-{4-[2-(4-chloro-phenoxy)-ethyl]-piperidin-1-ylmethyl}-2-cyclopropylmethyl-2,3-dihydro-isoindol-1-one | 16.1 mg, 85%, off-white solid | 7.35-7.37 (m, 2H), 7.21-7.26 (m, 2H), 6.80-6.85 (m, 2H), 4.44 (s, 2H), 3.98 (t, 2H), 3.54 (s, 2H), 3.47 (d, 2H), 2.86-2.89 (m, 2H), 1.98-2.06 (m, 2H), 1.71-1.78 (m, 4H), 1.42-1.58 (m, 1H), 1.36-1.41 (m, 2H), 1.02-1.10 (m, 1H), 0.56-0.61 (m, 2H), 0.34-0.36 (m, 2H) | |

-continued

| Example | Structure | Name | Yield | NMR | GTPγS EC50 |
|---|---|---|---|---|---|
| M58 | 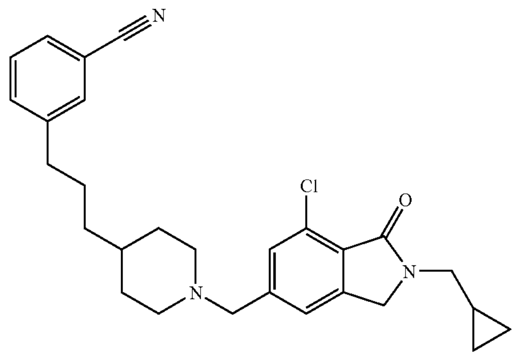 | 3-{3-[1-(7-Chloro-2-cyclopropyl-methyl-1-oxo-2,3-dihydro-1H-isoindol-5-ylmethyl)-piperidin-4-yl]-propyl}-benzonitrile | 13 mg, 70.3%, yellow oil | 7.41-7.50 (3H), 7.34-7.38 (m, 2H), 4.44 (s, 2H), 3.52 (s, 2H), 3.46 (d, 2H), 2.84-2.87 (m, 2H), 2.64 (t, 2H), 1.85-1.98 (m, 3H), 1.65-1.68 (m, 4H), 1.26-1.30 (m, 4H), 1.02-1.08 (m, 1H), 0.55-0.61 (m, 2H), 0.33-0.37 (m, 2H) | |
| M63 | 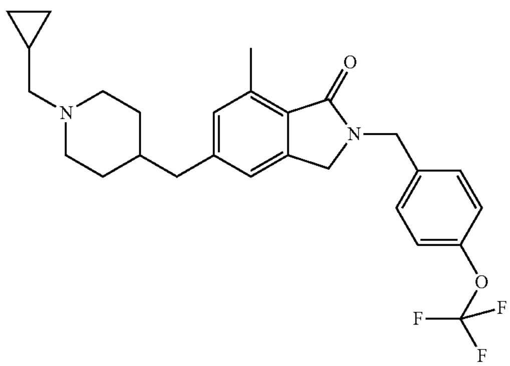 | 5-(1-Cyclopropyl-methyl-piperidin-4-ylmethyl)-7-methyl-2-(4-trifluoro-methoxy-benzyl)-2,3-dihydro-isoindol-1-one | 82.7 mg, 100%, yellow foam | 7.33-7.49 (m, 2H), 7.17-7.28 (m, 2H), 6.98 (d, 2H), 4.76 (s, 2H), 4.20 (s, 2h), 3.05-3.09 (m, 2H), 2.73 (s, 2H), 2.64-2.65 (m, 1H), 2.56-2.58 (m, 2H), 2.24-2.26 (d, 2H), 1.89-1.96 (m, 2H), 1.54-1.65 (m, 2H), 1.36-1.43 (m, 2H), 0.85-0.88 (m, 1H), 0.48-0.52 (m, 2H), 0.07-0.10 (m, 2H) | |

Example 168

7-Methyl-5-(1-pyridin-2-ylmethyl-piperidin-4-ylmethyl)-2-(4-trifluoromethoxy-benzyl)-2,3-dihydro-isoindol-1-one

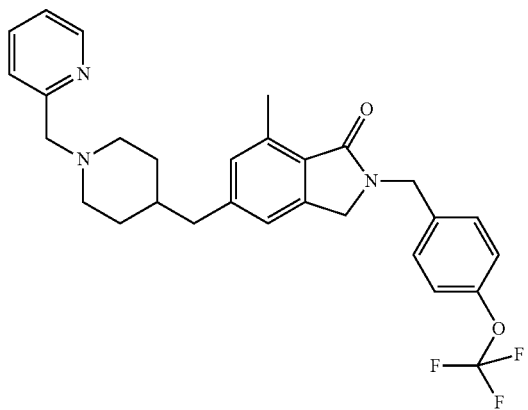

To a mixture of 2-chloromethylpyridine hydrochloride salt (16.9 mg, 0.103 mmol), 7-methyl-5-piperidin-4-ylmethyl-2-(4-trifluoromethoxy-benzyl)-2,3-dihydro-isoindol-1-one (50.0 mg, 0.120 mmol) and potassium carbonate (71.2 mg, 0.515 mmol) was added acetonitrile (3.0 mL). The mixture was allowed to stir at room temperature overnight. Water (2.0 mL) was added and the product was extracted with ethyl acetate. The organic layer was washed with water, brine, dried over sodium sulfate, filtered and concentrated. Column chromatography provided the title compound as a yellow oil (34.1 mg, 65%). $^1$H NMR (300 MHz, CDCl$_3$): δ 8.56 (d, 1H), 7.65 (t, 1H), 7.34 (m, 3H), 7.18 (m, 3H), 6.98 (d, 2H), 4.76 (s, 2H), 4.20 (s, 2H), 3.64 (s, 2H), 2.90 (d, 2H), 2.73 (s, 3H), 2.57 (d, 2H), 2.03 (t, 2H), 1.62 (m, 2H), 1.35 (m, 3H).

The following compounds were made in a similar fashion:

| Example | Structure | Name | Yield | NMR | GTPγS EC50 |
|---|---|---|---|---|---|
| 169 | 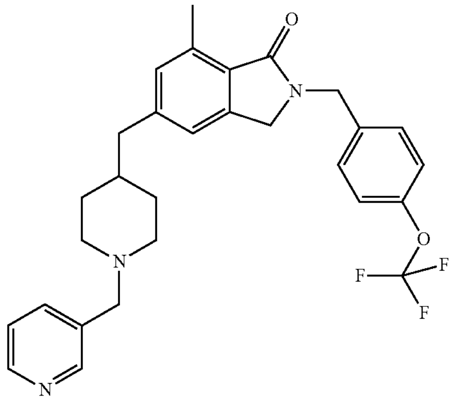 | 7-methyl-5-(1-pyridin-3-ylmethyl-piperidin-4-ylmethyl)-2-(4-trifluoromethoxy-benzyl)-2,3-dihydro-isoindol-1-one | 34.5 mg, 66.5% | ¹HNMR CDCl₃: 8.52 (broad s, 2H), 7.66 (d, 1H), 7.34 (d, 2H), 7.26 (m, 1H), 7.18 (d, 2H), 6.97 (d, 2H), 4.76 (s, 2H), 4.20 (s, 2H), 3.50 (s, 2H), 2.85 (d, 2H), 2.73 (s, 3H), 2.57 (d, 2H), 1.94 (t, 2H), 1.54 (m, 3H), 1.29 (m, 2H) | 0.14 |
| 170 | 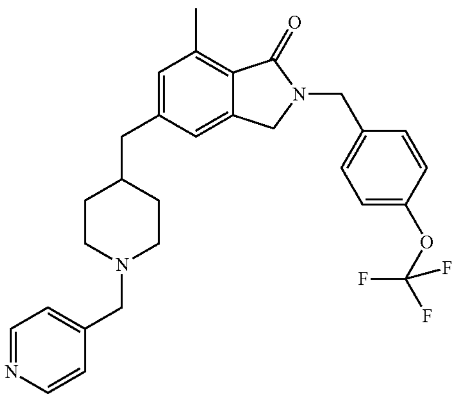 | 7-methyl-5-(1-pyridin-4-ylmethyl-piperidin-4-ylmethyl)-2-(4-trifluoromethoxy-benzyl)-2,3-dihydro-isoindol-1-one | 32.4 mg, 61.8% | 8.54 (broad s, 2H), 7.34 (d, 2H), 7.27 (m, 2H), 7.18 (d, 2H), 6.98 (d, 2H), 4.76 (s, 2H), 4.20 (s, 2H), 3.47 (s, 2H), 2.83 (d, 2H), 2.78 (s, 3H), 2.61 (d, 2H), 1.95 (t, 2H), 1.63 (m, 3H), 1.31 (m, 2H) | 0.08 |
| 171 | 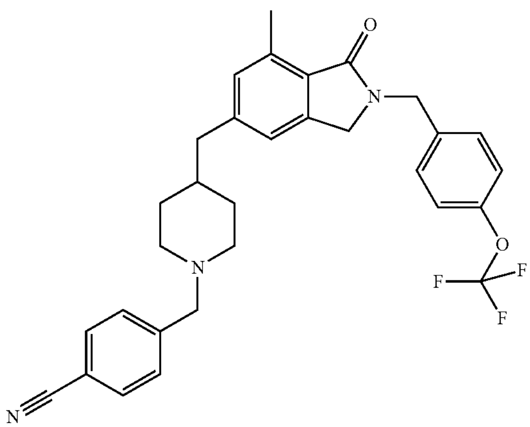 | 4-{4-[7-methyl-1-oxo-2-(4-trifluoromethoxy-benzyl)-2,3-dihydro-1H-isoindol-5-ylmethyl]-piperidin-1-ylmethyl}-benzonitrile | 43.1 mg, 78.3% | 7.66 (d, 1H), 7.59 (s, 1H), 7.44 (d, 2H), 7.35 (d, 2H), 7.20 (d, 2H), 6.98 (d, 2H), 4.76 (s, 2H), 4.20 (s, 2H), 3.54 (s, 2H), 2.84 (d, 2H), 2.73 (s, 3H), 2.57 (d, 2H), 1.95 (t, 2H), 1.61 (m, 3H), 1.28 (m, 2H) | 0.04 |
| 172 | 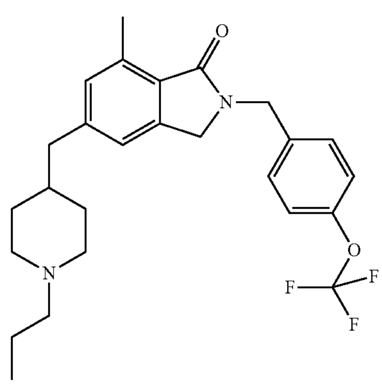 | 7-methyl-5-(1-propyl-piperidin-4-ylmethyl)-2-(4-trifluoromethoxy-benzyl)-2,3-dihydro-isoindol-1-one | 32.9 mg, 57.6% | 7.34 (d, 2H), 7.18 (d, 2H), 6.97 (s, 2H), 4.75 (s, 2H), 4.20 (s, 2H), 3.25 (d, 2H), 2.72 (s, 3H), 2.59 (m, 4H), 2.27 (m, 2H), 1.70 (m, 7H), 0.92 (t, 3H) | 1.51 |

| Example | Structure | Name | Yield | NMR | GTPγS EC50 |
|---|---|---|---|---|---|
| 173 | 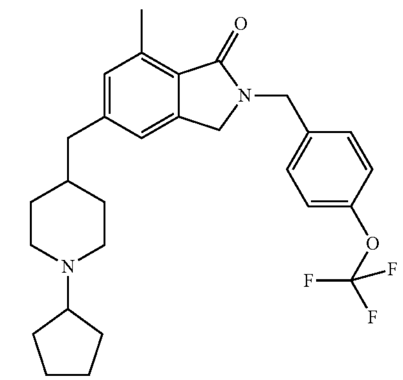 | 5-(1-cyclopentyl-piperidin-4-ylmethyl)-7-methyl-2-(4-trifluoromethoxy-benzyl)-2,3-dihydro-isoindol-1-one | 22.5 mg, 37.3% | 7.34 (d, 2H), 7.20 (d, 2H), 6.98 (d, 2H), 4.76 (s, 2H), 4.20 (s, 2H), 3.50 (d, 2H), 3.01 (m, 1H), 2.73 (s, 3H), 2.64 (d, 2H), 2.44 (m, 2H), 1.59-2.01 (m, 13H) | 0.82 |
| 174 | 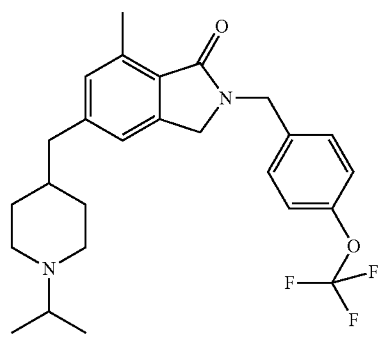 | 5-(1-isopropyl-piperidin-4-ylmethyl)-7-methyl-2-(4-trifluoromethoxy-benzyl)-2,3-dihydro-isoindol-1-one | 40.4 mg, 70.7% | 7.32 (d, 2H), 7.18 (d, 2H), 6.97 (s, 2H), 4.75 (2H), 4.19 (s, 2H), 3.05 (d, 2H,) 2.71 (s, 3H), 2.59 (d, 2H), 2.29 (t, 2H), 1.65 (m, 6H), 1.16 (d, 6H) | 0.74 |
| 175 | 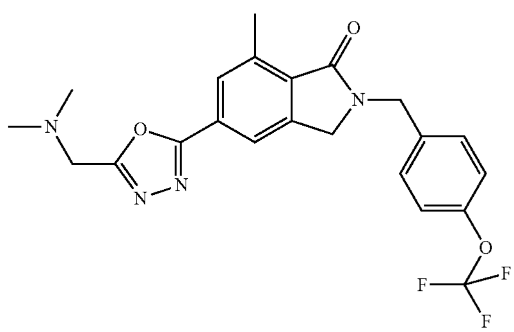 | 5-(5-Dimethylamino-methyl-[1,3,4]oxadiazol-2-yl)-7-methyl-2-(4-trifluoromethoxy-benzyl)-2,3-dihydro-isoindol-1-one | 8.43 mg, 100%, off white solid | 7.96 (s, 2H), 7.38 (d, 2H), 7.23 (d, 2H), 4.81 (s, 2H), 4.33 (s, 2H), 3.86 (s, 2H), 2.85 (s, 3H), 2.42 (s, 6H) | 6.40 |
| 176 | 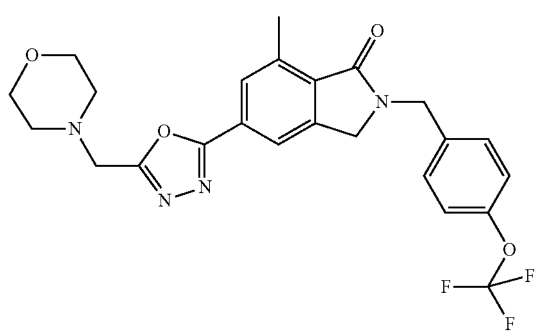 | 7-Methyl-5-(5-morpholin-4-ylmethyl-[1,3,4]oxadiazol-2-yl)-2-(4-trifluoromethoxy-benzyl)-2,3-dihydro-isoindol-1-one | 12.0 mg, 100% brown oil | 7.94 (d, 2H), 7.37 (d, 2H), 7.22 (d, 2H), 4.81 (s, 2H), 4.33 (s, 2H), 3.91 (s, 2H), 3.77 (t, 4H), 2.85 (s, 3H), 2.66 (t, 4H) | 1.29 |

-continued

| Example | Structure | Name | Yield | NMR | GTPγS EC50 |
|---|---|---|---|---|---|
| 177 | 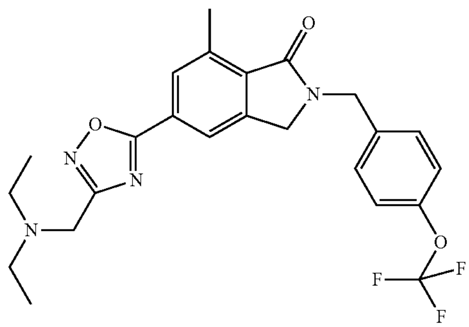 | 5-(3-Diethylamino methyl-[1,2,4]oxadiazol-5-yl)-7-methyl-2-(4-trifluoromethoxy-benzyl)-2,3-dihydro-isoindol-1-one | 18.6, 94%, yellow oil | 8.03 (d, 2H), 7.37 (d, 2H), 7.22 (d, 2H), 4.81 (s, 2H), 4.34 (s, 2H), 3.89 (s, 2H), 2.85 (s, 3H), 2.69 (q, 4H), 1.15 (t, 6H) | 0.14 |
| 178 | 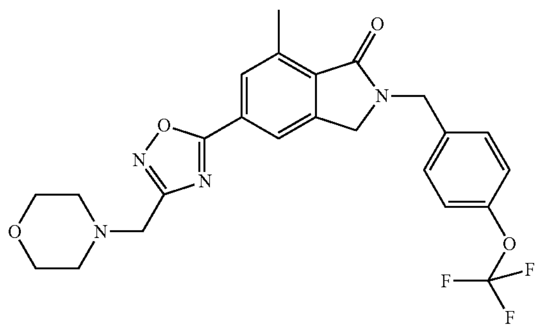 | 7-Methyl-5-(3-morpholin-4-ylmethyl-[1,2,4]oxadiazol-5-yl)-2-(4-trifluoromethoxy-benzyl)-2,3-dihydro-isoindol-1-one | 24.7 mg, 100%, off white oil | 8.03 (d, 2H), 7.37 (d, 2H), 7.23 (d, 2H), 4.81 (s, 2H), 4.34 (s, 2H), 3.78 (t, 6H), 2.85 (s, 3H), 2.65 (t, 4H) | 0.11 |
| 179 | 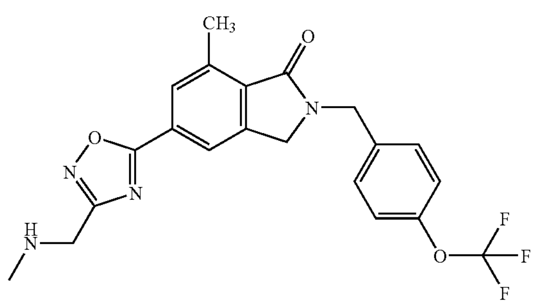 | 7-Methyl-5-(3-methylamino-methyl-[1,2,4]oxadiazol-5-yl)-2-(4-trifluoromethoxy-benzyl)-2,3-dihydro-isoindol-1-one | 18.5 mg, 100%, yellow solid | 8.01 (d, 2H), 7.38 (d, 2H), 7.22 (d, 2H), 4.81 (s, 2H), 4.34 (s, 2H), 4.00 (broad s, 2H), 2.85 (s, 3H), 2.54 (broad s, 3H) | 0.47 |
| 180 | 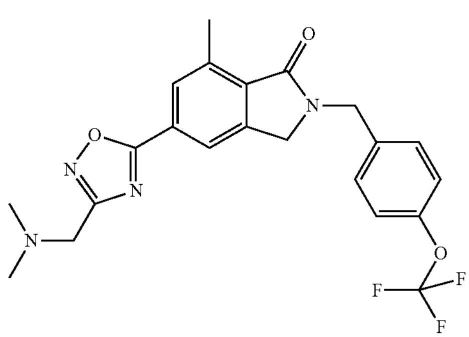 | 5-(3-Dimethylamino-methyl-[1,2,4]oxadiazol-5-yl)-7-methyl-2-(4-trifluoromethoxy-benzyl)-2,3-dihydro-isoindol-1-one | 19.8 mg, 100%, yellow oil | 8.05 (d, 2H), 7.37 (d, 2H), 7.23 (d, 2H), 4.81 (s, 2H), 4.34 (s, 2H), 3.71 (s, 2H), 2.85 (s, 3H), 2.40 (s, 6H) | 0.10 |

-continued

| Example | Structure | Name | Yield | NMR | GTPγS EC50 |
|---|---|---|---|---|---|
| 181 | 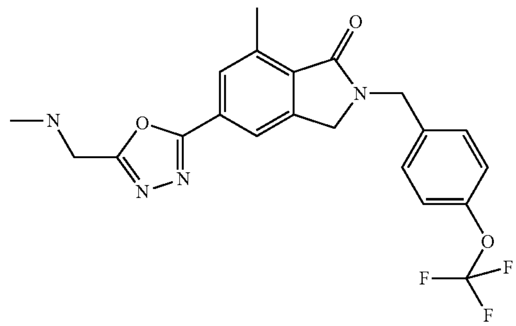 | 7-Methyl-5-(5-methylaminomethyl-[1,3,4]oxadiazol-2-yl)-2-(4-trifluoromethoxy-benzyl)-2,3-dihydro-isoindol-1-one | 8.1 mg, 68%, off white solid | 7.94 (s, 2H), 7.38 (d, 2H), 7.22 (d, 2H), 4.81 (s, 2H), 4.33 (s, 2H), 4.11 (s, 2H), 2.85 (s, 3H), 2.57 (s, 3H) | 2.12 |
| 182 | 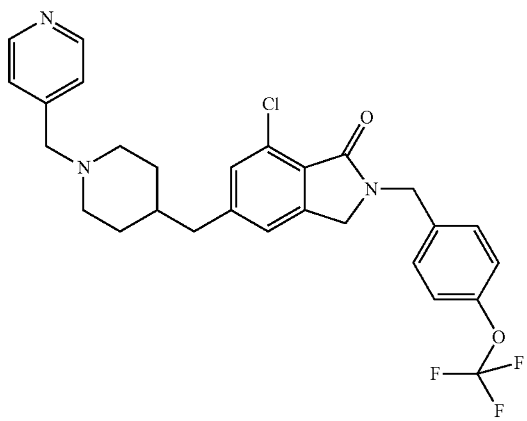 | 7-Chloro-5-(1-pyridin-4-ylmethyl]-piperidin-4-ylmethyl)-2-(4-trifluoromethoxy-benzyl)-2,3-dihydro-isoindol-1-one | 44.0 mg, 91% | 8.52 (d, 2H), 7.36 (d, 2H), 7.27 (m, 2H), 7.18 (d, 3H), 7.05 (s, 1H), 4.77 (s, 2H), 4.22 (s, 2H), 3.48 (s, 2H), 2.83 (d, 2H), 2.59 (d, 2H) 1.95 (t, 2H), 1.56 (m, 2H), 1.31 (m, 3H) | 0.04 |
| M5 | 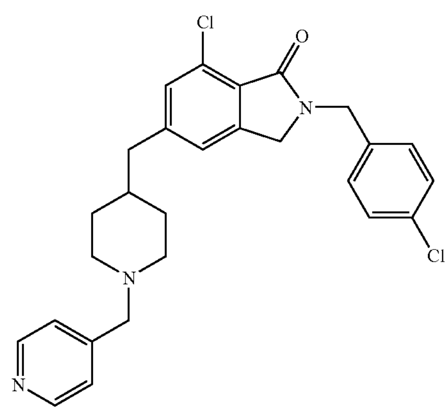 | 7-Chloro-2-(4-chloro-benzyl)-5-(1-ylmethyl-piperidin-4-ylmethyl-2,3-dihydro-isoindol-1-one | 12.1 mg, 41%, brown oil | 8.53-8.54 (m, 2H), 7.20-7.33 (m, 7H), 7.05 (s, 1H), 4.75 (s, 2H), 4.20 (s, 2H), 3.48 (s, 2H), 2.81-2.85 (m, 2H), 2.58-2.61 (d, 2H), 1.95 (t, 2H), 1.53-1.62 (m, 3H), 1.27-1.40 (m, 1H) | |
| M10 | 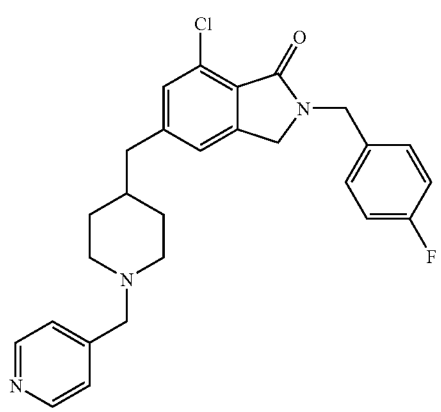 | 7-Chloro-2-(4-fluoro-benzyl)-5-(1-pyridin-ylmethyl-piperidin-4-ylmethyl-2,3-dihydro-isoindol-1-one | 8.61 mg, 37.2%, brown oil | 8.56-8.57 (m, 2H), 7.27-7.33 (m, 4H), 7.19 (s, 1H), 7.00-7.06 (m, 3H), 4.74 (s, 2H), 4.20 (m, 2H), 3.57 (br, 2H), 2.91-2.95 (m, 2H), 2.60 (d, 2H), 2.04-2.10 (m, 2H), 1.40-1.65 (m, 5H) | |

-continued

| Example | Structure | Name | Yield | NMR | GTPγS EC50 |
|---|---|---|---|---|---|
| M14 | 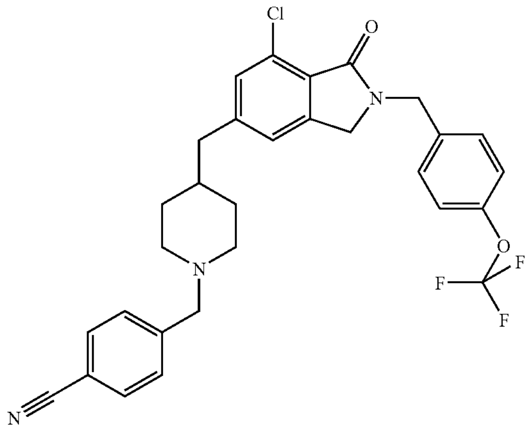 | 4-{4-[7-chloro-1-oxo-2-(4-trifluoromethoxy-benzyl)-2,3-dihydro-1H-isoindol-5-ylmethyl]-piperidin-1-ylmethyl}-benzonitrile | 39.04 mg, 99%, brown oil | 7.60 (d, 2H), 7.27-7.59 (m, 4H), 7.17-7.20 (m, 3H), 7.05 (s, 1H), 4.77 (s, 2H), 4.22 (s, 2H), 3.53 (s, 2H), 2.80-2.84 (m, 2H), 2.58-2.60 (m, 2H), 1.91 (t, 2H), 1.56-1.62 (m, 3H), 1.27-1.34 (m, 2H) | |
| M19 | 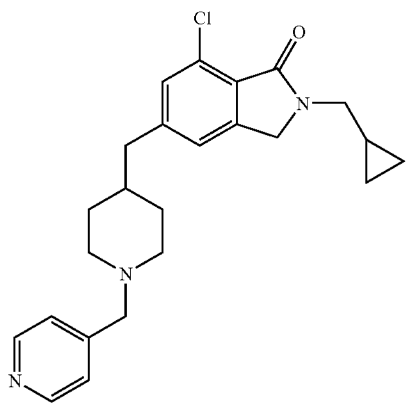 | 7-chloro-2-cyclopropyl-methyl-5-(1-pyridine-4-ylmethyl-piperidin-4-ylmethyl)-2,3-dihydro-isoindol-1-one | 14.4 mg, 59.5%, brown oil | 8.52-8.54 (m, 2H), 7.26 (s, 2H), 7.18 (s, 1H), 7H (s, 1H), 4.43 (s, 2H), 3.45-3.50 (m, 4H), 2.83-2.87 (m, 2H), 2.60-2.62 (m, 2H), 1.95-2.01 (m, 4H), 1.02-1.12 (m, 1H), 0.55-0.60 (m, 2H), 0.33-0.35 (m, 2H) | |
| M20 | 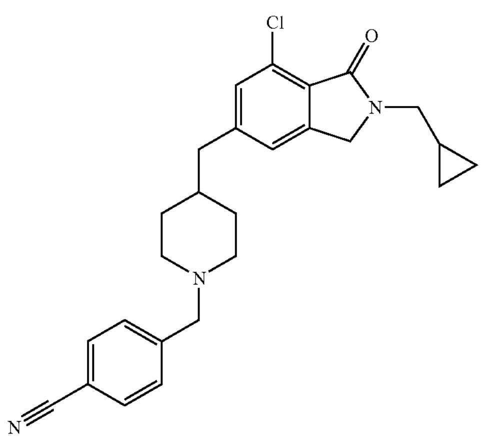 | 4-[4-(7-chloro-2-cyclopropyl-methyl-1-oxo-2,3-dihydro-1H-isoindol-5-ylmethyl)-piperidine-1-ylmethyl]-benzonitrile | 21.1 mg, 82.4%, brown oil | 7.59-7.62 (m, 2H), 7.45 (d, 2H), 7.18 (s, 1H), 4.43 (s, 2H), 3.53 (s, 2H), 3.46 (d, 2H), 2.81-2.85 (m, 2H), 2.60-2.62 (m, 2H), 1.92-1.99 (m, 2H), 1.50-1.64 (m, 3H), 1.27-1.35 (m, 2H), 0.98-1.05 (m, 1H), 0.55-0.60 (m, 2H), 0.33-0.35 (m, 2H) | |

-continued

| Example | Structure | Name | Yield | NMR | GTPγS EC50 |
|---|---|---|---|---|---|
| M27 | 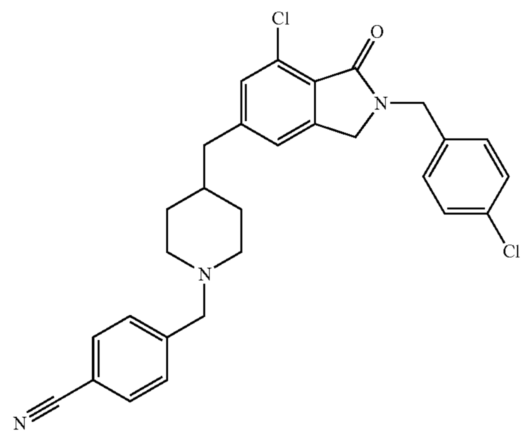 | 4-{4-[7-chloro-2-(4-chloro-benzyl)-1-oxo-2,3-dihydro-1H-isoindol-5-ylmethyl]-piperidin-1-ylmethyl}-benzonitrlle | 81.8 mg, 97.1%, yellow oil | 7.58-7.62 (m, 2H), 7.42-7.50 (m, 2H), 7.24-7.32 (m, 4H), 7.18 (s, 1H), 7.04 (s, 1H), 4.73 (s, 2H), 4.19 (s, 2H), 3.51 (s, 2H), 2.79-2.83 (m, 2H), 2.57-59 (m, 2H), 1.90-1.97 (m, 2H), 1.49-1.61 (m, 2H), 1.24-1.37 (m, 3H) | |
| M32 | 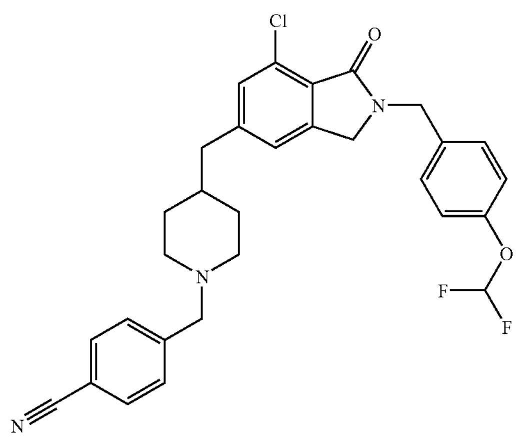 | 4-{4-[7-chloro-2-(4-difluorometh-oxy-benzyl)-1-oxo-2,3-dihydro-1H-isoindol-5-ylmethyl]-piperidin-1-ylmethyl}-benzonitrile | 35.2 mg, 72.9%, yellow oil | 7.59-7.61 (m, 2H), 7.42-7.45 (m, 2H), 7.30-7.35 (m, 2H), 7.19 (s, 1H), 7.05-7.11 (m, 3H), 6.26-6.75 (t, 1H), 4.75 (s, 2H), 4.21 (s, 2H), 3.52 (s, 2H), 2.79-2.83 (m, 2H), 2.58-2.60 (m, 2H), 1.88-1.98 (m, 2H), 1.51-1.62 (m, 3H), 1.25-1.37 (m, 2H) | |
| M33 | 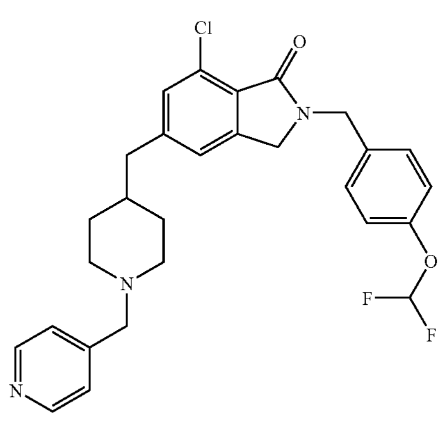 | 7-Chloro-2-(4-difluorometh-oxy-benzyl)-5-(1-pyridin-ylmethyl-piperidin-4-ylmethyl-2,3-dihydro-isoindol-1-one | 35.1 mg, 76.1%, yellow solid | 8.52-8.53 (m, 2H), 7.20-7.36 (m, 4H), 7.05-7.11 (m, 3H), 6.26-6.75 (t, 1H), 4.75 (s, 2H), 4.14 (s, 2H), 3.47 (s, 2H), 2.81-2.84 (m, 2H), 2.58-2.60 (m, 2H), 1.91-1.98 (m, 2H), 1.51-1.61 (m, 3H), 1.27-1.38 (m, 2H) | |

| Example | Structure | Name | Yield | NMR | GTPγS EC50 |
|---|---|---|---|---|---|
| M37 | 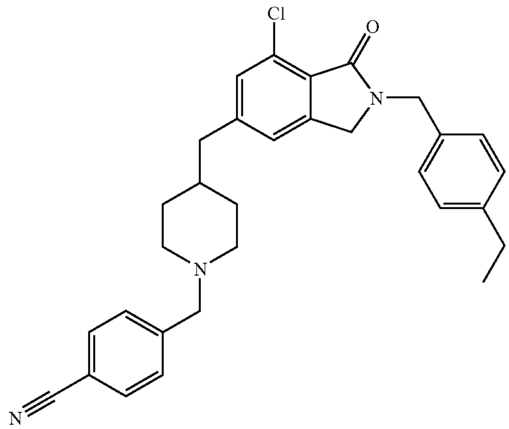 | 4-{4-[7-Chloro-2-(4-ethyl-benzyl)-1-oxo-2,3-dihydxo-1H-isoindol-5-ylmethyl]-piperidin-1-ylmethyl}-benzonitrile | 16.2 mg, 43.3%, yellow oil | 7.59-7.62 (m, 2H), 7.42-7.48 (m, 2H), 7.24-7.28 (m, 2H), 7.16-7.18 (m, 3H), 7.02 (s, 1H), 4.74 (s, 2H), 4.19 (s, 2H), 3.52 (s, 2H), 2.79-2.83 (m, 2H), 2.57-2.68 (m, 4H), 1.90-1.98 (m, 2H), 1.51-1.61 (m, 3H), 1.21-1.36 (m, 5H) | |
| M38 | 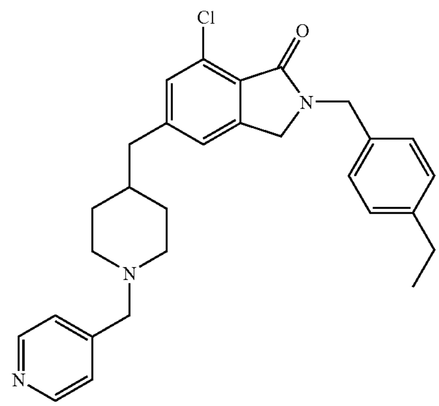 | 7-Chloro-2-(4-ethyl-benzyl)-5-(1-pyridin-4-ylmethyl-piperidin-4-ylmethyl)-2,3-dihydro-isoindol-1-one | 20.1 mg, 56.6%, yellow oil | 8.53 (br, 2H), 7.23-7.27 (m, 4H), 7.16-7.19 (m, 3H), 7.02 (s, 1H), 4.74 (s, 2H), 4.19 (s, 2H), 3.49 (s, 2H), 2.82-2.86 (m, 2H), 2.57-2.68 (m, 4H), 1.92-1.96 (m, 2H), 1.56-1.62 (m, 3H), 1.20-1.35 (m, 5H) | |

Preparation of Intermediates (Substituted Phenylpropyl Amines) for Examples 183

Example 183

3-(2-fluorophenyl)acrylonitrile

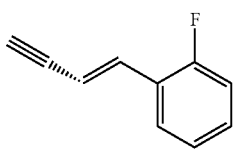

In a 500 mL round-bottomed flask, equipped with stir bar, septa, and nitrogen source, 2.4 g of a 60% mixture (oil) of sodium hydride (1.4 g, 60 mmol) in dimethylformamide (100 mL) was treated with diethyl (cyanomethyl)phosphonate (12 mL, 1.3.1 g, 74 mmol) and the reaction stirred at ambient temperature for 2 h. After this time, 2-fluorobenzaldehyde (6 mL, 7.2 g, 58 mmol) was added and the mixture stirred 16 hours at ambient temperature. After this time the reaction was quenched by the addition of water (100 mL). The mixture was transferred to a separatory funnel using diethyl ether (500 mL) and the phases equilibrated. The aqueous layer was removed and the remaining organic layer washed with water (4×100 ml) and brine (100 mL), dried over anhydrous MgSO$_4$, filtered and concentrated to afford the cis/trans mixture of 3-(2-fluorophenyl)acrylonitrile (9.36 g). GC/MS gave: m/z (rel.int.) 147 (M+, 100) and 120 (34).

Example 184

3-(2-fluorophenyl) propionitrile

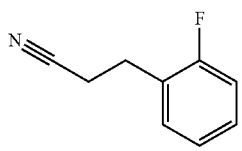

A solution of the cis/trans mixture of 3-(2-fluorophenyl) acrylonitrile (9.36 g) in ethanol (100 mL) was treated with Pearlman's catalyst (palladium hydroxide, 1 g, 20% Pd by wt. dry) and the mixture shook vigorously under 60 p.s.i. hydrogen for 30 minutes. The mixture was filtered and the filtrate concentrated to afford 3-(2-fluorophenyl) propionitrile (9.11 g). GC/MS gave: m/z (rel.int.) 149 (M+, 19), 109 (100) and 83 (15).

Example 185

3-(2-fluorophenyl)propylamine

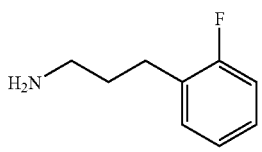

A solution of 3-(2-fluorophenyl) propionitrile (9.11 g) in tetrahydrofuran (200 mL) was heated to reflux and treated with borane-methyl sulfide complex (6 mL of ~10 M, 60 mmol). Approximately half of the volume of the reaction was then distilled off. The mixture was then cooled in a −15° C. bath and treated dropwise with ice water (100 mL). The mixture was then concentrated to a solid. The solid was then dissolved in water (100 mL) and treated with concentrated (12 N)HCl (50 mL). The mixture was heated at reflux for 1 h, cooled to ambient temperature, and equilibrated with diethyl ether (100 mL). The organic solution was removed and the resulting aqueous mixture, cooled by the addition of ice, and then basified (pH>10) by treatment with 10 N NaOH (70 mL). The resulting solution was extracted with diethyl ether (100 mL). The diethyl ether extract was removed, dried over anhydrous MgSO$_4$, filtered and concentrated to afford 3-(2-fluorophenyl)propylamine (3.62 g (41% from 2-fluorobenzaldehyde)). GC/MS gave: m/z (rel.int.) 153 (M+, 10), 136 (100), 109 (50), and 83 (22).

Example 186

3-(3-fluorophenyl)propylamine

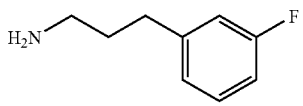

Reduction of 3-(3-fluorophenyl) propionitrile (9.43 g) with borane-methyl sulfide complex (6 mL of ~10 M, 60 mmol), followed by workup afforded 3-(3-fluorophenyl)propylamine (2.14 g (24% from 3-fluorobenzaldehyde)). GC/MS gave: m/z (rel.int.) 153 (M+, 9), 136 (100), 109 (55), and 83 (23).

Example 187

3-(4-fluorophenyl)propylamine

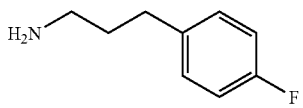

Reduction of 3-(4-fluorophenyl) propionitrile (9.05 g) with borane-methyl sulfide complex (6 mL of ~10 M, 60 mmol), followed by workup afforded 3-(4-fluorophenyl)propylamine (8.14 g (91% from 4-fluorobenzaldehyde)). GC/MS gave: m/z (rel.int.) 153 (M+, 4), 136 (100), 109 (51), and 83 (18).

Example 188

3-(2-bromophenyl)propylamine

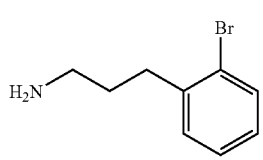

Reduction of 3-(2-bromophenyl) propionitrile (19.92 g) with borane-methyl sulfide complex (12 mL of ~10 M, 120 mmol), followed by workup afforded 3-(2-bromophenyl)propylamine (18.1 g, 93%). GC/MS gave: m/z (rel.int.) 214 (M+, 0.5), 198 (2), 196 (2), 171 (6), 169 (6), 134 (100), 117 (21), 106 (18), and 77 (18).

Example 189

3-(3-bromophenyl)propylamine

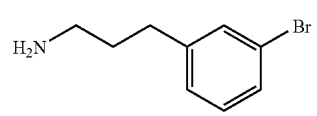

Reduction of 3-(3-bromophenyl) propionitrile (14 g, 65.4 mmol) with borane-methyl sulfide complex (8 mL of ~10 M, 80 mmol), followed by workup afforded 3-(3-bromophenyl)propylamine (7.86 g, 57%). GC/MS gave: m/z (rel.int.) 215 (M+, 15), 213 (M+16), 198 (97), 196 (98), 171(19), 169 (17), 117 (100), 103 (34), 91(59) and 77 (41).

Example 190

3-(4-bromophenyl)propylamine

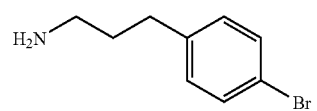

Reduction of 3-(4-bromophenyl) propionitrile (14.23 g, 67.7 mmol) with borane-methyl sulfide complex (8 mL of ~10 M, 80 mmol), followed by workup afforded 3-(4-bromophenyl)propylamine (6.21 g, 43%). GC/MS gave: m/z (rel.int.) 215 (M+, 15), 213 (M+5), 198 (63), 196 (66), 171 (14), 169 (15), 117 (100), 104 (25), 91 (29) and 77 (30).

Example 191

S-2-[1-(4-chlorophenyl)-ethyl]-2,3-dihydroisoindol-1-one

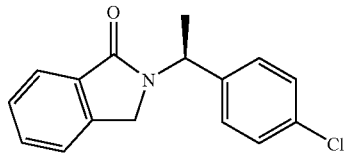

A mixture of 1-(4-chlorophenyl)-ethylamine (117 mg (0.75 mmol), 2-bromomethyl-benzoic acid methyl ester (172 mg, 0.75 mmol), and $K_2CO_3$ (207 mg, 1.5 mmol) in toluene (5 mL) was heated with stirring at 100° C. for 2 h. Workup and silica gel column chromatography using a gradient of hexanes to ethyl acetate afforded 38 mg of 2-[1-(4-chlorophenyl)-ethyl]-2,3-dihydroisoindol-1-one, as the racemic mixture. Chromatography (HPLC) of this material through ChrialCel OD (250×20 mm i.d., 10 μm) using 5% isopropanol in hexanes afforded 11.6 mg of R-2-[1-(4-chlorophenyl)-ethyl]-2,3-dihydro-isoindol-1-one and 8.3 mg of S-2-[1-(4-chlorophenyl)-ethyl]-2,3-dihydro-isoindol-1-one. GC/MS for S-2-[1-(4-chlorophenyl)-ethyl]-2,3-dihydroisoindol-1-one gave: m/z (rel.int.) 274 (M+, 9), 272 (M+, 56), 258 (26), 256 (57), 160 (20), 138 (32), 119 (100), 103 (50), 91 (65), and 77 (61).

Example 192

2-naphthalen-2-ylmethyl-2,3-dihydroisoindol-1-one

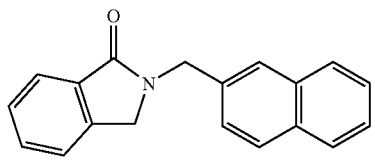

A mixture of naphthalen-2-yl-methylamine (47.2 mg, 0.3 mmol), 2-bromomethyl-benzoic acid methyl ester (68.7 mg, 0.3 mmol), and $K_2CO_3$ (83 mg, 0.6 mmol) in toluene (2 mL) was heated with stirring at 100° C. for 2 h. Workup and silica gel column chromatography using a gradient of hexanes to 50% ethyl acetate in hexanes afforded 2-naphthalen-2-ylmethyl-2,3-dihydroisoindol-1-one (57 mg, 70%). GC/MS gave: m/z (rel.int.) 273 (M+, 45), 141 (100), 119 (27), 115 (27), and 91 (25).

Example 193

2-[3-(2-fluorophenyl)-propyl]-2,3-dihydroisoindol-1-one

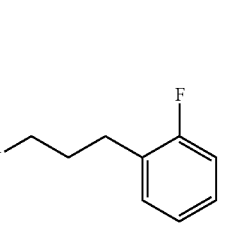

A mixture of 3-(2-fluorophenyl)-propylamine (306 mg, 2 mmol), 2-bromomethyl-benzoic acid methyl ester (458 mg, 2 mmol), and $K_2CO_3$ (200 mg, 1.45 mmol) in toluene (10 mL) was heated with stirring at 100° C. for 16 h. Workup and silica gel column chromatography using a gradient of hexanes to 50% ethyl acetate in hexanes afforded 2-[3-(2-fluorophenyl)-propyl]-2,3-dihydroisoindol-1-one (275 mg, 51%). GC/MS gave: m/z (rel.int.) 269 (M+, 32), 147 (89), 146 (100), 119 (29), 109 (25) and 91 (40).

Example 194

2-[3-(3-fluorophenyl)-propyl]-2,3-dihydroisoindol-1-one

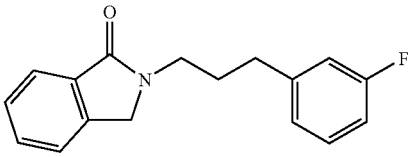

A mixture of 3-(3-fluorophenyl)-propylamine (306 mg, 2 mmol), 2-bromomethyl-benzoic acid methyl ester (458 mg, 2 mmol), and $K_2CO_3$ (200 mg, 1.45 mmol) in toluene (10 mL) was heated with stirring at 100° C. for 16 h. Workup and silica gel column chromatography using a gradient of hexanes to 50% ethyl acetate in hexanes afforded 2-[3-(3-fluorophenyl)-propyl]-2,3-dihydroisoindol-1-one (391 mg, 73%). GC/MS gave: m/z (rel.int.) 269 (M+, 32), 147 (100), 146 (100), 119 (37), 109 (26) and 91 (45).

Example 195

2-[3-(4-fluorophenyl)-propyl]-2,3-dihydroisoindol-1-one

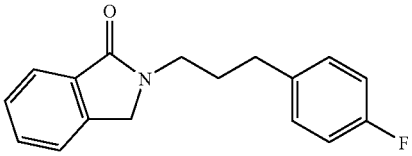

A mixture of 3-(4-fluorophenyl)-propylamine (306 mg, 2 mmol), 2-bromomethyl-benzoic acid methyl ester (458 mg, 2

Example 196

2-[3-(2-bromophenyl)-propyl]-2,3-dihydroisoindol-1-one

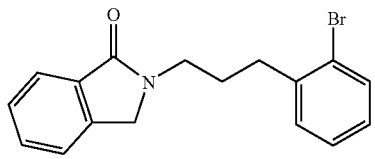

A mixture of 3-(2-bromophenyl)-propylamine (6.9 g, 30 mmol), 2-bromomethyl-benzoic acid methyl ester (6.42 g, 30 mmol), and $K_2CO_3$ (6.91 g, 50 mmol) in toluene (100 mL) was heated at reflux with stirring for 2 h. Workup and silica gel column chromatography using a gradient of hexanes to 50% ethyl acetate in hexanes afforded 2-[3-(2-bromophenyl)-propyl]-2,3-dihydroisoindol-1-one (5.7 g, 58%). GC/MS gave: m/z (rel.int.) 331 (M+, 3), 329 (M+, 3), 250 (42), 147 (82), 146 (100) 119 (27), and 91 (47). $^1$H NMR (300 MHz, CDCl$_3$): δ 2.00 (dt, 2H), 2.80 (t, 2H), 3.74 (t, 2H), 4.40 (s, 2H), 7.04 (dt, 1H), 7.19-7.27 (m, 3H), 7.43-7.53 (m, 3H), 7.76 (dd, 1H). $^{13}$C NMR (300 MHz, CDCl$_3$): δ 28.7, 33.7, 42.1, 50.0, 122.8, 123.8, 124.4, 127.7, 127.9, 128.1, 130.6, 131.3, 132.9, 133.1, 140.8, 141.3, 168.7.

Example 197

2-[3-(3-bromophenyl)-propyl]-2,3-dihydroisoindol-1-one

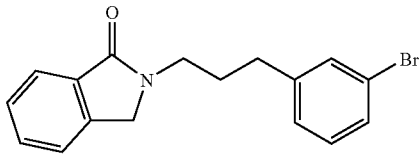

A mixture of 3-(3-bromophenyl)-propylamine (7.86 g, 36.7 mmol), 2-bromomethyl-benzoic acid methyl ester (8.45 g, 36.7 mmol), and $K_2CO_3$ (6.91 g, 50 mmol) in toluene (100 mL) was heated at reflux with stirring for 1.5 h. Workup and silica gel column chromatography using a gradient of hexanes to 50% ethyl acetate in hexanes afforded 2-[3-(3-bromophenyl)-propyl]-2,3-dihydroisoindol-1-one (8.81 g, 73%). GC/MS gave: m/z (rel.int.) 331 (M+, 10), 329 (M+, 10), 147-(100), 146 (72) 119 (25), and 91 (38). $^1$H NMR (300 MHz, CDCl$_3$): δ 2.00 (dt, 2H), 2.67 (t, 2H), 3.67 (t, 2H), 4.36 (s, 2H), 7.14 (dd, 2H), 7.31 (m, 1H), 7.35 (br s, 1H), 7.45 (m, 2H), 7.51 (dt, 1H), 7.85 (d, 1H). $^{13}$C NMR (300 MHz, CDCl$_3$): δ 29.9, 32.8, 42.0, 49.9, 122.4, 122.7, 123.6, 127.1, 128.0, 129.1, 130.0, 131.2, 131.3 132.8, 141.1, 143.7, 168.6.

Example 198

2-[3-(4-bromophenyl)-propyl]-2,3-dihydroisoindol-1-one

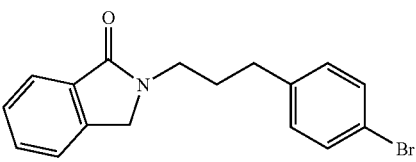

A mixture of 3-(4-bromophenyl)-propylamine (6.21 g, 29 mmol), 2-bromomethyl-benzoic acid methyl ester (6.57 g, 29 mmol), and $K_2CO_3$ (6.91 g, 50 mmol) in toluene (100 mL) was heated at reflux with stirring for 1.5 h. Workup and silica gel column chromatography using a gradient of hexanes to 50% ethyl acetate in hexanes afforded 2-[3-(4-bromophenyl)-propyl]-2,3-dihydroisoindol-1-one (7.24 g, 88%). GC/MS gave: m/z (rel.int.) 331 (M+, 9), 329 (M+, 9), 147 (100), 146 (54) 119 (34), and 91 (33). $^1$H NMR (300 MHz, CDCl$_3$): δ 1.97 (dt, 2H), 2.64 (t, 2H), 3.66 (t, 2H), 4.35 (s, 2H), 7.08 (dd, 2H), 7.38 (dd, 2H), 7.46 (m, 2H), 7.51 (dt, 1H), 7.85 (d, 1H). $^{13}$C NMR (300 MHz, CDCl$_3$): δ 29.9, 32.5, 41.9, 49.9, 119.7, 122.7, 123.6, 128.0, 130.2 (2C), 131.2, 131.4 (2C) 132.9, 140.3, 141.1, 168.5.

Example 199

2-(4-benzoylbenzyl)-2,3-dihydroisoindol-1-one

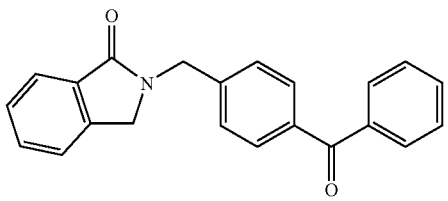

A mixture of 4-(bromomethyl)benzophenone (138 mg, 0.5 mmol), isoindolone (67 mg, 0.5 mmol), cesium carbonate (407 mg, 1.25 mmol), and 18-crown-6 (13 mg, 0.05 mmol) in acetone (10 mL) was stirred heating at reflux for 3 h. Workup and silica gel column chromatography using a gradient of hexanes to 50% ethyl acetate in hexanes afforded 2-(4-benzoylbenzyl)-2,3-dihydroisoindol-1-one (149 mg, 91%). GC/MS gave: m/z (rel.int.) 327 (M+, 97), 250 (5), 222 (42), 196 (20) 165 (31), 146 (31), 133 (53), 119 (94), 105 (71), 91 (100), and 77 (98). $^1$H NMR (300 MHz, CDCl$_3$): δ 4.33 (s, 2H), 4.89 (s, 2H), 7.42 (d, 2H), 7.45-7.59 (m, 6H), 7.77 (dd, 4H), 7.91 (dd, 1H).

Text preceding Example 196:

mmol), and $K_2CO_3$ (200 mg, 1.45 mmol) in toluene (10 mL) was heated with stirring at 100° C. for 16 h. Workup and silica gel column chromatography using a gradient of hexanes to 50% ethyl acetate in hexanes afforded 2-[3-(4-fluorophenyl)-propyl]-2,3-dihydroisoindol-1-one (432 mg, 80%). GC/MS gave: m/z (rel.int.) 269 (M+, 32), 147 (100), 146 (76), 119 (43), 109 (30) and 91 (39).

Example 200

2-[1-(4-phenoxyphenyl)-ethyl]-2,3-dihydroisoindol-1-one

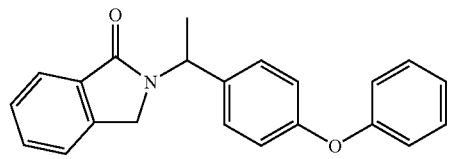

A mixture of 1-(4-phenoxyphenyl)ethylamine (213 mg, 1 mmol), 2-bromomethyl-benzoic acid methyl ester (250 mg, 1.1 mmol), and $K_2CO_3$ (1 g, 7.2 mmol) in toluene (10 mL) was heated at reflux with stirring for 16 h. Workup and silica gel column chromatography using a gradient of hexanes to 30% ethyl acetate in hexanes afforded 2-[1-(4-phenoxyphenyl)-ethyl]-2,3-dihydroisoindol-1-one (146 mg, 44%). GC/MS gave: m/z (rel.int.) 329 (M+, 46), 314 (100), 196 (8) and 77 (8). $^1$H NMR (300 MHz, $CDCl_3$): δ 1.68 (d, 3H), 4.03 (d, 1H), 4.34 (d, 1H), 5.80 (q, 1H), 6.98 (br t, 4H), 7.10 (t, 1H), 7.49 (dt, 2H), 7.33 (br m, 5H), 7.88 (dd, 1H).

Example 201

7-chloro-2-[1-(4-phenoxyphenyl)-ethyl]-2,3-dihydroisoindol-1-one

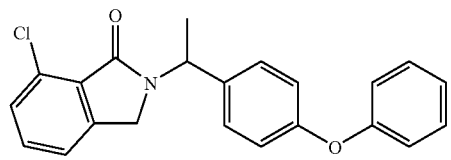

A mixture of 1-(4-phenoxyphenyl)ethylamine (121 mg, 0.57 mmol), 2-bromomethyl-6-chloro-benzoic acid methyl ester (150 mg, 0.57 mmol), and $K_2CO_3$ (1 g, 7.2 mmol) in toluene (10 mL) was heated at reflux with stirring for 16 h. Workup and silica gel column chromatography using a gradient of hexanes to 30% ethyl acetate in hexanes afforded 7-chloro-2-[1-(4-phenoxyphenyl)-ethyl]-2,3-dihydroisoindol-1-one (70 mg, 34%). GC/MS gave: m/z (rel.int.) 365 (M+, 9), 363 (M+23), 350 (25), 348 (63), 211 (32), 196 (65), 168 (33), 152 (54), 141 (27), 124 (27), 115 (27), 89 (35), and 77 (100). $^1$H NMR (300 MHz, $CDCl_3$): δ 1.68 (d, 3H), 3.99 (d, 1H), 4.15 (d, 1H), 5.79 (q, 1H), 6.98 (br t, 4H), 7.13 (t, 1H), 7.26-7.10 (br m, 7H).

Intermediate Compounds for Examples 203-278

Method 1

Step 1: Reduction of Phthalimide

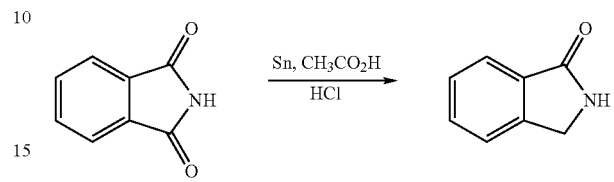

Example 202

2,3-dihydro-isoindol-1-one

Phthalimide (1.47 g, 10 mmol) was added to a mixture of glacial acetic acid (15 mL), concentrated hydrochloric acid (7 mL), and tin powder (2.97 g). The slurry was heated at reflux for 2 h. After this time GC-MS indicated that the reaction was completed. The residual tin was removed by filtration and the majority of the acetic acid evaporated. The resulting creamy material was dissolved in dichloromethane (60 mL) and washed with water (10 mL) and saturated aqueous NaCl solution (15 mL). The resulting organic solution was dried over anhydrous $MgSO_4$, filtered and concentrated. Silica gel column chromatography of the resulting material using ethyl acetate afforded 2,3-dihydro-isoindol-1-one (1 g, 75%) as an off-white solid. $^1$H NMR (300 MHz, $CDCl_3$): δ (ppm) 4.48 (s, 2H), 6.98 (s, 1H), 7.42-7.61 (m, 3H), 7.88 (d, 1H).

Step 2: Benzylation of Isoindolones

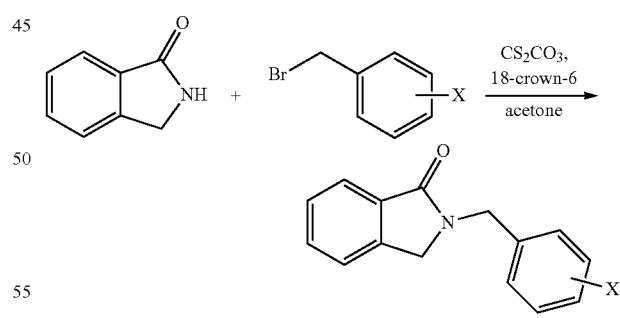

General Procedure

In a sealed vial, a mixture of the appropriately substituted benzyl halide (1 equiv.), isoindolone (1 equiv.), cesium carbonate (2.5 equiv.), and 18-crown-6 (0.1 equiv.) in acetone was stirred at 70° C. for 16 h. After this time the reaction was cooled and the remaining solids removed by filtration. The filtrate was concentrated. Silica gel column chromatography of the resulting material using combinations of hexane and ethyl acetate afforded the desired product.

The following final compounds were synthesized using general method 1 described above.

Example 203

2-(4-Fluoro-benzyl)-2,3-dihydro-isoindol-1-one

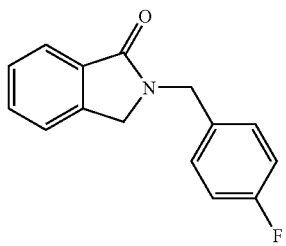

A mixture of 2,3-dihydro-isoindol-1-one (0.133 g, 1 mmol), 1-bromomethyl-4-fluoro-benzene (0.227 g, 1.2 mmol), $Cs_2CO_3$ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-fluoro-benzyl)-2,3-dihydro-isoindol-1-one (0.198 g, 82%). $^1$H NMR (300 MHz, $CDCl_3$): δ (ppm) 4.26 (s, 2H), 4.68 (s, 2H), 7.04 (t, 2H), 7.35-7.54 (m, 5H), 7.90 (d, 1H). GC-MS: m/z 241 (M)$^+$

Example 204

2-(2,4-difluoro-benzyl)-2,3-dihydro-isoindol-1-one

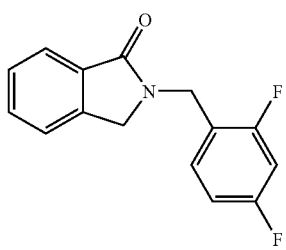

A mixture of 2,3-dihydro-isoindol-1-one (0.133 g, 1 mmol), 1-bromomethyl-2,4-difluoro-benzene (0.248 g, 1.2 mmol), $Cs_2CO_3$ (0.816 g, 2.5 mmol), and 18-crown-6 (0.026 g, 0.11 mmol) in acetone (5 mL) was stirred at 70° C. for 16 h. Workup and silica gel column chromatography using 30% ethyl acetate in hexane afforded 2-(2,4-difluoro-benzyl)-2,3-dihydro-isoindol-1-one (0.199 g, 77%). $^1$H NMR (300 MHz, $CDCl_3$): δ (ppm) 4.34 (s, 2H), 4.84 (s, 2H), 6.85 (m, 2H), 7.35-7.54 (m, 4H), 7.86 (d, 1H).

Example 205

2-(4-Chloro-benzyl)-2,3-dihydro-isoindol-1-one

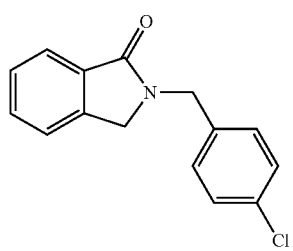

A mixture of 2,3-dihydro-isoindol-1-one (0.133 g, 1 mmol,), 1-bromomethyl-4-chloro-benzene (0.246 g, 1.2 mmol), $Cs_2CO_3$ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-chloro-benzyl)-2,3-dihydro-isoindol-1-one (0.125 g, 97%). $^1$H NMR (300 MHz, $CDCl_3$): δ (ppm) 4.24 (s, 2H), 4.76 (s, 2H), 7.22-7.54 (m, 7H), 7.90 (d, 1H).

Example 206

2-(4-Methyl-benzyl)-2,3-dihydro-isoindol-1-one

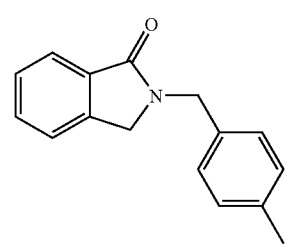

A mixture of 2,3-dihydro-isoindol-1-one (0.133 g, 1 mmol), 1-bromomethyl-4-methyl-benzene (0.222 g, 1.2 mmol), $Cs_2CO_3$ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-methyl-benzyl)-2,3-dihydro-isoindol-1-one (0.100 g, 84%). $^1$H NMR (300 MHz, CDCl₃): δ (ppm) 2.36 (s, 3H), 4.24 (s, 2H), 4.76 (s, 2H), 7.15-7.54 (m, 7H), 7.90 (d, 1H).

Example 207

2-(4-Methoxy-benzyl)-2,3-dihydro-isoindol-1-one

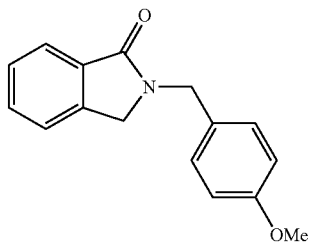

A mixture of 2,3-dihydro-isoindol-1-one (0.133 g, 1 mmol), 1-bromomethyl-4-methoxy-benzene (0.222 g, 1.2 mmol,), Cs₂CO₃ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-methoxy-benzyl)-2,3-dihydro-isoindol-1-one (0.080 g, 63%). ¹H NMR (300 MHz, CDCl₃): δ (ppm) 3.80 (s, 3H), 4.24 (s, 2H), 4.76 (s, 2H), 6.88 (d, 2H), 7.25 (d, 2H), 7.36-7.52 (m, 3H), 7.90 (d, 1H).

Example 208

2-(4-Trifluoromethyl-benzyl)-2,3-dihydro-isoindol-1-one

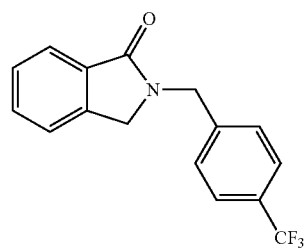

A mixture of 2,3-dihydro-isoindol-1-one (0.133 g, 1 mmol), 1-bromomethyl-4-trifluoromethyl-benzene (0.287 g, 1.2 mmol), Cs₂CO₃ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-trifluoromethyl-benzyl)-2,3-dihydro-isoindol-1-one (0.135 g, 93%). ¹H NMR (300 MHz, CDCl₃): δ (ppm) 4.28 (s, 2H), 4.86 (s, 2H), 7.39-7.62 (m, 7H), 7.90 (d, 1H).

Example 209

2-(4-Trifluoromethoxy-benzyl)-2,3-dihydro-isoindol-1-one

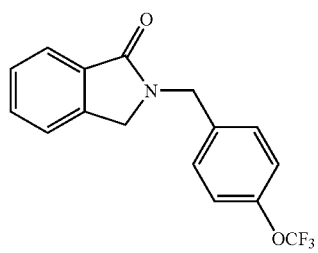

A mixture of 2,3-dihydro-isoindol-1-one (0.133 g, 1 mmol), 1-bromomethyl-4-trifluoromethoxy-benzene (0.306 g, 1.2 mmol), Cs₂CO₃ (0.816 g, 2.5 mmol), and 18-crown-6 (0.026 g, 0.1 mmol) in acetone (5 mL) was stirred at 70° C. for 16 h. Workup and silica gel column chromatography using 30% ethyl acetate in hexane afforded 2-(4-trifluoromethoxy-benzyl)-2,3-dihydro-isoindol-1-one (0.125 g, 81%). ¹H NMR (300 MHz, CDCl₃): δ (ppm) 4.28 (s, 2H), 4.82 (s, 2H), 7.16 (d, 2H), 7.32-7.52 (m, 5H), 7.90 (d, 1H).

Example 210

2-(3-chloro-benzyl)-2,3-dihydro-isoindol-1-one

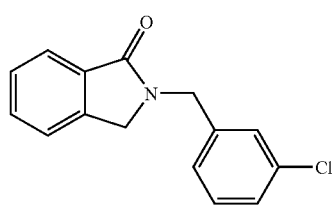

A mixture of 2,3-dihydro-isoindol-1-one (0.066 g, 0.5 mmol), 1-bromomethyl-3-chloro-benzene (0.123 g, 0.6 mmol), Cs₂CO₃ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(3-chloro-benzyl)-2,3-dihydro-isoindol-1-one (0.107 g, 85%). ¹H NMR (300 MHz, CDCl₃): δ (ppm) 4.28 (s, 2H), 4.78 (s, 2H), 7.16-7.52 (m, 7H), 7.90 (d, 1H).

Example 211

2-(3-Phenyl-propyl)-2,3-dihydro-isoindol-1-one

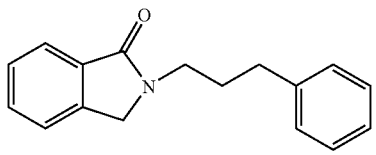

A mixture of 2,3-dihydro-isoindol-1-one (0.066 g, 0.5 mmol), 3-bromo-propyl-benzene (0.119 g, 0.6 mmol), Cs₂CO₃ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(3-phenyl-propyl)-2,3-dihydro-isoindol-1-one (0.100 g, 80%). ¹H NMR (300 MHz, CDCl₃): δ (ppm) 1.99 (m, 2H), 2.66 (t, 2H), 3.68 (t, 2H), 4.38 (s, 2H), 7.18-7.56 (m, 8H), 7.92 (d, 1H).

Example 212

2-(1-oxo-1,3-dihydro-isoindol-2-ylmethyl)-benzonitrile

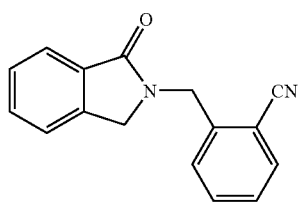

A mixture of 2,3-dihydro-isoindol-1-one (0.066 g, 0.5 mmol,), 2-bromomethyl-benzonitrile (0.117 g, 0.6 mmol), Cs₂CO₃ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(1-oxo-1,3-dihydro-isoindol-2-ylmethyl)-benzonitrile (0.055 g, 44%). ¹H NMR (300 MHz, CDCl₃): δ (ppm) 4.22 (s, 2H), 5.08 (s, 2H), 7.28-7.70 (m, 7H), 7.92 (d, 1H).

Example 213

2-(2-chloro-benzyl)-2,3-dihydro-isoindol-1-one

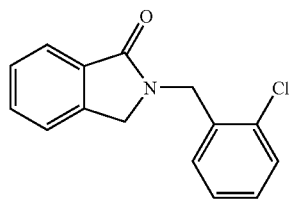

A mixture of 2,3-dihydro-isoindol-1-one (0.066 g, 0.5 mmol), 1-bromomethyl-2-chloro-benzene (0.123 g, 0.6 mmol), Cs₂CO₃ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(2-chloro-benzyl)-2,3-dihydro-isoindol-1-one (0.035 g, 27%). ¹H NMR (300 MHz, CDCl₃): δ (ppm) 4.28 (s, 2H), 4.94 (s, 2H), 7.16-7.52 (m, 7H), 7.90 (d, 1H).

Example 214

2-(3-Methoxy-benzyl)-2,3-dihydro-isoindol-1-one

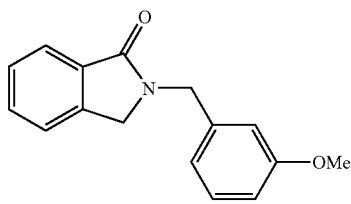

A mixture of 2,3-dihydro-isoindol-1-one (0.066 g, 0.5 mmol), 1-chloromethyl-3-methoxy-benzene (0.094 g, 0.6 mmol), Cs₂CO₃ (0.408 g, 1.25 mmol), and 18-crown-6 (0.013 g, 0.05 mmol) in acetone (5 mL) was stirred at 70° C. for 16 h. Workup and silica gel column chromatography using 30% ethyl acetate in hexane afforded 2-(3-methoxy-benzyl)-2,3-dihydro-isoindol-1-one (0.053 g, 42%). ¹H NMR (300 MHz, CDCl$_3$): δ (ppm) 3.80 (s, 3H), 4.26 (s, 2H), 4.80 (s, 2H), 6.88 (d, 3H), 7.22-7.52 (m, 4H), 7.90 (d, 1H).

Example 215

5-chloro-2-(1-oxo-1,3-dihydro-isoindol-2-ylmethyl)-benzonitrile

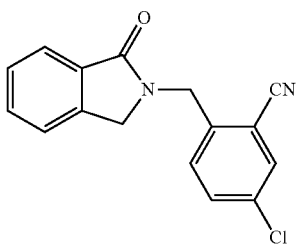

A mixture of 2,3-dihydro-isoindol-1-one (0.066 g, 0.5 mmol), 2-bromomethyl-4-chloro-benzonitrile (0.116 g, 0.6 mmol), Cs$_2$CO$_3$ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 5-chloro-2-(1-oxo-1,3-dihydroisoindol-2-ylmethyl)benzonitrile (0.057 g, 41%). $^1$H NMR (300 MHz, CDCl$_3$): δ (ppm) 4.48 (s, 2H), 5.08 (s, 2H), 7.42-7.65 (m, 6H), 7.92 (d, 1H). GC-MS: m/z 282 (M)$^+$.

Example 216

2-(2-Phenoxyethyl)-2,3-dihydroisoindol-1-one

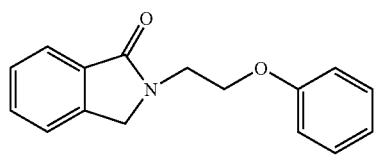

A mixture of 2,3-dihydroisoindol-1-one (0.066 g, 0.5 mmol,), 2-(bromoethoxy)benzene (0.121 g, 0.6 mmol), Cs$_2$CO$_3$ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(2-phenoxy-ethyl)-2,3-dihydro-isoindol-1-one (0.099 g, 78%). $^1$H NMR (300 MHz, CDCl$_3$): δ (ppm) 4.05 (t, 2H), 4.26 (t, 2H), 4.64 (s, 2H), 6.92 (m, 3H), 7.22-7.60 (m, 5H), 7.88 (d, 1H), GC-MS: m/z 253 (M)$^+$.

Example 217

2-(2-Phenyl-allyl)-2,3-dihydroisoindol-1-one

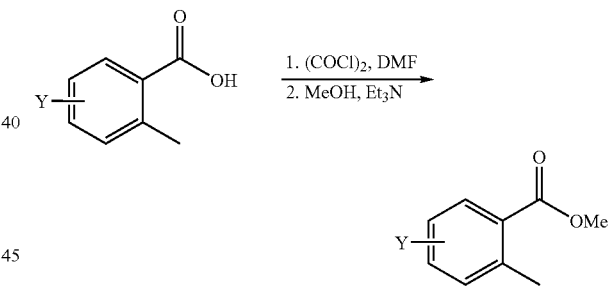

A mixture of 2,3-dihydroisoindol-1-one (0.066 g, 0.5 mmol), 3-bromo-propenyl-benzene (0.118 g, 0.6 mmol), Cs$_2$CO$_3$ (0.408 g, 1.25 mmol), and 18-crown-6 (0.013 g, 0.05 mmol) in acetone (3 mL) was stirred at 70° C. for 16 h. Workup and silica gel column chromatography using 30% ethyl acetate in hexane afforded 2-(2-phenyl-allyl)-2,3-dihydro-isoindol-1-one. $^1$H NMR (300 MHz, CDCl$_3$): δ (ppm) 4.42 (m, 4H), 6.22 (m, 1H), 6.60 (d, 1H), 7.22-7.60 (m, 8H), 7.88 (d, 1H). GC-MS: m/z 249 (M)$^+$.

Method 2

Step 1: Esterification of Carboxylic Acids

General Procedure

A stirred solution of the appropriately substituted carboxylic acid (1 equiv.) in dichloromethane was treated carefully with a 2 M solution of oxalyl chloride in dichloromethane (1.2-1.5 equivalent), followed by the careful addition of dimethylformamide (several drops). The resulting solution was stirred at ambient temperature for 2 h. The formation of carboxylic acid chloride was monitored (after quenching with methanol) by GC-MS. After completion of the reaction the solvent was evaporated. The residue was dissolved in methanol and the resulting solution treated with triethylamine (2 equiv.). The reaction mixture was allowed to stir at ambient temperature for 2 h. The solvent was evaporated and the residue equilibrated between water and dichloromethane (50 mL). The organic solution was removed and the remaining aqueous solution extracted with dichloromethane (2×50 mL). The combined organic extracts were dried over anhydrous MgSO$_4$, filtered and concentrated to afford the desired product. The material was used without further purification.

The following compounds were synthesized using general method 2, step 1 described above.

Example 218

2-methyl-benzoic acid methyl ester

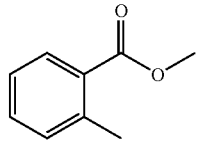

A solution of 2-methyl-benzoic acid (1.36 g, 10 mmol) in dichloromethane (10 mL) was treated with oxalyl chloride (6 mL, 12 mmol) and dimethylformamide (several drops) followed by treatment with methanol (10 mL) and triethylamine (2.78 mL, 20 mmol). Workup afforded 2-methyl-benzoic acid methyl ester. The material was used without further purification.

Example 219

2-Chloro-6-methyl-benzoic acid methyl ester

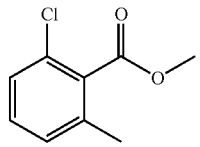

A solution of 2-chloro-6-methyl-benzoic acid (1.70 g, 10 mmol)) in dichloromethane (10 mL) was treated with oxalyl chloride (6 mL, 12 mmol) and dimethylformamide (several drops) followed by treatment with methanol (10 mL) and triethylamine (2.78 mL, 20 mmol). Workup afforded 2-chloro-6-methyl-benzoic acid methyl ester. The material was used without further purification.

Example 220

2-Iodo-6-methyl-benzoic acid methyl ester

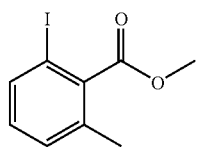

A solution of 2-iodo-6-methyl-benzoic acid (3.42 g, 13 mmol) in dichloromethane (25 mL) was treated with oxalyl chloride (7.5 mL, 15 mmol) and dimethylformamide (several drops) followed by treatment with methanol (30 mL) and triethylamine (2.78 mL, 20 mmol). Workup afforded 2-iodo-6-methyl-benzoic acid methyl ester. The material was used without further purification.

Step 2: Bromination

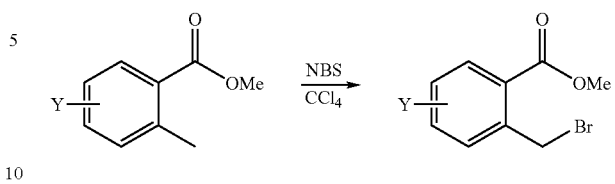

General Procedure

A mixture of the appropriately substituted carboxylic ester (1 equiv.), N-bromosuccinamide (1.1 equiv.), and benzoyl peroxide (0.02 equiv.) in carbon tetrachloride was refluxed until most of the starting materials were consumed (as analyzed by GC/MS). The resulting mixture was filtered and the filtrate concentrated to afforded the desired product. The material was used without further purification.

The following compounds were synthesized using general method 2, step 2 described above.

Example 221

2-bromomethyl-benzoic acid methyl ester

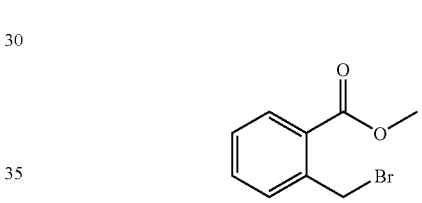

A mixture of 2-methyl-benzoic acid methyl ester (1.53 g, 10 mmol), N-bromosuccinamide (1.95 g, 11 mmol), and benzoyl peroxide (0.056 g, 0.21 mmol) in carbon tetrachloride (20 mL) was heated at reflux until the starting materials were mostly consumed. Workup and silica gel column chromatography using 5% ethyl acetate in hexane afforded 2-bromomethyl-benzoic acid methyl ester (2.0 g, 87%). GC-MS: m/z 230 (M1)$^+$.

Example 222

2-bromomethyl-6-chloro-benzoic acid methyl ester

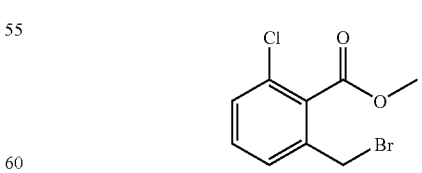

A mixture of 2-chloro-6-methyl-benzoic acid methyl ester (1.84 g, 10 mmol), N-bromosuccinamide (1.95 g, 11 mmol), and benzoyl peroxide (0.056 g, 0.21 mmol) in carbon tetrachloride (20 mL) was heated at reflux until the starting materials were mostly consumed. Workup afforded 2-bromomethyl-6-chloro-benzoic acid methyl ester. The material was used without further purification.

Example 223

2-Bromomethyl-6-iodo-benzoic acid methyl ester

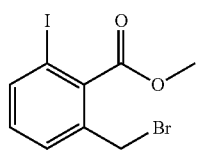

A mixture of 2-iodo-6-methyl-benzoic acid methyl ester (3.59 g, 13 mmol), N-bromosuccinamide (2.3 g, 13 mmol), and benzoyl peroxide (0.056 g, 0.21 mmol) in carbon tetrachloride (20 mL) was heated at reflux until the starting materials were mostly consumed. Workup afforded 2-bromomethyl-6-iodo-benzoic acid methyl ester. The material was used without further purification.

Step 3: Generation of Isoindolones from Bromo-Esters and Amines

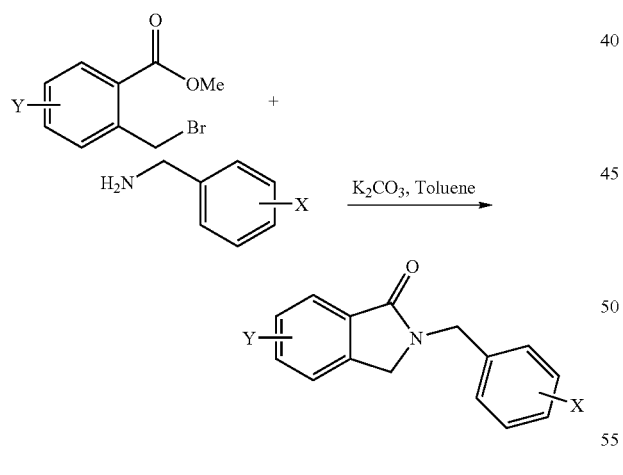

General Procedure

A mixture of the appropriately substituted benzyl amine (1.2 equiv.), the appropriately substituted bromo-ester (1.0 equiv.), and K$_2$CO$_3$ (2 equiv.) in toluene was heated with stirring at 100° C. for 2 h. The resulting mixture was filtered and the filtrate concentrated. Silica gel column chromatography of the resulting material using combinations of hexane and ethyl acetate (typically 30% ethyl acetate in hexane) afforded the desired product.

The following compounds were synthesized using general method 2, step 3 described above.

Example 224

2-(4-phenoxy-benzyl)-2,3-dihydro-isoindol-1-one

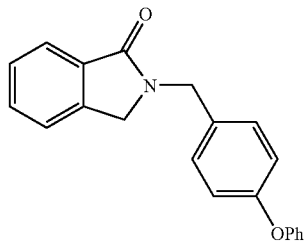

A mixture of 2-bromomethyl-benzoic acid methyl ester (0.115 g, 0.5 mmol), 4-phenoxy-benzylamine (0.106 mL, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-(4-phenoxy-benzyl)-2,3-dihydro-isoindol-1-one (0.095 g, 61%). $^1$H NMR (300 MHz, CDCl$_3$): δ (ppm) 4.28 (s, 2H), 4.79 (s, 2H), 6.98-7.54 (m, 12H), 7.89 (d, 1H). GC-MS: m/z 315 (M)$^+$.

Example 225

2-(3-phenoxy-benzyl)-2,3-dihydro-isoindol-1-one

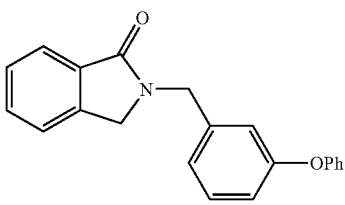

A mixture of 2-bromomethyl-benzoic acid methyl ester (0.115 g, 0.5 mmol), 3-phenoxy-benzylamine (0.106 mL, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-(3-phenoxy-benzyl)-2,3-dihydro-isoindol-1-one (0.064 g, 41%). $^1$H NMR (300 MHz, CDCl$_3$): δ (ppm) 4.26 (s, 2H), 4.82 (s, 2H), 6.90-7.56 (m, 12H), 7.89 (d, 1H). GC-MS: m/z 315 (M)$^+$.

Example 226

2-Biphenyl-4-ylmethyl-2,3-dihydro-isoindol-1-one

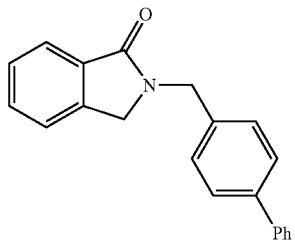

A mixture of 2-bromomethyl-benzoic acid methyl ester (0.115 g, 0.5 mmol), C-biphenyl-4-yl-methylamine (0.110 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-biphenyl-4-ylmethyl-2,3-dihydro-isoindol-1-one (0.079 g, 53%). $^1$H NMR (300 MHz, CDCl$_3$): δ (ppm) 4.26 (s, 2H), 4.84 (s, 2H), 7.32-7.56 (m, 12H), 7.89 (d, 1H). GC-MS: m/z 299 (M)$^+$.

Example 227

2-(1-Methyl-3-phenyl-propyl)-2,3-dihydro-isoindol-1-one

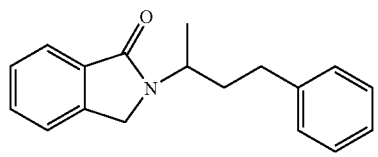

A mixture of 2-bromomethyl-benzoic acid methyl ester (0.115 g, 0.5 mmol), 1-methyl-3-phenyl-propylamine (0.090 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-(1-methyl-3-phenyl-propyl)-2,3-dihydro-isoindol-1-one (0.072 g, 54%). $^1$H NMR (300 MHz, CDCl$_3$):

δ (ppm) 1.32 (d, 3H), 1.92 (m, 2H), 2.64 (m, 2H), 4.34 (dd, 2H), 4.62 (m, 1H), 7.14-7.58 (m, 8H), 7.89 (d, 1H). GC-MS: m/z 265 (M)$^+$.

Example 228

2-[3-(2-chloro-phenyl)-propyl]-2,3-dihydro-isoindol-1-one

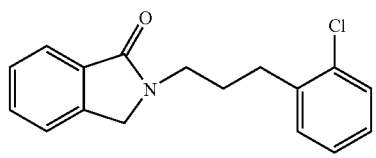

A mixture of 2-bromomethyl-benzoic acid methyl ester (0.115 g, 0.5 mmol), 3-(2-chloro-phenyl)-propylamine (0.102 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-[3-(2-chloro-phenyl)-propyl]-2,3-dihydro-isoindol-1-one (0.076 g, 51%). $^1$H NMR (300 MHz, CDCl$_3$): δ (ppm) 1.99 (m, 2H), 2.79 (t, 2H), 3.69 (t, 2H), 4.41 (s, 2H), 7.14-7.58 (m, 7H), 7.88 (d, 1H). GC-MS: m/z 285 (M)$^+$.

Example 229

2-[3-(4-chloro-phenyl)-propyl]-2,3-dihydro-isoindol-1-one

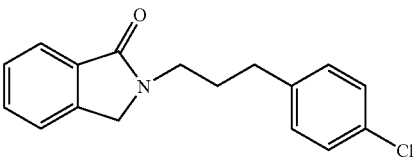

A mixture of 2-bromomethyl-benzoic acid methyl ester (0.115 g, 0.5 mmol), 3-(4-chloro-phenyl)-propylamine (0.102 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-[3-(4-chloro-phenyl)-propyl]-2,3-dihydro-isoindol-1-one (0.031 g, 23%). $^1$H NMR (300 MHz, CDCl$_3$): δ (ppm) 1.96 (m, 2H), 2.69 (t, 2H), 3.64 (t, 2H), 4.36 (s, 2H), 7.14-7.58 (m, 7H), 7.84 (d, 1H). GC-MS: m/z 285 (M)$^+$.

3.64 (t, 2H), 3.76 (s, 3H), 4.36 (s, 2H), 6.78 (d, 2H), 7.18 (d, 2H), 7.52 (m, 3H), 7.82 (d, 1H). GC-MS: m/z 281 (M)$^+$.

Example 230

2-[3-(3-chloro-phenyl)-propyl]-2,3-dihydro-isoindol-1-one

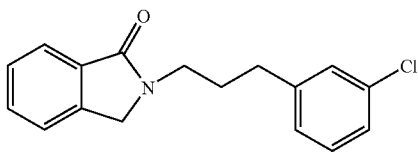

A mixture of 2-bromomethyl-benzoic acid methyl ester (0.115 g, 0.5 mmol), 3-(3-chloro-phenyl)-propylamine (0.102 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-[3-(3-chloro-phenyl)-propyl]-2,3-dihydro-isoindol-1-one (0.105 g, 71%). $^1$H NMR (300 MHz, CDCl$_3$): δ (ppm) 1.96 (m, 2H), 2.69 (t, 2H), 3.66 (t, 2H), 4.36 (s, 2H), 7.12-7.58 (m, 7H), 7.84 (d, 1H). GC-MS: m/z 285 (M)$^+$.

Example 232

2-[3-(3-methoxy-phenyl)-propyl]-2,3-dihydro-isoindol-1-one

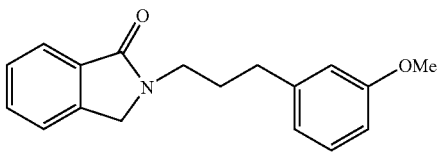

A mixture of 2-bromomethyl-benzoic acid methyl ester (0.115 g, 0.5 mmol), 3-(3-methoxy-phenyl)-propylamine (0.110 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-[3-(3-methoxy-phenyl)-propyl]-2,3-dihydro-isoindol-1-one (0.088 g, 62%). $^1$H NMR (300 MHz, CDCl$_3$): δ (ppm) 2.0 (m, 2H), 2.66 (t, 2H), 3.64 (t, 2H), 3.82 (s, 3H), 4.36 (s, 2H), 6.78 (m, 2H), 7.16-7.58 (m, 5H), 7.84 (d, 1H). GC-MS: m/z 281 (M)$^+$.

Example 231

2-[3-(4-methoxy-phenyl)-propyl]-2,3-dihydro-isoindol-1-one

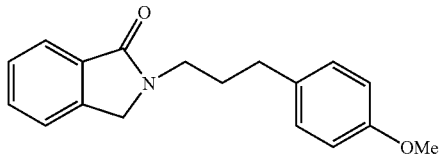

A mixture of 2-bromomethyl-benzoic acid methyl ester (0.115 g, 0.5 mmol), 3-(4-methoxy-phenyl)-propylamine (0.110 g, 0.6 mmol), and K$_2$CO$_3$ (0.207 g, 1.5 mmol) in toluene (3 mL) was heated with stirring at 100° C. for 2 h. Workup and silica gel column chromatography using 30% ethyl acetate in hexane afforded 2-[3-(4-methoxy-phenyl)-propyl]-2,3-dihydro-isoindol-1-one (0.114 g, 81%). $^1$H NMR (300 MHz, CDCl$_3$): δ (ppm) 1.98 (m, 2H), 2.63 (t, 2H),

Example 233

2-[3-(3-trifluoromethyl-phenyl)-propyl]-2,3-dihydro-isoindol-1-one

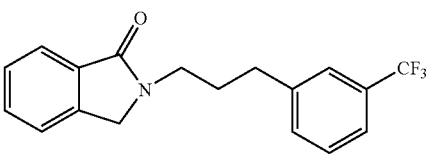

A mixture of 2-bromomethyl-benzoic acid methyl ester (1.13 g, 4.9 mmol), 3-(3-trifluoromethyl-phenyl)-propylamine (1 g, 4.9 mmol), and K$_2$CO$_3$ (1.13 g, 8.17 mmol) in toluene (10 mL) was heated with stirring at 100° C. for 2 h. Workup and silica gel column chromatography using 30% ethyl acetate in hexane afforded 2-[3-(3-trifluoromethyl-phenyl)-propyl]-2,3-dihydro-isoindol-1-one (0.658 g, 49%). $^1$H NMR (300 MHz, CDCl$_3$): δ (ppm) 2.02 (m, 2H), 2.76 (t, 2H), 3.69 (t, 2H), 4.36 (s, 2H), 7.36-7.56 (m, 7H), 7.84 (d, 1H). GC-MS: m/z 319 (M)$^+$.

Example 234

2-[3-(4-trifluoromethyl-phenyl)-propyl]-2,3-dihydro-isoindol-1-one

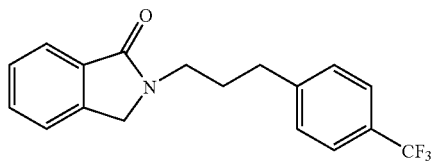

A mixture of 2-bromomethyl-benzoic acid methyl ester (1.13 g, 4.9 mmol), 3-(4-trifluoromethyl-phenyl)-propylamine (1 g, 4.9 mmol), and K$_2$CO$_3$ (1.13 g, 8.17 mmol) in toluene (10 mL) was heated with stirring at 100° C. for 2 h. Workup and silica gel column chromatography using 30% ethyl acetate in hexane afforded 2-[3-(4-trifluoromethyl-phenyl)-propyl]-2,3-dihydro-isoindol-1-one (0.314 g, 20%). $^1$H NMR (300 MHz, CDCl$_3$): δ (ppm) 2.02 (m, 2H), 2.76 (t, 2H), 3.69 (t, 2H), 4.36 (s, 2H), 7.29-7.56 (m, 7H), 7.83 (d, 1H). GC-MS: m/z 319 (M)$^+$.

Example 235

2-[3-(3-trifluoromethoxy-phenyl)-propyl]-2,3-dihydro-isoindol-1-one

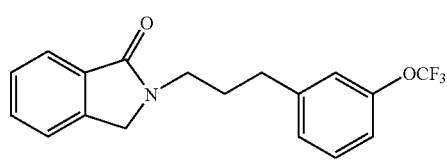

A mixture of 2-bromomethyl-benzoic acid methyl ester (0.23 g, 1.0 mmol), 3-(3-trifluoromethoxy-phenyl)-propylamine (0.219 g, 1.0 mmol), and K$_2$CO$_3$ (0.25 g, 1.8 mmol) in toluene (10 mL) was heated with stirring at 100° C. for 2 h. Workup and silica gel column chromatography using 30% ethyl acetate in hexane afforded 2-[3-(3-trifluoromethoxy-phenyl)-propyl]-2,3-dihydro-isoindol-1-one (0.153 g, 46%).

$^1$H NMR (300 MHz, CDCl$_3$): δ (ppm) 2.02 (m, 2H), 2.72 (t, 2H), 3.69 (t, 2H), 4.36 (s, 2H), 7.02-7.56 (m, 7H), 7.84 (d, 1H). GC-MS: m/z 335 (M)$^+$.

Example 236

2-[3-(4-trifluoromethoxy-phenyl)-propyl]-2,3-dihydro-isoindol-1-one

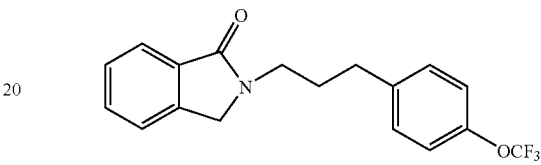

A mixture of 2-bromomethyl-benzoic acid methyl ester (0.460 g, 2.0 mmol), 3-(4-trifluoromethoxy-phenyl)-propylamine (0.438 g, 2.0 mmol), and K$_2$CO$_3$ (0.500 g, 3.6 mmol) in toluene (10 mL) was heated with stirring at 100° C. for 2 h. Workup and silica gel column chromatography using 30% ethyl acetate in hexane afforded 2-[3-(4-trifluoromethoxy-phenyl)-propyl]-2,3-dihydro-isoindol-1-one (0.248 g, 37%). $^1$H NMR (300 MHz, CDCl$_3$): δ (ppm) 1.97 (m, 2H), 2.70 (t, 2H), 3.69 (t, 2H), 4.36 (s, 2H), 7.09 (d, 2H), 7.23 (t, 2H), 7.42-7.56 (m, 3H), 7.86 (d, 1H). GC-MS: m/z 335 (M)$^+$.

Example 237

2-(2-Methyl-3-phenyl-propyl)-2,3-dihydro-isoindol-1-one

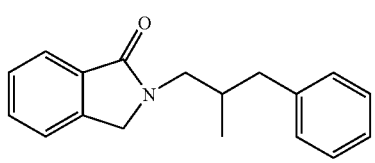

A mixture of 2-bromomethyl-benzoic acid methyl ester (0.460 g, 2.0 mmol), 2-methyl-3-phenyl-propylamine (0.298 g, 2.0 mmol), and K$_2$CO$_3$ (0.500 g, 3.6 mmol) in toluene (10 mL) was heated with stirring at 100° C. for 2 h. Workup and silica gel column chromatography using 30% ethyl acetate in hexane afforded 2-(2-methyl-3-phenyl-propyl)-2,3-dihydro-isoindol-1-one (0.265 g, 50%). $^1$H NMR (300 MHz, CDCl$_3$):

δ (ppm) 0.93 (d, 3H), 2.19 (m, 1H), 2.46 (m, 1H), 2.73 (m, 1H) 3.56 (d, 2H), 4.36 (dd, 2H), 7.14-7.56 (m, 8H), 7.86 (d, 1H). GC-MS: m/z 265 (M)+.

$^1$H NMR (300 MHz, CDCl$_3$): δ (ppm) 4.32 (s, 2H), 4.81 (s, 2H) 7.01-7.56 (m, 1H), 7.91 (d, 1H). GC-MS: m/z 383 (M)+.

Example 238

2-[4-(4-Fluoro-phenoxy)-benzyl]-2,3-dihydro-isoindol-1-one

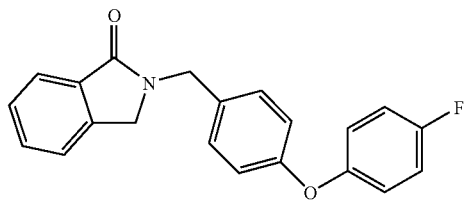

A mixture of 2-bromomethyl-benzoic acid methyl ester (0.108 g, 0.5 mmol), 4-(4-fluoro-phenoxy)-benzylamine (0.115 g, 0.5 mmol), and K$_2$CO$_3$ (0.235 g, 1.7 mmol) in toluene (5 mL) was heated with stirring at 100° C. for 2 h. Workup and silica gel column chromatography using 30% ethyl acetate in hexane afforded 2-[4-(4-fluoro-phenoxy)-benzyl]-2,3-dihydro-isoindol-1-one (0.100 g, 60%). $^1$H NMR (300 MHz, CDCl$_3$): δ (ppm) 4.29 (s, 2H), 4.78 (s, 2H) 6.83-7.56 (m, 1H), 7.89 (d, 1H). GC-MS: m/z 333 (M)+.

Example 239

2-[4-(4-Trifluoromethyl-phenoxy)-benzyl]-2,3-dihydro-isoindol-1-one

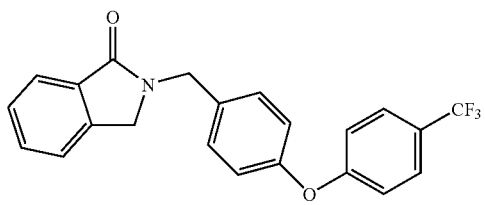

A mixture of 2-bromomethyl-benzoic acid methyl ester (0.115 g, 0.5 mmol), 4-(4-trifluoromethyl-phenoxy)-benzylamine (0.133 g, 0.5 mmol), and K$_2$CO$_3$ (0.235 g, 1.7 mmol) in toluene (5 mL) was heated with stirring at 100° C. for 2 h. Workup and silica gel column chromatography using 30% ethyl acetate in hexane afforded 2-[4-(4-trifluoromethyl-phenoxy)-benzyl]-2,3-dihydro-isoindol-1-one (0.116 g, 60%).

Example 240

2-(4-Phenylsulfanyl-benzyl)-2,3-dihydro-isoindol-1-one

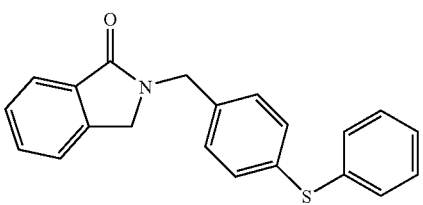

A mixture of 2-bromomethyl-benzoic acid methyl ester (0.230 g, 1 mmol), 4-phenylsulfanyl-benzylamine (0.215 g, 1 mmol), and K$_2$CO$_3$ (0.230 g, 1.67 mmol) in toluene (6 mL) was heated with stirring at 100° C. for 2 h. Workup and silica gel column chromatography using 30% ethyl acetate in hexane afforded 2-(4-phenylsulfanyl-benzyl)-2,3-dihydro-isoindol-1-one (0.175 g, 53%). $^1$H NMR (300 MHz, CDCl$_3$): δ (ppm) 4.27 (s, 2H), 4.77 (s, 2H) 7.22-7.49 (m, 12H), 7.88 (d, 1H). GC-MS: m/z 331 (M)+.

Example 241

2-Cyclohexylmethyl-2,3-dihydro-isoindol-1-one

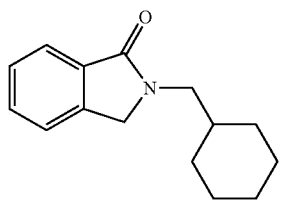

A mixture of 2-bromomethyl-benzoic acid methyl ester (0.230 g, 1 mmol), C-cyclohexyl-methylamine (0.190 g, 1 mmol), and K$_2$CO$_3$ (0.230 g, 1.67 mmol) in toluene (6 mL) was heated with stirring at 100° C. for 2 h. Workup and silica gel column chromatography using 30% ethyl acetate in hexane afforded 2-cyclohexylmethyl-2,3-dihydro-isoindol-1-one (0.085 g, 37%). $^1$H NMR (300 MHz, CDCl$_3$): δ (ppm)

1.18 (m, 5H), 1.72 (m, 6H), 3.46 (d, 2H), 4.38 (s, 2H) 7.42-7.53 (m, 3H), 7.85 (d, 1H). GC-MS: m/z 229 (M)+.

Example 242

2-Benzyl-7-chloro-2,3-dihydro-isoindol-1-one

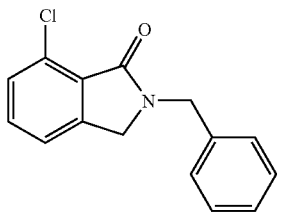

A mixture of 2-bromomethyl-6-chloro-benzoic acid methyl ester (0.132 g, 0.5 mmol), benzylamine (0.065 g, 0.6 mmol), and K$_2$CO$_3$ (0.207 g, 1.5 mmol) in toluene (4 mL) was heated with stirring at 100° C. for 2 h. Workup and silica gel column chromatography using 30% ethyl acetate in hexane afforded 2-benzyl-7-chloro-2,3-dihydro-isoindol-1-one (0.126 g, 99%). $^1$H NMR (300 MHz, CDCl$_3$): δ (ppm) 4.22 (s, 2H), 4.76 (s, 2H) 7.28-7.46 (m, 8H). GC-MS: m/z 257 (M)+.

Example 243

7-Chloro-2-(4-chloro-benzyl)-2,3-dihydro-isoindol-1-one

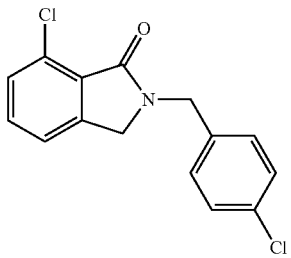

A mixture of 2-bromomethyl-6-chloro-benzoic acid methyl ester (0.132 g, 0.5 mmol), 4-chloro-benzylamine (0.073 g, 0.6 mmol), and K$_2$CO$_3$ (0.207 g, 1.5 mmol) in toluene (4 mL) was heated with stirring at 100° C. for 2 h. Workup and silica gel column chromatography using 30% ethyl acetate in hexane afforded 7-chloro-2-(4-chloro-benzyl)-2,3-dihydro-isoindol-1-one (0.116 g, 79%). $^1$H NMR (300 MHz, CDCl$_3$): δ (ppm) 4.24 (s, 2H), 4.74 (s, 2H) 7.24-7.46 (m, 7H). GC-MS: m/z 291 (M)+.

Example 244

7-Chloro-2-[1-(4-chloro-phenyl)-ethyl]-2,3-dihydro-isoindol-1-one

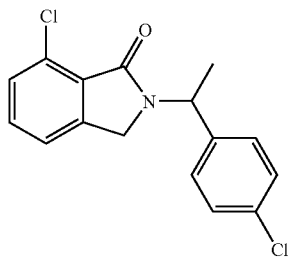

A mixture of 2-bromomethyl-6-chloro-benzoic acid methyl ester (0.132 g, 0.5 mmol), 1-(4-chlorophenyl)-ethylamine (0.117 g, 0.6 mmol), and K$_2$CO$_3$ (0.207 g, 1.5 mmol) in toluene (4 mL) was heated with stirring at 100° C. for 2 h. Workup and silica gel column chromatography using 30% ethyl acetate in hexane afforded 7-chloro-2-[1-(4-chlorophenyl)-ethyl]-2,3-dihydro-isoindol-1-one (0.132 g, 86%). $^1$H NMR (300 MHz, CDCl$_3$): δ (ppm) 1.66 (d, 3H), 3.95 (d, 1H), 4.34 (d, 1H), 5.84 (q, 1H) 7.26-7.46 (m, 7H). GC-MS: m/z 306 (M)+.

Example 245

(S)-7-Chloro-2-[1-(4-chloro-phenyl)-ethyl]-2,3-dihydro-isoindol-1-one

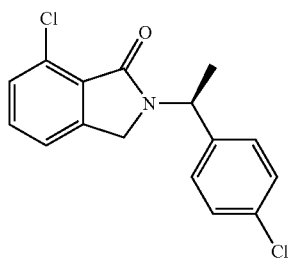

and (R)-7-Chloro-2-[1-(4-chloro-phenyl)-ethyl]-2,3-dihydro-isoindol-1-one

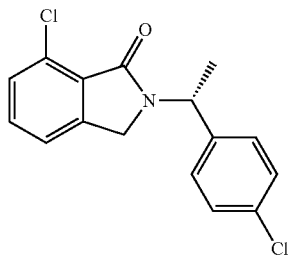

Chromatography (HPLC) of racemic mixture of 7-chloro-2-[1-(4-chloro-phenyl)-ethyl]-2,3-dihydro-isoindol-1-one (1.2 g) through ChrialCel OD (250×20 mm i.d., 10 µm)] using 5% isopropyl alcohol in hexanes as an eluent afforded (S)-7-Chloro-2-[1-(4-chloro-phenyl)-ethyl]-2,3-dihydro-isoindol-1-one (0.044 g) and (R)-7-Chloro-2-[1-(4-chloro-phenyl)-ethyl]-2,3-dihydro-isoindol-1-one (0.058 g)

Example 246

7-Chloro-2-(4-phenoxy-benzyl)-2,3-dihydro-isoindol-1-one

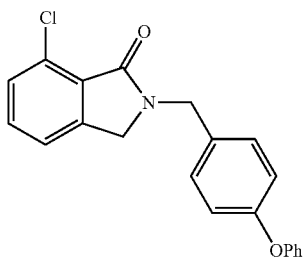

A mixture of 2-bromomethyl-6-chloro-benzoic acid methyl ester (0.132 g, 0.5 mmol), 4-phenoxy benzylamine (0.124 g, 0.7 mmol), and $K_2CO_3$ (0.152 g, 1.1 mmol) in toluene (4 mL) was heated with stirring at 100° C. for 2 h. Workup and silica gel column chromatography using 30% ethyl acetate in hexane afforded 7-chloro-2-(4-phenoxy-benzyl)-2,3-dihydro-isoindol-1-one (0.06 g, 34%). $^1$H NMR (300 MHz, $CDCl_3$): δ (ppm) 4.24 (s, 2H), 4.76 (s, 2H), 6.98-7.46 (m, 12H). GC-MS: m/z 349 (M)$^+$.

Example 247

7-Chloro-2-(4-methyl-benzyl) 2,3-dihydro-isoindol-1-one

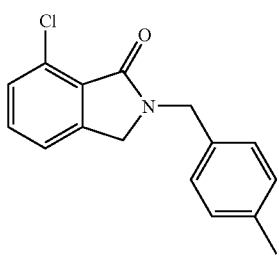

A mixture of 2-bromomethyl-6-chloro-benzoic acid methyl ester (0.132 g, 0.5 mmol,), 4-methyl benzylamine (0.102 mL, 0.8 mmol), and $K_2CO_3$ (0.276 g, 2.0 mmol) in toluene (5 mL) was heated with stirring at 100° C. for 2 h. Workup and silica gel column chromatography using 30% ethyl acetate in hexane afforded 7-chloro-2-(4-methyl-benzyl) 2,3-dihydro-isoindol-1-one (0.06 g, 34%). $^1$H NMR (300 MHz, $CDCl_3$): δ (ppm) 4.22 (s, 2H), 4.78 (s, 2H), 7.12-7.46 (m, 7H). GC-MS: m/z 271 (M)$^+$.

Example 248

7-Chloro-2-(4-trifluoromethoxy-benzyl)-2,3-dihydro-isoindol-1-one

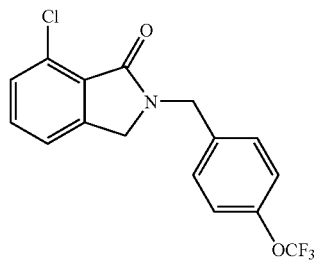

A mixture of 2-bromomethyl-6-chloro-benzoic acid methyl ester (0.105 g, 0.4 mmol), 4-methyl benzylamine (0.092 mL, 0.6 mmol), and $K_2CO_3$ (0.138 g, 1.0 mmol) in toluene (5 mL) was heated with stirring at 100° C. for 2 h. Workup and silica gel column chromatography using 30% ethyl acetate in hexane afforded 7-chloro-2-(4-trifluoromethoxy-benzyl)-2,3-dihydro-isoindol-1-one (0.06 g, 34%). $^1$H NMR (300 MHz, $CDCl_3$): δ (ppm) 4.31 (s, 2H), 4.78 (s, 2H), 7.15-7.46 (m, 7H). GC-MS: m/z 341 (M)$^+$.

Example 249

7-Chloro-2-dibenzo[1,4]dioxin-2-ylmethyl-2,3-dihydro-isoindol-1-one

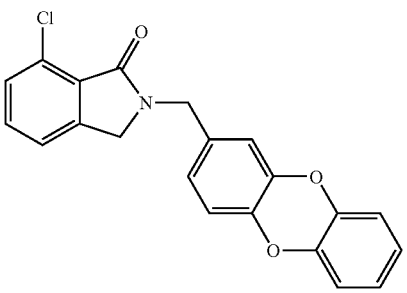

A mixture of 2-bromomethyl-6-chloro-benzoic acid methyl ester (0.148 g, 0.6 mmol), C-dibenzo[1,4]dioxin-2-yl-methylamine (0.213 g, 1.0 mmol), and $K_2CO_3$ (0.207 g, 1.5 mmol) in toluene (5 mL) was heated with stirring at 100° C. for 2 h. Workup and silica gel column chromatography using 30% ethyl acetate in hexane afforded 7-Chloro-2-dibenzo[1,4]dioxin-2-ylmethyl-2,3-dihydro-isoindol-1-one (0.023 g, 13%). $^1$H NMR (300 MHz, CDCl$_3$): δ (ppm) 4.34 (s, 2H), 4.65 (s, 2H), 6.85 (m, 8H), 7.40 (t, 2H). GC-MS: m/z 363 (M)$^+$.

Example 250

7-Chloro-2-(3-phenyl-propyl)-2,3-dihydro-isoindol-1-one

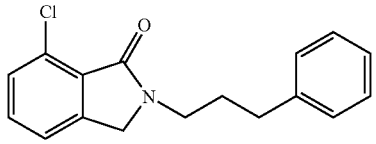

A mixture of 2-bromomethyl-6-chloro-benzoic acid methyl ester (0.132 g, 0.5 mmol), 3-phenyl-propylamine (0.081 mL, 0.6 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 7-chloro-2-(3-phenyl-propyl)-2,3-dihydro-isoindol-1-one (0.120 g, 84%). $^1$H NMR (300 MHz, CDCl$_3$): δ (ppm) 2.01 (m, 2H), 2.68 (t, 2H), 3.66 (t, 2H), 4.28 (s, 2H), 7.14-7.44 (m, 8H). GC-MS: m/z 285 (M)$^+$.

Example 251

2-Benzyl-5-chloro-2,3-dihydro-isoindol-1-one

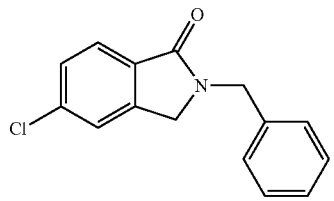

A mixture of 2-bromomethyl-4-chloro-benzoic acid methyl ester (0.120 g, 0.46 mmol), benzylamine (0.106 mL, 1.0 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 2-benzyl-5-chloro-2,3-dihydro-isoindol-1-one (0.047 g, 40%). $^1$H NMR (300 MHz, CDCl$_3$): δ (ppm) 4.26 (m, 2H), 4.80 (m, 2H), 7.32 (m, 7H), 7.83 (m, 1H). GC-MS: m/z 257 (M)$^+$, 180 (M−77)$^+$.

Example 252

2-Benzyl-6-chloro-2,3-dihydro-isoindol-1-one

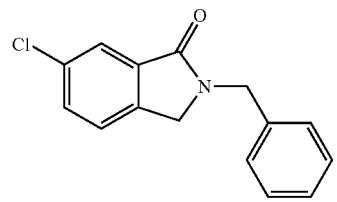

A mixture of 2-bromomethyl-5-chloro-benzoic acid methyl ester (0.200 g, 0.76 mmol), benzylamine (0.135 mL, 1.25 mmol), and K$_2$CO$_3$ (0.276 g, 3.5 mmol) in toluene (5 mL) was heated with stirring at 100° C. for 2 h. Workup and silica gel column chromatography using 30% ethyl acetate in hexane afforded 2-benzyl-6-chloro-2,3-dihydro-isoindol-1-one (0.118 g, 60%). $^1$H NMR (300 MHz, CDCl$_3$): δ (ppm) 4.23 (s, 2H), 4.68 (s, 2H), 7.29 (m, 7H), 7.76 (d, 1H). GC-MS: m/z 257 (M)$^+$, 180 (M−77)$^+$.

Example 253

2-Benzyl-4-chloro-2,3-dihydro-isoindol-1-one

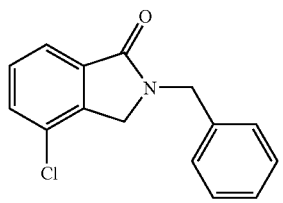

A mixture of 2-bromomethyl-3-chloro-benzoic acid methyl ester (0.132 g, 0.5 mmol), benzylamine (0.065 mL, 0.6 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 2-benzyl-4-chloro-2,3-dihydro-isoindol-1-one (0.129 g, 100%). $^1$H NMR (300 MHz, CDCl$_3$): δ (ppm) 4.24

(s, 2H), 4.70 (s, 2H), 7.27-7.48 (m, 7H), 7.80 (d, 1H). GC-MS: m/z 257 (M)+, 180 (M−77)+.

Example 254

2-Benzyl-7-iodo-2,3-dihydro-isoindol-1-one

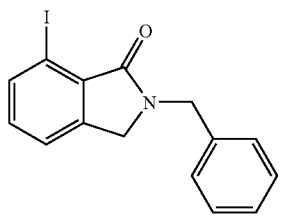

A mixture of 2-bromomethyl-6-iodo-benzoic acid methyl ester (1.07 g, 3.0 mmol), benzylamine (0.34 mL, 3.1 mmol), and $K_2CO_3$ (0.83 g, 6 mmol) in toluene (10 mL) was heated with stirring at 100° C. for 2 h. Workup and silica gel column chromatography using 30% ethyl acetate in hexane afforded 2-benzyl-7-iodo-2,3-dihydro-isoindol-1-one 0.586 g, 56%). $^1$H NMR (300 MHz, $CDCl_3$): δ (ppm) 4.16 (s, 2H), 4.82 (s, 2H) 7.18-7.40 (m, 7H), 7.90 (d, 1H). GC-MS: m/z 349 (M)+.

Example 255

7-Iodo-2-(3-phenyl-propyl)-2,3-dihydro-isoindol-1-one

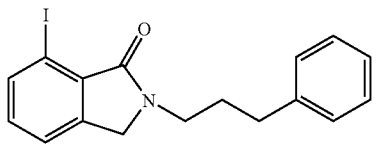

A mixture of 2-bromomethyl-6-iodo-benzoic acid methyl ester (0.107 g, 0.3 mmol), 3-phenyl-propylamine (0.071 mL, 0.5 mmol), and $K_2CO_3$ (0.138 g, 1 mmol) in toluene (5 mL) was heated with stirring at 100° C. for 2 h. Workup and silica gel column chromatography using 30% ethyl acetate in hexane afforded 7-iodo-2-(3-phenyl-propyl)-2,3-dihydro-isoindol-1-one (0.054 g, 48%). $^1$H NMR (300 MHz, $CDCl_3$): δ (ppm) 2.01 (m, 2H), 2.72 (t, 2H), 3.66 (t, 2H), 4.25 (s, 2H), 7.14-7.42 (m, 7H), 7.90 (d, 1H).

Example 256

2-[3-(3-Fluoro-phenyl)-propyl]-7-iodo-2,3-dihydro-isoindol-1-one

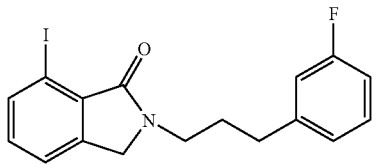

A mixture of 2-bromomethyl-6-iodo-benzoic acid methyl ester (0.150 g, 0.42 mmol), 3-(3-fluoro-phenyl)-propylamine (0.091 mL, 0.6 mmol), and $K_2CO_3$ (0.138 g, 1 mmol) in toluene (5 mL) was heated with stirring at 100° C. for 2 h. Workup and silica gel column chromatography using 30% ethyl acetate in hexane afforded 2-[3-(3-fluoro-phenyl)-propyl]-7-iodo-2,3-dihydro-isoindol-1-one (0.110 g, 69%). $^1$H NMR (300 MHz, $CDCl_3$): δ ppm) 2.01 (m, 2H), 2.72 (t, 2H), 3.66 (t, 2H), 4.25 (s, 2H), 6.82-7.24 (m, 5H), 7.41 (d, 1H), 7.92 (d, 1H).

Example 257

2-(4-Fluoro-benzyl)-7-iodo-2,3-dihydro-isoindol-1-one

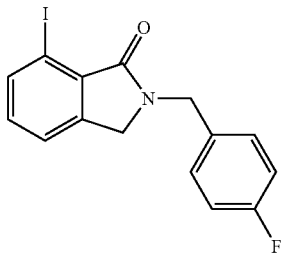

A mixture of 2-bromomethyl-6-iodo-benzoic acid methyl ester (0.200 g, 0.56 mmol), 4-fluoro-benzylamine (0.7 mmol), and $IC_2CO_3$ (0.166 g, 1.2 mmol) in toluene (5 mL) was heated with stirring at 100° C. for 2 h. Workup and silica gel column chromatography using 30% ethyl acetate in hexane afforded 2-(4-fluoro-benzyl)-7-iodo-2,3-dihydro-isoindol-1-one (0.082 g, 40%). $^1$H NMR (300 MHz, $CDCl_3$): δ (ppm) 4.16 (s, 2H), 4.75 (s, 2H), 7.01 (t, 2H), 7.28-7.40 (m, 4H), 7.89 (d, 1H). GC-MS: m/z 367 (M)+.

Example 258

2-(4-Chloro-benzyl)-7-iodo-2,3-dihydro-isoindol-1-one

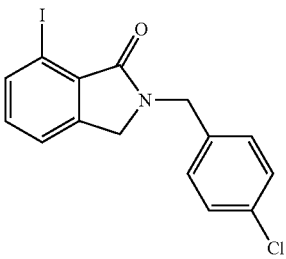

A mixture of 2-bromomethyl-6-iodo-benzoic acid methyl ester (0.200 g, 0.56 mmol), 4-chloro-benzylamine (0.7 mmol), and $K_2CO_3$ (0.166 g, 1.2 mmol) in toluene (5 mL) was heated with stirring at 100° C. for 2 h. Workup and silica gel column chromatography using 30% ethyl acetate in hexane afforded 2-(4-chloro-benzyl)-7-iodo-2,3-dihydro-isoindol- 1-one (0.084 g, 39%). $^1$H NMR (300 MHz, CDCl$_3$): δ (ppm) 4.16 (s, 2H), 4.75 (s, 2H), 7.16-7.40 (m, 6H), 7.92 (d, 1H). GC-MS: m/z 367 (M)$^+$.

$^1$H NMR (300 MHz, CDCl$_3$): δ (ppm) 2.01 (m, 2H), 2.68 (t, 2H), 3.67 (t, 2H), 4.28 (s, 2H), 6.86-7.42 (m, 11H), 7.88 (d, 1H).

Example 259

7-Iodo-2-(4-phenoxy-benzyl)-2,3-dihydro-isoindol-1-one

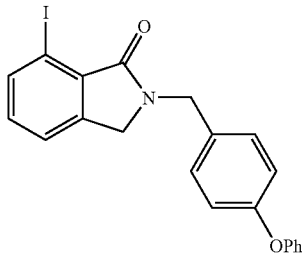

A mixture of 2-bromomethyl-6-iodo-benzoic acid methyl ester (0.200 g, 0.56 mmol), 4-phenoxy-benzylamine (0.7 mmol), and K$_2$CO$_3$ (0.166 g, 1.2 mmol) in toluene (5 mL) was heated with stirring at 100° C. for 2 h. Workup and silica gel column chromatography using 30% ethyl acetate in hexane afforded 7-iodo-2-(4-phenoxy-benzyl)-2,3-dihydro-isoindol-1-one (0.108 g, 44%). $^1$H NMR (300 MHz, CDCl$_3$): δ (ppm) 4.19 (s, 2H), 4.75 (s, 2H), 6.94-7.40 (m, 1H), 7.92 (d, 1H). GC-MS: m/z 441 (M)$^+$.

Example 261

2-{3-[4-(4-Fluoro-phenoxy)-phenyl]-propyl}-7-iodo-2,3-dihydro-isoindol-1-one

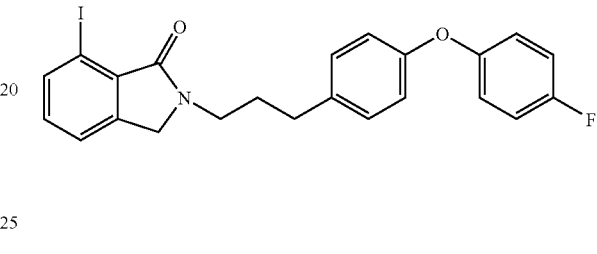

A mixture of 2-bromomethyl-6-iodo-benzoic acid methyl ester (0.245 g, 0.7 mmol), 3-[4-(4-fluoro-phenoxy)phenyl]-propylamine (0.193 g, 0.8 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 2-{3-[4-(4-fluoro-phenoxy)-phenyl]-propyl}-7-iodo-2,3-dihydro-isoindol-1-one (0.086 g, 25%). $^1$H NMR (300 MHz, CDCl$_3$): δ (ppm) 2.01 (m, 2H), 2.65 (t, 2H), 3.67 (t, 2H), 4.26 (s, 2H), 6.84-7.42 (m, 10H), 7.90 (d, 1H). GC-MS: m/z 487 (M)$^+$.

Example 260

7-Iodo-2-[3-(4-phenoxy-phenyl)-propyl]-2,3-dihydro-isoindol-1-one

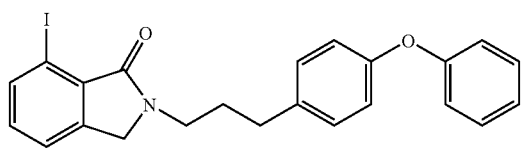

A mixture of 2-bromomethyl-6-iodo-benzoic acid methyl ester (0.106 g, 0.3 mmol), 3-(4-phenoxy-phenyl)-propylamine (0.136 g, 0.6 mmol), and K$_2$CO$_3$ (0.110 g, 0.8 mmol) in toluene (5 mL) was heated with stirring at 100° C. for 2 h. Workup and silica gel column chromatography using 30% ethyl acetate in hexane afforded 7-iodo-2-[3-(4-phenoxy-phenyl)-propyl]-2,3-dihydro-isoindol-1-one (0.025 g, 18%).

Example 262

7-iodo-2-[3-(4-methoxy-phenyl)-propyl]-2,3-dihydro-isoindol-1-one

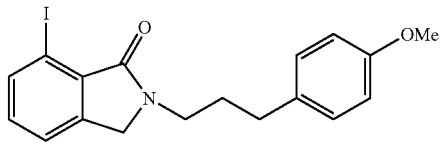

A mixture of 2-bromomethyl-6-iodo-benzoic acid methyl ester (0.245 g, 0.7 mmol), 3-(4-methoxy-phenyl)-propylamine (0.132 g, 0.8 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 7-iodo-2-[3-(4-methoxy-phenyl)-propyl]-2,3-dihydro-isoindol-1-one (0.125 g, 44%). $^1$H NMR (300 MHz, CDCl$_3$): δ (ppm) 2.01 (m, 2H), 2.63 (t, 2H), 3.64 (t, 2H), 3.79 (s, 3H), 4.24 (s, 2H), 6.80 (d, 2H), 7.08-7.44 (m, 4H), 7.90 (d, 1H). GC-MS: m/z 407 (M)$^+$.

Example 263

7-Iodo-2-(4-methoxy-benzyl)-2,3-dihydro-isoindol-1-one

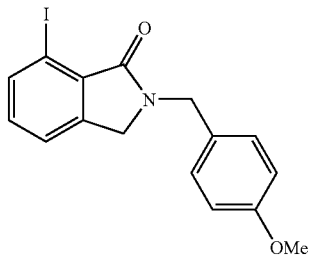

A mixture of 2-bromomethyl-6-iodo-benzoic acid methyl ester (0.245 g, 0.7 mmol), 4-methoxy-benzylamine (0.104 mL, 0.8 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 7-iodo-2-(4-methoxy-benzyl)-2,3-dihydro-isoindol-1-one (0.084 g, 31%). $^1$H NMR (300 MHz, CDCl$_3$): δ (ppm) 3.78 (s, 3H), 4.14 (s, 2H), 4.74 (s, 2H), 6.84 (d, 2H), 7.14-7.40 (m, 4H), 7.91 (d, 1H). GC-MS: m/z 379 (M)$^+$.

Example 264

7-Iodo-2-(3-methoxy-benzyl)-2,3-dihydro-isoindol-1-one

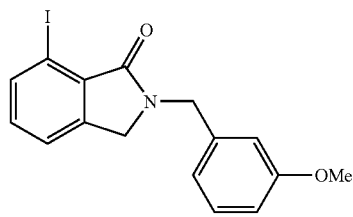

A mixture of 2-bromomethyl-6-iodo-benzoic acid methyl ester (0.107 g, 0.3 mmol), 3-methoxy-benzylamine (0.052 mL, 0.4 mmol), and K$_2$CO$_3$ (0.138 g, 1.0 mmol) in toluene (5 mL) was heated with stirring at 100° C. for 2 h. Workup and silica gel column chromatography using 30% ethyl acetate in hexane afforded 7-iodo-2-(3-methoxy-benzyl)-2,3-dihydro-isoindol-1-one (0.031 g, 27%). $^1$H NMR (300 MHz, CDCl$_3$): δ (ppm) 3.78 (s, 3H), 4.16 (s, 2H), 4.74 (s, 2H), 6.79 (m, 3H), 7.14-7.38 (m, 3H), 7.91 (d, 1H). GC-MS: m/z 379 (M)$^+$.

Example 265

7-Iodo-2-(4-methyl-benzyl)-2,3-dihydro-isoindol-1-one

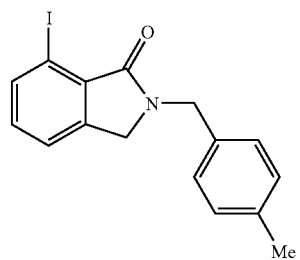

A mixture of 2-bromomethyl-6-iodo-benzoic acid methyl ester (0.245 g, 0.7 mmol), 4-methyl-benzylamine (0.102 mL, 0.8 mmol), and K$_2$CO$_3$ (0.207 g, 1.5 mmol) in toluene (5 mL) was heated with stirring at 100° C. for 2 h. Workup and silica gel column chromatography using 30% ethyl acetate in hexane afforded 7-iodo-2-(4-methyl-benzyl)-2,3-dihydro-isoindol-1-one (0.080 g, 31%). $^1$H NMR (300 MHz, CDCl$_3$): δ (ppm) 2.35 (s, 3H), 4.14 (s, 2H), 4.76 (s, 2H), 7.11-7.38 (m, 6H), 7.91 (d, 1H). GC-MS: m/z 363 (M)$^+$.

Example 266

7-Iodo-2-(2-methyl-benzyl)-2,3-dihydro-isoindol-1-one

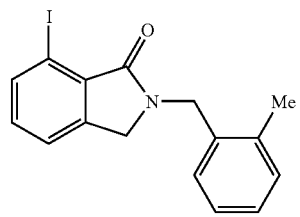

A mixture of 2-bromomethyl-6-iodo-benzoic acid methyl ester (0.107 g, 0.3 mmol), 2-methyl-benzylamine (0.063 mL, 0.5 mmol), and K$_2$CO$_3$ (0.138 g, 1.0 mmol) in toluene (4 mL) was heated with stirring at 100° C. for 2 h. Workup and silica gel column chromatography using 30% ethyl acetate in hexane afforded 7-iodo-2-(2-methyl-benzyl)-2,3-dihydro-isoindol-1-one (0.056 g, 51%). $^1$H NMR (300 MHz, CDCl$_3$): δ

(ppm) 2.35 (s, 3H), 4.14 (s, 2H), 4.82 (s, 2H), 7.11-7.38 (m, 6H), 7.91 (d, 1H). GC-MS: m/z 363 (M)+.

Example 267

7-Iodo-2-(3-methyl-benzyl)-2,3-dihydro-isoindol-1-one

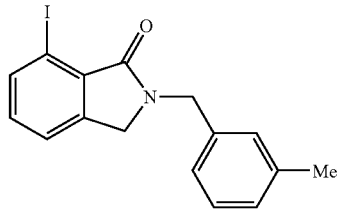

A mixture of 2-bromomethyl-6-iodo-benzoic acid methyl ester (0.107 g, 0.3 mmol), 3-methyl-benzylamine (0.063 mL, 0.5 mmol), and $K_2CO_3$ (0.138 g, 1.0 mmol) in toluene (4 mL) was heated with stirring at 100° C. for 2 h. Workup and silica gel column chromatography using 30% ethyl acetate in hexane afforded 7-iodo-2-(3-methyl-benzyl)-2,3-dihydro-isoindol-1-one (0.037 g, 34%). $^1$H NMR (300 MHz, $CDCl_3$): δ (ppm) 2.35 (s, 3H), 4.08 (s, 2H), 4.82 (s, 2H), 7.12-7.38 (m, 6H), 7.93 (d, 1H). GC-MS: m/z 363 (M)+.

Example 268

7-Iodo-2-(4-ethyl-benzyl)-2,3-dihydro-isoindol-1-one

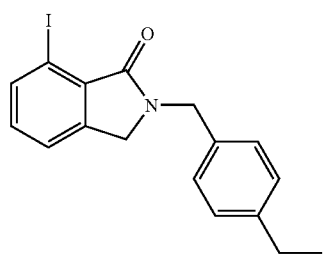

A mixture of 2-bromomethyl-6-iodo-benzoic acid methyl ester (0.107 g, 0.3 mmol), 4-ethyl-benzylamine (0.072 mL, 0.5 mmol), and $K_2CO_3$ (0.138 g, 1.0 mmol) in toluene (5 mL) was heated with stirring at 100° C. for 2 h. Workup and silica gel column chromatography using 30% ethyl acetate in hexane afforded 7-iodo-2-(4-ethyl-benzyl)-2,3-dihydro-isoindol-1-one (0.032 g, 28%). $^1$H NMR (300 MHz, $CDCl_3$): δ (ppm) 1.24 (t, 3H), 2.51 (q, 2H), 4.14 (s, 2H), 4.76 (s, 2H), 7.14-7.38 (m, 6H), 7.86 (d, 1H). GC-MS: m/z 377 (M)+, 348 (M−29)+.

Example 269

7-Iodo-2-(4-butyl-benzyl)-2,3-dihydro-isoindol-1-one

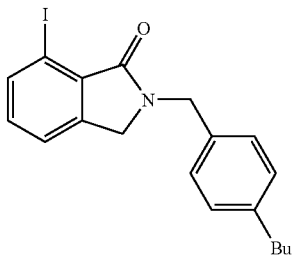

A mixture of 2-bromomethyl-6-iodo-benzoic acid methyl ester (0.107 g, 0.3 mmol), 4-butyl-benzylamine (0.088 mL, 0.5 mmol), and $K_2CO_3$ (0.083 g, 0.6 mmol) in toluene (5 mL) was heated with stirring at 100° C. for 2 h. Workup and silica gel column chromatography using 30% ethyl acetate in hexane afforded 7-iodo-2-(4-butyl-benzyl)-2,3-dihydro-isoindol-1-one (0.063 g, 50%). $^1$H NMR (300 MHz, $CDCl_3$): δ (ppm) 0.88 (t, 3H), 1.34 (m, 2H), 1.56 (m, 2H), 2.58 (t, 2H), 4.16 (s, 2H), 4.76 (s, 2H), 7.14-7.36 (m, 6H), 7.85 (d, 1H). GC-MS: m/z 405 (M)+, 348(M−57)+.

Example 270

7-Iodo-2-(2-p-tolyl-ethyl)-2,3-dihydro-isoindol-1-one

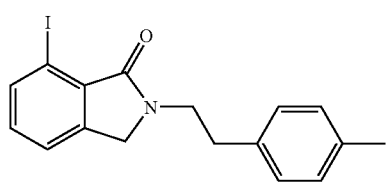

A mixture of 2-bromomethyl-6-iodo-benzoic acid methyl ester (0.107 g, 0.3 mmol), 2-p-tolyl-ethylamine (0.072 mL, 0.5 mmol), and $K_2CO_3$ (0.083 g, 0.6 mmol) in toluene (4 mL) was heated with stirring at 100° C. for 2 h. Workup and silica gel column chromatography using 30% ethyl acetate in hexane afforded 7-iodo-2-(2-p-tolyl-ethyl)-2,3-dihydro-isoindol-1-one (0.060 g, 53%). $^1$H NMR (300 MHz, $CDCl_3$): δ

(ppm) 2.28 (s, 3H), 2.94 (t, 2H), 3.81 (t, 2H), 4.76 (s, 2H), 7.12-7.36 (m, 6H), 7.86 (d, 1H). GC-MS: m/z 377 (M)+, 272(M−105)+.

Example 271

7-Iodo-2-(4-trifluoromethoxy-benzyl)-2,3-dihydro-isoindol-1-one

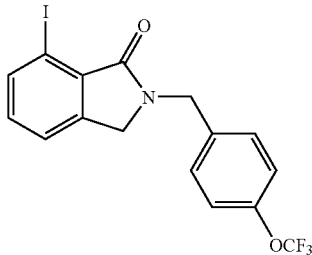

A mixture of 2-bromomethyl-6-iodo-benzoic acid methyl ester (0.245 g, 0.7 mmol), 4-trifluoromethoxy-benzylamine (0.122 mL, 0.8 mmol), and K₂CO₃ (0.207 g, 1.5 mmol) in toluene (5 mL) was heated with stirring at 100° C. for 2 h. Workup and silica gel column chromatography using 30% ethyl acetate in hexane afforded 7-iodo-2-(4-trifluoromethoxy-benzyl)-2,3-dihydro-isoindol-1-one (0.095 g, 31%). ¹H NMR (300 MHz, CDCl₃): δ (ppm) 4.21 (s, 2H), 4.82 (s, 2H), 6.84 (d, 2H), 7.14-7.40 (m, 4H), 7.92 (d, 1H). GC-MS: m/z 433 (M)+.

Example 272

7-Iodo-2-[3-(2-methoxy-phenoxy)-benzyl]-2,3-dihydro-isoindol-1-one

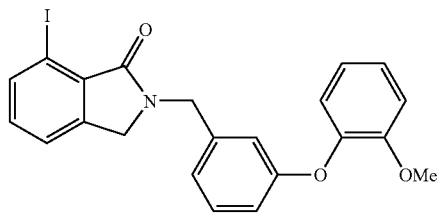

A mixture of 2-bromomethyl-6-iodo-benzoic acid methyl ester (0.178 g, 0.5 mmol), 3-(2-methoxy-phenoxy)-benzylamine (0.160 g, 0.6 mmol), and K₂CO₃ (0.138 g, 1.0 mmol) in toluene (5 mL) was heated with stirring at 100° C. for 2 h. Workup and silica gel column chromatography using 30% ethyl acetate in hexane afforded 7-iodo-2-[3-(2-methoxy-phenoxy)-benzyl]-2,3-dihydro-isoindol-1-one (0.056 g, 24%). ¹H NMR (300 MHz, CDCl₃): δ (ppm) 3.82 (s, 3H), 4.16 (s, 2H), 4.74 (s, 2H), 6.84-7.40 (m, 10H), 7.92 (d, 1H). GC-MS: m/z 471 (M)+.

Example 273

7-Iodo-2-(3-phenyl-butyl)-2,3-dihydro-isoindol-1-one

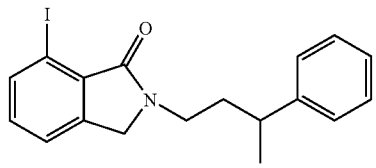

A mixture of 2-bromomethyl-6-iodo-benzoic acid methyl ester (0.178 g, 0.5 mmol), 3-phenyl-butylamine (0.090 g, 0.6 mmol), and K₂CO₃ (0.166 g, 1.2 mmol) in toluene (5 mL) was heated with stirring at 100° C. for 2 h. Workup and silica gel column chromatography using 30% ethyl acetate in hexane afforded 7-iodo-2-(3-phenyl-butyl)-2,3-dihydro-isoindol-1-one (0.046 g, 23%). ¹H NMR (300 MHz, CDCl₃): δ (ppm) 1.32 (d, 3H), 1.96 (m, 2H), 2.78 (m, 1H), 3.54 (m, 2H) 4.16 (s, 2H), 7.14-7.38 (m, 7H), 7.88 (d, 1H). GC-MS: m/z 391 (M)+.

Example 274

7-Iodo-2-(1-methyl-3-phenyl-propyl)-2,3-dihydro-isoindol-1-one

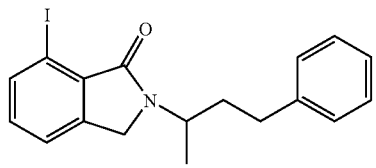

A mixture of 2-bromomethyl-6-iodo-benzoic acid methyl ester (0.107 g, 0.3 mmol), 1-methyl 3-phenyl-propylamine (0.065 g, 0.4 mmol), and K₂CO₃ (0.083 g, 0.6 mmol) in toluene (5 mL) was heated with stirring at 100° C. for 2 h. Workup and silica gel column chromatography using 30% ethyl acetate in hexane afforded 7-iodo-2-(1-methyl-3-phenyl-propyl)-2,3-dihydro-isoindol-1-one (0.098 g, 84%). ¹H NMR (300 MHz, CDCl₃): δ (ppm) 1.32 (d, 3H), 1.94 (m, 2H), 2.54-2.78 (m, 2H), 4.21 (dd, 2H), 4.64 (q, 1H), 7.12-7.24 (m, 6H), 7.41 (d, 1H), 7.88 (d, 1H). GC-MS: m/z 391 (M)+.

Example 275

2-Benzyl-4-iodo-2,3-dihydro-isoindol-1-one

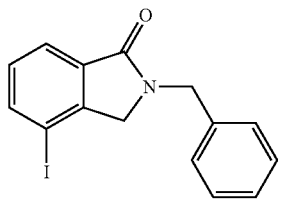

A mixture of 2-bromomethyl-6-iodo-benzoic acid methyl ester (0.708 g, 2.0 mmol), benzylamine (0.218 mL, 2.0 mmol), and $K_2CO_3$ (0.69 g, 5.0 mmol) in toluene (6 mL) was heated with stirring at 100° C. for 2 h. Workup and silica gel column chromatography using 30% ethyl acetate in hexane afforded 2-benzyl-4-iodo-2,3-dihydro-isoindol-1-one (0.325 g, 47%). $^1$H NMR (300 MHz, CDCl$_3$): δ (ppm) 4.18 (s, 2H), 4.84 (s, 2H), 7.21-7.38 (m, 6H), 7.86 (m, 2H). GC-MS: m/z 349 (M)+, 272 (M–77)+.

Example 276

2-Benzyl-5-bromo-2,3-dihydro-isoindol-1-one

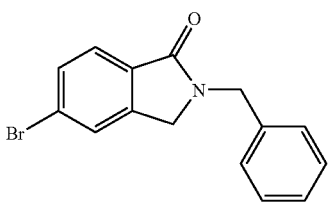

A mixture of 4-bromo-2-bromomethyl-benzoic acid methyl ester (0.308 g, 1.0 mmol), benzylamine (0.218 mL, 2.0 mmol), and $K_2CO_3$ (0.553 g, 4.0 mmol) in toluene (6 mL) was heated with stirring at 100° C. for 2 h. Workup and silica gel column chromatography using 30% ethyl acetate in hexane afforded 2-benzyl-5-bromo-2,3-dihydro-isoindol-1-one (0.150 g, 50%). $^1$H NMR (300 MHz, CDCl$_3$): δ (ppm) 4.22 (s, 2H), 4.76 (s, 2H), 7.21-7.38 (m, 5H), 7.52 (s, 1H), 7.61 (d, 1H), 7.76 (d, 1H). GC-MS: m/z 302 (M)+, 226 (M–76)+.

Example 277

2-Benzyl-6-trifluoromethyl-2,3-dihydroisoindo-1-one

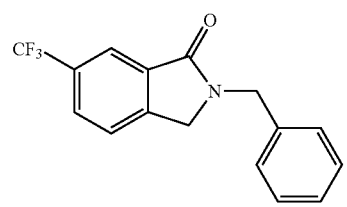

A mixture of 2-bromomethyl-5-trifluoromethyl-benzoic acid methyl ester (0.088 g, 0.3 mmol), benzylamine (0.055 mL, 0.5 mmol), and $K_2CO_3$ (0.083 g, 0.6 mmol) in toluene (4 mL) was heated with stirring at 100° C. for 2 h. Workup and silica gel column chromatography using 30% ethyl acetate in hexane afforded 2-benzyl-6-trifluoromethyl-2,3-dihydroisoindo-1-one. $^1$H NMR (300 MHz, CDCl$_3$): δ (ppm) 4.34 (s, 2H), 4.79 (s, 2H), 7.30 (m, 5H), 7.51 (d, 1H), 7.76 (d, 1H), 8.17 (s, 1H).

Example 278

2-Benzyl-6-fluoro-2,3-dihydro-isoindol-1-one

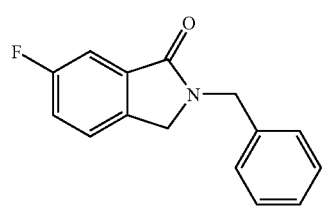

A mixture of 2-bromomethyl-5-fluoro-benzoic acid methyl ester (0.094 g, 0.5 mmol), benzylamine (0.076 mL, 0.7 mmol), and $K_2CO_3$ (0.207 g, 1.5 mmol) in toluene (5 mL) was heated with stirring at 100° C. for 2 h. Workup and silica gel column chromatography using 30% ethyl acetate in hexane afforded 2-benzyl-6-fluoro-2,3-dihydro-isoindol-1-one (0.085 g, 70.7%). $^1$H NMR (300 MHz, CDCl$_3$): δ (ppm) 4.24

(s, 2H), 4.79 (s, 2H), 7.18-7.39 (m, 7H), 7.55 (m, 1H). GC-MS: m/z 241 (M)⁺, 164 (M–77)⁺.

Example 279

2-Benzyl-4-methoxy-2,3-dihydro-isoindol-1-one

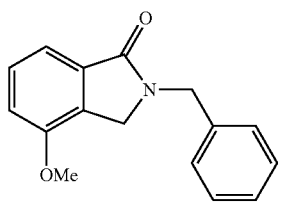

A mixture of 2-bromomethyl-3-methoxy-benzoic acid methyl ester (0.119 g, 0.5 mmol), benzylamine (0.065 mL, 0.6 mmol), and K₂CO₃ (0.207 g, 1.5 mmol) in toluene (5 mL) was heated with stirring at 100° C. for 2 h. Workup and silica gel column chromatography using 30% ethyl acetate in hexane afforded 2-benzyl-4-methoxy-2,3-dihydro-isoindol-1-one (0.078 g, 61.4%). ¹H NMR (300 MHz, CDCl₃): δ (ppm) 3.83 (s, 3H), 4.21 (s, 2H), 4.69 (s, 2H), 6.98 (d, 1H), 7.25-7.51 (m, 7H). GC-MS: m/z 253 (M)⁺, 176 (M–77)⁺.

Method 3

Preparation of 7-bromoisoindolones

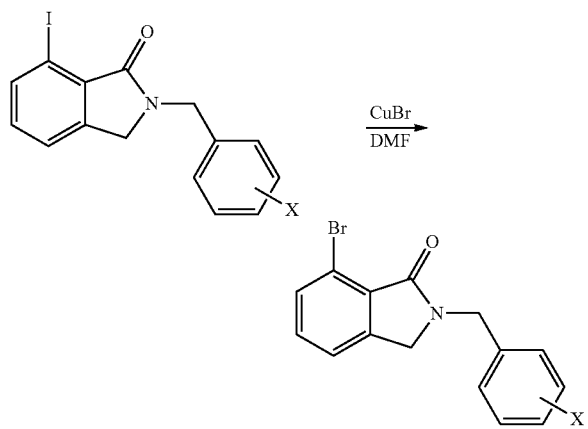

General Procedure

Copper(I) bromide (5 equiv.) was added to a stirred solution of the appropriately substituted 7-iodo-isoindolones (1 equiv.) in DMF. The mixture was heated at 140° C. for 1-2 h under a N₂ atmosphere. After the starting material was completely consumed (monitored using GC-MS and TLC), the reaction mixture was diluted with ethyl acetate. The solids were removed by filtration and the filtrate concentrated. Silica gel column chromatography (typically using 30% ethyl acetate in hexanes) of the resulting material afforded product.

The following compounds were synthesized using general method 3 described above.

Example 280

2-benzyl-7-bromo-2,3-dihydro-isoindol-1-one

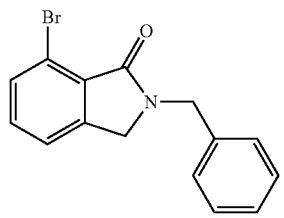

A mixture of 2-benzyl-7-iodo-2,3-dihydro-isoindol-1-one (0.069 g, 0.2 mmol) and CuBr (0.143 g, 1 mmol) in DMF (3 mL) was heated at 140° C. for 1-2 h under a N₂ atmosphere (measuring the consumption of starting material by GC-MS and TLC). Workup and silica gel column chromatography using 30% ethyl acetate in hexane afforded 2-benzyl-7-bromo-2,3-dihydro-isoindol-1-one (0.030 g, 50%). ¹H NMR (300 MHz, CDCl₃): δ (ppm) 4.21 (s, 2H), 4.77 (s, 2H), 7.34 (m, 7H), 7.61 (d, 1H). GC-MS: m/z 302 (M)⁺, 225 (M–77)⁺.

Example 281

7-Bromo-2-(4-methyl-benzyl)-2,3-dihydro-isoindol-1-one

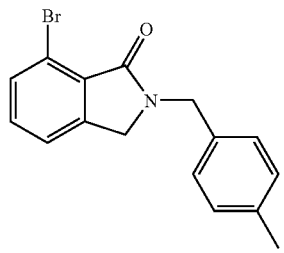

A mixture of 7-iodo-2-(4-methyl-benzyl)-2,3-dihydro-isoindol-1-one (0.05 g, 0.14 mmol) and CuBr (0.100 g, 0.7 mmol) in DMF (3 mL) was heated at 140° C. for 1-2 h under a N₂ atmosphere (measuring the consumption of starting material by GC-MS and TLC). Workup and silica gel column chromatography using 30% ethyl acetate in hexane afforded 7-bromo-2-(4-methyl-benzyl)-2,3-dihydro-isoindol-1-one (0.041 g, 93%). ¹H NMR (300 MHz, CDCl₃): δ (ppm) 2.34 (s, 3H), 4.19 (s, 2H), 4.74 (s, 2H), 7.15-7.34 (m, 6H), 7.61 (d, 1H). GC-MS: m/z 317 (M)$^+$, 302 (M−15)$^+$.

Example 282

7-Bromo-2-(4-phenoxy-benzyl)-2,3-dihydro-isoindol-1-one

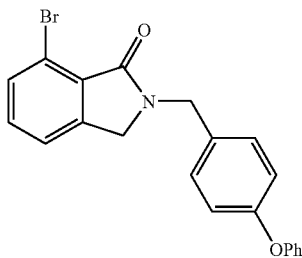

A mixture of 7-iodo-2-(4-phenoxy-benzyl)-2,3-dihydro-isoindol-1-one (0.100 g, 0.23 mmol) and CuBr (0.131 g, 0.92 mmol) in DMF (3 mL) was heated at 140° C. for 1-2 h under a N$_2$ atmosphere (measuring the consumption of starting material by GC-MS and TLC). Workup and silica gel column chromatography using 30% ethyl acetate in hexane afforded 7-bromo-2-(4-phenoxy-benzyl)-2,3-dihydro-isoindol-1-one (0.077 g, 85%). $^1$H NMR (300 MHz, CDCl$_3$): δ (ppm) 4.24 (s, 2H), 4.75 (s, 2H), 6.92-7.38 (m, 11H), 7.61 (m, 1H). GC-MS: m/z 395 (M+1)$^+$, 302 (M−93)$^+$.

Example 283

7-Bromo-2-(3-phenyl-propyl)-2,3-dihydro-isoindol-1-one

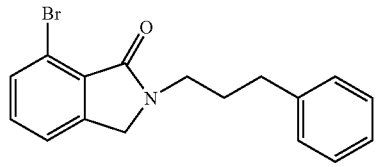

A mixture of 7-iodo-2-(3-phenyl-propyl)-2,3-dihydro-isoindol-1-one (0.06 g, 0.15 mmol) and CuBr (0.093 g, 0.65 mmol) in DMF (3 mL) was heated at 140° C. for 1-2 h under a N$_2$ atmosphere (measuring the consumption of starting material by GC-MS and TLC). Workup and silica gel column chromatography using 30% ethyl acetate in hexane afforded 7-bromo-2-(3-phenyl-propyl)-2,3-dihydro-isoindol-1-one (0.03 g, 59%). $^1$H NMR (300 MHz, CDCl$_3$): δ (ppm) 2.01 (m, 2H), 2.69 (t, 2H), 3.67 (t, 2H), 4.30 (s, 2H), 7.12-7.38 (m, 7H), 7.59 (m, 1H). GC-MS: m/z 331 (M+1)$^+$, 227 (M−104)$^+$.

Example 284

7-Bromo-2-[3-(3-fluoro-phenyl)-propyl]-2,3-dihydro-isoindol-1-one

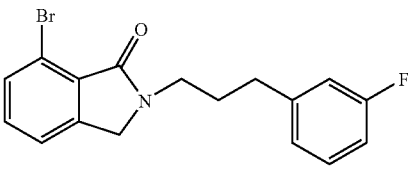

A mixture of 7-iodo-2-[3-(3-fluoro-phenyl)-propyl]-2,3-dihydro-isoindol-1-one (0.06 g, 0.15 mmol) and CuBr (0.114 g, 0.8 mmol) in DMF (3 mL) was heated at 140° C. for 1-2 h under a N$_2$ atmosphere (measuring the consumption of starting material by GC-MS and TLC). Workup and silica gel column chromatography using 30% ethyl acetate in hexane afforded 7-bromo-2-[3-(3-fluoro-phenyl)-propyl]-2,3-dihydro-isoindol-1-one (0.03 g, 58%). $^1$H NMR (300 MHz, CDCl$_3$): δ (ppm) 2.01 (m, 2H), 2.68 (t, 2H), 3.66 (t, 2H), 4.24 (s, 2H), 6.82-7.38 (m, 6H), 7.61 (m, 1H). GC-MS: m/z 349 (M+1)$^+$, 227 (M−122)$^+$.

Method 4

Synthesis of 7-Trifluoromethyl Isoindolone

Example 285

2-benzyl-7-trifluoromethyl-2,3-dihydro-isoindol-1-one

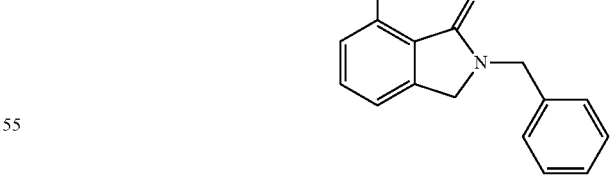

CuI (0.057 g, 0.3 mmol) and potassium fluoride (0.017 g, 0.3 mmol) were added under N$_2$ atmosphere to a stirred solution of 2-benzyl-7-iodo-2,3-dihydro-isoindol-1-one (0.089 g, 0.25 mmol) and chloro-difluoro-acetic acid methyl ester (0.053 mL, 0.5 mmol) in DMF (3 mL). The mixture was heated at 140° C. for 5-8 h. The reaction was cooled and the solvent evaporated. Silica gel column chromatography of the resulting material using 30% ethyl acetate in hexane afforded 2-benzyl-7-trifluoromethyl-2,3-dihydro-isoindol-1-one (0.03 g, 41%). $^1$H NMR (300 MHz, CDCl$_3$): δ (ppm) 4.28 (s, 2H), 4.79 (s, 2H), 7.33 (m, 5H), 7.59 (m, 2H), 7.76 (d, 1H). GC-MS: m/z 291 (M)$^+$, 270 (M−20)$^+$.

Method 5

Step 1: Preparation of Substituted Phthalides

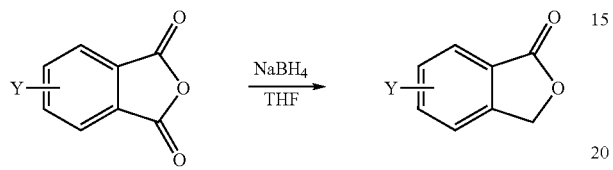

General Procedure

The ice cooled solution of appropriately substituted isobenzofuran-1,3-dione (1 equiv.), in THF was treated with sodium borohydride (0.8-1.1 equiv.) and stirred for 2 h at 0-10° C. The reaction was quenched by addition of water and the mixture was extracted with ether. The organic layer was separated, washed with brine, dried over anhydrous MgSO$_4$, filtered and concentrated. GC-MS of the mixture indicated the formation of 1:1 mixture of two isomers. The product was used without purification.

Step 2: Synthesis of Isoindolone

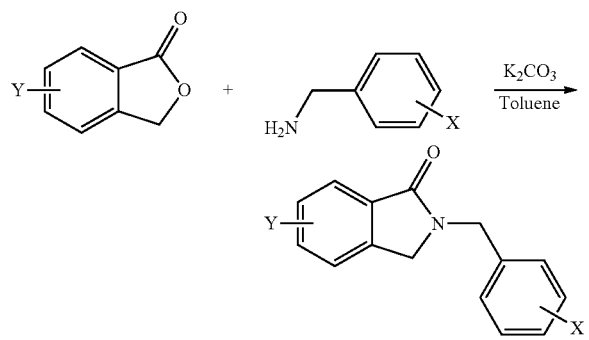

General Procedure

A mixture of the appropriately substituted phthalide (1 equiv.) and the appropriately substituted benzylamine (5-10 equiv.) was stirred at 150° C. for 16 h. The reaction mixture was cooled and poured into a mixture of ice and 10% aqueous HCl. The resulting solution was extracted with ether. The organic layer was removed, dried over anhydrous MgSO$_4$, filtered and concentrated. Silica gel column chromatography (typically 3:1 hexane-ethyl acetate) of the residue afforded the desired products.

The following compounds were synthesized using general method 5 described above.

Example 286

2-(4-Chloro-benzyl)-4-fluoro-2,3-dihydro-isoindol-1-one

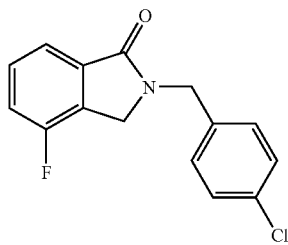

A mixture of the fluoro substituted phthalide (0.228 g, 1.5 mmol) and 4-chloro-benzylamine (2.12 g, 15 mmol) was stirred at 150° C. for 16 h. Workup and silica gel column chromatography (3:1 hexane-ethyl acetate) afforded 2-(4-chloro-benzyl)-4-fluoro-2,3-dihydro-isoindol-1-one (0.040 g, 19%). $^1$H NMR (300 MHz, CDCl$_3$): δ (ppm) 4.31 (s, 2H), 4.76 (s, 2H), 7.18-7.52 (m, 6H), 7.72 (d, 1H).

Example 287

6-Bromo-2-(3-phenyl-propyl)-2,3-dihydro-isoindol-1-one

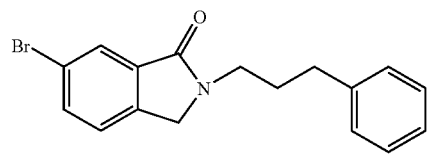

A mixture of the bromine substituted phthalide (0.642 g, 3.0 mmol) and 3-phenyl-propylamine (2.12 g, 15 mmol) was stirred at 150° C. for 16 h. Workup and silica gel column chromatography (3:1 hexane-ethyl acetate) afforded 6-bromo-2-(3-phenyl-propyl)-2,3-dihydro-isoindol-1-one (0.040 g, 16%). $^1$H NMR (300 MHz, CDCl$_3$): δ (ppm) 2.01 (m, 2H), 2.66 (t, 2H), 3.66 (t, 2H), 4.31 (s, 2H), 7.16-7.35 (m, 6H), 7.64 (d, 1H), 7.96 (s, 1H).

Example 288

2-(4-Phenyl-butyl)-2,3-dihydro-isoindol-1-one

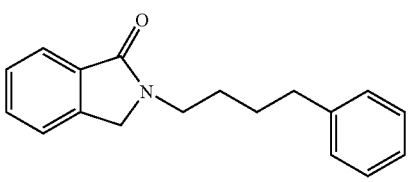

A mixture of phthalide (0.268 g, 2 mmol) and 4-phenyl-butylamine (0.316 mL, 2 mmol) was stirred at 150° C. for 16 h. Workup and silica gel column chromatography (2:1 hexane-ethyl acetate) afforded 2-(4-phenyl-butyl)-2,3-dihydro-isoindol-1-one (0.055 g, 11%). $^1$H NMR (300 MHz, CDCl$_3$): δ (ppm) 1.70 (m, 4H), 2.71 (t, 2H), 3.66 (t, 2H), 4.31 (s, 2H), 7.14-7.56 (m, 8H), 7.82 (s, 1H).

Method 6

Example 289

2-Benzyl-4-methyl-isoindole-1,3-dione

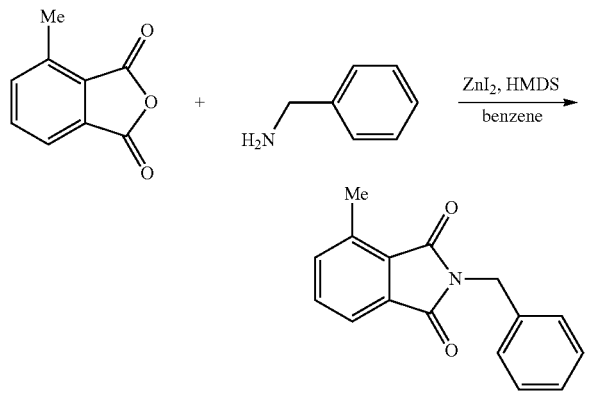

A solution of benzylamine (0.655 mL, 6 mmol) in benzene (5 mL) was added to a stirred solution of 4-methyl-isobenzofuran-1,3-dione (0.81 g, 5 mmol) in dry benzene (20 mL). An exothermic reaction was observed during this addition. The resulting solution was stirred for an additional 1 h. After this time, zinc iodide (1.92 g, 6 mmol) was added in one portion and the resulting mixture heated to 80° C. To this suspension HMDS (1.48 mL, 7 mmol) in benzene (10 mL) was added slowly and stirred at 80° C. for 1 h. The reaction mixture was cooled to room temperature and treated with 0.5 N HCl (15 mL). The organic phase was separated and the aqueous was extracted with ethyl acetate (2×25 mL). The combined organic extracts were washed with aqueous NaHCO$_3$ (10 mL), dried over MgSO$_4$, filtered and concentrated to afford 2-benzyl-4-methyl-isoindole-1,3-dione (1 g, 80%). $^1$H NMR (300 MHz, CDCl$_3$): δ (ppm) 2.69 (s, 3H), 4.83 (s, 2H), 7.26-7.59 (m, 7H), 7.67 (d, 1H).

Example 290

2-Benzyl-7-methyl-2,3-dihydro-isoindol-1-one and 2-Benzyl-4-methyl-2,3-dihydro-isoindol-1-one

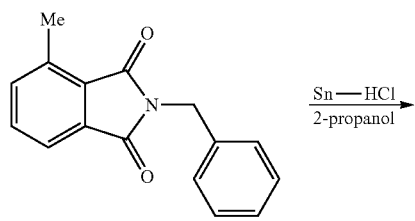

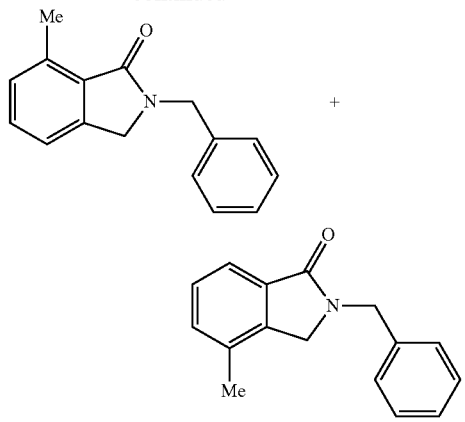

A mixture of 2-benzyl-4-methyl-isoindole-1,3-dione (0.500 g, 2 mmol), tin (0.59 g, 5 mmol) and concentrated HCl (2 mL) in isopropanol (10 mL) was heated at reflux for 2.5 h. After this time, the reaction mixture was cooled to ambient temperature, the solids removed by filtration and the filtrate concentrated. The resulting material was dissolved in dichloromethane (20 mL) and the solution washed with brine (7 mL). The organic solution was separated, dried over anhydrous MgSO$_4$, filtered, and concentrated to afford a mixture of regio isomers. Silica gel column chromatography of this mixture using 25% ethyl acetate in hexane afforded 2-benzyl-7-methyl-2,3-dihydro-isoindol-1-one (0.02 g, 9%); $^1$H NMR (300 MHz, CDCl$_3$): δ ppm) 2.68 (s, 3H), 4.23 (s, 2H), 4.77 (s, 2H), 7.15-7.40 (m, 8H) and GC-MS: m/z 237 (M)$^+$, 160 (M−77)$^+$; and 2-benzyl-4-methyl-2,3-dihydro-isoindol-1-one (0.02 g, 9%); $^1$H NMR (300 MHz, CDCl$_3$): δ (ppm) 2.68 (s, 3H), 4.23 (s, 2H), 4.77 (s, 2H), 7.15-7.40 (m, 8H) and GC-MS: m/z 237 (M)$^+$, 160 (M−77)$^+$.

Method 7

Preparation of Propargyl Amine Substituted Isoindolotie

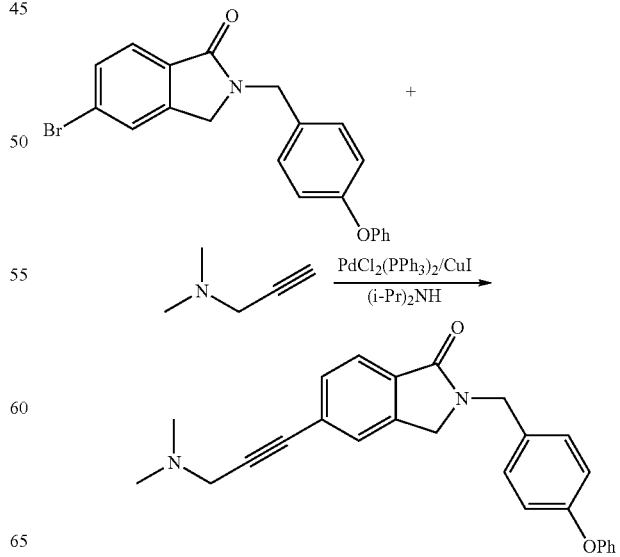

Example 291

5-(3-Dimethylamino-prop-1-ynyl)-2-(4-phenoxy-benzyl)-2,3-dihydro-isoindol-1-one A mixture of 5-bromo-2-(4-phenoxy-benzyl)-2,3-dihydro-isoindol-1-one (0.100 g, 0.25 mmol), PdCl$_2$(PPh$_3$)$_2$ (0.009 g, 0.013 mmol), and CuI (0.0025 g, 0.013 mmol) in diisopropylamine (4 mL) was treated with dimethyl-2-propynyl-amine (0.032 mL, 0.3 mmol). The reaction mixture was stirred at 100° C. for 2 h. After the complete consumption of bromo-isoindolone (monitored using GC-MS), the reaction mixture was cooled to ambient temperature and diluted with ethyl acetate (20 mL). The solids were removed by filtration and the filtrate was concentrated. Silica gel column chromatography of the resulting material using combinations of chloroform-methanol (typically 10:1 CHCl$_3$-MeOH) afforded 5-(3-dimethylamino-prop-1-ynyl)-2-(4-phenoxy-benzyl)-2,3-dihydro-isoindol-1-one (0.061 g, 62%). $^1$H NMR (300 MHz, CDCl$_3$): δ (ppm) 2.36 (s, 6H), 3.47 (s, 2H), 4.25 (s, 2H), 4.76 (s, 2H), 6.94-7.54 (m, 1H), 7.80 (d, 1H). GC-MS: 396 (M)$^+$, 353 (M–43)$^+$.

Hydrogenation of Alkyne

Example 292

5-(3-Dimethylamino-propyl)-2-(4-phenoxy-benzyl)-2,3-dihydro-isoindol-1-one

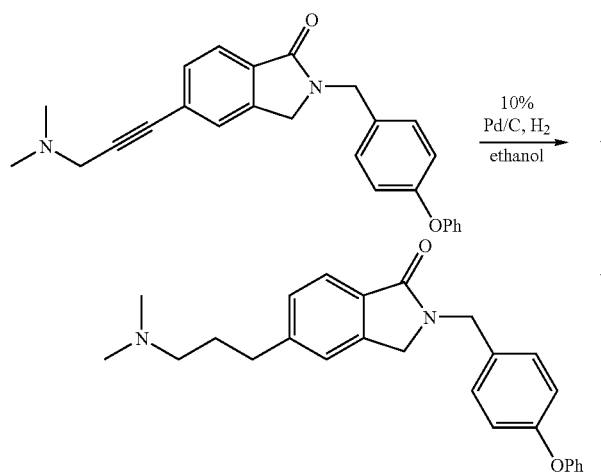

A solution of 5-(3-dimethylamino-prop-1-ynyl)-2-(4-phenoxy-benzyl)-2,3-dihydro-isoindol-1-one (0.055 g, 0.14 mmol) in ethanol (25 mL) was treated with 10% palladium on carbon (15 mg). The mixture was shook vigorously under 45 p.s.i. hydrogen for 3 h. The resulting reaction mixture was filtered through Celite and the filtrate concentrated under reduced pressure. Silica gel column chromatography of the resulting material using 5:1 CHCl$_3$-MeOH afforded 5-(3-dimethylamino-propyl)-2-(4-phenoxy-benzyl)-2,3-dihydro-isoindol-1-one (0.051 g, 83%). $^1$H NMR (300 MHz, CDCl$_3$): δ (ppm) 1.85 (m, 2H), 2.27 (s, 6H), 2.36 (t, 2H), 2.74 (t, 2H), 4.25 (s, 2H), 4.76 (s, 2H), 6.92-7.36 (m, 11H), 7.80 (d, 1H). GC-MS: 400 (M)$^+$

Method 8

Step 1: o-Chlorination of Benzoic Acid

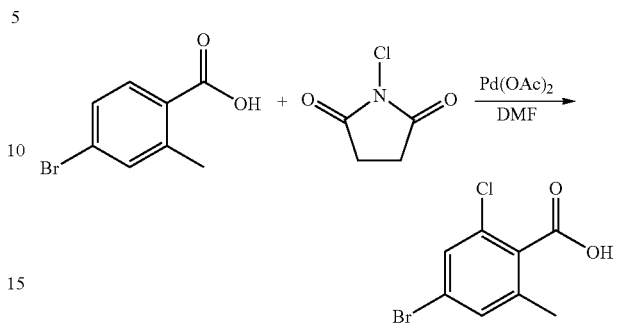

Example 293

4-bromo-2-chloro-6-methyl-benzoic acid

A mixture of 4-bromo-2-methyl-benzoic acid (6.45 g, 30 mmol,), N-chlorosuccinimide (4.67 g, 35 mmol), and palladium (II) acetate (0.675 g, 3 mmol) in dry DMF (35 mL) was heated under a nitrogen atmosphere at 100° C. for 36 h. After this time, the reaction mixture was cooled to ambient temperature and poured into water. The aqueous solution was extracted with ethyl acetate (2×100 mL) and the combined organic extracts washed with aqueous sodium thiosulphate (30 mL) and then brine (30 mL). The remaining organic solution was dried over anhydrous MgSO$_4$, filtered, and concentrated to give 4-bromo-2-chloro-6-methyl-benzoic acid. The product was used without further purification.

Step 2: Esterification of Carboxylic Acids

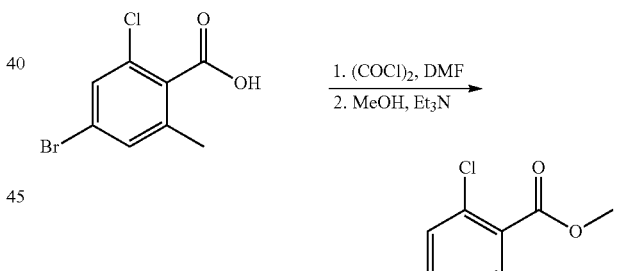

Example 294

4-bromo-2-chloro-6-methyl-benzoic acid methyl ester

A stirred solution of 4-bromo-2-chloro-6-methyl-benzoic acid (7.5 g, 30 mmol) in dichloromethane (100 mL) was treated carefully with a 2 M solution of oxalyl chloride in dichloromethane (25 mL, 50 mmol), followed by the careful addition of dimethylfomamide (several drops). The resulting solution was stirred at ambient temperature for 2 h. The formation of the acid chloride was monitored (after quenching with methanol) using GC-MS. After the completion of reaction, the solvent was evaporated.

The residue was dissolved in methanol (100 mL) and the resulting solution treated with triethylamine (8.8 mL, 60 mmol). The reaction mixture was allowed to stir at ambient temperature for 2 h. The solvent was evaporated and the residue equilibrated between water (20 mL) and dichloromethane (100 mL). The organic solution was removed and the remaining aqueous solution extracted with dichloromethane (2×50 mL). The combined organic extracts were dried over anhydrous MgSO$_4$, filtered and concentrated. Silica gel column chromatography using 10% ethyl acetate in hexane acetate afforded 4-bromo-2-chloro-6-methyl-benzoic acid methyl ester (2.45 g, 31%).
GC-MS: m/z 264 (M+1)$^+$.

Step 3: Bromination

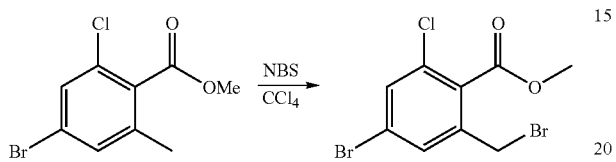

Example 295

4-bromo-2-bromomethyl-6-chloro-benzoic acid methyl ester

A mixture of 4-bromo-2-chloro-6-methyl-benzoic acid methyl ester (2.447 g, 9.27 mmol,), N-bromosuccinimide (1.815 g, 10.2 mmol), and benzoyl peroxide (0.051 g, 0.22 mmol) in carbon tetrachloride (30 mL) was refluxed until most of the starting materials were consumed (as analyzed by GC/MS). The resulting mixture was filtered and the filtrate concentrated to afford 4-bromo-2-bromomethyl-6-chlorobenzoic acid methyl ester. The product was used without further purification.

Step 4: Generation of Isoindolones from Bromo-Esters and Amines

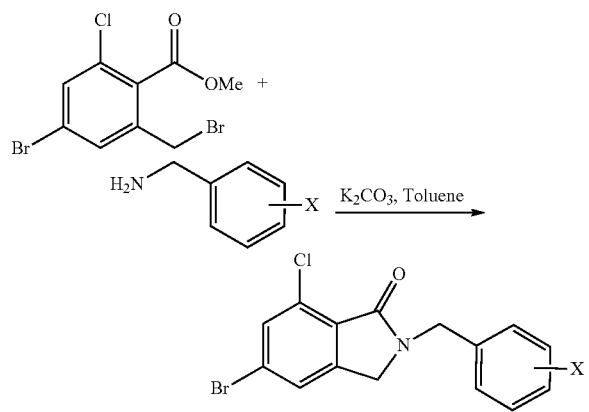

General Procedure

A mixture of the appropriately substituted benzyl amine (1.2 equiv.), the appropriately substituted-2-bromomethylbenzoic acid methyl ester (1.0 equiv.), and K$_2$CO$_3$ (2 equiv.) in toluene was heated with stirring at 100° C. for 2 h. The resulting mixture was filtered and the filtrate was concentrated. Silica gel column chromatography of the resulting material using combinations of hexane and ethyl acetate (typically 30% ethyl acetate in hexane) afforded the desired product.

The following compounds were synthesized using general method 8 described above.

Example 296

5-Bromo-7-chloro-2-(4-phenoxy-benzyl)-2,3-dihydro-isoindol-1-one

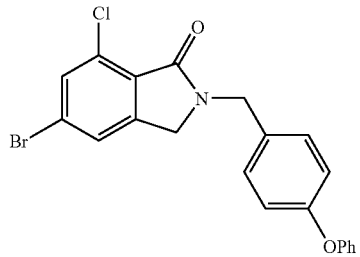

A mixture of 4-bromo-2-bromomethyl-6-chloro-benzoic acid methyl ester (0.492 g, 1.6 mmol), 4-phenoxy-benzylamine (0.256 mL, 2.0 mmol), and K$_2$CO$_3$ (0.414 g, 3 mmol) in toluene (5 mL) was heated with stirring at 100° C. for 2 h. Workup and silica gel column chromatography using 30% ethyl acetate in hexane afforded 5-bromo-7-chloro-2-(4-phenoxy-benzyl)-2,3-dihydro-isoindol-1-one (0.200 g, 32%).
GC-MS: m/z 429 (M)$^+$, 336 (M−93)$^+$.

Example 297

5-Bromo-7-chloro-2-(4-trifluoromethoxy-benzyl)-2,3-dihydro-isoindol-1-one

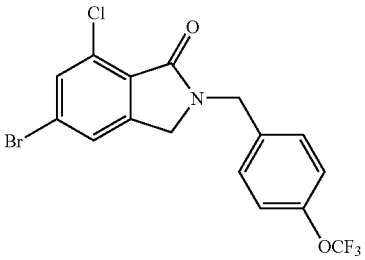

A mixture of 4-bromo-2-bromomethyl-6-chloro-benzoic acid methyl ester (1.54 g, 4.5 mmol), 4-trifluoromethoxybenzylamine (0.916 mL, 6.0 mmol), and K$_2$CO$_3$ (1.24 g, 9.0 mmol) in toluene (10 mL) was heated with stirring at 100° C. for 2 h. Workup and silica gel column chromatography using 30% ethyl acetate in hexane afforded 5-bromo-7-chloro-2-(4- trifluoromethoxy-benzyl)-2,3-dihydro-isoindol-1-one (0.781 g, 41%). GC-MS: m/z 421 (M)⁺, 336 (M−85)⁺.

Example 298

5-Bromo-7-chloro-2-(4-chloro-benzyl)-2,3-dihydro-isoindol-1-one

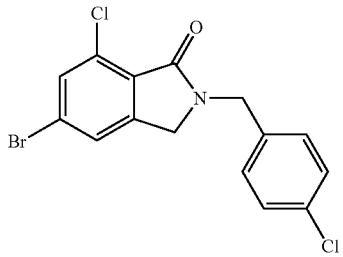

A mixture of 4-bromo-2-bromomethyl-6-chloro-benzoic acid methyl ester (0.900 g, 2.65 mmol), 4-chloro-benzylamine (0.391 mL, 3.2 mmol), and K₂CO₃ (0.69 g, 5.0 mmol) in toluene (10 mL) was heated with stirring at 100° C. for 2 h. Workup and silica gel column chromatography using 30% ethyl acetate in hexane afforded 5-bromo-7-chloro-2-(4-chloro-benzyl)-2,3-dihydro-isoindol-1-one (0.391 g, 41%). GC-MS: m/z 371 (M)⁺, 336 (M−35)⁺.

Example 299

5-Bromo-7-chloro-2-(4-trifluoromethyl-benzyl)-2,3-dihydro-isoindol-1-one

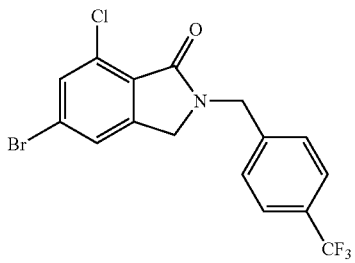

A mixture of 4-bromo-2-bromomethyl-6-chloro-benzoic acid methyl ester (1.4 g, 4.0 mmol), 4-trifluoromethyl-benzylamine (0.770 mL, 5.4 mmol), and K₂CO₃ (1.1 g, 8.0 mmol) in toluene (10 mL) was heated with stirring at 100° C. for 2 h. Workup and silica gel column chromatography using 30% ethyl acetate in hexane afforded 5-bromo-7-chloro-2-(4-trifluoromethyl-benzyl)-2,3-dihydro-isoindol-1-one (0.553 g, 35%). ¹H NMR (300 MHz, CDCl₃): δ (ppm) 4.23 (s, 2H), 4.83 (s, 2H), 7.28-7.64 (m, 6H). GC-MS: m/z 405 (M+1)⁺, 336 (M−68)⁺.

Example UR6

5-Bromo-7-chloro-2-(4-fluoro-benzyl)-2,3-dihydro-isoindol-1-one

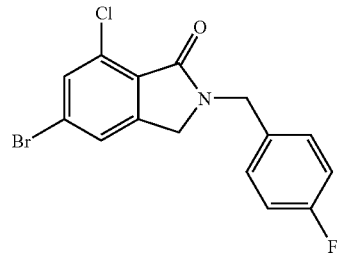

A mixture of 4-bromo-2-bromomethyl-6-chloro-benzoic acid methyl ester (1.06 g, 3.00 mmol), 4-fluoro-benzylamine (0.457 mL, 4.0 mmol), and K₂CO₃ (0.967 g, 7.0 mmol) in toluene (10 mL) was heated with stirring at 100° C. for 2 h. Workup and silica gel column chromatography using 30% ethyl acetate in hexane afforded 5-bromo-7-chloro-2-(4-fluoro-benzyl)-2,3-dihydro-isoindol-1-one (0.21 g, 20%). GC-MS: m/z 355 (M)⁺. ¹H NMR (300 MHz, CDCl₃): δ (ppm) 4.20 (s, 2H), 4.73 (s, 2H), 7.02 (t, 2H), 7.29-7.31 (m, 2H), 7.44 (s, 1H), 7.58 (s, 1H).

Example UR-8

5-Bromo-7-chloro-2-(4-ethyl-benzyl)-2,3-dihydro-isoindol-1-one

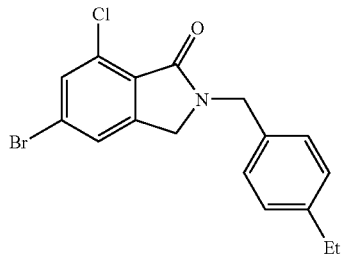

A mixture of 4-bromo-2-bromomethyl-6-chloro-benzoic acid methyl ester (1.06 g, 3.00 mmol), 4-ethyl-benzylamine (0.575 mL, 4.0 mmol), and K₂CO₃ (0.967 g, 7.0 mmol) in toluene (10 mL) was heated with stirring at 100° C. for 2 h. Workup and silica gel column chromatography using 30% ethyl acetate in hexane afforded 5-bromo-7-chloro-2-(4-ethyl-benzyl)-2,3-dihydro-isoindol-1-one (0.442 g, 41%). GC-MS: m/z 364 (M)⁺, 336 (M−28)⁺. ¹H NMR (300 MHz, CDCl₃): δ (ppm) 1.24 (t, 3H), 2.64 (q, 2H) 4.20 (s, 2H), 4.73 (s, 2H), 7.21 (m, 4H), 7.44 (s, 1H), 7.58 (s, 1H).

Example UR-14

5-Bromo-7-chloro-2-ethyl-2,3-dihydro-isoindol-1-one

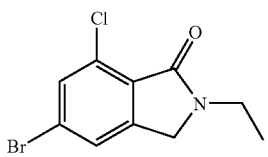

A mixture of 4-bromo-2-bromomethyl-6-chloro-benzoic acid methyl ester (0.684 g, 2.00 mmol), 2M THF solution of ethyl amine (1.3 mL, 2.6 mmol), and K₂CO₃ (0.552 g, 4.0 mmol) in toluene (5 mL) was heated with stirring at 100° C. for 2 h. Workup and silica gel column chromatography using 30% ethyl acetate in hexane afforded 5-bromo-7-chloro-2-ethyl-2,3-dihydro-isoindol-1-one (0.203 g, 37%). GC-MS: m/z 275 (M)⁺, 258 (M−27)⁺. ¹H NMR (300 MHz, CDCl₃): δ (ppm) 1.24 (t, 3H), 3.64 (q, 2H) 4.34 (s, 2H), 7.50 (s, 1H), 7.58 (s, 1H).

Example UR15

5-Bromo-7-chloro-2-(4-methoxy-benzyl)-2,3-dihydro-isoindol-1-one

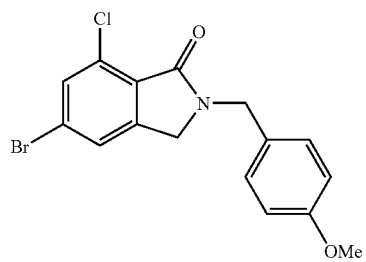

A mixture of 4-bromo-2-bromomethyl-6-chloro-benzoic acid methyl ester (1.06 g, 3.00 mmol), 4-methoxy-benzylamine (0.521 mL, 4.0 mmol), and K₂CO₃ (0.967 g, 7.0 mmol) in toluene (7 mL) was heated with stirring at 100° C. for 2 h. Workup and silica gel column chromatography using 30% ethyl acetate in hexane afforded 5-bromo-7-chloro-2-(4-methoxy-benzyl)-2,3-dihydro-isoindol-1-one (0.365 g, 33%). GC-MS: m/z 367 (M)⁺, 336 (M−31)⁺. ¹H NMR (300 MHz, CDCl₃): δ (ppm) 3.79 (S, 3H), 4.20 (s, 2H), 4.70 (s, 2H), 6.85 (d, 2H) 7.27 (d, 2H), 7.42 (s, 1H), 7.57 (s, 1H).

Example UR-23

5-Bromo-7-chloro-2-cyclopropylmethyl-2,3-dihydro-isoindol-1-one

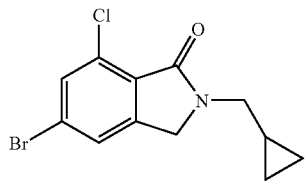

A mixture of 4-bromo-2-bromomethyl-6-chloro-benzoic acid methyl ester (0.684 g, 2.00 mmol), cyclopropyl methyl amine (0.22 mL, 2.6 mmol), and K₂CO₃ (0.552 g, 4.0 mmol) in toluene (5 mL) was heated with stirring at 100° C. for 2 h. Workup and silica gel column chromatography using 30% ethyl acetate in hexane afforded 5-bromo-7-chloro-2-cyclopropyl methyl-2,3-dihydro-isoindol-1-one (0.173 g, 29%). GC-MS: m/z 301 (M)⁺, 286 (M−15)⁺. ¹H NMR (300 MHz, CDCl₃): δ (ppm) 0.34 (m, 2H), 0.59 (m, 2H), 1.05 (m, 1H), 3.47 (d, 2H) 4.44 (s, 2H), 7.50 (s, 1H), 7.58 (s, 1H).

Example UR-63

5-Bromo-7-chloro-2-[1-(4-trifluoromethoxy-phenyl)-ethyl]-2,3-dihydro-isoindol-1-one

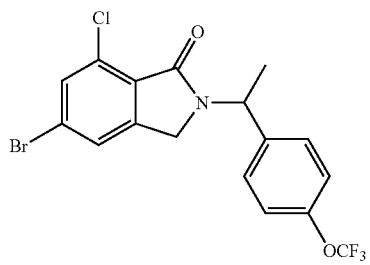

A mixture of 4-bromo-2-bromomethyl-6-chloro-benzoic acid methyl ester (0.409 g, 1.2 mmol), 1-(4-trifluoromethoxy-phenyl)-ethyl-amine (0.288 g, 10.4 mmol), and K₂CO₃ (0.331 g, 2.4 mmol) in toluene (10 mL) was heated with stirring at 100° C. for 2 h. Workup and silica gel column chromatography using 30% ethyl acetate in hexane afforded 5-Bromo-7-chloro-2-[1-(4-trifluoromethoxy-phenyl)-ethyl]-2,3-dihydro-isoindol-1-one (0.202 g, 39%). ¹H NMR (300 MHz, CDCl₃): δ (ppm) 1.67 (d, 3H), 3.96 (d, 1H), 4.20 (d, 1H), 5.77 (q, 1H) 7.21 (d, 2H), 7.41 (m, 3H), 7.58 (s, 1H). GC-MS: m/z 434 (M)⁺, 420 (M−14)⁺.

Step 5: Preparation of Propargyl Amine Substituted Isoindolones

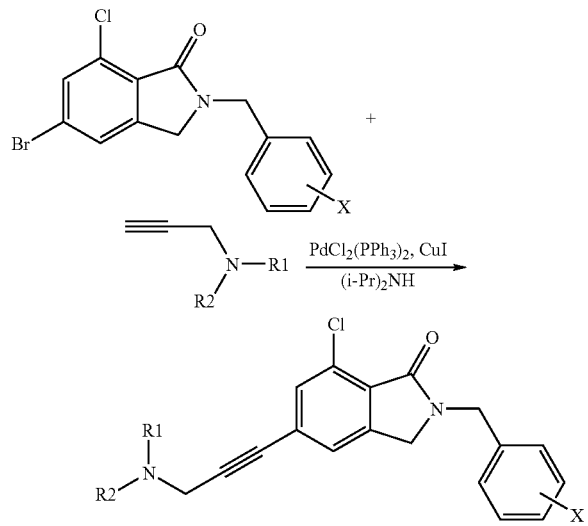

General Procedure

The appropriately substituted propargylamine (1.3 equiv.) was added to a mixture of the appropriately substituted isoindolone (1 equiv.), PdCl$_2$(PPh$_3$)$_2$ (5 mol %), and CuI (5 mol %) in diisopropyl amine. The reaction mixture was stirred at 100° C. for 2 h. After the complete consumption of bromo-isoindolone (monitored using GC-MS) the reaction mixture was cooled to ambient temperature and diluted with ethyl acetate (20 mL). The solids were removed by filtration and the filtrate concentrated. Silica gel column chromatography of the resulting material using combinations of chloroform-methanol (typically 10:1 CHCl$_3$-MeOH) afforded the desired product.

The following compounds were synthesized using general method 8, step 5 described above.

Example 300

7-Chloro-5-(3-dimethylamino-prop-1-ynyl)-2-(4-phenoxy-benzyl)-2,3-dihydro-isoindol-1-one

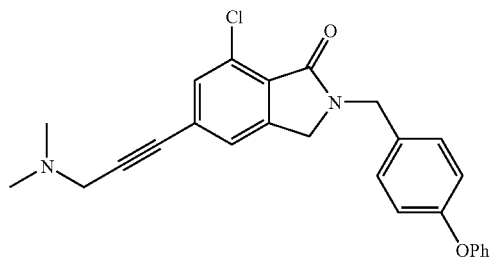

A mixture of dimethyl-prop-2-ynyl-amine (0.036 mL, 0.32 mmol), 5-bromo-7-chloro-2-(4-phenoxy-benzyl)-2,3-dihydro-isoindol-1-one (0.120 g, 0.28 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-chloro-5-(3-dimethylamino-prop-1-ynyl)-2-(4-phenoxy-benzyl)-2,3-dihydro-isoindol-1-one (0.095 g, 79%). $^1$H NMR (300 MHz, CDCl$_3$): δ (ppm) 2.36 (s, 6H), 3.46 (s, 2H), 4.23 (s, 2H), 4.76 (s, 2H), 6.93-7.38 (m, 10H), 7.43 (s, 1H).

Example 301

7-Chloro-2-(4-phenoxy-benzyl)-5-(3-pyrrolidin-1-yl-prop-1-ynyl)-2,3-dihydro-isoindol-1-one

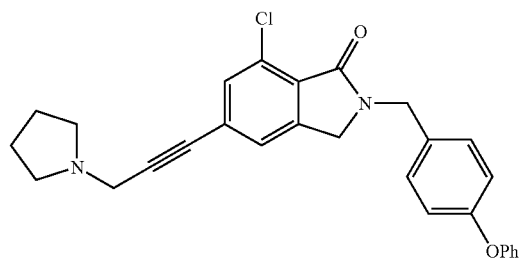

A mixture of 1-prop-2-ynyl-pyrrolidine (0.024 mL, 0.22 mmol), 5-bromo-7-chloro-2-(4-phenoxy-benzyl)-2,3-dihydro-isoindol-1-one (0.086 g, 0.20 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-chloro-2-(4-phenoxy-benzyl)-5-(3-pyrolidin-1-yl-prop-1-ynyl)-2,3-dihydro-isoindol-1-one (0.061 g, 66%). $^1$H NMR (300 MHz, CDCl$_3$): δ (ppm) 1.83 (m, 4H), 2.65 (m, 4H), 3.64 (s, 2H), 4.23 (s, 2H), 4.76 (s, 2H), 6.93-7.38 (m, 10H), 7.43 (s, 1H).

Example 302

7-Chloro-5-[3-(4-methyl-piperazin-1-yl)-prop-1-ynyl]-2-(4-phenoxy-benzyl)-2,3-dihydro-isoindol-1-one

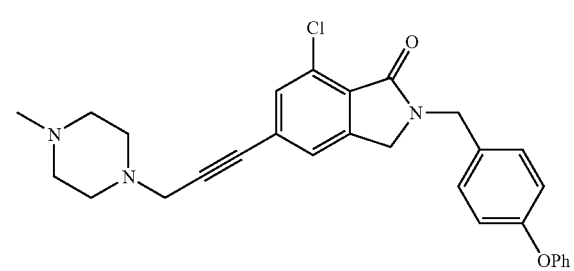

A mixture of 1-methyl-4-prop-2-ynyl-piperazine (0.046 mL, 0.3 mmol), 5-bromo-7-chloro-2-(4-phenoxy-benzyl)-2,3-dihydro-isoindol-1-one (0.100 g, 0.23 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-chloro-5-[3-(4-methyl-piperazin-1-yl)-prop-1-ynyl)-2-(4-phenoxy-benzyl)-2,3-dihydro-isoindol-1-one (0.075 g, 71%).

Example 303

7-Chloro-5-(3-dimethylamino-prop-1-ynyl)-2-(4-trifluoromethoxy-benzyl)-2,3-dihydro-isoindol-1-one

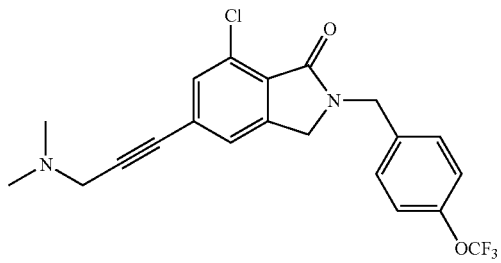

A mixture of dimethyl-prop-2-ynyl-amine (0.036 mL, 0.32 mmol), 5-bromo-7-chloro-2-(4-trifluoromethoxy-benzyl)-2,3-dihydro-isoindol-1-one (0.120 g, 0.28 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-chloro-5-(3-dimethylamino-prop-1-ynyl)-2-(4-trifluoromethoxy-benzyl)-2,3-dihydro-isoindol-1-one (0.122 g, 79%). $^1$H NMR (300 MHz, CDCl$_3$): δ (ppm) 2.36 (s, 6H), 3.44 (s, 2H), 4.21 (s, 2H), 4.77 (s, 2H), 7.14-7.36 (m, 5H), 7.43 (s, 1H).

Example 304

7-Chloro-2-(4-chloro-benzyl)-5-[3-(4-methyl-piperazin-1-yl)-prop-1-ynyl]-2,3-dihydro-isoindol-1-one

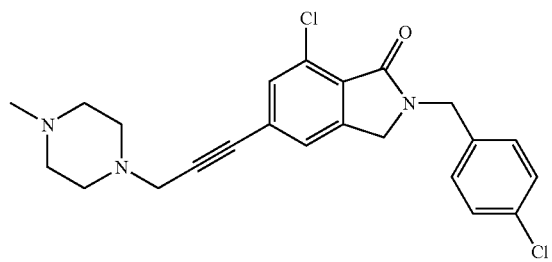

A mixture of 1-methyl-4-prop-2-ynyl-piperazine (0.061 mL, 0.4 mmol), 5-bromo-7-chloro-2-(4-chloro-benzyl)-2,3-dihydro-isoindol-1-one (0.11 g, 0.3 mmol), PdCl$_2$(PPh$_3$)$_2$ (0.011 g, 0.015 mmol), and CuI (0.0028 g, 0.015 mmol) in diisopropylamine (4 mL) was stirred at 100° C. for 2 h. Workup and silica gel column chromatography using 10:1 CHCl$_3$-MeOH afforded 7-chloro-2-(4-chloro-benzyl)-5-[3-(4-methyl-piperazin-1-yl)-prop-1-ynyl]-2,3-dihydro-isoindol-1-one (0.090 g, 70%). $^1$H NMR (300 MHz, CDCl$_3$): δ (ppm) 2.31 (s, 3H), 2.32-2.74 (m, 8H), 3.54 (s, 2H), 4.18 (s, 2H), 4.74 (s, 2H), 7.22-7.36 (m, 5H), 7.44 (s, 1H).

Example 305

7-Chloro-5-[3-(4-methyl-piperazin-1-yl)-prop-1-ynyl]-2-(4-trifluoromethyl-benzyl)-2,3-dihydro-isoindol-1-one

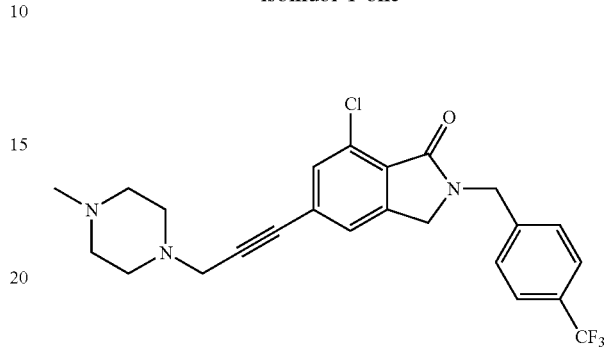

A mixture of 1-methyl-4-prop-2-ynyl-piperazine (0.122 mL, 0.79 mmol), 5-bromo-7-chloro-2-(4-trifluoromethyl-benzyl)-2,3-dihydro-isoindol-1-one (0.240 g, 0.6 mmol), PdCl$_2$(PPh$_3$)$_2$ (0.023 g, 0.03 mmol), and CuI (0.006 g, 0.03 mmol) in diisopropyl amine (4 mL) was stirred at 100° C. for 2 h. Workup and silica gel column chromatography using 10:1 CHCl$_3$-MeOH afforded 7-chloro-5-[3-(4-methyl-piperazin-1-yl)-prop-1 ynyl)-2-(4-trifluoromethyl-benzyl)-2,3-dihydro-isoindol-1-one (0.250 g, 90%). $^1$H NMR (300 MHz, CDCl$_3$): δ (ppm) 2.34 (s, 3H), 2.32-2.54 (m, 8H), 3.57 (s, 2H), 4.20 (s, 2H), 4.81 (s, 2H), 7.34 (s, 1H), 7.41-7.63 (m, 5H).

Step 6: Hydrogenation of Alkyne

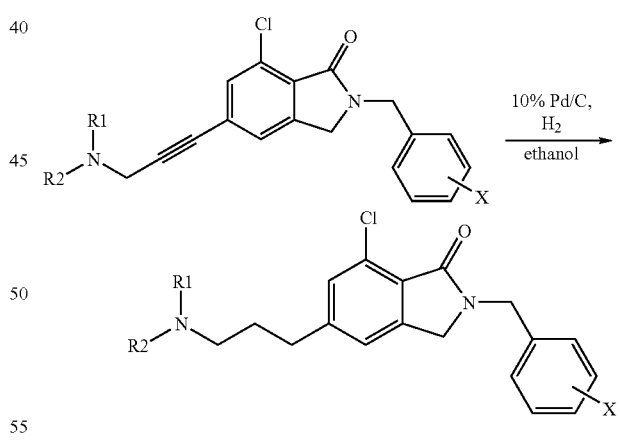

General Procedure

A solution of the propargyl-amine substituted isoindolone in ethanol was treated with 10% palladium on carbon (10 mg-50 mg) and shook vigorously under 45 p.s.i. hydrogen for 2-3 h. The resulting reaction mixture was filtered through Celite and the filtrate concentrated under reduced pressure. Silica gel column chromatography of the resulting material using combinations of chloroform-methanol (typically 5:1) CHCl$_3$-MeOH) afforded the desired product.

The following compounds were synthesized using general method 8, step 6 described above.

Example 306

7-Chloro-5-(3-dimethylamino-propyl)-2-(4-phenoxy-benzyl)-2,3-dihydro-isoindol-1-one

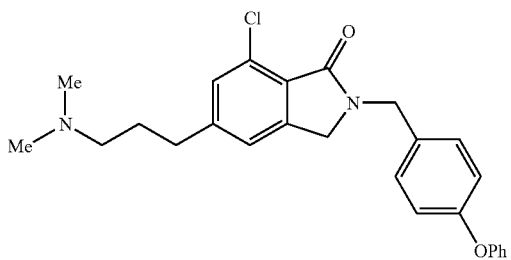

A mixture of 7-chloro-5-(3-dimethylamino-prop-1-ynyl)-2-(4-phenoxy-benzyl)-2,3-dihydro-isoindol-1-one (0.047 g, 0.11 mmol) and 10% palladium-carbon (0.015 g) in ethanol (25 mL) was reduced under 45 p.s.i. hydrogen. Workup and silica gel column chromatography using 5:1 $CHCl_3$-MeOH afforded 7-chloro-5-(3-dimethylamino-propyl)-2-(4-phenoxy-benzyl)-2,3-dihydro-isoindol-1-one (0.020 g, 42%). $^1$H NMR (300 MHz, $CDCl_3$): δ (ppm) 1.78 (m, 2H), 2.2 (m, 6H), 2.31 (t, 2H), 2.66 (t, 2H), 4.22 (s, 2H), 4.74 (s, 2H), 6.88-7.38 (m, 11H).

Example 307

7-Chloro-2-(4-phenoxy-benzyl)-5-(3-pyrrolidin-1-yl-propyl)-2,3-dihydro-isoindol-1-one

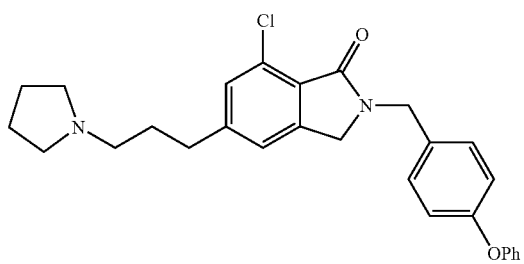

A mixture of 7-chloro-2-(4-phenoxy-benzyl)-5-(3-pyrrolidin-1-yl-prop-1-ynyl)-2,3-dihydro-isoindol-1-one (0.049 g, 0.11 mmol) and 10% palladium-carbon (0.015 g) in ethanol (25 mL) was reduced under 45 p.s.i. hydrogen. Workup and silica gel column chromatography using 5:1 $CHCl_3$-MeOH afforded 7-chloro-2-(4-phenoxy-benzyl)-5-(3-pyrrolidin-1-yl-propyl)-2,3-dihydro-isoindol-1-one (0.025 g, 50%). $^1$H NMR (300 MHz, $CDCl_3$): δ (ppm) 1.80 (m, 6H), 2.5 (m, 6H), 2.68 (t, 2H), 4.22 (s, 2H), 4.74 (s, 2H), 6.88-7.38 (m, 11H).

Example 308

7-Chloro-5-[3-(4-methyl-piperazin-1-yl)-propyl]-2-(4-phenoxy-benzyl)-2,3-dihydro-isoindol-1-one

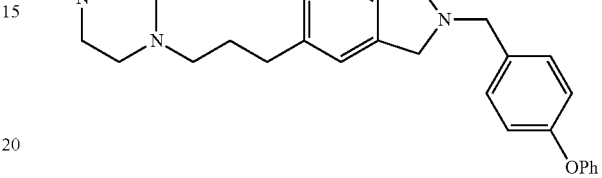

A mixture of 7-chloro-5-[3-(4-methyl-piperazin-1-yl)-prop-1-ynyl)-2-(4-phenoxy-benzyl)-2,3-dihydro-isoindol-1-one (0.073 g, 0.15 mmol) and 10% palladium-carbon (0.015 g) in ethanol (25 mL) was reduced under 45 p.s.i hydrogen. Workup and silica gel column chromatography using 5:1 $CHCl_3$-MeOH afforded 7-chloro-5-[3-(4-methyl-piperazin-1-yl)-propyl]-2-(4-phenoxy-benzyl)-2,3-dihydro-isoindol-1-one (0.035 g, 50%). $^1$H NMR (300 MHz, $CDCl_3$): δ (ppm) 1.79 (m, 2H), 2.22-2.60 (m, 13H), 2.66 (t, 2H), 4.22 (s, 2H), 4.74 (s, 2H), 6.86-7.38 (m, 11H).

Example 309

7-Chloro-5-(3-dimethylamino-propyl)-2-(4-trifluoromethoxy-benzyl)-2,3-dihydro-isoindol-1-one

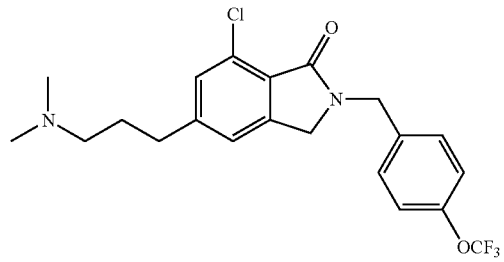

A mixture of 7-chloro-5-(3-dimethylamino-prop-1-ynyl)-2-(4-trifluoromethoxy-benzyl)-2,3-dihydro-isoindol-1-one (0.102 g, 0.24 mmol) and 10% palladium-carbon (0.015 g) in ethanol (25 mL) was reduced under 45 p.s.i. hydrogen. Workup and silica gel column chromatography using 5:1 $CHCl_3$-MeOH afforded 7-chloro-5-(3-dimethylamino-propyl)-2-(4-trifluoromethoxy-benzyl)-2,3-dihydro-isoindol-1-one (0.050 g, 50%). $^1$H NMR (300 MHz, $CDCl_3$): δ (ppm)

1.84 (m, 2H), 2.4 (s, 6H), 2.48 (t, 2H), 2.72 (t, 2H), 4.22 (s, 2H), 4.76 (s, 2H), 7.15-7.39 (m, 6H).

Example 310

7-Chloro-5-[3-(4-methyl-piperazin-1-yl)-propyl]-2-(4-trifluoromethoxy-benzyl)-2,3-dihydro-isoindol-1-one

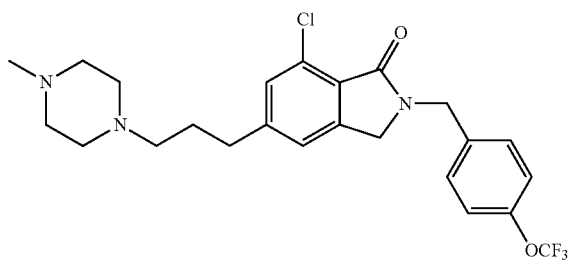

A mixture of 7-chloro-5-[3-(4-methyl-piperazin-1-yl)-prop-1-ynyl)-2-(4-trifluoromethoxy-benzyl)-2,3-dihydro-isoindol-1-one (0.057 g, 0.12 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-chloro-5-[3-(4-methyl-piperazin-1-yl)-propyl]-2-(4-trifluoromethoxy-benzyl)-2,3-dihydro-isoindol-1-one (0.036 g, 63%). 1H NMR (300 MHz, CDCl$_3$): δ (ppm) 1.79 (m, 2H), 2.22-2.60 (m, 13H), 2.66 (t, 2H), 4.20 (s, 2H), 4.76 (s, 2H), 7.08-7.38 (m, 6H).

Example 311

7-Chloro-2-(4-chloro-benzyl)-5-[3-(4-methyl-piperazin-1-yl)-propyl]-2,3-dihydro-isoindol-1-one

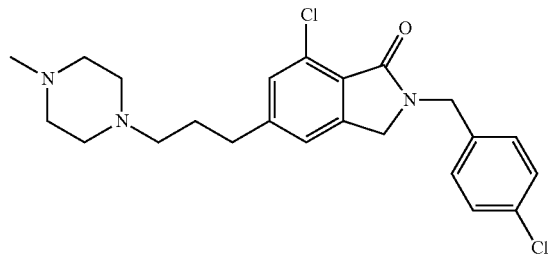

A mixture of 7-chloro-2-(4-chloro-benzyl)-5-[3-(4-methyl-piperazin-1-yl)-prop-1-ynyl)-2,3-dihydro-isoindol-1-one (0.078 g, 0.18 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-chloro-2-(4-chloro-benzyl)-5-[3-(4-methyl-piperazin-1-yl)-propyl]-2,3-dihydro-isoindol-1-one (0.065 g, 83%). $^1$H NMR (300 MHz, CDCl$_3$): δ (ppm) 1.79 (m, 2H), 2.31-2.72 (m, 15H), 4.18 (s, 2H), 4.74 (s, 2H), 7.08 (s, 1H), 7.28 (m, 5H).

Example 312

7-Chloro-5-[3-(4-methyl-piperazin-1-yl)-propyl]-2-(4-trifluoromethyl-benzyl)-2,3-dihydro-isoindol-1-one

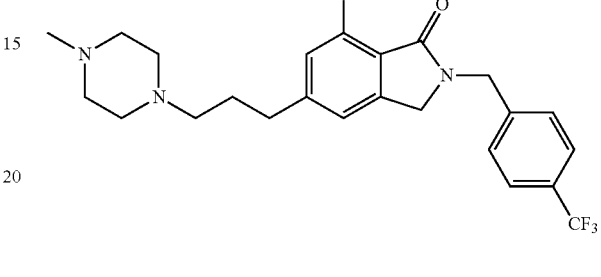

A mixture of 7-chloro-5-[3-(4-methyl-piperazin-1-yl)-prop-1-ynyl)-2-(4-trifluoromethyl-benzyl)-2,3-dihydro-isoindol-1-one (0.125 g, 0.27 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-chloro-5-[3-(4-methyl-piperazin-1-yl)-propyl]-2-(4-trifluoromethyl-benzyl)-2,3-dihydro-isoindol-1-one (0.034 g, 30%). $^1$H NMR (300 MHz, CDCl$_3$): 5 (ppm) 1.79 (m, 2H), 2.23-2.60 (m, 13H), 2.64 (t, 2H), 4.18 (s, 2H), 4.80 (s, 2H), 7.08 (s, 1H), 7.24 (s, 1H), 7.42 (d, 2H), 7.59 (d, 2H).

Method 9

Step 1: o-Iodination of Benzoic Acid

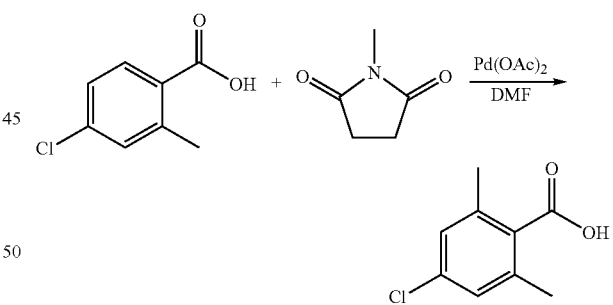

Example 313

4-chloro-2-iodo-6-methyl-benzoic acid

A mixture of 4-chloro-2-methyl-benzoic acid (3.40 g, 20 mmol,), N-iodosuccinamide (4.4 g, 22 mmol) and palladium (II) acetate (0.448 g, 2 mmol) in dry DMF (35 mL) was heated at 100° C. for 36 h under nitrogen atmosphere. After this time, the reaction mixture was cooled to ambient temperature and poured into water. The aqueous solution was extracted with ethyl acetate (2×100 mL) and the combined organic extracts were washed with aqueous sodium thiosulphate (30 mL) and brine (30 mL). The organic solution was dried over anhydrous

341

MgSO₄, filtered and concentrated to afford 4-chloro-2-iodo-6-methyl-benzoic acid. The product was used without further purification.

Step 2: Esterification

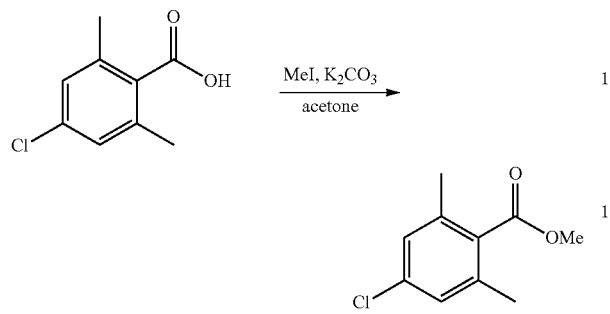

Example 314

4-chloro-2-iodo-6-methyl-benzoic acid methyl ester

A solution of 4-chloro-2-iodo-6-methyl-benzoic acid (5.9 g, 20.0 mmol) in acetone (50 mL) was treated with anhydrous K₂CO₃ (4.14 g, 30 mmol) followed by methyl iodide (1.5 g, 24 mmol). The reaction mixture was stirred at 70° C. for 2 h. GC-MS and TLC indicated that the reaction was completed. The solids were removed by filtration and the filtrate was evaporated under reduced pressure. Silica gel column chromatography of the resulting material using 10% ethyl acetate in hexanes afforded 4-chloro-2-iodo-6-methyl-benzoic acid methyl ester (2.91 g, 47%). GC-MS: m/z 310 (M)⁺, 279 (M−31)⁺.

Bromination

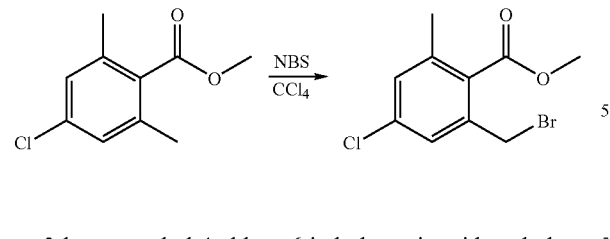

2-bromomethyl-4-chloro-6-iodo-benzoic acid methyl ester

A mixture of 4-chloro-2-iodo-6-methyl-benzoic acid methyl ester (4.19 g, 13.5 mmol), N-bromosuccinamide (2.67 g, 15.0 mmol), and benzoyl peroxide (0.072 g, 0.290 mmol) in carbon tetrachloride (50 mL) was heated at reflux until majority of ester was consumed (as analyzed by GC/MS). The resulting mixture was filtered and the filtrate concentrated to afforded 2-bromomethyl-4-chloro-6-trifluoromethyl-benzoic acid methyl ester. The material was used without further purification.

342

Generation of Isoindolones from Bromo-Esters and Amines General Procedure

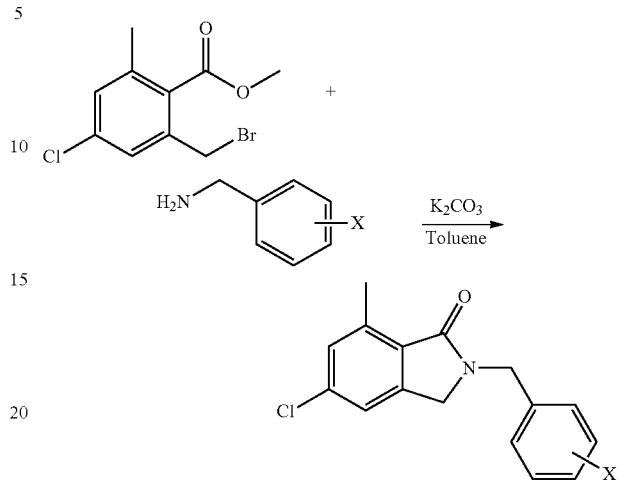

A mixture of the appropriately substituted benzyl amine (1.2 equiv.), 4-chloro-2-bromomethyl-6-trifluoromethyl-benzoic acid methyl ester (1.0 equiv.), and K₂CO₃ (2 equiv.) in toluene was heated with stirring at 100° C. for 2 h. The resulting mixture was filtered and concentrated. Silica gel column chromatography using combinations of hexane and ethyl acetate (typically 30% ethyl acetate in hexane) afforded the desired product.

The following compounds were synthesized using the general method described above.

Example UR-11

5-chloro-7-iodo-2-(4-trifluoromethoxy-benzyl)-2,3-dihydro-isoindol-1-one

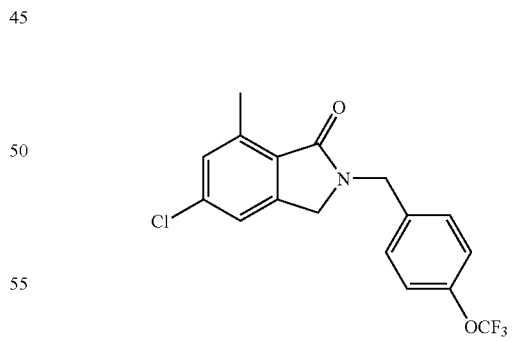

A mixture of 4-chloro-2-bromomethyl-6-iodo-benzoic acid methyl ester (0.78 g, 2.0 mmol), 4-trifluoromethoxy-benzylamine (0.458 mL, 3.0 mmol), and K₂CO₃ (0.552 g, 4.0 mmol) in toluene (5 mL) was heated with stirring at 100° C. for 2 h. Workup and silica gel column chromatography of the product using 30% ethyl acetate in hexane afforded 5-chloro-7-iodo-2-(4-trifluoromethoxy-benzyl)-2,3-dihydro-isoindol-1-one (0.356 g, 38%). ¹H NMR (300 MHz, CDCl₃): δ

(ppm) 4.17 (s, 2H), 4.78 (s, 2H) 7.20 (d, 2H), 7.37 (t, 3H), 7.93 (s, 1H). GC-MS: m/z 467 (M)⁺, 382 (M−85)⁺.

3H), 4.12 (s, 2H), 4.71 (s, 2H) 6.86 (d, 2H), 7.25 (m, 2H), 7.36 (s, 1H), 7.90 (s, 1H). GC-MS: m/z 413 (M)⁺, 382 (M−31)⁺.

Example UR-19

5-chloro-7-iodo-2-(4-fluoro-benzyl)-2,3-dihydro-isoindol-1-one

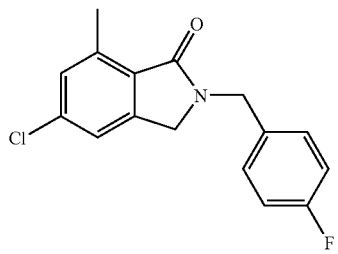

A mixture of 4-chloro-2-bromomethyl-6-iodo-benzoic acid methyl ester (0.389 g, 1.0 mmol), 4-fluoro-benzylamine (0.137 mL, 1.2 mmol), and K₂CO₃ (0.276 g, 2.0 mmol) in toluene (5 mL) was heated with stirring at 100° C. for 2 h. Workup and silica gel column chromatography of the product using 30% ethyl acetate in hexane afforded 5-chloro-7-iodo-2-(4-fluoro-benzyl)-2,3-dihydro-isoindol-1-one (0.149 g, 37%). ¹H NMR (300 MHz, CDCl₃): δ (ppm) 4.15 (s, 2H), 4.75 (s, 2H) 7.02 (t, 2H), 7.27 (t, 2H), 7.36 (s, 1H), 7.92 (s, 1H). GC-MS: m/z 401 (M)⁺.

Example UR-25

5-chloro-7-iodo-2-(4-chloro-benzyl)-2,3-dihydro-isoindol-1-one

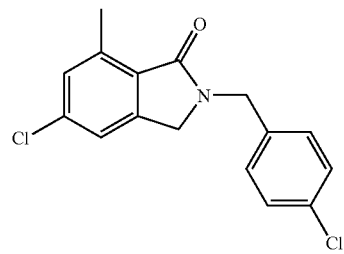

A mixture of 4-chloro-2-bromomethyl-6-iodo-benzoic acid methyl ester (0.389 g, 1.0 mmol), 4-chloro-benzylamine (0.158 mL, 1.2 mmol), and K₂CO₃ (0.276 g, 2.0 mmol) in toluene (5 mL) was heated with stirring at 100° C. for 2 h. Workup and silica gel column chromatography of the product using 30% ethyl acetate in hexane afforded 5-chloro-7-iodo-2-(4-chloro-benzyl)-2,3-dihydro-isoindol-1-one (0.115 g, 28%). ¹H NMR (300 MHz, CDCl₃): δ (ppm) 4.15 (s, 2H), 4.74 (s, 2H) 7.22-7.38 (m, 5H), 7.92 (s, 1H). GC-MS: m/z 417 (M−1)⁺, 382 (M−36)⁺.

Example UR-24

5-chloro-7-iodo-2-(4-methoxy-benzyl)-2,3-dihydro-isoindol-1-one

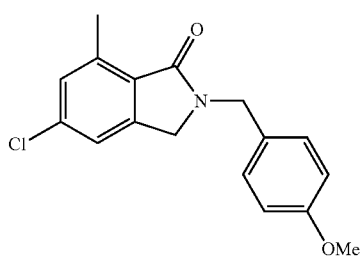

A mixture of 4-chloro-2-bromomethyl-6-iodo-benzoic acid methyl ester (0.389 g, 1.0 mmol), 4-methoxy-benzylamine (0.169 mL, 1.2 mmol), and K₂CO₃ (0.276 g, 2.0 mmol) in toluene (5 mL) was heated with stirring at 100° C. for 2 h. Workup and silica gel column chromatography of the product using 30% ethyl acetate in hexane afforded 5-chloro-7-iodo-2-(4-methoxy-benzyl)-2,3-dihydro-isoindol-1-one (0.111 g, 27%). ¹H NMR (300 MHz, CDCl₃): δ (ppm) 3.79 (s, Example UR-29

2-Cyclopropyl methyl-5-chloro-7-iodo-2,3-dihydro-isoindol-1-one

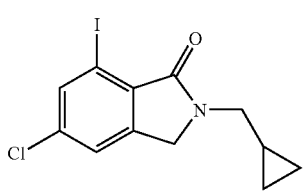

A mixture of cyclopropyl-methylamine (1.3 mmol, 0.111 mL), 2-bromomethyl-4-chloro-6-iodo-benzoic acid methyl ester (0.389 g, 1.0 mmol), and K₂CO₃ (0.277 g, 2 mmol) in toluene (4 mL) was heated with stirring at 100° C. for 2 h. The resulting mixture was filtered and concentrated. Silica gel column chromatography using 30% ethyl acetate in hexane afforded 2-Cyclopropyl methyl-5-chloro-7-iodo-2,3-dihydro-isoindol-1-one (0.123 g, 35%). ¹H NMR (300 MHz, CDCl$_3$): δ (ppm) 0.32 (m, 2H), 0.60 (m, 2H), 1.04 (m, 1H), 3.46 (d, 2H), 4.36 (s, 2H), 7.43 (s, 1H), 7.90 (s, 1H). GC-MS: m/z 347 (M)$^+$ 0.332 (M−15)$^+$

Example 315

Synthesis of 7-trifluoromethyl isoindolone

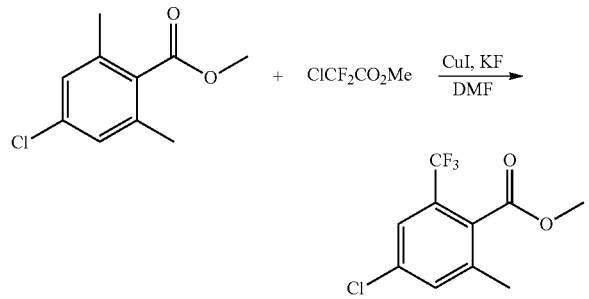

Example 316

4-chloro-2-trifluoromethyl-6-methyl-benzoic acid methyl ester

CuI (1.9 g, 10 mmol) and potassium fluoride (0.58 g, 10 mmol) were added under an N$_2$ atmosphere to a solution of 4-chloro-2-iodo-6-methyl-benzoic acid methyl ester (2.9 g, 9.4 mmol) and chloro-difluoro-acetic acid methyl ester (1.2 mL, 11 mmol) in DMF (25 mL). The mixture was stirred at 140° C. for 18 h. The reaction was cooled and the solvent evaporated. Silica gel column chromatography using 10% ethyl acetate in hexane afforded 4-chloro-2-trifluoromethyl-6-methyl-benzoic acid methyl ester (1.6 g, 67%). GC-MS: m/z 252 (M−1)$^+$, 221 (M−31)$^+$.

Bromination

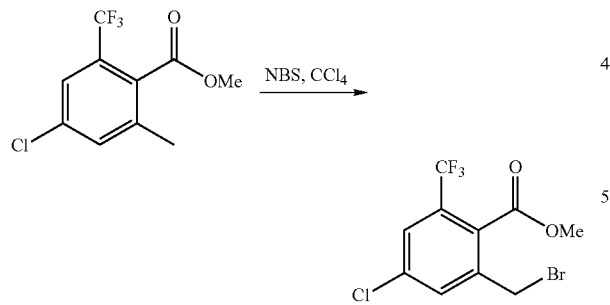

Example 317

2-bromomethyl-4-chloro-6-trifluoromethyl-benzoic acid methyl ester

A mixture of 4-chloro-2-trifluoromethyl-6-methyl-benzoic acid methyl ester (1.6 g, 6.3 mmol), N-bromosuccinamide (1.23 g, 6.93 mmol), and benzoyl peroxide (0.050 g, 0.20 mmol) in carbon tetrachloride (50 mL) was heated at reflux until majority of ester was consumed (as analyzed by GC/MS). The resulting mixture was filtered and the filtrate concentrated to afforded 2-bromomethyl-4-chloro-6-trifluoromethyl-benzoic acid methyl ester. The material was used without further purification.

Generation of Isoindolones from Bromo-Esters and Amines

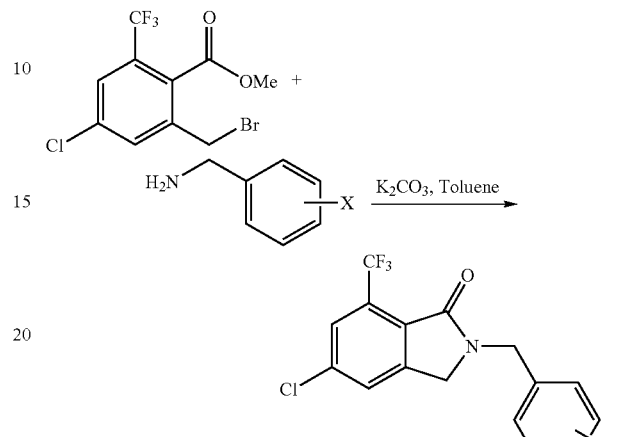

General Procedure

A mixture of the appropriately substituted benzyl amine (1.2 equiv.), 4-chloro-2-bromomethyl-6-trifluoromethyl-benzoic acid methyl ester (1.0 equiv.), and K$_2$CO$_3$ (2 equiv.) in toluene was heated with stirring at 100° C. for 2 h. The resulting mixture was filtered and concentrated. Silica gel column chromatography using combinations of hexane and ethyl acetate (typically 30% ethyl acetate in hexane) afforded the desired product.

The following compounds were synthesized using general method 9 described above.

Example 318

5-chloro-2-(4-trifluoromethoxy-benzyl)-7-trifluoromethyl-2,3-dihydro-isoindol-1-one

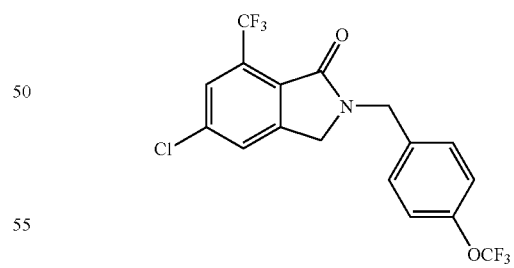

A mixture of 4-chloro-2-bromomethyl-6-trifluoromethyl-benzoic acid methyl ester (1.33 g, 4.0 mmol), 4-trifluoromethoxy-benzylamine (0.610 mL, 4.1 mmol), and K$_2$CO$_3$ (0.691 g, 5.0 mmol) in toluene (10 mL) was heated with stirring at 100° C. for 2 h. Workup and silica gel column chromatography of the product using 30% ethyl acetate in hexane afforded 5-chloro-2-(4-trifluoromethoxy-benzyl)-7-trifluoromethyl-2,3-dihydro-isoindol-1-one (0.770 g, 47%). $^1$H NMR (300 MHz, CDCl$_3$): δ (ppm) 4.34 (s, 2H), 4.80 (s, 2H) 7.20 (d, 2H), 7.36 (d, 2H), 7.59 (s, 1H), 7.78 (s, 1H). GC-MS: m/z 409 (M)+, 388 (M−21)+.

3H), 2.65 (q, 2H), 4.27 (s, 2H), 4.78 (s, 2H) 7.20-7.56 (m, 6H). GC-MS: m/z 337 (M)+, 318 (M−19)+.

Example 319

5-chloro-2-(4-ethyl-benzyl)-7-trifluoromethyl-2,3-dihydro-isoindol-1-one

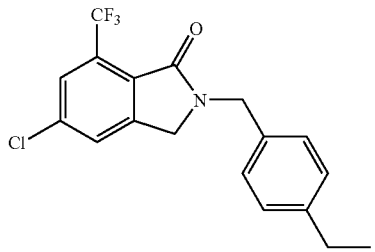

A mixture of 4-chloro-2-bromomethyl-6-trifluoromethyl-benzoic acid methyl ester (0.995 g, 3.0 mmol), 4-ethyl-benzylamine (0.520 mL, 3.6 mmol), and K$_2$CO$_3$ (0.621 g, 4.5 mmol) in toluene (10 mL) was heated with stirring at 100° C. for 2 h. Workup and silica gel column chromatography using 30% ethyl acetate in hexane afforded 5-chloro-2-(4-ethyl-benzyl)-7-trifluoromethyl-2,3-dihydro-isoindol-1-one (0.30 g, 28%). $^1$H NMR (300 MHz, CDCl$_3$): δ (ppm) 1.24 (t, 3H), 2.63 (q, 2H), 4.27 (s, 2H), 4.76 (s, 2H) 7.20 (m, 4H), 7.59 (s, 1H), 7.78 (s, 1H). GC-MS: m/z 353 (M)+, 338 (M−15)+, 324 (M−29)+.

Example UR-53

5-fluoro-2-(4-chloro-benzyl)-7-trifluoromethyl-2,3-dihydro-isoindol-1-one

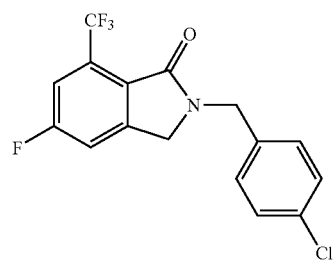

A mixture of 4-fluoro-2-bromomethyl-6-trifluoromethyl-benzoic acid methyl ester (0.100 g, 0.32 mmol), 4-chloro-benzylamine (0.051 mL, 0.42 mmol), and K$_2$CO$_3$ (0.088 g, 0.64 mmol) in toluene (4 mL) was heated with stirring at 100° C. for 2 h. Workup and silica gel column chromatography using 30% ethyl acetate in hexane afforded 5-fluoro-2-(4-chloro-benzyl)-7-trifluoromethyl-2,3-dihydro-isoindol-1-one (0.048 g, 44%). $^1$H NMR (300 MHz, CDCl$_3$): δ (ppm) 4.28 (s, 2H), 4.75 (s, 2H) 7.24-7.51 (m, 6H). GC-MS: m/z 343 (M)+, 322 (M−21)+.

Example UR-52

5-fluoro-2-(4-ethyl-benzyl)-7-trifluoromethyl-2,3-dihydro-isoindol-1-one

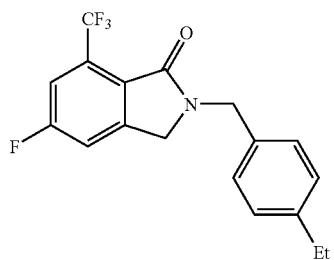

A mixture of 4-fluoro-2-bromomethyl-6-trifluoromethyl-benzoic acid methyl ester (0.100 g, 0.32 mmol), 4-ethyl-benzylamine (0.06 mL, 0.42 mmol), and K$_2$CO$_3$ (0.088 g, 0.64 mmol) in toluene (4 mL) was heated with stirring at 100° C. for 2 h. Workup and silica gel column chromatography using 30% ethyl acetate in hexane afforded 5-fluoro-2-(4-ethyl-benzyl)-7-trifluoromethyl-2,3-dihydro-isoindol-1-one (0.36 g, 33%). $^1$H NMR (300 MHz, CDCl$_3$): δ (ppm) 1.22 (t, Example UR-54

5-fluoro-2-(4-trifluoromethyl-benzyl)-7-trifluoromethyl-2,3-dihydro-isoindol-1-one

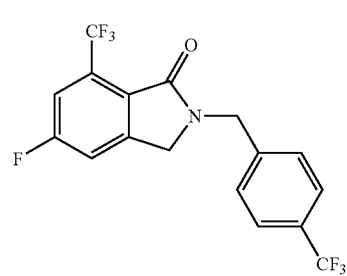

A mixture of 4-fluoro-2-bromomethyl-6-trifluoromethyl-benzoic acid methyl ester (0.100 g, 0.32 mmol), 4-trifluoromethyl-benzylamine (0.06 mL, 0.42 mmol), and K$_2$CO$_3$ (0.088 g, 0.64 mmol) in toluene (4 mL) was heated with stirring at 100° C. for 2 h. Workup and silica gel column chromatography using 30% ethyl acetate in hexane afforded 5-fluoro-2-(4-trifluoromethyl-benzyl)-7-trifluoromethyl-2,3-dihydroisoindol-1-one (0.39 g, 33%). ¹H NMR (300 MHz, CDCl₃): δ (ppm) 4.34 (s, 2H), 4.84 (s, 2H) 7.20-7.50 (m, 6H). GC-MS: m/z 377 (M)⁺, 356 (M−21)⁺.

Example UR-55

5-fluoro-2-(3-fluoro-4-methyl-benzyl)-7-trifluoromethyl-2,3-dihydro-isoindol-1-one

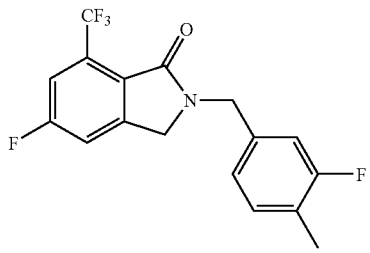

A mixture of 4-fluoro-2-bromomethyl-6-trifluoromethyl-benzoic acid methyl ester (0.100 g, 0.32 mmol), 3-fluoro-4-methyl-benzylamine (0.060 mL, 0.42 mmol), and K₂CO₃ (0.088 g, 0.64 mmol) in toluene (4 mL) was heated with stirring at 100° C. for 2 h. Workup and silica gel column chromatography using 30% ethyl acetate in hexane afforded 5-fluoro-2-(3-fluoro-4-methyl-benzyl)-7-trifluoromethyl-2,3-dihydro-isoindol-1-one (0.034 g, 31%). ¹H NMR (300 MHz, CDCl₃): δ (ppm) 2.25 (s, 3H), 4.28 (s, 2H), 4.74 (s, 2H) 6.98 (t, 2H), 7.16 (t, 1H), 7.27 (d, 1H), 7.51 (d, 1H). GC-MS: m/z 341 (M)⁺, 320 (M−21)⁺.

Example UR-56

2-[1-(4-chloro-phenyl-ethyl]-5-fluoro-7-trifluoromethyl-2,3-dihydro-isoindol-1-one

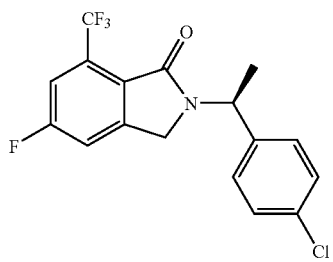

A mixture of 4-fluoro-2-bromomethyl-6-trifluoromethyl-benzoic acid methyl ester (0.100 g, 0.32 mmol), 1-(4-chlorophenyl)-ethylamine (0.059 mL, 0.42 mmol), and K₂CO₃ (0.088 g, 0.64 mmol) in toluene (4 mL) was heated with stirring at 100° C. for 2 h. Workup and silica gel column chromatography using 30% ethyl acetate in hexane afforded 2-[1-(4-chloro-phenyl-ethyl]-5-fluoro-7-trifluoromethyl-2,3-dihydro-isoindol-1-one (0.031 g, 27%). ¹H NMR (300 MHz, CDCl₃): δ (ppm) 1.65 (d, 3H), 3.97-4.38 (dd, 2H), 5.78 (q, 1H) 7.34-7.51 (m, 6H). GC-MS: m/z 357 (M)⁺, 342 (M−15)⁺.

Example UR-78

2-[4-(2,2-difluoroethoxy-benzyl)]-5-fluoro-7-trifluoromethyl-2,3-dihydro-isoindol-1-one

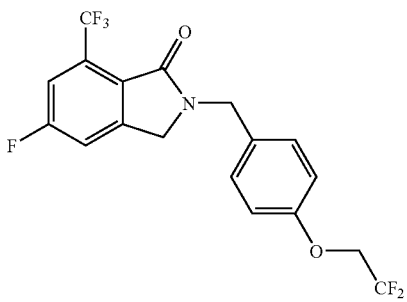

A mixture of 4-fluoro-2-bromomethyl-6-trifluoromethyl-benzoic acid methyl ester (0.100 g, 0.32 mmol), 4-(2,2-difluoroethoxy)-benzylamine (0.065 g, 0.35 mmol), and K₂CO₃ (0.088 g, 0.64 mmol) in toluene (4 mL) was heated with stirring at 100° C. for 2 h. Workup and silica gel column chromatography using 30% ethyl acetate in hexane afforded 2-[4-(2,2-difluoroethoxy-benzyl)]-5-fluoro-7-trifluoromethyl-2,3-dihydro-isoindol-1-one (0.033 g, 27%). ¹H NMR (300 MHz, CDCl₃): δ (ppm) 3.98 (m, 2H), 4.08 (s, 2H), 4.54 (s, 2H) 5.70-6.07 (m, 1H), 6.7 (d, 2H), 7.10 (m, 3H), 7.30 (d, 1H). GC-MS: m/z 389 (M)⁺, 368 (M−21)⁺.

Method

Preparation of Trifluoromethyl Substituted Isoindolone

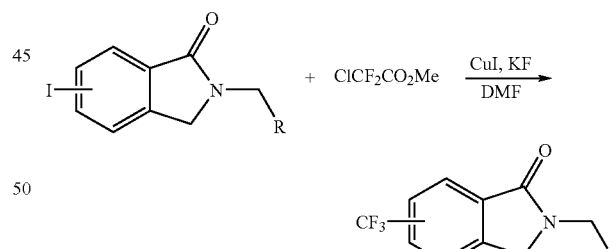

General Procedure:

CuI (0.076 g, 0.4 mmol) and potassium fluoride (0.023 g, 0.4 mmol) were added under an N₂ atmosphere to a solution appropriately substituted-7-iodo-2,3-dihydro-isoindol-1-one (0.149 g, 0.37 mmol) and chloro-difluoro-acetic acid methyl ester (0.046 mL, 0.43 mmol) in DMF (4 mL). The mixture was stirred at 140° C. for 18 h. The reaction was cooled and the solvent evaporated. Silica gel column chromatography using 30% ethyl acetate in hexane afforded appropriately substituted-7-trifluoromethyl-2,3-dihydro-isoindol-1-ones The following compounds were synthesized using the general method described above.

Example UR-20

5-chloro-2-(4-fluoro-benzyl)-7-trifluoromethyl-2,3-dihydro-isoindol-1-one

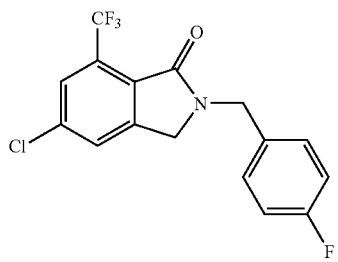

CuI (0.076 g, 0.4 mmol) and potassium fluoride (0.023 g, 0.4 mmol) were added under an $N_2$ atmosphere to a solution 5-chloro-2-(4-fluoro-benzyl)-7-iodo-2,3-dihydro-isoindol-1-one (0.149 g, 0.37 mmol) and chloro-difluoro-acetic acid methyl ester (0.046 mL, 0.43 mmol) in DMF (4 mL). The mixture was stirred at 140° C. for 18 h. The reaction was cooled and the solvent evaporated. Silica gel column chromatography using 30% ethyl acetate in hexane afforded 5-chloro-2-(4-fluoro-benzyl)-7-trifluoromethyl-2,3-dihydro-isoindol-1-one (0.025 g, 20%). $^1$H NMR (300 MHz, CDCl$_3$): δ (ppm) 4.37 (s, 2H), 4.76 (s, 2H) 7.05 (m, 2H), 7.26 (m, 2H), 7.56 (s, 1H), 7.78 (s, 1H). GC-MS: m/z 343 (M)$^+$, 322 (M–21)$^+$.

Example UR-26

5-chloro-2-(4-methoxy-benzyl)-7-trifluoromethyl-2,3-dihydro-isoindol-1-one

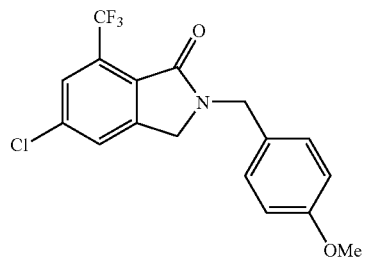

CuI (0.076 g, 0.4 mmol) and potassium fluoride (0.055 g, 0.29 mmol) were added under an $N_2$ atmosphere to a solution 5-chloro-2-(4-methoxy-benzyl)-7-iodo-2,3-dihydro-isoindol-1-one (0.100 g, 0.24 mmol) and chloro-difluoro-acetic acid methyl ester (0.031 mL, 0.29 mmol) in DMF (4 mL). The mixture was stirred at 140° C. for 18 h. The reaction was cooled and the solvent evaporated. Silica gel column chromatography using 30% ethyl acetate in hexane afforded 5-chloro-2-(4-methoxy-benzyl)-7-trifluoromethyl-2,3-dihydro-isoindol-1-one (0.042 g, 50%). $^1$H NMR (300 MHz, CDCl$_3$): δ (ppm) 3.79 (s, 3H), 4.25 (s, 2H), 4.72 (s, 2H) 6.86 (d, 2H), 7.25 (d, 2H), 7.56 (s, 1H), 7.73 (s, 1H). GC-MS: m/z 355 (M)$^+$, 334 (M–21)$^+$.

Example UR-30

5-chloro-2-cyclopropyl methyl-7-trifluoromethyl-2,3-dihydro-isoindol-1-one

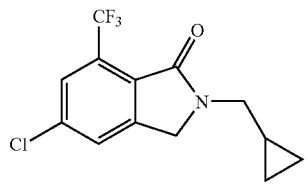

CuI (0.080 g, 0.42 mmol) and potassium fluoride (0.024 g, 0.42 mmol) were added under an $N_2$ atmosphere to a solution 5-chloro-2-cyclopropyl methyl-7-iodo-2,3-dihydro-isoindol-1-one (0.123 g, 0.35 mmol) and chloro-difluoro-acetic acid methyl ester (0.046 mL, 0.42 mmol) in DMF (4 mL). The mixture was stirred at 140° C. for 18 h. The reaction was cooled and the solvent evaporated. Silica gel column chromatography using 30% ethyl acetate in hexane afforded 5-chloro-2-cyclopropyl methyl-7-trifluoromethyl-2,3-dihydro-isoindol-1-one (0.020 g, 20%). $^1$H NMR (300 MHz, CDCl$_3$): δ (ppm) 0.33 (s, 2H), 0.59 (m, 2H), 1.05 (m, 1H), 3.48 (d, 2H) 4.53 (s, 2H), 7.64 (s, 1H), 7.73 (s, 1H). GC-MS: m/z 289 (M)$^+$, 274 (M-15)$^+$.

Example: UR-4

5-fluoro-7-trifluoromethyl-2-(4-trifluoromethoxy-benzyl)-2,3-dihydro-isoindol-1-one

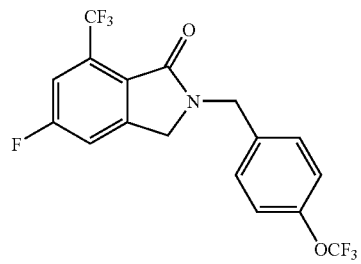

CuI (0.129 g, 0.68 mmol) and potassium fluoride (0.039 g, 0.68 mmol) were added under an $N_2$ atmosphere to a solution 5-fluoro-7-iodo-2-(4-trifluoromethoxy-benzyl)-2,3-dihydro-isoindol-1-one (0.260 g, 0.58 mmol) and chloro-difluoro-acetic acid methyl ester (0.072 mL, 0.098 mmol) in DMF (4 mL). The mixture was stirred at 140° C. for 18 h. The reaction was cooled and the solvent evaporated. Silica gel column chromatography using 30% ethyl acetate in hexane afforded 5-fluoro-7-trifluoromethyl-2-(4-trifluoromethoxybenzyl)-2,3-dihydro-isoindol-1-one (0.070 g, 31%). $^1$H NMR (300 MHz, CDCl$_3$): δ (ppm) 4.41 (s, 2H), 4.85 (s, 2H) 7.23-7.58 (m, 6H).

Example: UR-65

2-(3-trifluoro-4-methyl-benzyl)-7-methyl-5-trifluoromethyl)-2,3-dihydro-isoindol-1-one

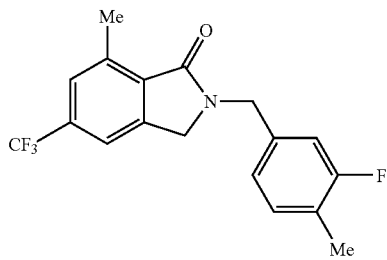

CuI (0.068 g, 0.36 mmol) and potassium fluoride (0.021 g, 0.36 mmol) were added under an N$_2$ atmosphere to a solution 2-(3-trifluoro-4-methyl-benzyl)-7-methyl-5-iodo-2,3-dihydro-isoindol-1-one (0.096 g, 0.24 mmol) and chloro-difluoro-acetic acid methyl ester (0.051 mL, 0.48 mmol) in DMF (4 mL). The mixture was stirred at 140° C. for 18 h. The reaction was cooled and the solvent evaporated. Silica gel column chromatography using 30% ethyl acetate in hexane afforded 2-(3-trifluoro-4-methyl-benzyl)-7-methyl-5-trifluoromethyl)-2,3-dihydro-isoindol-1-one (0.049 g, 60%). $^1$H NMR (300 MHz, CDCl$_3$): δ (ppm) 2.25 (s, 3H), 2.82 (s, 3H), 4.27 (s, 2H), 4.74 (s, 2H) 6.99 (t, 2H), 7.16 (t, 1H), 7.45 (d, 2H). GC-MS: m/z 337 (M)$^+$, 322 (M–15)$^+$.

Method 10

Step 1: Preparation of Benzonitrile Derivative

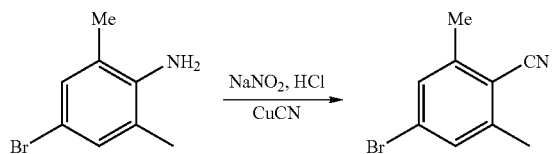

Example 320

4-bromo-2,6-dimethyl-benzonitrile

4-Bromo-2,6-dimethylaniline (10.1 g, 50 mmol) was treated with concentrated HCl (50 mL) and the mixture stirred in an ice bath to maintain a temperature of below 5° C. A solution of sodium nitrite (6.9 g, 100 mmol) in water (20 mL) was added. After stirring for 20 min in the ice bath the reaction mixture was carefully neutralized with sodium carbonate to afford the diazotized aniline.

A solution of cuprous cyanide was prepared by adding copper cyanide (5.4 g, 60 mmol) to sodium cyanide (7.2 g, 150 mmol) in water (40 mL). This solution was cooled to below 5° C. (ice bath) and toluene (25 mL) was added to the aqueous solution. This bi-phasic solution was then treated slowly with the above diazotized aniline. The resulting mixture was stirred in an ice bath for 30 min and then allowed to warm to room temperature. After 3 h of stirring at room temperature, the reaction mixture was heated at 60° C. for 30 minutes without stirring. The resulting solution was cooled to ambient temperature and then extracted with ethyl acetate (2×400 mL). The combined organic extracts were washed with brine (50 mL), dried over MgSO$_4$, filtered, and concentrated to afford 4-bromo-2,6-dimethyl-benzonitrile (8.0 g, 76%). The material was used without further purification.

Step 2: Hydrolysis of Cyanide

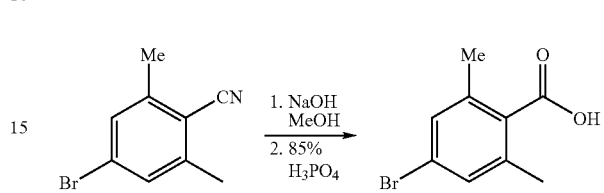

Example 321

4-bromo-2,6-dimethyl-benzoic acid

A solution of 4-bromo-2,6-dimethyl-benzonitrile (8.0 g, 38 mmol), 5N NaOH (60 mL), and MeOH (60 mL) was stirred at 80° C. for 17 h. The reaction mixture was cooled to ambient temperature and the methanol evaporated. The resulting solution was extracted with dichloromethane (2×200 mL). The combined organic extracts were dried over anhydrous MgSO$_4$, filtered, and concentrated. GC-MS indicated that 70% of benzonitrile was converted to benzamide derivative. This material (7.0 g) was treated with 85% phosphoric acid (20 mL) and stirred at 150° C. for 18 h. After this time, the reaction mixture was cooled to ambient temperature and treated with water (30 mL). The resulting solution was extracted with ethyl acetate (2×200 mL). The combined organic extracts were dried over anhydrous MgSO$_4$, filtered, and concentrated to afford 4-bromo-2,6-dimethyl-benzoic acid. The material was used without further purification.

Step 3: Esterification

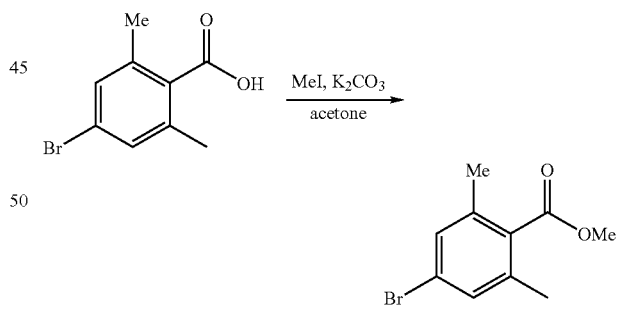

Example 322

4-bromo-2,6-dimethyl-benzoic acid methyl ester

A solution of 4-bromo-2,6-dimethyl-benzoic acid (4.04 g, 17.6 mmol) in acetone (50 mL), was treated with anhydrous K$_2$CO$_3$ (4.14 g, 30 mmol) followed by methyl iodide (1.43 g, 21 mmol). The reaction mixture was stirred at 70° C. for 2 h. GC-MS and TLC indicated that the reaction was completed. The solids were removed by filtration and the filtrate evaporated under reduced pressure. Silica gel column chromatography using 10% ethyl acetate in hexanes afforded 4-bromo-2,6-dimethyl-benzoic acid methyl ester (3.44 g, 80%). GC-MS: m/z 244 M+.

Step 4: Bromination

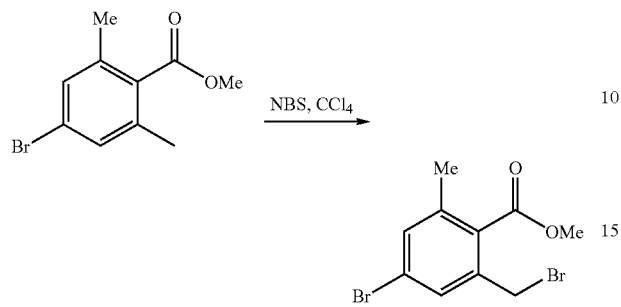

Example 323

4-bromo-2-bromomethyl-6-methyl-benzoic acid methyl ester

A mixture of 4-bromo-2,6-dimethyl-benzoic acid methyl ester (3.4 g, 14.2 mmol), N-bromosuccinamide (2.5 g, 14.2 mmol), and benzoyl peroxide (0.060 g, 0.25 mmol) in carbon tetrachloride (50 mL) was heated at reflux until majority of ester was consumed (as analyzed by GC/MS). The resulting mixture was filtered and the filtrate concentrated to afford 4-bromo-2-bromomethyl-6-methyl-benzoic acid methyl ester. The product obtained was used without further purification.

Step 5: Generation of Isoindolones from Bromo-Esters and Amines

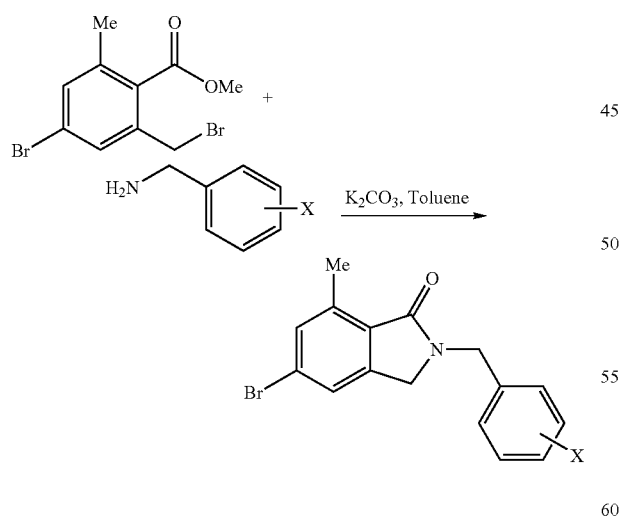

General Procedure

A mixture of the appropriately substituted benzyl amine (1.2 equiv.), 4-bromo-2-bromomethyl-6-methyl-benzoic acid methyl ester (1.0 equiv.), and K$_2$CO$_3$ (2 equiv.) in toluene was heated with stirring at 100° C. for 2 h. The resulting mixture was filtered and concentrated. Silica gel column chromatography using combinations of hexane and ethyl acetate (typically 30% ethyl acetate in hexane) afforded the desired product.

The following compounds were synthesized using general method 10 described above.

Example 324

5-Bromo-7-methyl-2-(4-phenoxy-benzyl)-2,3-dihydro-isoindol-1-one

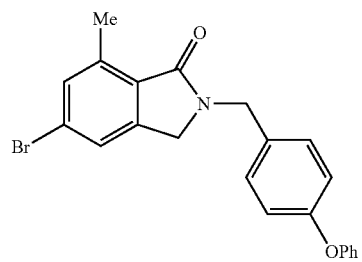

A mixture of 4-bromo-2-bromomethyl-6-methyl-benzoic acid methyl ester (0.500 g, 1.6 mmol), 4-phenoxy-benzylamine (0.342 mL, 1.92 mmol), and K$_2$CO$_3$ (0.484 g, 3.5 mmol) in toluene (5 mL) was heated with stirring at 100° C. for 2 h. Workup and silica gel column chromatography using 30% ethyl acetate in hexane afforded 5-bromo-7-methyl-2-(4-phenoxy-benzyl)-2,3-dihydro-isoindol-1-one (0.212 g, 32%). GC-MS: m/z 407 (M)+, 314 (M−93)+.

Example 325

5-Bromo-7-methyl-2-(4-trifluoromethoxy-benzyl)-2,3-dihydro-isoindol-1-one

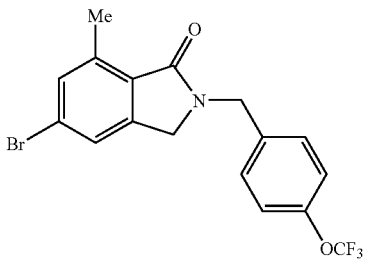

A mixture of 4-bromo-2-bromomethyl-6-methyl-benzoic acid methyl ester (1.61 g, 5.0 mmol), 4-trifluoromethoxy-benzylamine (0.916 mL, 6.0 mmol), and K$_2$CO$_3$ (1.24 g, 9.0 mmol) in toluene (10 mL) was heated with stirring at 100° C. for 2 h. Workup and silica gel column chromatography using 30% ethyl acetate in hexane afforded 5-bromo-7-methyl-2-

(4-trifluoromethoxy-benzyl)-2,3-dihydro-isoindol-1-one (1.21 g, 60%). GC-MS: m/z 399 (M)+, 316 (M–83)+.

Example 326

5-Bromo-7-methyl-2-(4-chloro-benzyl)-2,3-dihydro-isoindol-1-one

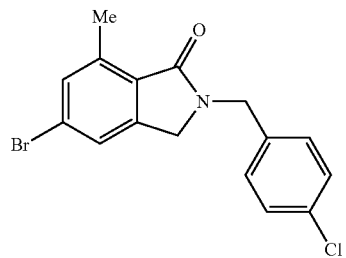

A mixture of 4-bromo-2-bromomethyl-6-methyl-benzoic acid methyl ester (0.966 g, 3.0 mmol), 4-chloro-benzylamine (0.462 mL, 3.8 mmol), and K$_2$CO$_3$ (0.829 g, 6.0 mmol) in toluene (10 mL) was heated with stirring at 100° C. for 2 h. Workup and silica gel column chromatography using 30% ethyl acetate in hexane afforded 5-bromo-7-methyl-2-(4-chloro-benzyl)-2,3-dihydro-isoindol-1-one (0.725 g, 69%). GC-MS: m/z 350 (M)+, 314 (M–36)+.

Step 6: Preparation of Propargyl Amine Substituted Isoindolones

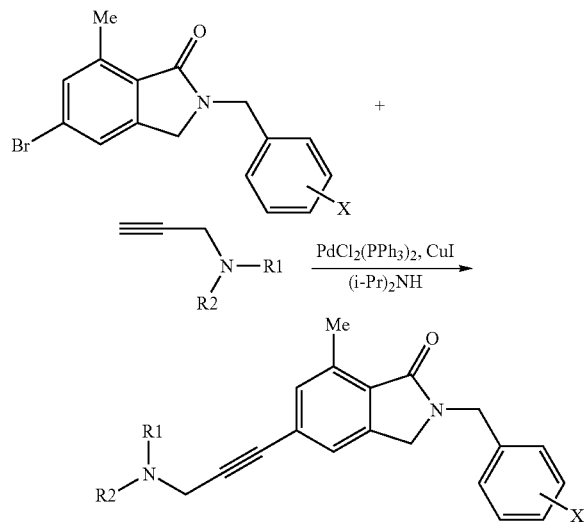

General Procedure

The appropriately substituted propargylamine (1.3 equiv.) was added to a mixture of appropriately substituted isoindolone (1 equiv.), PdCl$_2$(PPh$_3$)$_2$ (5 mol %), and CuI (5 mol %) in diisopropyl amine. The reaction mixture was stirred at 100° C. for 2 h. After the complete consumption of bromo-isoindolone (monitored using GC-MS), the reaction mixture was cooled to ambient temperature and diluted with ethyl acetate (20 mL). The solids were removed by filtration and the filtrate concentrated. Silica gel column chromatography of the product using combinations of chloroform-methanol (typically 10:1 CHCl$_3$-MeOH) afforded the desired product.

The following compounds were synthesized using the general method described above.

Example 327

7-Methyl-5-[3-(4-methyl-piperazin-1-yl)-prop-1-ynyl)-2-(4-phenoxy-benzyl)-2,3-dihydro-isoindol-1-one

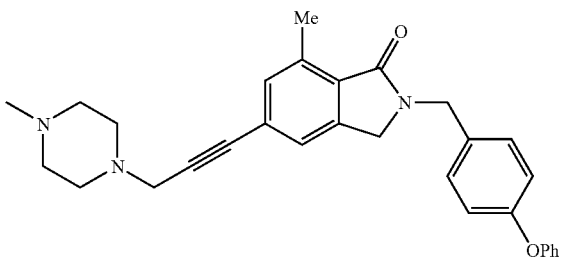

A mixture of 1-methyl-4-prop-2-ynyl-piperazine (0.033 mL, 0.33 mmol), 5-bromo-7-methyl-2-(4-phenoxy-benzyl)-2,3-dihydro-isoindol-1-one (0.102 g, 0.25 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-methyl-5-[3-(4-methyl-piperazin-1-yl)-prop-1-ynyl)-2-(4-phenoxy-benzyl)-2,3-dihydro-isoindol-1-one (0.05 g, 43%).

Example 328

7-Methyl-5-[3-(4-methyl-piperazin-1-yl)-prop-1-ynyl)-2-(4-trifluoromethoxy-benzyl)-2,3-dihydro-isoindol-1-one

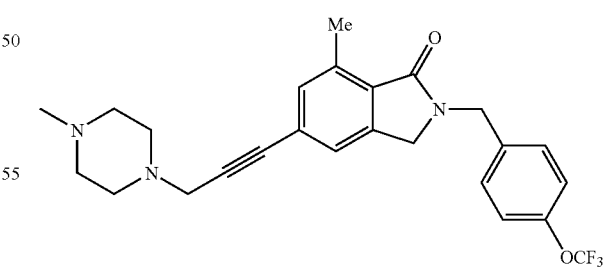

A mixture of 1-methyl-4-prop-2-ynyl-piperazine (0.033 mL, 0.33 mmol), 5-bromo-7-methyl-2-(4-trifluoromethoxy-benzyl)-2,3-dihydro-isoindol-1-one (0.100 g, 0.25 mmol), PdCl$_2$(PPh$_3$)$_2$ (0.011 g, 0.015 mmol), and CuI (0.0028 g, 0.015 mmol) in diisopropyl amine (4 mL) was stirred at 100° C. for 2 h. Workup and silica gel column chromatography using 10:1 CHCl$_3$-MeOH afforded 7-Methyl-5-[3-(4-methyl-piperazin-1-yl)-prop-1-ynyl)-2-(4-trifluoromethoxy-benzyl)-2,3-dihydro-isoindol-1-one (0.076 g, 67%).

The following compounds were synthesized using the general method described above.

Example 329

7-Methyl-2-(4-chloro-benzyl)-5-[3-(4-methyl-piperazin-1-yl)-prop-1-ynyl]-2,3-dihydro-isoindol-1-one

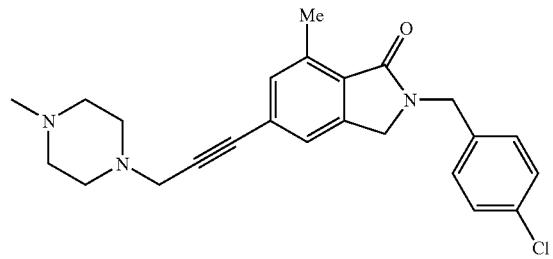

A mixture of 1-methyl-4-prop-2-ynyl-piperazine (0.061 mL, 0.4 mmol), 5-bromo-7-methyl-2-(4-chloro-benzyl)-2,3-dihydro-isoindol-1-one (0.105 g, 0.3 mmol), PdCl$_2$(PPh$_3$)$_2$ (0.011 g, 0.015 mmol), and CuI (0.0028 g, 0.015 mmol) in diisopropylamine (4 mL) was stirred at 100° C. for 2 h. Workup and silica gel column chromatography using 10:1 CHCl$_3$-MeOH afforded 7-methyl-2-(4-chloro-benzyl)-5-[3-(4-methyl-piperazin-1-yl)-prop-1-ynyl)-2,3-dihydro-isoindol-1-one (0.100 g, 81%).

Step 7: Hydrogenation of Alkyne

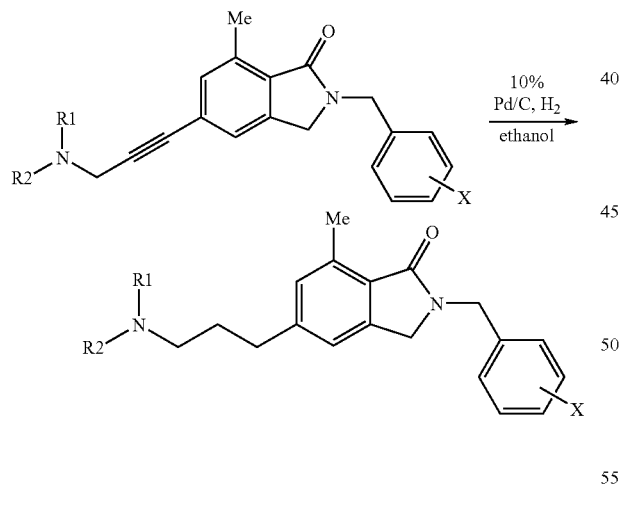

General Procedure

A solution of a propargyl-substituted isoindolone in ethanol was treated with 10% palladium on carbon (10 mg-50 mg) and shook vigorously under 45 p.s.i. hydrogen for 2-3 h. The resulting reaction mixture was filtered through Celite and the filtrate concentrated under reduced pressure. Silica gel column chromatography using combinations of chloroform-methanol (typically 5:1 CHCl$_3$-MeOH) afforded the desired product.

Example 330

7-Methyl-5-[3-(4-methyl-piperazin-1-yl)-propyl]-2-(4-phenoxy-benzyl)-2,3-dihydro-isoindol-1-one

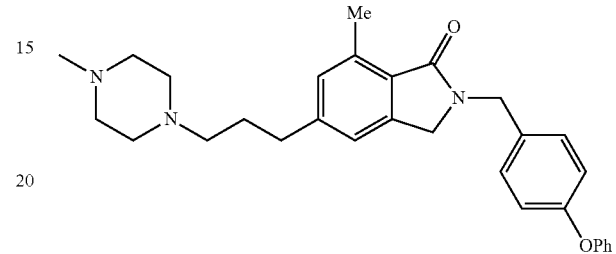

A mixture of 7-methyl-5-[3-(4-methyl-piperazin-1-yl)-prop-1-ynyl)-2-(4-phenoxy-benzyl)-2,3-dihydro-isoindol-1-one (0.056 g, 0.11 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-Methyl-5-[3-(4-methyl-piperazin-1-yl)-propyl]-2-(4-phenoxy-benzyl)-2,3-dihydro-isoindol-1-one (0.056 g, 100%). $^1$H NMR (300 MHz, CDCl$_3$): δ (ppm) 1.79 (m, 2H), 2.23-2.66 (m, 18H), 4.18 (s, 2H), 4.72 (s, 2H), 6.88-7.38 (m, 11H).

Example 331

7-Methyl-5-[3-(4-methyl-piperazin-1-yl)-propyl]-2-(4-trifluoromethoxy-benzyl)-2,3-dihydro-isoindol-1-one A mixture of 7-methyl-5-[3-(4-methyl-piperazin-1-yl)-prop-1-ynyl)-2-(4-trifluoromethoxy-benzyl)-2,3-dihydro-isoindol-1-one (0.076 g, 0.17 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-methyl-5-[3-(4-methyl-piperazin-1-yl)-propyl]-2-(4-trifluoromethoxy-benzyl)-2,3-dihydro-isoindol-1-one (0.074 g, 95%). $^1$H NMR (300

MHz, CDCl$_3$): δ (ppm) 1.79 (m, 2H), 2.22-2.78 (m, 18H), 4.20 (s, 2H), 4.76 (s, 2H), 7.02 (d, 2H), 7.18 (d, 2H), 7.36 (d, 2H).

Example 332

7-Methyl-2-(4-chloro-benzyl)-5-[3-(4-methyl-piperazin-1-yl)-propyl]-2,3-dihydro-isoindol-1-one

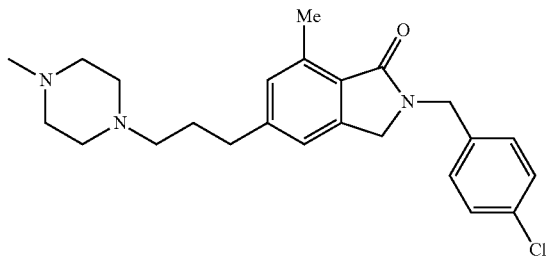

A mixture of 7-methyl-2-(4-chloro-benzyl)-5-[3-(4-methyl-piperazin-1-yl)-prop-1-ynyl]-2,3-dihydro-isoindol-1-one (0.100 g, 0.24 mmol) and 10% palladium-carbon (0.015 g) in ethanol (25 mL) was reduced under 45 p.s.i. hydrogen. Workup and silica gel column chromatography using 5:1 CHCl$_3$-MeOH afforded 7-methyl-2-(4-chloro-benzyl)-5-[3-(4-methyl-piperazin-1-yl)-propyl]-2,3-dihydro-isoindol-1-one (0.063 g, 64%). $^1$H NMR (300 MHz, CDCl$_3$): δ (ppm) 1.79 (m, 2H), 2.24-2.77 (m, 18H), 4.15 (s, 2H), 4.72 (s, 2H), 7.08 (d, 1H), 7.28 (m, 5H).

Method 11

Preparation of Piperazine Containing Isoindolones

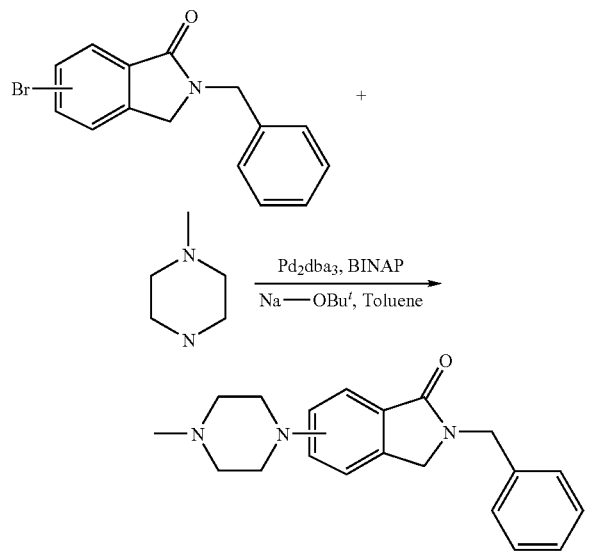

General Procedure

In a sealed vial, a mixture of the appropriately substituted bromo-isoindolones (1 equiv.), 1-methyl piperazine (1.2 equiv.), Pd$_2$.dba$_3$ (3 mol %), BINAP (6 mol %), and sodium tertiary-butoxide (1.5 equiv.) in toluene was heated to reflux for 2-3 h. The reaction was monitored using GC-MS for the disappearance of starting materials. After completion of the reaction, the mixture was cooled to ambient temperature and the solvent evaporated. Silica gel column chromatography using, typically, 30% ethyl acetate in hexane afforded product.

The following compounds were synthesized using the general method described above.

Example 333

6-(4-Methyl-piperazin-1-yl)-2-[2-(4-phenoxy-phenyl)-ethyl]-2,3-dihydro-isoindol-1-one

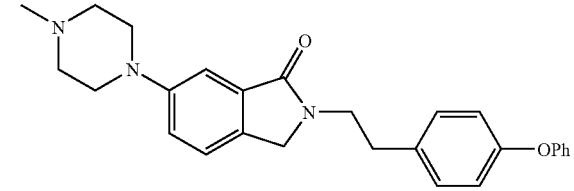

A mixture of 6-Bromo-2-[2-(4-phenoxy-phenyl)-ethyl]-2,3-dihydro-isoindol-1-one (0.134 g, 0.33 mmol), 1-methyl piperazine (0.048 mL, 0.43 mmol), Pd$_2$.dba$_3$ (0.009 g, 0.01 mmol), BINAP (0.012 g, 0.02 mmol), and sodium tertiary-butoxide (0.048 g, 0.5 mmol) in toluene (3 mL) was heated to reflux for 3 h. Workup and silica gel column chromatography using 30% ethyl acetate in hexane afforded 6-(4-Methyl-piperazin-1-yl)-2-[2-(4-phenoxy-phenyl)-ethyl]-2,3-dihydro-isoindol-1-one (0.03 g, 41%). $^1$H NMR (300 MHz, CDCl$_3$): δ (ppm) 2.36 (s, 3H), 2.57 (m, 4H), 2.93 (t, 2H), 3.32 (m, 4H), 3.81 (t, 2H), 4.16 (s, 2H), 6.82-7.35 (m, 11H), 7.68 (d, 1H).

Example 334

5-(4-Methyl-piperazin-1-yl)-2-[2-(4-phenoxy-phenyl)-ethyl]-2,3-dihydro-isoindol-1-one

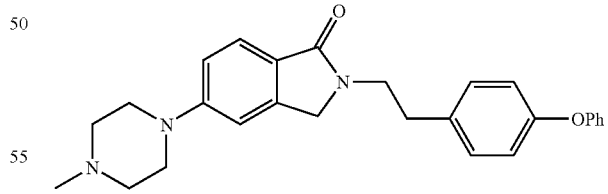

A mixture of 5-bromo-2-[2-(4-phenoxy-phenyl)-ethyl]-2,3-dihydro-isoindol-1-one (0.128 g, 0.31 mmol), 1-methyl piperazine (0.046 mL, 0.41 mmol), Pd$_2$.dba$_3$ (0.009 g, 0.01 mmol), BINAP (0.012 g, 0.02 mmol), and sodium tertiary-butoxide (0.048 g, 0.5 mmol) in toluene (3 mL) was heated to reflux for 3 h. Workup and silica gel column chromatography using 30% ethyl acetate in hexane afforded 5-(4-Methyl-piperazin-1-yl)-2-[2-(4-phenoxy-phenyl)-ethyl]-2,3-dihydro-isoindol-1-one (0.039 g, 29%). $^1$H NMR (300 MHz, CDCl$_3$): δ (ppm) 2.36 (s, 3H), 2.58 (m, 4H), 2.94 (t, 2H), 3.32 (m, 4H), 3.81 (t, 2H), 4.16 (s, 2H), 6.82-7.35 (m, 1H), 7.69 (d, 1H).

Example 335

5-(4-Methyl-piperazin-1-yl)-2-(4-phenoxy-benzyl)-2,3-dihydro-isoindol-1-one

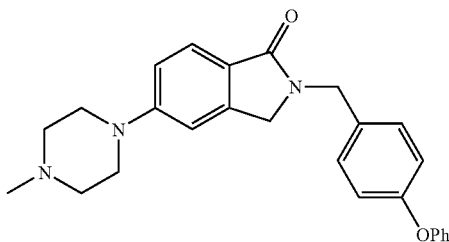

A mixture of 5-bromo-2-(4-phenoxy-benzyl)-2,3-dihydro-isoindol-1-one (0.039 g, 0.1 mmol), 1-methyl piperazine (0.022 mL, 0.2 mmol), Pd$_2$.dba$_3$ (0.009 g, 0.01 mmol), BINAP (0.012 g, 0.02 mmol), and sodium tertiary-butoxide (0.030 g, 0.3 mmol) in toluene (3 mL) was heated to reflux for 3 h. Workup and silica gel column chromatography using 30% ethyl acetate in hexane afforded 5-(4-Methyl-piperazin-1-yl)-2-(4-phenoxy-benzyl)-2,3-dihydro-isoindol-1-one (0.017 g, 41%). $^1$H NMR (300 MHz, CDCl$_3$): δ (ppm) 2.37 (s, 3H), 2.58 (m, 4H), 3.32 (m, 4H), 4.20 (s, 2H), 4.72 (s, 2H), 6.83-7.36 (m, 11H), 7.75 (d, 1H).

Example 336

5-(4-Methyl-piperazin-1-yl)-2-(4-trifluoromethoxy-benzyl)-2,3-dihydro-isoindol-1-one

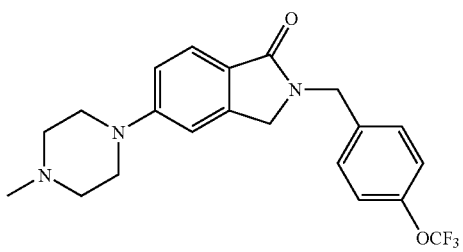

A mixture of 5-bromo-2-(4-trifluoromethoxy-benzyl)-2,3-dihydro-isoindol-1-one (0.104 g, 0.27 mmol), 1-methyl piperazine (0.047 mL, 0.4 mmol), Pd$_2$.dba$_3$ (0.009 g, 0.01 mmol), BINAP (0.012 g, 0.02 mmol), and sodium tertiary-butoxide (0.040 g, 0.4 mmol) in toluene (3 mL) was heated to reflux for 3 h. Workup and silica gel column chromatography using 30% ethyl acetate in hexane afforded 5-(4-methyl-piperazin-1-yl)-2-(4-trifluoromethoxy-benzyl)-2,3-dihydro-isoindol-1-one (0.017 g, 41%). $^1$H NMR (300 MHz, CDCl$_3$): δ (ppm) 2.36 (s, 3H), 2:58 (m, 4H), 3.32 (m, 4H), 4.20 (s, 2H), 4.76 (s, 2H), 6.83-7.32 (m, 6H), 7.73 (d, 1H).

Example 337

5-(4-Methyl-piperazin-1-yl)-2-(4-trifluoromethoxy-benzyl)-7-trifluoromethyl-2,3-dihydro-isoindol-1-one

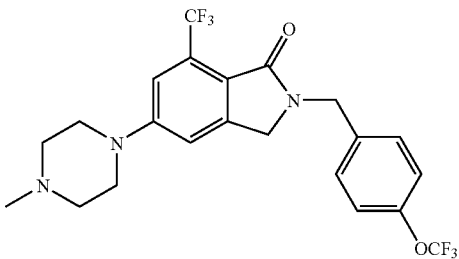

A mixture of 5-bromo-2-(4-trifluoromethoxy-benzyl)-7-trifluoromethyl-2,3-dihydro-isoindol-1-one (0.110 g, 0.25 mmol), 1-methyl piperazine (0.037 mL, 0.33 mmol), Ni(COD)$_2$ (0.013 g, 0.004 mmol), 1,10-phenanthroline (0.005 g, 0.025 mmol), and sodium tertiary-butoxide (0.034 g, 0.35 mmol) in pyridine (2 mL) was heated to reflux for 3 h. Workup and silica gel column chromatography using 30% ethyl acetate in hexane afforded 5-(4-methyl-piperazin-1-yl)-2-(4-trifluoromethoxy-benzyl)-7-trifluoromethyl-2,3-dihydro-isoindol-1-one (0.037 g, 31%). $^1$H NMR (300 MHz, CDCl$_3$/CD$_3$OD): δ (ppm) 2.26 (s, 3H), 2.52 (m, 2H), 2.80 (m, 4H), 3.40 (m, 2H), 4.36 (s, 2H), 4.76 (s, 2H), 7.20-7.52 (m, 6H).

Method 12

Step 1: Preparation of Nitrile Derivative of Isoindolones

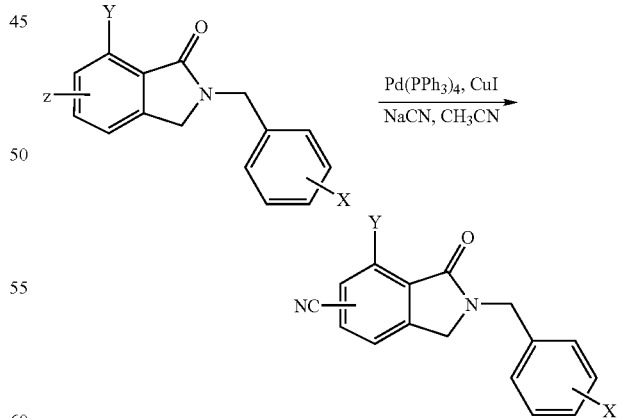

General Procedure

A mixture of an appropriately substituted bromo-isoindolone (1 equiv.), Pd(PPh$_3$)$_4$ (10 mol %), sodium cyanide (2-5 equiv.), and CuI (10 mol %) in acetonitrile (10 mL) was stirred at 80° C. for 18 h. After complete consumption of bromo-isoindolones (monitored by GC-MS), the mixture was cooled to ambient temperature and diluted with ethyl acetate (25 mL). The solids were removed by filtration and the filtrate was concentrated. Silica gel column chromatography using 2:1 hexanes-ethyl acetate afforded the desired product.

The following compounds were synthesized using general method 12, step 1 described above.

Example 338

2-Benzyl-1-oxo-2,3-dihydro-1H-isoindole-5-carbonitrile

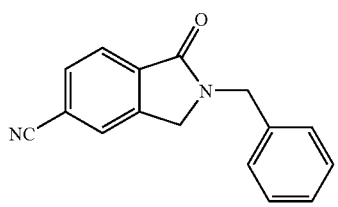

A mixture of 5-bromo-2,3-dihydro-1H-isoindole-1-one (0.065 g, 0.22 mmol), Pd(PPh$_3$)$_4$ (0.025 g, 0.02 mmol), sodium cyanide (0.023 g, 0.5 mmol), and CuI (0.004 g, 0.02 mmol) in acetonitrile (4 mL) was stirred at 80° C. for 18 h. Workup and silica gel column chromatography using 2:1 hexanes-ethyl acetate (typically 2:1 hexane-EtOAc) afforded 2-benzyl-1-oxo-2,3-dihydro-1H-isoindole-5-carbonitrile (0.047 g, 85%). $^1$H NMR (300 MHz, CDCl$_3$): δ (ppm) 4.32 (s, 2H), 4.81 (s, 2H), 7.33 (m, 5H), 7.68 (s, 1H), 7.76 (d, 1H), 7.98 (d, 1H). GC-MS: m/z 248 (M)$^+$, 171 (M–77)$^+$.

Example 339

Benzyl-1-oxo-2,3-dihydro-1H-isoindole-7-carbonitrile

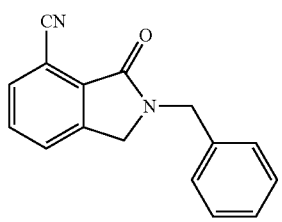

A mixture of 7-iodo-2,3-dihydro-1H-isoindole-1-one (0.087 g, 0.25 mmol), Pd(PPh$_3$)$_4$ (0.031 g, 0.025 mmol), sodium cyanide (0.028 g, 0.6 mmol), and CuI (0.006 g, 0.025 mmol) in acetonitrile (4 mL) was stirred at 80° C. for 18 h. Workup and silica gel column chromatography using 2:1 hexanes-ethyl acetate (typically 2:1 hexane-EtOAc) afforded 2-benzyl-1-oxo-2,3-dihydro-1H-isoindole-7-carbonitrile (0.042 g, 68%). $^1$H NMR (300 MHz, CDCl$_3$): δ (ppm) 4.32 (s, 2H), 4.82 (s, 2H), 7.33 (m, 5H), 7.61 (d, 2H), 7.78 (t, 1H).

Example 340

7-Chloro-1-oxo-2-(4-trifluoromethoxy-benzyl)-2,3-dihydro-1H-isoindole-5-carbonitrile

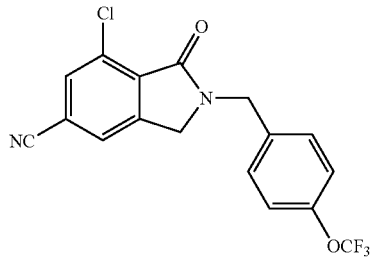

A mixture of 5-bromo-7-chloro-2-(4-trifluoromethoxy-benzyl)-2,3-dihydro-isoindol-1-one (0.349 g, 0.83 mmol), Pd(PPh$_3$)$_4$ (0.317 g, 0.25 mmol), sodium cyanide (0.048 g, 0.946 mmol), CuI (0.016 g, 0.086 mmol), acetonitrile (4 mL) was stirred at 80° C. for 18 h. Workup and silica gel column chromatography using 2:1 hexanes-ethyl acetate (typically 2:1 hexane-EtOAc) afforded 7-chloro-1-oxo-2-(4-trifluoromethoxy-benzyl)-2,3-dihydro-1H-isoindole-5-carbonitrile (0.100 g, 33%). $^1$H NMR (300 MHz, CDCl$_3$): δ (ppm) 4.32 (s, 2H), 4.79 (s, 2H), 7.20 (d, 2H), 7.35 (d, 2H), 7.58 (s, 1H), 7.70 (s, 1H). GC-MS: m/z 366 (M–1)$^+$, 281 (M–85)$^+$.

Example 341

7-Methyl-1-oxo-2-(4-trifluoromethoxy-benzyl)-2,3-dihydro-1H-isoindole-5-carbonitrile

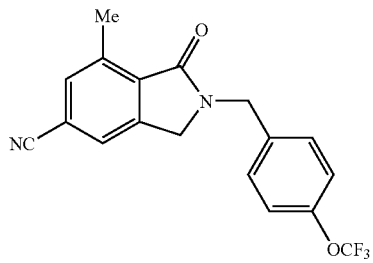

A mixture of 5-bromo-7-methyl-2-(4-trifluoromethoxy-benzyl)-2,3-dihydro-isoindol-1-one (0.600 g, 1.5 mmol), Pd(PPh$_3$)$_4$ (0.175 g, 0.14 mmol), sodium cyanide (0.163 g, 3.4 mmol), and CuI (0.029 g, 0.15 mmol) in acetonitrile (6 mL) was stirred at 80° C. for 18 h. Workup and silica gel column chromatography using 2:1 hexanes-ethyl acetate (typically 2:1 hexane-EtOAc) afforded 7-methyl-1-oxo-2-(4-trifluoromethoxy-benzyl)-2,3-dihydro-1H-isoindole-5-carbonitrile (0.491 g, 95%). ¹H NMR (300 MHz, CDCl₃): δ (ppm) 2.78 (s, 3H), 4.26 (s, 2H), 4.79 (s, 2H), 7.18 (d, 2H), 7.35 (d, 2H), 7.52 (s, 2H).

Example 342

7-Methyl-1-oxo-2-(4-chloro-benzyl)-2,3-dihydro-1H-isoindole-5-carbonitrile

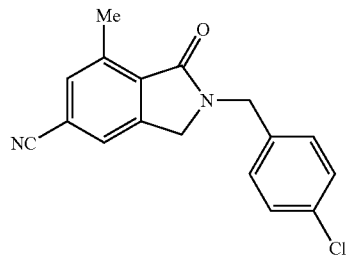

A mixture of 5-bromo-7-methyl-2-(4-chloro-benzyl)-2,3-dihydro-isoindol-1-one (0.205 g, 0.59 mmol), Pd(PPh₃)₄ (0.070 g, 0.06 mmol), sodium cyanide (0.038 g, 0.8 mmol), and CuI (0.013 g, 0.07 mmol) in acetonitrile (3 mL) was stirred at 80° C. for 18 h. Workup and silica gel column chromatography using 2:1 hexanes-ethyl acetate (typically 2:1 hexane-EtOAc) afforded 7-methyl-1-oxo-2-(4-chloro-benzyl)-2,3-dihydro-1H-isoindole-5-carbonitrile (0.93 g, 54%). ¹H NMR (300 MHz, CDCl₃): δ (ppm) 2.78 (s, 3H), 4.26 (s, 2H), 4.65 (s, 2H), 7.24 (d, 2H), 7.33 (d, 2H), 7.52 (d, 2H). GC-MS: m/z 296 (M)⁺, 261 (M−35)⁺.

Example 343

6-Chloro-3-oxo-2-(4-phenoxy-benzyl)-2,3-dihydro-1H-isoindole-4-carbonitrile

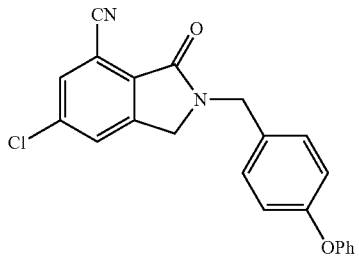

A mixture of 5-chloro-7-iodo-2-(4-phenoxy-benzyl)-2,3-dihydro-isoindol-1-one (0.675 g, 1.42 mmol), Pd(PPh₃)₄ (0.162 g, 0.14 mmol), sodium cyanide (0.089 g, 1.85 mmol), and CuI (0.027 g, 0.14 mmol) in acetonitrile (5 mL) was stirred at 80° C. for 18 h. Workup and silica gel column chromatography using 2:1 hexanes-ethyl acetate (typically 2:1 hexane-EtOAc) afforded 6-chloro-3-oxo-2-(4-phenoxy-benzyl)-2,3-dihydro-1H-isoindole-4-carbonitrile (0.307 g, 58%). ¹H NMR (300 MHz, CDCl₃): δ (ppm) 4.32 (s, 2H), 4.77 (s, 2H), 6.95-7.38 (m, 9H), 7.63 (s, 1H), 7.75 (s, 1H). GC-MS: m/z 374 (M)⁺, 297 (M−77)⁺, 281 (M−93)⁺.

Example UR-9

6-fluoro-3-oxo-2-(4-trifluoromethoxy-benzyl)-2,3-dihydro-1H-isoindole-4-carbonitrile

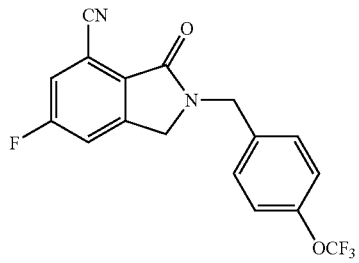

A mixture of 5-fluoro-7-iodo-2-(4-trifluoromethoxy-benzyl)-2,3-dihydro-isoindol-1-one (0.100 g, 0.22 mmol), Pd(PPh₃)₄ (0.022 g, 0.24 mmol), sodium cyanide (0.014 g, 0.285 mmol), and CuI (0.004 g, 0.022 mmol) in acetonitrile (5 mL) was stirred at 80° C. for 18 h. Workup and silica gel column chromatography using 2:1 hexanes-ethyl acetate afforded 6-fluoro-3-oxo-2-(4-trifluoromethoxy-benzyl)-2,3-dihydro-1H-isoindole-4-carbonitrile (0.035 g, 45%). ¹H NMR (300 MHz, CDCl₃): δ (ppm) 4.32 (s, 2H), 4.80 (s, 2H), 7.20 (d, 2H), 7.37 (m, 3H), 7.49 (d, 1H). GC-MS: m/z 350 (M)⁺.

Example UR-10

6-methoxy-3-oxo-2-(4-trifluoromethoxy-benzyl)-2,3-dihydro-1H-isoindole-4-carbonitrile

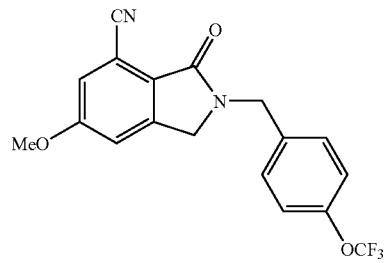

A mixture of 5-methoxy-7-iodo-2-(4-trifluoromethoxy-benzyl)-2,3-dihydro-isoindol-1-one (0.060 g, 0.13 mmol), Pd(PPh₃)₄ (0.015 g, 0.013 mmol), sodium cyanide (0.013 g, 0.26 mmol), and CuI (0.003 g, 0.013 mmol) in acetonitrile (5 mL) was stirred at 80° C. for 18 h. Workup and silica gel column chromatography using 2:1 hexanes-ethyl acetate afforded 6-methoxy-3-oxo-2-(4-trifluoromethoxy-benzyl)-2,3-dihydro-1H-isoindole-4-carbonitrile (0.032 g, 68%). ¹H NMR (300 MHz, CDCl$_3$): δ (ppm) 3.89 (s, 3H), 4.36 (s, 2H), 4.77 (s, 2H), 7.10 (s, 1H), 7.17 (d, 2H), 7.25 (s, 1H), 7.36 (d, 2H). GC-MS: m/z 362 (M$^+$.

Example UR-12

6-chloro-3-oxo-2-(4-trifluoromethoxy-benzyl)-2,3-dihydro-1H-isoindole-4-carbonitrile

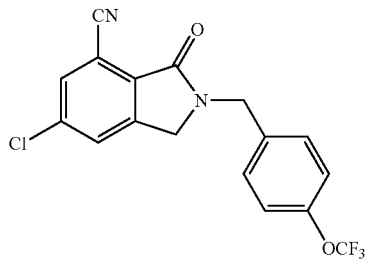

A mixture of 5-chloro-7-iodo-2-(4-trifluoromethoxy-benzyl)-2,3-dihydro-isoindol-1-one (0.339 g, 0.73 mmol), Pd(PPh$_3$)$_4$ (0.084 g, 0.073 mmol), sodium cyanide (0.046 g, 0.95 mmol), and CuI (0.017 g, 0.073 mmol) in acetonitrile (5 mL) was stirred at 80° C. for 18 h. Workup and silica gel column chromatography using 2:1 hexanes-ethyl acetate afforded 6-chloro-3-oxo-2-(4-trifluoromethoxy-benzyl)-2,3-dihydro-1H-isoindole-4-carbonitrile (0.184 g, 69%). $^1$H NMR (300 MHz, CDCl$_3$): δ (ppm) 4.31 (s, 2H), 4.81 (s, 2H), 7.20 (d, 2H), 7.37 (d, 2H), 7.62 (s, 1H), 7.76 (s, 1H). GC-MS: m/z 366 (M)$^+$.

Example UR-38

5-fluoro-3-oxo-2-(4-trifluoromethoxy-benzyl)-2,3-dihydro-1H-isoindole-4-carbonitrile

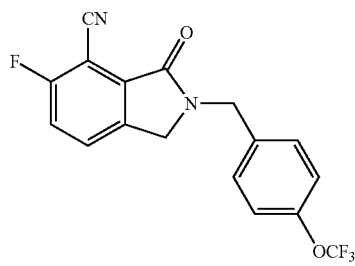

A mixture of 6-fluoro-7-iodo-2-(4-trifluoromethoxy-benzyl)-2,3-dihydro-isoindol-one (0.100 g, 0.22 mmol), PdCl$_2$(dppf)$_2$ (0.008 g, 0.011 mmol), zinc cyanide (0.051 g, 0.44 mmol), and zinc (0.007 g, 0.011 mmol) in DMF (5 mL) was stirred at 80° C. for 18 h. Workup and silica gel column chromatography using 2:1 hexanes-ethyl acetate afforded 5-fluoro-3-oxo-2-(4-trifluoromethoxy-benzyl)-2,3-dihydro-1H-isoindole-4-carbonitrile (0.015 g, 19%). $^1$H NMR (300 MHz, CDCl$_3$): δ (ppm) 4.31 (s, 2H), 4.81 (s, 2H), 7.19 (d, 2H), 7.37 (m, 3H), 7.64 (m, 1H). GC-MS: m/z 350 (M)$^+$.

Example 344

1-Oxo-2-(4-trifluoromethoxy-benzyl)-7-trifluoromethyl-2,3-dihydro-1H-isoindole-5-carbonitrile

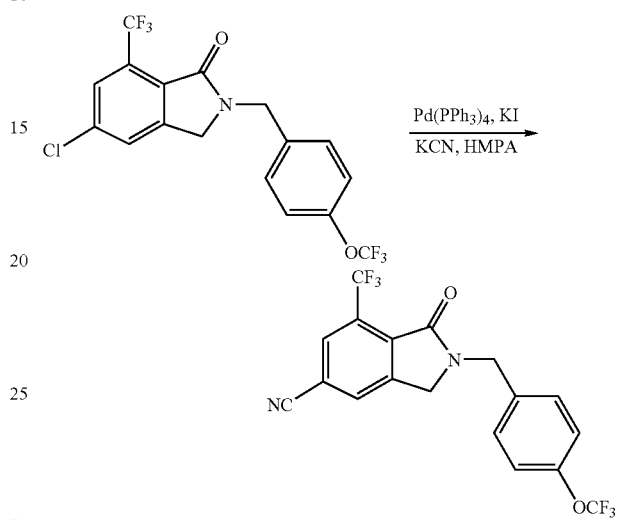

A mixture of 5-chloro-2-(4-trifluoromethoxy-benzyl)-7-trifluoromethyl-2,3-dihydro-isoindol-1-one (0.123 g, 0.3 mmol), Pd(PPh$_3$)$_4$ (0.035 g, 0.03 mmol), KCN (0.057 g, 0.88 mmol), and KI (0.125 g, 0.75 mmol) in HMPA (3 mL) was stirred at 80° C. for 18 h. Workup and silica gel column chromatography using 2:1 hexanes-ethyl acetate afforded 1-Oxo-2-(4-trifluoromethoxy-benzyl)-7-trifluoromethyl-2,3-dihydro-1H-isoindole-5-carbonitrile (0.112 g, 93%). $^1$H NMR (300 MHz, CDCl$_3$): δ (ppm) 4.39 (s, 2H), 4.72 (s, 2H), 7.22 (d, 2H), 7.37 (d, 2H), 7.89 (s, 1H), 8.06 (s, 1H) GC-MS: m/z 400 (M)$^+$, 379 (M−21)$^+$.

The following compound was synthesized using the method as described above in Example 308.

Example 345

3-Oxo-2-(4-trifluoromethoxy-benzyl)-2,3-dihydro-1H-isoindole-4,6-dicarbonitrile

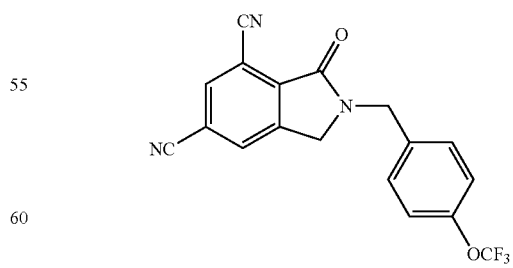

A mixture of 5-bromo-7-chloro-2-(4-trifluoromethoxy-benzyl)-2,3-dihydro-isoindol-1-one (0.781, 1.86 mmol), Pd(PPh$_3$)$_4$ (0.635 g, 0.55 mmol), KCN (0.357 g, 5.5 mmol), and KI (0.77 g, 4.65 mmol) in HMPA (8 mL) was stirred at 80° C. for 18 h. Workup and silica gel column chromatography using 2:1 hexanes-ethyl acetate (typically 2:1 hexane-EtOAc) afforded 3-Oxo-2-(4-trifluoromethoxy-benzyl)-2,3-dihydro-1H-isoindole-4,6-dicarbonitrile (0.300 g, 44%). $^1$H NMR (300 MHz, CDCl$_3$): δ (ppm) 4.41 (s, 2H), 4.83 (s, 2H), 7.22 (d, 2H), 7.39 (d, 2H), 7.92 (s, 1H), 8.08 (s, 1H) GC-MS: m/z 357 (M)$^+$, 272 (M-85)$^+$.

Step 2: Reduction of Nitrile to Amine

Example 346

5-Aminomethyl-7-methyl-2-(4-trifluoromethoxy-benzyl)-2,3-dihydro-isoindol-1-one

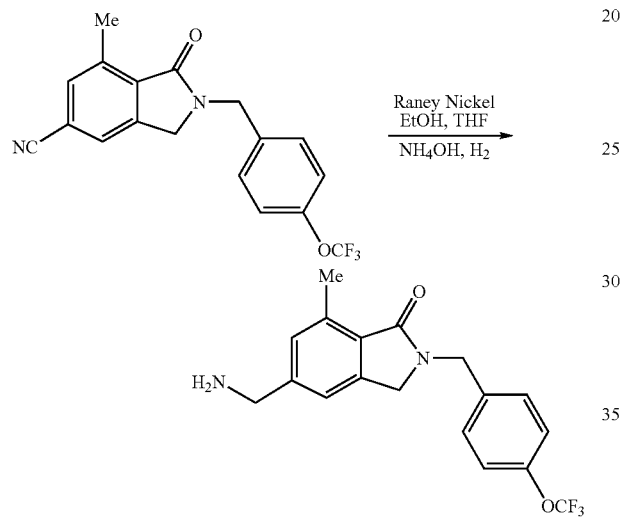

A solution of 7-methyl-1-oxo-2-(4-trifluoromethoxy-benzyl)-2,3-dihydro-1H-isoindole-5-carbonitrile (0.104 g, 0.3 mmol) in THF (1 mL) and ethanol (4 mL) was treated with a suspension of Raney nickel in water (1 mL) and aqueous NH$_4$OH (0.5 mL). The mixture was stirred at ambient temperature for 12 h under hydrogen atmosphere (1 atm.). After this time GC-MS indicated that all the starting material was consumed. The reaction mixture was filtered and concentrated to afford the desired product. The material was used without purification.

Step 3: Reductive Alkylation

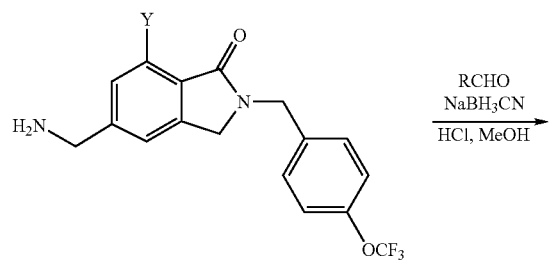

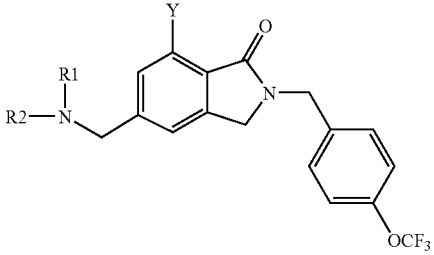

General Procedure

The appropriate carbonyl compound (2 equiv.), NaCNBH$_3$ (1.8 equiv.) and anhydrous MgSO$_4$ (50-100 mg) was added to a stirred solution of an appropriately substituted isoindolone (1 equiv.) in methanol (10 mL). The mixture was stirred for 6 h and then treated dropwise with 1M HCl. The solution was stirred for additional 1 h and diluted with diethyl ether. The organic layer was separated, washed with 1N NaOH, dried over anhydrous MgSO$_4$ and concentrated. Silica gel column chromatography (typically using 10:1 CHCl$_3$-MeOH) afforded the desired product.

The following compounds were synthesized using general method 12, step 3 described above.

Example 347

5-dimethylaminomethyl-7-methyl-2-(4-trifluoromethoxy-benzyl)-2,3-dihydro-isoindol-1-one

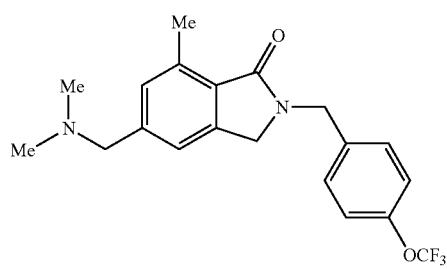

A mixture of 5-aminomethyl-7-methyl-2-(4-trifluoromethoxy-benzyl)-2,3-dihydro-isoindol-1-one (0.070 g, 0.2 mmol), paraformaldehyde (0.025 g), NaCNBH$_3$ (0.023 g, 0.36 mmol), and anhydrous MgSO$_4$ (0.050 g) in methanol (10 mL) was stirred for 6 h. workup and silica gel column chromatography of product typically using 10:1 CHCl$_3$-MeOH afforded 5-dimethylaminomethyl-7-methyl-2-(4-trifluoromethoxy-benzyl)-2,3-dihydro-isoindol-1-one (0.040 g, 53%). $^1$H NMR (300 MHz, CDCl$_3$): δ (ppm) 2.24 (s, 6H), 2.73 (s, 3H), 3.42 (s, 2H) 4.21 (s, 2H), 4.75 (s, 2H), 7.15 (m, 4H), 7.35 (d, 2H). GC-MS: m/z 378 (M)⁺, 335 (M–43)⁺.

Example 348

7-Methyl-5-[(1-phenyl-ethylamino)-methyl]-2-(4-trifluoromethoxy-benzyl)-2,3-dihydro-isoindol-1-one

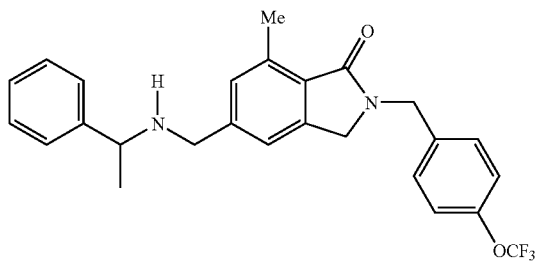

A mixture of 5-aminomethyl-7-methyl-2-(4-trifluoromethoxybenzoyl)-2,3-dihydro-isoindol-1-one (0.053 g, 0.15 mmol), acetophenone (0.036 g, 0.30 mmol), Ti(i-OPr)₄ (1 mL), and NaBH₃CN (0.1 g, 1.6 mmol) in EtOH (2 mL) was stirred for 6 h. Workup and silica gel column chromatography using 10:1 CHCl₃-MeOH afforded 7-methyl-5-[(1-phenyl-ethylamino)-methyl]-2-(4-trifluoromethoxy-benzyl)-2,3-dihydro-isoindol-1-one (0.030 g, 44%). ¹H NMR (300 MHz, CDCl₃): δ (ppm) 1.38 (d, 3H), 1.64 (bs, 1H), 2.73 (s, 3H), 3.62 (dd, 2H), 3.82 (q, 1H), 4.21 (s, 2H), 4.75 (s, 2H), 7.08-7.39 (m, 11H). GC-MS: m/z 439 (M–15)⁺.

Example 349

5-[(Isopropyl-methyl-amino)-methyl]-2-(4-trifluoromethoxy-benzyl)-7-trifluoromethyl-2,3-dihydro-isoindol-1-one

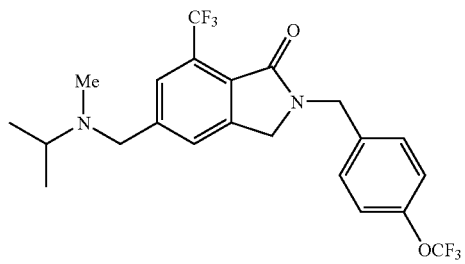

A mixture of 5-aminomethyl-2-(4-trifluoromethoxy-benzyl)-7-trifluoromethyl-2,3-dihydro-isoindol-1-one (0.040 g, 0.1 mmol), paraformaldehyde (0.025 g), acetone (0.5 mL), NaCNBH₃ (0.013 g, 0.2 mmol), and anhydrous MgSO₄ (0.050 g) in MeOH (6 mL) was stirred for 6 h. Workup and silica gel column chromatography using 10:1 CHCl₃-MeOH afforded 5-[(isopropyl-methyl-amino)-methyl]-2-(4-trifluoromethoxy-benzyl)-7-trifluoromethyl-2,3-dihydro-isoindol-1-one (0.017 g, 39%). ¹H NMR (300 MHz, CDCl₃): δ ppm) 1.02 (d, 6H), 2.12 (s, 3H), 2.88 (q, 1H), 3.61 (s, 2H) 4.24 (s, 2H), 4.78 (s, 2H), 7.18 (d, 2H), 7.37 (d, 2H), 7.58 (s, 1H), 7.71 (s, 1H). GC-MS: m/z 445 (4-15)⁺, 367 (M–93)⁺.

Synthesis of Piperazine Derivatives

Example 350

7-methyl-5-(4-methyl-piperazin-1-ylmethyl)-2-(4-trifluoromethoxy-benzyl)-2,3-dihydro-isoindol-1-one

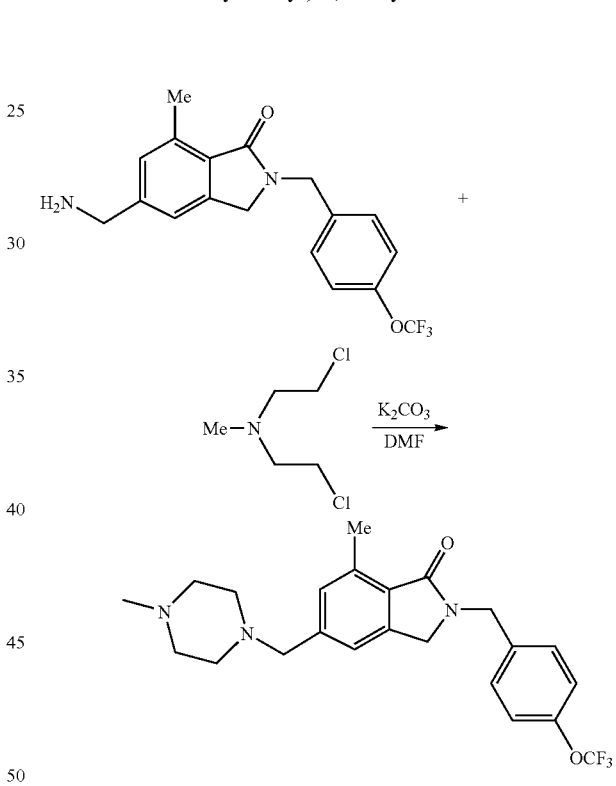

In sealed vial, a mixture of 5-aminomethyl-7-methyl-2-(4-trifluoromethoxy-benzyl)-2,3-dihydro-isoindol-1-one (0.104 g, 0.3 mmol), bis(2-chloro-ethyl)-methyl-amine (0.077 g, 0.4 mmol), and K₂CO₃ (0.083 g, 0.6 mmol) in DMF (3 mL) was stirred at 110° C. for 16 h. After this time, the GC-MS of the reaction mixture indicated the completion of reaction. The reaction was cooled to ambient temperature and the solids removed by filtration. The filtrate was concentrated. Silica gel column chromatography of the resulting material using 5:1 CHCl₃-MeOH afforded 7-methyl-5-(4-methyl-piperazin-1-ylmethyl)-2-(4-trifluoromethoxy-benzyl)-2,3-dihydro-isoindol-1-one (0.040 g, 31%). ¹H NMR (300 MHz, CDCl₃): δ (ppm) 2.24 (s, 3H), 2.34-2.52 (m, 8H), 2.74 (s, 3H), 3.49 (s, 2H), 4.20 (s, 2H), 4.76 (s, 2H), 7.15-7.37 (m, 6H). GC-MS: m/z 433 (M)⁺.

Preparation of Ethoxy Amine-Isoindolone Derivatives

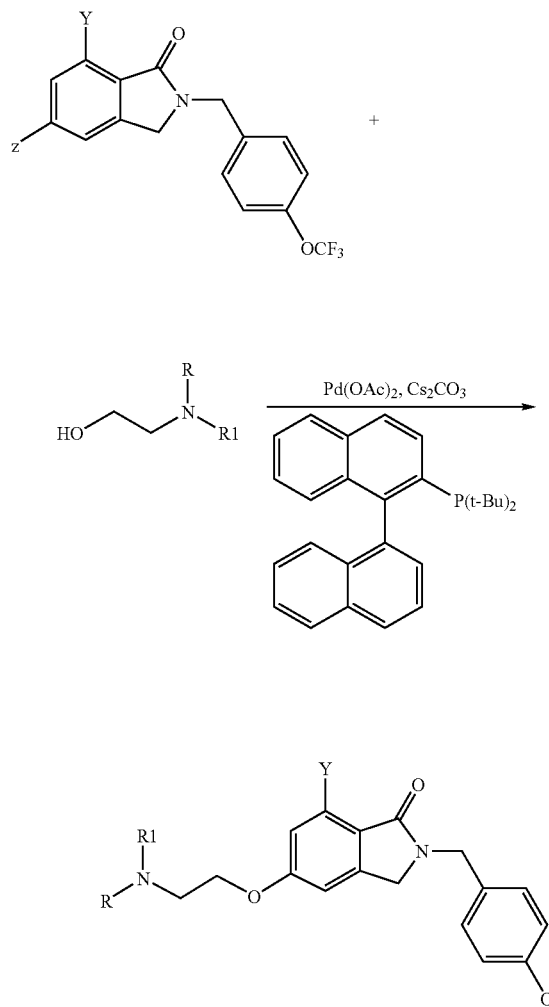

General Procedure

The ethoxy amine-isoindolones were prepared using a previously reported method (*JACS*, 2001, 123, 10770). A mixture of the appropriately substituted isoindolones (1 equiv.), the appropriately substituted ethanol amines (2 equiv.), palladium(II) acetate (1 mol %), cesium carbonate (2 equiv.), and [1,1']-Binaphthalenyl-2-yl-di-tert-butyl-phosphane (2 mol %) in toluene was stirred at 100° C. for 24 h. The reaction was monitored using GC-MS and TLC. After complete consumption of starting material the reaction mixture was diluted with chloroform, filtered and the filtrate was concentrated. Silica gel column chromatography, typically using 5:1 CHCl$_3$-MeOH, of the resulting material afforded the desired product.

The following compounds were synthesized using the general method described above.

Example 351

5-(2-Dimethylamino-ethoxy)-7-methyl-2-(4-trifluoromethoxy-benzyl)-2,3-dihydro-isoindol-1-one

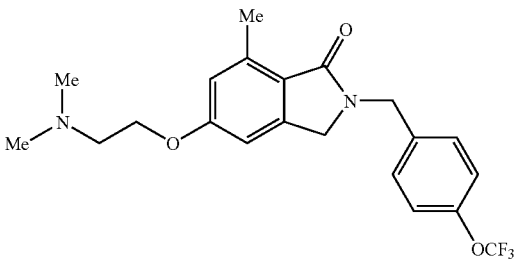

A mixture of 5-bromo-7-methyl-2-(4-trifluoromethoxy-benzyl)-2,3-dihydro-isoindol-1-one (0.078 g, 0.2 mmol), 2-dimethylamino-ethanol (0.04 mL, 0.4 mmol), Pd(OAc)$_2$ (0.001 g, 0.004 mmol), and Cs$_2$CO$_3$ (0.130 g, 0.4 mmol) in toluene (3 mL) was stirred at 100° C. for 24 h. Workup and silica gel column chromatography using 5:1 CHCl$_3$-MeOH afforded 5-(2-dimethylamino-ethoxy)-7-methyl-2-(4-trifluoromethoxy-benzyl)-2,3-dihydro-isoindol-1-one (0.020 g, 25%). $^1$H NMR (300 MHz, CDCl$_3$): δ (ppm) 2.32 (s, 6H), 2.70 (m, 5H), 4.06 (t, 2H), 4.18 (s, 2H), 4.74 (s, 2H), 6.70 (d, 2H), 7.15-7.37 (m, 4H).

Example 352

5-(2-Dimethylamino-ethoxy)-2-(4-trifluoromethoxy-benzyl)-7-trifluoromethyl-2,3-dihydro-isoindol-1-one

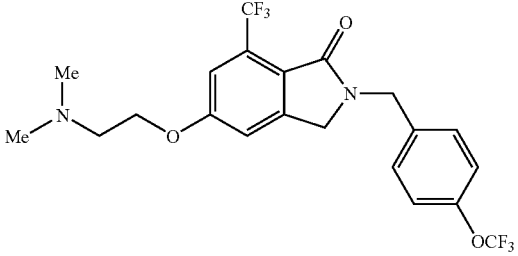

A mixture of 5-bromo-7-trifluoromethyl-2-(4-trifluoromethoxy-benzyl)-2,3-dihydro-isoindol-1-one (0.123 g, 0.3 mmol), 2-dimethylamino-ethanol (0.05 mL, 0.5 mmol), Pd(OAc)$_2$ (0.002 g, 0.006 mmol), and Cs$_2$CO$_3$ (0.195 g, 0.6 mmol) in toluene (3 mL) was stirred at 100° C. for 24 h. Workup and silica gel column chromatography using 5:1 CHCl$_3$-MeOH afforded 5-(2-dimethylamino-ethoxy)-2-(4-trifluoromethoxy-benzyl)-7-trifluoromethyl-2,3-dihydro-isoindol-1-one (0.050 g, 36%). $^1$H NMR (300 MHz, CDCl$_3$):

δ (ppm) 2.35 (s, 6H), 2.73 (t, 2H), 4.13 (t, 2H), 4.23 (s, 2H), 4.74 (s, 2H), 7.04-7.38 (m, 6H).

Example 353

7-Methyl-5-[2-(4-methyl-piperazin-1-yl)-ethoxy]-2-(4-trifluoromethoxy-benzyl)-2,3-dihydro-isoindol-1-one

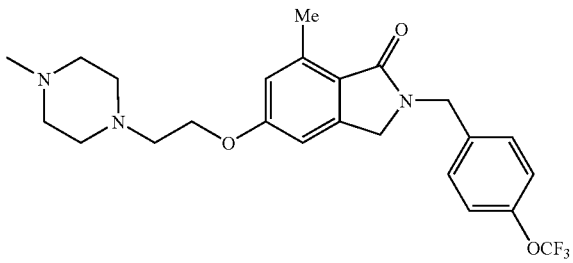

A mixture of 5-bromo-7-methyl-2-(4-trifluoromethoxy-benzyl)-2,3-dihydro-isoindol-1-one (0.120 g, 0.3 mmol), 2-(4-methyl-piperazin-1yl)-ethanol (0.074 mL, 0.6 mmol), Pd(OAc)$_2$ (0.002 g, 0.006 mmol), and Cs$_2$CO$_3$ (0.195 g, 0.6 mmol) in toluene (3 mL) was stirred at 100° C. for 24 h. Workup and silica gel column chromatography using 5:1 CHCl$_3$-MeOH afforded 7-methyl-5-[2-(4-methyl-piperazin-1-yl)-ethoxy]-2-(4-trifluoromethoxy-benzyl)-2,3-dihydro-isoindol-1one (0.025 g, 18%). $^1$H NMR (300 MHz, CDCl$_3$): δ (ppm) 2.49 (bs, 8H), 2.75 (s, 3H), 2.83 (t, 2H), 4.16 (m, 5H), 4.73 (s, 2H), 6.70 (d, 2H), 7.13-7.37 (m, 4H).

Method 13

Step 1: Hydrolysis of Cyanide

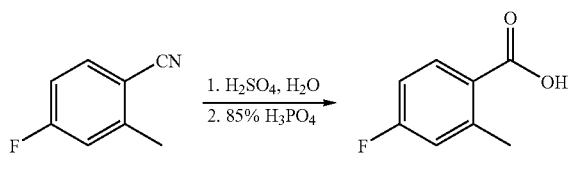

Example 354

4-fluoro-2-methyl-benzoic acid

A solution of 4-fluoro-2-methyl-benzonitrile (5.0 g, 37 mmol), H$_2$SO$_4$ (20 mL) and H$_2$O (15 mL) was stirred at 80° C. for 17 h. The reaction mixture was cooled to ambient temperature and intermediate carboxamide collected as a precipitate. The material was used without purification. The intermediate carboxamide (5.7 g) was treated with 85% phosphoric acid (20 mL) and stirred at 150° C. for 18 h. After this time, the reaction mixture was cooled to ambient temperature and treated with water (30 mL). The resulting solution was extracted with ethyl acetate (2×200 mL). The combined organic extracts were dried over anhydrous MgSO$_4$, filtered, and concentrated to afford 4-fluoro-2-methyl-benzoic acid. The material was without further purification.

Step 2: o-Iodination of Benzoic Acid

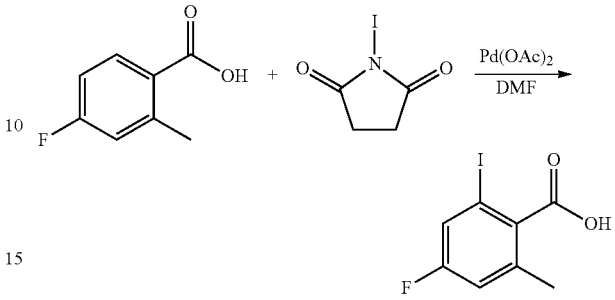

Example 355

4-fluoro-2-iodo-6-methyl-benzoic acid

A mixture of 4-fluoro-2-methyl-benzoic acid (4.90 g, 31.8 mmol,), N-iodosuccinamide (7.87 g, 35 mmol), palladium (II) acetate (0.714 g, 3.18 mmol) and dry DMF (40 mL) was heated under nitrogen atmosphere at 100° C. for 15-36 h. After this time, the reaction mixture was cooled, to ambient temperature and poured into water. The aqueous solution was extracted with ethyl acetate (2×100 mL) and the combined organic extracts washed with aqueous sodium thiosulphate (30 mL) and then brine (30 mL). The remaining organic solution was dried over anhydrous MgSO$_4$, filtered and concentrated to the product. The product was used without further purification.

Step 3: Esterification

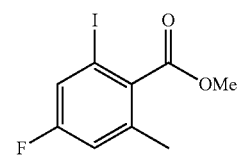

Example 356

4-fluoro-2-iodo-6-methyl-benzoic acid methyl ester

A solution of 4-fluoro-2-iodo-6-methyl-benzoic acid (8.87 g, 31.8 mmol) in acetone (80 mL) was treated with anhydrous K$_2$CO$_3$ (6.91 g, 50 mmol) followed by methyl iodide (2.72 mL, 40 mmol). The reaction mixture was stirred at 70° C. for 2 h. GC-MS and TLC indicated that the reaction was completed. The solids were removed by filtration and the filtrate evaporated under reduced pressure. Silica gel column chromatography of the resulting material using 10% ethyl acetate in hexanes afforded 4-fluoro-2-iodo-6-methyl-benzoic acid methyl ester (1.1 g, 12%).

Step 4: Bromination

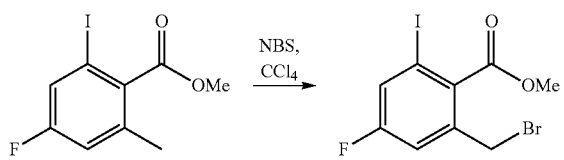

Example 357

2-Bromomethyl-4-fluoro-6-iodo-benzoic acid methyl ester

A mixture of 4-fluoro-2-iodo-6-methyl-benzoic acid methyl ester (1.14 g, 3.74 mmol), N-bromosuccinamide (0.796 g, 4.5 mmol), and benzoyl peroxide (0.024 g, 0.146 mmol) in carbon tetrachloride (50 mL) was heated at reflux until majority of ester was consumed (as analyzed by GC/MS). The resulting mixture was filtered, the filtrate was concentrated to afford 2-bromomethyl-4-fluoro-6-iodo-benzoic acid methyl ester. The material was used without further purification Step 5: Generation of Isoindolones from Bromo-Esters and Amines

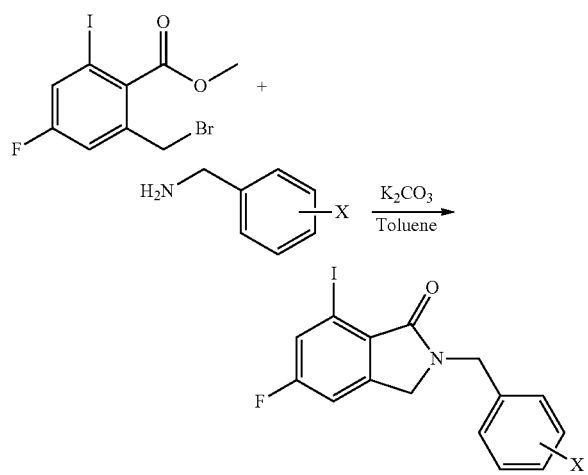

General Procedure

A mixture of the appropriately substituted benzyl amine (1.2 equiv.), the appropriately substituted-2-bromomethyl-benzoic acid methyl ester (1.0 equiv.), and $K_2CO_3$ (2 equiv.) in toluene was heated with stirring at 100° C. for 2 h. The resulting mixture was filtered and the filtrate was concentrated. Silica gel column chromatography of the resulting material using combinations of hexane and ethyl acetate (typically 30% ethyl acetate in hexane) afforded the desired product.

The following compounds were synthesized using the general method described above.

Example 358

5-Fluoro-7-iodo-2-(4-trifluoromethoxy-benzyl)-2,3-dihydro-isoindol-1-one

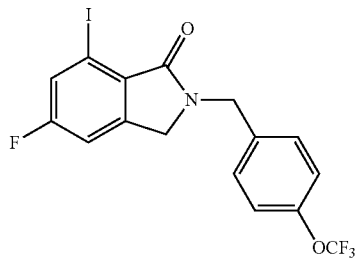

A mixture of 4-trifluoromethoxy-benzyl amine (0.092 mL, 0.6 mmol), 2-bromomethyl-4-fluoro-6-iodo-benzoic acid methyl ester (0.181 g, 0.49 mmol), and $K_2CO_3$ (0.138 g, 1 mmol) in toluene was heated with stirring at 100° C. for 2 h. The resulting mixture was filtered and concentrated. Silica gel column chromatography using 30% ethyl acetate in hexane afforded 5-fluoro-7-iodo-2-(4-trifluoromethoxy-benzyl)-2,3-dihydro-isoindol-1-one (0.080 g, 36%). $^1$H NMR (300 MHz, CDCl$_3$): δ (ppm) 4.19 (s, 2H), 4.79 (s, 2H), 7.06-7.38 (m, 5H), 7.67 (d, 1H). GC-MS: m/z 451 (M)$^+$, 382 (M−69)$^+$.

Example UR-31

5-Fluoro-7-iodo-2-(4-chloro-benzyl)-2,3-dihydro-isoindol-1-one

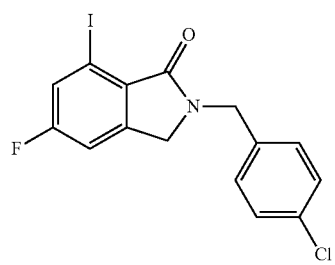

A mixture of 4-chloro-benzyl amine (1.3 mmol), 2-bromomethyl-4-fluoro-6-iodo-benzoic acid methyl ester (0.374 g, 1.0 mmol), and $K_2CO_3$ (0.277 g, 2 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-chloro-benzyl)-2,3-dihydro-isoindol-1-one (0.204 g, 50%). $^1$H NMR (300 MHz, CDCl$_3$): δ (ppm)

4.15 (s, 2H), 4.74 (s, 2H), 7.10 (d, 1H), 7.23-7.33 (m, 4H), 7.67 (d, 11H). GC-MS: m/z 401 (M)+.

Example UR-32

5-Fluoro-7-iodo-2-(4-ethyl-benzyl)-2,3-dihydro-isoindol-1-one

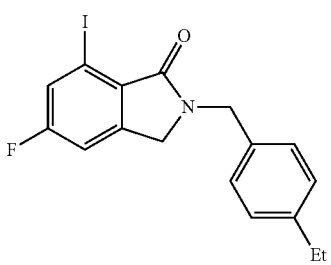

A mixture of 4-ethyl-benzyl amine (1.3 mmol), 2-bromomethyl-4-fluoro-6-iodo-benzoic acid methyl ester (0.374 g, 1.0 mmol), and K$_2$CO$_3$ (0.277 g, 2 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-ethyl-benzyl)-2,3-dihydro-isoindol-1-one (0.184 g, 47%). $^1$H NMR (300 MHz, CDCl$_3$): δ (ppm) 1.20 (t, 3H), 2.65 (q, 2H), 4.16 (s, 2H), 4.74 (s, 2H), 7.10 (d, 1H), 7.23-7.33 (m, 4H), 7.63 (d, 1H). GC-MS: m/z 395 (M)+.

Example UR-33

2-Cyclopropyl methyl-5-Fluoro-7-iodo-2,3-dihydro-isoindol-1-one

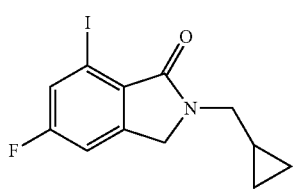

A mixture of cyclopropyl-methylamine (1.3 mmol), 2-bromomethyl-4-fluoro-6-iodo-benzoic acid methyl ester (0.374 g, 1.0 mmol), and K$_2$CO$_3$ (0.277 g, 2 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-ethyl-benzyl)-2,3-dihydro-isoindol-1-one (0.090 g, 27%). $^1$H NMR (300 MHz, CDCl$_3$): δ (ppm) 0.32 (m, 2H), 0.60 (m, 2H), 1.05 (m, 1H), 3.46 (d, 2H), 4.38 (s, 2H), 7.16 (d, 1H), 7.64 (d, 1H). GC-MS: m/z 331 (M)+ 0.316 (M−15)+.

Example UR-41

5-Fluoro-7-iodo-2-(4-cyano-benzyl)-2,3-dihydro-isoindol-1-one

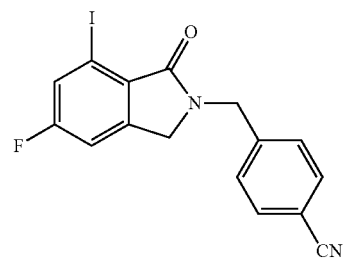

A mixture of 4-cyano-benzyl amine (0.218 g, 1.3 mmol), 2-bromomethyl-4-fluoro-6-iodo-benzoic acid methyl ester (0.374 g, 1.0 mmol), and K$_2$CO$_3$ (0.277 g, 2 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-cyano-benzyl)-2,3-dihydro-isoindol-1-one (0.160 g, 41%). $^1$H NMR (300 MHz, CDCl$_3$): δ (ppm) 4.19 (s, 2H), 4.83 (s, 2H), 7.13 (d, 1H), 7.42 (d, 2H), 7.64 (m, 3H). GC-MS: m/z 392 (M)$_4$.

Example UR-43

5-Fluoro-7-iodo-2-[1-(4-trifluoromethoxy-phenyl)-ethyl]-2,3-dihydro-isoindol-1-one

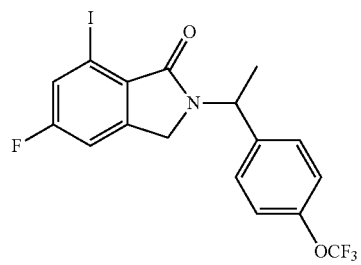

A mixture of 1-(4-trifluoromethoxy-phenyl)-ethylamine (0.246 mL, 1.2 mmol), 2-bromomethyl-4-fluoro-6-iodo-benzoic acid methyl ester (0.372 g, 1.0 mmol), and K$_2$CO$_3$ (0.276 g, 2 mmol) in toluene (3 mL) was heated with stirring at 100° C. for 2 h. The resulting mixture was filtered and concentrated. Silica gel column chromatography using 30% ethyl acetate in hexane afforded 5-Fluoro-7-iodo-2-[1-(4-trifluoromethoxy-phenyl)-ethyl]-2,3-dihydro-isoindol-1-one (0.192 g, 41%). $^1$H NMR (300 MHz, CDCl$_3$): δ (ppm) 1.68

(d, 3H), 3.88-4.26 (dd, 2H), 5.78 (q, 1H), 7.06 (d, 1H), 7.20 (d, 2H), 7.41 (d, 2H), 7.67 (d, 1H). GC-MS: m/z 465 (M)$^+$, 450 (M–15)$^+$.

Example UR-45

5-Fluoro-7-iodo-2-(4-trifluoromethyl-benzyl)-2,3-dihydro-isoindol-1-one

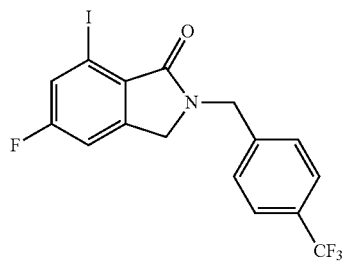

A mixture of 4-trifluoromethyl-benzyl amine (0.142 mL, 1.0 mmol), 2-bromomethyl-4-fluoro-6-iodo-benzoic acid methyl ester (0.270 g, 0.73 mmol), and K$_2$CO$_3$ (0.207 g, 1.5 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-trifluoromethyl-benzyl)-2,3-dihydro-isoindol-1-one (0.110 g, 35%). $^1$H NMR (300 MHz, CDCl$_3$): δ (ppm) 4.18 (s, 2H), 4.84 (s, 2H), 7.10 (d, 1H), 7.42 (d, 2H), 7.60 (m, 2H), 7.66 (d, 1H). GC-MS: m/z 435 (M)$^+$, 416 (M–19)$^+$.

Example UTR-46

5-Fluoro-7-iodo-2-(4-difluoromethoxy-benzyl)-2,3-dihydro-isoindol-1-one

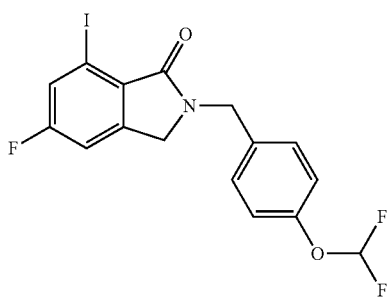

A mixture of 4-difluoromethoxy-benzyl amine (0.173 g, 1.0 mmol), 2-bromomethyl-4-fluoro-6-iodo-benzoic acid methyl ester (0.270 g, 0.73 mmol), and K$_2$CO$_3$ (0.207 g, 1.5 mmol) in toluene (4 mL) was heated with stirring at 100° C. for 2 h. The resulting mixture was filtered and concentrated. Silica gel column chromatography using 30% ethyl acetate in hexane afforded 5-fluoro-7-iodo-2-(4-difluoromethoxy-benzyl)-2,3-dihydro-isoindol-1-one (0.110 g, 35%). $^1$H NMR (300 MHz, CDCl$_3$): δ (ppm) 4.18 (s, 2H), 4.84 (s, 2H), 6.52 (t, 1H), 7.10 (m, 3H), 7.28 (d, 2H), 7.64 (d, 1H). GC-MS: m/z 433 (M)$^+$.

Generation of Isoidolones from Bromo-Esters and Amines

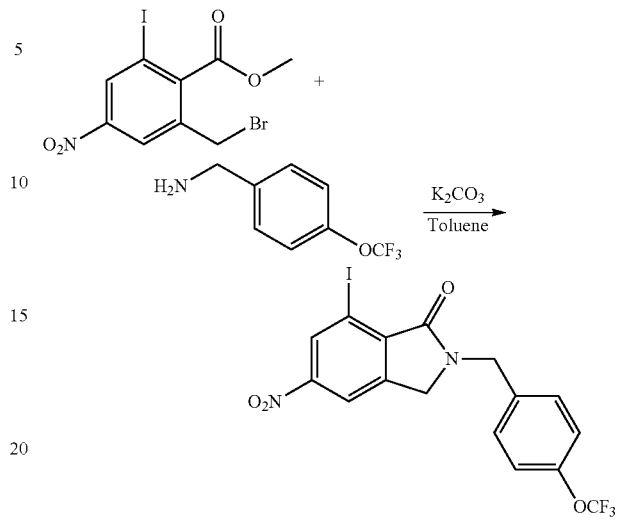

Example UR-17

5-nitro-7-iodo-2-(4-trifluoromethoxy-benzyl)-2,3-dihydro-isoindol-1-one

A mixture of 4-trifluoromethoxy-benzyl amine (0.586 mL, 3.84 mmol), 2-bromomethyl-4-nitro-6-iodo-benzoic acid methyl ester (1.18 g, 2.95 mmol), and K$_2$CO$_3$ (0.815 g, 0.815 mmol) in toluene (7 mL) was heated with stirring at 100° C. for 2 h. The resulting mixture was filtered and concentrated. Silica gel column chromatography using 30% ethyl acetate in hexane afforded 5-nitro-7-iodo-2-(4-trifluoromethoxy-benzyl)-2,3-dihydro-isoindol-1-one (0.144 g, 10%). $^1$H NMR (300 MHz, CDCl$_3$): δ (ppm) 4.31 (s, 2H), 4.82 (s, 2H), 7.19 (d, 2H), 7.38 (d, 2H), 8.24 (s, 1H), 8.78 (s, 1H). GC-MS: m/z 478 (M)$^+$, 409 (M–69)$^+$.

Generation of Isoindolones from Bromo-Esters and Amines

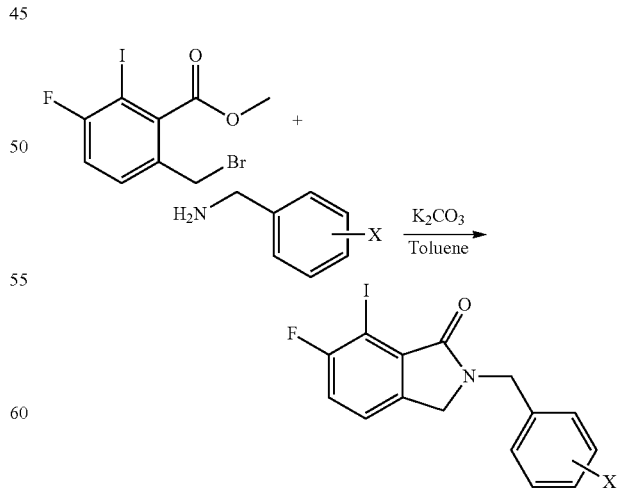

General Procedure

A mixture of the appropriately substituted benzyl amine (1.2 equiv.), the appropriately substituted-2-bromomethyl-

Example UR-28

6-Fluoro-7-iodo-2-(4-trifluoromethoxy-benzyl)-2,3-dihydro-isoindol-1-one

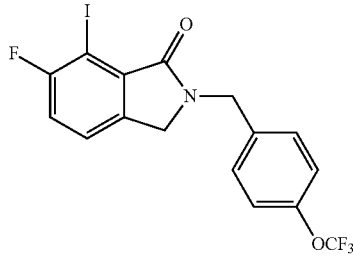

A mixture of 4-trifluoromethoxy-benzyl amine (0.763 mL, 5.0 mmol), 2-bromomethyl-5-fluoro-6-iodo-benzoic acid methyl ester (1.49 g, 4.0 mmol), and K$_2$CO$_3$ (0.828 g, 1 mmol) in toluene (7 mL) was heated with stirring at 100° C. for 2 h. The resulting mixture was filtered and concentrated. Silica gel column chromatography using 30% ethyl acetate in hexane afforded 6-fluoro-7-iodo-2-(4-trifluoromethoxy-benzyl)-2,3-dihydro-isoindol-1-one (0.717 g, 40%). $^1$H NMR (300 MHz, CDCl$_3$): δ (ppm) 4.18 (s, 2H), 4.79 (s, 2H), 7.14-7.38 (m, 6H). GC-MS: m/z 451 (M)$^+$, 366 (M−85)$^+$.

Example UR-39

6-Fluoro-7-iodo-2-(4-cyano-benzyl)-2,3-dihydro-isoindol-1-one

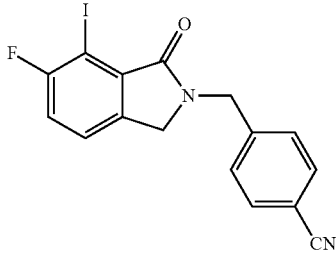

A mixture of 4-cyano-benzyl amine hydrochloride (0.218 g, 5.0 mmol), 2-bromomethyl-5-fluoro-6-iodo-benzoic acid methyl ester (0.373 g, 1.0 mmol), and K$_2$CO$_3$ (0.276 g, 2 mmol) in toluene (4 mL) was heated with stirring at 100° C. for 2 h. The resulting mixture was filtered and concentrated. Silica gel column chromatography using 30% ethyl acetate in hexane afforded 6-fluoro-7-iodo-2-(4-cyano-benzyl)-2,3-dihydro-isoindol-1-one (0.100 g, 26%). $^1$H NMR (300 MHz, CDCl$_3$): δ (ppm) 4.19 (s, 2H), 4.84 (s, 2H), 7.22-7.68 (m, 6H). GC-MS: m/z 392 (M)$^+$.

Method: Generation of Isoindolone by Reaction of Bromo Esters and aq. Ammonium Hydroxide

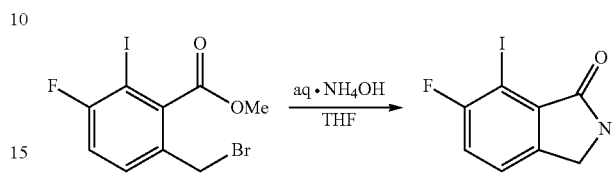

Example

6-Fluoro-7-iodo-2,3-dihydro-isoindol-1-one

A solution of 2-bromomethyl-5-fluoro-6-iodo-benzoic acid methyl ester (0.373 g, 1.0 mmol), in THF (4 mL) was treated with 30% aq. Ammonium hydroxide (0.256 mL, 2.2 mmol) and heated with stirring at 100° C. for 2 h. After this time, the resulting mixture was concentrated. Silica gel column chromatography using 30% ethyl acetate in hexane afforded 6-fluoro-7-iodo-2,3-dihydro-isoindol-1-one (0.070 g, 25%). GC-MS: m/z 277 (M)$^+$, 249 (M−28)$^+$.

Example UR-40

6-Fluoro-7-iodo-2-(2-cyano-benzyl)-2,3-dihydro-isoindol-1-one

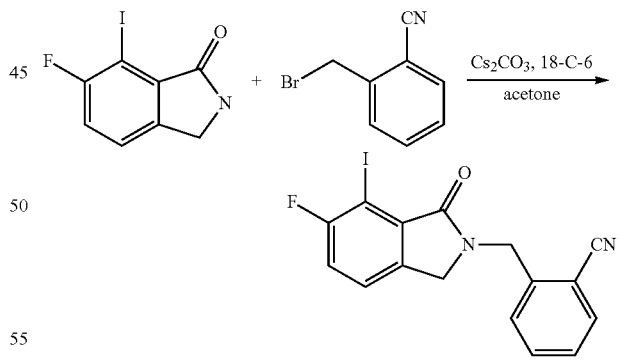

A mixture of 6-fluoro-7-iodo-2,3-dihydro-isoindol-1-one (0.070 g, 0.25 mmol), 1-bromomethyl-2-cyano-benzene (0.059 g, 0.3 mmol), Cs$_2$CO$_3$ (0.098 g, 0.3 mmol), and 18-crown-6 (0.007 g, 0.025 for mmol) in acetone (5 mL) was stirred at 70° C. for 2 h. Workup and silica gel column chromatography using 30% ethyl acetate in hexane afforded 6-fluoro-7-iodo-2-(2-cyano-benzyl)-2,3-dihydro-isoindol-1-one (0.040 g, 41%). $^1$H NMR (300 MHz, CDCl$_3$): δ (ppm) 4.33 (s, 2H), 5.04 (s, 2H), 7.04-7.71 (m, 6H), GC-MS: m/z 392 (M)$^+$.

Method
Difluoro and Trifluoro Ethoxy Substituted Isoindolones

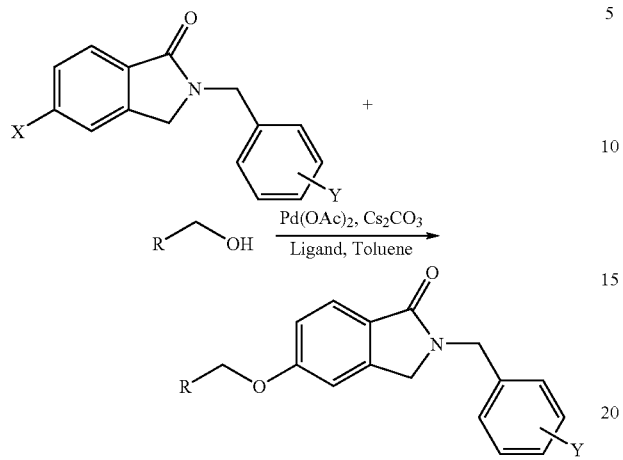

General Method:

A mixture of appropriately substituted isoindolone (1 equiv.), palladium(II) acetate (0.02 equiv.), rac-2-(di-t-butylphosphino)-1,1'-binaphthyl (0.025 equiv.), and cesium carbonate (1.5 equiv.) in toluene was treated with appropriately substituted ethanol (2 equiv.) and stirred at 110° C. for 8-12 h. After this time the solvent was evaporated and silica gel column chromatography using, typically 30% ethyl acetate in hexane, afforded the desired product.

The following compounds were synthesized using the general method described above.

Example UR-66

5-(2,2-Difluoro-ethoxy)-7-methyl-2-(4-trifluoromethoxy-benzyl)-2,3-dihydro-isoindol-1-one

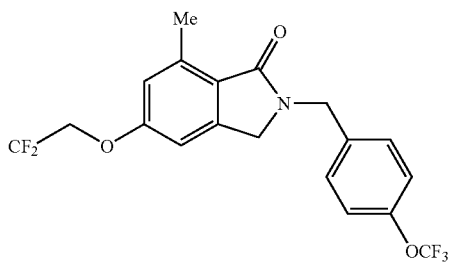

A mixture of 5-bromo-7-methyl-2-(4-trifluoromethoxy-benzyl)-2,3-dihydro-isoindol-1-one (0.400 g, 1 mmol), palladium(II) acetate (0.004 g, 0.02 mmol), rac-2-(di-t-butylphosphino)-1,1'-binaphthyl (0.009 g, 0.025 mmol), and cesium carbonate (0.488 g, 1.5 mmol) in toluene (5 mL) was treated with 2,2-difluoro ethanol (0.164 mL, 2 mmol) and stirred at 110° C. for 8-12 h. After this time the solvent was evaporated and silica gel column chromatography using, typically 30% ethyl acetate in hexane, afforded the desired product (0.082 g, 20%). $^1$H NMR (300 MHz, CDCl$_3$): δ (ppm) 2.74 (s, 3H), 4.22 (m, 4H), 4.73 (s, 2H), 5.94-6.32 (m, 1H), 6.75 (d, 2H), 7.18 (d, 2H), 7.35 (d, 2H). GC-MS: m/z 401 (M)$^+$, 316 (M−85)$^+$.

Example UR-68

5-(2,2-Difluoro-ethoxy)-7-chloro-2-(4-trifluoromethoxy-benzyl)-2,3-dihydro-isoindol-1-one

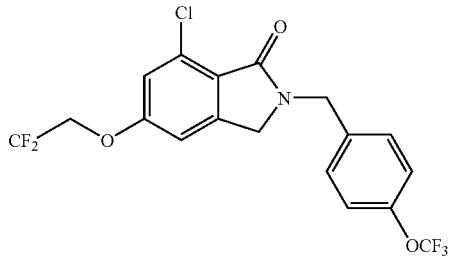

A mixture of 5-bromo-7-chloro-2-(4-trifluoromethoxy-benzyl)-2,3-dihydro-isoindol-1-one (0.126 g, 1 mmol), palladium(II) acetate (0.004 g, 0.02 mmol), rac-2-(di-t-butylphosphino)-1,1'-binaphthyl (0.009 g, 0.025 mmol), and cesium carbonate (0.163 g, 0.5 mmol) in toluene (5 mL) was treated with 2,2-difluoro ethanol (0.05 mL, 0.6 mmol) and stirred at 110° C. for 0.12 h. After this time the solvent was evaporated and silica gel column chromatography using, typically 30% ethyl acetate in hexane, afforded the desired product (0.06 g, 50%). $^1$H NMR (300 MHz, CDCl$_3$): δ (ppm) 4.21 (m, 4H), 4.76 (s, 2H), 5.94-6.32 (m, 1H), 6.82 (s, 1H), 6.97 (s, 1H), 7.18 (d, 2H), 7.35 (d, 2H). GC-MS: m/z 421 (M)$^+$.

Example UR-69

5-(2,2,2-trifluoro-ethoxy)-7-chloro-2-(4-trifluoromethoxy-benzyl)-2,3-(hydro-isoindol-1-one

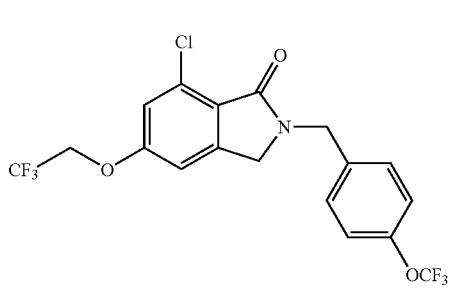

A mixture of 5-bromo-7-chloro-2-(4-trifluoromethoxy-benzyl)-2,3-dihydro-isoindol-1-one (0.126 g, 0.3 mmol), palladium(II) acetate (0.004 g, 0.02 mmol), rac-2-(di-t-butylphosphino)-1,1'-binaphthyl (0.009 g, 0.025 mmol), and cesium carbonate (0.163 g, 0.5 mmol) in toluene (5 mL) was treated with 2,2,2-trifluoro ethanol (0.045 mL, 0.45 mmol) and stirred at 110° C. for 12 h. After this time the solvent was evaporated and silica gel column chromatography using, typically 30% ethyl acetate in hexane, afforded the desired product (0.048 g, 37%). ¹H NMR (300 MHz, CDCl₃): δ (ppm) 4.21 (s, 2H), 4.39 (q, 2H), 4.76 (s, 2H), 6.86 (s, 1H), 6.97 (s, 1H), 7.34 (d, 2H). GC-MS: m/z 439 (M)+0.354, (M−85)⁺.

Example UR-70

5-(2,2-Difluoro-ethoxy)-7-chloro-2-(4-chloro-benzyl)-2,3-dihydro-isoindol-1-one

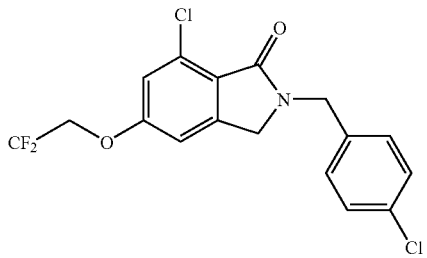

A mixture of 5-bromo-7-chloro-2-(4-chloro-benzyl)-2,3-dihydro-isoindol-1-one (0.110 g, 0.297 mmol), palladium(II) acetate (0.004 g, 0.02 mmol), rac-2-(di-t-butylphosphino)-1,1'-binaphthyl (0.009 g, 0.025 mmol), and cesium carbonate (0.163 g, 0.5 mmol) in toluene (5 mL) was treated with 2,2-difluoro ethanol (0.05 mL, 0.6 mmol) and stirred at 110° C. for 12 h. After this time the solvent was evaporated and silica gel column chromatography using, typically 30% ethyl acetate in hexane, afforded the desired product (0.055 g, 50%). ¹H NMR (300 MHz, CDCl₃): δ (ppm) 4.14-4.26 (m, 4H), 4.72 (s, 2H), 5.92-6.32 (m, 1H), 6.82 (s, 1H), 6.97 (s, 1H), 7.23-7.33 (m, 4H). GC-MS: m/z 371 (M)⁺, 336 (M−35)⁺.

Example UR-71

5-(2,2,2-trifluoro-ethoxy)-7-chloro-2-(4-chloro-benzyl)-2,3-dihydro-isoindol-1-one

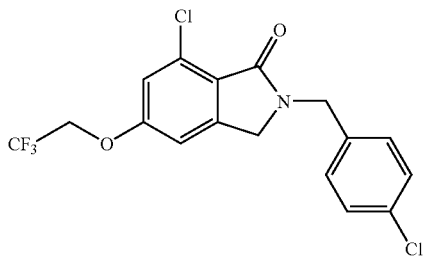

A mixture of 5-bromo-7-chloro-2-(4-chloro-benzyl)-2,3-dihydro-isoindol-1-one (0.110 g, 0.298 mmol), palladium(II) acetate (0.004 g, 0.02 mmol), rac-2-(di-t-butylphosphino)-1,1'-binaphthyl (0.009 g, 0.025 mmol), and cesium carbonate (0.163 g, 0.5 mmol) in toluene (5 mL) was treated with 2,2,2-trifluoro ethanol (0.061 mL, 0.6 mmol) and stirred at 110° C. for 12 h. After this time the solvent was evaporated and silica gel column chromatography using, typically 30% ethyl acetate in hexane, afforded the desired product (0.040 g, 34%). ¹H NMR (300 MHz, CDCl₃): δ (ppm) 4.19 (s, 2H), 4.39 (q, 2H), 4.73 (s, 2H), 6.86 (s, 1H), 6.98 (s, 1H), 7.23 (d, 2H), 7.34 (d, 2H). GC-MS: m/z 389 (M)⁺0.354, (M−35)⁺.

Example UR-75

5-(2,2,2-trifluoro-ethoxy)-7-chloro-2-(4-bromo-benzyl)-2,3-dihydro-isoindol-1-one

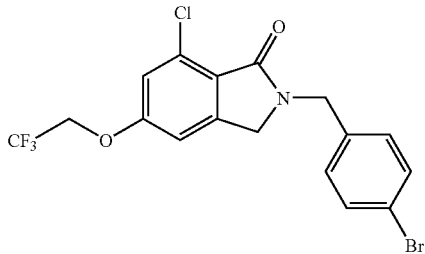

A mixture of 5,7-dichloro-2-(4-bromo-benzyl)-2,3-dihydro-isoindol-1-one (0.148 g, 0.4 mmol), palladium(II) acetate (0.004 g, 0.02 mmol), rac-2-(di-t-butylphosphino)-1,1'-binaphthyl (0.009 g, 0.025 mmol), and cesium carbonate (0.228 g, 0.7 mmol) in toluene (5 mL) was treated with 2,2,2-trifluoro ethanol (0.082 μL, 0.8 mmol) and stirred at 110° C. for 12 h. After this time the solvent was evaporated and silica gel column chromatography using, typically 30% ethyl acetate in hexane, afforded the desired product (0.110 g, 64%). ¹H NMR (300 MHz, CDCl₃): δ (ppm) 4.02 (s, 2H), 4.53 (m, 4H), 6.86 (s, 1H), 6.91 (s, 1H), 6.93 (d, 2H), 7.37 (d, 2H). GC-MS: m/z 435 (M)⁺.

Example UR-76

5-(2,2,2-trifluoro-ethoxy)-7-methyl-2-(4-chloro-benzyl)-2,3-dihydro-isoindol-1-one

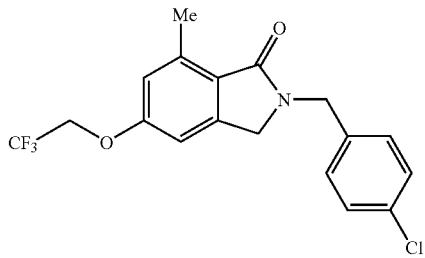

A mixture of 5-iodo 7-methyl-2-(4-chloro-benzyl)-2,3-dihydro-isoindol-1-one (0.148 g, 0.4 mmol), palladium(II) acetate (0.004 g, 0.02 mmol), rac-2-(di-t-butylphosphino)-1,1'-binaphthyl (0.009 g, 0.025 mmol), and cesium carbonate (0.156 g, 0.48 mmol) in toluene (5 mL) was treated with 2,2-difluoro ethanol (0.03 g, 0.36 mmol) and stirred at 110° C. for 12 h. After this time the solvent was evaporated and silica gel column chromatography using, typically 30% ethyl acetate in hexane, afforded the desired product (0.047 g, 56%). ¹H NMR (300 MHz, CDCl₃): δ (ppm) 4.12-4.26 (m, 4H), 4.68 (s, 2H), 5.86-6.24 (m, 1H), 6.70 (d, 2H), 7.16-7.37 (m, 4H). GC-MS: m/z 351 (M)+, 316 (M−35)+.

Method 14

Methoxylation

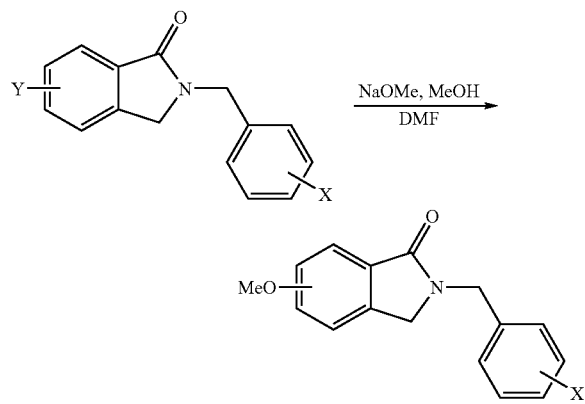

General Procedure

A solution of appropriately substituted isoindolones (1 equiv.) in methanol was treated with a solution of 30% sodium methoxide-methanol and DMF. The mixture was stirred at 100° C. for 1 h. After cooling the reaction mixture was diluted with ethyl acetate and washed with water. The organic layer was separated, dried over anhydrous MgSO_4, filtered and concentrated. Silica gel column chromatography using, typically 30% ethyl acetate in hexane, afforded the desired product.

The following compounds were synthesized using general method 14 described above.

Example 359

7-Iodo-5-methoxy-2-(4-trifluoromethoxy-benzyl)-2,3-dihydro-isoindol-1-one

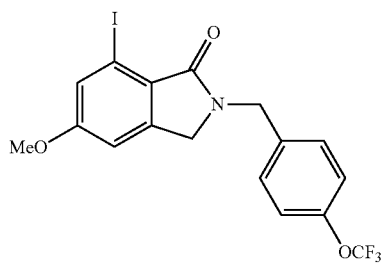

A mixture of 5-fluoro-7-iodo-2-(4-trifluoromethoxy-benzyl)-2,3-dihydro-isoindol-1-one (0.226 g, 0.5 mmol), 30% sodium methoxide-methanol (0.7 mL) and DMF (0.12 mL) was stirred at 100° C. for 1 h. Workup and silica gel column chromatography using 30% ethyl acetate in hexane afforded 7-iodo-5-methoxy-2-(4-trifluoromethoxy-benzyl)-2,3-dihydro-isoindol-1-one (0.071 g, 31%). $^1$H NMR (300 MHz, CDCl_3): δ (ppm) 3.83 (s, 3H), 4.12 (s, 2H), 4.75 (s, 2H), 6.87 (bs, 1H), 7.17 (d, 2H), 7.33 (d, 2H), 7.44 (bs, 1H). GC-MS: m/z 463 (M)+, 394 (M−69)+, 378 (M−85)+.

Example 360

2-Benzyl-5-methoxy-2,3-dihydro-isoindol-1-one

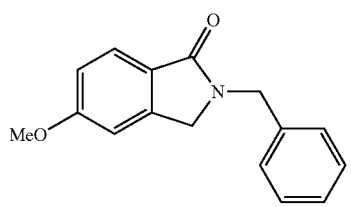

A mixture of 2-benzyl-5-bromo-2,3-dihydro-isoindol-1-one (0.065 g, 0.22 mmol), 30% sodium methoxide-methanol (0.06 mL, 0.33 mmol), and CuBr (0:004 g, 0.03 mmol) in methanol (4 mL) was stirred at 100° C. for 1 h. Workup and silica gel column chromatography using 30% ethyl acetate in hexane afforded 2-benzyl-5-methoxy-2,3-dihydro-isoindol-1-one (0.03 g, 54%). $^1$H NMR (300 MHz, CDCl_3): δ (ppm) 3.86 (s, 3H), 4.22 (s, 2H), 4.78 (s, 2H), 6.82-7.29 (m, 7H), 7.79 (d, 1H).

Example UR-2

7-methyl-5-methoxy-2-(4-trifluoromethoxy-benzyl)-2,3-dihydro-isoindol-1-one

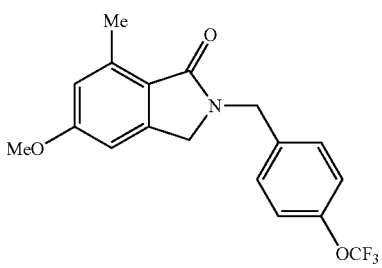

A mixture of 7-methyl-5-bromo-2-(4-trifluoromethoxy-benzyl)-2,3-dihydro-isoindol-1-one (0.100 g, 0.25 mmol), 30% sodium methoxide-methanol (0.5 mL), and CuBr (0.005 g, 0.04 mmol) in methanol (4 mL) was stirred at 100° C. for 1 h. Workup and silica gel column chromatography using 30% ethyl acetate in hexane afforded 7-methyl-5-methoxy-2-(4-trifluoromethoxy-benzyl)-2,3-dihydro-isoindol-1-one (0.035 g, 41%). ¹H NMR (300 MHz, CDCl₃): δ (ppm) 2.80 (s, 3H), 3.91 (s, 3H), 4.26 (s, 2H), 4.83 (s, 2H), 6.82 (d, 2H), 7.26 (d, 2H), 7.42 (d, 2H).

Example UR-5

7-trifluoromethyl-5-methoxy-2-(4-trifluoromethoxy-benzyl)-2,3-dihydro-isoindol-1-one

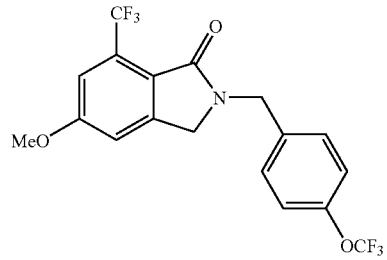

A mixture of 7-trifluoromethyl-5-bromo-2-(4-trifluoromethoxy-benzyl)-2,3-dihydro-isoindol-1-one (0.060 g, 0.15 mmol), and 30% sodium methoxide-methanol (0.21 mL) in methanol (4 mL) was stirred at 100° C. for 1 h. Workup and silica gel column chromatography using 30% ethyl acetate in hexane afforded 7-trifluoromethyl-5-methoxy-2-(4-trifluoromethoxy-benzyl)-2,3-dihydro-isoindol-1-one (0.043 g, 70%). ¹H NMR (300 MHz, CDCl₃): δ (ppm) 3.88 (s, 3H), 4.25 (s, 2H), 4.76 (s, 2H), 7.02 (s, 1H), 7.17 (d, 2H), 7.28 (s, 1H), 7.37 (d, 2H).

Example UR-72

5-(2,2-Difluoro-ethoxy)-7-methoxy-2-(4-trifluoromethoxy-benzyl)-2,3-dihydro-isoindol-1-one

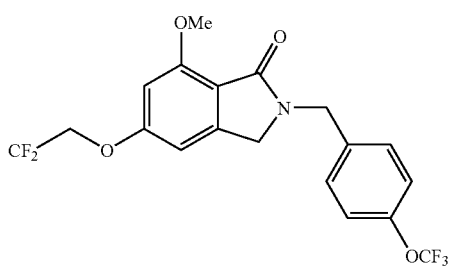

A mixture of 7-chloro-5-(2,2-Difluoro-ethoxy)-2-(4-trifluoromethoxy-benzyl)-2,3-dihydro-isoindol-1-one (0.057 g, 0.14 mmol), and 30% sodium methoxide-methanol (0.12 mL) in methanol (4 mL) was stirred at 100° C. for 1 h. Workup and silica gel column chromatography using 30% ethyl acetate in hexane afforded 5-(2,2-Difluoro-ethoxy)-7-methoxy-2-(4-trifluoromethoxy-benzyl)-2,3-dihydro-isoindol-1-one (0.030 g, 51%). ¹H NMR (300 MHz, CDCl₃): δ (ppm) 3.96 (s, 3H), 4.22 (m, 4H), 4.73 (s, 2H), 5.94-6.32 (m, 1H), 6.45 (d, 2H), 7.17 (d, 2H), 7.35 (d, 2H). GC-MS: m/z 417 (M)⁺, 399 (M−18)⁺.

Example UR-73

5-(2,2,2-trifluoro-ethoxy)-7-methoxy-2-(4-trifluoromethoxy-benzyl)-2,3-dihydro-isoindol-1-one

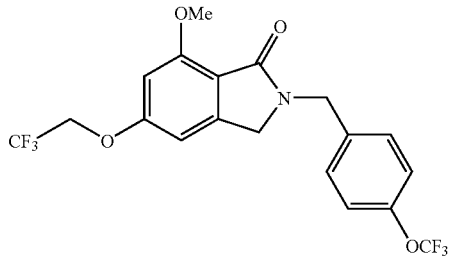

A mixture of 7-chloro-5-(2,2,2-trifluoro-ethoxy)-2-(4-trifluoromethoxy-benzyl)-2,3-dihydro-isoindol-1-one (0.025 g, 0.06 mmol), and 300% sodium methoxide-methanol (0.06 mL) in methanol (4 mL) was stirred at 100° C. for 1 h. Workup and silica gel column chromatography using 30% ethyl acetate in hexane afforded 5-(2,2,2-trifluoro-ethoxy)-7-methoxy-2-(4-trifluoromethoxy-benzyl)-2,3-dihydro-isoindol-1-one (0.030 g, 51%). ¹H NMR (300 MHz, CDCl₃): δ (ppm) 3.73 (s, 3H), 4.02 (s, 2H), 4.22 (q, 2H), 4.54 (s, 2H), 6.32 (m, 2H), 6.94 (d, 2H), 7.17 (d, 2H). GC-MS: m/z 435 (M)⁺, 417 (M−18)⁺.

Method 15

Preparation of Chloro-Isoindolones

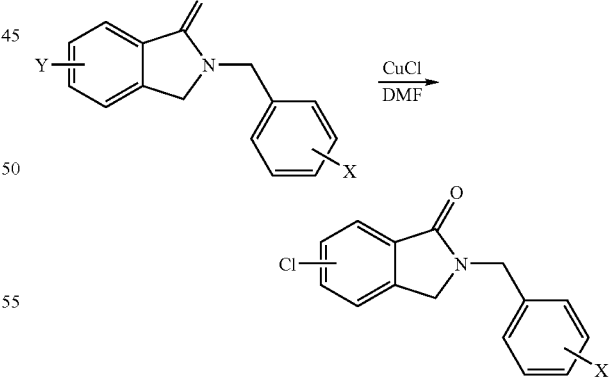

General Procedure

A solution of the appropriately substituted isoindolone (1 equiv.) in DMF was treated with CuCl (4 equiv.) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded the desired product.

The following compounds were synthesized using the general method described above.

Example 361

5,7-Dichloro-2-(4-trifluoromethoxy-benzyl)-2,3-dihydro-isoindol-1-one

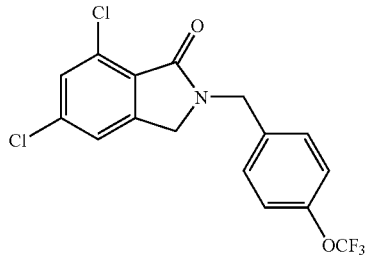

A mixture of 5-bromo-7-chloro-2-(4-trifluoromethoxy-benzyl)-2,3-dihydro-isoindol-1-one (0.100 g, 0.24 mmol) and CuCl (0.099 g, 1 mmol) in DMF (3 mL) was stirred at 140° C. for 2 h. Workup and silica gel column chromatography using combinations 30% ethyl acetate in hexane afforded 5,7-dichloro-2-(4-trifluoromethoxy-benzyl)-2,3-dihydro-isoindol-1-one (0.090 g, 100%). H NMR (300 MHz, CDCl$_3$): δ (ppm) 4.22 (s, 2H), 4.78 (s, 2H), 7.17-7.44 (m, 6H). GC-MS: m/z 376 (M)$^+$.

Example 362

5-Fluoro-7-chloro-2-(4-trifluoromethoxy-benzyl)-2,3-dihydro-isoindol-1-one

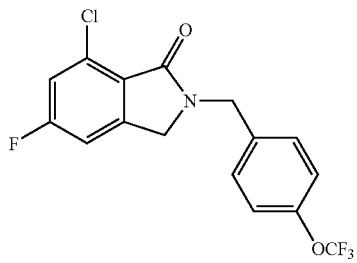

A mixture of 5-fluoro-7-iodo-2-(4-trifluoromethoxy-benzyl)-2,3-dihydro-isoindol-1-one (0.065 g, 0.14 mmol) and CuCl (0.049 g, 0.56 mmol) in DMF (3 mL) was stirred at 140° C. for 2 h. Workup and silica gel column chromatography using combinations 30% ethyl acetate in hexane afforded 5-fluoro-7-chloro-2-(4-trifluoromethoxy-benzyl)-2,3-dihydro-isoindol-1-one (0.030 g, 60%). $^1$H NMR (300 MHz, CDCl$_3$): δ (ppm) 4.23 (s, 2H), 4.75 (s, 2H), 7.01 (dd, 1H), 7.15 (m, 3H), 7.34 (d, 2H). GC-MS: m/z 359 (M)$^+$, 274 (M−85)$^+$.

Example 363

7-chloro-5-methoxy-2-(4-trifluoromethoxy-benzyl)-2,3-dihydro-isoindol-1-one

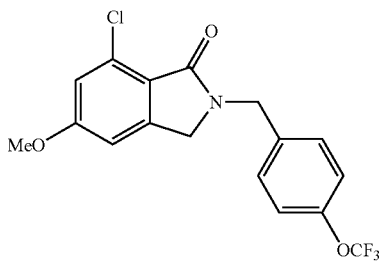

A mixture of 7-iodo-5-methoxy-2-(4-trifluoromethoxy-benzyl)-2,3-dihydro-isoindol-1-one (0.055 g, 0.12 mmol) and CuCl (0.059 g, 0.6 mmol) in DMF (3 mL) was stirred at 140° C. for 2 h. Workup and silica gel column chromatography using combinations 30% ethyl acetate in hexane afforded 7-chloro-5-methoxy-2-(4-trifluoromethoxy-benzyl)-2,3-dihydro-isoindol-1-one (0.018 g, 40%). $^1$H NMR (300 MHz, CDCl$_3$): δ (ppm) 3.83 (s, 3H), 4.19 (s, 2H), 4.74 (s, 2H), 6.78 (s, 1H), 6.92 (s, 1H), 7.18 (d, 2H), 7.34 (d, 2H). GC-MS: m/z 371 (M)$^+$, 302 (M−69)$^+$.

Example UR-22

5,7-Dichloro-2-(4-chloro-benzyl)-2,3-dihydro-isoindol-1-one

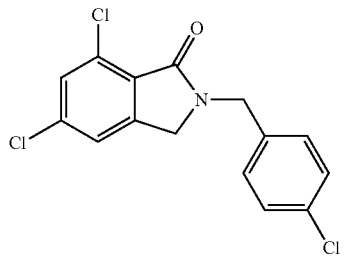

A mixture of 5-bromo-7-chloro-2-(4-chloro-benzyl)-2,3-dihydro-isoindol-1-one (0.100 g, 0.27 mmol) and CuCl (0.112 g, 1.13 mmol) in DMF (3 mL) was stirred at 140° C. for 2 h. Workup and silica gel column chromatography using combinations 30% ethyl acetate in hexane afforded 5,7-dichloro-2-(4-chloro-benzyl)-2,3-dihydro-isoindol-1-one (0.062 g, 70%). $^1$H NMR (300 MHz, CDCl$_3$): δ (ppm) 4.21 (s, 2H), 4.73 (s, 2H), 7.23-7.44 (m, 6H). GC-MS: m/z 326 (M)$^+$, 290 (M−36)$^+$.

Example UR-18

5,7-Dichloro-2-(4-methoxy-benzyl)-2,3-dihydro-isoindol-1-one

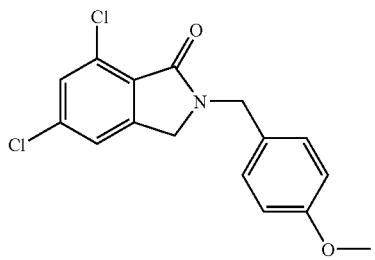

A mixture of 5-bromo-7-chloro-2-(4-methoxy-benzyl)-2,3-dihydro-isoindol-1-one (0.178 g, 0.49 mmol) and CuCl (0.188 g, 1.9 mmol) in DMF (3 mL) was stirred at 140° C. for 2 h. Workup and silica gel column chromatography using combinations 30% ethyl acetate in hexane afforded 5,7-dichloro-2-(4-methoxy-benzyl)-2,3-dihydro-isoindol-1-one (0.079 g, 50%). $^1$H NMR (300 MHz, CDCl$_3$): δ (ppm) 3.78 (s, 3H), 4.19 (s, 2H), 4.70 (s, 2H), 6.80 (d, 2H), 7.25 (d, 3H), 7.41 (s, 1).

Example UR-27

5,7-Dichloro-2-cyclopropyl methyl-2,3-dihydro-isoindol-1-one

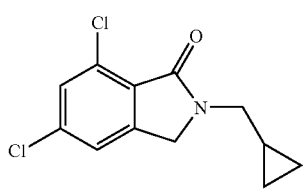

A mixture of 5-bromo-7-chloro-2-cyclopropyl methyl-2, 3-dihydro-isoindol-1-one (0.150 g, 0.5 mmol) and CuCl (0.196 g, 2.0 mmol) in DMF (3 mL) was stirred at 140° C. for 2 h. Workup and silica gel column chromatography using combinations 30% ethyl acetate in hexane afforded 5,7-dichloro-2-cyclopropyl-methyl-2,3-dihydro-isoindol-1-one (0.099 g, 77%). $^1$H NMR (300 MHz, CDCl$_3$): δ (ppm) 0.30 (m, 2H), 0.59 (m, 2H), 1.04 (m, 1H), 3.45 (d, 2H), 4.46 (s, 2H), 7.41 (s, 1H), 7.42 (s, 1H). GC-MS: m/z 256 (M)$^+$, 240 (M−16)$^+$.

Example UR-35

5-Fluoro-7-chloro-2-(4-ethyl-benzyl)-2,3-dihydro-isoindol-1-one

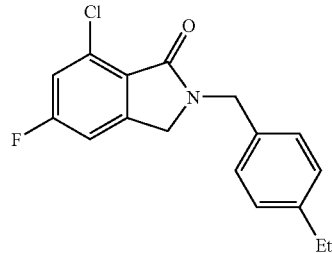

A mixture of 5-fluoro-7-iodo-2-(4-ethyl-benzyl)-2,3-dihydro-isoindol-1-one (0:164 g, 0.41 mmol) and CuCl (0.151 g, 1.6 mmol) in DMF (3 mL) was stirred at 140° C. for 2 h. Workup and silica gel column chromatography using combinations 30% ethyl acetate in hexane afforded 5-fluoro-7-chloro-2-(4-ethyl-benzyl)-2,3-dihydro-isoindol-1-one (0.079 g, 63%). $^1$H NMR (300 MHz, CDCl$_3$): δ (ppm) 1.22 (t, 3H), 2.62 (q, 2H), 4.30 (s, 2H), 4.72 (s, 2H), 6.99-7.32 (m, 6H). GC-MS: m/z 303 (M)$^+$, 274 (M−29)$^+$.

Example UR-34

5-Fluoro-7-chloro-2-(4-chloro-benzyl)-2,3-dihydro-isoindol-1-one

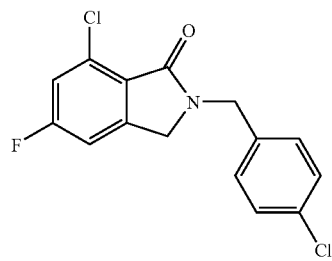

A mixture of 5-fluoro-7-iodo-2-(4-chloro-benzyl)-2,3-dihydro-isoindol-1-one (0.180 g, 0.45 mmol) and CuCl (0.178 g, 1.8 mmol) in DMF (3 mL) was stirred at 140° C. for 2 h. Workup and silica gel column chromatography using combinations 30% ethyl acetate in hexane afforded 5-fluoro-7-chloro-2-(4-chloro-benzyl)-2,3-dihydro-isoindol-1-one (0.073 g, 52%). ¹H NMR (300 MHz, CDCl₃): δ (ppm) 4.23 (s, 2H), 4.75 (s, 2H), 6.99-7.32 (m, 6H). GC-MS: m/z 399 (M–1)⁺, 274 (M–35)⁺.

Example UR-36

5-fluoro-7-chloro-2-cyclopropyl methyl-2,3-dihydro-isoindol-1-one

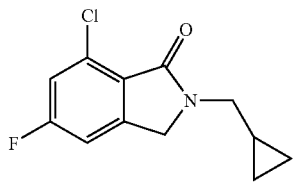

A mixture of 5-fluoro-7-iodo-2-cyclopropyl methyl-2,3-dihydro-isoindol-1-one (0.075 g, 0.23 mmol) and CuCl (0.091 g, 0.92 mmol) in DMF (3 mL) was stirred at 140° C. for 2 h. Workup and silica gel column chromatography using combinations 30% ethyl acetate in hexane afforded 5-fluoro-7-chloro-2-cyclopropyl-methyl-2,3-dihydro-isoindol-1-one (0.034 g, 62%). ¹H NMR (300 MHz, CDCl₃): δ (ppm) 0.32 (m, 2H), 0.57 (m, 2H), 1.04 (m, 1H), 3.44 (d, 2H), 4.46 (s, 2H), 7.09 (d, 1H), 7.14 (d, 1H). GC-MS: m/z 239 (M)⁺, 224 (M–15)⁺.

Example UR-37

6-Fluoro-7-chloro-2-(4-trifluoromethoxy-benzyl)-2,3-dihydro-isoindol-1-one

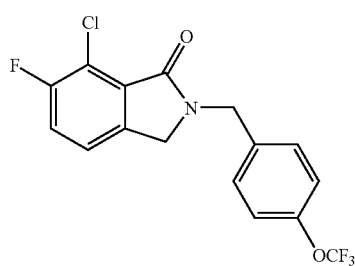

A mixture of 6-fluoro-7-iodo-2-(4-trifluoromethoxy-benzyl)-2,3-dihydro-isoindol-1-one (0.10 g, 0.22 mmol) and CuCl (0.099 g, 1.0 mmol) in DMF (3 mL) was stirred at 140° C. for 2 h. Workup and silica gel column chromatography using combinations 30% ethyl acetate in hexane afforded 6-fluoro-7-chloro-2-(4-trifluoromethoxy-benzyl)-2,3-dihy-dro-isoindol-1-one (0.040 g, 50%). ¹H NMR (300 MHz, CDCl₃): δ (ppm) 4.22 (s, 2H), 4.78 (s, 2H), 7.20-7.37 (m, 6H). GC-MS: m/z 359 (M)⁺.

Example UR-42

5-Fluoro-7-chloro-2-(4-cyano-benzyl)-2,3-dihydro-isoindol-1-one

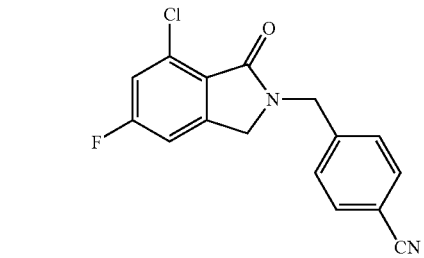

A mixture of 5-fluoro-7-iodo-2-(4-cyano-benzyl)-2,3-dihydro-isoindol-1-one (0.136 g, 0.35 mmol) and CuCl (0.173 g, 1.75 mmol) in DMF (3 mL) was stirred at 140° C. for 2 h. Workup and silica gel column chromatography using combinations 30% ethyl acetate in hexane afforded 5-fluoro-7-chloro-2-(4-cyano-benzyl)-2,3-dihydro-isoindol-1-one (0.05 g, 50%). ¹H NMR (300 MHz, CDCl₃): δ ppm) 4.25 (s, 2H), 4.81 (s, 2H), 7.02 (d, 1H), 7.17 (d, 1H), 7.43 (d, 2H), 7.65 (d, 2H). GC-MS: m/z 300 (M–1)⁺.

Example UR-21

7-chloro-5-nitro-2-(4-trifluoromethoxy-benzyl)-2,3-dihydro-isoindol-1-one

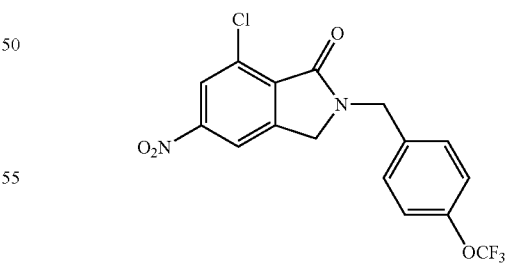

A mixture of 7-iodo-5-nitro-2-(4-trifluoromethoxy-benzyl)-2,3-dihydro-isoindol-1-one (0.100 g, 0.21 mmol) and CuCl (0.083 g, 0.84 mmol) in DMF (3 mL) was stirred at 140° C. for 2 h. Workup and silica gel column chromatography using combinations 30% ethyl acetate in hexane afforded 7-chloro-5-nitro-2-(4-trifluoromethoxy-benzyl)-2,3-dihy-dro-isoindol-1-one (0.040 g, 50%). ¹H NMR (300 MHz, CDCl₃): δ (ppm) 4.37 (s, 2H), 4.82 (s, 2H), 7.21 (d, 2H), 7.37 (d, 2H), 8.15 (s, 1H), 8.31 (s, 1H). GC-MS: m/z 385 (M)⁺.

Example UR-47

7-chloro-5-fluoro-2-[1-(4-trifluoromethoxy-phenyl)-ethyl]-2,3-dihydro-isoindol-1-one

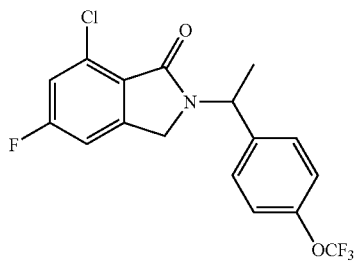

A mixture of 7-iodo-5-fluoro-2-[1-(4-trifluoromethoxy-phenyl)-ethyl]-2,3-dihydro-isoindol-1-one (0.185 g, 0.4 mmol) and CuCl (0.198 g, 2.0 mmol) in DMF (3 mL) was stirred at 140° C. for 2 h. Workup and silica gel column chromatography using combinations 30% ethyl acetate in hexane afforded 5-fluoro-7-chloro-5-fluoro-2-[1-(4-trifluoromethoxy-phenyl)-ethyl]-2,3-dihydro-isoindol-1-one (0.098 g, 66%). ¹H NMR (300 MHz, CDCl₃): δ (ppm) 1.68 (d, 3H), 3.99-4.33 (dd, 2H), 5.78 (q, 1H), 7.01 (d, 1H), 7.14-7.42 (m, 5H). GC-MS: m/z 373 (M)⁺, 358 (M−15)⁺.

Example UR-48

5-Fluoro-7-chloro-2-(4-trifluoromethyl-benzyl)-2,3-dihydro-isoindol-1-one

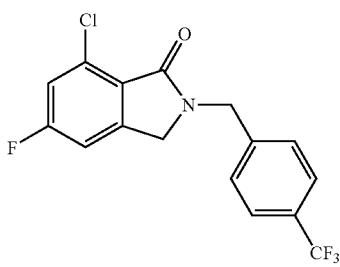

A mixture of 5-fluoro-7-iodo-2-(4-trifluoromethyl-benzyl)-2,3-dihydro-isoindol-1-one (0.110 g, 0.26 mmol) and CuCl (0.125 g, 1.27 mmol) in DMF (3 mL) was stirred at 140° C. for 2 h. Workup and silica gel column chromatography using combinations 30% ethyl acetate in hexane afforded 5-fluoro-7-chloro-2-(4-trifluoromethyl-benzyl)-2,3-dihydro-isoindol-1-one (0.04 g, 45%). ¹H NMR (300 MHz, CDCl₃): δ (ppm) 4.24 (s, 2H), 4.82 (s, 2H), 7.02 (d, 1H), 7.17 (d, 1H), 7.43 (d, 2H), 7.61 (d, 2H). GC-MS: m/z 343 (M)⁺, 324 (M−19)⁺.

Example UR-49

5-Fluoro-7-chloro-2-(4-fluoro-benzyl)-2,3-dihydro-isoindol-1-one

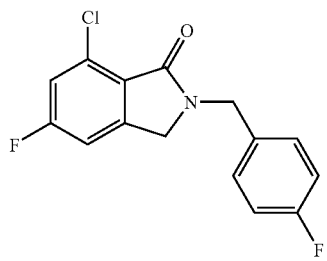

A mixture of 5-fluoro-7-iodo-2-(4-fluoro-benzyl)-2,3-dihydro-isoindol-1-one (0.107 g, 0.28 mmol) and CuCl (0.136 g, 1.38 mmol) in DMF (3 mL) was stirred at 140° C. for 2 h. Workup and silica gel column chromatography using combinations 30% ethyl acetate in hexane afforded 5-fluoro-7-chloro-2-(4-fluoro-benzyl)-2,3-dihydro-isoindol-1-one (0.05 g, 61%). ¹H NMR (300 MHz, CDCl₃): δ (ppm) 4.22 (s, 2H), 4.74 (s, 2H), 6.95-7.35 (m, 6H). GC-MS: m/z 293 (M)⁺.

Example UR-50

5-Fluoro-7-chloro-2-(4-difluoromethoxy-benzyl)-2,3-dihydro-isoindol-1-one

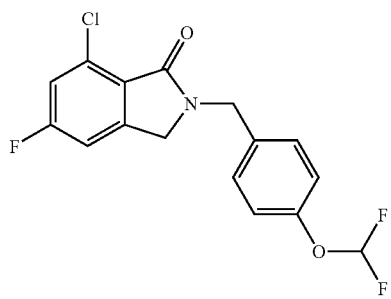

A mixture of 5-fluoro-7-iodo-2-(4-difluoromethoxy-benzyl)-2,3-dihydro-isoindol-1-one (0.120 g, 0.28 mmol) and CuCl (0.138 g, 1.4 mmol) in DMF (3 mL) was stirred at 140° C. for 2 h. Workup and silica gel column chromatography using combinations 30% ethyl acetate in hexane afforded 5-fluoro-7-chloro-2-(4-difluoromethoxy-benzyl)-2,3-dihydro-isoindol-1-one (0.036 g, 38%). ¹H NMR (300 MHz, CDCl$_3$): δ (ppm) 4.22 (s, 2H), 4.74 (s, 2H), 6.49 (t, 1H), 7.01-7.34 (m, 6H). GC-MS: m/z 341 (M)$^+$.

Example UR-64

7-chloro-2-[1-(4-chloro-benzyl)-ethyl]-5-fluoro-2,3-dihydro-isoindol-1-one

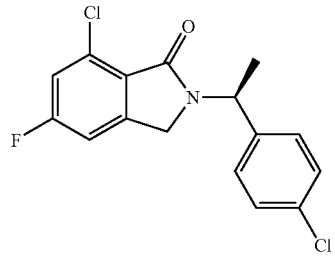

A mixture of 7-iodo-2-[1-(4-chloro-benzyl)-ethyl]-5-fluoro-2,3-dihydro-isoindol-1-one (0.075 g, 0.18 mmol) and CuCl (0.09 g, 0.91 mmol) in DMF (3 mL) was stirred at 140° C. for 2 h. Workup and silica gel column chromatography using combinations 30% ethyl acetate in hexane afforded 7-chloro-2-[1-(4-chloro-benzyl)-ethyl]-5-fluoro-2,3-dihydro-isoindol-1-one (0.025 g, 43%). $^1$H NMR (300 MHz, CDCl$_3$): δ (ppm) 1.67 (d, 3H), 3.94 (d, 1H), 4.30 (d, 1H), 5.75 (q, 1H), 6.97-7.32 (m, 6H). GC-MS: m/z 323 (M−1)$^+$, 308 (M−15)$^+$.

Example UR-51

5-chloro-7-methoxy-2-(4-trifluoromethoxy-benzyl)-2,3-dihydro-isoindol-1-one

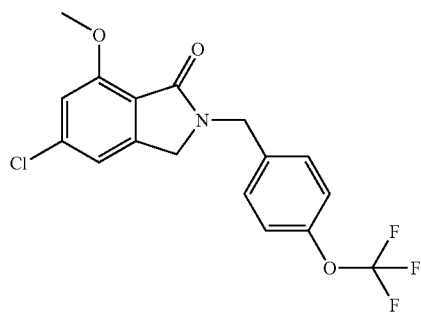

A mixture of 5-bromo-7-methoxy-2-(4-trifluoromethoxy-benzyl)-2,3-dihydro-isoindol-1-one (0.250 g, 0.6 mmol) and CuCl (0.297 g, 3.0 mmol) in DMF (3 mL) was stirred at 140° C. for 2 h. Workup and silica gel column chromatography using combinations 30% ethyl acetate in hexane afforded 5-chloro-7-methoxy-2-(4-trifluoromethoxy-benzyl)-2,3-dihydro-isoindol-1-one (0.080 g, 36%). $^1$H NMR (300 MHz, CDCl$_3$): δ (ppm) 3.97 (s, 3H), 4.19 (s, 2H), 4.74 (s, 2H), 6.92 (d, 2H), 7.15-7.39 (m, 4H). GC-MS: m/z 371 (M)$^+$.

Example UR-3

5-chloro-7-methyl-2-(4-trifluoromethoxy-benzyl)-2,3-dihydro-isoindol-1-one

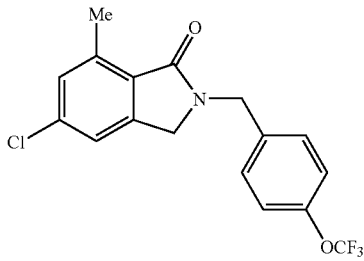

A mixture of 5-chloro-7-methyl-2-(4-trifluoromethoxy-benzyl)-2,3-dihydro-isoindol-1-one (0.120 g, 0.3 mmol) and CuCl (0.118 g, 1.20 mmol) in DMF (3 mL) was stirred at 140° C. for 2 h. Workup and silica gel column chromatography using combinations 30% ethyl acetate in hexane afforded 5-chloro-7-methyl-2-(4-trifluoromethoxy-benzyl)-2,3-dihydro-isoindol-1-one (0.106 g, 100%). $^1$H NMR (300 MHz, CDCl$_3$): δ (ppm) 2.83 (s, 3H), 4.29 (s, 2H), 4.84 (s, 2H), 7.24-7.44 (m, 6H). GC-MS: m/z 355 (M)$^+$, 270 (M−85)$^+$.

Method

Step 1: Preparation of Chloro-Benzoic Esters

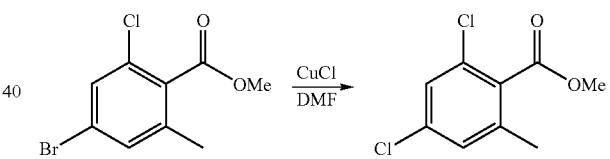

2,4-dichloro-6-methyl-benzoic acid methyl ester

A solution of the 4-bromo-2-chloro-6-methyl-benzoic acid methyl ester (1.31 g, 5 mmol) in DMF was treated with CuCl (1.96 g, 20 mmol) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded 2,4-dichloro-6-methyl-benzoic acid methyl ester (0.72 g, 65%).

Step 2: Bromination

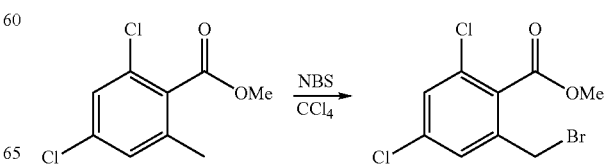

Example

2-Bromomethyl-4,6-dichloro-benzoic acid methyl ester

A mixture of 2,4-dichloro-6-methyl-benzoic acid methyl ester (0.71 g, 3.23 mmol), N-bromosuccinamide (0.693 g, 3.9 mmol), and benzoyl peroxide (0.012 g, 0.05 mmol) in carbon tetrachloride (20 mL) was heated at reflux until majority of ester was consumed (as analyzed by GC/MS). The resulting mixture was filtered, the filtrate was concentrated to afford 2-Bromomethyl-4,6-dichloro-benzoic acid methyl ester. The material was used without further purification.

Step 3: Generation of Isoindolones from Bromo-Esters and Amines

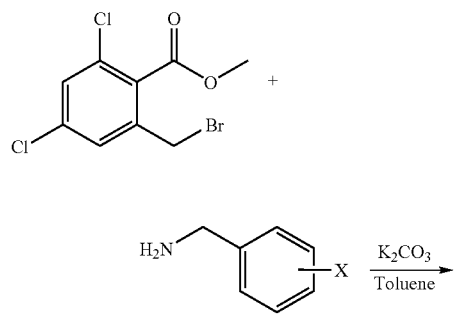

General Procedure

A mixture of the appropriately substituted benzyl amine (1.2 equiv.), the appropriately substituted-2-bromomethyl-benzoic acid methyl ester (1.0 equiv.), and $K_2CO_3$ (2 equiv.) in toluene was heated with stirring at 100° C. for 2 h. The resulting mixture was filtered and the filtrate was concentrated. Silica gel column chromatography of the resulting material using combinations of hexane and ethyl acetate (typically 30% ethyl acetate in hexane) afforded the desired product.

The following compounds were synthesized using the general method described above.

Example UR-57

(S)-5,7-dichloro-2-[1-(4-chloro-phenyl)-ethyl]-2,3-dihydro-isoindol-1-one

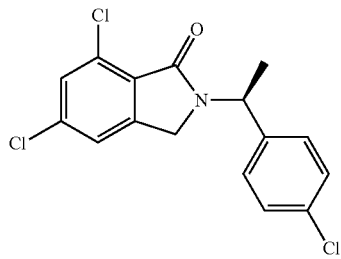

A mixture of 2-Bromomethyl-4,6-dichloro-benzoic acid methyl ester (0.119 g, 0.4 mmol), (S)-1-(4-chloro-phenyl)-ethyl amine (0.067 mL, 0.48 mmol), and $K_2CO_3$ (0.104 g, 0.8 mmol) in toluene (5 mL) was heated with stirring at 100° C. for 2 h. Workup and silica gel column chromatography of the product using 30% ethyl acetate in hexane afforded (S)-5,7-dichloro-2-[1-(4-chloro-phenyl)-ethyl]-2,3-dihydro-isoindol-1-one (0.047 g, 35%). $^1$H NMR (300 MHz, CDCl$_3$): δ (ppm) 1.64 (d, 3H), 3.94 (d, 1H), 4.26 (d, 1H), 5.74 (q, 1H) 7.22-7.42 (m, 6H). GC-MS: m/z 340 (M)$^+$.

Example UR-67

5,7-dichloro-2-(4-difluoromethoxy-benzyl)-2,3-dihydro-isoindol-1-one

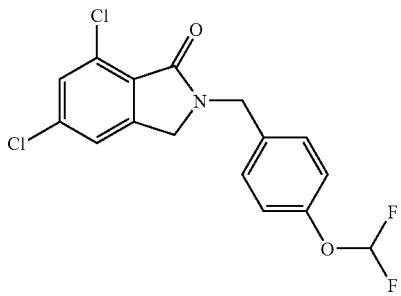

A mixture of 2-Bromomethyl-4,6-dichloro-benzoic acid methyl ester (0.150 g, 0.5 mmol), 4-difluoromethoxy-benzyl amine (0.101 g, 0.6 mmol), and $K_2CO_3$ (0.138 g, 1.0 mmol) in toluene (4 mL) was heated with stirring at 100° C. for 2 h. Workup and silica gel column chromatography of the product using 30% ethyl acetate in hexane afforded 5,7-dichloro-2-(4-difluoromethoxy-benzyl)-2,3-dihydro-isoindol-1-one (0.036 g, 20%). $^1$H NMR (300 MHz, CDCl$_3$): δ (ppm) 4.22 (s, 2H), 4.74 (s, 214), 6.49 (t, 1H) 7.11 (d, 2H), 7.26-7.32 (m, 3H), 7.42 (s, 1H). GC-MS: m/z 357 (M)+.

Example UR-77

5,7-dichloro-2-(4-difluoro-ethoxy-benzyl)-2,3-dihydro-isoindol-1-one

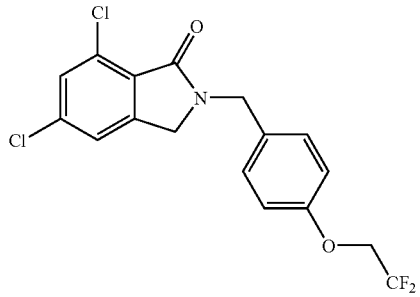

A mixture of 2-Bromomethyl-4,6-dichloro-benzoic acid methyl ester (0.096 g, 0.32 mmol), 4-difluoro-ethoxy-benzyl amine (0.071 g, 0.38 mmol), and $K_2CO_3$ (0.088 g, 0.64 mmol) in toluene (4 mL) was heated with stirring at 100° C. for 2 h. Work-up and silica gel column chromatography of the product using 30% ethyl acetate in hexane afforded 5,7-dichloro-2-(4-difluoro-ethoxy-benzyl)-2,3-dihydro-isoindol-1-one (0.063 g, 53%). $^1$H NMR (300 MHz, $CDCl_3$): δ ppm) 4.09-4.21 (m, 4H), 4.67 (s, 2H), 5.86-6.25 (m, 1H) 6.85 (d, 2H), 7.24 (m, 3H), 7.39 (s, 1H). GC-MS: m/z 371 (M)+, 306 (M−65)+.

Method

Step 1: Preparation of Cyano Derivatives

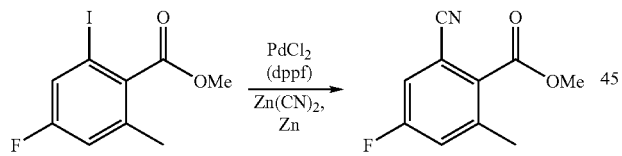

Example 2-cyano-4-fluoro-6-methyl-benzoic acid methyl ester

A mixture of 2-iodo-4-fluoro-6-methyl-benzoic acid methyl ester (0.294 g, 1.0 mmol), $PdCl_2(dppf)_2$ (0.018 g, 0.025 mmol), zinc (0.002 g, 0.03 mmol), Zinc cyanide (0.234 g, 2 mmol) and DMF (3 mL) was stirred at 150° C. for 1 h. The reaction mixture was cooled to room temperature, dissolved in ethyl acetate (50 mL) and washed with water. Combined organic layer was dried ($MgSO_4$), filtered and concentrated. Silica gel column chromatography using 10:1 hexane-ethyl acetate afforded 2-cyano-4-fluoro-6-methyl-benzoic acid methyl ester (0.175 g, 91%).

Step 2: Bromination

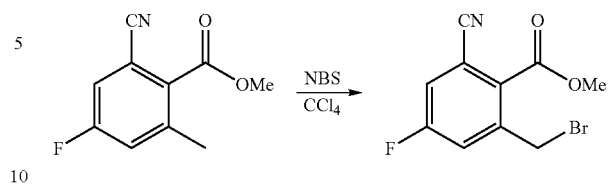

Example 357

2-Bromomethyl-4-fluoro-6-cyano-benzoic acid methyl ester

A mixture of 4-fluoro-2-cyano-6-methyl-benzoic acid methyl ester (1.04 g, 5.38 mmol), N-bromosuccinamide (1.25 g, 7.0 mmol), and benzoyl peroxide (0.024 g, 0.146 mmol) in carbon tetrachloride (50 mL) was heated at reflux until majority of ester was consumed (as analyzed by GC/MS). The resulting mixture was filtered, the filtrate was concentrated to afford 2-bromomethyl-4-fluoro-6-cyano-benzoic acid methyl ester. The material was used without further purification.

Step 3: Generation of Isoindolones from Bromo-Esters and Amines

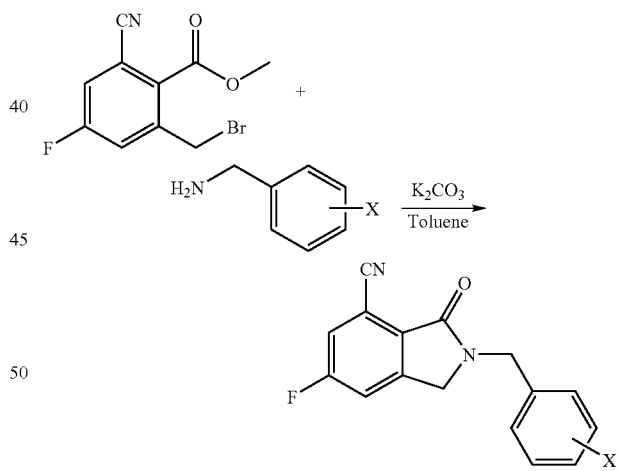

General Procedure

A mixture of the appropriately substituted benzyl amine (1.2 equiv.), the appropriately substituted-2-bromomethyl-benzoic acid methyl ester (1.0 equiv.), and $K_2CO_3$ (2 equiv.) in toluene was heated with stirring at 100° C. for 2 h. The resulting mixture was filtered and the filtrate was concentrated. Silica gel column chromatography of the resulting material using combinations of hexane and ethyl acetate (typically 30% ethyl acetate in hexane) afforded the desired product.

The following compounds were synthesized using the general method described above.

Example UR-58

2-(4-chloro-benzyl)-6-fluoro-3-oxo-2,3-dihydroisoindolone-4-carbonitrile

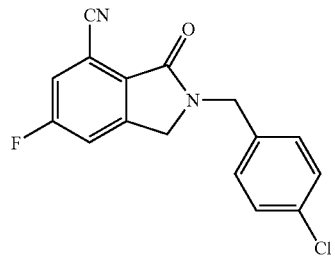

A mixture of 2-bromomethyl-4-fluoro-6-cyano-benzoic acid methyl ester (0.100 g, 0.37 mmol), 4-chlorobenzyl amine (0.058 mL, 0.48 mmol), and $K_2CO_3$ (0.103 g, 0.74 mmol) in toluene (4 mL) was heated with stirring at 100° C. for 2 h. Workup and silica gel column chromatography of the product using 30% ethyl acetate in hexane afforded 2-(4-chloro-benzyl)-6-fluoro-3-oxo-2,3-dihydroisoindolone-4-carbonitrile (0.038 g, 34%). $^1$H NMR (300 MHz, CDCl$_3$): δ (ppm) 4.29 (s, 2H), 4.77 (s, 2H), 7.22-7.53 (m, 6H). GC-MS: m/z 300 (M)$^+$, 265 (M−35)$^+$.

Example UR-59

2-(4-trifluoromethyl-benzyl)-6-fluoro-3-oxo-2,3-dihydroisoindolone-4-carbonitrile

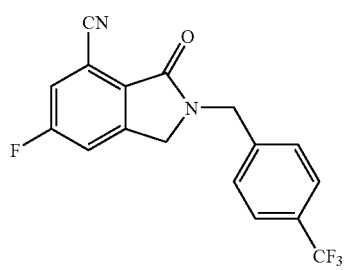

A mixture of 2-bromomethyl-4-fluoro-6-cyano-benzoic acid methyl ester (0.100 g, 0.37 mmol), 4-trifluoromethyl-benzyl amine (0.067 mL, 0.48 mmol), and $K_2CO_3$ (0.103 g, 0.74 mmol) in toluene (4 mL) was heated with stirring at 100° C. for 2 h. Workup and silica gel column chromatography of the product using 30% ethyl acetate in hexane afforded 2-(4-trifluoromethyl-benzyl)-6-fluoro-3-oxo-2,3-dihydroisoindolone-4-carbonitrile (0.040 g, 34%). $^1$H NMR (300 MHz, CDCl$_3$): δ (ppm) 4.31 (s, 2H), 5.01 (s, 2H), 7.34-7.53 (m, 4H), 7.71 (d, 1H). GC-MS: m/z 334 (M)$^+$.

Example UTR-60

2-(3-fluoro-4-methyl-benzyl)-6-fluoro-3-oxo-2,3-dihydroisoindolone-4-carbonitrile

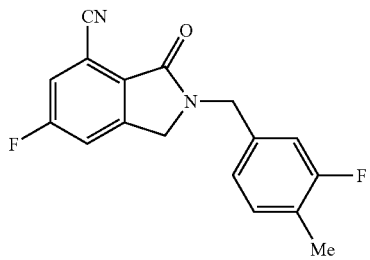

A mixture of 2-bromomethyl-4-fluoro-6-cyano-benzoic acid methyl ester (0.100 g, 0.37 mmol), 4-trifluoromethyl-benzyl amine (0.066 g, 0.48 mmol), and $K_2CO_3$ (0.103 g, 0.74 mmol) in toluene (4 mL) was heated with stirring at 100° C. for 2 h. Workup and silica gel column chromatography of the product using 30% ethyl acetate in hexane afforded 2-(3-fluoro-4-methyl-benzyl)-6-fluoro-3-oxo-2,3-dihydroisoindolone-4-carbonitrile (0.031 g, 28%). $^1$H NMR (300 MHz, CDCl$_3$): δ (ppm) 2.24 (s, 3H), 4.30 (s, 2H), 4.75 (s, 2H), 7.01 (t, 2H), 7.16 (t, 1H), 7.35 (d, 1H), 7.49 (d, 1H). GC-MS: m/z 298 (M)$^+$, 283 (M−15)$^+$.

Example UR-61

(S)-2-[1-(4-chloro-phenyl)-ethyl]-6-fluoro-3-oxo-2,3-dihydroisoindolone-4-carbonitrile

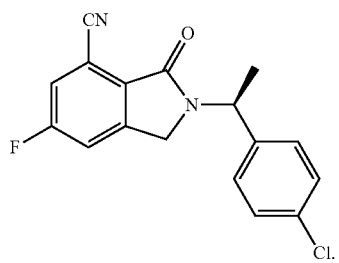

A mixture of 2-bromomethyl-4-fluoro-6-cyano-benzoic acid methyl ester (0.100 g, 0.37 mmol), (S)-1-(4-chloro-phenyl)-ethyl amine (0.067 mL, 0.48 mmol), and $K_2CO_3$ (0.104 g, 0.8 mmol) in toluene (5 mL) was heated with stirring at 100° C. for 2 h. Workup and silica gel column chromatography of the product using 30% ethyl acetate in hexane afforded (S)-2-[1-(4-chloro-phenyl)-ethyl]-6-fluoro-3-oxo-2,3-dihydroisoindolone-4-carbonitrile (0.031 g, 27%). $^1$H NMR (300

MHz, CDCl$_3$): δ (ppm) 1.69 (d, 3H), 3.98 (d, 1H), 4.33 (d, 1H), 5.76 (q, 1H) 7.32 (m, 5H), 7.46 (d, 1H). GC-MS: m/z 314 (M)$^+$, 299 (M–15)$^+$.

Example UR-62

2-[1-(4-trifluoromethoxy-phenyl)-ethyl]-6-fluoro-3-oxo-2,3-dihydroisoindolone-4-carbonitrile

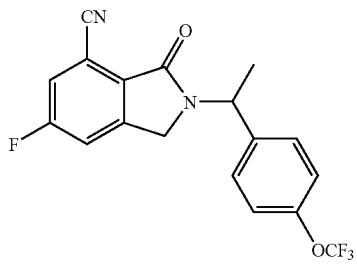

A mixture of 2-bromomethyl-4-fluoro-6-cyano-benzoic acid methyl ester (0.100 g, 0.37 mmol), 1-(4-trifluoromethoxy-phenyl)-ethyl amine (0.092 g, 0.45 mmol), and K$_2$CO$_3$ (0.102 g, 0.74 mmol) in toluene (5 mL) was heated with stirring at 100° C. for 2 h. Workup and silica gel column chromatography of the product using 30% ethyl acetate in hexane afforded 2-[1-(4-trifluoromethoxy-phenyl)-ethyl]-6-fluoro-3-oxo-2,3-dihydroisoindolone-4-carbonitrile (0.079 g, 59%). $^1$H NMR (300 MHz, CDCl$_3$): δ (ppm) 1.71 (d, 3H), 4.04 (d, 1H), 4.41 (d, 1H), 5.78 (q, 1H) 7.19-7.50 (m, 6H).

Method 16

Step 1: Preparation of Alkynyl-Isoindolones

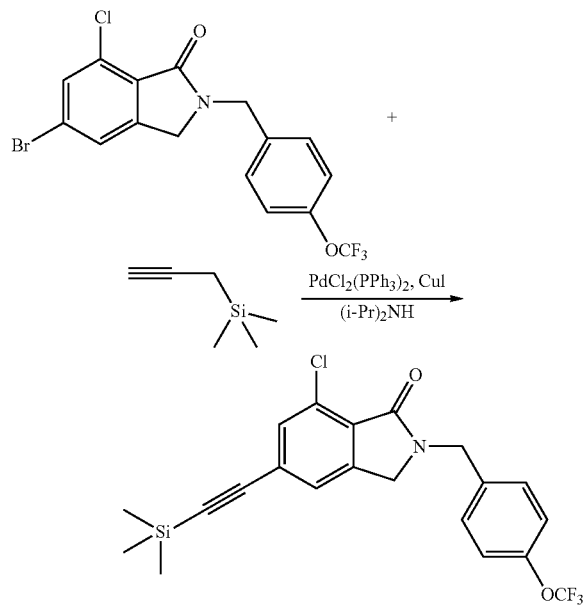

Example 364

7-Chloro-2-(4-trifluoromethoxy-benzyl)-5-trimethyl-silanylethynyl-2,3-dihydro-isoindol-1-one A mixture of 5-bromo-7-chloro-2-(4-trifluoromethoxy-benzyl)-2,3-dihydro-isoindol-1-one (0.210 g, 0.5 mmol), PdCl$_2$(PPh$_3$)$_2$ (0.019 g, 0.05 mmol), and CuI (0.010 g, 0.05 mmol) in diisopropyl amine (4 mL) was treated with trimethyl-prop-2-ynyl-silane (0.141 mL, 1 mmol) and stirred at ambient temperature for 16 h. The reaction mixture diluted with dichloromethane (20 mL) filtered and concentrated. Silica gel column chromatography using 3:1 hexane-ethyl acetate afforded 7-chloro-2-(4-trifluoromethoxy-benzyl)-5-trimethylsilanylethynyl-2,3-dihydro-isoindol-1-one (0.100 g, 46%). GC-MS: 437 (M)$^+$, 356 (M-81)$^+$.

Step 2: Removal of Trimethyl Silyl Group

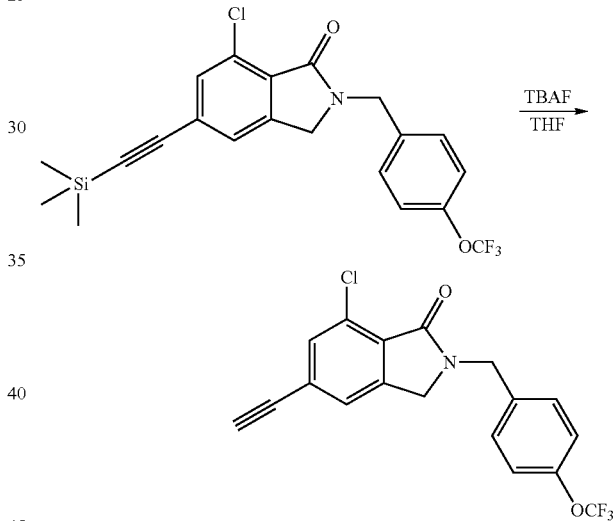

Example 365

7-Chloro-5-ethynyl-2-(4-trifluoromethoxy-benzyl)-2,3-dihydro-isoindol-1-one

A solution of 7-chloro-2-(4-trifluoromethoxy-benzyl)-5-trimethylsilanylethynyl-2,3-dihydro-isoindol-1-one (0.100 g, 0.22 mmol) in THF (1 mL) was treated with a 1M solution of tertiary-butyl amino fluoride-THF (1 mL). The reaction mixture was stirred at ambient temperature for 2 h. After this time, GC-MS indicated that the reaction was completed. The reaction solution was poured into water (7 mL) and extracted with diethyl ether (2×20 mL). The combined organic extracts were dried over anhydrous MgSO$_4$, filtered and concentrated to afford 7-chloro-5-ethynyl-2-(4-trifluoromethoxy-benzyl)-2,3-dihydro-isoindol-1-one. The material was used without purification.

Step 3: Hydrogenation of Alkyne

Example 366

7-chloro-5-ethyl-2-(4-trifluoromethoxy-benzyl)-2,3-dihydro-isoindol-1-one

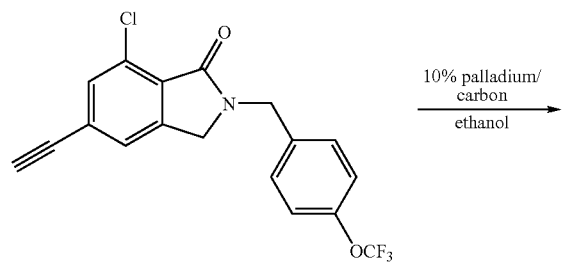

A solution of 7-chloro-5-ethynyl-2-(4-trifluoromethoxy-benzyl)-2,3-dihydro-isoindol-1-one (0.080 g, 0.22 mmol) in ethanol (25 mL) was treated with 10% palladium on carbon (20 mg) and shook vigorously under 45 p.s.i. hydrogen for 2-3 h. The resulting mixture was filtered through Celite and the filtrate concentrated under reduced pressure. Silica gel column chromatography using combinations of hexane-ethyl acetate (typically 3:1 hexane-ethyl acetate) afforded 7-chloro-5-ethyl-2-(4-trifluoromethoxy-benzyl)-2,3-dihydro-isoindol-1-one (0.051 g, 63%). $^1$H NMR (300 MHz, CDCl$_3$): δ (ppm) 1.28 (t, 3H), 2.74 (q, 2H), 4.23 (s, 2H), 4.81 (s, 2H), 7.12-7.39 (m, 6H). GC-MS: m/z 369 (M)$^+$, 300 (M−69)$^+$.

The following compound was synthesized using general method 16, step 3 as described above.

Example 367

7-Chloro-5-ethyl-2-(4-trifluoromethyl-benzyl)-2,3-dihydro-isoindol-1-one

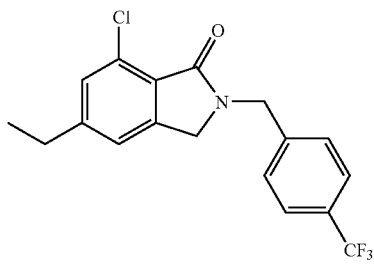

A mixture of 7-chloro-5-ethynyl-2-(4-trifluoromethyl-benzyl)-2,3-dihydro-isoindol-1-one (0.035 g, 0.1 mmol) and 10% palladium on carbon (20 mg) in ethanol (25 mL) was reduced under 45 p.s.i. hydrogen. Workup and silica gel column chromatography using combinations 3:1 hexane-ethyl acetate afforded 7-chloro-5-ethyl-2-(4-trifluoromethyl-benzyl)-2,3-dihydro-isoindol-1-one (0.015 g, 43%). $^1$H NMR (300 MHz, CDCl$_3$): δ (ppm) 1.23 (t, 3H), 2.69 (q, 2H), 4.20 (s, 2H), 4.81 (s, 2H), 7.09 (s, 1H), 7.24 (d, 1H), 7.42 (d, 2H), 7.59 (d, 2H). GC-MS: m/z 353 (M)$^+$, 334 (M−29)$^+$, 284 (M−50)$^+$.

Method

Step 1: Preparation of Alkenes

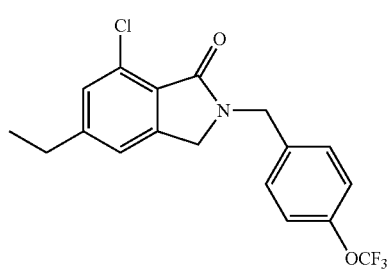

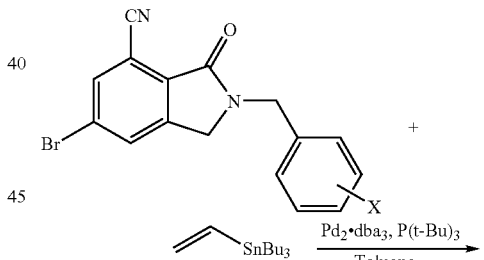

A mixture of appropriately substituted isoindolones (1 equiv.), tributyl vinl tin (1.2 equiv.) Pd$_2$dba$_3$ (1 mol %), tris-t-butyl-phosphine (0.005 mL, 0.02 mmol) and toluene (3 mL) was added to a vial and stirred at 100° C. for 24 h. After this time the reaction mixture was cooled to room temperature and stirred with potassium fluoride (200 mg) for 45 min. The solids were filtered and filtrate was concentrated. Silica gel column chromatography using combinations 3:1 hexane-ethyl acetate afforded 7-chloro-5-vinyl-2,3-dihydro-isoindol-1-one derivatives.

Step 2: Reduction of Alkenes to Alkanes

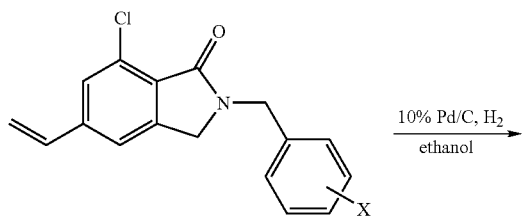

A mixture of appropriately substituted isoindolones (1 equiv.) and 10% palladium on carbon (20 mg) in ethanol (25 mL) was reduced under 45 p.s.i. hydrogen. Workup and silica gel column chromatography using combinations 3:1 hexane-ethyl acetate afforded the product.

The following compounds were synthesized using the general method described above.

Example UR-7

7-Chloro-5-ethyl-2-(4-chloro-benzyl)-2,3-dihydro-isoindol-1-one

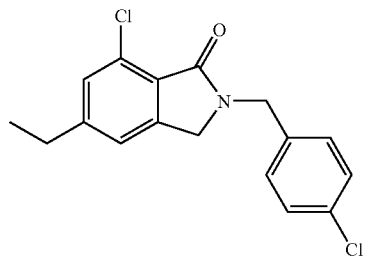

A mixture of 7-chloro-5-ethenyl-2-(4-chloro-benzyl)-2,3-dihydro-isoindol-1-one (0.032 g, 0.1 mmol) and 10% palladium on carbon (20 mg) in ethanol (25 mL) was reduced under 45 p.s.i. hydrogen. Workup and silica gel column chromatography using combinations 3:1 hexane-ethyl acetate afforded 7-chloro-5-ethyl-2-(4-chloro-benzyl)-2,3-dihydro-isoindol-1-one (0.020 g, 63%). $^1$H NMR (300 MHz, CDCl$_3$): δ (ppm) 1.23 (t, 3H), 2.68 (q, 2H), 4.18 (s, 2H), 4.72 (s, 2H), 7.09 (s, 1H), 7.22-7.32 (m, 5H). GC-MS: m/z 319 (M–1)$^+$, 284 (M–35)$^+$.

Example UR-13

7-Chloro-5-ethyl-2-(4-ethyl-benzyl)-2,3-dihydro-isoindol-1-one

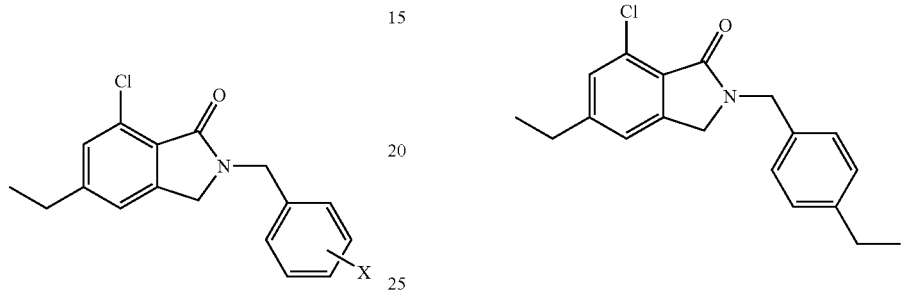

A mixture of 7-chloro-5-ethenyl-2-(4-ethyl-benzyl)-2,3-dihydro-isoindol-1-one (0.062 g, 0.2 mmol) and 10% palladium on carbon (20 mg) in ethanol (25 mL) was reduced under 45 p.s.i. hydrogen. Workup and silica gel column chromatography using combinations 3:1 hexane-ethyl acetate afforded 7-chloro-5-ethyl-2-(4-ethyl-benzyl)-2,3-dihydro-isoindol-1-one (0.031 g, 50%). $^1$H NMR (300 MHz, CDCl$_3$): δ (ppm) 1.23 (t, 6H), 2.68 (q, 4H), 4.18 (s, 2H), 4.72 (s, 2H), 7.07 (s, 1H), 7.14-7.36 (m, 5H). GC-MS: m/z 313 (M)$^+$, 284 (M–29)$^+$.

Example UR-16

7-Chloro-5-ethyl-2-(4-fluoro-benzyl)-2,3-dihydro-isoindol-1-one

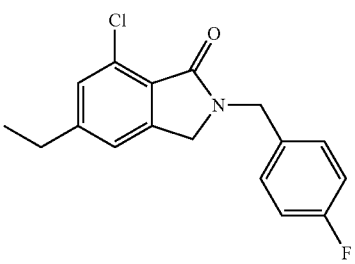

A mixture of 7-chloro-5-ethenyl-2-(4-fluoro-benzyl)-2,3-dihydro-isoindol 1-one (0.134 g, 0.45 mmol) and 10% palladium on carbon (20 mg) in ethanol (25 mL) was reduced under 45 p.s.i. hydrogen. Workup and silica gel column chromatography using combinations 3:1 hexane-ethyl acetate afforded 7-chloro-5-ethyl-2-(4-fluoro-benzyl)-2,3-dihydro-isoindol-1-one (0.068 g, 50%). $^1$H NMR (300 MHz, CDCl$_3$):

δ (ppm) 1.24 (t, 3H), 2.68 (q, 2H), 4.19 (s, 2H), 4.74 (s, 2H), 6.98-7.32 (m, 6H). GC-MS: m/z 303 (M)+.

Example UR-1

7-Chloro-5-propyl-2-(4-trifluoromethoxy-benzyl)-2,3-dihydro-isoindol-1-one

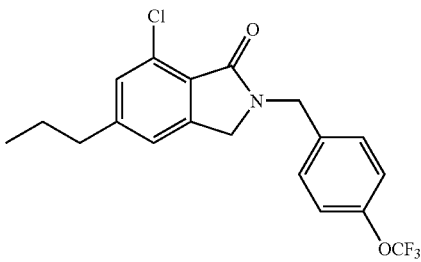

A mixture of 7-chloro-5-propynyl-2-(4-trifluoromethoxy-benzyl)-2,3-dihydro-isoindol-1-one (0.082 g, 0.19 mmol) and 10% palladium on carbon (20 mg) in ethanol (25 mL) was reduced under 45 p.s.i. hydrogen. Workup and silica gel column chromatography using combinations 3:1 hexane-ethyl acetate afforded 7-Chloro-5-propyl-2-(4-trifluoromethoxy-benzyl)-2,3-dihydro-isoindol-1-one (0.050 g, 69%). $^1$H NMR (300 MHz, CDCl$_3$): δ (ppm) 0.94 (t, 3H), 1.64 (m, 2H), 2.63 (t, 2H), 4.20 (s, 2H), 4.78 (s, 2H), 7.09 (s, 1H), 7.14-7.38 (m, 5H). GC-MS: m/z 383 (M)+, 354 (M−29)+.

Method

Reduction of Alkene

Example UR-44

7-ethyl-5-fluoro-2-(4-trifluoromethoxy-benzyl)-2,3-dihydro-isoindol-1-one

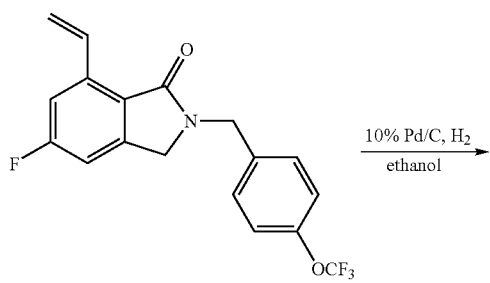

-continued

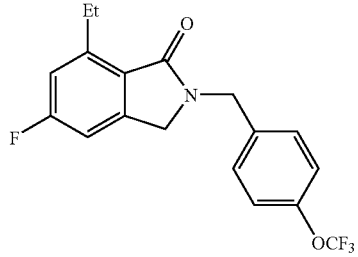

A solution of 7-ethyl-5-fluoro-2-(4-trifluoromethoxy-benzyl)-2,3-dihydro-isoindol-1-one (0.100 g, 0.28 mmol) in ethanol (25 mL), dichloromethane (5 mL) was treated with 10% palladium on carbon (20 mg) and shook vigorously under 45 p.s.i. hydrogen for 2-3 h. The resulting mixture was filtered through Celite and the filtrate concentrated under reduced pressure. Silica gel column chromatography using combinations of hexane-ethyl acetate (typically 3:1 hexane-ethyl acetate) afforded 7-ethyl-5-fluoro-2-(4-trifluoromethoxy-benzyl)-2,3-dihydro-isoindol-1-one (0.087 g, 88%). $^1$H NMR (300 MHz, CDCl$_3$): δ (ppm) 1.28 (t, 3H), 3.22 (q, 2H), 4.21 (s, 2H), 4.75 (s, 2H), 6.95 (dd, 2H), 7.19 (d, 21); 7.35 (d, 2H). GC-MS: m/z 353 (M)+.

Method

Step 2: Bromination

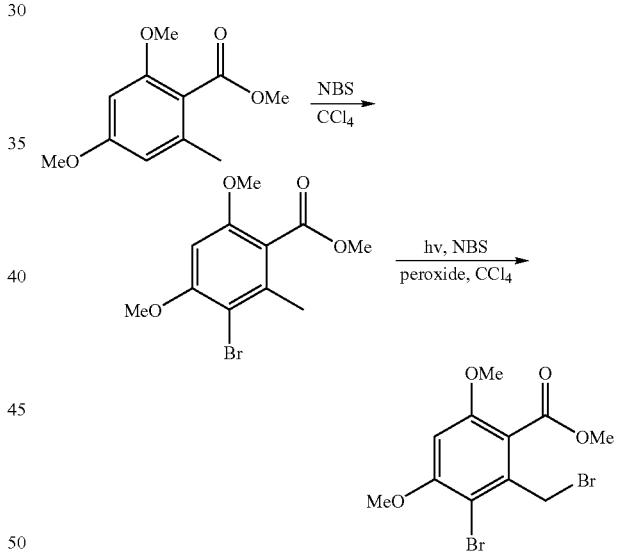

Example 3-bromo-2-Bromomethyl-4,6-dimethoxy-benzoic acid methyl ester

A mixture of 2,4-dimethoxy-6-methyl-benzoic acid methyl ester (1.90 g, 8.5 mmol), N-bromosuccinamide (1.81 g, 10.2 mmol), and benzoyl peroxide (0.12 g, 0.5 mmol) in carbon tetrachloride (20 mL) was heated at reflux until majority of ester was consumed (as analyzed by GC/MS). The resulting mixture was filtered, to the filtrate benzoyl peroxide (0.12 g, 0.5 mmol) was added and refluxed in the presence of UV lamp (60 Hz) for 12 h. After this time, reaction mixture was filtered and the filtrate was concentrated to afford 3-bromo-2-Bromomethyl-4,6-dimethoxy-benzoic acid methyl ester. The material was used without further purification.

Step 2: Generation of Isoindolones from Bromo-Esters and Amines

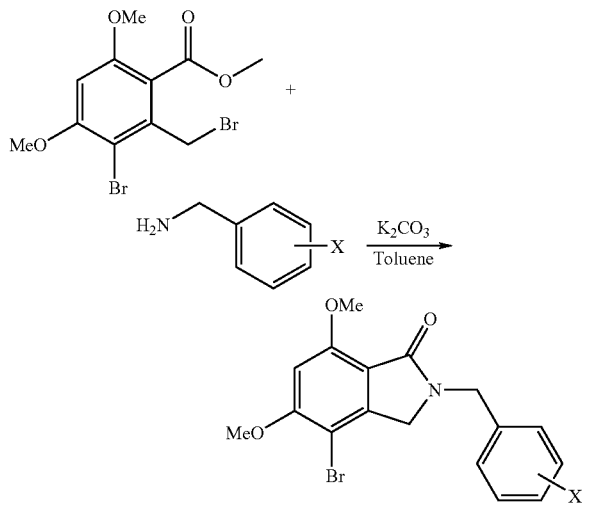

General Procedure

A mixture of the appropriately substituted benzyl amine (1.2 equiv.), the appropriately substituted-3-bromo-2-bromomethyl-benzoic acid methyl ester (1.0 equiv.), and $K_2CO_3$ (2 equiv.) in toluene was heated with stirring at 100° C. for 2 h. The resulting mixture was filtered and the filtrate was concentrated. Silica gel column chromatography of the resulting material using combinations of hexane and ethyl acetate (typically 30% ethyl acetate in hexane) afforded the desired product.

Step 3: Reduction of Aryl Bromides

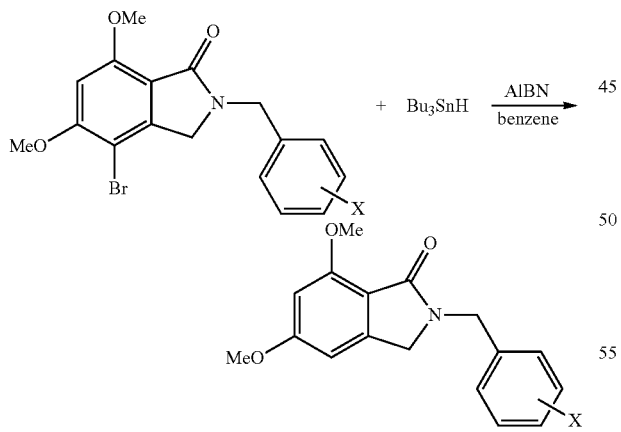

General Procedure

To a solution of appropriately substituted isoindolones (1 equiv.) in benzene under N2 atmosphere was added 2,2'-azobis(2-methyl propionitrile) AIBN (5.0 mg), followed by tributyl tin hydride (2 equiv.). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The product was purified using column chromatography (typically 40% ethyl acetate in hexanes).

The following compounds were synthesized using the procedure described above.

Example UR-81

5,7-Dimethoxy-2-(4-trifluoromethoxy-benzyl)-2,3-dihydro-isoindol-1-one

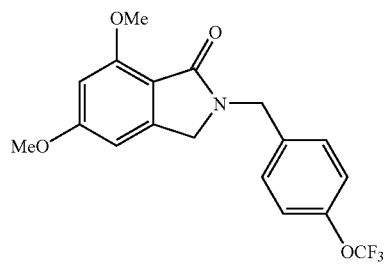

To a solution of 4-bromo-5,7-Dimethoxy-2-(4-trifluoromethoxy-benzyl)-2,3-dihydro-isoindol-1 one (0.200 g, 0.45 mmol) in benzene under N2 atmosphere was added 2,2'-azobis(2-methyl propionitrile) AIBN (5.0 mg), followed by tributyl tin hydride (0.238 mL, 0.9 mmol). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-(4-trifluoromethoxy-benzyl)-2,3-dihydro-isoindol-1one (0.106 g, 64%). $^1$H NMR (300 MHz, CDCl$_3$): δ (ppm) 3.82 (s, 3H), 3.95 (s, 3H), 4.17 (s, 2H), 4.72 (s, 2H), 6.43 (d, 2H), 7.16 (d, 2H), 7.32 (d, 2H). GC-MS: m/z 367 (M)$^+$, 349 (M−18)$^+$.

Example UR-82

5,7-Dimethoxy-2-(4-chloro-benzyl)-2,3-dihydro-isoindol-1-one

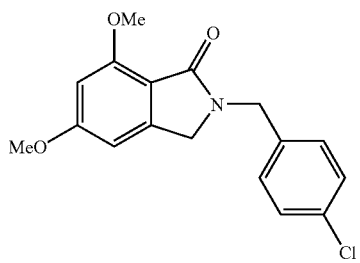

To a solution of 4-bromo-5,7-Dimethoxy-2-(4-chloro-benzyl)-2,3-dihydro-isoindol-1-one (0.100 g, 0.25 mmol) in benzene under N2 atmosphere was added 2,2'-azobis(2-methyl propionitrile) AIBN (5.0 mg), followed by tributyl tin hydride (0.132 mL, 0.5 mmol). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-(4-chloro-benzyl)-2,3-dihydro-isoindol-1one (0.035 g, 44%). $^1$H NMR (300 MHz, CDCl$_3$): δ (ppm) 3.82 (s, 3H), 3.95 (s, 3H), 4.15 (s, 2H), 4.69 (s, 2H), 6.43 (d, 2H), 7.25 (m, 4H). GC-MS: m/z 317 (M)$^+$, 299 (M−18)$^+$.

Example UR-83

5,7-Dimethoxy-2-[1-(4-chloro-phenyl)-ethyl]-2,3-dihydro-isoindol-1-one

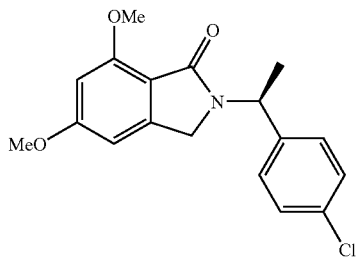

To a solution of 4-bromo-5,7-Dimethoxy-2-[1-(4-chloro-phenyl)-ethyl]-2,3-dihydro-isoindol-1 one (0.112 g, 0.27 mmol) in benzene under N2 atmosphere was added 2,2'-azobis(2-methyl propionitrile) AIBN (5.0 mg), followed by tributyl tin hydride (0.145 mL, 0.55 mmol). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-[1-(4-chloro-phenyl)-ethyl]-2,3-dihydro-isoindol-1one (0.056 g, 63%). $^1$H NMR (300 MHz, CDCl$_3$): δ (ppm) 1.43 (d, 3H), 3.63 (s, 3H), 3.68 (d, 1H), 3.74 (s, 3H), 3.99 (d, 1H), 5.53 (q, 1H), 6.23 (dd, 2H), 7.15 (m, 4H). GC-MS: m/z 331 (M)$^+$, 316 (M−15)$^+$.

Method

Step 1: Demethylation

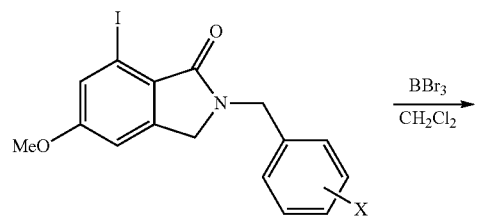

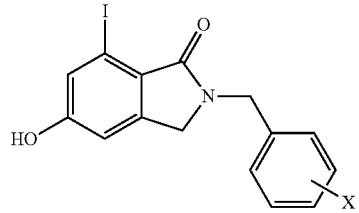

General Procedure:

A solution of appropriately substituted 5-methoxy-7-iodo-isoindolone (1 equiv.) in dichloromethane (10 mL) was treated with 1M solution of tribromoborane (3 equiv.) at −78° C. The reaction mixture was allowed to warm up to room temperature slowly and stirred at room temperature for 2 h. Reaction mixture was diluted with ethyl acetate, washed with water. Combined organic layer was dried and concentrated to give appropriately substituted 5-hydroxy-7-iodo-isoindolones.

Step 2: Synthesis of Iodo-Difluoromethoxy Isoindolones

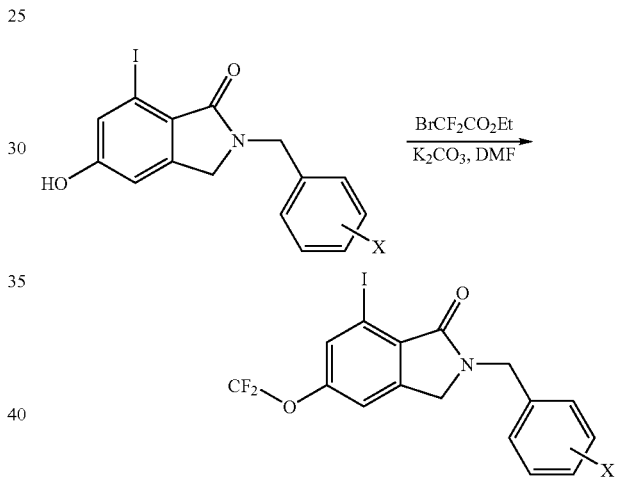

General Procedure

A mixture of appropriately substituted 5-hydroxy-7-iodo-isoindolones (1 equiv.), bromo-difluoro-acetic acid-ethyl ester (1.5 equiv.), potassium carbonate (2 equiv.) and DMF was stirred at 100° C. for 6 h. After complete consumption of starting material, the solids were filtered off and the filtrate was concentrated. Silica Gel column chromatography of product using 30% ethyl acetate in hexane gave products.

Step 3: Synthesis of Chloro-Difluoromethoxy-Isoindolones

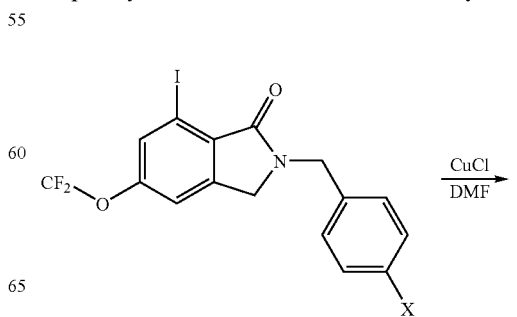

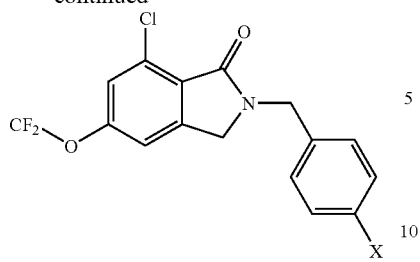

General Procedure

A solution of the appropriately substituted 5-difluoromethoxy-7-iodo-isoindolones (1 equiv.) in DMF was treated with CuCl (5 equiv.) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded products.

The following compounds were synthesized using the general method described above.

Example UR-79

7-Chloro-2-(4-chloro-benzyl)-5-difluoromethoxy-2,3-dihydro-isoindolone

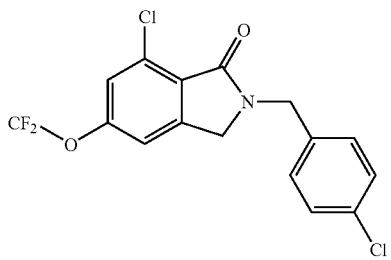

A solution of the 7-iodo-5-difluoromethoxy-2-(4-bromobenzyl)-2,3-dihydro-isoindolone (0.072 g, 0.15 mmol) in DMF (5 mL) was treated with CuCl (0.101 g, 1.02 mmol) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded 7-chloro-2-(4-chloro-benzyl)-5-difluoromethoxy-2,3-dihydro-isoindolone (0.04 g, 74%). $^1$H NMR (300 MHz, CDCl$_3$): δ (ppm) 4.02 (s, 2H), 4.54 (s, 2H), 6.37 (t, 1H), 6.88 (s, 1H), 7.01-7.16 (m, 5H). GC-MS: m/z 357 (M−1)$^+$, 322 (M−35)$^+$.

Example UR-80

7-Chloro-2-(4-trifluoromethoxy-benzyl)-5-difluoromethoxy-2,3-dihydro-isoindolone

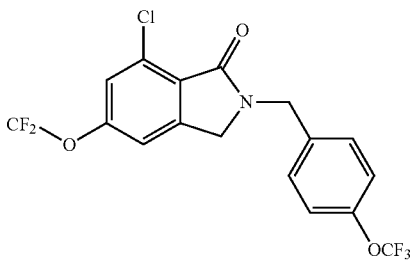

A solution of the 7-iodo-5-difluoromethoxy-2-(4-trifluoromethoxy-benzyl)-2,3-dihydro-isoindolone (0.082 g, 0.16 mmol) in DMF (5 mL) was treated with CuCl (0.064 g, 0.65 mmol) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded 7-Chloro-2-(4-trifluoromethoxy-benzyl)-5-difluoromethoxy-2,3-dihydro-isoindolone (0.02 g, 31%). $^1$H NMR (300 MHz, CDCl$_3$): δ (ppm) 4.08 (s, 2H), 4.58 (s, 2H), 6.37 (t, 1H), 6.87 (s, 1H), 7.01 (m, 3H), 7.17 (d, 2H). GC-MS: m/z 407 (M)$^+$, 322 (M−85)$^+$.

Example UR-85

7-Chloro-2-[1-(4-chloro-phenyl)-ethyl]-5-difluoromethoxy-2,3-dihydro-isoindolone

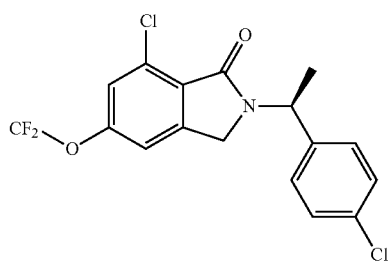

A solution of the 7-iodo-2-[1-(4-chloro-phenyl)-ethyl]-5-difluoromethoxy-2,3-dihydro-isoindolone (0.122 g, 0.26 mmol) in DMF (5 mL) was treated with CuCl (0.130 g, 1.31 mmol) and stirred at 140° C. for 1-2 h. After this time, the reaction mixture was diluted with dichloromethane (15 mL) and the solids removed by filtration. The filtrate was concentrated. Silica gel column chromatography using, typically 30% ethyl acetate in hexane, afforded 7-Chloro-2-[1-(4-chloro-phenyl)-ethyl]-5-difluoromethoxy-2,3-dihydro-isoindolone (0.05 g, 52%). $^1$H NMR (300 MHz, CDCl$_3$): δ

(ppm) 1.66 (d, 3H), 3.94 (d, 1H), 4.27 (d, 1H), 5.74 (q, 1H), 6.54 (t, 1H), 7.17 (s, 1H), 7.26 (s, 1H), 7.31 (m, 4H). GC-MS: m/z 371 (M)+, 356 (M−15)+.

Example UR-84

6-difluoromethoxy-3-oxo-2-(4-trifluoromethoxy-benzyl)-2,3-dihydro-1H-isoindole-4-carbonitrile

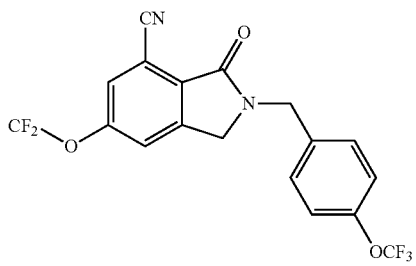

A mixture of 7-iodo-2-(4-trifluoromethoxy-benzyl)-5-difluoromethoxy-2,3-dihydro-isoindolone (0.125 g, 0.25 mmol), $PdCl_2(dppf)_2$ (0.009 g, 0.012 mmol), zinc (0.002 g, 0.03 mmol), zinc cyanide (0.035 g, 0.3 mmol) and DMF (3 mL) was stirred at 150° C. for 1 h. The reaction mixture was cooled to room temperature, dissolved in ethyl acetate (50 mL) and washed with water. Combined organic layer was dried ($MgSO_4$), filtered and concentrated. Silica gel column chromatography using 10:1 hexane-ethyl acetate afforded 6-difluoromethoxy-3-oxo-2-(4-trifluoromethoxy-benzyl)-2,3-dihydro-1H-isoindole-4-carbonitrile (0.02 g, 20%). $^1$H NMR (300 MHz, $CDCl_3$): δ (ppm) 4.32 (s, 2H), 4.80 (s, 2H), 6.60 (t, 1H), 6.87 (s, 1H), 7.21 (d, 2H), 7.37 (d, 2H), 7.42 (s, 1H), 7.53 (s, 1H). GC-MS: m/z 398 (M)+, 313 (M−85)+

J26: 7-Chloro-2-(4-chloro-benzyl)-5-(1H-imidazol-4-yl)-2,3-dihydro-isoindol-1-one

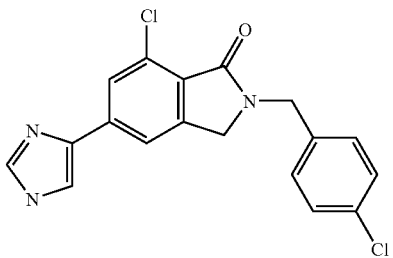

A mixture of 5-Bromo-7-chloro-2-(4-chloro-benzyl)-2,3-dihydro-isoindol-1-one (127 mg, 0.343 mmol), 4-Tributyl-stannanyl-1-trityl-1H-imidazole (300 mg, 0.514 mmol), and Pd(PPh$_3$)$_4$ (79 mg, 0.0514 mmol) in toluene (15 mL) stirred overnight at 110° C. The mixture was cooled, diluted with water and extracted with ethyl acetate. The organics were washed with brine, dried over anhydrous sodium sulfate, filtered and concentrated. The resulting residue (7-Chloro-2-(4-chloro-benzyl)-5-(1-trityl-1H-imidazol-4-yl)-2,3-dihydro-isoindol-1-one) was dissolved in formic acid (5 mL) and stirred at room temperature for 18 hrs. The solvent was removed in vacuo and the residue was dissolved in ethyl acetate. The organics were washed with 3N HCl (2×30 ml) and the aqueous washes were combined, neutralized with 1N NaOH, and extracted with ethyl acetate. The organics were washed with brine, and dried over anhydrous sodium sulfate, filtered and concentrated. Column chromatography (100% Ethyl acetate—5% 2M $NH_3$ in MeOH/$CH_2Cl_2$) provided the title compound (22 mg, 18%). $^1$H NMR (300 MHz, $CDCl_3$): δ 7.80 (s, 2H), 7.7.75 (s, 1H), 7.46 (s, 1H), 7.35-7.30 (m, 4H), 4.77 (s, 2H), 4.27 (s, 2H).

J98: 5-(5-Dimethylaminomethyl-pyridin-3-yl)-7-methyl-2-(4-trifluoromethoxy-benzyl)-2,3-dihydro-isoindol-1-one

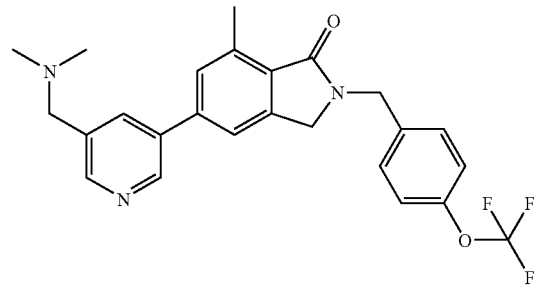

Methanesulfonic acid 5-[7-methyl-1-oxo-2-(4-trifluoromethoxy-benzyl)-2,3-dihydro-1H-isoindol-5-yl]-pyridin-3-ylmethyl ester (70 mg, 0.138 mmol) was dissolved in 2M dimethylamine in THF (5 mL) and stirred at 50° C. for 18 hrs. The mixture was cooled, diluted with water, and extracted with ethyl acetate. The organics were washed with brine, dried over anhydrous sodium sulfate, filtered and concentrated. Column chromatography (5% 2M N13 in MeOH/$CH_2Cl_2$) provided the title compound (37 mg, 59%) as a brown oil. $^1$H NMR (300 MHz, $CDCl_3$): δ 8.75 (s, 1H), 8.53 (s, 1H), 7.89 (s, 1H), 7.44 (d, 2H), 7.37 (d, 2H), 7.20 (d, 2H), 4.81 (s, 2H), 4.31 (s, 2H), 3.52 (s, 2H), 2.84 (s, 3H), 2.30 (s, 6H).

The following compounds were made using the above general procedure:

| Example | Structure | Name | Yield | NMR |
| --- | --- | --- | --- | --- |
| J109 | 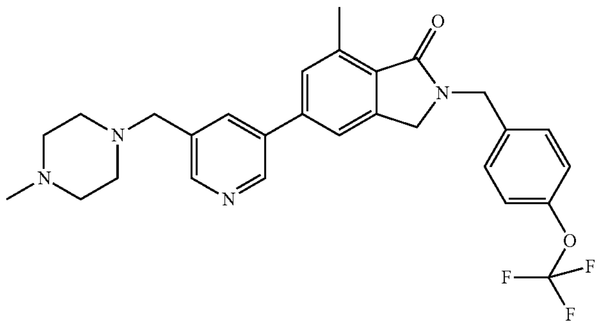 | 7-Methyl-5-[5-(4-methyl-piperazin-1-ylmethyl)-pyridin-3-yl]-2-(4-trifluoromethoxy-benzyl)-2,3-dihydro-isoindol-1-one | 24 mg 67% yellow oil | 8.73 (s, 1H), 8.56 (s, 1H), 7.86 (s, 1H), 7.42 (d, 2H), 7.37 (d, 2H), 7.19 (d, 2H), 4.82 (s, 2H), 4.32 (s, 2H), 3.60 (s, 2H), 2.85 (s, 3H), 2.52-2.42 (br s, 8H), 2.30 (s, 3H) |
| J110 | 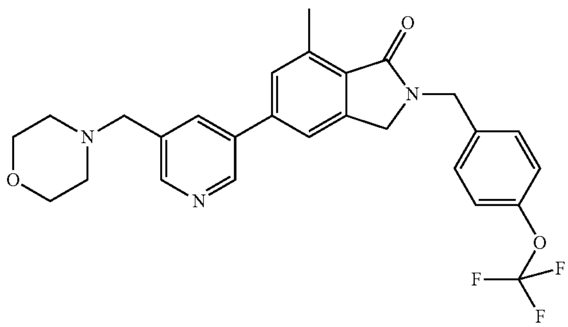 | 7-Methyl-5-(5-morpholin-4-ylmethyl-pyridin-3-yl)-2-(4-trifluoromethoxy-benzyl)-2,3-dihydro-isoindol-1-one | 23 mg 66% yellow oil | 8.75 (br s, 1H), 8.58 (br s, 1H), 7.88 (s, 1H), 7.43 (s, 2H), 7.37 (d, 2H), 7.21 (d, 2H), 4.82 (s, 2H), 4.33 (s, 2H), 3.73 (t, 4H), 3.60 (s, 2H), 2.85 (s, 3H), 2.50 (t, 4H) |
| J119 | 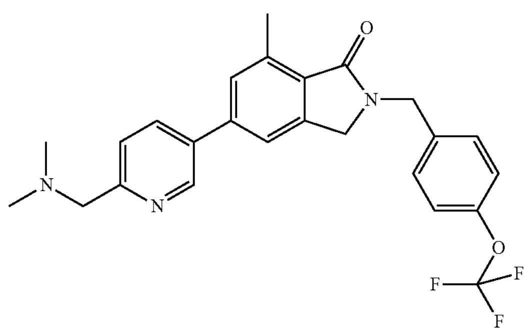 | 5-(6-Dimethylamino methyl-pyridin-3-yl)-7-methyl-2-(4-trifluoromethoxy-benzyl)-2,3-dihydro-isoindol-1-one | 26 mg 48% brown oil | 8.78 (s, 1H), 7.87 (d, 1H), 7.49 (s, 1H), 7.48-7.35 (m, 4H), 7.20 (d, 2H), 4.81 (s, 2H), 4.32 (s, 2H), 3.65 (s, 2H), 2.84 (s, 3H), 2.34 (s, 6H) |
| J120 | 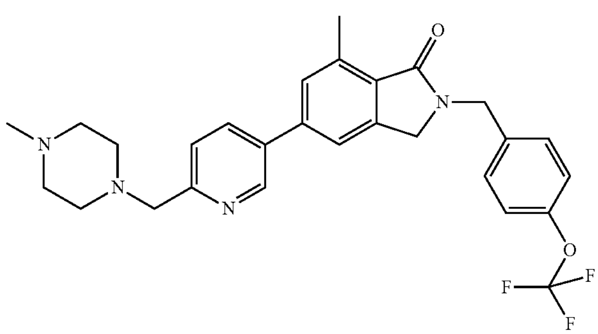 | 7-Methyl-5-{6-(4-methyl-piperazin-1-ylmethyl)-pyridin-3-yl]-2-(4-trifluoromethoxy-benzyl)-2,3-dihydro-iso indol-1-one | 48 mg 80% brown oil | 8.78 (s, 1H), 7.85 (s, 1H), 7.50 (d, 1H), 7.40-7.34 (m, 4H), 7.20 (d, 2H), 4.81 (s, 2H), 4.32 (s, 2H), 3.73 (s, 2H), 2.84 (s, 3H), 2.60-2.52 (br d, 8H), 2.31 (s, 3H) |

| Example | Structure | Name | Yield | NMR |
|---|---|---|---|---|
| J121 | 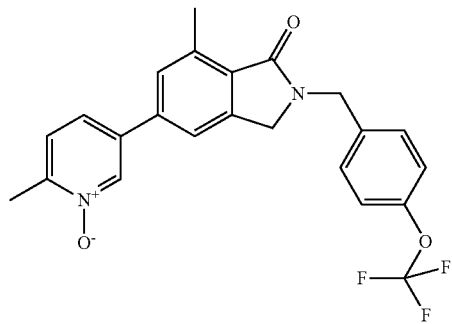 | 7-Methyl-5-(6-morpholin-4-ylmethyl-pyridin-3-yl)-2-(4-trifluoromethoxy-benzyl)-2,3-dihydro-isoindol-1-one | 54 mg 92% brown oil | 8.79 (s, 1H), 7.86 (s, 1H), 7.51 (d, 2H), 7.40-7.35 (m, 4H), 7.20 (d, 2H), 4.81 (s, 2H), 4.32 (s, 2H), 3.77 (t, 4H), 3.72 (s, 2H), 2.84 (s, 3H), 2.56 (t, 4H) |

J114: 7-Methyl-5-(6-methyl-1-oxy-pyridin-3-yl)-2-(4-trifluoromethoxy-benzyl)-2,3-dihydro-isoindol-1-one J128: 7-Chloro-5-[(piperidin-4-ylmethyl)-amino]-2-(4-trifluoromethoxy-benzyl)-2,3-dihydro-isoindol-1-one A solution of 7-Methyl-5-(6-methyl-pyridin-3-yl)-2-(4-trifluoromethoxy-benzyl)-2,3-dihydro-isoindol-1-one (117 mg, 0.284 mmol) in chloroform (7 mL) was chilled to 0° C. in an ice bath and 3-Chloro-benzenecarboperoxoic acid (120 mg, 0.680 mmol) was added. The mixture stirred at room temperature for 3 hours and was washed with saturated sodium bicarbonate and water, dried over anhydrous sodium sulfate, filtered and concentrated. Column chromatography (4% MeOH in $CH_2Cl_2$) provided the title compound (120 mg, 100%) as a colorless solid. $^1$H NMR (300 MHz, $CDCl_3$): δ 8.55 (s, 1H), 7.40-7.34 (m, 6H), 7.21 (d, 2H), 4.81 (s, 2H), 4.32 (s, 2H), 2.83 (s, 3H), 2.50 (s, 3H).

4-{[7-Chloro-1-oxo-2-(4-trifluoromethoxy-benzyl)-2,3-dihydro-1H-isoindol-5-ylamino]-methyl}-piperidine-1-carboxylic acid tert-butyl ester (47 mg, 0.0848 mmol) was stirred in formic acid (4 mL) overnight at room temperature and the solvent was removed under vacuum. The resulting residue was triturated with ether to provide the title compound (29 mg, 74%) as a colorless solid. $^1$H NMR (300 MHz, $CDCl_3$): δ 8.44 (s, 2H), 7.59 (s, 1H), 7.53 (s, 1H), 7.46 (d, 2H), 7.29 (d, 2H), 4.84 (s, 2H), 4.41 (s, 2H), 4.08 (s, 2H), 3.43-3.39 (m, 2H), 3.03-2.94 (m, 2H), 2.77 (d, 2H), 2.05-2.00 (m, 2H), 1.46-1.42 (m, 2H).

The following compound was made using the above general procedure:

| Example | Structure | Name | Yield | NMR |
|---|---|---|---|---|
| J131 | 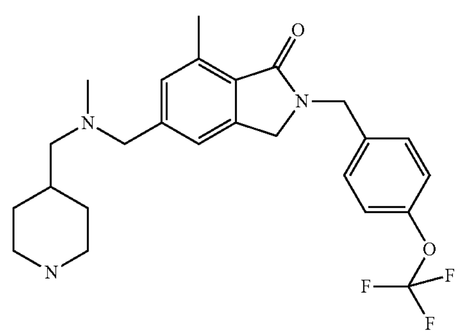 | 7-Methyl-5-[(methyl-piperidin-4-ylmethyl-amino)-methyl]-2-(4-trifluoromethoxy-benzyl)-2,3-dihydro-isoindol-1-one | 35 mg 85% yellow oil | 7.35 (d, 2H), 7.20-7.14 (m, 4H), 4.78 (s, 2H), 4.22 (s, 2H), 3.75-3.68 (br d, 2H), 3.48 (s, 2H), 3.23 (d, 2H), 2.75 (s, 3H), 2.75-2.66 (m, 2H), 2.23 (d, 2H), 2.15 (s, 3H), 1.90-1.86 (m, 2H), 1.70-1.66 (m, 1H) |

J132: 7-Methyl-5-{[methyl-(1-methyl-piperidin-4-ylmethyl)-amino]-methyl}-2-(4-trifluoromethoxy-benzyl)-2,3-dihydro-isoindol-1-one

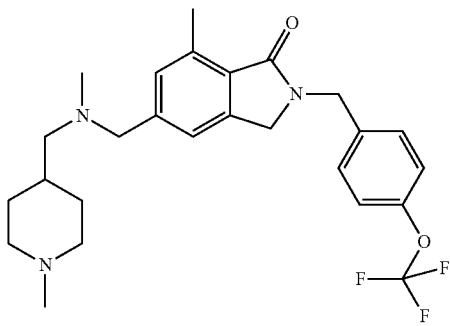

To a solution of 7-Methyl-5-[(methyl-piperidin-4-ylmethyl-amino)-methyl]-2-(4-trifluoromethoxy-benzyl)-2,3-dihydro-isoindol-1-one (30 mg, 0.065 mmol) in methanol (1.5 mL) was added formic acid (0.02 ml), formaldehyde (0.1 mL), and Sodium cyanoborohydride (0.2 mL, 0.1 M in THF) respectively. The mixture stirred at room temperature for 1 hour and was then diluted with water and extracted with ethyl acetate. The organics were washed with brin, dried over anhydrous sodium sulfate, filtered and concentrated to provide the title compound (15 mg, 38%) as a colorless oil. $^1$H NMR (300 MHz, CDCl$_3$): δ 7.35 (d, 2H), 7.21-7.14 (m, 4H), 4.78 (s, 2H), 4.22 (s, 2H), 3.48 (s, 2H), 2.94 (d, 2H), 2.75 (s, 3H), 2.33 (s, 3H), 2.23 (d, 2H), 2.16 (s, 3H), 2.01 (t, 2H), 1.84-1.80 (m, 2H), 1.54-1.51 (m, 1H), 1.25-1.20 (m, 2H).

M55: 5-(1-Cyclopropyl-piperidin-4-ylmethyl)-7-methyl-2-(4-trifluoromethoxy-benzyl)-2,3-dihydro-isoindol-1-one

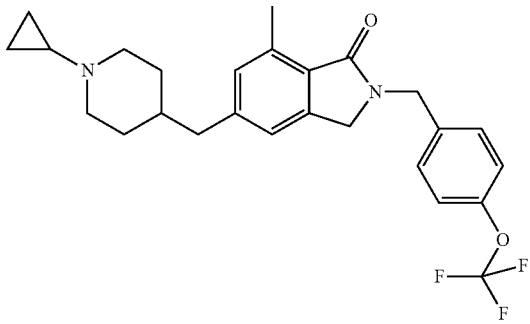

To a solution of 7-Methyl-5-piperidin-4-ylmethyl-2-(4-trifluoromethoxy-benzyl)-2,3-ihydro-isoindol-1-one (100 mg, 0.247 mmol) in MeOH (10 ml), acetic acid (148.2 mg, 2.47 mmol) was added at 0° C. 5 mins later, [(1-ethoxycyclopropyl)oxy]trimethylsilane (86 mg, 0.494 mmol) was added dropwise at 0-10° C., followed by sodium cyanoborohydride (0.5 ml, 0.494 mmol). The resulting mixture was allowed to reflux for 28 days. After removal of MeOH, the residue was quenched with saturated sodium bicarbonate solution in water to pH=9-10. The product was extracted with EtOAc. The combined organic layer was washed with water, brine, dried over anhydrous sodium sulfate, filtered and concentrated. Column chromatography (4% MeOH/EtOAc to 20% 2M ammonia in MeOH/EtOAc) provided the title compound (31 mg, 27.4%) as a yellow solid. $^1$H NMR (300 MHz, CDCl$_3$): δ 7.33-7.36 (m, 2H), 7.15-7.20 (m, 2H), 6.98 (d, 2H), 4.76 (s, 2H), 4.21 (s, 2H), 3.02-3.06 (m, 2H), 2.73 (s, 3H), 2.55-2.66 (m, 3H), 2.10-2.14 (m, 2H), 1.55-1.63 (m, 2H), 1.23-1.30 (m, 3H), 0.43-0.46 (m, 4H). GTPγS 0.0715.

I2: 5-Bromo-7-chloro-2-(3-phenylprop-2-ynyl)-2,3-dihydroisoindol-1-one

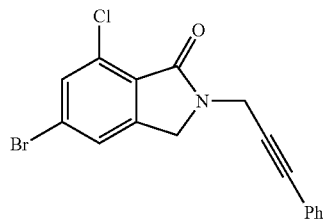

To a solution of 5-bromo-7-chloro-2-prop-2-ynyl-2,3-dihydroisoindol-1-one (100 mg, 0.352 mmol), iodobenzene (0.527 mmol), and CuI (8.03 mg, 0.042 mmol) in triethylamine (4 mL) was added tetrakis(triphenylphosphine)palladium (16.3 mg, 0.014 mmol). After 4 hours the mixture was concentrated and purified by column chromatography (20% EtOAc/hexanes) to provide the title compound (64 mg, 51%). $^1$H NMR (300 MHz, CDCl$_3$): δ (ppm) 7.60 (s, 1H), 7.54 (s, 1H), 7.44 (m, 2H), 7.33 (m, 3H), 4.67 (s, 2H), 4.53 (s, 2H).

I3: 7-Chloro-2-(3-phenylprop-2-ynyl)-5-(1-pyridin-2-ylmethyl-1H-pyrazol-4-yl)-2,3-dihydroisoindol-1-one

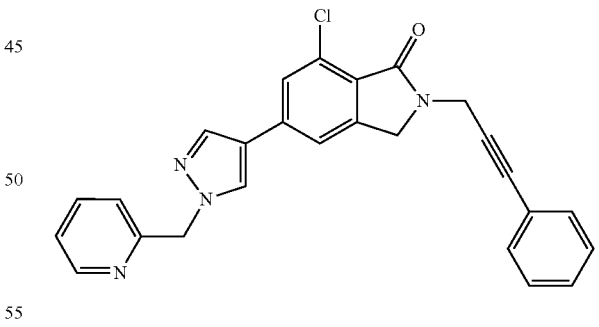

To a solution of 5-bromo-7-chloro-2-(3-phenylprop-2-ynyl)-2,3-dihydroisoindol-1-one (60 mg, 0.167 mmol) in DMF (4 mL) was added 2-[4-(4,4,5,5-tetramethyl-[1,3,2]-dioxaborolan-2-yl)pyrazol-1-ylmethyl]pyridine (61.71 mg, 0.216 mmol), PdCl$_2$ (13.57 mg, 0.017 mmol), and K$_2$CO$_3$ (70 mg, 0.5 mmol). The mixture was heated at 110° C. overnight, then poured into water and extracted with EtOAc. The organic phase was washed with brine, dried (Na$_2$SO$_4$), filtered, and concentrated. Column chromatography (4% (2M NH$_3$ in MeOH)/CH$_2$Cl$_2$) provided the title compound (46.9 mg, 64%). $^1$H NMR (300 MHz, CDCl$_3$): δ (ppm) 8.61 (d, 1H), 7.90 (dd, 1H), 7.45 (m, 4H), 7.32 (m, 5H), 7.18 (d, 1H), 5.49 (s, 2H), 4.66 (s, 2H), 4.53 (s, 2H).

I4: 7-Chloro-2-(3-phenylpropyl)-5-(1-pyridin-2-ylmethyl-1H-pyrazol-4-yl)-2,3-dihydroisoindol-1-one

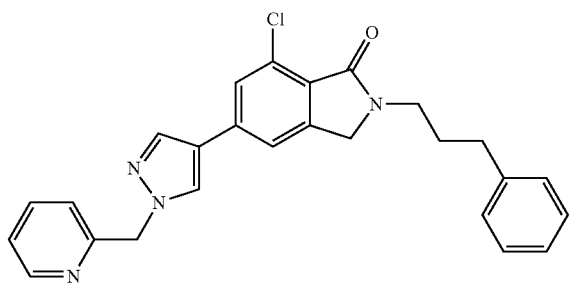

To a solution of 7-chloro-2-(3-phenylprop-2-ynyl)-5-(1-pyridin-2-ylmethyl-1H-pyrazol-4-yl)-2,3-dihydroisoindol-1-one (30 mg, 0.07 mmol) in EtOH (5 mL) was added 10% Pd on carbon (16.5 mg). A $H_2$ balloon was attached to the flask. After 16 hours the reaction was filtered and concentrated to provide the title compound (29.7 mg, 98%) as a yellow oil. $^1$H NMR (300 MHz, CDCl$_3$): δ (ppm) 8.61 (ddpg, 1H), 7.88 (m, 2H), 7.70 (t, 1H), 7.48 (d, 2H), 7.40 (d, 2H), 7.23 (m, 8H), 5.49 (s, 2H), 4.32 (s, 2H), 3.68 (t, 2H), 2.70 (t, 2H), 2.00 (tt, 2H).

What is claimed is:

1. A compound according to formula I:

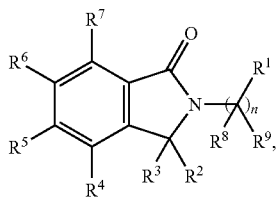

wherein:

$R^1$ is a phenyl ring substituted by one or more A;

$R^2$ and $R^3$ are H;

$R^4$ and $R^6$ are H;

$R^5$ is a 5- to 7-membered ring that may contain one or more heteroatoms independently selected from the group consisting of N, O and S, wherein $R^5$ may be substituted by one or more A;

$R^7$ is selected from the group consisting of H, F, Cl, Br, I and $C_{1-6}$-alkyl;

$R^8$ and $R^9$ are independently H or $C_{1-6}$-alkyl;

n is selected from the group consisting of 1, 2, 3, 4, 5, 6, 7 and 8; and

A is $C_{1-6}$-alkylheterocyclyl or $OC_{1-6}$-alkylhalo;

or a pharmaceutically acceptable salt or optical isomer thereof.

2. A compound according to claim 1 selected from the group consisting of:

7-chloro-5-(1-(pyridin-4-ylmethyl)-1H-pyrazol-4-yl)-2-(4-(trifluoromethoxy)benzyl)isoindolin-1-one;

7-chloro-5-(1-(pyridin-3-ylmethyl)-1H-pyrazol-4-yl)-2-(4-(trifluoromethoxy)benzyl)isoindolin-1-one;

7-chloro-5-(1-(pyridin-2-ylmethyl)-1H-pyrazol-4-yl)-2-(4-(trifluoromethoxy)benzyl)isoindolin-1-one;

7-methyl-5-(1-(pyridin-4-ylmethyl)-1H-pyrazol-4-yl)-2-(4-(trifluoromethoxy)benzyl)isoindolin-1-one;

7-methyl-5-(1-(pyridin-3-ylmethyl)-1H-pyrazol-4-yl)-2-(4-(trifluoromethoxy)benzyl)isoindolin-1-one, and 7-methyl-5-(1-(pyridin-2-ylmethyl)-1H-pyrazol-4-yl)-2-(4-(trifluoromethoxy)benzyl)isoindolin-1-one or a pharmaceutically acceptable salt of any foregoing compound.

3. A pharmaceutical composition comprising a compound according to claim 1 and a pharmaceutically acceptable carrier or excipient.

4. A pharmaceutical composition comprising a compound according to claim 2 and a pharmaceutically acceptable carrier or excipient.

* * * * *